US006858710B2

(12) United States Patent
Bangur et al.

(10) Patent No.: US 6,858,710 B2
(45) Date of Patent: Feb. 22, 2005

(54) COMPOSITIONS AND METHODS FOR THE THERAPY AND DIAGNOSIS OF OVARIAN CANCER

(75) Inventors: Chaitanya S. Bangur, Seattle, WA (US); Marc W. Retter, Carnation, WA (US); Gary R. Fanger, Mill Creek, WA (US); Paul Hill, Duvall, WA (US)

(73) Assignee: Corixa Corporation, Seattle, WA (US)

( * ) Notice: Subject to any disclaimer, the term of this patent is extended or adjusted under 35 U.S.C. 154(b) by 204 days.

(21) Appl. No.: 10/198,053

(22) Filed: Jul. 17, 2002

(65) Prior Publication Data

US 2003/0124140 A1 Jul. 3, 2003

Related U.S. Application Data

(63) Continuation-in-part of application No. 09/907,969, filed on Jul. 17, 2001, which is a continuation-in-part of application No. 09/884,441, filed on Jun. 18, 2001, which is a continuation-in-part of application No. 09/827,271, filed on Apr. 4, 2001, which is a continuation-in-part of application No. 09/667,857, filed on Sep. 20, 2000, which is a continuation-in-part of application No. 09/636,801, filed on Aug. 10, 2000, now abandoned, which is a continuation-in-part of application No. 09/617,747, filed on Jul. 17, 2000, now abandoned, which is a continuation-in-part of application No. 09/404,879, filed on Sep. 24, 1999, now Pat. No. 6,468,546, which is a continuation-in-part of application No. 09/338,933, filed on Jun. 23, 1999, now Pat. No. 6,488,931, which is a continuation-in-part of application No. 09/216,003, filed on Dec. 17, 1998, now Pat. No. 6,670,463, which is a continuation-in-part of application No. 09/215,681, filed on Dec. 17, 1998, now Pat. No. 6,528,253.

(51) Int. Cl.[7] ...................... A61K 35/14; A61K 39/395; A61K 51/00; C07K 1/00; C07K 16/00

(52) U.S. Cl. .................. 530/386; 424/1.11; 424/130.1; 530/387.1; 530/388.1; 530/388.8

(58) Field of Search ........................... 435/252.3, 320.1; 536/23.1, 24.1; 424/1.11, 130.1; 530/386, 387.1, 388.1, 388.8

(56) References Cited

FOREIGN PATENT DOCUMENTS

| | | |
|---|---|---|
| WO | WO 00/36107 | 6/2000 |
| WO | WO 01/16318 | 3/2001 |
| WO | WO 01/57272 | 8/2001 |
| WO | WO 02/02587 | 1/2002 |
| WO | WO 02/02624 | 1/2002 |
| WO | WO 02/10187 | 2/2002 |
| WO | WO 02/16429 | 2/2002 |
| WO | WO 02/16581 | 2/2002 |

OTHER PUBLICATIONS

Jin et al., "Human T cell leukemia virus type 1 oncoprotein tax targets the human mitotic checkpoint protein MA1," *Cell 93*:81–91, Apr. 3, 1998.

Köhler et al., "Immunotherapy of Ovarian Carcinoma with the Monoclonal Anti–Idiotype Antibody ACA125—Results of the Phase LB Study," *Gebrutshilfe und Fraenheilkunde, 58*(4):180–186, Apr. 1998.

Ma et al., "Use of encapsulated single chain antibodies for induction of anti–idiotypic humoral and cellular immune responses," *Journal of Pharmaceutical Sciences, 87*(11):1375–1378, Nov. 1998.

Parker et al., "Scheme for ranking potential HLA–A2 binding peptides based on independent binding of individual peptide side–chains," *The Journal of Immunology 152*(1):163–175, Jan. 1, 1994.

Perez–Vilar and Hill, "The structure and assembly of secreted mucins," *The Journal of Biological Chemistry 274*(45):31751–31754, Nov. 5, 1999.

Peoples et al., "Ovarian cancer–associated lymphocyte recognition of folate binding protein peptides," *Annals of Surgical Oncology, 5*(8):743–750, Dec. 1998.

Schena et al., "Parallel human genome analysis: Microarray–based expression monitoring of 1000 genes," *Proc. Natl. Acad. Sci., 93*:10614–10619, Oct. 1996.

Yee et al., "Isolation of tyrosinase–specific $CD8^+$ and $CD4^+$ T cell clones from the peripheral blood of melanoma patients following in vitro stimulation with recombinant vaccinia virus," *The Journal of Immunology 157*: 4079–4086, 1996.

Bookman et al., "Biological therapy of ovarian cancer: Current directions," *Seminars in Oncology, 25*(3):381–396, 1998.

Gibson et al., "Novel method for real time quantitative RT–PCR," *Genome Research 6*:995–1001, Oct. 1996.

Gillespie et al., "Mage, Bage and Gage: Tumour antigen expression in benign and malignant ovarian tissue," *British Journal of Cancer, 78*(6):816–821, Sep. 1998.

Heid et al., "Real time quantitative PCR," *Genome Research 6*:986–994; Oct. 1996.

Heller et al., "Discovery and analysis of inflammatory disease–related genes using cDNA microarrays," *Proc. Natl. Acad. Sci. USA 94*:2150–2155, Mar. 1997.

Ishikawa et al., "Prediction of the coding sequence of unidentified human genes. The complete sequence of 100 new cDNA clones from brain which can code for large proteins in vitro," *DNA Res., 5*:169–176, 1998.

Hovig, E. et al., "CA125: The End of the Beginning," *Tumor Biology 22*: 345–347, 2001.

(List continued on next page.)

*Primary Examiner*—John Brusca
*Assistant Examiner*—Shubo (Joe) Zhou
(74) *Attorney, Agent, or Firm*—Seed IP Law Group PLLC

(57) ABSTRACT

Compositions and methods for the therapy and diagnosis of cancer, particularly ovarian cancer, are disclosed. Illustrative compositions comprise one or more ovarian tumor polypeptides, immunogenic portions thereof, polynucleotides that encode such polypeptides, antigen presenting cell that expresses such polypeptides, and T cells that are specific for cells expressing such polypeptides. The disclosed compositions are useful, for example, in the diagnosis, prevention and/or treatment of diseases, particularly ovarian cancer.

8 Claims, 101 Drawing Sheets

OTHER PUBLICATIONS

O'Brien, T.J. et al., "The CA 125 Gene: A Newly Discovered Extension of the Glycosylated N–Terminal Domain Doubles the Size of This Extracellular Superstructure," *Tumor Biology 23*: 154–169, 2002.

O'Brien, T.J. et al., "The CA 125 Gene: An Extracellular Superstructure Dominated by Repeat Sequences," *Tumor Biology 22*: 348–366, 2001.

Schummer, M. et al., "Comparative hybridization of an array of 21 500 ovarian cDNAs for the discovery of genes overexpressed in ovarian carcinomas," *Gene 238*: 375–385, 1999.

Whitehouse, C. et al., "NBR1 interacts with fasciculation and elongation protein zeta–1 (FEZ1) and calcium and integrin binding protein (CIB) and shows developmentally restricted expression in the neural tube," *Eur. J. Biochem. 269*: 538–545, 2002.

Yin and Lloyd, "Molecular Cloning of the CA125 Ovarian Cancer Antigen. Identification as a new mucin, MUC16," *Journal of Biological Chemistry 276*(29): 27371–27375, Jul. 20, 2001.

Yin, B.W.T. et al., "Ovarian cancer antigen CA125 is encoded by the *MUC16* mucin gene," *International Journal of Cancer 98*: 737–740, 2002.

11729.1 contg

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC

11729-45.21.21.cons1

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA

11729-45.21.21.cons2

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC

11731.1contig

TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

*Fig. 1A*

11731.2contig

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA 11734.1contig AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC 11734.2contig GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC 11736.1contg GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA

*Fig. 1B*

11736.2contig

AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG

11739-1&2

CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA

11740.1.contig

GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA

*Fig. 1C*

11766.1.contig

CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT 11766.2.contig GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCCGGTCGCCTGCGTGCCGGAGTGTGTGCGAGGGAGGGGGAGGGCGTCGGGGGGGTGGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA 11773.2.contig AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG 11775-1&2

ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA

*Fig. 1D*

11777.1&2.cons

CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG

11779.2.contig

AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA

11781 & 37.cons

CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT

CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA 11784-1 & 2

GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC 11785.2.contig GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT

*Fig. 1F*

11718-1&2 cons

TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA 13690.4

CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC 13693.1

TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG 13694.1

CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG

GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG 13695.1

GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAANGGAAAGAAACTTA
GAAGCTCAACAAGCTGAAGATAATCCCATCAGGCATTTCCCATAGGCCTTGCAACTCTGTTCACTGAGAGATGTTA
TCCTG 13695.2

AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAAATGATCATAATTTTAGCATAAACCGAGCAATC
GGCGACCCC 13697.1

TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC 13699.1&2

CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA 13703.3

CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA 13705.1

TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG

TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC 13707.4

TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC 13708.1&2

GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT 13709.1

TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T 13722.3

CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA 13722.4

GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT 13724-13698-13748

GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC

GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA 13732.1

ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG 13732.2

ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA

GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG 13735.2

CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG 13736.1

AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC 13737.1&2

CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA 13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC 13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG 13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA 14351.1

ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT 14351.2

ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA 14354.2

AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT 14354.1

CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T

*Fig. 1P*

```
TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG
```

16432-1

```
GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA
```

16432-2

```
GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC
```

17184.3

```
TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG
```

17184.4

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG 17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCCGGCTCCCAGTACCTGAAAAACCAAGGCCTACTGNCTTTTGGATGCTCTCTTGGGCCACG 17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC 17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC

CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC 17191.2&89.2

TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT

*Fig. 1S*

```
AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA
```

*Fig. 2A*

ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA

*Fig. 2B*

ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA

*Fig. 2C*

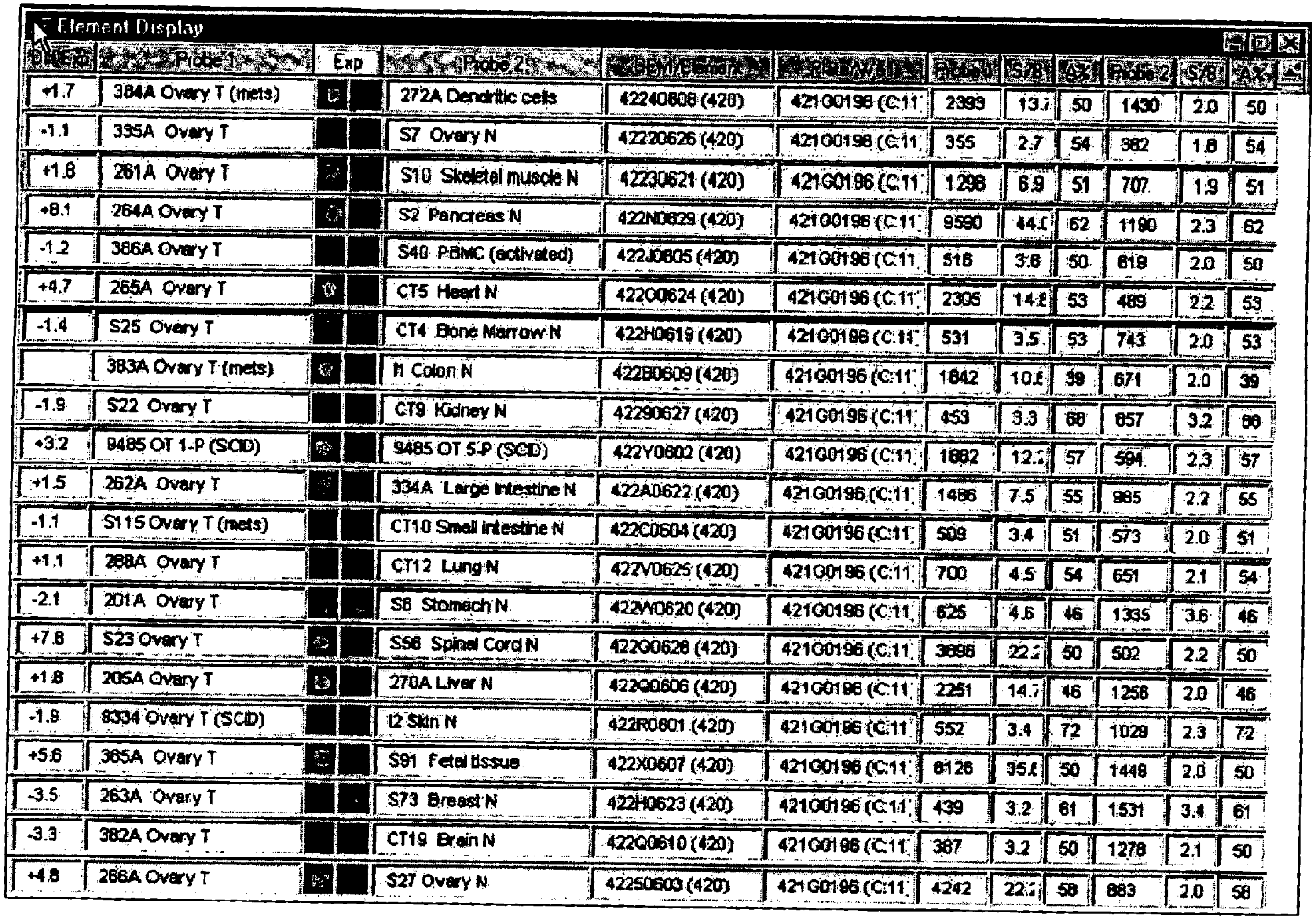

Element Display

| [illegible] | Probe 1 | Exp | Probe 2 | [illegible] | [illegible] | Probe1 | S/B | A% | Probe 2 | S/B | A% |
|---|---|---|---|---|---|---|---|---|---|---|---|
| +1.7 | 384A Ovary T (mets) | | 272A Dendritic cells | 42240608 (420) | 421G0198 (C11 | 2393 | 13.7 | 50 | 1430 | 2.0 | 50 |
| -1.1 | 335A Ovary T | | S7 Ovary N | 42220626 (420) | 421G0198 (C11 | 355 | 2.7 | 54 | 382 | 1.8 | 54 |
| +1.8 | 261A Ovary T | | S10 Skeletal muscle N | 42230621 (420) | 421G0196 (C11 | 1298 | 6.9 | 51 | 707 | 1.9 | 51 |
| +8.1 | 264A Ovary T | | S2 Pancreas N | 422N0629 (420) | 421G0198 (C11 | 9590 | 44. | 62 | 1190 | 2.3 | 62 |
| -1.2 | 386A Ovary T | | S40 PBMC (activated) | 422J0805 (420) | 421G0196 (C11 | 516 | 3.8 | 50 | 618 | 2.0 | 50 |
| +4.7 | 265A Ovary T | | CT5 Heart N | 422O0624 (420) | 421G0196 (C11 | 2305 | 14. | 53 | 489 | 2.2 | 53 |
| -1.4 | S25 Ovary T | | CT4 Bone Marrow N | 422H0619 (420) | 421G0198 (C11 | 531 | 3.5 | 53 | 743 | 2.0 | 53 |
| | 383A Ovary T (mets) | | H Colon N | 422B0609 (420) | 421G0196 (C11 | 1642 | 10.6 | 39 | 671 | 2.0 | 39 |
| -1.9 | S22 Ovary T | | CT9 Kidney N | 42290627 (420) | 421G0196 (C11 | 453 | 3.3 | 66 | 857 | 3.2 | 66 |
| +3.2 | 9485 OT 1-P (SCID) | | 9485 OT 5-P (SCID) | 422Y0602 (420) | 421G0196 (C11 | 1882 | 12. | 57 | 594 | 2.3 | 57 |
| +1.5 | 262A Ovary T | | 334A Large Intestine N | 422A0622 (420) | 421G0196 (C11 | 1486 | 7.5 | 55 | 985 | 2.2 | 55 |
| -1.1 | S115 Ovary T (mets) | | CT10 Small Intestine N | 422C0604 (420) | 421G0196 (C11 | 509 | 3.4 | 51 | 573 | 2.0 | 51 |
| +1.1 | 288A Ovary T | | CT12 Lung N | 422V0625 (420) | 421G0196 (C11 | 700 | 4.5 | 54 | 651 | 2.1 | 54 |
| -2.1 | 201A Ovary T | | S8 Stomach N | 422W0620 (420) | 421G0196 (C11 | 625 | 4.6 | 46 | 1335 | 3.6 | 46 |
| +7.8 | S23 Ovary T | | S56 Spinal Cord N | 422G0628 (420) | 421G0196 (C11 | 3896 | 22. | 50 | 502 | 2.2 | 50 |
| +1.8 | 205A Ovary T | | 270A Liver N | 422Q0606 (420) | 421G0196 (C11 | 2251 | 14.7 | 46 | 1258 | 2.0 | 46 |
| -1.9 | 9334 Ovary T (SCID) | | 12 Skin N | 422R0601 (420) | 421G0196 (C11 | 552 | 3.4 | 72 | 1029 | 2.3 | 72 |
| +5.6 | 365A Ovary T | | S91 Fetal tissue | 422X0607 (420) | 421G0196 (C11 | 8128 | 35. | 50 | 1448 | 2.0 | 50 |
| -3.5 | 263A Ovary T | | S73 Breast N | 422H0623 (420) | 421G0196 (C11 | 439 | 3.2 | 61 | 1531 | 3.4 | 61 |
| -3.3 | 382A Ovary T | | CT19 Brain N | 422Q0610 (420) | 421G0198 (C11 | 387 | 3.2 | 50 | 1278 | 2.1 | 50 |
| +4.8 | 266A Ovary T | | S27 Ovary N | 42250603 (420) | 421G0196 (C11 | 4242 | 22. | 58 | 883 | 2.0 | 58 |

*Fig. 3*

TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 4*

TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC

*Fig. 5*

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

Fig. 7B

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7A and 7B*

TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA

*Fig. 8*

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 9*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42100188 (D3) | +7.0 | 205A Ovary T | | | 270A Liver N | 422Q0606 | 8620 | 1240 | 57.7 | 65 | 2.2 | 65 |
| 42100188 (D3) | +5.9 | S23 Ovary T | | | S56 Spinal Cord N | 422G0628 | 5894 | 1002 | 35.3 | 89 | 3.9 | 89 |
| 42100188 (D3) | +5.7 | 385A Ovary T | | | S91 Fetal tissue | 422X0607 | 12151 | 2121 | 54.3 | 73 | 2.8 | 73 |
| 42100188 (D3) | +5.1 | 426A Ovary T (mets | | | 415A Aorta N | 422X0611 | 7487 | 1480 | 53.0 | 73 | 9.7 | 73 |
| 42100188 (D3) | +3.5 | 263A Ovary T | | | S73 Breast N | 422H0623 | 7302 | 2116 | 39.2 | 84 | 4.5 | 84 |
| 42100188 (D3) | +3.3 | 383A Ovary T (mets | | | I1 Colon N | 422B0609 | 3714 | 1113 | 20.4 | 83 | 2.6 | 83 |
| 42100188 (D3) | +3.0 | 9334 Ovary T (SCID | | | I2 Skin N | 422R0601 | 2435 | 814 | 12.1 | 75 | 2.1 | 75 |
| 42100188 (D3) | +2.6 | 384A Ovary T (mets | | | 272A Dendritic cells | 42240608 | 4578 | 1754 | 25.0 | 69 | 2.3 | 69 |
| 42100188 (D3) | +2.2 | 264A Ovary T | | | S2 Pancreas N | 422N0629 | 7904 | 3596 | 38.5 | 81 | 5.6 | 81 |
| 42100188 (D3) | +2.0 | 386A Ovary T | | | S40 PBMC (activat | 422J0605 | 2191 | 1081 | 14.0 | 90 | 2.9 | 90 |
| 42100188 (D3) | +2.0 | S115 Ovary T (mets | | | CT10 Small intestin | 422C0604 | 1979 | 971 | 10.4 | 80 | 2.7 | 80 |
| 42100188 (D3) | +2.0 | 265A Ovary T | | | CT5 Heart N | 422O0624 | 1911 | 964 | 13.9 | 93 | 3.4 | 93 |
| 42100188 (D3) | +2.0 | 335A Ovary T | | | S7 Ovary N | 42220626 | 1666 | 817 | 9.8 | 100 | 3.0 | 100 |
| 42100188 (D3) | -1.9 | 428A Ovary T (mets | | | 243A Esophagus N | 42240612 | 1827 | 3480 | 13.4 | 97 | 9.5 | 97 |
| 42100188 (D3) | +1.6 | 261A Ovary T | | | S10 Skeletal muscle | 42230621 | 5914 | 3653 | 30.4 | 86 | 6.0 | 86 |
| 42100188 (D3) | +1.6 | 266A Ovary T | | | S27 Ovary N | 42250603 | 2039 | 1274 | 11.9 | 50 | 2.6 | 50 |
| 42100188 (D3) | +1.6 | S22 Ovary T | | | CT9 Kidney N | 42290627 | 1736 | 1072 | 11.0 | 92 | 4.0 | 92 |
| 42100188 (D3) | +1.4 | 9485 OT 1-P (SCID | | | 9485 OT 5-P (SCID | 422Y0602 | 4204 | 3074 | 23.0 | 93 | 7.7 | 93 |
| 42100188 (D3) | +1.4 | 262A Ovary T | | | 334A Large Intestir | 422A0622 | 3002 | 2101 | 16.6 | 89 | 4.0 | 89 |
| 42100188 (D3) | +1.3 | S25 Ovary T | | | CT4 Bone Marrow | 422H0619 | 1643 | 1297 | 9.6 | 90 | 3.1 | 90 |
| 42100188 (D3) | +1.2 | 429A Ovary T (mets | | | 364A Ovary N | 422I0614 | 2521 | 2084 | 22.0 | 65 | 23.9 | 65 |
| 42100188 (D3) | +1.2 | 382A Ovary T | | | CT19 Brain N | 422Q0610 | 2072 | 1663 | 10.9 | 88 | 2.3 | 88 |
| 42100188 (D3) | +1.2 | 288A Ovary T | | | CT12 Lung N | 422V0625 | 1840 | 1473 | 10.7 | 87 | 3.8 | 87 |
| 42100188 (D3) | +1.1 | 201A Ovary T | | | S6 Stomach N | 422W0620 | 1329 | 1204 | 9.1 | 90 | 3.5 | 90 |

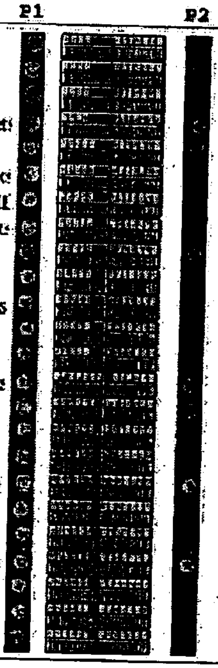

*Fig. 10*

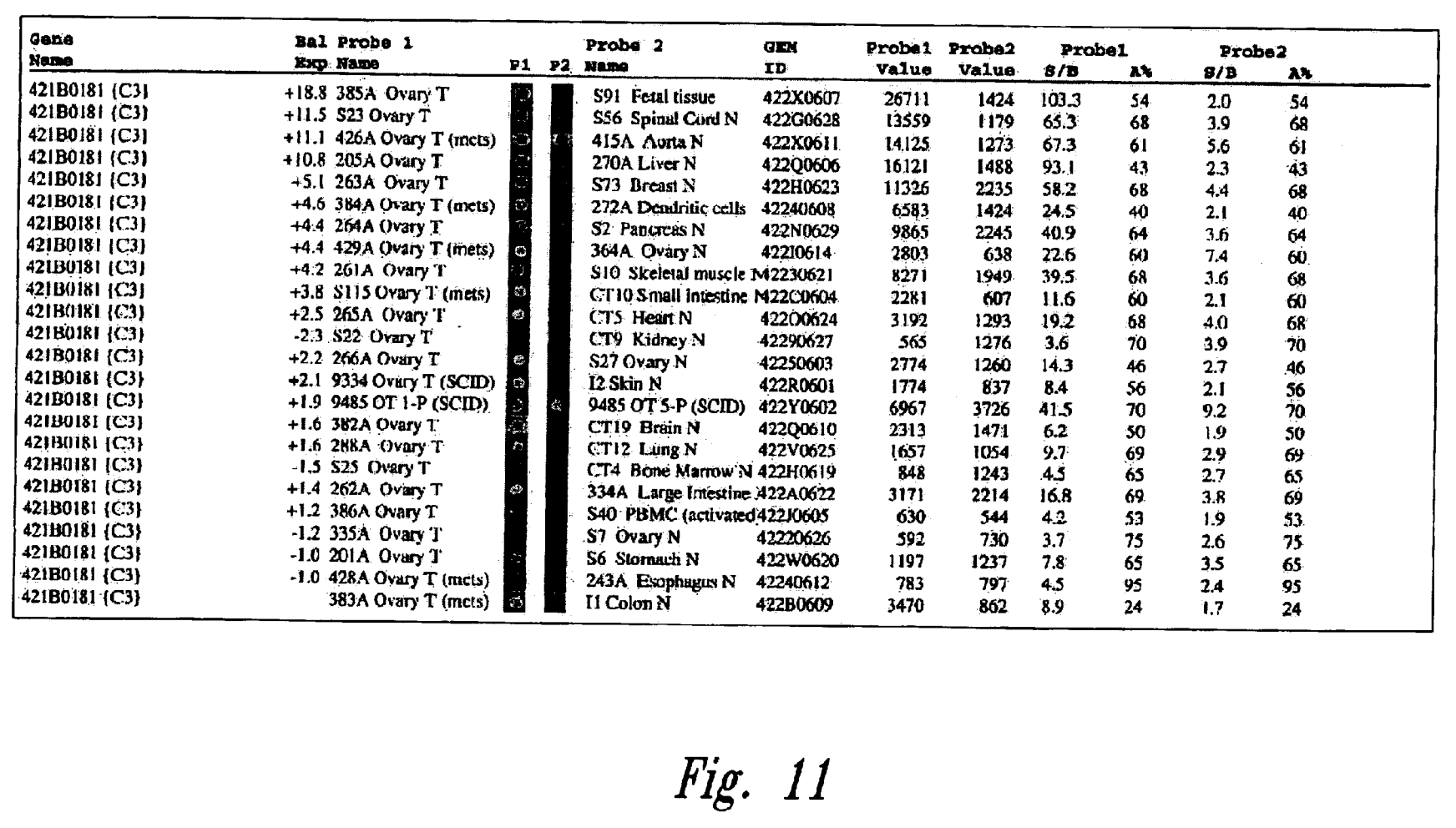

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 (C3) | +18.8 | 385A Ovary T | | | S91 Fetal tissue | 422X0607 | 26711 | 1424 | 103.3 | 54 | 2.0 | 54 |
| 421B0181 (C3) | +11.5 | S23 Ovary T | | | S56 Spinal Cord N | 422G0628 | 13559 | 1179 | 65.3 | 68 | 3.9 | 68 |
| 421B0181 (C3) | +11.1 | 426A Ovary T (mets) | | | 415A Aorta N | 422X0611 | 14125 | 1273 | 67.3 | 61 | 5.6 | 61 |
| 421B0181 (C3) | +10.8 | 205A Ovary T | | | 270A Liver N | 422Q0606 | 16121 | 1488 | 93.1 | 43 | 2.3 | 43 |
| 421B0181 (C3) | +5.1 | 263A Ovary T | | | S73 Breast N | 422H0623 | 11326 | 2235 | 58.2 | 68 | 4.4 | 68 |
| 421B0181 (C3) | +4.6 | 384A Ovary T (mets) | | | 272A Dendritic cells | 42240608 | 6583 | 1424 | 24.5 | 40 | 2.1 | 40 |
| 421B0181 (C3) | +4.4 | 264A Ovary T | | | S2 Pancreas N | 422N0629 | 9865 | 2245 | 40.9 | 64 | 3.6 | 64 |
| 421B0181 (C3) | +4.4 | 429A Ovary T (mets) | | | 364A Ovary N | 422I0614 | 2803 | 638 | 22.6 | 60 | 7.4 | 60 |
| 421B0181 (C3) | +4.2 | 261A Ovary T | | | S10 Skeletal muscle | M2230621 | 8271 | 1949 | 39.5 | 68 | 3.6 | 68 |
| 421B0181 (C3) | +3.8 | S115 Ovary T (mets) | | | CT10 Small intestine | M22C0604 | 2281 | 607 | 11.6 | 60 | 2.1 | 60 |
| 421B0181 (C3) | +2.5 | 265A Ovary T | | | CT5 Heart N | 422O0624 | 3192 | 1293 | 19.2 | 68 | 4.0 | 68 |
| 421B0181 (C3) | -2.3 | S22 Ovary T | | | CT9 Kidney N | 42290627 | 565 | 1276 | 3.6 | 70 | 3.9 | 70 |
| 421B0181 (C3) | +2.2 | 266A Ovary T | | | S27 Ovary N | 42250603 | 2774 | 1260 | 14.3 | 46 | 2.7 | 46 |
| 421B0181 (C3) | +2.1 | 9334 Ovary T (SCID) | | | I2 Skin N | 422R0601 | 1774 | 837 | 8.4 | 56 | 2.1 | 56 |
| 421B0181 (C3) | +1.9 | 9485 OT 1-P (SCID) | | | 9485 OT 5-P (SCID) | 422Y0602 | 6967 | 3726 | 41.5 | 70 | 9.2 | 70 |
| 421B0181 (C3) | +1.6 | 382A Ovary T | | | CT19 Brain N | 422Q0610 | 2313 | 1471 | 6.2 | 50 | 1.9 | 50 |
| 421B0181 (C3) | +1.6 | 288A Ovary T | | | CT12 Lung N | 422V0625 | 1657 | 1054 | 9.7 | 69 | 2.9 | 69 |
| 421B0181 (C3) | -1.5 | S25 Ovary T | | | CT4 Bone Marrow N | 422H0619 | 848 | 1243 | 4.5 | 65 | 2.7 | 65 |
| 421B0181 (C3) | +1.4 | 262A Ovary T | | | 334A Large Intestine | 422A0622 | 3171 | 2214 | 16.8 | 69 | 3.8 | 69 |
| 421B0181 (C3) | +1.2 | 386A Ovary T | | | S40 PBMC (activated | 422J0605 | 630 | 544 | 4.2 | 53 | 1.9 | 53 |
| 421B0181 (C3) | -1.2 | 335A Ovary T | | | S7 Ovary N | 42220626 | 592 | 730 | 3.7 | 75 | 2.6 | 75 |
| 421B0181 (C3) | -1.0 | 201A Ovary T | | | S6 Stomach N | 422W0620 | 1197 | 1237 | 7.8 | 65 | 3.5 | 65 |
| 421B0181 (C3) | -1.0 | 428A Ovary T (mets) | | | 243A Esophagus N | 42240612 | 783 | 797 | 4.5 | 95 | 2.4 | 95 |
| 421B0181 (C3) | | 383A Ovary T (mets) | | | I1 Colon N | 422B0609 | 3470 | 862 | 8.9 | 24 | 1.7 | 24 |

*Fig. 11*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 (H7) | +16.7 | 426A Ovary T (met: | 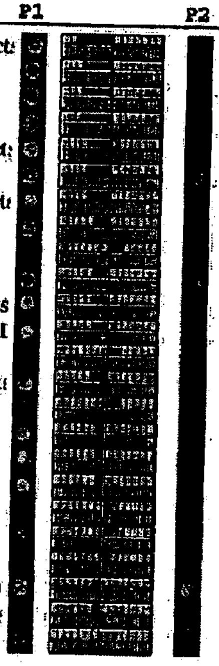 | | 415A Aorta N | 422X0611 | 7706 | 462 | 46.3 | 75 | 3.5 | 75 |
| 42110182 (H7) | +10.7 | 205A Ovary T | | | 270A Liver N | 422Q0606 | 10171 | 950 | 61.2 | 41 | 1.8 | 41 |
| 42110182 (H7) | +9.9 | 385A Ovary T | | | S91 Fetal tissue | 422X0607 | 14415 | 1459 | 62.1 | 48 | 2.2 | 48 |
| 42110182 (H7) | +8.8 | S23 Ovary T | | | S56 Spinal Cord N | 422Q0628 | 7781 | 880 | 47.3 | 73 | 3.4 | 73 |
| 42110182 (H7) | +6.4 | 383A Ovary T (met: | | | I1 Colon N | 422B0609 | 4807 | 748 | 27.6 | 47 | 2.2 | 47 |
| 42110182 (H7) | +5.1 | 263A Ovary T | | | S73 Breast N | 422H0623 | 9815 | 1909 | 57.1 | 74 | 4.2 | 74 |
| 42110182 (H7) | +4.9 | 429A Ovary T (met: | | | 364A Ovary N | 422I0614 | 2661 | 543 | 20.3 | 61 | 6.7 | 61 |
| 42110182 (H7) | +3.5 | 264A Ovary T | | | S2 Pancreas N | 422N0629 | 7934 | 2274 | 38.8 | 71 | 3.9 | 71 |
| 42110182 (H7) | -2.9 | S25 Ovary T | | | CT4 Bone Marrow | 422H0619 | 480 | 1375 | 3.5 | 80 | 3.0 | 80 |
| 42110182 (H7) | +2.8 | 261A Ovary T | | | S10 Skeletal muscl | 42230621 | 8993 | 3245 | 34.6 | 69 | 5.1 | 69 |
| 42110182 (H7) | +2.5 | S115 Ovary T (mets | | | CT10 Small intestin | 422C0604 | 1864 | 738 | 8.1 | 67 | 2.2 | 67 |
| 42110182 (H7) | +2.3 | 9334 Ovary T (SCII | | | I2 Skin N | 422R0601 | 2552 | 1113 | 12.7 | 41 | 2.6 | 41 |
| 42110182 (H7) | -2.3 | S22 Ovary T | | | CT9 Kidney N | 42290627 | 386 | 889 | 3.2 | 69 | 3.4 | 69 |
| 42110182 (H7) | +2.2 | 384A Ovary T (met: | | | 272A Dendritic cell | 42240608 | 3516 | 1567 | 18.7 | 55 | 2.2 | 55 |
| 42110182 (H7) | -2.2 | 382A Ovary T | | | CT19 Brain N | 422Q0610 | 608 | 1320 | 4.2 | 60 | 2.3 | 60 |
| 42110182 (H7) | +1.9 | 265A Ovary T | | | CT5 Heart N | 422O0624 | 2063 | 1080 | 13.6 | 87 | 3.5 | 87 |
| 42110182 (H7) | +1.8 | 266A Ovary T | | | S27 Ovary N | 42250603 | 1550 | 847 | 7.0 | 58 | 2.1 | 58 |
| 42110182 (H7) | +1.5 | 262A Ovary T | | | 334A Large Intestir | 422A0622 | 2559 | 1651 | 13.2 | 73 | 3.2 | 73 |
| 42110182 (H7) | -1.4 | 386A Ovary T | | | S40 PBMC (activat | 422J0605 | 534 | 738 | 3.9 | 62 | 2.2 | 62 |
| 42110182 (H7) | -1.3 | 288A Ovary T | | | CT12 Lung N | 422V0625 | 893 | 1120 | 5.3 | 66 | 3.1 | 66 |
| 42110182 (H7) | -1.3 | 335A Ovary T | | | S7 Ovary N | 42220626 | 440 | 567 | 3.3 | 60 | 2.2 | 60 |
| 42110182 (H7) | +1.2 | 9485 OT 1-P (SCID | | | 9485 OT 5-P (SCID | 422Y0602 | 4188 | 3529 | 21.6 | 66 | 9.5 | 66 |
| 42110182 (H7) | +1.1 | 428A Ovary T (met: | | | 243A Esophagus N | 42240612 | 725 | 689 | 6.2 | 65 | 2.8 | 65 |
| 42110182 (H7) | -1.0 | 201A Ovary T | | | S6 Stomach N | 422W0620 | 1008 | 1018 | 7.4 | 62 | 3.2 | 62 |

*Fig. 12*

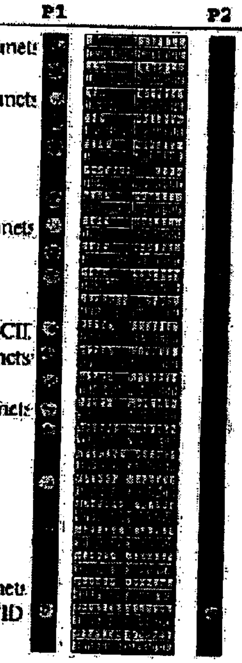

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 {D1} | +33.2 | 426A Ovary T (mets | | | 415A Aorta N | 422X0611 | 8072 | 243 | 55.2 | 67 | 2.4 | 67 |
| 421V0189 {D1} | +13.7 | S23 Ovary T | | | S56 Spinal Cord N | 422G0628 | 7367 | 537 | 42.6 | 69 | 2.5 | 69 |
| 421V0189 {D1} | +12.6 | 429A Ovary T (mets | | | 364A Ovary N | 422I0614 | 2850 | 227 | 21.7 | 64 | 3.5 | 64 |
| 421V0189 {D1} | +8.0 | 385A Ovary T | | | S91 Fetal tissue | 422X0607 | 11711 | 1469 | 54.0 | 58 | 2.2 | 58 |
| 421V0189 {D1} | +7.3 | 263A Ovary T | | | S73 Breast N | 422H0623 | 6949 | 952 | 37.8 | 69 | 2.6 | 69 |
| 421V0189 {D1} | -5.8 | S25 Ovary T | | | CT4 Bone Marrow | 422H0619 | 208 | 1210 | 2.1 | 44 | 2.9 | 44 |
| 421V0189 {D1} | +5.0 | 205A Ovary T | | | 270A Liver N | 422Q0606 | 8676 | 1737 | 52.3 | 57 | 2.6 | 57 |
| 421V0189 {D1} | +4.5 | 383A Ovary T (mets | | | 11 Colon N | 422B0609 | 3149 | 707 | 17.4 | 57 | 2.0 | 57 |
| 421V0189 {D1} | +4.4 | 261A Ovary T | | | S10 Skeletal muscl | 42230621 | 6332 | 1443 | 29.1 | 77 | 2.9 | 77 |
| 421V0189 {D1} | +4.2 | 264A Ovary T | | | S2 Pancreas N | 422N0629 | 7612 | 1809 | 38.1 | 79 | 3.3 | 79 |
| 421V0189 {D1} | -3.2 | 382A Ovary T | | | CT19 Brain N | 422Q0610 | 468 | 1508 | 3.4 | 60 | 2.3 | 60 |
| 421V0189 {D1} | +2.9 | 9334 Ovary T (SCII | | | I2 Skin N | 422R0601 | 2500 | 860 | 12.3 | 51 | 2.1 | 51 |
| 421V0189 {D1} | +2.5 | S115 Ovary T (mets | | | CT10 Small intestin | 422C0604 | 1424 | 569 | 6.7 | 61 | 2.1 | 61 |
| 421V0189 {D1} | +2.4 | 265A Ovary T | | | CT5 Heart N | 422O0624 | 1742 | 723 | 11.8 | 70 | 2.8 | 70 |
| 421V0189 {D1} | +2.3 | 384A Ovary T (mets | | | 272A Dendritic cell | 42240608 | 3083 | 1342 | 17.0 | 62 | 2.0 | 62 |
| 421V0189 {D1} | +1.9 | 266A Ovary T | | | S27 Ovary N | 42250603 | 1370 | 732 | 8.0 | 47 | 2.0 | 47 |
| 421V0189 {D1} | -1.9 | 386A Ovary T | | | S40 PBMC (activat | 422J0605 | 307 | 580 | 2.6 | 41 | 2.0 | 41 |
| 421V0189 {D1} | +1.7 | 262A Ovary T | | | 334A Large Intestir | 422A0622 | 2097 | 1202 | 11.2 | 86 | 2.7 | 86 |
| 421V0189 {D1} | -1.3 | 335A Ovary T | | | S7 Ovary N | 42220626 | 373 | 470 | 2.9 | 47 | 2.0 | 47 |
| 421V0189 {D1} | -1.1 | 288A Ovary T | | | CT12 Lung N | 422V0625 | 969 | 1094 | 5.6 | 72 | 2.9 | 72 |
| 421V0189 {D1} | +1.1 | 201A Ovary T | | | S6 Stomach N | 422W0620 | 750 | 672 | 5.6 | 62 | 2.4 | 62 |
| 421V0189 {D1} | +1.1 | 428A Ovary T (mets | | | 243A Esophagus N | 42240612 | 498 | 446 | 4.2 | 73 | 2.1 | 73 |
| 421V0189 {D1} | -1.0 | 9485 OT 1-P (SCID | | | 9485 OT 5-P (SCID | 422Y0602 | 3117 | 3174 | 16.7 | 91 | 8.2 | 91 |
| 421V0189 {D1} | | S22 Ovary T | | | CT9 Kidney N | 42290627 | 224 | 409 | 2.3 | 48 | 2.3 | 48 |

*Fig. 13*

Figure 14:
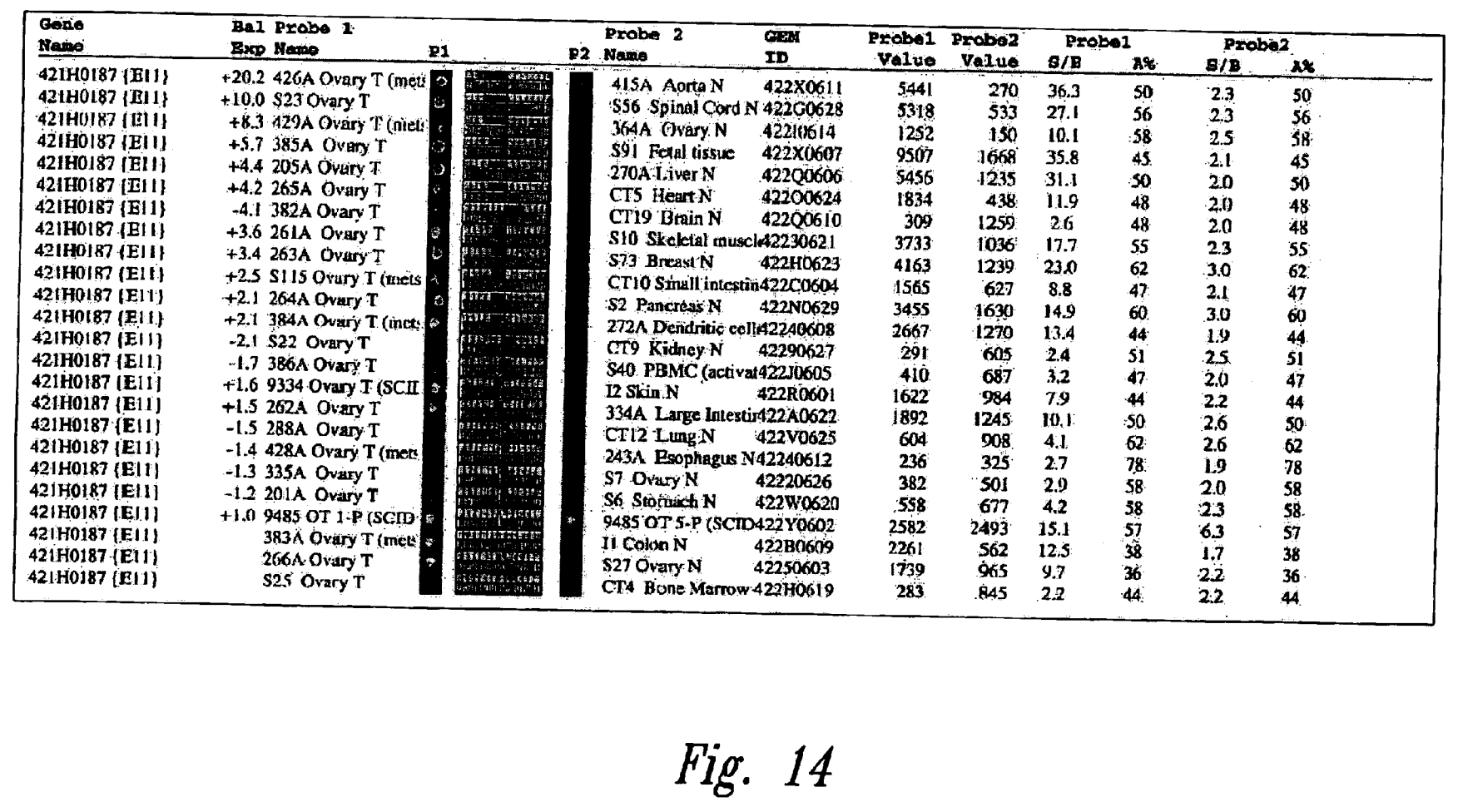

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421H0187 {E11} | +20.2 | 426A Ovary T (mets | | | 415A Aorta N | 422X0611 | 5441 | 270 | 36.3 | 50 | 2.3 | 50 |
| 421H0187 {E11} | +10.0 | S23 Ovary T | | | S56 Spinal Cord N | 422G0628 | 5318 | 533 | 27.1 | 56 | 2.3 | 56 |
| 421H0187 {E11} | +8.3 | 429A Ovary T (mets | | | 364A Ovary N | 422I0614 | 1252 | 150 | 10.1 | 58 | 2.5 | 58 |
| 421H0187 {E11} | +5.7 | 385A Ovary T | | | S91 Fetal tissue | 422X0607 | 9507 | 1668 | 35.8 | 45 | 2.1 | 45 |
| 421H0187 {E11} | +4.4 | 205A Ovary T | | | 270A Liver N | 422Q0606 | 5456 | 1235 | 31.1 | 50 | 2.0 | 50 |
| 421H0187 {E11} | +4.2 | 265A Ovary T | | | CT5 Heart N | 422O0624 | 1834 | 438 | 11.9 | 48 | 2.0 | 48 |
| 421H0187 {E11} | -4.1 | 382A Ovary T | | | CT19 Brain N | 422Q0610 | 309 | 1259 | 2.6 | 48 | 2.0 | 48 |
| 421H0187 {E11} | +3.6 | 261A Ovary T | | | S10 Skeletal muscl | 4223062 1 | 3733 | 1036 | 17.7 | 55 | 2.3 | 55 |
| 421H0187 {E11} | +3.4 | 263A Ovary T | | | S73 Breast N | 422H0623 | 4163 | 1239 | 23.0 | 62 | 3.0 | 62 |
| 421H0187 {E11} | +2.5 | S115 Ovary T (mets | | | CT10 Small intestin | 422C0604 | 1565 | 627 | 8.8 | 47 | 2.1 | 47 |
| 421H0187 {E11} | +2.1 | 264A Ovary T | | | S2 Pancreas N | 422N0629 | 3455 | 1630 | 14.9 | 60 | 3.0 | 60 |
| 421H0187 {E11} | +2.1 | 384A Ovary T (mets | | | 272A Dendritic cell | 4224O608 | 2667 | 1270 | 13.4 | 44 | 1.9 | 44 |
| 421H0187 {E11} | -2.1 | S22 Ovary T | | | CT9 Kidney N | 4229O627 | 291 | 605 | 2.4 | 51 | 2.5 | 51 |
| 421H0187 {E11} | -1.7 | 386A Ovary T | | | S40 PBMC (activat | 422J0605 | 410 | 687 | 3.2 | 47 | 2.0 | 47 |
| 421H0187 {E11} | +1.6 | 9334 Ovary T (SCII | | | I2 Skin N | 422R0601 | 1622 | 984 | 7.9 | 44 | 2.2 | 44 |
| 421H0187 {E11} | +1.5 | 262A Ovary T | | | 334A Large Intestir | 422A0622 | 1892 | 1245 | 10.1 | 50 | 2.6 | 50 |
| 421H0187 {E11} | -1.5 | 288A Ovary T | | | CT12 Lung N | 422V0625 | 604 | 908 | 4.1 | 62 | 2.6 | 62 |
| 421H0187 {E11} | -1.4 | 428A Ovary T (mets | | | 243A Esophagus N | 4224O612 | 236 | 325 | 2.7 | 78 | 1.9 | 78 |
| 421H0187 {E11} | -1.3 | 335A Ovary T | | | S7 Ovary N | 4222O626 | 382 | 501 | 2.9 | 58 | 2.0 | 58 |
| 421H0187 {E11} | -1.2 | 201A Ovary T | | | S6 Stomach N | 422W0620 | 558 | 677 | 4.2 | 58 | 2.3 | 58 |
| 421H0187 {E11} | +1.0 | 9485 OT 1-P (SCID | | | 9485 OT 5-P (SCID | 422Y0602 | 2582 | 2493 | 15.1 | 57 | 6.3 | 57 |
| 421H0187 {E11} | | 383A Ovary T (mets | | | I1 Colon N | 422B0609 | 2261 | 562 | 12.5 | 38 | 1.7 | 38 |
| 421H0187 {E11} | | 266A Ovary T | | | S27 Ovary N | 4225O603 | 1739 | 965 | 9.7 | 36 | 2.2 | 36 |
| 421H0187 {E11} | | S25 Ovary T | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG 11721-2

AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA 11724-1

TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG 11724-2

TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT

AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC 11726-1&2

CAAGCTTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT 11727-1&2

AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA

TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG 11728.2.40.19.19

CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG 11730-1

GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT 11730-2

AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC

*Fig. 15C*

11732.1contig

GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT 11732.2contig GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT 11735-1-2

AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA 11740.2.contig AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA

*Fig. 15D*

11765.2&64.2.contig

CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT 11767.2.contig CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA 11768-1&2

GGGAATGCAACAACTTTATTGAAAGGAAAGTGCAATGAAATTTGTTGAAACCTTAAAAGGGGAAACTTAGACACCC
CCCCTCRAgCGMAGKACCARGTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT

AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT 11769.1.contig ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT 11769.2.contig AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC 11770.1.contig GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGGCC
AGGCCTCAGCCATACTCCTGGGCGCGGGTTTCGGTGAGCAAGGCACAGTCCCAGAGGTGATATCAAGGCCT

*Fig. 15F*

11770.2.contig

GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA 11773.1.contig TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG 11778.1.contig GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG 11778-2&30-2

CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC

*Fig. 15G*

11782.1.contig

ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC 11782.2.contig CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC 11783-1 & 2

CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG 11786.1.contig GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC

*Fig. 15H*

11786.2.contig

CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA

13691.1&2

AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA

13692.1&2

TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC

13693.2

TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC

CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC 13700.1

CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC 13700.2

TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA 13701.1

AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT 13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT 13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA 13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG 13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA 13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG 13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA 13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT 13721.1

TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG 13721.2

GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA 13723.1

CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC 13727.2

ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG 13728.1&2

TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC 13731.1&2

TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC

TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT 13736.2

ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT 13744.2-13696.2

GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCTTGARACTGCCGTGCTCTTGGGGTCCTACGCTTGTGCATGCCAAGTTTGGGGACTACC
ACCAAGAAG 13746.1&2-13720.1&2

GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG

CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT 14347.2

CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA 14348.2&14350.1&2

TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC 14349.1&2

TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC

GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT 14353.1

AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA 14353.2

TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC 17182.1&2

AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA

GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG 17186.1&2

TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG 17187.1&2

TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG 17191.1&89.1

GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA

TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA

*Fig. 15U*

16443.1.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC 16443.2.edit AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA 16444.2.edit AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA 16445.1.edit AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA

*Fig. 15V*

16445.2.edit

TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT 16446.1.edit TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT 16446.2.edit AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA 16447.1.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT

*Fig. 15W*

16447.2.edit

AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA 16449.1.edit AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG 16450.1.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA 16450.2.edit AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT

*Fig. 15X*

16451.1.edit

AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA 16451.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT 16452.1.edit AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC 16452.2.edit TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA 16453.2.edit TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT 16454.1.edit AGCGTGGNTGCGGACGACGCCCACAAAGCCATTGTATGTAGTTTTANTTCAGCTGCAAANAATACCNCCAGCATCC
ACCTTACTAACCAGCATATGCAGACA 16454.2.edit TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT 16455.2.edit AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA 16456.1.edit AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC 16456.2.edit TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG

*Fig. 15A-1*

16459.1.edit

TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT 16459.2.edit AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA 16460.1.edit TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT 16460.2.edit AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA

*Fig. 15B-1*

16461.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA 16461.2.edit TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT 16463.1.edit AGCGTGGNNGCGGCCGAGGTATAAATATCCAGNCCATATCCTCCCTCCACACGCTGANAGATGAAGCTGTNCAAAG
ATCTCAGGGTGGANAAAACCAT 16463.2.edit TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 15C-1*

16464.1.edit

CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA 16464.2.edit AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG 16465.1.edit AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG 16465.2.edit TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT 16466.2.edit TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT 16467.2.edit TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA

*Fig. 15D-1*

01_16469.edit

AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15E-1*

06_16471.edit

AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN

*Fig. 15F-1*

11_16474.edit

```
AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN
```

12_16474.edit

```
TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC
```

13_16475.edit

```
TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT
```

*Fig. 15G-1*

14_16475.edit

AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT

15_16476.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT

*Fig. 15H-1*

17_16477.edit

TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT

18_16477.edit

AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

22_16479.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA

*Fig. 15I-1*

24_16480.edit

TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT

26_16481.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA

27_16482.edit

TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT

*Fig. 15J-1*

28_16482.edit

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

29_16483.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT

31_16484.edit

TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT

37_16487.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG

*Fig. 15K-1*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15L-1*

46_16491.edit

GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN

48_16492.edit

TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG

*Fig. 15M-1*

49_16493.edit

```
TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG
```

55_16496.edit

```
AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA
```

56_16496.edit

```
TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT
```

59_16498.edit

```
TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT
```

*Fig. 15N-1*

60_16473.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA

60_16498.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN

61_16499.edit

AGCGTGGTCGCGGCCGAGGTCNAGG

62_16483.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT

*Fig. 15O-1*

63_16500.edit

AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA

64_16500.edit

TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT

*Fig. 15P-1*

16501.edit

TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT 16501.2.edit GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC 16502.1.edit AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC 16502.2.edit TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG

*Fig. 15Q-1*

16503.1.edit

AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAACCTGTGGAAAAGCCCCTTATTTCTGCCCCATAATTTGGTTCT
CCTAATCNCTCTGAAATCACTATTTCCCTGGAANGTTTGGGAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA 16503.2.edit AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT 16504.1.edit TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT 16504.2.edit AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 15R-1*

16505.1.edit

CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG 16505.2.edit AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG 16506.1.edit TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC 16506.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA

*Fig. 15S 1*

16507.1.edit

AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG 16507.2.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT 16508.1.edit CGAGCGGCCGCCCGGGCAGGTCCCCCCCCTTTTTTTTTTTTTTTTTTTTTTTTTTTTTTTTTTTTTTTTTTTTTTT
TTTTTTTTTTTTTTTTTTT 16508.2.edit AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT

*Fig. 15T-1*

16509.1.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC 16509.2.edit TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC 16510.1.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA 16510.2.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT

*Fig. 15U-1*

16511.1.edit

TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC 16511.2.edit AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC 16512.1.edit AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA 16512.2.edit TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT

*Fig. 15V-1*

16514.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC 16514.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT 16515.1.edit AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA 16515.2.edit TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT

*Fig. 15W-1*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG 16516.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA 16517.1.edit

ANCGNGGTCGCGGCCGANGTNTTTTTTCTTNTTTTTTT 16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC 16518.2.edit TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15X-1*

16519.1.edit

AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC 16519.2.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA 16520.1.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAANGTCAAGCCTTNTGGGTTCAA 16520.2.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC 16521.2.edit TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15Y-1*

16522.1.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC 16522.2.edit TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG 16523.1.edit

AGCGTGGNCGCGGACGANGACAACAACCCC 16523.2.edit

TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT 16524.1.edit AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG

*Fig. 15Z-1*

16524.2.edit

TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT 16526.1.edit TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG 16526.2.edit ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT 16527.1.edit AGCGTGGTCGCGGCCGAGGTTGTACAAGCTTTTTTTTTTTTTTTTTTTTTTTTTTTTTTTTTTTTTTTTTTTTTTTTT
TTTTTTTTTTTTTTTTTTTTTTTTT 16527.2.edit TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT

*Fig. 15A-2*

16528.1.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG 16528.2.edit AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG 16529.1.edit TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC 16529.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG

*Fig. 15B-2*

16530.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG 16530.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG 16531.1.edit TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA 16531.2.edit AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA 16532.1.edit TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG

*Fig. 15C-2*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15D-2*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

*Fig. 15E-2*

O8E Surface Expression

B305D/HEK stained with anti-O8E antibody
O8E/HEK stained with anti-O8E antibody
O8E/HEK stained with an irrelevant antibody O8E Surface Expression O8E expression in HEK293 Cells
(probed with anti-O8E rabbit polyclonal sera #2333L)

O8E Rabbits 01212000

Date:1/21/99

| Antigen on Plate | Sera Sample | Antibody Dilutions | | | | | | | | | | | |
|---|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E (#632-24) | Preimmune sera (#2576L):11/10/99 | 0.13 | 0.09 | 0.08 | 0.07 | 0.07 | 0.07 | 0.07 | 0.06 | 0.07 | 0.07 | 0.07 | 0.07 |
| | | 0.10 | 0.08 | 0.07 | 0.07 | 0.07 | 0.07 | 0.07 | 0.06 | 0.06 | 0.07 | 0.06 | 0.07 |
| | Average | 0.11 | 0.08 | 0.07 | 0.07 | 0.07 | 0.07 | 0.07 | 0.06 | 0.07 | 0.07 | 0.06 | 0.07 |
| | α-O8E (#2576K):1/11/2000 | 2.92 | 2.81 | 2.74 | 2.70 | 2.58 | 2.08 | 1.61 | 1.01 | 0.68 | 0.40 | 0.24 | 0.15 |
| | | 2.93 | 2.77 | 2.74 | 2.69 | 2.48 | 2.08 | 1.57 | 1.00 | 0.66 | 0.40 | 0.23 | 0.16 |
| | Average | 2.93 | 2.79 | 2.74 | 2.69 | 2.53 | 2.08 | 1.59 | 1.00 | 0.67 | 0.40 | 0.23 | 0.16 |
| | Preimmune sera (#2333L):11/10/99 | 0.09 | 0.07 | 0.06 | 0.06 | 0.07 | 0.07 | 0.07 | 0.07 | 0.07 | 0.07 | 0.07 | 0.07 |
| | | 0.08 | 0.07 | 0.06 | 0.07 | 0.10 | 0.07 | 0.07 | 0.07 | 0.07 | 0.07 | 0.07 | 0.07 |
| | Average | 0.08 | 0.07 | 0.06 | 0.06 | 0.08 | 0.07 | 0.07 | 0.07 | 0.07 | 0.07 | 0.07 | 0.07 |
| | α-O8E (#2333L):1/11/2000 | 2.73 | 2.75 | 2.64 | 2.48 | 2.30 | 1.78 | 1.41 | 0.92 | 0.58 | 0.32 | 0.20 | 0.14 |
| | | 2.73 | 2.76 | 2.51 | 2.60 | 2.37 | 1.93 | 1.44 | 0.88 | 0.58 | 0.35 | 0.20 | 0.14 |
| | Average | 2.73 | 2.76 | 2.57 | 2.54 | 2.33 | 1.85 | 1.43 | 0.90 | 0.58 | 0.33 | 0.20 | 0.14 |

*Fig. 23* affi-pure O8E #2576L 739.87A&B

| Date: 5/2/2000 | | |
|---|---|---|
| Antibody Name<br>Rabbit #, Bleed Date<br>Purification Method<br>Buffer<br>Notebook | O8E polyclonal<br>2576L, 1/11/2000<br>affinity<br>PBS<br>#705, p150 | |
| lot #<br>Antibody Concentration<br>Initial Amount | 739.87A<br>1.4mg/ml<br>18mg | 739.87B<br>1.7mg/ml<br>3mg |

| Antigen on Plate | Sera Sample | Antibody Dilutions | | | | | | | | | | | |
|---|---|---|---|---|---|---|---|---|---|---|---|---|---|
| | | 1:1000 | 1:2000 | 1:4000 | 1:8000 | 1:16000 | 1:32000 | 1:64000 | 1:128000 | 1:256000 | 1:512000 | 1:1024000 | 1:2048000 |
| O8E #632-24 | preimmune sera (2576L) | 0.15 | 0.11 | 0.09 | 0.08 | 0.08 | 0.07 | 0.07 | 0.07 | 0.07 | 0.08 | 0.07 | 0.08 |
| | | 0.14 | 0.10 | 0.09 | 0.08 | 0.07 | 0.07 | 0.07 | 0.07 | 0.07 | 0.07 | 0.07 | 0.07 |
| | Average | 0.14 | 0.10 | 0.09 | 0.08 | 0.07 | 0.07 | 0.07 | 0.07 | 0.07 | 0.08 | 0.07 | 0.08 |
| | α-O8E (2576K):2/8/2000 | 2.74 | 2.71 | 2.63 | 2.49 | 2.29 | 1.87 | 1.39 | 0.92 | 0.57 | 0.33 | 0.20 | 0.14 |
| | | 2.72 | 2.68 | 2.64 | 2.47 | 2.26 | 1.93 | 1.42 | 0.94 | 0.57 | 0.34 | 0.21 | 0.14 |
| | Average | 2.73 | 2.70 | 2.63 | 2.48 | 2.27 | 1.90 | 1.41 | 0.93 | 0.57 | 0.34 | 0.21 | 0.14 |
| | affinity pure α-O8E poly salt peak 739-87A | 2.69 | 2.60 | 2.50 | 2.21 | 1.83 | 1.34 | 0.99 | 0.64 | 0.38 | 0.22 | 0.15 | 0.11 |
| | | 2.59 | 2.48 | 2.38 | 2.21 | 1.82 | 1.33 | 1.00 | 0.62 | 0.37 | 0.22 | 0.14 | 0.11 |
| | Average | 2.64 | 2.54 | 2.44 | 2.21 | 1.83 | 1.34 | 1.00 | 0.63 | 0.37 | 0.22 | 0.15 | 0.11 |
| | affinity pure α-O8E poly acid peak 739-67B | 2.46 | 2.39 | 2.40 | 2.34 | 2.08 | 1.73 | 1.29 | 0.81 | 0.49 | 0.29 | 0.19 | 0.13 |
| | | 2.65 | 2.66 | 2.61 | 2.45 | 2.14 | 1.76 | 1.30 | 0.82 | 0.48 | 0.29 | 0.19 | 0.13 |
| | Average | 2.56 | 2.53 | 2.51 | 2.39 | 2.11 | 1.74 | 1.30 | 0.81 | 0.49 | 0.29 | 0.19 | 0.13 |

*Fig. 24*

COMPOSITIONS AND METHODS FOR THE THERAPY AND DIAGNOSIS OF OVARIAN CANCER

BACKGROUND OF THE INVENTION

1. Field of the Invention

The present invention relates generally to therapy and diagnosis of cancer, such as ovarian cancer. The invention is more specifically related to polypeptides, comprising at least a portion of an ovarian tumor protein, and to polynucleotides encoding such polypeptides. Such polypeptides and polynucleotides are useful in pharmaceutical compositions, e.g., vaccines, and other compositions for the diagnosis and treatment of ovarian cancer.

2. Description of the Related Art

Cancer is a significant health problem throughout the world. Although advances have been made in detection and therapy of cancer, no vaccine or other universally successful method for prevention and/or treatment is currently available. Current therapies, which are generally based on a combination of chemotherapy or surgery and radiation, continue to prove inadequate in many patients.

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

In spite of considerable research into therapies for these and other cancers, ovarian cancer remains difficult to diagnose and treat effectively. Accordingly, there is a need in the art for improved methods for detecting and treating such cancers. The present invention fulfills these needs and further provides other related advantages.

BRIEF SUMMARY OF THE INVENTION

In one aspect, the present invention provides polynucleotide compositions comprising a sequence selected from the group consisting of:

(a) sequences provided in SEQ ID NOs: 1–311, 313–387, 391, 457, 460–477, 512–570 and 619–622;

(b) complements of the sequences provided in SEQ ID NOs: 1–311, 313–387, 391, 457, 460–477, 512–570 and 619–622;

(c) sequences consisting of at least 20, 25, 30, 35, 40, 45, 50, 75 and 100 contiguous residues of a sequence provided in SEQ ID NOs: 1–311, 313–387, 391, 457, 460–477, 512–570 and 619–622;

(d) sequences that hybridize to a sequence provided in SEQ ID NOs: 1–311, 313–387, 391, 457, 460–477, 512–570 and 619–622, under moderate or highly stringent conditions;

(e) sequences having at least 75%, 80%, 85%, 90%, 95%, 96%, 97%, 98% or 99% identity to a sequence of SEQ ID NOs: 1–311, 313–387, 391, 457, 460–477, 512–570 and 619–622;

(f) degenerate variants of a sequence provided in SEQ ID NOs: 1–311, 313–387, 391, 457, 460–477, 512–570 and 619–622.

In one preferred embodiment, the polynucleotide compositions of the invention are expressed in at least about 20%, more preferably in at least about 30%, and most preferably in at least about 50% of ovarian tumors samples tested, at a level that is at least about 2-fold, preferably at least about 5-fold, and most preferably at least about 10-fold higher than that for normal tissues.

The present invention, in another aspect, provides polypeptide compositions comprising an amino acid sequence that is encoded by a polynucleotide sequence described above.

The present invention further provides polypeptide compositions comprising an amino acid sequence selected from the group consisting of sequences recited in SEQ ID NOs: 312, 388–389, 392–455, 458–459, 478–511, 571–618 and 623–624.

In certain preferred embodiments, the polypeptides and/or polynucleotides of the present invention are immunogenic, i.e., they are capable of eliciting an immune response, particularly a humoral and/or cellular immune response, as further described herein.

The present invention further provides fragments, variants and/or derivatives of the disclosed polypeptide and/or polynucleotide sequences, wherein the fragments, variants and/or derivatives preferably have a level of immunogenic activity of at least about 50%, preferably at least about 70% and more preferably at least about 90% of the level of immunogenic activity of a polypeptide sequence set forth in SEQ ID NOs: 312, 388–389, 392–455, 458–459, 478–511, and 571–618 and 623–624 or a polypeptide sequence encoded by a polynucleotide sequence set forth in SEQ ID NOs: 1–311, 313–387, 391, 457, 460–477, 512–570 and 619–622.

The present invention further provides polynucleotides that encode a polypeptide described above, expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, the pharmaceutical compositions, e.g., vaccine compositions, are provided for prophylactic or therapeutic applications. Such compositions generally comprise an immunogenic polypeptide or polynucleotide of the invention and an immunostimulant, such as an adjuvant.

The present invention further provides pharmaceutical compositions that comprise: (a) an antibody or antigen-binding fragment thereof that specifically binds to a polypeptide of the present invention, or a fragment thereof; and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Illustrative antigen presenting cells include dendritic cells, macrophages, monocytes, fibroblasts and B cells.

Within related aspects, pharmaceutical compositions are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins, typically in the form of pharmaceutical compositions, e.g., vaccine compositions, comprising a physiologically acceptable carrier and/or an immunostimulant. The fusions proteins may comprise multiple immunogenic polypeptides or portions/variants thereof, as described herein, and may further comprise one or more polypeptide segments for facilitating the expression, purification and/or immunogenicity of the polypeptide(s).

Within further aspects, the present invention provides methods for stimulating an immune response in a patient, preferably a T cell response in a human patient, comprising administering a pharmaceutical composition described herein. The patient may be afflicted with ovarian cancer, in which case the methods provide treatment for the disease, or patient considered at risk for such a disease may be treated prophylactically.

Within further aspects, the present invention provides methods for inhibiting the development of a cancer in a patient, comprising administering to a patient a pharmaceutical composition as recited above. The patient may be afflicted with ovarian cancer, in which case the methods provide treatment for the disease, or patient considered at risk for such a disease may be treated prophylactically.

The present invention further provides, within other aspects, methods for removing tumor cells from a biological sample, comprising contacting a biological sample with T cells that specifically react with a polypeptide of the present invention, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a polypeptide of the present invention, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated t cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of polypeptide disclosed herein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer, preferably an ovarian cancer, in a patient comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample, e.g., tumor sample, serum sample, etc., obtained from a patient with an oligonucleotide that hybridizes to a polynucleotide that encodes a polypeptide of the present invention; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a polypeptide of the present invention; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIGS. 1A–1S (SEQ ID NO: 1–71) depict partial sequences of polynucleotides encoding representative secreted ovarian carcinoma antigens.

FIGS. 2A–2C depict full insert sequences for three of the clones of FIG. 1. FIG. 2A shows the sequence designated O7E (11731; SEQ ID NO: 72), FIG. 2B shows the sequence designated 09E (11785; SEQ ID NO: 73) and FIG. 2C shows the sequence designated O8E (13695; SEQ ID NO: 74).

FIG. 3 presents results of microarray expression analysis of the ovarian carcinoma sequence designated O8E.

FIG. 4 presents a partial sequence of a polynucleotide (designated 3g; SEQ ID NO: 75) encoding an ovarian carcinoma sequence that is a splice fusion between the human T-cell leukemia virus type I oncoprotein TAX and osteonectin.

FIG. 5 presents the ovarian carcinoma polynucleotide designated 3f (SEQ ID NO: 76).

FIG. 6 presents the ovarian carcinoma polynucleotide designated 6b (SEQ ID NO: 77).

FIGS. 7A and 7B present the ovarian carcinoma polynucleotides designated 8e (SEQ ID NO: 78) and 8h (SEQ ID NO: 79).

FIG. 8 presents the ovarian carcinoma polynucleotide designated 12c (SEQ ID NO: 80).

FIG. 9 presents the ovarian carcinoma polynucleotide designated 12h (SEQ ID NO: 81).

FIG. 10 depicts results of microarray expression analysis of the ovarian carcinoma sequence designated 3f.

FIG. 11 depicts results of microarray expression analysis of the ovarian carcinoma sequence designated 6b.

FIG. 12 depicts results of microarray expression analysis of the ovarian carcinoma sequence designated 8e.

FIG. 13 depicts results of microarray expression analysis of the ovarian carcinoma sequence designated 12c.

FIG. 14 depicts results of microarray expression analysis of the ovarian carcinoma sequence designated 12h.

FIGS. 15A–15I depict partial sequences of additional polynucleotides encoding representative secreted ovarian carcinoma antigens (SEQ ID NO: 82–310).

FIG. 23 shows the ELISA analysis of anti-08E rabbit sera.

FIG. 24 shows the ELISA analysis of affinity purified rabbit anti-08E polyclonal antibody.

BRIEF DESCRIPTION OF THE SEQUENCE IDENTIFIERS

Figure 16:
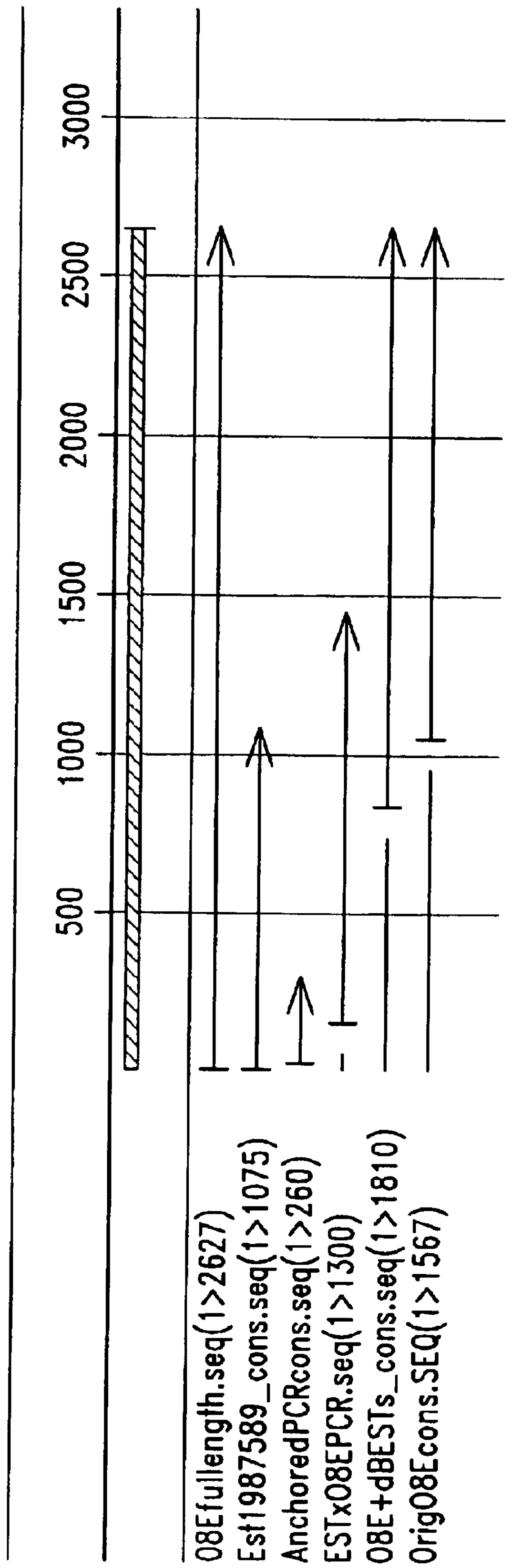
FIG. 16 is a diagram illustrating the location of various partial O8E sequences within the full length sequence.

SEQ ID NO: 1–71 are ovarian carcinoma antigen polynucleotides shown in FIGS. 1A–1S.

SEQ ID NO: 72–74 are ovarian carcinoma antigen polynucleotides shown in FIGS. 2A–2C.

SEQ ID NO: 75 is the ovarian carcinoma polynucleotide 3g (FIG. 4).

SEQ ID NO: 76 is the ovarian carcinoma polynucleotide 3f (FIG. 5).

SEQ ID NO: 77 is the ovarian carcinoma polynucleotide 6b (FIG. 6).

SEQ ID NO: 78 is the ovarian carcinoma polynucleotide 8e (FIG. 7A).

SEQ ID NO: 79 is the ovarian carcinoma polynucleotide 8h (FIG. 7B).

SEQ ID NO: 80 is the ovarian carcinoma polynucleotide 12e (FIG. 8).

SEQ ID NO: 81 is the ovarian carcinoma polynucleotide 12h (FIG. 9).

SEQ ID NO: 82–310 are ovarian carcinoma antigen polynucleotides shown in FIGS. 15A–15E2.

SEQ ID NO: 311 is a full length sequence of ovarian carcinoma polynucleotide O772P.

SEQ ID NO: 312 is the O772P amino acid sequence.

SEQ ID NO: 313–384 are ovarian carcinoma antigen polynucleotides.

SEQ ID NO: 385 represents the cDNA sequence of a form of the clone O772P, designated 21013.

SEQ ID NO: 386 represents the cDNA sequence of a form of the clone O772P, designated 21003.

SEQ ID NO: 387 represents the cDNA sequence of a form of the clone O772P, designated 21008.

SEQ ID NO: 388 is the amino acid sequence corresponding to SEQ ID NO: 385.

SEQ ID NO: 389 is the amino acid sequence corresponding to SEQ ID NO: 386.

SEQ ID NOs: 390 is the amino acid sequence corresponding to SEQ ID NO: 387.

SEQ ID NO: 391 is a full length sequence of ovarian carcinoma polynucleotide O8E.

SEQ ID NO: 392–393 are protein sequences encoded by O8E.

SEQ ID NO: 394–415 are peptide sequences corresponding to the OE8 antibody epitopes.

SEQ ID NO: 416–435 are potential HLA-A2 10-mer binding peptides predicted using the full length open-reading frame from OE8.

SEQ ID NO: 436–455 are potential HLA-A2 9-mer binding peptides predicted using the full length open-reading frame from OE8.

SEQ ID NO: 456 is a truncated nucleotide sequence of the full length Genbank sequence showing homology to O772P SEQ ID NO: 457 is the full length Genbank sequence showing significant homology to O772P SEQ ID NO: 458 is a protein encoding a truncated version of the full length Genbank sequence showing homology to O772P SEQ ID NO: 459 is the full length protein sequence from Genbank showing significant homology to the protein sequence for O772P SEQ ID NO: 460 encodes a unique N-terminal portion of O772P contained in residues 1–70.

SEQ ID NO: 461 contains unique sequence and encodes residues 1–313 of SEQ ID NO: 456.

SEQ ID NO: 462 is the hypothetical sequence for clone O772P.

SEQ ID NO: 463 is the cDNA sequence for clone FLJ14303.

SEQ ID NO: 464 is a partial cDNA sequence for clone O772P.

SEQ ID NO: 465 is a partial cDNA sequence for clone O772P.

SEQ ID NO: 466 is a partial cDNA sequence for clone O772P.

SEQ ID NO: 467 is a partial cDNA sequence for clone O772P.

SEQ ID NO: 468 is a partial cDNA sequence for clone O772P.

SEQ ID NO: 469 is a partial cDNA sequence for clone O772P.

SEQ ID NO: 470 is a partial cDNA sequence for clone O772P.

SEQ ID NO: 471 is a partial cDNA sequence for clone O772P.

SEQ ID NO: 472 is a partial cDNA sequence for clone O772P.

SEQ ID NO: 473 is a partial cDNA sequence for clone O772P.

SEQ ID NO: 474 is a partial cDNA sequence for clone O772P.

SEQ ID NO: 475 is a partial cDNA sequence for clone O772P.

SEQ ID NO: 476 is a partial cDNA sequence for clone O772P.

SEQ ID NO: 477 represents the novel 5'-end of the ovarian tumor antigen O772P.

SEQ ID NO: 478 is the amino acid sequence encoded by SEQ ID NO: 462.

SEQ ID NO: 479 is the amino acid sequence encoded by SEQ ID NO: 463.

SEQ ID NO: 480 is a partial amino acid sequence encoded by SEQ ID NO: 472.

SEQ ID NO: 481 is a partial amino acid sequence encoded by a possible open reading frame of SEQ ID NO: 471.

SEQ ID NO: 482 is a partial amino acid sequence encoded by a second possible open reading frame of SEQ ID NO: 471.

SEQ ID NO: 483 is a partial amino acid sequence encoded by SEQ ID NO: 467.

SEQ ID NO: 484 is a partial amino acid sequence encoded by a possible open reading frame of SEQ ID NO: 466.

SEQ ID NO: 485 is a partial amino acid sequence encoded by a second possible open reading frame of SEQ ID NO: 466.

SEQ ID NO: 486 is a partial amino acid sequence encoded by SEQ ID NO: 465.

SEQ ID NO: 487 is a partial amino acid sequence encoded by SEQ ID NO: 464.

SEQ ID NO: 488 represents the extracellular, transmembrane and cytoplasmic regions of O772P.

SEQ ID NO: 489 represents the predicted extracellular domain of O772P.

SEQ ID NO: 490 represents the amino acid sequence of peptide #2 which corresponds to an O772P specific antibody epitope.

SEQ ID NO: 491 represents the amino acid sequence of peptide #6 which corresponds to an O772P specific antibody epitope.

SEQ ID NO: 492 represents the amino acid sequence of peptide #7 which corresponds to an O772P specific antibody epitope.

SEQ ID NO: 493 represents the amino acid sequence of peptide #8 which corresponds to an O772P specific antibody epitope.

SEQ ID NO: 494 represents the amino acid sequence of peptide #9 which corresponds to an O772P specific antibody epitope.

SEQ ID NO: 495 represents the amino acid sequence of peptide #11 which corresponds to an O772P specific antibody epitope.

SEQ ID NO: 496 represents the amino acid sequence of peptide #13 which corresponds to an O772P specific antibody epitope.

SEQ ID NO: 497 represents the amino acid sequence of peptide #22 which corresponds to an O772P specific antibody epitope.

SEQ ID NO: 498 represents the amino acid sequence of peptide #24 which corresponds to an O772P specific antibody epitope.

SEQ ID NO: 499 represents the amino acid sequence of peptide #27 which corresponds to an O772P specific antibody epitope.

SEQ ID NO: 500 represents the amino acid sequence of peptide #40 which corresponds to an O772P specific antibody epitope.

SEQ ID NO: 501 represents the amino acid sequence of peptide #41 which corresponds to an O772P specific antibody epitope.

SEQ ID NO: 502 represents the amino acid sequence of peptide #47 which corresponds to an O772P specific antibody epitope.

SEQ ID NO: 503 represents the amino acid sequence of peptide #50 which corresponds to an O772P specific antibody epitope.

SEQ ID NO: 504 represents the amino acid sequence of peptide #51 which corresponds to an O772P specific antibody epitope.

SEQ ID NO: 505 represents the amino acid sequence of peptide #52 which corresponds to an O772P specific antibody epitope.

SEQ ID NO: 506 represents the amino acid sequence of peptide #53 which corresponds to an O772P specific antibody epitope.

SEQ ID NO: 507 represents the amino acid sequence of peptide #58 which corresponds to an O772P specific antibody epitope.

SEQ ID NO: 508 represents the amino acid sequence of peptide #59 which corresponds to an O772P specific antibody epitope.

SEQ ID NO: 509 represents the amino acid sequence of peptide #60 which corresponds to an O772P specific antibody epitope.

SEQ ID NO: 510 represents the amino acid sequence of peptide #61 which corresponds to an O772P specific antibody epitope.

SEQ ID NO: 511 represents the amino acid sequence of peptide #71 which corresponds to an O772P specific antibody epitope.

SEQ ID NO: 512 (O772P repeat1) represents an example of a cDNA sequence corresponding to repeat number 21 from the 5' variable region of O772P.

SEQ ID NO: 513 (O772P repeat2) represents an example of a cDNA sequence corresponding to repeat number 20 from the 5' variable region of O772P.

SEQ ID NO: 514 (O772P repeat3) represents an example of a cDNA sequence corresponding to repeat number 19 from the 5' variable region of O772P.

SEQ ID NO: 515 (O772P repeat4) represents an example of a cDNA sequence corresponding to repeat number 18 from the 5' variable region of O772P.

SEQ ID NO: 516 (O772P repeat5) represents an example of a cDNA sequence corresponding to repeat number 17 from the 5' variable region of O772P.

SEQ ID NO: 517 (HB repeat1) represents an example of a cDNA sequence corresponding to repeat number 21 from the 5' variable region of O772P.

SEQ ID NO: 518 (HB repeat2) represents an example of a cDNA sequence corresponding to repeat number 20 from the 5' variable region of O772P.

SEQ ID NO: 519 (HB repeat3) represents an example of a cDNA sequence corresponding to repeat number 19 from the 5' variable region of O772P.

SEQ ID NO: 520 (HB repeat4) represents an example of a cDNA sequence corresponding to repeat number 18 from the 5' variable region of O772P.

SEQ ID NO: 521 (HB repeat5) represents an example of a cDNA sequence corresponding to repeat number 17 from the 5' variable region of O772P.

SEQ ID NO: 522 (HB repeat6 5'-end) represents an example of a cDNA sequence corresponding to repeat number 16 from the 5' variable region of O772P.

SEQ ID NO: 523 (1043400.1 repeat1) represents an example of a cDNA sequence corresponding to repeat number 9 from the 5' variable region of O772P.

SEQ ID NO: 524 (1043400.1 repeat2) represents an example of a cDNA sequence corresponding to repeat number 10 from the 5' variable region of O772P.

SEQ ID NO: 525 (1043400.1 repeat3) represents an example of a cDNA sequence corresponding to repeat number 10/11 from the 5' variable region of O772P.

SEQ ID NO: 526 (1043400.1 repeat4) represents an example of a cDNA sequence corresponding to repeat number 11 from the 5' variable region of O772P.

SEQ ID NO: 527 (1043400.1 repeat5) represents an example of a cDNA sequence corresponding to repeat number 14 from the 5' variable region of O772P.

SEQ ID NO: 528 (1043400.1 repeat6) represents an example of a cDNA sequence corresponding to repeat number 17 from the 5' variable region of O772P.

SEQ ID NO: 529 (1043400.3 repeat1) represents an example of a cDNA sequence corresponding to repeat number 20 from the 5' variable region of O772P.

SEQ ID NO: 530 (1043400.3 repeat2) represents an example of a cDNA sequence corresponding to repeat number 21 from the 5' variable region of O772P.

SEQ ID NO: 531 (1043400.5 repeat1) represents an example of a cDNA sequence corresponding to repeat number 8 from the 5' variable region of O772P.

SEQ ID NO: 532 (1043400.5 repeat2) represents an example of a cDNA sequence corresponding to repeat number 9 from the 5' variable region of O772P, in addition containing intron sequence.

SEQ ID NO: 533 (1043400.5 repeat2) represents an example of a cDNA sequence corresponding to repeat number 9 from the 5' variable region of O772P.

SEQ ID NO: 534 (1043400.8 repeat1) represents an example of a cDNA sequence corresponding to repeat number 17 from the 5' variable region of O772P.

SEQ ID NO: 535 (1043400.8 repeat2) represents an example of a cDNA sequence corresponding to repeat number 18 from the 5' variable region of O772P.

SEQ ID NO: 536 (1043400.8 repeat3) represents an example of a cDNA sequence corresponding to repeat number 19 from the 5' variable region of O772P.

SEQ ID NO: 537 (1043400.9 repeat1) represents an example of a cDNA sequence corresponding to repeat number 4 from the 5' variable region of O772P.

SEQ ID NO: 538 (1043400.9 repeat2) represents an example of a cDNA sequence corresponding to repeat number 5 from the 5' variable region of O772P.

SEQ ID NO: 539 (1043400.9 repeat3) represents an example of a cDNA sequence corresponding to repeat number 7 from the 5' variable region of O772P.

SEQ ID NO: 540 (1043400.9 repeat4) represents an example of a cDNA sequence corresponding to repeat number 8 from the 5' variable region of O772P.

SEQ ID NO: 541 (1043400.11 repeat1) represents an example of a cDNA sequence corresponding to repeat number 1 from the 5' variable region of O772P.

SEQ ID NO: 542 (1043400.11 repeat2) represents an example of a cDNA sequence corresponding to repeat number 2 from the 5' variable region of O772P.

SEQ ID NO: 543 (1043400.11 repeat3) represents an example of a cDNA sequence corresponding to repeat number 3 from the 5' variable region of O772P.

SEQ ID NO: 544 (1043400.11 repeat4) represents an example of a cDNA sequence corresponding to repeat number 11 from the 5' variable region of O772P.

SEQ ID NO: 545 (1043400.11 repeat5) represents an example of a cDNA sequence corresponding to repeat number 12 from the 5' variable region of O772P.

SEQ ID NO: 546 (1043400.12 repeat1) represents an example of a cDNA sequence corresponding to repeat number 20 from the 5' variable region of O772P.

SEQ ID NO: 547 (PB repeatA) represents an example of a cDNA sequence corresponding to repeat number 1 from the 5' variable region of O772P.

SEQ ID NO: 548 (PB repeatB) represents an example of a cDNA sequence corresponding to repeat number 2 from the 5' variable region of O772P.

SEQ ID NO: 549 (PB repeatE) represents an example of a cDNA sequence corresponding to repeat number 3 from the 5' variable region of O772P.

SEQ ID NO: 550 (PB repeatG) represents an example of a cDNA sequence corresponding to repeat number 4 from the 5' variable region of O772P.

SEQ ID NO: 551 (PB repeatC) represents an example of a cDNA sequence corresponding to repeat number 4 from the 5' variable region of O772P.

SEQ ID NO: 552 (PB repeatH) represents an example of a cDNA sequence corresponding to repeat number 6 from the 5' variable region of O772P.

SEQ ID NO: 553 (PB repeatJ) represents an example of a cDNA sequence corresponding to repeat number 7 from the 5' variable region of O772P.

SEQ ID NO: 554 (PB repeatK) represents an example of a cDNA sequence corresponding to repeat number 8 from the 5' variable region of O772P.

SEQ ID NO: 555 (PB repeatD) represents an example of a cDNA sequence corresponding to repeat number 9 from the 5' variable region of O772P.

SEQ ID NO: 556 (PB repeatI) represents an example of a cDNA sequence corresponding to repeat number 10 from the 5' variable region of O772P.

SEQ ID NO: 557 (PB repeatM) represents an example of a cDNA sequence corresponding to repeat number 11 from the 5' variable region of O772P.

SEQ ID NO: 558 (PB repeat9) represents an example of a cDNA sequence corresponding to repeat number 12 from the 5' variable region of O772P.

SEQ ID NO: 559 (PB repeat8.5) represents an example of a cDNA sequence corresponding to repeat number 13 from the 5' variable region of O772P.

SEQ ID NO: 560 (PB repeat8) represents an example of a cDNA sequence corresponding to repeat number 14 from the 5' variable region of O772P.

SEQ ID NO: 561 (PB repeat7) represents an example of a cDNA sequence corresponding to repeat number 15 from the 5' variable region of O772P.

SEQ ID NO: 562 (PB repeat6) represents an example of a cDNA sequence corresponding to repeat number 16 from the 5' variable region of O772P.

SEQ ID NO: 563 (PB repeat5) represents an example of a cDNA sequence corresponding to repeat number 17 from the 5' variable region of O772P.

SEQ ID NO: 564 (PB repeat4) represents an example of a cDNA sequence corresponding to repeat number 18 from the 5' variable region of O772P.

SEQ ID NO: 565 (PB repeat3) represents an example of a cDNA sequence corresponding to repeat number 19 from the 5' variable region of O772P.

SEQ ID NO: 566 (PB repeat2) represents an example of a cDNA sequence corresponding to repeat number 20 from the 5' variable region of O772P.

SEQ ID NO: 567 (PB repeat1) represents an example of a cDNA sequence corresponding to repeat number 21 from the 5' variable region of O772P.

SEQ ID NO: 568 represents the cDNA sequence form the 3' constant region.

SEQ ID NO: 569 represents a cDNA sequence containing the consensus sequences of the 21 repeats, the 3' constant region and the 3' untranslated region.

SEQ ID NO: 570 represents the cDNA sequence of the consensus repeat sequence.

SEQ ID NO: 571 represents the consensus amino acid sequence of one potential open reading frame of repeat number 1 from the 5' variable region of O772P.

SEQ ID NO: 572 represents the consensus amino acid sequence of a second potential open reading frame of repeat number 1 from the 5' variable region of O772P.

SEQ ID NO: 573 represents the consensus amino acid sequence of a third potential open reading frame of repeat number 1 from the 5' variable region of O772P.

SEQ ID NO: 574 represents the consensus amino acid sequence of repeat number 2 from the 5' variable region of O772P.

SEQ ID NO: 575 represents the consensus amino acid sequence of repeat number 3 from the 5' variable region of O772P.

SEQ ID NO: 576 represents the consensus amino acid sequence of repeat number 4 from the 5' variable region of O772P.

SEQ ID NO: 577 represents the consensus amino acid sequence of repeat number 5 from the 5' variable region of O772P.

SEQ ID NO: 578 represents the consensus amino acid sequence of repeat number 6 from the 5' variable region of O772P.

SEQ ID NO: 579 represents the consensus amino acid sequence of repeat number 7 from the 5' variable region of O772P.

SEQ ID NO: 580 represents the consensus amino acid sequence of repeat number 8 from the 5' variable region of O772P.

SEQ ID NO: 581 represents the consensus amino acid sequence of repeat number 9 from the 5' variable region of O772P.

SEQ ID NO: 582 represents the consensus amino acid sequence of repeat number 10 from the 5' variable region of O772P.

SEQ ID NO: 583 represents the consensus amino acid sequence of repeat number 11 from the 5' variable region of O772P.

SEQ ID NO: 584 represents the consensus amino acid sequence of repeat number 12 from the 5' variable region of O772P.

SEQ ID NO: 585 represents the consensus amino acid sequence of repeat number 13 from the 5' variable region of O772P.

SEQ ID NO: 586 represents the consensus amino acid sequence of repeat number 14 from the 5' variable region of O772P.

SEQ ID NO: 587 represents the consensus amino acid sequence of repeat number 15 from the 5' variable region of O772P.

SEQ ID NO: 588 represents the consensus amino acid sequence of repeat number 16 from the 5' variable region of O772P.

SEQ ID NO: 589 represents the consensus amino acid sequence of repeat number 17 from the 5' variable region of O772P.

SEQ ID NO: 590 represents the consensus amino acid sequence of repeat number 18 from the 5' variable region of O772P.

SEQ ID NO: 591 represents the consensus amino acid sequence of repeat number 19 from the 5' variable region of O772P.

SEQ ID NO: 592 represents the consensus amino acid sequence of repeat number 20 from the 5' variable region of O772P.

SEQ ID NO: 593 represents the consensus amino acid sequence of repeat number 21 from the 5' variable region of O772P.

SEQ ID NO: 594 represents the amino acid sequence of the 3' constant region.

SEQ ID NO: 595 represents an amino acid sequence containing the consensus sequences of the 21 repeats and the 3' constant region.

SEQ ID NO: 596 represents the amino acid sequence of the consensus repeat sequence.

SEQ ID NO: 597 represents the amino acid sequence for Peptide #1, a 30-mer peptide that corresponds to the predicted extracellular domain of O772P.

SEQ ID NO: 598 represents the amino acid sequence for Peptide #2, a 30-mer peptide that corresponds to the predicted extracellular domain of O772P.

SEQ ID NO: 599 represents the amino acid sequence for Peptide #3, a 30-mer peptide that corresponds to the predicted extracellular domain of O772P.

SEQ ID NO: 600 represents the amino acid sequence of Peptide #1 from O8E, which corresponds to amino acids 1–20.

SEQ ID NO: 601 represents the amino acid sequence of Peptide #2 from O8E, which corresponds to amino acids 16–35.

SEQ ID NO: 602 represents the amino acid sequence of Peptide #3 from O8E, which corresponds to amino acids 31–50.

SEQ ID NO: 603 represents the amino acid sequence of Peptide #4 from O8E, which corresponds to amino acids 46–65.

SEQ ID NO: 604 represents the amino acid sequence of Peptide #5 from O8E, which corresponds to amino acids 61–80.

SEQ ID NO: 605 represents the amino acid sequence of Peptide #6 from O8E, which corresponds to amino acids 76–95.

SEQ ID NO: 606 represents the amino acid sequence of Peptide #7 from O8E, which corresponds to amino acids 91–110.

SEQ ID NO: 607 represents the amino acid sequence of Peptide #8 from O8E, which corresponds to amino acids 106–125.

SEQ ID NO: 608 represents the amino acid sequence of Peptide #9 from O8E, which corresponds to amino acids 120–140.

SEQ ID NO: 609 represents the amino acid sequence of Peptide #10 from O8E, which corresponds to amino acids 136–155.

SEQ ID NO: 610 represents the amino acid sequence of Peptide #11 from O8E, which corresponds to amino acids 151–170.

SEQ ID NO: 61 1 represents the amino acid sequence of Peptide #12 from O8E, which corresponds to amino acids 166–185.

SEQ ID NO: 612 represents the amino acid sequence of Peptide #13 from O8E, which corresponds to amino acids 181–200.

SEQ ID NO: 613 represents the amino acid sequence of Peptide #14 from O8E, which corresponds to amino acids 196–215.

SEQ ID NO: 614 represents the amino acid sequence of Peptide #15 from O8E, which corresponds to amino acids 211–230.

SEQ ID NO: 615 represents the amino acid sequence of Peptide #16 from O8E, which corresponds to amino acids 225–245.

SEQ ID NO: 616 represents the amino acid sequence of Peptide #17 from O8E, which corresponds to amino acids 241–260.

SEQ ID NO: 617 represents the amino acid sequence of Peptide #18 from O8E, which corresponds to amino acids 256–275.

SEQ ID NO: 618 represents the amino acid sequence of Peptide #19 from O8E, which corresponds to amino acids 263–282.

SEQ ID NO: 619 is the DNA sequence for the O8E PCR primer, O8E-UP1.

SEQ ID NO: 620 is the DNA sequence for the O8E reverse PCR primer designated O8E-DN1.

SEQ ID NO: 621 is a DNA sequence corresponding to the O8E Rhesus orthologs.

SEQ ID NO: 622 is a DNA sequence corresponding to the O8E mouse ortholog.

SEQ ID NO: 623 is an amino acid sequence corresponding to the O8E Rhesus orthologs.

SEQ ID NO: 624 is an amino acid sequence corresponding to the O8E mouse ortholog.

DETAILED DESCRIPTION OF THE INVENTION

U.S. patents, U.S. patent application publications, U.S. patent applications, foreign patents, foreign patent applications and non-patent publications referred to in this specification and/or listed in the Application Data Sheet, are incorporated herern by reference, in their entirety.

The present invention is directed generally to compositions and their use in the therapy and diagnosis of cancer, particularly ovarian cancer. As described further below, illustrative compositions of the present invention include, but are not restricted to, polypeptides, particularly immunogenic polypeptides, polynucleotides encoding such polypeptides, antibodies and other binding agents, antigen presenting cells (APCs) and immune system cells (e.g., T cells).

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Sambrook, et al., *Molecular Cloning: A Laboratory Manual* (2nd Edition, 1989); Maniatis et al., *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

Polypeptide Compositions

As used herein, the term "polypeptide" "is used in its conventional meaning, i.e., as a sequence of amino acids. The polypeptides are not limited to a specific length of the product; thus, peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising epitopes, i.e., antigenic determinants substantially responsible for the immunogenic properties of a polypeptide and being capable of evoking an immune response.

Particularly illustrative polypeptides of the present invention comprise those encoded by a polynucleotide sequence set forth in any one of SEQ ID NOs: 1–311, 313–387, 391, 457, 460–477, 512–570 and 619–622, or a sequence that hybridizes under moderately stringent conditions, or, alternatively, under highly stringent conditions, to a polynucleotide sequence set forth in any one of SEQ ID NOs: 1–311, 313–387, 391, 457, 460–477, 512–570 and 619–622. Certain other illustrative polypeptides of the invention comprise amino acid sequences as set forth in any one of SEQ ID NOs: 312, 388–389, 392–455, 458–459, 478–511, and 571–618.

The polypeptides of the present invention are sometimes herein referred to as ovarian tumor proteins or ovarian tumor polypeptides, as an indication that their identification has been based at least in part upon their increased levels of expression in ovarian tumor samples. Thus, an "ovarian tumor polypeptide" or "ovarian tumor protein," refers generally to a polypeptide sequence of the present invention, or a polynucleotide sequence encoding such a polypeptide, that is expressed in a substantial proportion of ovarian tumor samples, for example preferably greater than about 20%, more preferably greater than about 30%, and most preferably greater than about 50% or more of ovarian tumor samples tested, at a level that is at least two fold, and preferably at least five fold, greater than the level of expression in normal tissues, as determined using a representative assay provided herein. A ovarian tumor polypeptide sequence of the invention, based upon its increased level of expression in tumor cells, has particular utility both as a diagnostic marker as well as a therapeutic target, as further described below.

In certain preferred embodiments, the polypeptides of the invention are immunogenic, i.e., they react detectably within an immunoassay (such as an ELISA or T-cell stimulation assay) with antisera and/or T-cells from a patient with ovarian cancer. Screening for immunogenic activity can be performed using techniques well known to the skilled artisan. For example, such screens can be performed using methods such as those described in Harlow and Lane, *Antibodies: A Laboratory Manual*, Cold Spring Harbor Laboratory, 1988. In one illustrative example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As would be recognized by the skilled artisan, immunogenic portions of the polypeptides disclosed herein are also encompassed by the present invention. An "immunogenic portion," as used herein, is a fragment of an immunogenic polypeptide of the invention that itself is immunologically reactive (i.e., specifically binds) with the B-cells and/or T-cell surface antigen receptors that recognize the polypeptide. Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well-known techniques.

In one preferred embodiment, an immunogenic portion of a polypeptide of the present invention is a portion that reacts with antisera and/or T-cells at a level that is not substantially less than the reactivity of the full-length polypeptide (e.g., in an ELISA and/or T-cell reactivity assay). Preferably, the level of immunogenic activity of the immunogenic portion is at least about 50%, preferably at least about 70% and most preferably greater than about 90% of the immunogenicity for the full-length polypeptide. In some instances, preferred immunogenic portions will be identified that have a level of immunogenic activity greater than that of the corresponding full-length polypeptide, e.g., having greater than about 100% or 150% or more immunogenic activity.

In certain other embodiments, illustrative immunogenic portions may include peptides in which an N-terminal leader sequence and/or transmembrane domain have been deleted. Other illustrative immunogenic portions will contain a small N- and/or C-terminal deletion (e.g., 1–30 amino acids, preferably 5–15 amino acids), relative to the mature protein.

In another embodiment, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof.

In another embodiment of the invention, polypeptides are provided that comprise one or more polypeptides that are capable of eliciting T cells and/or antibodies that are immunologically reactive with one or more polypeptides described herein, or one or more polypeptides encoded by contiguous nucleic acid sequences contained in the polynucleotide sequences disclosed herein, or immunogenic fragments or variants thereof, or to one or more nucleic acid sequences which hybridize to one or more of these sequences under conditions of moderate to high stringency.

The present invention, in another aspect, provides polypeptide fragments comprising at least about 5, 10, 15, 20, 25, 50, or 100 contiguous amino acids, or more, including all intermediate lengths, of a polypeptide compositions set forth herein, such as those set forth in SEQ ID NOs: 312, 388–389, 392–455, 458–459, 478–511, and 571–618, or those encoded by a polynucleotide sequence set forth in a sequence of SEQ ID NOs: 1–311, 313–387, 391, 457, 460–477, 512–570 and 619–622.

In another aspect, the present invention provides variants of the polypeptide compositions described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequences set forth herein.

In one preferred embodiment, the polypeptide fragments and variants provided by the present invention are immunologically reactive with an antibody and/or T-cell that reacts with a full-length polypeptide specifically set forth herein.

In another preferred embodiment, the polypeptide fragments and variants provided by the present invention exhibit a level of immunogenic activity of at least about 50%, preferably at least about 70%, and most preferably at least about 90% or more of that exhibited by a full-length polypeptide sequence specifically set forth herein.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating their immunogenic activity as described herein and/or using any of a number of techniques well known in the art.

For example, certain illustrative variants of the polypeptides of the invention include those in which one or more portions, such as an N-terminal leader sequence or transmembrane domain, have been removed. Other illustrative variants include variants in which a small portion (e.g., 1–30 amino acids, preferably 5–15 amino acids) has been removed from the N- and/or C-terminal of the mature protein.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |

TABLE 1-continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within +1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

When comparing polypeptide sequences, two sequences are said to be "identical" if the sequence of amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O., (1978) *A model of evolutionary change in proteins—Matrices for detecting distant relationships*. In Dayhoff, M. O. (ed.) *Atlas of Protein Sequence and Structure*, National Biomedical Research Foundation, Washington D.C. Vol. 5, Suppl. 3, pp. 345–358; Hein J. (1990) *Unified Approach to Alignment and Phylogenes*, pp. 626–645 *Methods in Enzymology* vol. 183, Academic Press, Inc., San Diego, Calif.; Higgins, D. G. and Sharp, P. M., *CABIOS* 5:151–153 (1989); Myers, E. W. and Muller W., *CABIOS*4:11–17 (1988); Robinson, E. D., *Comb. Theor*11:105 (1971); Saitou, N. Nei, M., *Mol. Biol. Evol.* 4:406–425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726–730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389–3402 (1977), and Altschul et al., *J. Mol. Biol.* 215:403–410 (1990), respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one preferred approach, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Within other illustrative embodiments, a polypeptide may be a xenogeneic polypeptide that comprises an polypeptide having substantial sequence identity, as described above, to the human polypeptide (also termed autologous antigen) which served as a reference polypeptide, but which xenogeneic polypeptide is derived from a different, non-human species. One skilled in the art will recognize that "self" antigens are often poor stimulators of CD8+ and CD4+ T-lymphocyte responses, and therefore efficient immunotherapeutic strategies directed against tumor polypeptides require the development of methods to overcome immune tolerance to particular self tumor polypeptides. For example, humans immunized with prostase protein from a xenogeneic (non human) origin are capable of mounting an immune response against the counterpart human protein, e.g., the human prostase tumor protein present on human tumor cells. Accordingly, the present invention provides methods for purifying the xenogeneic form of the tumor proteins set forth herein, such as the polypeptides set forth in SEQ ID NOs: 312, 388–389, 392–455, 458–459, 478–511, and 571–618, or those encoded by polynucleotide sequences set forth in SEQ ID NOs: 1–311, 313–387, 391, 457, 460–477, 512–570 and 619–622.

Therefore, one aspect of the present invention provides xenogeneic variants of the polypeptide compositions described herein. Such xenogeneic variants generally encompassed by the present invention will typically exhibit at least about 70%, 75%, 80%, 85%, 90%, 91%, 92%, 93%, 94%, 95%, 96%, 97%, 98%, or 99% or more identity along their lengths, to a polypeptide sequences set forth herein.

More particularly, the invention is directed to mouse, rat, monkey, porcine and other non-human polypeptides which can be used as xenogeneic forms of human polypeptides set forth herein, to induce immune responses directed against tumor polypeptides of the invention.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46,1985; Murphy et al., *Proc. Natl. Acad. Sci. USA* 83:8258–8262,1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.,* 336:86–91,1997).

In one preferred embodiment, the immunological fusion partner is derived from a Mycobacterium sp., such as a *Mycobacterium tuberculosis*-derived Ra12 fragment. Ra12 compositions and methods for their use in enhancing the expression and/or immunogenicity of heterologous polynucleotide/polypeptide sequences is described in U.S. Patent Application 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. Patent Application 60/158,585; see also, Skeiky et al., *Infection and Immun.* 67:3998–4007 (1999), incorporated herein by reference). C-terminal fragments of the MTB32A coding sequence express at high levels and remain as a soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292,1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of $CD4^+$ T-cells specific for the polypeptide.

Polypeptides of the invention are prepared using any of a variety of well known synthetic and/or recombinant techniques, the latter of which are further described below. Polypeptides, portions and other variants generally less than about 150 amino acids can be generated by synthetic means, using techniques well known to those of ordinary skill in the art. In one illustrative example, such polypeptides are synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

In general, polypeptide compositions (including fusion polypeptides) of the invention are isolated. An "isolated" polypeptide is one that is removed from its original environment. For example, a naturally-occurring protein or polypeptide is isolated if it is separated from some or all of the coexisting materials in the natural system. Preferably, such polypeptides are also purified, e.g., are at least about 90% pure, more preferably at least about 95% pure and most preferably at least about 99% pure.

Polynucleotide Compositions

The present invention, in other aspects, provides polynucleotide compositions. The terms "DNA" and "polynucleotide" are used essentially interchangeably herein to refer to a DNA molecule that has been isolated free of total genomic DNA of a particular species. "Isolated," as used herein, means that a polynucleotide is substantially away from other coding sequences, and that the DNA molecule does not contain large portions of unrelated coding DNA, such as large chromosomal fragments or other functional genes or polypeptide coding regions. Of course, this refers to the DNA molecule as originally isolated, and does not exclude genes or coding regions later added to the segment by the hand of man.

As will be understood by those skilled in the art, the polynucleotide compositions of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

As will be also recognized by the skilled artisan, polynucleotides of the invention may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a polypeptide/protein of the invention or a portion thereof) or may comprise a sequence that encodes a variant or derivative, preferably and immunogenic variant or derivative, of such a sequence.

Therefore, according to another aspect of the present invention, polynucleotide compositions are provided that comprise some or all of a polynucleotide sequence set forth in any one of SEQ ID NOs: 1–311, 313–387, 391, 457, 460–477, 512–570 and 619–622, complements of a polynucleotide sequence set forth in any one of SEQ ID NOs: 1–311, 313–387, 391, 457, 460–477, 512–570 and 619–622, and degenerate variants of a polynucleotide sequence set forth in any one of SEQ ID NOs: 1–311, 313–387, 391, 457, 460–477, 512–570 and 619–622. In certain preferred embodiments, the polynucleotide sequences set forth herein encode immunogenic polypeptides, as described above.

In other related embodiments, the present invention provides polynucleotide variants having substantial identity to the sequences disclosed herein in SEQ ID NOs: 1–311, 313–387, 391, 457, 460–477, 512–570 and 619–622, for example those comprising at least 70% sequence identity, preferably at least 75%, 80%, 85%, 90%, 95%, 96%, 97%, 98%, or 99% or higher, sequence identity compared to a polynucleotide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the immunogenicity of the polypeptide encoded by the variant polynucleotide is not substantially diminished relative to a polypeptide encoded by a polynucleotide sequence specifically set forth herein). The term "variants" should also be understood to encompasses homologous genes of xenogenic origin.

In additional embodiments, the present invention provides polynucleotide fragments comprising or consisting of various lengths of contiguous stretches of sequence identical to or complementary to one or more of the sequences disclosed herein. For example, polynucleotides are provided by this invention that comprise or consist of at least about 10, 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200–500; 500–1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of the disclosed sequence or at both ends of the disclosed sequence.

In another embodiment of the invention, polynucleotide compositions are provided that are capable of hybridizing under moderate to high stringency conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60–65° C. or 65–70° C.

In certain preferred embodiments, the polynucleotides described above, e.g., polynucleotide variants, fragments and hybridizing sequences, encode polypeptides that are immunologically cross-reactive with a polypeptide sequence specifically set forth herein. In other preferred embodiments, such polynucleotides encode polypeptides that have a level of immunogenic activity of at least about 50%, preferably at least about 70%, and more preferably at least about 90% of that for a polypeptide sequence specifically set forth herein.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345–358; Hein J., *Unified Approach to Alignment and Phylogenes*, pp. 626–645 (1990); *Methods in Enzymology vol.*183, Academic Press, Inc., San Diego, Calif.; Higgins, D. G. and Sharp, P. M., *CABIOS* 5:151–153 (1989); Myers, E. W. and Muller W., *CABIOS* 4:11–17 (1988); Robinson, E. D., *Comb. Theor* 11:105 (1971); Santou, N. Nes, M., *Mol. Biol. Evol.* 4:406–425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726–730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389–3402 (1977), and Altschul et al., *J. Mol. Biol.* 215:403–410 (1990), respectively. BLAST and BLAST 2.0 can be used, for example with the parameters described herein, to determine percent sequence identity for the polynucleotides of the invention. Software for performing BLAST analyses is publicly available through the National Center for Biotechnology Information. In one illustrative example, cumulative scores can be calculated using, for nucleotide sequences, the parameters M (reward score for a pair of matching residues; always>0) and N (penalty score for mismatching residues; always<0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Therefore, in another embodiment of the invention, a mutagenesis approach, such as site-specific mutagenesis, is employed for the preparation of immunogenic variants and/or derivatives of the polypeptides described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the immunogenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants of the present invention, recursive sequence recombination, as described in U.S. Pat. No. 5,837,458, may be employed. In this approach, iterative cycles of recombination and screening or selection are performed to "evolve" individual polynucleotide variants of the invention having, for example, enhanced immunogenic activity.

In other embodiments of the present invention, the polynucleotide sequences provided herein can be advantageously used as probes or primers for nucleic acid hybridization. As such, it is contemplated that nucleic acid segments that comprise or consist of a sequence region of at least about a 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10–14, 15–20, 30, 50, or even of 100–200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch (es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15–25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequences set forth herein, or to any continuous portion of the sequences, from about 15–25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

According to another embodiment of the present invention, polynucleotide compositions comprising antisense oligonucleotides are provided. Antisense oligonucleotides have been demonstrated to be effective and targeted inhibitors of protein synthesis, and, consequently, provide a therapeutic approach by which a disease can be treated by inhibiting the synthesis of proteins that contribute to the disease. The efficacy of antisense oligonucleotides for inhibiting protein synthesis is well established. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., *Science Jun.* 10, 1988; 240(4858):1544–6; Vasanthakumar and Ahmed, Cancer Commun. 1989;1 (4):225–32; Peris et al., *Brain Res Mol Brain Res. Jun.* 15, 1998; 57(2):310–20; U.S. Pat. Nos. 5,801,154; 5,789,573; 5,718,709 and 5,610,288). Antisense constructs have also been described that inhibit and can be used to treat a variety of abnormal cellular proliferations, e.g., cancer (U.S. Pat. Nos. 5,747,470; 5,591,317 and 5,783,683).

Therefore, in certain embodiments, the present invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein. Selection of antisense compositions specific for a given gene sequence is based upon analysis of the chosen target sequence and determination of secondary structure, $T_m$, binding energy, and relative stability. Antisense compositions may be selected based upon their relative inability to form dimers, hairpins, or other secondary structures that would reduce or prohibit specific binding to the target mRNA in a host cell. Highly preferred target regions of the mRNA, are those which are at or near the AUG translation initiation codon, and those sequences which are substantially complementary to 5' regions of the mRNA. These secondary structure analyses and target site selection considerations can be performed, for example, using v0.4 of the OLIGO primer analysis software and/or the BLASTN 2.0.5 algorithm software (Altschul et al., Nucleic Acids Res. 1997, 25(17):3389–402).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., Nucleic Acids Res. Jul. 15, 1997; 25(14):2730–6). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane.

According to another embodiment of the invention, the polynucleotide compositions described herein are used in the design and preparation of ribozyme molecules for inhibiting expression of the tumor polypeptides and proteins of the present invention in tumor cells. Ribozymes are RNA-protein complexes that cleave nucleic acids in a site-specific fashion. Ribozymes have specific catalytic domains that possess endonuclease activity (Kim and Cech, *Proc. Natl. Acad. Sci. USA. December* 1997; 84(24):8788–92; Forster and Symons, Cell. Apr. 24, 1987; 49(2):211–20). For example, a large number of ribozymes accelerate phosphoester transfer reactions with a high degree of specificity, often cleaving only one of several phosphoesters in an oligonucleotide substrate (Cech et al., Cell. Dec. 27, 1981; (3 Pt 2):487–96; Michel and Westhof, J Mol Biol. Dec, 5, 1990; 216(3):585–610; Reinhold-Hurek and Shub, Nature. May 14, 1992; 357(6374):173–6). This specificity has been attributed to the requirement that the substrate bind via specific base-pairing interactions to the internal guide sequence ("IGS") of the ribozyme prior to chemical reaction.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., *Proc. Natl. Acad. Sci. USA. Aug.* 15, 1992; 89(16):7305–9). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. Nucleic Acids Res. Sep. 11, 1992; 20(17):4559–65. Examples of hairpin motifs are described by Hampel et al. (Eur. Pat. Appl. Publ. No. EP 0360257), Hampel and Tritz, Biochemistry Jun. 13, 1989; 28(12):4929–33; Hampel et al., Nucleic Acids Res. Jan. 25, 1990; 18(2):299–304 and U.S. Pat. No. 5,631,359. An example of the hepatitis δ virus motif is described by Perrotta and Been, Biochemistry. Dec. 1, 1992; 31 (47):11843–52; an example of the RNaseP motif is described by Guerrier-Takada et al., Cell. December 1993; 35(3 Pt 2):849–57; Neurospora VS RNA ribozyme motif is described by Collins (Saville and Collins, Cell. May 18, 1990; 61 (4):685–96; Saville and Collins, *Proc. Natl. Acad. Sci. USA,* 88(19):8826–30 (Oct. 1, 1991); Collins and Olive, *Biochemistry* 32(11):2795–9 (Mar. 23, 1993); and an example of the Group I intron is described in (U.S. Pat. No. 4,987,071). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Int. Pat. Appl. Publ. No. WO 93/15187; Int. Pat. Appl. Publ. No. WO 91/03162; Eur. Pat. Appl. Publ. No. 92110298.4; U.S. Pat. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol II). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells Ribozymes expressed from such promoters have been shown to function in mammalian cells. Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

In another embodiment of the invention, peptide nucleic acids (PNAs) compositions are provided. PNA is a DNA mimic in which the nucleobases are attached to a pseudopeptide backbone (Good and Nielsen, Antisense Nucleic Acid Drug Dev. 1997 7(4) 431–37). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (*Trends Biotechnol* 15(6):224–9 (June 1997)). As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., *Science* 254(5037):1497–500 (Dec. 6, 1991); Hanvey et al., *Science* 258(5087):1481–5 (Nov. 27, 1992); Hyrup and Nielsen, *Bioorg. Med. Chem.* 4(1):5–23 (January 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc or Fmoc protocols for solid-phase peptide synthesis, although other methods, including a modified Merrifield method, have been used.

PNA monomers or ready-made oligomers are commercially available from PerSeptive Biosystems (Framingham, Mass.). PNA syntheses by either Boc or Fmoc protocols are straightforward using manual or automated protocols (Norton et al., *Bioorg. Med. Chem.* 3(4):437–45 (April 1995)). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography, providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (for example, Norton et al., *Bioorg Med Chem* 3(4):437–45 (April 1995); Petersen et al., *J Pept Sci* 1(3):175–83 (May–June 1995); Orum et al., *Biotechniques* 19(3):472–80 (September 1995); Footer et al., *Biochemistry.* 1996 August 20;35(33):10673–9; Griffith et al., *Nucleic Acids Res* 23(15):3003–8 (Aug. 11, 1995); Pardridge et al., *Proc. Natl. Acad. Sci. USA.*

92(12):5592–6 (Jun. 6, 1995); Boffa et al., *Proc. Natl. Acad. Sci. USA*. 92(6):1901–5 (Mar. 14, 1995); Gambacorti-Passerini et al., *Blood* 88(4):1411–7 (Aug. 15, 1996); Armitage et al., *Proc. Natl. Acad. Sci. USA*. 94(23):12320–5 (Nov. 11, 1997); Seeger et al., *Biotechniques* 23(3):512–7 (September 1997)). U.S. Pat. No. 5,700,922 discusses PNA-DNA-PNA chimeric molecules and their uses in diagnostics, modulating protein in organisms, and treatment of conditions susceptible to therapeutics.

Methods of characterizing the antisense binding properties of PNAs are discussed in Rose (*Anal Chem* 65(24):3545–9 (Dec. 15, 1993) and Jensen et al. (Biochemistry. Apr. 22, 1997; 36(16):5072–7). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs that have been described and will be apparent to the skilled artisan include use in DNA strand invasion, antisense inhibition, mutational analysis, enhancers of transcription, nucleic acid purification, isolation of transcriptionally active genes, blocking of transcription factor binding, genome cleavage, biosensors, in situ hybridization, and the like.

Polynucleotide Identification, Characterization and Expression

Polynucleotides compositions of the present invention may be identified, prepared and/or manipulated using any of a variety of well established techniques (see generally, Sambrook et al., *Molecular Cloning: A Laboratory Manual*, Cold Spring Harbor Laboratories, Cold Spring Harbor, N.Y., 1989, and other like references). For example, a polynucleotide may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using the microarray technology of Affymetrix, Inc. (Santa Clara, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155,1997). Alternatively, polynucleotides may be amplified from cDNA prepared from cells expressing the proteins described herein, such as tumor cells.

Many template dependent processes are available to amplify a target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Any of a number of other template dependent processes, many of which are variations of the PCR™ amplification technique, are readily known and available in the art. Illustratively, some such methods include the ligase chain reaction (referred to as LCR), described, for example, in Eur. Pat. Appl. Publ. No. 320,308 and U.S. Pat. No. 4,883,750; Qbeta Replicase, described in PCT Intl. Pat. Appl. Publ. No. PCT/US87/00880; Strand Displacement Amplification (SDA) and Repair Chain Reaction (RCR). Still other amplification methods are described in Great Britain Pat. Appl. No. 2 202 328, and in PCT Intl. Pat. Appl. Publ. No. PCT/US89/01025. Other nucleic acid amplification procedures include transcription-based amplification systems (TAS) (PCT Intl. Pat. Appl. Publ. No. WO 88/10315), including nucleic acid sequence based amplification (NASBA) and 3SR. Eur. Pat. Appl. Publ. No. 329,822 describes a nucleic acid amplification process involving cyclically synthesizing single-stranded RNA ("ssRNA"), ssDNA, and double-stranded DNA (dsDNA). PCT Intl. Pat. Appl. Publ. No. WO 89/06700 describes a nucleic acid sequence amplification scheme based on the hybridization of a promoter/primer sequence to a target single-stranded DNA ("ssDNA") followed by transcription of many RNA copies of the sequence. Other amplification methods such as "RACE" (Frohman, 1990), and "one-sided PCR" (Ohara, 1989) are also well-known to those of skill in the art.

An amplified portion of a polynucleotide of the present invention may be used to isolate a full length gene from a suitable library (e.g., a tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, amplification techniques, such as those described above, can be useful for obtaining a full length coding sequence from a partial cDNA sequence. One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215–223, Horn, T. et al. (1980) *Nucl. Acids Res. Symp. Ser.* 225–232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202–204) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, W H Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described, for example, in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the pBLUESCRIPT phagemid (Stratagene, La Jolla, Calif.) or pSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, any of a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as pBLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503–5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516–544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307–311. Alternatively, plant promoters such as the small subunit of RUBISCO or heat shock promoters may be used (Coruzzi, G. et al. (1984) *EMBO J.* 3:1671–1680; Broglie, R. et al. (1984) *Science* 224:838–843; and Winter, J. et al. (1991) *Results Probl. Cell Differ.* 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191–196).

An insect system may also be used to express a polypeptide of interest. For example, in one such system, Autographa californica nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224–3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Prob. Cell Differ.* 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, COS, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223–32) and adenine phosphoribosyltransferase (Lowy, I. et al. (1990) *Cell* 22:817–23) genes which can be employed in tk.sup.- or aprt.sup.- cells, respectively. Also, antimetabolite, antibiotic or herbicide resistance can be used as the basis for selection; for example, dhfr which confers resistance to methotrexate (Wigler, M. et al. (1980)

*Proc. Natl. Acad. Sci.* 77:3567–70); npt, which confers resistance to the aminoglycosides, neomycin and G-418 (Colbere-Garapin, F. et al (1981) *J. Mol. Biol.* 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047–51). The use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells that contain and express a desired polynucleotide sequence may be identified by a variety of procedures known to those of skill in the art. These procedures include, but are not limited to, DNA—DNA or DNA-RNA hybridizations and protein bioassay or immunoassay techniques which include, for example, membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif.* 3:263–281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441–453).

In addition to recombinant production methods, polypeptides of the invention, and fragments thereof, may be produced by direct peptide synthesis using solid-phase techniques (Merrifield J. (1963) *J. Am. Chem. Soc.* 85:2149–2154). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

Antibody Compositions, Fragments Thereof and Other Binding Agents

According to another aspect, the present invention further provides binding agents, such as antibodies and antigen-binding fragments thereof, that exhibit immunological binding to a tumor polypeptide disclosed herein, or to a portion, variant or derivative thereof. An antibody, or antigen-binding fragment thereof, is said to "specifically bind," "immunogically bind," and/or is "immunologically reactive" to a polypeptide of the invention if it reacts at a detectable level (within, for example, an ELISA assay) with the polypeptide, and does not react detectably with unrelated polypeptides under similar conditions.

Immunological binding, as used in this context, generally refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439–473.

An "antigen-binding site," or "binding portion" of an antibody refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions," or "FRs". Thus the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

Binding agents may be further capable of differentiating between patients with and without a cancer, such as ovarian cancer, using the representative assays provided herein. For example, antibodies or other binding agents that bind to a tumor protein will preferably generate a signal indicating the presence of a cancer in at least about 20% of patients with the disease, more preferably at least about 30% of patients. Alternatively, or in addition, the antibody will generate a negative signal indicating the absence of the disease in at least about 90% of individuals without the cancer. To determine whether a binding agent satisfies this requirement, biological samples (e.g., blood, sera, sputum, urine and/or tumor biopsies) from patients with and without a cancer (as determined using standard clinical tests) may be assayed as described herein for the presence of polypeptides that bind to the binding agent. Preferably, a statistically significant number of samples with and without the disease will be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

A number of therapeutically useful molecules are known in the art which comprise antigen-binding sites that are capable of exhibiting immunological binding properties of an antibody molecule. The proteolytic enzyme papain preferentially cleaves IgG molecules to yield several fragments, two of which (the "F(ab)" fragments) each comprise a covalent heterodimer that includes an intact antigen-binding site. The enzyme pepsin is able to cleave IgG molecules to provide several fragments, including the "$F(ab')_2$" fragment which comprises both antigen-binding sites. An "Fv" fragment can be produced by preferential proteolytic cleavage of an IgM, and on rare occasions IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat Acad. Sci.*

*USA* 69:2659–2662; Hochman et al. (1976) *Biochem* 15:2706–2710; and Ehrlich et al. (1980) *Biochem* 19:4091–4096.

A single chain Fv ("sFv") polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879–5883. A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

Each of the above-described molecules includes a heavy chain and a light chain CDR set, respectively interposed between a heavy chain and a light chain FR set which provide support to the CDRS and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRS. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

A number of "humanized" antibody molecules comprising an antigen-binding site derived from a non-human immunoglobulin have been described, including chimeric antibodies having rodent V regions and their associated CDRs fused to human constant domains (Winter et al. (1991) *Nature* 349:293–299; Lobuglio et al. (1989) *Proc. Nat. Acad. Sci. USA* 86:4220–4224; Shaw et al. (1987) *J Immunol.* 138:4534–4538; and Brown et al. (1987) *Cancer Res.* 47:3577–3583), rodent CDRs grafted into a human supporting FR prior to fusion with an appropriate human antibody constant domain (Riechmann et al. (1988) *Nature* 332:323–327; Verhoeyen et al. (1988) *Science* 239:1534–1536; and Jones et al. (1986) *Nature* 321:522–525), and rodent CDRs supported by recombinantly veneered rodent FRs (European Patent Publication No. 519,596, published Dec. 23, 1992). These "humanized" molecules are designed to minimize unwanted immunological response toward rodent antihuman antibody molecules which limits the duration and effectiveness of therapeutic applications of those moieties in human recipients.

As used herein, the terms "veneered FRs" and "recombinantly veneered FRs" refer to the selective replacement of FR residues from, e.g., a rodent heavy or light chain V region, with human FR residues in order to provide a xenogeneic molecule comprising an antigen-binding site which retains substantially all of the native FR polypeptide folding structure. Veneering techniques are based on the understanding that the ligand binding characteristics of an antigen-binding site are determined primarily by the structure and relative disposition of the heavy and light chain CDR sets within the antigen-binding surface. Davies et al. (1990) *Ann. Rev. Biochem.* 59:439–473. Thus, antigen binding specificity can be preserved in a humanized antibody only wherein the CDR structures, their interaction with each other, and their interaction with the rest of the V region domains are carefully maintained. By using veneering techniques, exterior (e.g., solvent-accessible) FR residues which are readily encountered by the immune system are selectively replaced with human residues to provide a hybrid molecule that comprises either a weakly immunogenic, or substantially non-immunogenic veneered surface.

The process of veneering makes use of the available sequence data for human antibody variable domains compiled by Kabat et al., in Sequences of Proteins of Immunological Interest, 4th ed., (U.S. Dept. of Health and Human Services, U.S. Government Printing Office, 1987), updates to the Kabat database, and other accessible U.S. and foreign databases (both nucleic acid and protein). Solvent accessibilities of V region amino acids can be deduced from the known three-dimensional structure for human and murine antibody fragments. There are two general steps in veneering a murine antigen-binding site. Initially, the FRs of the variable domains of an antibody molecule of interest are compared with corresponding FR sequences of human variable domains obtained from the above-identified sources. The most homologous human V regions are then compared residue by residue to corresponding murine amino acids. The residues in the murine FR which differ from the human counterpart are replaced by the residues present in the human moiety using recombinant techniques well known in the art. Residue switching is only carried out with moieties which are at least partially exposed (solvent accessible), and care is exercised in the replacement of amino acid residues which may have a significant effect on the tertiary structure of V region domains, such as proline, glycine and charged amino acids.

In this manner, the resultant "veneered" murine antigen-binding sites are thus designed to retain the murine CDR residues, the residues substantially adjacent to the CDRs, the residues identified as buried or mostly buried (solvent inaccessible), the residues believed to participate in non-covalent (e.g., electrostatic and hydrophobic) contacts between heavy and light chain domains, and the residues from conserved structural regions of the FRs which are believed to influence the "canonical" tertiary structures of the CDR loops. These design criteria are then used to prepare recombinant nucleotide sequences which combine the CDRs of both the heavy and light chain of a murine antigen-binding site into human-appearing FRs that can be used to transfect mammalian cells for the expression of recombinant human antibodies which exhibit the antigen specificity of the murine antibody molecule.

In another embodiment of the invention, monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

T Cell Compositions

The present invention, in another aspect, provides T cells specific for a tumor polypeptide disclosed herein, or for a variant or derivative thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a polypeptide, polynucleotide encoding a polypeptide and/or an antigen presenting cell (APC) that expresses such a polypeptide. Such stimulation is performed under conditions and for a time sufficient to permit the generation of T cells that are specific for the polypeptide of interest. Preferably, a tumor polypeptide or polynucleotide of the invention is present within a delivery vehicle, such as a microsphere, to facilitate the generation of specific T cells.

T cells are considered to be specific for a polypeptide of the present invention if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070,1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a tumor polypeptide (100 ng/ml–100 μg/ml, preferably 200 ng/ml–25 μg/ml) for 3–7 days will typically result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a tumor polypeptide, polynucleotide or polypeptide-expressing APC may be $CD4^+$ and/or $CD8^+$. Tumor polypeptide-specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to a tumor polypeptide, polynucleotide or APC can be expanded in number either in vitro or in vivo. Proliferation of such T cells in vitro may be accomplished in a variety of ways. For example, the T cells can be re-exposed to a tumor polypeptide, or a short peptide corresponding to an immunogenic portion of such a polypeptide, with or without the addition of T cell growth factors, such as interleukin-2, and/or stimulator cells that synthesize a tumor polypeptide. Alternatively, one or more T cells that proliferate in the presence of the tumor polypeptide can be expanded in number by cloning. Methods for cloning cells are well known in the art, and include limiting dilution.

T Cell Receptor Compositions

The T cell receptor (TCR) consists of 2 different, highly variable polypeptide chains, termed the T-cell receptor α and β chains, that are linked by a disulfide bond (Janeway, Travers, Walport. Immunobiology. Fourth Ed., 148–159. Elsevier Science Ltd/Garland Publishing. 1999). The α/β heterodimer complexes with the invariant CD3 chains at the cell membrane. This complex recognizes specific antigenic peptides bound to MHC molecules. The enormous diversity of TCR specificities is generated much like immunoglobulin diversity, through somatic gene rearrangement. The β chain genes contain over 50 variable (V), 2 diversity (D), over 10 joining (J) segments, and 2 constant region segments (C). The α chain genes contain over 70 V segments, and over 60 J segments but no D segments, as well as one C segment. During T cell development in the thymus, the D to J gene rearrangement of the β chain occurs, followed by the V gene segment rearrangement to the DJ. This functional VDJβ exon is transcribed and spliced to join to a Cβ. For the α chain, a Vα gene segment rearranges to a Jα gene segment to create the functional exon that is then transcribed and spliced to the Cα. Diversity is further increased during the recombination process by the random addition of P and N-nucleotides between the V, D, and J segments of the b chain and between the V and J segments in the a chain (Janeway, Travers, Walport. Immunobiology. Fourth Ed., 98 and 150. Elsevier Science Ltd/Garland Publishing. 1999).

The present invention, in another aspect, provides TCRs specific for a polypeptide disclosed herein, or for a variant or derivative thereof. In accordance with the present invention, polynucleotide and amino acid sequences are provided for the V-J or V-D-J junctional regions or parts thereof for the alpha and beta chains of the T-cell receptor which recognize tumor polypeptides described herein. In general, this aspect of the invention relates to T-cell receptors which recognize or bind tumor polypeptides presented in the context of MHC. In a preferred embodiment the tumor antigens recognized by the T-cell receptors comprise a polypeptide of the present invention. For example, cDNA encoding a TCR specific for a ovarian tumor peptide can be isolated from T cells specific for a tumor polypeptide using standard molecular biological and recombinant DNA techniques.

This invention further includes the T-cell receptors or analogs thereof having substantially the same function or activity as the T-cell receptors of this invention which recognize or bind tumor polypeptides. Such receptors include, but are not limited to, a fragment of the receptor, or a substitution, addition or deletion mutant of a T-cell receptor provided herein. This invention also encompasses polypeptides or peptides that are substantially homologous to the T-cell receptors provided herein or that retain substantially the same activity. The term "analog" includes any protein or polypeptide having an amino acid residue sequence substantially identical to the T-cell receptors provided herein in which one or more residues, preferably no more than 5 residues, more preferably no more than 25 residues have been conservatively substituted with a functionally similar residue and which displays the functional aspects of the T-cell receptor as described herein.

The present invention further provides for suitable mammalian host cells, for example, non-specific T-cells, that are transfected with a polynucleotide encoding TCRs specific for a polypeptide described herein, thereby rendering the host cell specific for the polypeptide. The α and β chains of the TCR may be contained on separate expression vectors or alternatively, on a single expression vector that also contains an internal ribosome entry site (IRES) for cap-independent translation of the gene downstream of the IRES. Said host cells expressing TCRs specific for the polypeptide may be used, for example, for adoptive immunotherapy of ovarian cancer as discussed further below.

In further aspects of the present invention, cloned TCRs specific for a polypeptide recited herein may be used in a kit for the diagnosis of ovarian cancer. For example, the nucleic acid sequence or portions thereof, of tumor-specific TCRs can be used as probes or primers for the detection of expression of the rearranged genes encoding the specific TCR in a biological sample. Therefore, the present invention further provides for an assay for detecting messenger RNA or DNA encoding the TCR specific for a polypeptide.

Pharmaceutical Compositions

In additional embodiments, the present invention concerns formulation of one or more of the polynucleotide, polypeptide, T-cell, TCR, and/or antibody compositions disclosed herein in pharmaceutically-acceptable carriers for administration to a cell or an animal, either alone, or in combination with one or more other modalities of therapy.

It will be understood that, if desired, a composition as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Therefore, in another aspect of the present invention, pharmaceutical compositions are provided comprising one or more of the polynucleotide, polypeptide, antibody, TCR, and/or T-cell compositions described herein in combination with a physiologically acceptable carrier. In certain preferred embodiments, the pharmaceutical compositions of the invention comprise immunogenic polynucleotide and/or polypeptide compositions of the invention for use in prophylactic and theraputic vaccine applications. Vaccine preparation is generally described in, for example, M. F. Powell and M. J. Newman, eds., "Vaccine Design (the subunit and adjuvant approach)," Plenum Press (NY, 1995). Generally, such compositions will comprise one or more polynucleotide and/or polypeptide compositions of the present invention in combination with one or more immunostimulants.

It will be apparent that any of the pharmaceutical compositions described herein can contain pharmaceutically acceptable salts of the polynucleotides and polypeptides of the invention. Such salts can be prepared, for example, from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

In another embodiment, illustrative immunogenic compositions, e.g., vaccine compositions, of the present invention comprise DNA encoding one or more of the polypeptides as described above, such that the polypeptide is generated in situ. As noted above, the polynucleotide may be administered within any of a variety of delivery systems known to those of ordinary skill in the art. Indeed, numerous gene delivery techniques are well known in the art, such as those described by Rolland, *Crit. Rev. Therap. Drug Carrier Systems* 15:143–198, 1998, and references cited therein. Appropriate polynucleotide expression systems will, of course, contain the necessary regulatory DNA regulatory sequences for expression in a patient (such as a suitable promoter and terminating signal). Alternatively, bacterial delivery systems may involve the administration of a bacterium (such as Bacillus-Calmette-Guerrin) that expresses an immunogenic portion of the polypeptide on its cell surface or secretes such an epitope.

Therefore, in certain embodiments, polynucleotides encoding immunogenic polypeptides described herein are introduced into suitable mammalian host cells for expression using any of a number of known viral-based systems. In one illustrative embodiment, retroviruses provide a convenient and effective platform for gene delivery systems. A selected nucleotide sequence encoding a polypeptide of the present invention can be inserted into a vector and packaged in retroviral particles using techniques known in the art. The recombinant virus can then be isolated and delivered to a subject. A number of illustrative retroviral systems have been described (e.g., U.S. Pat. No. 5,219,740; Miller and Rosman (1989) *Bio Techniques* 7:980–990; Miller, A. D. (1990) *Human Gene Therapy* 1:5–14; Scarpa et al. (1991) *Virology* 180:849–852; Burns et al. (1993) *Proc. Natl. Acad. Sci. USA* 90:8033–8037; and Boris-Lawrie and Temin (1993) *Cur. Opin. Genet. Develop.* 3:102–109.

In addition, a number of illustrative adenovirus-based systems have also been described. Unlike retroviruses which integrate into the host genome, adenoviruses persist extrachromosomally thus minimizing the risks associated with insertional mutagenesis (Haj-Ahmad and Graham (1986) *J. Virol.* 57:267–274; Bett et al. (1993) *J. Virol.* 67:5911–5921; Mittereder et al. (1994) *Human Gene Therapy* 5:717–729; Seth et al. (1994) *J. Virol.* 68:933–940; Barr et al. (1994) *Gene Therapy* 1:51–58; Berkner, K. L. (1988) *Bio Techniques* 6:616–629; and Rich et al. (1993) *Human Gene Therapy* 4:461–476).

Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) *Molec. Cell. Biol.* 8:3988–3996; Vincent et al. (1990) *Vaccines* 90 (Cold Spring Harbor Laboratory Press); Carter, B. J. (1992) *Current Opinion in Biotechnology* 3:533–539; Muzyczka, N. (1992) *Current Topics in Microbiol. and Immunol.* 158:97–129; Kotin, R. M. (1994) *Human Gene Therapy* 5:793–801; Shelling and Smith (1994) *Gene Therapy* 1:165–169; and Zhou et al. (1994) *J. Exp. Med.* 179:1867–1875.

Additional viral vectors useful for delivering the polynucleotides encoding polypeptides of the present invention by gene transfer include those derived from the pox family of viruses, such as vaccinia virus and avian poxvirus. By way of example, vaccinia virus recombinants expressing the novel molecules can be constructed as follows. The DNA encoding a polypeptide is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the polypeptide of interest into the viral genome. The resulting TK.sup.(−) recombinant can be selected by culturing the cells in the presence of bromodeoxyuridine and picking viral plaques resistant thereto.

A vaccinia-based infection/transfection system can be conveniently used to provide for inducible, transient expression or coexpression of one or more polypeptides described herein in host cells of an organism. In this particular system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide or polynucleotides of interest, driven by a T7 promoter. The polymerase expressed in the cytoplasm from the vaccinia virus recombinant transcribes the transfected DNA into RNA which is then translated into polypeptide by the host translational machinery. The method provides for high level, transient, cytoplasmic production of large quantities of RNA and its translation products. See, e.g., Elroy-Stein and Moss, *Proc. Natl. Acad. Sci. USA* 87:6743–6747 (1990); Fuerst et al., *Proc. Natl. Acad. Sci. USA* 83:8122–8126 (1986).

Alternatively, avipoxviruses, such as the fowlpox and canarypox viruses, can also be used to deliver the coding sequences of interest. Recombinant avipox viruses, expressing immunogens from mammalian pathogens, are known to confer protective immunity when administered to non-avian species. The use of an Avipox vector is particularly desirable in human and other mammalian species since members of the Avipox genus can only productively replicate in susceptible avian species and therefore are not infective in mammalian cells. Methods for producing recombinant Avipoxviruses are known in the art and employ genetic recombination, as described above with respect to the production of vaccinia viruses. See, e.g., WO 91/12882; WO 89/03429; and WO 92/03545.

Any of a number of alphavirus vectors can also be used for delivery of polynucleotide compositions of the present invention, such as those vectors described in U.S. Pat. Nos. 5,843,723; 6,015,686; 6,008,035 and 6,015,694. Certain vectors based on Venezuelan Equine Encephalitis (VEE) can also be used, illustrative examples of which can be found in U.S. Pat. Nos. 5,505,947 and 5,643,576.

Moreover, molecular conjugate vectors, such as the adenovirus chimeric vectors described in Michael et al. *J. Biol. Chem.* 268:6866–6869 (1993) and Wagner et al., *Proc. Natl. Acad. Sci. USA* 89:6099–6103 (1992), can also be used for gene delivery under the invention.

Additional illustrative information on these and other known viral-based delivery systems can be found, for example, in Fisher-Hoch et al., *Proc. Natl. Acad. Sci. USA* 86:317–321,1989; Flexner et al., *Ann. N.Y. Acad. Sci.* 569:86–103, 1989; Flexner et al., *Vaccine* 8:17–21,1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627,1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502,1993; Guzman et al., *Circulation* 88:2838–2848,1993; and Guzman et al., *Cir. Res.* 73:1202–1207, 1993.

In certain embodiments, a polynucleotide may be integrated into the genome of a target cell. This integration may be in the specific location and orientation via homologous recombination (gene replacement) or it may be integrated in a random, non-specific location (gene augmentation). In yet further embodiments, the polynucleotide may be stably maintained in the cell as a separate, episomal segment of DNA. Such polynucleotide segments or "episomes" encode sequences sufficient to permit maintenance and replication independent of or in synchronization with the host cell cycle. The manner in which the expression construct is delivered to a cell and where in the cell the polynucleotide remains is dependent on the type of expression construct employed.

In another embodiment of the invention, a polynucleotide is administered/delivered as "naked" DNA, for example as described in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In still another embodiment, a composition of the present invention can be delivered via a particle bombardment approach, many of which have been described. In one illustrative example, gas-driven particle acceleration can be achieved with devices such as those manufactured by Powderject Pharmaceuticals PLC (Oxford, UK) and Powderject Vaccines Inc. (Madison, Wis.), some examples of which are described in U.S. Pat. Nos. 5,846,796; 6,010,478; 5,865,796; 5,584,807; and EP Patent No. 0500 799. This approach offers a needle-free delivery approach wherein a dry powder formulation of microscopic particles, such as polynucleotide or polypeptide particles, are accelerated to high speed within a helium gas jet generated by a hand held device, propelling the particles into a target tissue of interest.

In a related embodiment, other devices and methods that may be useful for gas-driven needle-less injection of compositions of the present invention include those provided by Bioject, Inc. (Portland, Oreg.), some examples of which are described in U.S. Pat. Nos. 4,790,824; 5,064,413; 5,312,335; 5,383,851; 5,399,163; 5,520,639 and 5,993,412.

According to another embodiment, the pharmaceutical compositions described herein will comprise one or more immunostimulants in addition to the immunogenic polynucleotide, polypeptide, antibody, T-cell, TCR, and/or APC compositions of this invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Certain adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is preferably one that induces an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173,1989.

Certain preferred adjuvants for eliciting a predominantly Th1-type response include, for example, a combination of monophosphoryl lipid A, preferably 3-de-O-acylated monophosphoryl lipid A, together with an aluminum salt. MPL® adjuvants are available from Corixa Corporation (Seattle, Wash.; see, for example, U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352, 1996. Another preferred adjuvant comprises a saponin, such as Quil A, or derivatives thereof, including QS21 and QS7 (Aquila Biopharmaceuticals Inc., Framingham, Mass.); Escin; Digitonin; or Gypsophila or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol$^R$ to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion is described in WO 95/17210.

Another enhanced adjuvant system involves the combination of a CpG-containing oligonucleotide and a saponin derivative particularly the combination of CpG and QS21 is disclosed in WO 00/09159. Preferably the formulation additionally comprises an oil in water emulsion and tocopherol.

Additional illustrative adjuvants for use in the pharmaceutical compositions of the invention include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Enhanzyn®) (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula $$HO(CH_2CH_2O)_n—A—R, \qquad (I)$$

wherein, n is 1–50, A is a bond or —C(O)—, R is $C_1l_{50}$ alkyl or Phenyl $C_{1-50}$ alkyl.

One embodiment of the present invention consists of a vaccine formulation comprising a polyoxyethylene ether of general formula (I), wherein n is between 1 and 50, preferably 4–24, most preferably 9; the R component is $C_{1-50}$, preferably $C_4$–$C_{20}$ alkyl and most preferably $C_{12}$ alkyl, and A is a bond. The concentration of the polyoxyethylene ethers should be in the range 0.1–20%, preferably from 0.1–10%, and most preferably in the range 0.1–1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

According to another embodiment of this invention, an immunogenic composition described herein is delivered to a host via antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide of the invention (or portion or other variant thereof) such that the encoded polypeptide, or an immunogenic portion thereof, is expressed on the cell surface. Such transfection may take place ex vivo, and a pharmaceutical composition comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the tumor polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

While any suitable carrier known to those of ordinary skill in the art may be employed in the pharmaceutical compositions of this invention, the type of carrier will typically vary depending on the mode of administration. Compositions of the present invention may be formulated for any appropriate manner of administration, including for example, topical, oral, nasal, mucosal, intravenous, intracranial, intraperitoneal, subcutaneous and intramuscular administration.

Carriers for use within such pharmaceutical compositions are biocompatible, and may also be biodegradable. In certain embodiments, the formulation preferably provides a relatively constant level of active component release. In other embodiments, however, a more rapid rate of release immediately upon administration may be desired. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

In another illustrative embodiment, biodegradable microspheres (e.g., polylactate polyglycolate) are employed as carriers for the compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344, 5,407,609 and 5,942,252. Modified hepatitis B core protein carrier systems, such as described in WO/99 40934, and references cited therein, will also be useful for many applications. Another illustrative carrier/delivery system employs a carrier comprising particulate-protein complexes, such as those described in U.S. Pat. No. 5,928,647, which are capable of inducing a class I-restricted cytotoxic T lymphocyte responses in a host.

In another illustrative embodiment, calcium phosphate core particles are employed as carriers, vaccine adjuvants, or as controlled release matrices for the compositions of this invention. Exemplary calcium phosphate particles are disclosed, for example, in published patent application No. WO/0046147.

The pharmaceutical compositions of the invention will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

The pharmaceutical compositions described herein may be presented in unit-dose or multi-dose containers, such as sealed ampoules or vials. Such containers are typically sealed in such a way to preserve the sterility and stability of the formulation until use. In general, formulations may be stored as suspensions, solutions or emulsions in oily or aqueous vehicles. Alternatively, a pharmaceutical composition may be stored in a freeze-dried condition requiring only the addition of a sterile liquid carrier immediately prior to use.

The development of suitable dosing and treatment regimens for using the particular compositions described herein in a variety of treatment regimens, including e.g., oral, parenteral, intravenous, intranasal, and intramuscular administration and formulation, is well known in the art, some of which are briefly discussed below for general purposes of illustration.

In certain applications, the pharmaceutical compositions disclosed herein may be delivered via oral administration to an animal. As such, these compositions may be formulated with an inert diluent or with an assimilable edible carrier, or they may be enclosed in hard-or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, for example, Mathiowitz et al., Nature Mar. 27, 1997; 386(6623):410–4; Hwang et al., Crit Rev Ther Drug Carrier Syst.1998;15(3):243–84; U.S. Pat. Nos. 5,641,515; 5,580,579 and 5,792,451). Tablets, troches, pills, capsules and the like may also contain any of a variety of additional components, for example, a binder, such as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Of course, any material used in preparing any dosage unit form should be pharmaceutically pure and substantially non-toxic in the amounts employed. In addition, the active compounds may be incorporated into sustained-release preparation and formulations.

Typically, these formulations will contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

In certain circumstances it will be desirable to deliver the pharmaceutical compositions disclosed herein parenterally, intravenously, intramuscularly, or even intraperitoneally. Such approaches are well known to the skilled artisan, some of which are further described, for example, in U.S. Pat. Nos. 5,543,158; 5,641,515 and 5,399,363. In certain embodiments, solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations generally will contain a preservative to prevent the growth of microorganisms.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. Moreover, for human administration, preparations will of course preferably meet sterility, pyrogenicity, and the general safety and purity standards as required by FDA Office of Biologics standards.

In another embodiment of the invention, the compositions disclosed herein may be formulated in a neutral or salt form. Illustrative pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" refers to molecular entities and compositions that do not produce an allergic or similar untoward reaction when administered to a human.

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described, e.g., in U.S. Pat. Nos. 5,756,353 and 5,804,212. Likewise, the delivery of drugs using intranasal microparticle resins (Takenaga et al., J Controlled Release Mar. 2, 1998; 52(1–2):81–7) and lysophosphatidyl-glycerol compounds (U.S. Pat. No. 5,725,871) are also well-known in the pharmaceutical arts. Likewise, illustrative transmucosal drug delivery in the form of a polytetrafluoroetheylene support matrix is described in U.S. Pat. No. 5,780,045.

In certain embodiments, liposomes, nanocapsules, microparticles, lipid particles, vesicles, and the like, are used for the introduction of the compositions of the present invention into suitable host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Lasic, Trends Biotechnol Jul. 16, 1998;(7):307–21; Takakura, Nippon Rinsho March 1998;56(3):691–5; Chandran et al., Indian J Exp Biol. August 1997;35(8):801–9; Margalit, Crit Rev Ther Drug Carrier Syst. 1995;12(2–3):233–61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally difficult to transfect by other procedures, including T cell suspensions, primary hepatocyte cultures and PC 12 cells (Renneisen et al., J Biol Chem. Sep. 25, 1990; 265(27):16337–42; Muller et al., DNA Cell Biol. Apr. 9, 1990(3):221–9). In addition, liposomes are free of the DNA length constraints that are typical of viral-based delivery systems. Liposomes have been used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery.

In certain embodiments, liposomes are formed from phospholipids that are dispersed in an aqueous medium and spontaneously form multilamellar concentric bilayer vesicles (also termed multilamellar vesicles (MLVs).

Alternatively, in other embodiments, the invention provides for pharmaceutically-acceptable nanocapsule formulations of the compositions of the present invention. Nanocapsules can generally entrap compounds in a stable and reproducible way (see, for example, Quintanar-Guerrero et al., Drug Dev Ind Pharm. Dec. 24, 1998(12):1113–28). To avoid side effects due to intracellular polymeric overloading, such ultrafine particles (sized around 0.1 μm) may be designed using polymers able to be degraded in vivo. Such particles can be made as described, for example, by Couvreur et al., Crit Rev Ther Drug Carrier Syst. 1988;5(1):1–20; zur Muhlen et al., Eur J Pharm Biopharm. March 1998; 45(2):149–55; Zambaux et al. J Controlled Release. Jan. 2, 1998; 50(1–3):31–40; and U.S. Pat. No. 5,145,684.

Cancer Therapeutic Methods

Immunologic approaches to cancer therapy are based on the recognition that cancer cells can often evade the body's defenses against aberrant or foreign cells and molecules, and that these defenses might be therapeutically stimulated to regain the lost ground, e.g., pgs. 623–648 in Klein, Immunology (Wiley—Interscience, New York, 1982). Numerous recent observations that various immune effectors can directly or indirectly inhibit growth of tumors has led to renewed interest in this approach to cancer therapy, e.g., Jager, et al., Oncology 2001;60(1):1–7; Renner, et al., Ann Hematol December 2000; 79(12):651–9.

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins that are responsible for lysing and processing the immunoglobulin-coated target invader cells; iii) natural killer lymphocytes having two mechanisms for the destruction of tumor cells, antibody-dependent cellular cytotoxicity and natural killing; and iv) T-lymphocytes possessing antigen-specific receptors and having the capacity to recognize a tumor cell carrying complementary marker molecules (Schreiber, H., 1989, in Fundamental Immunology (ed). W. E. Paul, pp. 923–955).

Cancer immunotherapy generally focuses on inducing humoral immune responses, cellular immune responses, or both. Moreover, it is well established that induction of $CD4^+$ T helper cells is necessary in order to secondarily induce either antibodies or cytotoxic $CD8^+$ T cells. Polypeptide antigens that are selective or ideally specific for cancer cells, particularly ovarian cancer cells, offer a powerful approach for inducing immune responses against ovarian cancer, and are an important aspect of the present invention.

Therefore, in further aspects of the present invention, the pharmaceutical compositions described herein may be used to stimulate an immune response against cancer, particularly for the immunotherapy of ovarian cancer. Within such methods, the pharmaceutical compositions described herein are administered to a patient, typically a warm-blooded animal, preferably a human. A patient may or may not be afflicted with cancer. Pharmaceutical compositions and vaccines may be administered either prior to or following surgical removal of primary tumors and/or treatment such as administration of radiotherapy or conventional chemotherapeutic drugs. As discussed above, administration of the pharmaceutical compositions may be by any suitable method, including administration by intravenous, intraperitoneal, intramuscular, subcutaneous, intranasal, intradermal, anal, vaginal, topical and oral routes.

Within certain embodiments, immunotherapy may be active immunotherapy, in which treatment relies on the in vivo stimulation of the endogenous host immune system to react against tumors with the administration of immune response-modifying agents (such as polypeptides and polynucleotides as provided herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Monoclonal antibodies may be labeled with any of a variety of labels for desired selective usages in detection, diagnostic assays or therapeutic applications (as described in U.S. Pat. Nos. 6,090,365; 6,015,542; 5,843,398; 5,595,721; and 4,708,930, hereby incorporated by reference in their entirety as if each was incorporated individually). In each case, the binding of the labelled monoclonal antibody to the determinant site of the antigen will signal detection or delivery of a particular therapeutic agent to the antigenic determinant on the non-normal cell. A further object of this invention is to provide the specific monoclonal antibody suitably labelled for achieving such desired selective usages thereof.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast and/or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177,1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions described herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

Cancer Detection and Diagnostic Compositions, Methods and Kits

In general, a cancer may be detected in a patient based on the presence of one or more ovarian tumor proteins and/or polynucleotides encoding such proteins in a biological sample (for example, blood, sera, sputum urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of antigen that binds to the agent in the biological sample.

Polynucleotide primers and probes may be used to detect the level of mRNA encoding a tumor protein, which is also indicative of the presence or absence of a cancer. In general, a tumor sequence should be present at a level that is at least two-fold, preferably three-fold, and more preferably five-fold or higher in tumor tissue than in normal tissue of the same type from which the tumor arose. Expression levels of a particular tumor sequence in tissue types different from that in which the tumor arose are irrelevant in certain diagnostic embodiments since the presence of tumor cells can be confirmed by observation of predetermined differential expression levels, e.g., 2-fold, 5-fold, etc, in tumor tissue to expression levels in normal tissue of the same type.

Other differential expression patterns can be utilized advantageously for diagnostic purposes. For example, in one aspect of the invention, overexpression of a tumor sequence in tumor tissue and normal tissue of the same type, but not in other normal tissue types, e.g., PBMCs, can be exploited diagnostically. In this case, the presence of metastatic tumor cells, for example in a sample taken from the circulation or some other tissue site different from that in which the tumor arose, can be identified and/or confirmed by detecting expression of the tumor sequence in the sample, for example using RT-PCR analysis. In many instances, it will be desired to enrich for tumor cells in the sample of interest, e.g., PBMCs, using cell capture or other like techniques.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian tumor proteins and polypeptide portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use tumor polypeptides to detect antibodies that bind to such polypeptides in a biological sample. The detection of such tumor protein specific antibodies may correlate with the presence of a cancer.

A cancer may also, or alternatively, be detected based on the presence of T cells that specifically react with a tumor protein in a biological sample. Within certain methods, a biological sample comprising $CD4^+$ and/or $CD8^+$ T cells isolated from a patient is incubated with a tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of tumor polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a tumor protein in a biological sample. For example, at least two oligonucleotide primers may be employed in a polymerase chain reaction (PCR) based assay to amplify a portion of a tumor cDNA derived from a biological sample, wherein at least one of the oligonucleotide primers is specific for (i.e., hybridizes to) a polynucleotide encoding the tumor protein. The amplified cDNA is then separated and detected using techniques well known in the art, such as gel electrophoresis.

Similarly, oligonucleotide probes that specifically hybridize to a polynucleotide encoding a tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a tumor protein of the invention that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence as disclosed herein. Techniques for both PCR based assays and hybridization assays are well known in the art (see, for example, Mullis et al., *Cold Spring Harbor Symp. Quant. Biol.,* 51:263, 1987; Erlich ed., PCR *Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another aspect of the present invention, cell capture technologies may be used in conjunction, with, for example, real-time PCR to provide a more sensitive tool for detection of metastatic cells expressing ovarian tumor antigens. Detection of ovarian cancer cells in biological samples, e.g., bone marrow samples, peripheral blood, and small needle aspiration samples is desirable for diagnosis and prognosis in ovarian cancer patients.

Immunomagnetic beads coated with specific monoclonal antibodies to surface cell markers, or tetrameric antibody complexes, may be used to first enrich or positively select cancer cells in a sample. Various commercially available kits may be used, including Dynabeads® Epithelial Enrich (Dynal Biotech, Oslo, Norway), StemSep™ (StemCell Technologies, Inc., Vancouver, BC), and RosetteSep (StemCell Technologies). A skilled artisan will recognize that other methodologies and kits may also be used to enrich or positively select desired cell populations. Dynabeads® Epithelial Enrich contains magnetic beads coated with mAbs specific for two glycoprotein membrane antigens expressed on normal and neoplastic epithelial tissues. The coated beads may be added to a sample and the sample then applied to a magnet, thereby capturing the cells bound to the beads. The unwanted cells are washed away and the magnetically isolated cells eluted from the beads and used in further analyses.

RosetteSep can be used to enrich cells directly from a blood sample and consists of a cocktail of tetrameric antibodies that targets a variety of unwanted cells and crosslinks them to glycophorin A on red blood cells (RBC) present in the sample, forming rosettes. When centrifuged over Ficoll, targeted cells pellet along with the free RBC. The combination of antibodies in the depletion cocktail determines which cells will be removed and consequently which cells will be recovered. Antibodies that are available include, but are not limited to: CD2, CD3, CD4, CD5, CD8, CD10, CD11 b, CD14, CD15, CD16, CD19, CD20, CD24, CD25, CD29, CD33, CD34, CD36, CD38, CD41, CD45, CD45RA, CD45RO, CD56, CD66B, CD66e, HLA-DR, IgE, and TCRαβ.

Additionally, it is contemplated in the present invention that mAbs specific for ovarian tumor antigens can be generated and used in a similar manner. For example, mAbs that bind to tumor-specific cell surface antigens may be conjugated to magnetic beads, or formulated in a tetrameric antibody complex, and used to enrich or positively select metastatic ovarian tumor cells from a sample. Once a sample is enriched or positively selected, cells may be lysed and RNA isolated. RNA may then be subjected to RT-PCR analysis using ovarian tumor-specific primers in a real-time PCR assay as described herein. One skilled in the art will recognize that enriched or selected populations of cells may be analyzed by other methods (e.g., in situ hybridization or flow cytometry).

In another embodiment, the compositions described herein may be used as markers for the progression of cancer. In this embodiment, assays as described above for the diagnosis of a cancer may be performed over time, and the change in the level of reactive polypeptide(s) or polynucleotide(s) evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a tumor protein in a biological sample. Such kits generally comprise at least one oligonucleotide probe or primer, as described above, that hybridizes to a polynucleotide encoding a tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a tumor protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NO: 1 to 71. Three complete insert sequences are shown in FIGS. 2A–2C (SEQ ID NO: 72 to 74). Other clones having known sequences are presented in FIGS. 15A–15EEE (SEQ ID NO: 82 to 310). Database searches identified the following sequences that were substantially identical to the sequences presented in FIGS. 15A–15EEE.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO: 75. Osteonectin, unspliced and unaltered, was also identified from such assays independently.

Further clones identified by this method are referred to herein as 3f, 6b, 8e, 8h, 12c and 12h. Sequences of these clones are shown in FIGS. 5 to 9 and SEQ ID NO: 76 to 81. Microarray analyses were performed as described above, and are presented in FIGS. 10 to 14. A full length sequence encompassing clones 3f, 6b, 8e and 12h was obtained by screening an ovarian tumor (SCID-derived) cDNA library. This 2996 base pair sequence (designated O772P) is presented in SEQ ID NO: 311, and the encoded 914 amino acid protein sequence is shown in SEQ ID NO: 312. PSORT analysis indicates a Type 1a transmembrane protein localized to the plasma membrane.

In addition to certain of the sequences described above, this screen identified the following sequences which are described in detail in Table 2:

TABLE 2

| Sequence | Comments |
|---|---|
| OV4vG11 (SEQ ID NO:313) | human clone 1119D9 on chromosome 20p12 |
| OV4vB11 (SEQ ID NO:314) | human UWGC:y14c094from chromosome 6p21 |
| OV4vD9 (SEQ ID NO:315) | human clone 1049G16 chromosome 20q12-13.2 |
| OV4vD5 (SEQ ID NO:316) | human KIAA0014 gene |
| OV4vC2 (SEQ ID NO:317) | human KIAA0084 gene |
| OV4vF3 (SEQ ID NO:318) | human chromosome 19 cosmid R31167 |
| OV4VC1 (SEQ ID NO:319) | Novel |
| OV4vH3 (SEQ ID N0:320) | Novel |
| OV4vD2 (SEQ ID NO:321) | novel |
| O815P (SEQ ID NO:322) | novel |
| OV4vC12 (SEQ ID NO:323) | novel |
| OV4vA4 (SEQ ID NO:324) | novel |
| OV4vA3 (SEQ ID NO:325) | novel |
| OV4v2A5 (SEQ ID NO:326) | novel |
| O819P (SEQ ID NO:327) | novel |
| O818P (SEQ ID NO:328) | novel |
| O817P (SEQ ID NO:329) | novel |
| O816P (SEQ ID NO:330) | novel |
| Ov4vC5 (SEQ ID NO:331) | novel |
| 21721 (SEQ ID NO:332) | human lumican |
| 21719 (SEQ ID NO:333) | human retinoic acid-binding protein II |
| 21717 (SEQ ID NO:334) | human26S proteasome ATPase subunit |
| 21654 (SEQ ID NO:335) | human copine I |
| 21627 (SEQ ID NO:336) | human neuron specific gamma-2 enolase |
| 21623 (SEQ ID NO:337) | human geranylgeranyl transferase II |
| 21621 (SEQ ID NO:338) | human cyclin-dependent protein kinase |

TABLE 2-continued

| Sequence | Comments |
|---|---|
| 21616 (SEQ ID NO:339) | human prepro-megakaryocyte potentiating factor |
| 21612 (SEQ ID NO:340) | human UPH1 |
| 21558 (SEQ ID NO:341) | human RalGDS-like 2 (RGL2) |
| 21555 (SEQ ID NO:342) | human autoantigen P542 |
| 21548 (SEQ ID NO:343) | human actin-related protein (ARP2) |
| 21462 (SEQ ID NO:344) | human huntingtin interacting protein |
| 21441 (SEQ ID NO:345) | human 90K product (tumor associated antigen) |
| 21439 (SEQ ID NO:346) | human guanine nucleotide regulator protein (tim1) |
| 21438 (SEQ ID NO:347) | human Ku autoimmune (p70/p80) antigen |
| 21237 (SEQ ID NO:348) | human S-laminin |
| 21436 (SEQ ID NO:349) | human ribophorin I |
| 21435 (SEQ ID NO:350) | human cytoplasmic chaperonin hTRiC5 |
| 21425 (SEQ ID NO:351) | humanEMX2 |
| 21423 (SEQ ID NO:352) | human p87/p89 gene |
| 21419 (SEQ ID NO:353) | human HPBRII-7 |
| 21252 (SEQ ID NO:354) | human T1-227H |
| 21251 (SEQ ID NO:355) | human cullin I |
| 21247 (SEQ ID NO:356) | kunitz type protease inhibitor (KOP) |
| 21244-1 (SEQ ID NO:357) | human protein tyrosine phosphatase receptor F (PTPRF) |
| 21718 (SEQ ID NO:358) | human LTR repeat |
| OV2-90 (SEQ ID NO:359) | novel |
| Human zinc finger (SEQ ID NO:360) | |
| Human polyA binding protein (SEQ ID NO:361) | |
| Human pleitrophin (SEQ ID NO:362) | |
| Human PAC clone 278C19 (SEQ ID NO:363) | |
| Human LLRep3 (SEQ ID NO:364) | |
| Human Kunitz type protease inhib (SEQ ID NO:365) | |
| Human KIAA0106 gene (SEQ ID NO:366) | |
| Human keratin (SEQ ID NO:367) | |
| Human HIV-1TAR (SEQ ID NO:368) | |
| Human glia derived nexin (SEQ ID NO:369) | |
| Human fibronectin (SEQ ID NO:370) | |
| Human ECMproBM40 (SEQ ID NO:371) | |
| Human collagen (SEQ ID NO:372) | |
| Human alpha enolase (SEQ ID NO:373) | |
| Human aldolase (SEQ ID NO:374) | |
| Human transf growth factor BIG H3 (SEQ ID NO:375) | |
| Human SPARC osteonectin (SEQ ID NO:376) | |
| Human SLP1 leucocyte protease (SEQ ID NO:377) | |
| Human mitochondrial ATP synth (SEQ ID NO:378) | |
| Human DNA seq clone 461P17 (SEQ ID NO:379) | |
| Human dbpB pro Y box (SEQ ID NO:380) | |
| Human 40 kDa keratin (SEQ ID NO:381) | |
| Human arginosuccinate synth (SEQ ID NO:382) | |
| Human acidic ribosomal phosphoprotein (SEQ ID NO:383) | |
| Human colon carcinoma laminin binding pro (SEQ ID NO:384) | |

This screen further identified multiple forms of the clone O772P, referred to herein as 21013, 21003 and 21008. PSORT analysis indicates that 21003 (SEQ ID NO: 386; translated as SEQ ID NO: 389) and 21008 (SEQ ID NO: 387; translated as SEQ ID NO: 390) represent Type 1a transmembrane protein forms of O772P. 21013 (SEQ ID NO: 385; translated as SEQ ID NO: 388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO: 391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (EST×O8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO: 393) begins with a putative start methionine. A second form "b" (SEQ ID NO: 392) includes 27 additional upstream residues to the 5' end of the nucleotide sequence.

Example 3

This example discloses the identification and characterization of antibody epitopes recognized by the O8E polyclonal anti-sera.

Rabbit anti-sera was raised against *E. coli* derived O8E recombinant protein and tested for antibody epitope recognition against 20 or 21 mer peptides that correspond to the O8E amino acid sequence. Peptides spanning amino acid regions 31 to 65, 76 to 110, 136 to 200 and 226 to 245 of the full length O8E protein were recognized by an acid eluted peak and/or a salt eluted peak from affinity purified anti-O8E sera. Thus, the corresponding amino acid sequences of the above peptides constitute the antibody epitopes recognized by affinity purified anti-O8E antibodies.

ELISA analysis of anti-O8E rabbit sera is shown in FIG. 23, and ELISA analysis of affinity purified rabbit anti-O8E polyclonal antibody is shown in FIG. 24.

Figure 17:
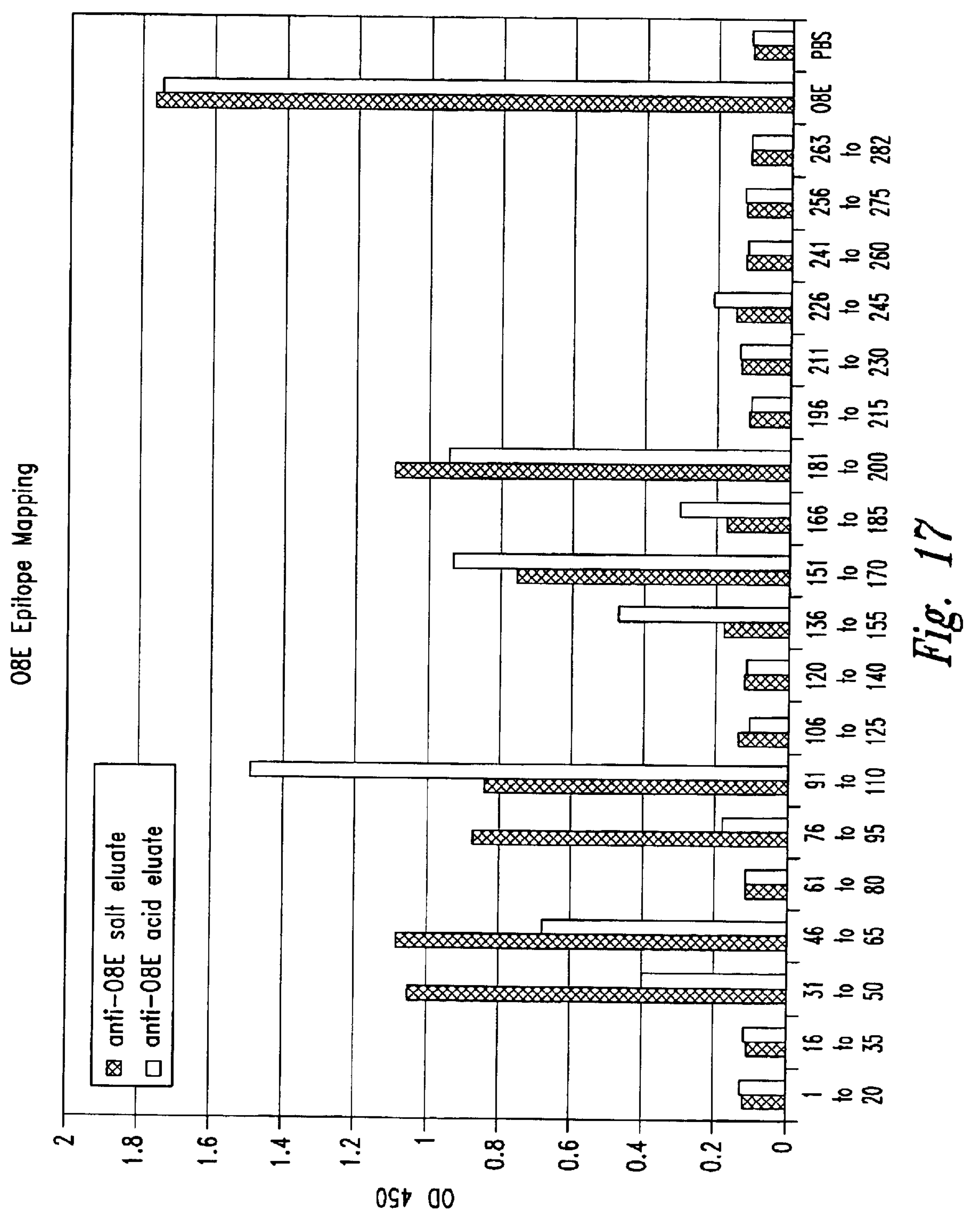
FIG. 17 is a graph illustrating the results of epitope mapping studies on O8E protein.

For epitope mapping, 20 or 21 mer peptides corresponding to the O8E protein were synthesized. For antibody affinity purification, rabbit anti-O8E sera was run over an O8E-sepharose column, then antibody was eluted with a salt buffer containing 0.5 M NaCl and 20 mM $PO_4$, followed by an acid elution step using 0.2 M Glycine, pH 2.3. Purified antibody was neutralized by the addition of 1 M Tris, pH 8 and buffer exchanged into phosphate buffered saline (PBS). For enzyme linked immunosorbant assay (ELISA) analysis, O8E peptides and O8E recombinant protein were coated onto 96 well flat bottom plates at 2 $\mu$g/ml for 2 hours at room temperature (RT). Plates were then washed 5 times with PBS+0.1% Tween 20 and blocked with PBS+1% bovine serum albumin (BSA) for 1 hour. Affinity purified anti-O8E antibody, either an acid or salt eluted fraction, was then added to the wells at 1 $\mu$g/ml and incubated at RT for 1 hr. Plates were again washed, followed by the addition of donkey anti-rabbit-Ig-horseradish peroxidase (HRP) antibody for 1 hour at RT. Plates were washed, then developed by the addition of the chromagenic substrate 3, 3', 5, 5'-tetramethylbenzidine (TMB) (described by Bos et al., *J. of Immunoassay* 2:187–204 (1981); available from Sigma (St. Louis, Mo.)). The reaction was incubated 15 minutes at RT and-then stopped by the addition of 1 N $H_2SO_4$. Plates were read at an optical density of 450 (OD450) in an automated plate reader. The sequences of peptides corresponding to the OE8 antibody epitopes are disclosed herein as SEQ ID NO: 394–415. Antibody epitopes recognized by the O8E polyclonal anti-sera are disclosed herein in FIG. 17.

Example 4

This example discloses IHC analysis of O8E expression in ovarian cancer tissue samples.

For immunohistochemistry studies, paraffin-embedded formalin fixed ovarian cancer tissue was sliced into 8 micron sections. Steam heat induced epitope retrieval (SHIER) in 0.1 M sodium citrate buffer (pH 6.0) was used for optimal staining conditions. Sections were incubated with 10% serum/PBS for 5 minutes. Primary antibody (anti-O8E rabbit affinity purified polyclonal antibody) was added to each section for 25 min followed by a 25 min incubation with an anti-rabbit biotinylated antibody. Endogenous peroxidase activity was blocked by three 1.5 min incubations with hydrogen peroxidase. The avidin biotin complex/horse radish peroxidase system was used along with DAB chromogen to visualize antigen expression. Slides were counterstained with hematoxylin. One (papillary serous carcinoma) of six ovarian cancer tissue sections displayed O8E immunoreactivity. Upon optimization of the staining conditions, 4/5 ovarian cancer samples stained positive using the O8E polyclonal antibody. O8E expression was localized to the plasma membrane.

Six ovarian cancer tissues were analyzed with the anti-O8E rabbit polyclonal antibody. One (papillary serous carcinoma) of six ovarian cancer tissue samples stained positive for O8E expression. O8E expression was localized to the surface membrane.

Example 5

This example discloses OBE peptides that are predicted to bind HLA-A2 and to be immunogenic for CD8 T cell responses in humans.

Potential HLA-A2 binding peptides of O8E were predicted by using the full-length open-reading frame (ORF) from O8E and running it through "Episeek," a program used to predict MHC binding peptides. The program used is based on the algorithm published by Parker, K. C. et al., *J. Immunol.* 152(1):163–175 (1994) (incorporated by reference herein in its entirety). 10-mer and 9-mer peptides predicted to bind HLA-0201 are disclosed herein as SEQ ID NO: 416–435 and SEQ ID NO: 436–455, respectively.

Example 6

This example discloses O8E cell surface expression measured by fluoresence activated cell sorting.

Figure 18:
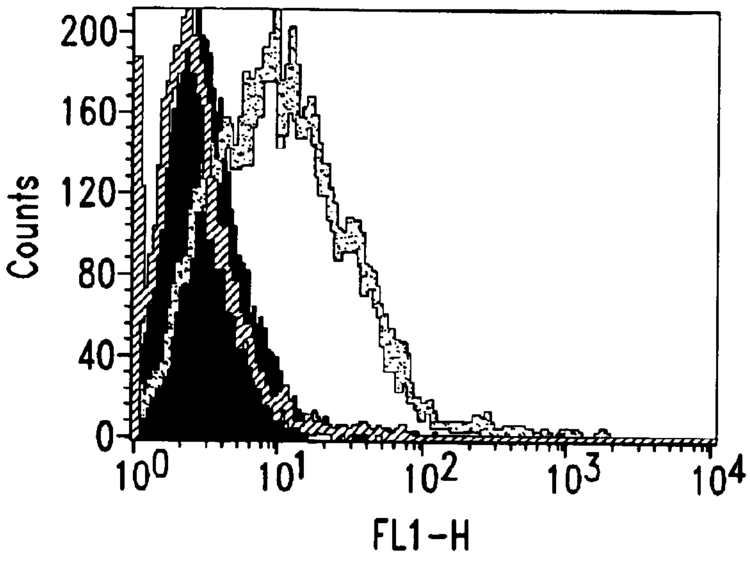
FIG. 18 is graph of a fluorescence activated cell sorting (FACS) analysis of O8E cell surface expression.
Figure 19:
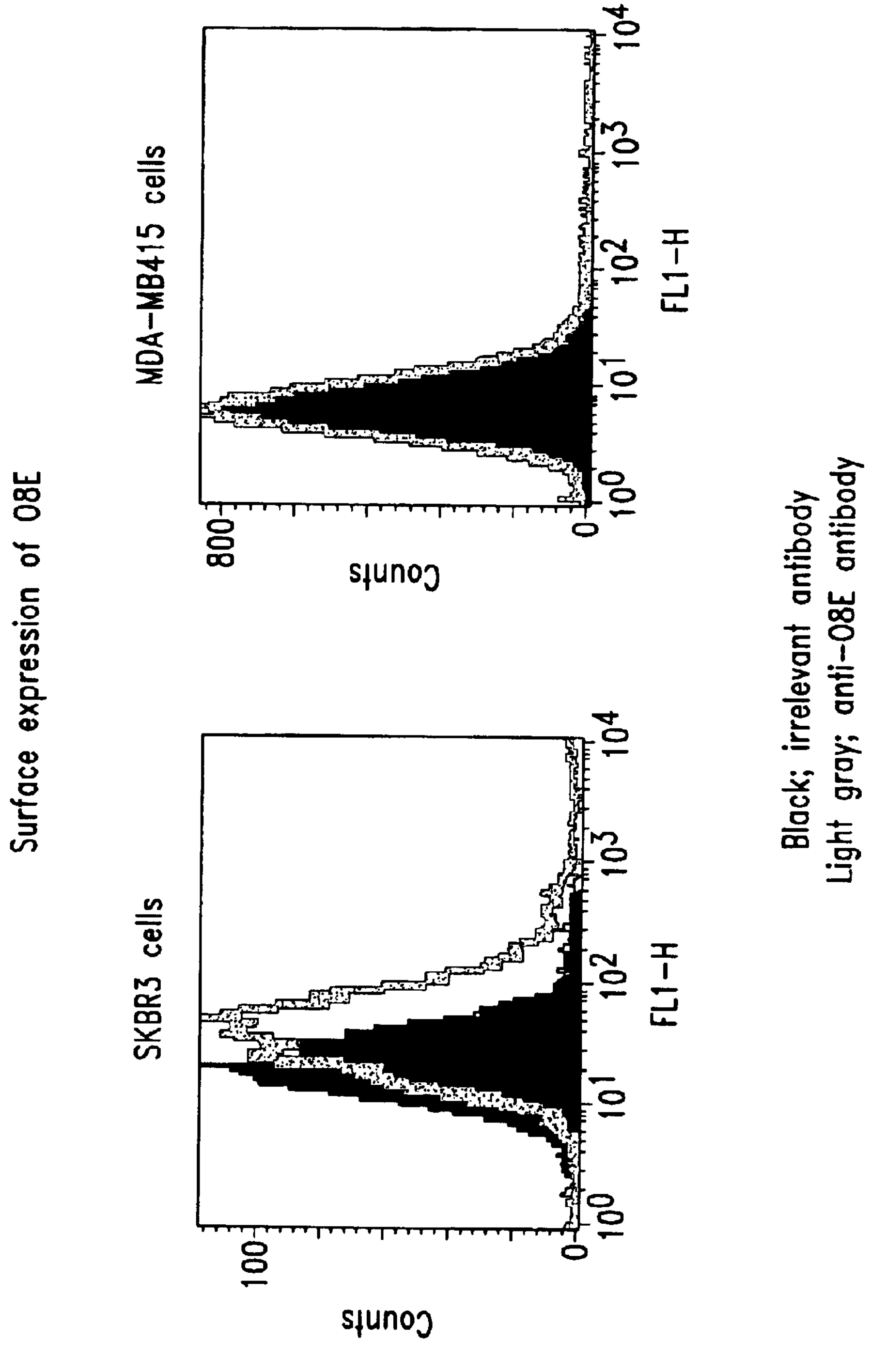
FIG. 19 is graph of a FACS analysis of O8E cell surface expression.

For FACS analysis, cells were washed with ice cold staining buffer (PBS/1% BSA/azide). Next, the cells were incubated for 30 minutes on ice with 10 micrograms/ml of affinity purified rabbit anti-B305D polyclonal antibody. The cells were washed 3 times with staining buffer and then incubated with a 1:100 dilution of a goat anti-rabbit Ig (H+L)-FITC reagent (Southern Biotechnology) for 30 minutes on ice. Following 3 washes, the cells were resuspended in staining buffer containing prodium iodide, a vital stain that allows for identification of permeable cells, and analyzed by FACS. O8E surface expression was confirmed on SKBR3 breast cancer cells and HEK293 cells that stably overexpress the cDNA for O8E. Neither MB415 cells nor HEK293 cells stably transfected with a control irrelevant plasmid DNA showed surface expression of O8E (FIGS. 18 and 19).

Example 7

This example further evaluates the expression and surface localization of O8E.

For expression and purification of antigen used for immunization, O8E expressed in an *E. coli* recombinant expression system was grown overnight in LB Broth with the appropriate antibiotics at 37° C. in a shaking incubator. The next morning, 10 ml of the overnight culture was added to 500 ml of 2×YT plus appropriate antibiotics in a 2L-baffled Erlenmeyer flask. When the Optical Density (at 560 nanometers) of the culture reached 0.4–0.6 the cells were induced with IPTG (1 mM). 4 hours after induction with IPTG the cells were harvested by centrifugation. The cells were then washed with phosphate buffered saline and centrifuged again. The supernatant was discarded and the cells were either frozen for future use or immediately processed. Twenty milliliters of lysis buffer was added to the cell pellets and vortexed. To break open the *E. coli* cells, this mixture was then run through the French Press at a pressure of 16,000 psi. The cells were then centrifuged again and the supernatant and pellet were checked by SDS-PAGE for the partitioning of the recombinant protein. For protein that localized to the cell pellet, the pellet was resuspended in 10 mM Tris pH 8.0, 1% CHAPS and the inclusion body pellet was washed and centrifuged again. This procedure was repeated twice more. The washed inclusion body pellet was solubilized with either 8 M urea or 6 M guanidine HCl containing 10 mM Tris pH 8.0 plus 10 mM imidazole. The solubilized protein was added to 5 ml of nickel-chelate resin (Qiagen) and incubated for 45 min to 1 hour at room temperature with continuous agitation. After incubation, the resin and protein mixture were poured through a disposable column and the flow through was collected. The column was then washed with 10–20 column volumes of the solubilization buffer. The antigen was then eluted from the column using 8M urea, 10 mM tris pH 8.0 and 300 mM imidazole and collected in 3 ml fractions. A SDS-PAGE gel was run to determine which fractions to pool for further purification. As a final purification step, a strong anion exchange resin such as Hi-Prep Q (Biorad) was equilibrated with the appropriate buffer and the pooled fractions from above were loaded onto the column. Each antigen was eluted off of the column with an increasing salt gradient. Fractions were collected as the column was run and another SDS-PAGE gel was run to determine which fractions from the column to pool. The pooled fractions were dialyzed against 10 mM Tris pH 8.0. This material was then evaluated for acceptable purity as determined by SDS-PAGE or HPLC, concentration as determined by Lowry assay or Amino Acid Analysis, identity as determined by amino terminal protein sequence, and endotoxin level as determined by the Limulus (LAL) assay. The proteins were then vialed after filtration through a 0.22 micron filter and the antigens were frozen until needed for immunization.

For generation of polyclonal anti-sera, 400 micrograms of each prostate antigen was combined with 100 micrograms of muramyldipeptide (MDP). Equal volume of Incomplete Freund's Adjuvant (IFA) was added and then mixed. Every four weeks animals were boosted with 100 micrograms of antigen mixed with an equal volume of IFA. Seven days following each boost the animal was bled. Sera was generated by incubating the blood at 4° C. for 12–24 hours followed by centrifugation.

For characterization of polyclonal antisera, 96 well plates were coated with antigen by incubating with 50 microliters (typically 1 microgram) at 4° C. for 20 hrs. 250 microliters of BSA blocking buffer was added to the wells and incubated at RT for 2 hrs. Plates were washed 6 times with PBS/0.01% tween. Anti-O8E rabbit sera or affinity purified anti-O8e antibody was diluted in PBS. Fifty microliters of diluted antibody was added to each well and incubated at RT for 30 min. Plates were washed as described above before 50 microliters of goat anti-rabbit horse radish peroxidase (HRP) at a 1:10000 dilution was added and incubated at RT for 30 min. Plates were washed as described above and 100 microliters of TMB microwell Peroxidase Substrate was added to each well. Following a 15 minute incubation in the dark at room temperature the colorimetric reaction was stopped with 100 microliters of 1 N H2SO4 and read immediately at 450 nm. All polyclonal antibodies showed immunoreactivity to the O8E antigen.

For recombinant expression in mammalian HEK293 cells, full length O8E cDNA was subcloned into the mammalian expression vectors pcDNA3.1+ and pCEP4 (Invitrogen) which were modified to contain His and FLAG epitope tags, respectively. These constructs were transfected into HEK293 cells (ATCC) using Fugene 6 reagent (Roche). Briefly, HEK293 cells were plated at a density of 100,000 cells/ml in DMEM (Gibco) containing 10% FBS (Hyclone) and grown overnight. The following day, 2 ul of Fugene6 was added to 100 ul of DMEM containing no FBS and incubated for 15 minutes at room temperature. The Fugene6/DMEM mixture was then added to 1 ug of O8E/pCEP4 or O8E/pcDNA3.1 plasmid DNA and incubated for 15 minutes at room temperature. The Fugene/DNA mix was then added to the HEK293 cells and incubated for 48–72 hrs at 37° C. with 7% CO2. Cells were rinsed with PBS then collected and pelleted by centrifugation. For Western blot analysis, whole cell lysates were generated by incubating the cells in Triton-X100 containing lysis buffer for 30 minutes on ice. Lysates were then cleared by centrifugation at 10,000 rpm for 5 minutes at 4 C. Samples were diluted with SDS-PAGE loading buffer containing beta-mercaptoethanol, then boiled for 10 minutes prior to loading the SDS-PAGE gel. Protein was transferred to nitrocellulose and probed using anti-O8E rabbit polyclonal sera #2333L at a dilution of 1:750. The blot was revealed with a goat anti-rabbit Ig coupled to HRP followed by incubation in ECL substrate.

For FACS analysis, cells were washed further with ice cold staining buffer (PBS+1% BSA+Azide). Next, the cells were incubated for 30 minutes on ice with 10 ug/ml of Protein A purified anti-O8E polyclonal sera. The cells were washed 3 times with staining buffer and then incubated with a 1:100 dilution of a goat anti-rabbit Ig(H+L)-FITC reagent (Southern Biotechnology) for 30 minutes on ice. Following 3 washes, the cells were resuspended in staining buffer containing Propidium Iodide (PI), a vital stain that allows for the identification of permeable cells, and analyzed by FACS.

Figure 20:
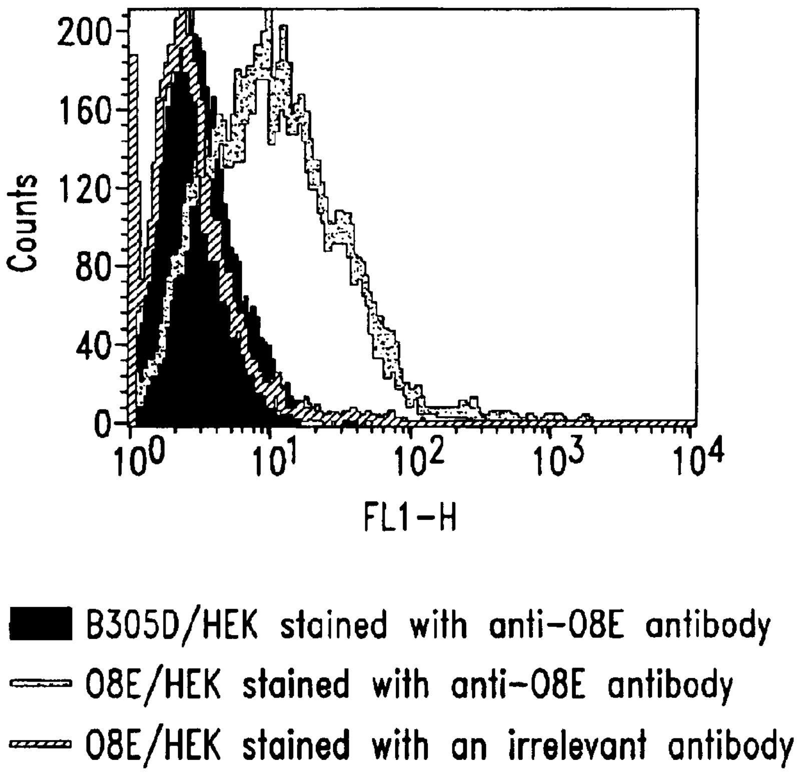
FIG. 20 shows FACS analysis results for O8E transfected HEK293 cells demonstrating cell surface expression of O8E.
Figure 21:
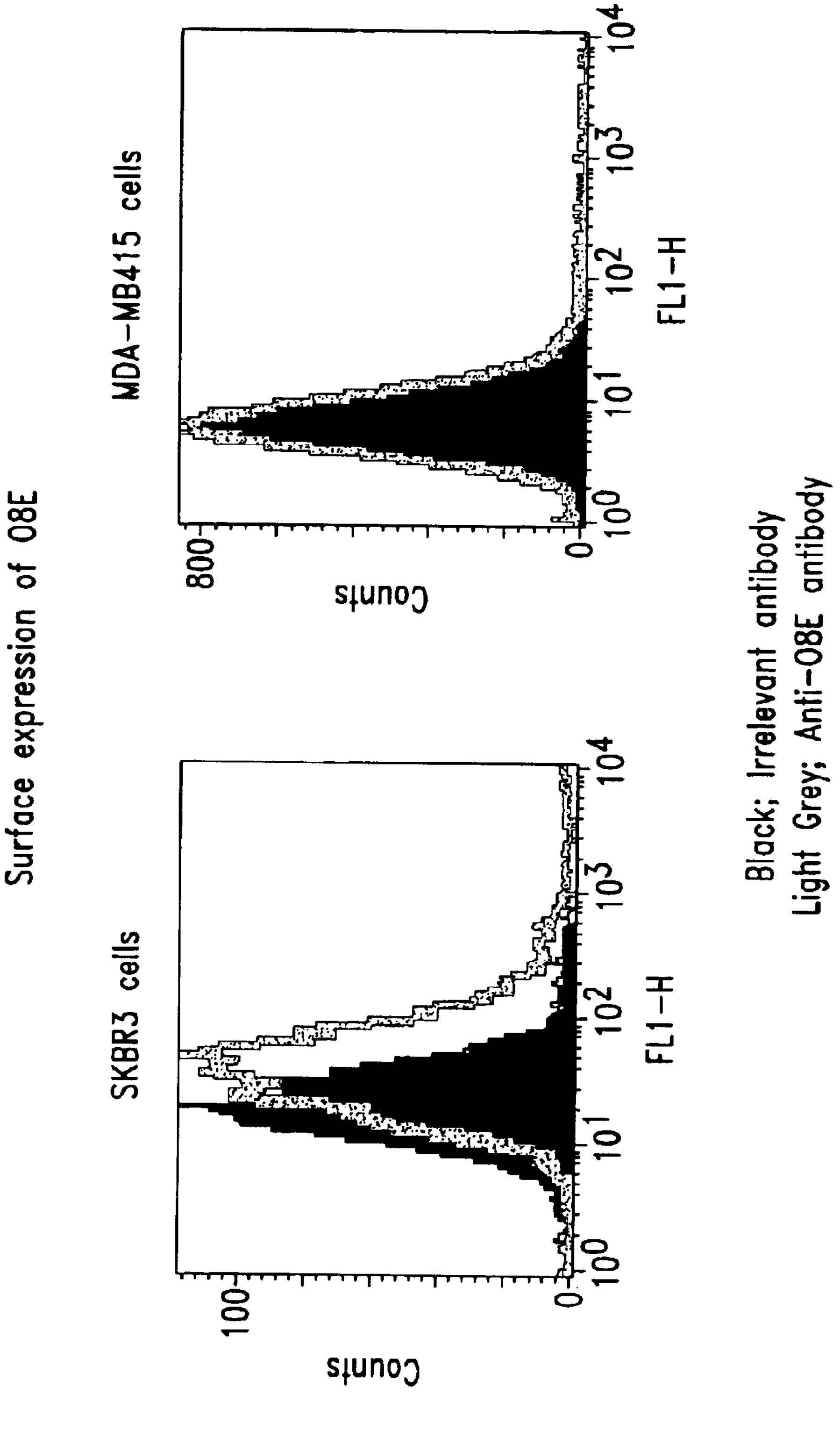
FIG. 21 shows FACS analysis results for SKBR3 breast tumor cells demonstrating cell surface expression of O8E.
Figure 22:
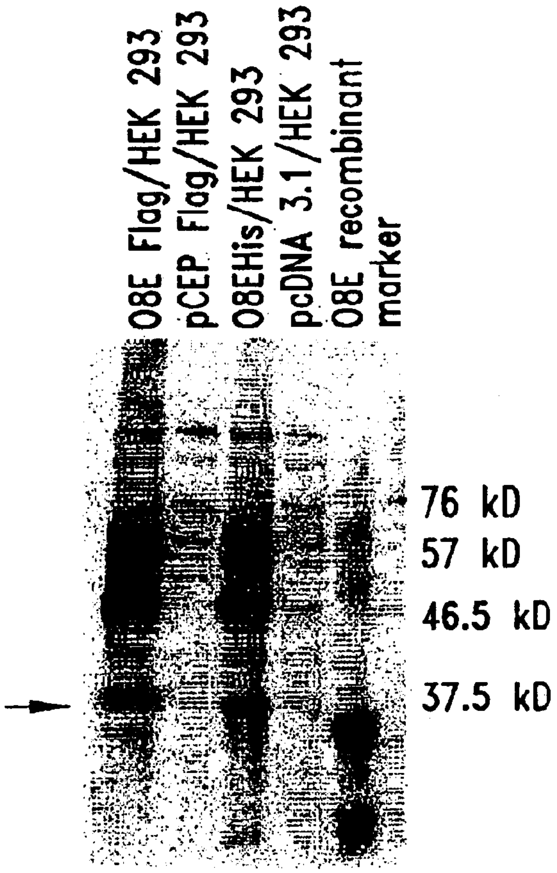
FIG. 22 shows O8E expression in HEK 293 cells. The cells were probed with anti-O8E rabbit polyclonal antisera #2333L.

From these experiments, the results of which are illustrated in FIGS. 20–21, O8E expression was detected on the surface of transfected HEK293 cells and SKBR3 cells by FACS analysis using rabbit anti-O8E sera. Expression was also detected in transfected HEK293 cell lysates by Western blot analysis (FIG. 22).

Example 8

Generation and Characterization of Anti-O8E MABS

Mouse monoclonal antibodies were raised against *E. coli* derived O8E proteins as follows. A/J mice were immunized intraperitoneally (IP) with Complete Freund's Adjuvant (CFA) containing 50 μg recombinant O8E, followed by a subsequent IP boost with Incomplete Freund's Adjuvant (IFA) containing 10 μg recombinant O8E protein. Three days prior to removal of the spleens, the mice were immunized intravenously with approximately 50 μg of soluble O8E recombinant protein. The spleen of a mouse with a positive titer to O8E was removed, and a single-cell suspension made and used for fusion to SP2/0 myeloma cells to generate B cell hybridomas. The supernatants from the hybrid clones were tested by ELISA for specificity to recombinant O8E, and epitope mapped using peptides that spanned the entire O8E sequence. The mAbs were also tested by flow cytometry for their ability to detect O8E on the surface of cells stably transfected with O8E and on the surface of a breast tumor cell line.

For ELISA analysis, 96 well plates were coated with either recombinant O8E protein or overlapping 20-mer peptides spanning the entire O8E molecule at a concentration of either 1–2 μg/ml or 10 μg/ml, respectively. After coating, the plates were washed 5 times with washing buffer (PBS+0.1% Tween-20) and blocked with PBS containing 0.5% BSA, 0.4% Tween-20. Hybrid supernatants or purified mAbs were then added and the plates incubated for 60 minutes at room temperature. The plates were washed 5 times with washing buffer and the secondary antibody, donkey-anti mouse Ig linked to horseradish peroxidase (HRP)(Jackson ImmunoResearch), was added for 60 minutes. The plates were again washed 5 times in washing buffer, followed by the addition of the peroxidase substrate. Of the hybridoma clones generated, 15 secreted mAbs that recognized the entire O8E protein. Epitope mapping revealed that of these 15 clones, 14 secreted mAbs that recognized the O8E amino acid residues 61–80 and one clone secreted a mAb that recognized amino acid residues 151–170.

For flow cytometric analysis, HEK293 cells which had been stably transfected with O8E and SKBR3 cells which express O8E mRNA, were harvested and washed in flow staining buffer (PBS+1%BSA+Azide). The cells were incubated with the supernatant from the mAb hybrids for 30 minutes on ice followed by 3 washes with staining buffer. The cells were incubated with goat-anti mouse Ig-FITC for 30 minutes on ice, followed by three washes with staining buffer before being resuspended in wash buffer containing propidium iodide. Flow cytometric analysis revealed that 15/15 mAbs were able to detect O8E protein expressed on the surface of O8E-transfected HEK293 cells. 6/6 mAbs tested on SKBR3 cells were able to recognize surface expressed O8E.

Example 9

Extended DNA and Protein Sequence Analysis of Sequence O772P

A full-length sequence encompassing clones 3f, 6b, 8e, and 12 was obtained by screening an ovarian tumor (SCID-derived) cDNA library described in detail in Example 2. This 2996 base pair sequence, designated O772P, is presented in SEQ ID NO: 311, and the encoded 914 amino acid protein sequence is shown in SEQ ID NO: 312. The DNA sequence O772P was searched against public databases including Genbank and showed a significant hit to Genbank Accession number AK024365 (SEQ ID NO: 457). This Genbank sequence was found to be 3557 base pairs in length and encodes a protein 1156 amino acids in length (SEQ ID NO: 459). A truncated version of this sequence, residues 25–3471, in which residue 25 corresponds to the first ATG initiation codon in the Genbank sequence, (SEQ ID NO: 456), encodes a protein that is 1148 amino acids in length (SEQ ID NO: 458). The published DNA sequence (SEQ ID NO: 457) differs from O772P in that it has a 5 base pair insertion corresponding to bases 958–962 of SEQ ID NO: 457. This insertion results in a frame shift such that SEQ ID NO: 457 encodes an additional N-terminal protein sequence relative to O772P (SEQ ID NO: 312). In addition, O772P encodes a unique N-terminal portion contained in residues 1–79 (SEQ ID NO: 460). The N-terminal portion of SEQ ID NO: 456, residues 1–313, also contains unique sequence and is listed as SEQ ID NO: 461.

Example 10

The Generation of Polyclonal Antibodies for Immunohistochemistry and Flow Cytometric Analysis of the Cell Associated Expression Pattern of Molecule O772P The O772P molecule was identified in Examples 2 and 9 of this application. To evaluate the subcellular localization and specificity of antigen expression in various tissues, polyclonal antibodies were generated against O772P. To produce these antibodies, O772P-1 (amino acids 44–772 of SEQ ID NO: 312) and O772P-2 (477–914 of SEQ ID NO: 312) were expressed in an *E. coli* recombinant expression system and grown overnight at 37° C. in LB Broth. The following day, 10 ml of the overnight culture was added to 500 ml of 2×YT containing the appropriate antibiotics. When the optical density of the cultures (560 nanometers) reached 0.4–0.6 the cells were induced with IPTG. Following induction, the cells were harvested, washed, lysed and run through a French Press at a pressure of 16000 psi. The cells were then centrifuged and the pellet checked by SDS-PAGE for the partitioning of the recombinant protein. For proteins that localize to the cell pellet, the pellet was resuspended in 10 mM Tris, pH 8.0, 1% CHAPS and the inclusion body pellet washed and centrifuged. The washed inclusion body was solubilized with either 8M urea or 6M guanidine HCL containing 10 mM Tris, pH 8.0, plus 10 mM imidazole. The solubilized protein was then added to 5 ml of nickel-chelate resin (Qiagen) and incubated for 45 minutes at room temperature.

Following the incubation, the resin and protein mixture was poured through a column and the flow through collected. The column was washed with 10–20 column volumes of buffer and the antigen eluted using 8M urea, 10 mM Tris, pH 8.0, and 300 mM imidazole and collected in 3 ml fractions. SDS-PAGE was run to determine which fractions to pool for further purification. As a final purification step, a strong anion exchange resin was equilibrated with the appropriate buffer and the pooled fractions were loaded onto the column. Each antigen was eluted from the column with an increasing salt gradient. Fractions were collected and analyzed by a SDS-PAGE to determine which fractions from the column to pool. The pooled fractions were dialyzed against 10 mM Tris, pH 8.0, and the resulting protein was submitted for quality control for final release. The release criteria were: (a) purity as determined by SDS-PAGE or HPLC, (b) concentration as determined by Lowry assay or Amino Acid Analysis, (c) identity as determined by amino terminal protein, and (d) endotoxin levels as determined by the Limulus (LAL) assay. The proteins were then filtered through a 0.22 μM filter and frozen until needed for immunizations.

To generate polyclonal antisera, 400 μg of O772P-1 or O772P-2 was combined with 100 μg of muramyldipeptide (MDP). The rabbits were immunized every 4 weeks with 100 μg of antigen mixed with an equal volume of Incomplete Freund's Adjuvant (IFA). Seven days following each boost, the animals were bled and sera was generated by incubating the blood at 4° C. for 12–24 hours followed by centrifugation.

To characterize the antisera, 96 well plates were coated with antigen followed by blocking with BSA. Rabbit sera was diluted in PBS and added to each well. The plates were then washed, and goat anti-rabbit horseradish peroxidase (HRP). The plates were again washed and TMB microwell Peroxidase Substrate was added. Following this incubation, the colormetric reaction was stopped and the plates read immediately at 450 nm. All polyclonal antibodies showed immunoreactivity to the appropriate antigen.

Immunohistochemistry analysis of O772P expression was performed on paraffin-embedded formalin fixed tissue. O772P was found to be expressed in normal ovary and ovarian tumor, but not in normal heart, kidney, colon, lung or liver. Additionally, immunohistochemistry and flow cytometric analysis indicates that O772P is a plasma membrane-associated molecule. O772P contains 1 plasma transmembrane domain predicted to be encoded by amino acids 859–880. The N-terminus of O772P is extracellular and is encoded by amino acids 1–859, while the C-terminus is intracellular. Sequence analysis shows that there are 17 potential N-linked glycosylation sites.

Example 11

O772P is Expressed on the Surface of Primary Ovarian Tumor Cells

For recombinant expression in mammalian cells, the O772P-21008 (SEQ ID NO: 387) and O772P full length cDNA (SEQ ID NO: 311 encoding the protein of SEQ ID NO: 312) were subcloned into mammalian expression vectors pBIB or pCEP4 respectively. These constructs were transfected into HEK293 cells using Fugene 6 (Roche). The HEK cells were then plated at a density of 100,000 cells/ml in DMEM containing fetal bovine serum (FBS) and grown overnight. The following day, 2 μl of Fugene 6 was added to 100 μl of DMEM, which contained no FBS, and incubated for 15 minutes at room temperature. The Fugene 6/DMEM mixture was then added to 1 μg of O772P/pBIB or O772P/pCEP4 plasmid DNA and incubated for an additional 15 minutes at room temperature. The Fugene 6/DNA mix was then added to the HEK293 cells and incubated for 48–72 hours at 37° C. with 7% $CO_2$. The cells were rinsed and pelleted by centrifugation.

For Western Blot analysis, whole cell lysates were generated by incubating the cells in lysis buffer followed by clarification by centrifugation. The samples were diluted and run on SDS-PAGE. The gel was then transferred to nitrocellulose and probed using purified anti-O772P-2 rabbit polyclonal antibody. The blot was revealed with a goat anti-rabbit Ig coupled to HRP followed by incubation in ECL substrate. Western Blot analysis revealed that O772P-21008 could be detected in HEK293 cells that had been transfected with O772P.

To determine the cell expression profile of O772P in cells, primary ovarian tumor cells were grown in SCID mice. The cells were retrieved from the mice and analyzed by flow cytometry. Briefly, cells washed in cold staining buffer containing PBS, 1% BSA, and Na Azide. The cells were incubated for 30 minutes with 10 μg/ml of purified anti-O772P-1 and O772P-2 polyclonal sera. Following this incubation, the cells were washed three times in staining buffer and incubated with goat anti-rabbit Ig (H+L) conjugated to FITC (Southern Biotechnology). The cells were washed and resuspended in staining buffer containing Propidium Iodide (PI), a vital stain that identifies non-viable cells. The cells were then analyzed using Fluorescence Activated Cell Sorting (FACS). FACS analysis revealed that O772P was present on the cells surface. Surface expression of O772P on tumor cells allows for immune targeting by therapeutic antibodies.

Example 12

Functional Characterization of Anti-O8E Monoclonal Antibodies

Figure 25:
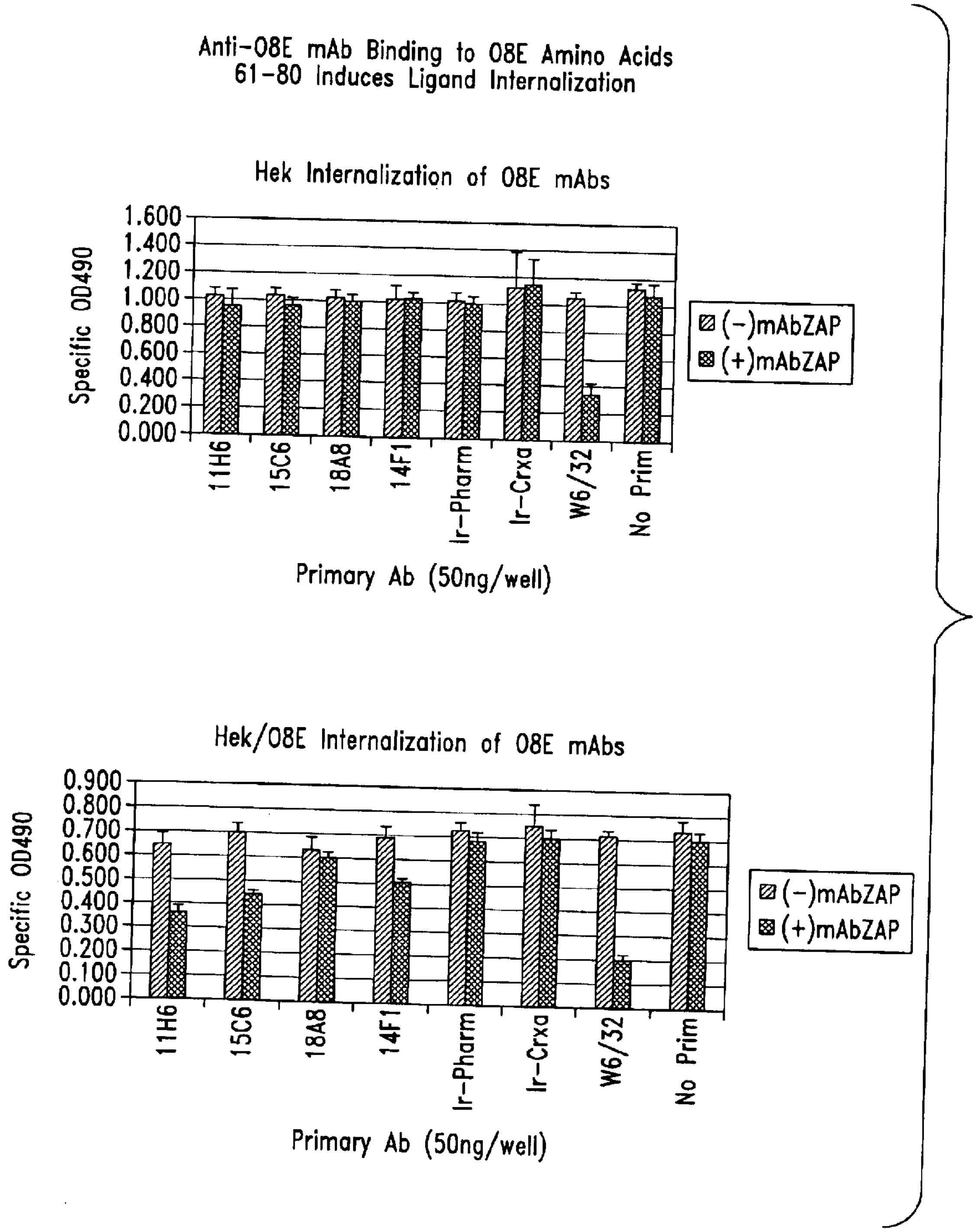
FIG. 25 is a graph determining antibody internalization of anti-O8E mAb showing that mAbs against amino acids 61–80 induces ligand internalization.

Mouse monoclonal antibodies (mAb) raised against *E. coli* derived O8E, as described in Example 8, were tested for their ability to promote O8E antigen internalization. Internalization of the antibody was determined using an in vitro cytotoxicity assay. Briefly, HEK293 and O8E/HEK transfected cells were plated into 96 well plates containing DME plus 10% heat-inactivated FBS in the presence of 50ng/well of purified anti-O8E or control antibodies. The isotype of the anti-O8E mAbs are as follows: 11A6-IgG1/kappa, 15C6-IgG2b/kappa, 18A8-IgG2b/kappa, and 14F1-IgG2a/kappa. W6/32 is a pan anti-human MHC class I mouse monoclonal antibody that serves as a positive control, and two irrelevant mAbs, Ir-Pharm and Ir-Crxa were included as negative controls. Following incubation with the O8E specific antibodies or the relevant controls antibodies, the mAb-zap, a goat anti-mouse Ig-saporin conjugated secondary antibody (Advanced Targeting Systems) was added at a concentration of 100 ng/ml to half of the wells, and the plates were incubated for 48 to 72 hours at 37° C. in a 7% $CO_2$ incubator. This assay takes advantage of the toxic nature of saporin, a ribozyme inactivating protein, which when internalized has a cytotoxic effect. Following incubation with the mAb-zap, internalization was quantitated by the addition of MTS reagent, followed by reading the OD490 of the plate on a microplate ELISA reader. FIG. 25 depicts the results from these assays. The top panel represents HEK cells that have not been transfected with O8E and therefore O8E antibody should not bind and be internalized. Levels of proliferation were the same in all samples whether they were incubated with or without the mAb-zap, with the exception of the positive control Ab, W6/32. The lower panel represents cells that have been transfected with O8E and therefore should bind O8E specific antibodies. Antibodies from the hybridomas 11H6, 14F1, and 15C6, which recognize the amino acids 61–80 of O8E were able to promote internalization of the O8E surface protein as measured by decreased levels of proliferation due to the toxic nature of the mAb-zap (See FIG. 25). The antibody generated by the hybridoma 18A8, which recognizes amino acids 151–170 of O8E, was unable to promote internalization as determined by normal levels of proliferation either in the absence or presence of the mAb-zap.

Example 13

Characterization of the Ovarian Tumor Antigen, O772P

The cDNA and protein sequences for multiple forms of the ovarian tumor antigen O772P have been described in the above (e.g., Examples 2 and 9). A Genbank search indicated that O772P has a high degree of similarity with FLJ14303 (Accession#AK024365; SEQ ID NO: 457 and 463). Protein sequences corresponding to O772P and FLJ14303 are disclosed in SEQ ID NO: 478 and 479, respectively. FLJ14303 was identical to the majority of O772P, with much of the 3'-end showing 100% homology. However, the 5'-end of FLJ14303 was found to extend further 5' than O772P. In addition, FLJ14303 contained a 5 bp insert (SEQ ID NO: 457) resulting in a frame shift of the amino-terminus protein sequence such that FLJ14303 utilizes a different starting methionine than O772P and therefore encodes a different protein. This insertion was present in the genomic sequence and seen in all EST clones that showed identity to this region, suggesting that FLJ14303 (SEQ ID NO: 457) represents a splice variant of O772P, with an ORF that contains an extended and different amino-terminus. The additional 5'-nucleotide sequence included repeat sequences that were identified during the genomic mapping of O772P. The 5'-end of O772P and the corresponding region of FLJ14303 showed between 90–100% homology. Taken together, this suggests that O772P and FLJ14303 are different splice variants of the same gene, with different unique repeat sequences being spliced into the 5'-end of the gene.

The identification of an additional ten or more repeat sequences within the same region of chromosome 19, indicates that there may be many forms of O772P, each with a different 5'-end, due to differential splicing of different repeat sequences. Northern blot analysis of O772P demonstrated multiple O772P-hybridizing transcripts of different sizes, some in excess 10 kb.

Upon further analysis, 13 additional O772P-related sequences were identified, the cDNA and amino acid sequences of which are described in Table 3.

TABLE 3

| SEQ ID NO: | Description | Transmembrane Domains |
|---|---|---|
| 464 | LS #1043400.1 (cDNA) | nd |
| 465 | LS #1043400.10 (cDNA) | 0 |
| 466 | LS #1043400.11 (cDNA) | 2 |
| 467 | LS #1043400.12 (cDNA) | 2 |
| 468 | LS #1043400.2 (cDNA) | nd |
| 469 | LS #1043400.3 (cDNA) | |
| 470 | LS #1043400.5 (cDNA) | nd |
| 471 | LS #1043400.8 (CDNA) | 1 |
| 472 | LS #1043400.9 (cDNA) | 0 |
| 473 | LS #1043400.6 (cDNA) | nd |
| 474 | LS #1043400.7 (cDNA) | nd |
| 475 | LS #1043400.4 (cDNA) | nd |
| 476 | LS #1397610.1 (cDNA) | 0 |
| 477 | 1043400.10 Novel 5' (cDNA) | — |
| 480 | LS #1043400.9 (amino acid) | — |
| 481 | LS #1043400.8B (amino acid) Contains a transmembrane domain | — |
| 482 | LS #1043400.8A (amino acid) | — |
| 483 | LS #1043400.12 (amino acid) Contains a transmembrane domain | — |
| 484 | LS #1043400.11B (amino acid) Contains a transmembrane domain | — |
| 485 | LS #1043400.11A (amino acid) | — |
| 486 | LS #1043400.10 (amino acid) | — |
| 487 | LS #1043400.1 (amino acid) | — |

nd = not determined

Initially it appeared that these sequences represented overlapping and/or discrete sequences of O772P splice forms that were capable of encoding polypeptides unique to the specific splice forms of O772P. However, nucleotide alignment of these sequences failed to identify any identical regions within the repeat elements. This indicates that the sequences may represent different specific regions of a single O772P gene, one that contains 16 or more repeat domains, all of which form a single linear transcript. The 5'-end of sequence LS #1043400.10 (Table 2; SEQ ID NO: 465) is unique to both O772P and FLJ14303 and contains no repeat elements, indicating that this sequence may represent the 5'-end of O772P.

Previously, transmembrane prediction analysis had indicated that O772P contained between 1 and 3 transmembrane spanning domains. This was verified by the use of immunohistochemistry and flow cytometry, which demonstrated the existence of a plasma membrane-associated molecule representing O772P. However, immunohistochemistry also indicated the presence of secreted form(s) of O772P, possibly resulting from an alternative splice form of O772P or from a post-translational cleavage event. Analysis of several of the sequences presented in Table 2 showed that sequences 1043400B.12, 1043400.8B, and 1043400.11B all contained transmembrane regions, while 1043400.8A, 1043400.10, 1043400.1, 1043400.11A, and 1043400.9 were all lacking transmembrane sequences, suggesting that these proteins may be secreted.

Analysis indicates a part of O772P is expressed and/or retained on the plasma membrane, making O772P an attractive target for directing specific immunotherapies, e.g., therapeutic antibodies, against this protein. The predicted extracellular domain of O772P is disclosed in SEQ ID NO: 489 and secretion of O772P is likely to occur as a result of a cleavage event within the sequence:

SLVEQVFLDKTLNASFHWLGSTYQLVDIHVTEM ESSVYQP.

Proteolytic cleavage is most likely to occur at the Lysine (K) at position 10 of SEQ ID NO: 489. The extracellular, transmembrane, and cytoplasmic regions of O772P are all disclosed in SEQ ID NO: 488:

```
Extracellular:
SLVEQVFLDKTLNASFHWLGSTYQLVDIHVTEMESSVYQPTSSSSTQHFY

LNFTITNLPYSQDKAQPGTTNYQRNKRNIEDALNQLFRNSSIKSYFSDCQ

VSTFRSVPNRHHTGVDSLCNFSPLARRVDRVAIYEEFLRMTRNGTQLQNF

TLDRSSVLVDGYFPNRNEPLTGNSDLPF

Transmembrane:
WAVILIGLAGLLGLITCLICGVLVTT

Cytoplasmic:
RRRKKEGEYNVQQQCPGYYQSHLDLEDLQ
```

Example 14

Immunohistochemistry (IHC) Analysis of O8E Expression in Ovarian Cancer and Normal Tissues In order to determine which tissues express the ovarian cancer antigen O8E, IHC analysis was performed on a diverse range of tissue sections using both polyclonal and monoclonal antibodies specific for O8E. The generation of O8E specific polyclonal antibodies is described in detail in Example 8. The monoclonal antibodies used for staining were 11A6 and 14F1, both of which are specific for amino acids 61–80 of O8E and 18A8, which recognizes amino acids 151–170 of O8E (see Example 12 for details on generation).

To perform staining, tissue samples were fixed in formalin solution for 12–24 hours and embedded in paraffin before being sliced into 8 micron sections. Steam heat induced epitope retrieval (SHEIR) in 0.1M sodium citrate buffer (pH 6.0) was used for optimal staining conditions. Sections were incubated with 10% serum/PBS for 5 minutes. Primary antibody was then added to each section for 25 minutes followed by 25 minutes of incubation with either anti-rabbit or anti-mouse biotinylated antibody. Endogenous peroxidase activity was blocked by three 1.5 minute incubations with hydrogen peroxidase. The avidin biotin complex/horse radish peroxidase (ABC/HRP) system was used along with DAB chromogen to visualize the antigen expression. Slides were counterstained with hematoxylin to visualize the cell nuclei.

Results using rabbit affinity purified polyclorial antibody to O8E (a.a. 29–283; for details on the generation of this Ab, see Example 3) are presented in Table 3. Results using the three monoclonal antibodies are presented in Table 4.

TABLE 4

Immunohistochemistry analysis of O8E using polyclonal antibodies

| Tissue | O8E Expression |
|---|---|
| Ovarian Cancer | Positive |
| Breast Cancer | Positive |
| Normal Ovary | Positive |
| Normal Breast | Positive |
| Blood Vessel | Positive |
| Kidney | Negative |
| Lung | Negative |
| Colon | Negative |
| Liver | Negative |
| Heart | Negative |

TABLE 5

Immunohistochemistry analysis of O8E using monoclonal antibodies

| Normal | 11A6 | | 18A8 | | 14F1 | |
|---|---|---|---|---|---|---|
| Tissue | Endothelial | Epithelial | Endothelial | Epithelial | Endothelial | Epithelial |
| Skin | 2 | 2 | 0 | 0 | 1 | 1 |
| Skin | 1 | 1 | 0 | 0 | 1 | 1 |
| Breast | 0 | 1 | n/a | n/a | 1 | 1 |
| Colon | 0 | 0 | 0 | 0 | 0 | 0 |
| Jejunum | 0 | 0 | 0 | 0 | 0 | 0 |
| Colon | 0 | 0 | 0 | 0 | 0 | 0 |
| Colon | 0 | 0 | 0 | 0 | 0 | 0 |
| Ovary | 0 | 0 | 0 | 0 | 1 | 0 |
| Colon | 0 | 0 | 0 | 0 | 0 | 1 |
| Liver | 0 | 0 | 0 | 0 | 1 | 2 |
| Skin | 0 | 0 | 0 | 0 | 1 | 0 |
| Duodenum and Pancreas | 0 | 0 | 0 | 0 | 0 | 0 |
| Appendix | 0 | 0 | 0 | 0 | 0 | 0 |
| Ileum | 0 | 0 | 0 | 0 | 0 | 0 |

0 = no staining,
1 = light staining,
2 = moderate staining,
n/a = not available

Example 15

Epitope Mapping of O772P Polyclonal Antibodies

To perform epitope mapping of O772P, peptides were generated, the sequences of which were derived from the sequence of O772P. These peptides were 15 mers that overlapped by 5 amino acids and were generated via chemical synthesis on membrane supports. The peptides were covalently bound to Whatman 50 cellulose support by their C-terminus with the N-terminus unbound. In order to determine epitope specificity, the membranes were wet with 100% ethanol for 1 minute, and then blocked for 16 hours in TBS/Tween/Triton buffer (50 mM Tris, 137 mM NaCl, 2.7 mM KCl, 0.5% BSA, 0.05% Tween 20, 0.05% Triton X-100, pH 7.5). The peptides were then probed with 2 O772P specific antibodies, O772P-1 (amino acids 44–772 of SEQ ID NO: 312) and O772P-2 (477–914 of SEQ ID NO: 312; see Example 10 for details of antibody generation), as well 15 as irrelevant rabbit antibodies for controls. The antibodies were diluted to 1 μg/ml and incubated with the membranes for 2 hours at room temperature. The membranes were then washed for 30 minutes in TBS/Tween/Triton buffer, prior to being incubated with a 1:10,000 dilution of HRP-conjugated anti-rabbit secondary antibody for 2 hours. The membranes were again washed for 30 minutes in TBS/Triton and anti-peptide reactivity was visualized using ECL. Specific epitope binding specificity for each of the O772P-polyclonal antibodies is described in Table 6.

TABLE 6

| SEQ ID NO: | Peptide # | Anti-O772P1 | Anti-O772P2 | Peptide Sequence |
|---|---|---|---|---|
| 490 | 2 | *** | — | TCGMRRTCSTLAPGS |
| 491 | 6 | * | */— | CRLTLLRPEKDGTAT |
| 492 | 7 | * | — | DGTATGVDAICTHHP |
| 493 | 8 | — | — | CTHHPDPKSPRLDRE |
| 494 | 9 | *** | *** | RLDREQLYWELSQLT |
| 495 | 11 | */— | — | LGPYALDNDSLFVNG |
| 496 | 13 | **** | — | SVSTTSTPGTPTYVL |

TABLE 6-continued

| SEQ ID NO: | Peptide # | Anti-O772P1 | Anti-O772P2 | Peptide Sequence |
|---|---|---|---|---|
| 497 | 22 | — | — | LRPEKDGEATGVDAI |
| 498 | 24 | ** | */— | DPTGPGLDREQLYLE |
| 499 | 27 | */— | — | LDRDSLYVNGFTHRS |
| 500 | 40 | */— | — | GPYSLDKDSLYLNGY |
| 501 | 41 | — | — | YLNGYNEPGPDEPPT |
| 502 | 47 | *** | *** | ATFNSTEGVLQHLLR |
| 503 | 50 | — | *** | QLISLRPEKDGAATG |
| 504 | 51 | — | ** | GAATGVDTTCTYHPD |
| 505 | 52 | — | */— | TYHPDPVGPGLDIQQ |
| 506 | 53 | — | * | LDIQQLYWELSQLTH |
| 507 | 58 | — | * | HIVNWNLSNPDPTSS |
| 508 | 59 | — | * | DPTSSEYITLLRDIQ |
| 509 | 60 | — | * | LRDIQDKVTTLYKGS |
| 510 | 61 | — | *** | LYKGSQLHDTFRFCL |
| 511 | 71 | — | ** | DKAQPGTTNYQRNKR |

* = relative reactive level, —; no binding, ****; maximal binding

Example 16

Identification of a Novel N-Terminal Repeat Structure Associated with O772P

Various O772P cDNA and protein forms have been identified and characterized as detailed above (e.g., Examples 1, 2, 9, and 14). Importantly, O772P RNA and protein have been demonstrated to be over-expressed in ovarian cancer tissue relative to normal tissues and thus represents an attractive target for ovarian cancer diagnostic and therapeutic applications.

Using bioinformatic analysis of open reading frames (ORFs) from genomic nucleotide sequence identified previously as having homology with O772P, multiple nucleotide repeat sequences were identified in the 5' region of the gene encoding the O772P protein. A number of these repeat sequences were confirmed by RT-PCR using primers specific for the individual repeats. Fragments which contained multiple repeats were amplified from cDNA, thus confirming the presence of specific repeats and allowing an order of these repeats to be established.

Unexpectedly, when various sets of O772P sequences derived from different database and laboratory sources were analyzed, at least 20 different repeat structures, each having substantial levels of identity with each other (see Table 6), were identified in the 5' region of the O772P gene and the corresponding N-terminal region of the O772P protein. Each repeat comprises a contiguous open reading frame encoding a polypeptide unit that is capable of being spliced to one or more other repeats such that concatomers of the repeats are formed in differing numbers and orders. Interestingly, other molecules have been described in the scientific literature that have repeating structural domains analogous to those described herein for O772P. For example, the mucin family of proteins, which are the major glycoprotein component of the mucous which coats the surfaces of cells lining the respiratory, digestive and urogenital tracts, have been shown to be composed of tandemly repeated sequences that vary in number, length and amino acid sequence from one mucin to another (Perez-Vilar and Hill, *J. Biol. Chem.* 274(45):31751–31754, 1999).

The various identified repeat structures set forth herein are expected to give rise to multiple forms of O772P, most likely by alternative splicing. The cDNA sequences of the identified repeats are set forth in SEQ ID NOs: 513–540, 542–546, and 548–567. The encoded amino acid sequences of the repeats are set forth in SEQ ID NOs: 574–593. In many instances these amino acid sequences represent consensus sequences that were derived from the alignment of more than one experimentally derived sequence.

Each of these splice forms is capable of encoding a unique O772P protein with multiple repeat domains attached to a constant carboxy terminal protein portion of O772P that contains a trans membrane region. The cDNA sequence of the O772P constant region is set forth in SEQ ID NO: 568 and the encoded amino acid sequence is set forth in SEQ ID NO: 594.

All of the available O772P sequences that were obtained were broken down into their identifiable repeats and these sequences were compared using the Clustal method with weighted residue weight table (MegAlign software within DNASTAR sequence analysis package) to identify the relationship between the repeat sequences. Using this information, the ordering data provided by the RT-PCR, and sequence alignments (automatic and manual) using SeqMan (DNASTAR), one illustrative consensus full length O772P contig was identified comprising 20 distinct repeat units. The cDNA for this O772P cDNA contig is set forth in SEQ ID NO: 569 and the encoded amino acid sequence is set forth in SEQ ID NO: 595. This form of the O772P protein includes the following consensus repeat structures in the following order:

```
SEQ ID NO:572-SEQ ID NO:574-SEQ ID NO:575-SEQ ID
NO:576-SEQ ID NO 577-SEQ ID NO:578-SEQ ID NO:579-
SEQ ID NO:580-SEQ ID NO:581-SEQ ID NO:582-SEQ ID
NO:583-SEQ ID NO:584-SEQ ID NO:585-SEQ ID NO:586-
SEQ ID NO:587-SEQ ID NO:588-SEQ ID NO:589-SEQ ID
NO:590-SEQ ID NO:591-SEQ ID NO:592-SEQ ID NO:593.
```

SEQ ID NO: 595, therefore, represents one illustrative full-length consensus sequence for the O772P protein. As discussed above, however, based on current knowledge of this protein and based upon scientific literature describing proteins containing analogous repeating structures, many other forms of O772P are expected to exist with either more or less repeats. In addition, many forms of O772P are expected to have differing arrangements, e.g., different orders, of these N-terminal repeat structures. The existence of multiple forms of O772P having differing numbers of repeats is supported by Northern analysis of O772P. In this study, Northern hybridization of a O772P-specific probe resulted in a smear of multiple O772P-hybridizing transcripts, some in excess 10 kb.

Thus, the variable repeat region of the O772 protein can be illustratively represented by the structure Xn-Y, wherein X comprises a repeat structure having at least 50% identity with the consensus repeat sequence set forth in SEQ ID NO: 596; n is the number of repeats present in the protein and is expected to typically be a integer from 1 to about 35; Y comprise the O772P constant region sequence set forth in SEQ ID NO: 594 or sequences having at least 80% identity with SEQ ID NO: 594. Each X present in the Xn repeat region of the O772 molecule is different.

To determine the consensus sequences of each of the 20 repeat regions, sequences that were experimentally determined for a discrete repeat region were aligned and a consensus sequence determined. In addition to determining the consensus sequences for individual repeat regions, a consensus repeat sequence was also determined. This sequence was obtained by aligning the 20 individual consensus sequences. Variability of the repeats was determined by aligning the consensus amino acid sequences from each of the individual repeat regions with the over all repeat consensus sequence. Identity data is presented in Table 6.

TABLE 7

Percent identities of Repeat Sequences with Reference to the Consensus Repeat Sequence

| Repeat Number (amino acid) | SEQ ID NO: | Percent Identity to Consensus Repeat Sequence |
|---|---|---|
| 2 | 574 | 88 |
| 3 | 575 | 84 |
| 4 | 576 | 88 |
| 5 | 577 | 89 |
| 6 | 578 | 93 |
| 7 | 579 | 90 |
| 8 | 580 | 91 |
| 9 | 581 | 88 |
| 10 | 582 | 85 |
| 11 | 583 | 86 |
| 12 | 584 | 87 |
| 13 | 585 | 87 |
| 14 | 586 | 89 |
| 15 | 587 | 89 |
| 16 | 588 | 89 |
| 17 | 589 | 83 |
| 18 | 590 | 84 |
| 19 | 591 | 83 |
| 20 | 592 | 57 |
| 21 | 593 | 68 |

Example 17

Generation and Characterization of Anti-O772P Monoclonal Antibodies

Monoclonal antibodies were generated against the O772P-2 protein, specifically amino acid residues 447–914 of SEQ ID NO: 312. To produce these antibodies, A/J mice were immunized i.p. with 50 μg of recombinant O772P-2 (rO772P-2) mixed with Complete Freud's Adjuvant, followed by a second immunization with 10 μg of rO772P-2 in Incomplete Freud's Adjuvant. Three days prior to the animals being sacrificed, the mice were immunized i.v. with 50 μg of soluble rO772P-2 protein. The spleens from mice with positive titers of O772P-2 were harvested, and a single cell suspension was made and used for fusion to SP2/0 myeloma cells to generate B cell hybridomas.

The supernatants from the resulting hybrid clones were tested by ELISA for specificity to the rO772P-2 protein. Briefly, 96 well plates were coated with rO772P-2 or with one of three 30 mer peptides, which corresponded to the extracelluair domain of the O772P protein. Sequences corresponding to these peptides are disclosed in SEQ ID NO: 597–599. The rO772P protein or peptides were coated at a concentration of 1–2 μg/ml and 10 μg/ml, respectively, and allowed to incubate for 60 minutes at room temperature. Following coating, the plates were washed five times with PBS containing 0.1% Tween-20, and then blocked with PBS containing 0.5% BSA and 0.4% Tween-20 for 1–2 hours at room temperature. Following the addition of the hybridoma supernatants the plates were again incubated for 60 minutes at room temperature. The plates were then washed as above and donkey-anti-mouse Ig-HRP linked secondary antibody (Jackson ImmunoResearch) was added and incubated for 60 minutes at room temperature, followed by a final wash. TMB peroxidase substrate was then added and incubated for 5–15 minutes at room temperature in the dark. The reaction was stopped by the addition of 1 N $H_2SO_4$ and the optical density was read at 450 nm. Epitope mapping using ELISA revealed that there was 1 hybridoma that recognized peptide #1 (SEQ ID NO: 597).

The hybrid supernatants were also tested using flow cytometry to determine if they were capable of recognizing surface expressed epitopes of the O772P protein. Briefly, transiently transfected O772P-08/HEK293, O772P-3rpt/HEK293, O772P-7rpt/HEK293 cells were harvested and washed, followed by incubation with the hybridoma supernatants on ice for 30 minutes. The cells were then washed in staining buffer (1×PBS, 0.5%BSA and 0.01% sodium azide), followed by incubation with goat-anti-mouse Ig-FITC for 30 minutes on ice. The cells were again washed, and resuspended in staining buffer containing 1% propidium iodide (to determine cell viability). The cells were then analyzed for surface expression of the mAbs. Flow cytometry analysis revealed that the 3 of the hybridomas tested were able to detect O772P protein expressed in the surface of O772P-transfected HEK293 cells.

Example 18

Characterization of Human Anti-O8E Monoclonal Antibodies

Monoclonal antibodies (mAb) were generated against the O8E protein, the amino acid sequence of which is disclosed in SEQ ID NO: 392. To produce these mAbs, Medarex mice were i.p. immunized repeatedly with multiple forms if recombinant O8E antigens, including O8E protein produced using *E. coli*, O8E plasmid DNA and O8E expressing CHO-1 cells. Spleens from mice with positive titers to O8E were collected and used for fusion to myeloma cells in order to generate B cell hybrids. The supernatants from the resulting hybrids were tested by ELISA for specificity to O8E recombinant protein as well as being tested by flow cytometry for recognition of surface expressed epitopes of the O8E protein and in internalization assays.

For ELISA analysis, 96 well plates were coated with recombinant O8E (rO8E) protein or with pools of 5 overlapping 20-mer peptides that span the entire O8E molecule (peptides 1–19, the sequences of which are disclosed in SEQ ID NOs: 600–618). Recombinant proteins and peptides were coated at a concentration of 1–2 μg/ml and 10 μg/ml, respectively, and then allowed to incubate for 60 minutes at room temperature. After coating, the plates were washed five times with PBS containing 0.1% Tween-20 and then blocked with PBS containing 0.5% BSA and 0.4% Tween-20 for 1–2 hours at room temperature. Following the addition of the hybridoma supernatants, the plates were incubated for 60 minutes at room temperature. The plates were washed as above and mouse anti-human IgG-HRP linked secondary antibody was added and incubated for 60 minutes at room temperature, followed by a final washing as above. TMB peroxidase substrate was added and incubated for 5–15 minutes at room temperature in the dark. The reaction was stopped by the addition of 1 N $H_2SO_4$ and the OD was read at 450 nm. Hybridoma 7F5 was shown to react with peptides 11–15, corresponding to amino acids 151–230. No other hybridoma demonstrated reactivity against the O8E specific peptides. Results from this study are presented in Table 7, column 2.

For flow cytometric analysis, HEK293 cells stably transfected with O8E or SKBR3 cells, which naturally express O8E, were harvested and washed, then incubated with the hybridoma supernatants for 30 minutes on ice. Following this incubation, the cells were washed with staining buffer (1×PBS, 0.5% BSA, and 0.01% sodium azide). Next, mouse anti-human kappa-FITC was added to the cells and allowed to incubate for 30 minutes on ice. Again, the cells were washed followed by resuspension in wash buffer containing 1% propidium iodide. The cells were then subjected to flow cytometric analysis. Results from these experiments are presented in Table 8, column 3.

For internalization assays, $1\times10^3$ SKBR3 cells/well were plated into 96 well plates containing DME plus 10% heat inactivated fetal bovine serum in the presence of 50 ng/well of human anti-O8E hybridoma supernatants or a control antibody. A mouse anti-human Ig-saporin conjugated secondary antibody was then added at various concentrations to the wells, and the plates were incubated for 4 days at 37" C. in a 7% $CO_2$ incubator. To measure any decreases in the amount of proliferation MTS (20 μl/ml: Promega) was added to the cells for 1 to 2 hours. Proliferation was then measured by reading the OD490 of the plate. The majority of the hybridomas tested were internalized resulting in a decrease in the amount of proliferation detected. The results from these studies are summarized in Table 8, column 6. These findings indicate that the hybridomas can be used to deliver toxins, either directly or indirectly conjugated to the anti-O8E antibodies, to cells that express O8E on their cell surface. This allows for the specific targeting and death of cells that express the ovarian tumor antigen, O8E.

TABLE 8

Summary of anti-O8E hybridoma data

| Clone | ELISA (O8E Ag) | Facs* | HEK (MFI) | 08E/HEK (MFI) | SKBR3 % death |
|---|---|---|---|---|---|
| 7H4 | − | + | 2.29 | 96.08 | 50 |
| 9C10 | − | + | 2.85 | 105.98 | 40 |
| 12B9 | − | + | 2.22 | 113.63 | 12 |
| 6F9 | − | + | 4.78 | 100.36 | 25 |
| 11C11 | − | nt | 2.44 | 26.64 | 20 |
| 2A7 | + | + | 2.52 | 153.61 | 25 |
| 5A7 | + | + | 2.45 | 22.76 | 25 |
| 14D2 | − | + | 3.92 | 55.45 | 15 |
| 12B10 | − | + | 2.21 | 23.74 | 40 |
| 12E.1 | + | + | 2.27 | 10.87 | 50 |
| 6E.2 | − | + | 2.45 | 31.89 | 12 |
| 2G6 | − | + | 2.43 | 86.7 | 30.7 |
| 3C7 | − | + | 2.61 | 112.2 | 5.6 |
| 3D8 | − | + | 2.47 | 105.02 | 24.2 |
| 4B8 | − | + | 2.74 | 128 | 29.6 |
| 4G5 | − | + | 2.64 | 68.56 | 14.1 |
| 8D5 | − | + | 2.55 | 131.99 | 8.2 |
| 8G9 | − | + | 2.64 | 123.4 | 18 |
| 9A5 | − | + | 2.43 | 89.43 | 12.3 |
| 9B6 | − | + | 2.51 | 175.81 | 16.3 |
| 14A4 | − | + | 2.52 | 197.33 | 4.5 |
| 18H6 | − | + | 2.58 | 90.29 | −16.2 |
| 19C9 | − | + | 2.44 | 47.11 | −14.1 |
| 20E8 | − | + | 2.51 | 111.2 | −14.9 |
| 21B9 | − | + | 2.46 | 137.36 | −2.2 |
| 22G5 | − | + | 2.88 | 54.66 | 16.3 |
| 23F9 | − | + | 2.53 | 30.02 | 13.5 |
| 24C2 | − | + | 2.59 | 57.9 | 24 |
| 2A7.G4 | + | + | 2.45 | 42.87 | 40.5 |
| 2A7.G7 | + | + | 2.48 | 47.28 | 46.4 |
| 2A7.H5 | + | + | 2.47 | 43.57 | 37 |
| 2A7.H8 | + | + | 2.42 | 45.76 | 40 |
| 2A7.D12 | + | + | 2.67 | 51.83 | 44.3 |
| 1E9 | − | + | 2.67 | 26.14 | 68.5 |
| 2A2 | − | + | 2.59 | 156.82 | 49.4 |
| 2D4 | − | + | 2.56 | 115.79 | 50 |
| 2E4 | − | + | 2.54 | 32.5 | 58.1 |
| 2F9 | − | + | 2.46 | 92.78 | 59.5 |

TABLE 8-continued

Summary of anti-O8E hybridoma data

| Clone | ELISA (O8E Ag) | Facs* | HEK (MFI) | 08E/HEK (MFI) | SKBR3 % death |
|---|---|---|---|---|---|
| 4C7 | − | + | nt | nt | nt |
| 5C6 | − | + | 2.54 | 88.19 | 64.2 |
| 5H5 | − | + | 2.66 | 100.82 | 52 |
| 6F1 | − | + | 2.45 | 57.81 | 49.8 |
| 7H12 | − | + | 2.56 | 172 | 45 |
| 8A10 | − | + | 2.41 | 16.47 | 58.3 |
| 8B7 | − | + | nt | nt | nt |
| 9E11 | − | + | nt | nt | nt |
| 10D4 | − | + | nt | nt | nt |
| 10G7 | − | + | 2.5 | 3.04 | 59.1 |
| 11H8 | − | + | 2.43 | 5.22 | 9 |
| 13A4 | − | + | 2.45 | 53.58 | 37.5 |

MFI = mean fluorescence intensity;
Facs = fluorescence activated cells sorter Internalization assay − 1% death = average OD (+) toxin/average OD (−) toxins × 100

Example 19

Immunohistochemical Analysis Ovarian Cancer using Human Anti-O8E Monoclonal Antibodies Anti-O8E immunoreactivity was tested in breast cancer, ovarian cancer and normal tissues. In order to perform this analysis, paraffin embedded formalin fixed tissues were sliced into 8 micron sections. Steam heat induced epitope retrieval (SHIER) in 0.1 M sodium, citrate buffer (pH 6.0) was used for optimal staining conditions. Sections were incubated in PBS containing 10% serum for 5 minutes. Primary O8E mAb (described in detail in Example 18) was then added to each section for 25 minutes followed by a 25 minute incubation with an anti-mouse biotinylated antibody. Endogenous peroxidase was blocked by three 1.5 minute incubations with hydrogen peroxidase. The avidin biotin complex/horse radish peroxidase (ABC/HRP) system was used along with DAB chromogen to visualize antigen expression. Slides were counterstained with hematoxylin.

O8E expression was detected in the majority of ovarian tumor samples but not in normal ovary. O8E expression was also observed in breast cancer samples and at very low levels in normal breast. Of the normal tissues tested (blood vessel, heart, liver, kidney, colon, stomach, skin and lung), only stomach and skin tested positive.

Example 20

Expression of O8E Orthologs

The identification and characterization of related forms of the ovarian specific antigen O8E has been described above, one representative DNA sequence for which is set forth in SEQ ID NO: 391, encoding amino acid sequences set forth in SEQ ID NOs: 392–393. O8E is a plasma membrane associated protein that is over-expressed in ovarian and other cancers. In this example, O8E orthologs from monkey and mouse are identified.

For the cloning of the Rhesus monkey O8E, a PCR primer set was designed using the human O8E open reading frame sequence. The O8E forward primer, designated O8E-UP1, 5'CAGMGCTTATGGCTTCCCTGGGGCAGACT-3' (SEQ ID NO: 619) corresponds to the first 21 nucleotides of the human O8E ORF including the start codon, with a HindIII restriction site added at the 5'-end. The O8E reverse primer, designated O8E-DN1, 5'CAGCGGCCGCTTATTIIAGC- ATCAGGTMGG-3' (SEQ ID NO: 620) corresponds to the last 21 nucleotides of the human O8E ORF including the stop codon, with a NotI restriction site added to the 5'-end. The monkey O8E was then amplified from Rhesus monkey placenta cDNA sample using the above-described primer set and cloned into pCEP4 mammalian expression vector. Sequence analysis showed that the O8E sequence derived from the Rhesus (rhO8E) cDNA demonstrated 97.9% identity at the cDNA level and 98.2% identity at the protein level when compared to human O8E. Representative protein and cDNA sequences are disclosed in SEQ ID NOs: 623 and 621, respectively.

For the cloning of the mouse O8E cDNA, the moue EST database was searched using the human O8E sequence. This search resulted in the identification of several mouse ESTs that shared greater than 80% identity to the human O8E cDNA sequence. Three of the mouse EST clones were obtained and sequenced. One clone, 557246, (Genebank Accession number AA117088) contained the full-length cDNA insert for the mouse O8E in a mammalian expression vector, pCMV-SPORT2. Sequence analysis showed that the mouse O8E (rmO8E) shared 82.7% identity at the cDNA level and 86.6% identity at the protein level with human O8E. Representative protein and cDNA sequences are disclosed in SEQ ID NOs: 624 and 622, respectively.

Example 21

Characterization of the Expression Profile of O8E Orthologs

This example demonstrates that mAbs generated against human O8E were capable of recognizing cells transfected with either Rhesus O8E or mouse O8E.

For expression of the O8E orthologs, HEK293 cells were plated at a density of 250,000 cells/well in DMEM containing 10% FBS and incubated for 4 hours. At the end of the incubation period, 2 μl of Lipofectamine 2000 (Invitrogen) was added to 50 μl of Optimen 1 (Invitrogen) containing no FBS and incubated for 5 minutes at room temperature. In a different tube 50 μl of Optimen 1 was mixed with ~1.0 μg of pCEP4 vector, pCEP/rhesus monkey O8E, or pCMV-Spert2/mouse O8E plasmid DNA and the mixture was transferred to the Lipofectamine 2000/Optimen mix. The combined mixture was incubated for 20 minutes at room temperature and then transferred to the HEK293 cells containing 2 ml of fresh DMEM containing 10% FBS. The transformed HEK293 cells were incubated for approximately 72 hours at 37° C. with 7% $CO_2$.

For Fluorescence Activated Cell Sorting (FACS) analysis, cells were collected and washed with ice cold staining buffer (PBS containing 1% BSA and Azide). HEK293/human O8E stable transfectants were used as a positive control for the FACS analysis. The cells were incubated for 45 minutes at room temperature with human mAbs generated against the human O8E protein (identified in Example 18) then washed 2 times with staining buffer followed by incubation with 20 μl of anti-human IgG-FITC reagent (Pharminigen) for 30 minutes ay room temperature. Following 2 washes, the cells were resuspended in staining buffer containing Propidium Iodide (PI), a vital stain that allows for identification of dead cells, and analyzed by FACS.

Cells transfected with human O8E, monkey O8E and mouse O8E demonstrated O8E specific staining with all human O8E mAbs tested. The results of this study are summarized in Table 9.

TABLE 9

Summary of O8E Staining Using Cells Expressing Human O8E, Mouse O8E, and Rhesus OBE Orthologs

| | Geometric Mean Fluorescent Intensity (GeoMFI) | | | |
|---|---|---|---|---|
| Human mAb | HEK293-pCEP4 | HEK293-huO8E | HEK293-rmO8E | HEK293-mO8E |
| Human IgG (control) | 24.45 | 24.88 | 38.96 | 49.65 |
| 1G11 | 26.40 | 275.60 | 301.06 | 300.97 |
| 2A7 | 26.35 | 419.46 | 474.83 | 448.04 |
| 2D4 | 28.57 | 352.71 | 416.72 | 436.11 |
| 2F9 | 28.51 | 381.29 | 446.81 | 426.47 |
| 5A4 | 27.08 | 77.78 | 72.64 | 141.51 |
| 5C6 | 31.47 | 395.61 | 464.40 | 377.79 |
| 5H5 | 32.58 | 220.14 | 302.87 | 323.77 |
| 6F1 | 27.01 | 214.72 | 211.47 | 157.42 |
| 6F9 | 29.22 | 241.65 | 272.48 | 212.39 |
| 7H12 | 27.48 | 365.52 | 416.14 | 403.88 |
| 7H4 | 27.58 | 279.54 | 333.76 | 305.97 |
| 8A10 | 29.59 | 371.75 | 438.83 | 402.82 |
| 9B6 | 26.04 | 267.77 | 442.83 | 415.75 |
| 9C10 | 28.34 | 260.90 | 273.98 | 113.19 |
| 12B10 | 25.38 | 199.61 | 258.99 | 99.53 |
| 12B9 | 23.26 | 272.40 | 284.54 | 116.58 |
| 12E1 | 25.74 | 302.00 | 68.24 | 47.49 |
| 13A12 | 27.03 | 172.35 | 196.80 | 99.19 |
| 13D8 | 25.03 | 386.35 | 462.70 | 430.94 |
| 14A4 | 27.45 | 408.81 | 471.49 | 440.18 |
| 14D2 | 27.58 | 243.74 | 295.29 | 212.84 |
| 15C8 | 30.12 | 392.47 | 448.20 | 440.61 |
| 18H6 | 26.27 | 160.84 | 222.63 | 213.72 |

Example 22

Analysis of cDNA Expression using Real-Time PCR

Real-time PCR (see Gibson et al., *Genome Research* 6:995–1001, 1996; Heid et al., *Genome Research* 6:986–994,1996) is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR is performed, for example, using a Perkin Elmer/Applied Biosystems (Foster City, Calif.) 7700 Prism instrument. Matching primers and fluorescent probes are designed for genes of interest using, for example, the primer express program provided by Perkin Elmer/Applied Biosystems (Foster City, Calif.). Optimal concentrations of primers and probes are initially determined by those of ordinary skill in the art, and control (e.g., β-actin) primers and probes are obtained commercially from, for example, Perkin Elmer/Applied Biosystems (Foster City, Calif.). To quantitate the amount of specific RNA in a sample, a standard curve is generated using a plasmid containing the gene of interest. Standard curves are generated using the Ct values determined in the real-time PCR, which are related to the initial cDNA concentration used in the assay. Standard dilutions ranging from 10–$10^6$ copies of the gene of interest are generally sufficient. In addition, a standard curve is generated for the control sequence. This permits standardization of initial RNA content of a tissue sample to the amount of control for comparison purposes.

An alternative real-time PCR procedure can be carried out as follows: The first-strand cDNA to be used in the quantitative real-time PCR is synthesized from 20 μg of total RNA that is first treated with DNase I (e.g., Amplification Grade, Gibco BRL Life Technology, Gaitherburg, Md.), using Superscript Reverse Transcriptase (RT) (e.g., Gibco BRL Life Technology, Gaitherburg, Md.). Real-time PCR is performed, for example, with a GeneAmp™ 5700 sequence detection system (PE Biosystems, Foster City, Calif.). The 5700 system uses SYBR™ green, a fluorescent dye that only intercalates into double stranded DNA, and a set of gene-specific forward and reverse primers. The increase in fluorescence is monitored during the whole amplification process. The optimal concentration of primers is determined using a checkerboard approach and a pool of cDNAs from ovarian tumors is used in this process. The PCR reaction is performed in 25 μl volumes that include 2.5 μl of SYBR green buffer, 2 μl of cDNA template and 2.5 μl each of the forward and reverse primers for the gene of interest. The cDNAs used for RT reactions are diluted approximately 1:10 for each gene of interest and 1:100 for the β-actin control. In order to quantitate the amount of specific cDNA (and hence initial mRNA) in the sample, a standard curve is generated for each run using the plasmid DNA containing the gene of interest. Standard curves are generated using the Ct values determined in the real-time PCR which are related to the initial cDNA concentration used in the assay. Standard dilution ranging from $20–2\times10^6$ copies of the gene of interest are used for this purpose. In addition, a standard curve is generated for β-actin ranging from 200 fg–2000 fg. This enables standardization of the initial RNA content of a tissue sample to the amount of β-actin for comparison purposes. The mean copy number for each group of tissues tested is normalized to a constant amount of β-actin, allowing the evaluation of the over-expression levels seen with each of the genes.

Example 23

Peptide Priming of T-Helper Lines

Generation of $CD4^+$ T helper lines and identification of peptide epitopes derived from tumor-specific antigens that are capable of being recognized by $CD4^+$ T cells in the context of HLA class II molecules, is carried out as follows:

Fifteen-mer peptides overlapping by 10 amino acids, derived from a tumor-specific antigen, are generated using standard procedures. Dendritic cells (DC) are derived from PBMC of a normal donor using GM-CSF and IL-4 by standard protocols. $CD4^+$ T cells are generated from the same donor as the DC using MACS beads (Miltenyi Biotec, Auburn, Calif.) and negative selection. DC are pulsed overnight with pools of the 15-mer peptides, with each peptide at a final concentration of 0.25 μg/ml. Pulsed DC are washed and plated at $1\times10^4$ cells/well of 96-well V-bottom plates and purified $CD4^+$ T cells are added at $1\times10^5$/well. Cultures are supplemented with 60 ng/ml IL-6 and 10 ng/ml IL-12 and incubated at 37° C. Cultures are restimulated as above on a weekly basis using DC generated and pulsed as above as antigen presenting cells, supplemented with 5 ng/ml IL-7 and 10 U/ml IL-2. Following 4 in vitro stimulation cycles, resulting $CD4^+$ T cell lines (each line corresponding to one well) are tested for specific proliferation and cytokine production in response to the stimulating pools of peptide with an irrelevant pool of peptides used as a control.

Example 24

Generation of Tumor-Specific CTL Lines using in Vitro Whole-Gene Priming

Using in vitro whole-gene priming with tumor antigen-vaccinia infected DC (see, for example, Yee et al, *The Journal of Immunology,* 157(9):4079–86, 1996), human CTL lines are derived that specifically recognize autologous fibroblasts transduced with a specific tumor antigen, as determined by interferon-γ ELISPOT analysis. Specifically, dendritic cells (DC) are differentiated from monocyte cultures derived from PBMC of normal human donors by growing for five days in RPMI medium containing 10% human serum, 50 ng/ml human GM-CSF and 30 ng/ml human IL-4. Following culture, DC are infected overnight with tumor antigen-recombinant vaccinia virus at a multiplicity of infection (M.O.I) of five, and matured overnight by the addition of 3 μg/ml CD40 ligand. Virus is then inactivated by UV irradiation. CD8+ T cells are isolated using a magnetic bead system, and priming cultures are initiated using standard culture techniques. Cultures are restimulated every 7–10 days using autologous primary fibroblasts retrovirally transduced with previously identified tumor antigens. Following four stimulation cycles, CD8+ T cell lines are identified that specifically produce interferon-γ when stimulated with tumor antigen-transduced autologous fibroblasts. Using a panel of HLA-mismatched B-LCL lines transduced with a vector expressing a tumor antigen, and measuring interferon-γ production by the CTL lines in an ELISPOT assay, the HLA restriction of the CTL lines is determined.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated antibody, or antigen-binding fragment thereof, that specifically binds to a polypeptide having the amino acid sequence set forth in SEQ ID NO: 312.

2. A diagnostic kit comprising at least one antibody according to claim 1 and a detection reagent, wherein the detection reagent comprises a reporter group.

3. An isolated antibody of claim 1, wherein the antibody specifically binds to amino acid residues of SEQ ID NO: 312 selected from the group consisting of 54–68, 94–108, 104–118, 124–138, 164–178, 274–288, 504–518, 534–548, 544–558, 564–578, 614–628, 624–638, 634–648, 644–658, 744–758, and 774–801.

4. An isolated antibody of claim 1, wherein the antibody is a polyclonal antibody.

5. An isolated antibody of claim 1, wherein the antibody is a monoclonal antibody.

6. An isolated antibody of claim 1, wherein the antibody is a humanized antibody.

7. An isolated antibody of claim 1 said antibody coupled to a radionuclide.

8. An isolated antibody of claim 7, wherein the radionuclide is selected from the group consisting of $^{90}$Y, $^{123}$I, $^{125}$I, $^{131}$I, $^{186}$Re, $^{188}$Re, $^{211}$At, and $^{212}$Bi.

* * * * *

SEQUENCE LISTING

```
<160> NUMBER OF SEQ ID NOS: 624
<210> SEQ ID NO 1
<211> LENGTH: 461
<212> TYPE: DNA
<213> ORGANISM: Homo sapiens

<400> SEQUENCE: 1

ttagagaggc acagaaggaa gaagagttaa aagcagcaaa gccgggtttt tttgttttgt      60

tttgttttgt tttgttttga gatggagtct cactctgttg cccaagctgg agtacaacgg     120

catgatctca gctcgctgca acctccgcct cccacgttca agtgattctc ctgcctcagc     180
```

-continued

```
ctcccaagta gctgggatta caggcgcccg ccaccacgct cagctaattt tttttgtatt    240

tttagtagag acagggtttc accaggttgg ccaggctgct cttgaactcc tgacctcagg    300

tgatccaccc gcctcggcct cccaaagtgc tgggattaca ggcgtgagcc accacgcccg    360

gcccccaaag ctgtttcttt tgtctttagc gtaaagctct cctgccatgc agtatctaca    420

taactgacgt gactgccagc aagctcagtc actccgtggt c                        461


<210> SEQ ID NO 2
<211> LENGTH: 540
<212> TYPE: DNA
<213> ORGANISM: Homo sapiens

<400> SEQUENCE: 2

taggatgtgt tggaccctct gtgtcaaaaa aaacctcaca aagaatcccc tgctcattac     60

agaagaagat gcatttaaaa tatgggttat tttcaacttt ttatctgagg acaagtatc     120

attaattatt gtgtcagaag agattgaata cctgcttaag aagcttacag aagctatggg    180

aggaggttgg cagcaagaac aatttgaaca ttataaaatc aactttgatg acagtaaaaa    240

tggcctttct gcatgggaac ttattgagct tattggaaat ggacagttta gcaaaggcat    300

ggaccggcag actgtgtcta tggcaattaa tgaagtcttt aatgaactta tattagatgt    360

gttaaagcag ggttacatga tgaaaaaggg ccacagacgg aaaaactgga ctgaaagatg    420

gtttgtacta aaacccaaca taatttctta ctatgtgagt gaggatctga aggataagaa    480

aggagacatt ctcttggatg aaaattgctg tgtagagtcc ttgcctgaca aagatggaaa    540


<210> SEQ ID NO 3
<211> LENGTH: 461
<212> TYPE: DNA
<213> ORGANISM: Homo sapiens

<400> SEQUENCE: 3

ttagagaggc acagaaggaa gaagagttaa aagcagcaaa gccgggtttt tttgttttgt     60

tttgttttgt tttgttttga gatggagtct cactctgttg cccaagctgg agtacaacgg    120

catgatctca gctcgctgca acctccgcct cccacgttca agtgattctc ctgcctcagc    180

ctcccaagta gctgggatta caggcgcccg ccaccacgct cagctaattt tttttgtatt    240

tttagtagag acagggtttc accaggttgg ccaggctgct cttgaactcc tgacctcagg    300

tgatccaccc gcctcggcct cccaaagtgc tgggattaca ggcgtgagcc accacgcccg    360

gcccccaaag ctgtttcttt tgtctttagc gtaaagctct cctgccatgc agtatctaca    420

taactgacgt gactgccagc aagctcagtc actccgtggt c                        461


<210> SEQ ID NO 4
<211> LENGTH: 531
<212> TYPE: DNA
<213> ORGANISM: Homo sapiens
<220> FEATURE:
<221> NAME/KEY: misc_feature
<222> LOCATION: 454, 492, 526
<223> OTHER INFORMATION: n = A,T,C or G

<400> SEQUENCE: 4

tctttttctt tcgatttcct tcaatttgtc acgtttgatt ttatgaagtt gttcaagggc     60

taactgctgt gtattatagc tttctctgag ttccttcagc tgattgttaa atgaatccat    120

ttctgagagc ttagatgcag tttctttttc aagagcatct aattgttctt taagtctttg    180
```

-continued

```
gcataattct tccttttctg atgacttttt atgaagtaaa ctgatccctg aatcaggtgt    240

gttactgagc tgcatgtttt taattctttc gtttaatagc tgcttctcag ggaccagata    300

gataagctta ttttgatatt ccttaagctc ttgttgaagt tgtttgattt ccataatttc    360

caggtcacac tgtttatcca aaacttctag ctcagtcttt tgtgtttgct ttctgatttg    420

gacatcttgt agtctgcctg agatctgctg atgntttcca ttcactgctt ccagttccag    480

gtggagactt tnctttctgg agctcagcct gacaatgcct tcttgntccc t             531
```

<210> SEQ ID NO 5
<211> LENGTH: 531
<212> TYPE: DNA
<213> ORGANISM: Homo sapiens

<400> SEQUENCE: 5

```
agccagatgg ctgagagctg caagaagaag tcaggatcat gatggctcag tttcccacag     60

cgatgaatgg agggccaaat atgtgggcta ttacatctga agaacgtact aagcatgata    120

aacagtttga taacctcaaa ccttcaggag gttacataac aggtgatcaa gcccgtactt    180

ttttcctaca gtcaggtctg ccggccccgg ttttagctga aatatgggcc ttatcagatc    240

tgaacaagga tgggaagatg gaccagcaag agttctctat agctatgaaa ctcatcaagt    300

taaagttgca gggccaacag ctgcctgtag tcctccctcc tatcatgaaa caacccccta    360

tgttctctcc actaatctct gctcgttttg ggatgggaag catgcccaat ctgtccattc    420

atcagccatt gcctccagtt gcacctatag caacaccctt gtcttctgct acttcaggga    480

ccagtattcc tcccctaatg atgcctgctc ccctagtgcc ttctgttagt a             531
```

<210> SEQ ID NO 6
<211> LENGTH: 531
<212> TYPE: DNA
<213> ORGANISM: Homo sapiens

<400> SEQUENCE: 6

```
aatagattta atgcagagtg tcaacttcaa ttgattgata gtggctgcct agagtgctgt     60

gttgagtagg tttctgagga tgcaccctgg cttgaagaga aagactggca ggattaacaa    120

tatctaaaat ctcacttgta ggagaaacca caggcaccag agctgccact ggtgctggca    180

ccagctccac caaggccagc gaagagccca aatgtgagag tggcggtcag gctggcacca    240

gcactgaagc caccactggt gctggcactg gcactggcac tgttattggt actggtactg    300

gcaccagtgc tggcactgcc actctcttgg gctttggctt tagcttctgc tcccgcctgg    360

atccgggctt tggcccaggg tccgatatca gcttcgtccc agttgcaggg cccggcagca    420

ttctccgagc cgagcccaat gcccattcga gctctaatct cggccctagc cttggcttca    480

gctgcagcct cagctgcagc cttcaaatcc gcttccatcg cctctcggta c             531
```

<210> SEQ ID NO 7
<211> LENGTH: 531
<212> TYPE: DNA
<213> ORGANISM: Homo sapiens

<400> SEQUENCE: 7

```
gccaagaaag cccgaaaggt gaagcatctg gatggggaag aggatggcag cagtgatcag     60

agtcaggctt ctggaaccac aggtggccga agggtctcaa aggccctaat ggcctcaatg    120

gcccgcaggg cttcaagggg tcccatagcc ttttgggccc gcagggcatc aaggactcgg    180

ttggctgctt gggcccggag agccttgctc tccctgagat cacctaaagc ccgtaggggc    240
```

-continued

```
aaggctcgcc gtagagctgc caagctccag tcatcccaag agcctgaagc accaccacct    300

cgggatgtgg ccccttttgca agggagggca aatgatttgg tgaagtacct tttggctaaa    360

gaccagacga agattcccat caagcgctcg gacatgctga aggacatcat caaagaatac    420

actgatgtgt accccgaaat cattgaacga gcaggctatt ccttggagaa ggtatttggg    480

attcaattga aggaaattga taagaatgac cacttgtaca ttcttctcag c             531
```

<210> SEQ ID NO 8
<211> LENGTH: 531
<212> TYPE: DNA
<213> ORGANISM: Homo sapiens
<220> FEATURE:
<221> NAME/KEY: misc_feature
<222> LOCATION: 481
<223> OTHER INFORMATION: n = A,T,C or G

<400> SEQUENCE: 8

```
gaggtctcac tatgttgccc aggctgttct tgaactcctg ggatcaagca atccacccat     60

gttggtctcc aaaagtgctg ggatcatagg cgtgagccac ctcacccagc caccaatttt    120

caatcaggaa gactttttcc ttcttcaaga agtgaagggt ttccagagta tagctacact    180

attgcttgcc tgagggtgac tacaaaattg cttgctaaaa ggttaggatg ggtaaagaat    240

tagattttct gaatgcaaaa ataaaatgtg aactaatgaa ctttaggtaa tacatattca    300

taaaataatt attcacatat ttcctgattt atcacagaaa taatgtatga aatgctttga    360

gtttcttgga gtaaactcca ttactcatcc caagaaacca tattataagt atcactgata    420

ataagaacaa caggaccttg tcataaattc tggataagag aaatagtctc tgggtgtttg    480

ntcttaattg ataaaattta cttgtccatc ttttagttca gaatcacaaa a             531
```

<210> SEQ ID NO 9
<211> LENGTH: 531
<212> TYPE: DNA
<213> ORGANISM: Homo sapiens
<220> FEATURE:
<221> NAME/KEY: misc_feature
<222> LOCATION: 528
<223> OTHER INFORMATION: n = A,T,C or G

<400> SEQUENCE: 9

```
aagcggaaat gagaaaggag ggaaaatcat gtggtattga gcggaaaact gctggatgac     60

agggctcagt cctgttggag aactctgggt ggtgctgtag aacagggcca ctcacagtgg    120

ggtgcacaga ccagcacggc tctgtgacct gtttgttaca ggtccatgat gaggtaaaca    180

atacactgag tataagggtt ggtttagaaa ctcttacagc aatttgacaa agtaatcttc    240

tgtgcagtga atctaagaaa aaaattgggg ctgtatttgt atgttccttt ttttcatttc    300

atgttctgag ttacctattt ttattgcatt ttacaaaagc atccttccat gaaggaccgg    360

aagttaaaaa caaagcaggt cctttatcac agcactgtcg tagaacacag ttcagagtta    420

tccacccaag gagccaggga gctgggctaa accaaagaat tttgcttttg gttaatcatc    480

aggtacttga gttggaattg ttttaatccc atcattacca ggctggangt g             531
```

<210> SEQ ID NO 10
<211> LENGTH: 861
<212> TYPE: DNA
<213> ORGANISM: Homo sapiens

<400> SEQUENCE: 10

-continued

```
ccgcggctcc tgtccagacc ctgaccctcc ctcccaaggc tcaaccgtcc cccaacaacc     60

gccagccttg tactgatgtc ggctgcgaga gcctgtgctt aagtaagaat caggccttat    120

tggagacatt caagcaaagg ttggacaact acttttccag aacagaaagg aaactcatgc    180

atcagaaaag gtgactaata aaggtaccag aagaatatgg ctgcacaaat accagaatct    240

gatcagataa aacagtttaa ggaatttctg ggacctaca ataaacttac agagacctgc    300

tttttggact gtgttagaga cttcacaaca agagaagtaa aacctgaaga gaccacctgt    360

tcagaacatt gcttacagaa atatttaaaa atgacacaaa gaatatccat gagatttcag    420

gaatatcata ttcagcagaa tgaagccctg gcagccaaag caggactcct tggccaacca    480

cgatagagaa gtcctgatgg atgaactttt gatgaaagat tgccaacagc tgctttattg    540

gaaatgagga ctcatctgat agaatcccct gaaagcagta gccaccatgt tcaaccatct    600

gtcatgactg tttggcaaat ggaaaccgct ggagaaacaa aattgctatt taccaggaat    660

aatcacaata gaaggtctta ttgttcagtg aaataataag atgcaacatt tgttgaggcc    720

ttatgattca gcagcttggt cacttgatta gaaaaataaa ccattgtttc ttcaattgtg    780

actgttaatt ttaaagcaac ttatgtgttc gatcatgtat gagatagaaa aatttttatt    840

actcaaagta aaataaatgg a                                              861
```

<210> SEQ ID NO 11
<211> LENGTH: 541
<212> TYPE: DNA
<213> ORGANISM: Homo sapiens

<400> SEQUENCE: 11

```
gaaaaaaaat ataaaacaca cttttgcgaa aacggtggcc ctaaaagagg aaaagaattt     60

caccaatata aatccaattt tatgaaaact gacaatttaa tccaagaatc acttttgtaa    120

atgaagctag caagtgatga tatgataaaa taaacgtgga ggaaataaaa acacaagact    180

tggcataaga tatatccact tttgatatta aacttgtgaa gcatattctt cgacaaattg    240

tgaaagcgtt cctgatcttg cttgttctcc atttcaaata aggaggcata tcacatccca    300

agagtaacag aaaaagaaaa aagacatttt tgcattttga gatgaaccaa agacacaaaa    360

caaaacgaac aaagtgtcat gtctaattct agcctctgaa ataaaccttg aacatctcct    420

acaaggcacc gtgatttttg taattctaac ctgaagaaat gtgatgactt ttgtggacat    480

gaaaatcaga tgagaaaact gtggtctttc caaagcctga actcccctga aaacctttgc    540

a                                                                    541
```

<210> SEQ ID NO 12
<211> LENGTH: 541
<212> TYPE: DNA
<213> ORGANISM: Homo sapiens

<400> SEQUENCE: 12

```
ctgggatcat ttctcttgat gtcataaaag actcttcttc ttcctcttca tcctcttctt     60

catcctcttc tgtacagtgc tgccgggtac aacggctatc tttgtcttta tcctgagatg    120

aagatgatgc ttctgtttct cctaccataa ctgaagaaat ttcgctggaa gtcgtttgac    180

tggctgtttc tctgacttca ccttctttgt caaacctgag tctttttacc tcatgcccct    240

cagcttccac agcatcttca tctggatgtt tatttttcaa agggctcact gaggaaactt    300

ctgattcaga ggtcgaagag tcactgtgat ttttctcctc attttgctgc aaatttgcct    360

ctttgctgtc tgtgctctca ggcaacccat ttgttgtcat gggggctgac aaagaaacct    420
```

ttggtcgatt aagtggcctg ggtgtcccag gcccatttat attagacctc tcagtatagc 480
ttggtgaatt tccaggaaac ataacaccat tcattcgatt taaactattg gaattggttt 540
t 541

<210> SEQ ID NO 13
<211> LENGTH: 441
<212> TYPE: DNA
<213> ORGANISM: Homo sapiens

<400> SEQUENCE: 13
gagggttggt ggtagcggct tggggaggtg ctcgctctgt cggtcttgct ctctcgcacg 60
cttcccccgg ctcccttcgt ttcccccccc cggtcgcctg cgtgccggag tgtgtgcgag 120
ggagggggag ggcgtcgggg gggtgggggg aggcgttccg gtccccaaga gacccgcgga 180
gggaggcgga ggctgtgagg gactccggga agccatggac gtcgagaggc tccaggaggc 240
gctgaaagat tttgagaaga gggggaaaaa ggaagtttgt cctgtcctgg atcagtttct 300
ttgtcatgta gccaagactg gagaaacaat gattcagtgg tcccaattta aaggctattt 360
tattttcaaa ctggagaaag tgatggatga tttcagaact tcagctcctg agccaagagg 420
tcctcccaac cctaatgtcg a 441

<210> SEQ ID NO 14
<211> LENGTH: 131
<212> TYPE: DNA
<213> ORGANISM: Homo sapiens
<220> FEATURE:
<221> NAME/KEY: misc_feature
<222> LOCATION: 126
<223> OTHER INFORMATION: n = A,T,C or G

<400> SEQUENCE: 14
aagcaggcgg ctcccgcgct cgcagggccg tgccacctgc ccgcccgccc gctcgctcgc 60
tcgcccgccg cgccgcgctg ccgaccgcca gcatgctgcc gagagtgggc tgccccgcgc 120
tgccgntgcc g 131

<210> SEQ ID NO 15
<211> LENGTH: 692
<212> TYPE: DNA
<213> ORGANISM: Homo sapiens

<400> SEQUENCE: 15
atctcttgta tgccaaatat ttaatataaa tctttgaaac aagttcagat gaaataaaaa 60
tcaaagtttg caaaaacgtg aagattaact taattgtcaa atattcctca ttgccccaaa 120
tcagtatttt ttttatttct atgcaaaagt atgccttcaa actgcttaaa tgatatatga 180
tatgatacac aaaccagttt tcaaatagta aagccagtca tcttgcaatt gtaagaaata 240
ggtaaaagat tataagacac cttacacaca cacacacaca cacacacgtg tgcacgccaa 300
tgacaaaaaa caatttggcc tctcctaaaa taagaacatg aagaccctta attgctgcca 360
ggagggaaca ctgtgtcacc cctccctaca atccaggtag tttcctttaa tccaatagca 420
aatctgggca tatttgagag gagtgattct gacagccacg ttgaaatcct gtggggaacc 480
attcatgtcc acccactggt gccctgaaaa aatgccaata atttttcgct cccacttctg 540
ctgctgtctc ttccacatcc tcacatagac cccagacccg ctggcccctg gctgggcatc 600
gcattgctgg tagagcaagt cataggtctc gtctttgacg tcacagaagc gatacaccaa 660

-continued

```
attgcctggt cggtcattgt cataaccaga ga                                 692


<210> SEQ ID NO 16
<211> LENGTH: 728
<212> TYPE: DNA
<213> ORGANISM: Homo sapiens

<400> SEQUENCE: 16

cagacggggt ttcactatgt tggctaggct ggtcttgaac tcctgacttc aggtgatctg     60

cctgccttgg cctcccaaag tgctgggatt acaggcataa gccactgcgc ccggctgatc    120

tgatggtttc ataaggcttt tccccctttt gctcagcact tctccttcct gccgccatgt    180

gaagaaggac atgtttgctt cccctccac cacgattgta agttgtttcc tgaggcctcc    240

ccggccatgc tgaactgtga gtcaattaaa cctctttcct ttataaatta tccagttttg    300

ggtatgtctt tattagtaga atgagaacag actaatacaa cccttaaagg agactgacgg    360

agaggattct tcctggatcc cagcacttcc tctgaatgct actgacattc ttcttgagga    420

ctttaaactg ggagatagaa aacagattcc atggctcagc agcctgagag cagggaggga    480

gccaagctat agatgacatg ggcagcctcc cctgaggcca ggtgtggccg aacctgggca    540

gtgctgccac ccaccccacc agggccaagt cctgtccttg gagagccaag cctcaatcac    600

tgctagcctc aagtgtcccc aagccacagt ggctaggggg actcagggaa cagttcccag    660

tctgccctac ttctcttacc tttaccccctc atacctccaa agtagaccat gttcatgagg    720

tccaaagg                                                             728


<210> SEQ ID NO 17
<211> LENGTH: 531
<212> TYPE: DNA
<213> ORGANISM: Homo sapiens
<220> FEATURE:
<221> NAME/KEY: misc_feature
<222> LOCATION: 518, 528
<223> OTHER INFORMATION: n = A,T,C or G

<400> SEQUENCE: 17

aagcgaggaa gccactgcgg ctcctggctg aaaagcggcg ccaggctcgg gaacagaggg     60

aacgcgaaga acaggagcgg aagctgcagg ctgaaaggga caagcgaatg cgagaggagc    120

agctggcccg ggaggctgaa gcccgggctg aacgtgaggc cgaggcgcgg agacgggagg    180

agcaggaggc tcgagagaag gcgcaggctg agcaggagga gcaggagcga ctgcagaagc    240

agaaagagga agccgaagcc cggtcccggg aagaagctga gcgccagcgc caggagcggg    300

aaaagcactt tcagaaggag gaacaggaga gacaagagcg aagaaagcgg ctggaggaga    360

taatgaagag gactcggaaa tcagaagccg ccgaaaccaa gaagcaggat gcaaaggaga    420

ccgcagctaa caattccggc ccagaccctt gtgaaagctg tagagactcg gccctctggg    480

cttccagaaa ggattctatt gcagaaagga aggagctngg ccccccangg a            531


<210> SEQ ID NO 18
<211> LENGTH: 1041
<212> TYPE: DNA
<213> ORGANISM: Homo sapiens
<220> FEATURE:
<221> NAME/KEY: misc_feature
<222> LOCATION: 544
<223> OTHER INFORMATION: n = A,T,C or G

<400> SEQUENCE: 18

ctctgtggaa aactgatgag gaatgaattt accattaccc atgttctcat ccccaagcaa     60
```

-continued

```
agtgctgggt ctgattactg caacacagag aacgaagaag aacttttcct catacaggat    120
cagcagggcc tcatcacact gggctggatt catactcacc ccacacagac cgcgtttctc    180
tccagtgtcg acctacacac tcactgctct taccagatga tgttgccaga gtcagtagcc    240
attgtttgct cccccaagtt ccaggaaact ggattcttta aactaactga ccatggacta    300
gaggagattt cttcctgtcg ccagaaagga tttcatccac acagcaagga tccacctctg    360
ttctgtagct gcagccacgt gactgttgtg gacagagcag tgaccatcac agaccttcga    420
tgagcgtttg agtccaacac cttccaagaa caacaaaacc atatcagtgt actgtagccc    480
cttaatttaa gctttctaga aagctttgga agtttttgta gatagtagaa agggggcat    540
cacntgagaa agagctgatt ttgtatttca ggtttgaaaa gaaataactg aacatatttt    600
ttaggcaagt cagaaagaga acatggtcac ccaaaagcaa ctgtaactca gaaattaagt    660
tactcagaaa ttaagtagct cagaaattaa gaaagaatgg tataatgaac ccccatatac    720
ccttccttct ggattcacca attgttaaca tttttttcct ctcagctatc cttctaattt    780
ctctctaatt tcaatttgtt tatatttacc tctgggctca ataagggcat ctgtgcagaa    840
atttggaagc catttagaaa atcttttgga ttttcctgtg gtttatggca atatgaatgg    900
agcttattac tggggtgagg gacagcttac tccatttgac cagattgttt ggctaacaca    960
tcccgaagaa tgattttgtc aggaattatt gttatttaat aaatatttca ggatattttt   1020
cctctacaat aaagtaacaa t                                             1041
```

<210> SEQ ID NO 19
<211> LENGTH: 1043
<212> TYPE: DNA
<213> ORGANISM: Homo sapiens

<400> SEQUENCE: 19

```
ctctgtggaa aactgatgag gaatgaattt accattaccc atgttctcat ccccaagcaa     60
agtgctgggt ctgattactg caacacagag aacgaagaag aacttttcct catacaggat    120
cagcagggcc tcatcacact gggctggatt catactcacc ccacacagac cgcgtttctc    180
tccagtgtcg acctacacac tcactgctct taccagatga tgttgccaga gtcagtagcc    240
attgtttgct cccccaagtt ccaggaaact ggattcttta aactaactga ccatggacta    300
gaggagattt cttcctgtcg ccagaaagga tttcatccac acagcaagga tccacctctg    360
ttctgtagct gcagccacgt gactgttgtg gacagagcag tgaccatcac agaccttcga    420
tgagcgtttg agtccaacac cttccaagaa caacaaaacc atatcagtgt actgtagccc    480
cttaatttaa gctttctaga aagctttgga agtttttgta gatagtagaa agggggcat    540
cacctgagaa agagctgatt ttgtatttca ggtttgaaaa gaaataactg aacatatttt    600
ttaggcaagt cagaaagaga acatggtcac ccaaaagcaa ctgtaactca gaaattaagt    660
tactcagaaa ttaagtagct cagaaattaa gaaagaatgg tataatgaac ccccatatac    720
ccttccttct ggattcacca attgttaaca tttttttcct ctcagctatc cttctaattt    780
ctctctaatt tcaatttgtt tatatttacc tctgggctca ataagggcat ctgtgcagaa    840
atttggaagc catttagaaa atcttttgga ttttcctgtg gtttatggca atatgaatgg    900
agcttattac tggggtgagg gacagcttac tccatttgac cagattgttt ggctaacaca    960
tcccgaagaa tgattttgtc aggaattatt gttatttaat aaatatttca ggatattttt   1020
cctctacaat aaagtaacaa tta                                           1043
```

-continued

<210> SEQ ID NO 20
<211> LENGTH: 448
<212> TYPE: DNA
<213> ORGANISM: Homo sapiens

<400> SEQUENCE: 20
ggacgacaag gccatggcga tatcggatcc gaattcaagc ctttggaatt aaataaacct 60
ggaacaggga aggtgaaagt tggagtgaga tgtcttccat atctatacct ttgtgcacag 120
ttgaatggga actgtttggg tttagggcat cttagagttg attgatggaa aaagcagaca 180
ggaactggtg ggaggtcaag tggggaagtt ggtgaatgtg gaataactta cctttgtgct 240
ccacttaaac cagatgtgtt gcagctttcc tgacatgcaa ggatctactt taattccaca 300
ctctcattaa taaattgaat aaaagggaat gttttggcac ctgatataat ctgccaggct 360
atgtgacagt aggaaggaat ggtttcccct aacaagccca atgcactggt ctgactttat 420
aaattattta ataaaatgaa ctattatc 448

<210> SEQ ID NO 21
<211> LENGTH: 411
<212> TYPE: DNA
<213> ORGANISM: Homo sapiens

<400> SEQUENCE: 21
ggcagtgaca ttcaccatca tgggaaccac cttccctttt cttcaggatt ctctgtagtg 60
gaagagagca cccagtgttg ggctgaaaac atctgaaagt agggagaaga acctaaaata 120
atcagtatct cagagggctc taaggtgcca agaagtctca ctggacattt aagtgccaac 180
aaaggcatac tttcggaatc gccaagtcaa aactttctaa cttctgtctc tctcagagac 240
aagtgagact caagagtcta ctgctttagt ggcaactaca gaaaactggt gttacccaga 300
aaaacaggag caattagaaa tggttccaat atttcaaagc tccgcaaaca ggatgtgctt 360
tcctttgccc atttagggtt tcttctcttt cctttctctt tattaaccac t 411

<210> SEQ ID NO 22
<211> LENGTH: 896
<212> TYPE: DNA
<213> ORGANISM: Homo sapiens
<220> FEATURE:
<221> NAME/KEY: misc_feature
<222> LOCATION: 230, 320
<223> OTHER INFORMATION: n = A,T,C or G

<400> SEQUENCE: 22
tgcgctgaaa acaacggcct cctttactgt taaaatgcag ccacaggtgc ttagccgtgg 60
gcatctcaac caccagcctc tgtggggggc aggtgggcgt ccctgtgggc ctctgggccc 120
acgtccagcc tctgtcctct gccttccgtt cttcgacagt gttcccggca tccctggtca 180
cttggtactt ggcgtgggcc tcctgtgctg ctccagcagc tcctccaggn ggtcggcccg 240
cttcaccgca gcctcatgtt gtgtccggag gctgctcacg gcctcctcct tcctcgcgag 300
ggctgtcttc accctccggn gcacctcctc cagctccagc tgctggcggg cctgcagcgt 360
ggccagctcg gccttggcct gccgcgtctc ctcctcarag gctgccagcc ggtcctcgaa 420
ctcctggcgg atcacctggg ccaggttgct gcgctcgcta gaaagctgct cgttcaccgc 480
ctgcgcatcc tccagcgccc gctccttctg ccgcacaagg ccctgcagac gcagattctc 540
gccctcggcc tccccaagct ggcccttcag ctccgagcac cgctcctgaa gcttccgctc 600
cgactgctcc agctcggaga gctcggcctc gtacttgtcc cgtaagcgct tgatgcggct 660

-continued ctcggcagcc ttctcactct cctccttggc cagcgccatg tcggcctcca gccggtgaat 720
gaccagctca atctccttgt cccggccttt ccggatttct tccctcagct cctgttcccg 780
gttcagcagc cacgcctcct ccttcctggt gcggccggcc tcccacgcct gcctctccag 840
ctccagctgc tgcttcaggg tattcagctc catctggcgg gcctgcagcg tggcca 896

<210> SEQ ID NO 23
<211> LENGTH: 111
<212> TYPE: DNA
<213> ORGANISM: Homo sapiens

<400> SEQUENCE: 23
caacttatta cttgaaatta taatatagcc tgtccgtttg ctgtttccag gctgtgatat 60
attttcctag tggtttgact ttaaaaataa ataaggttta attttctccc c 111

<210> SEQ ID NO 24
<211> LENGTH: 531
<212> TYPE: DNA
<213> ORGANISM: Homo sapiens
<220> FEATURE:
<221> NAME/KEY: misc_feature
<222> LOCATION: 472, 494
<223> OTHER INFORMATION: n = A,T,C or G

<400> SEQUENCE: 24
tgcaagtcac gggagtttat ttatttaatt tttttcccca gatggagact ctgtcgccca 60
ggctggagtg caatggtgtg atcttggctc actgcaacct ccacctcctg ggttcaagcg 120
attctcctgc cacagcctcc cgagtagctg ggattacagg tgcccgccac cacacccagc 180
taatttttat atttttagta aagacagggt ttccccatgt tggccaggct ggtcttgaac 240
ttctgacctc aggtgatcca cctgcctcgg cctcccaaag tgttgggatt acaggcgtga 300
gctacccgtg cctggccagc cactggagtt taaaggacag tcatgttggc tccagcctaa 360
ggcggcattt tcccccatca gaaagcccgc ggctcctgta cctcaaaata gggcacctgt 420
aaagtcagtc agtgaagtct ctgctctaac tggccacccg gggccattgg cntctgacac 480
agccttgcca ggangcctgc atctgcaaaa gaaaagttca cttcctttcc g 531

<210> SEQ ID NO 25
<211> LENGTH: 471
<212> TYPE: DNA
<213> ORGANISM: Homo sapiens
<220> FEATURE:
<221> NAME/KEY: misc_feature
<222> LOCATION: 377
<223> OTHER INFORMATION: n = A,T,C or G

<400> SEQUENCE: 25
cagagaatct kagaaagatg tcgcgttttc ttttaatgaa tgagagaagc ccatttgtat 60
ccctgaatca ttgagaaaag gcggcggtgg cgacagcggc gacctaggga tcgatctgga 120
gggacttggg gagcgtgcag agacctctag ctcgagcgcg agggacctcc cgccgggatg 180
cctggggagc agatggaccc tactggaagt cagttggatt cagatttctc tcagcaagat 240
actccttgcc tgataattga agattctcag cctgaaagcc aggttctaga ggatgattct 300
ggttctcact tcagtatgct atctcgacac cttcctaatc tccagacgca caaagaaaat 360
cctgtgttgg atgttgngtc caatccttga acaaacagct ggagaagaac gaggagaccg 420
gtaatagtgg gttcaatgaa catttgaaag aaaaccaggt tgcagaccct g 471

-continued

<210> SEQ ID NO 26
<211> LENGTH: 541
<212> TYPE: DNA
<213> ORGANISM: Homo sapiens

<400> SEQUENCE: 26
gactgtcctg aacaagggac ctctgaccag agagctgcag gagatgcaga gtggtggcag 60
gagtggaagc caaagaacac ccaccttcct cccttgaagg agtagagcaa ccatcagaag 120
atactgtttt attgctctgg tcaaacaagt cttcctgagt tgacaaaacc tcaggctctg 180
gtgacttctg aatctgcagt ccactttcca taagttcttg tgcagacaac tgttcttttg 240
cttccatagc agcaacagat gctttggggc taaaaggcat gtcctctgac cttgcaggtg 300
gtggattttg ctcttttaca acatgtacat ccttactggg ctgtgctgtc acagggatgt 360
ccttgctgga ctgttctgct atggggatat cttcgttgga ctgttcttca tgcttaattg 420
cagtattagc atccacatca gacagcctgg tataaccaga gttggtggtt actgattgta 480
gctgctcttt gtccacttca tatggcacaa gtattttcct caacatcctg gctctgggaa 540
g 541

<210> SEQ ID NO 27
<211> LENGTH: 461
<212> TYPE: DNA
<213> ORGANISM: Homo sapiens
<220> FEATURE:
<221> NAME/KEY: misc_feature
<222> LOCATION: 367
<223> OTHER INFORMATION: n = A,T,C or G

<400> SEQUENCE: 27
gaaatgtata tttaatcatt ctcttgaacg atcagaactc traaatcagt tttctataac 60
arcatgtaat acagtcaccg tggctccaag gtccaggaag gcagtggtta acacatgaag 120
agtgtgggaa gggggctgga aacaaagtat tcttttcctt caaagcttca ttcctcaagg 180
cctcaattca agcagtcatt gtccttgctt tcaaaagtct gtgtgtgctt catggaaggt 240
atatgtttgt tgccttaatt tgaattgtgg ccaggaaggg tctggagatc taaattcaga 300
gtaagaaaac ctgagctaga actcaggcat ttctcttaca gaacttggct tgcagggtag 360
aatgaangga aagaaactta gaagctcaac aagctgaaga taatcccatc aggcatttcc 420
cataggcctt gcaactctgt tcactgagag atgttatcct g 461

<210> SEQ ID NO 28
<211> LENGTH: 541
<212> TYPE: DNA
<213> ORGANISM: Homo sapiens

<400> SEQUENCE: 28
agtctggagt gagcaaacaa gagcaagaaa caarragaag ccaaaagcag aaggctccaa 60
tatgaacaag ataaatctat cttcaaagac atattagaag ttgggaaaat aattcatgtg 120
aactagacaa gtgtgttaag agtgataagt aaaatgcacg tggagacaag tgcatcccca 180
gatctcaggg acctccccct gcctgtcacc tggggagtga gaggacagga tagtgcatgt 240
tctttgtctc tgaattttta gttatatgtg ctgtaatgtt gctctgagga agcccctgga 300
aagtctatcc caacatatcc acatcttata ttccacaaat taagctgtag tatgtaccct 360
aagacgctgc taattgactg ccacttcgca actcaggggc ggctgcattt tagtaatggg 420
tcaaatgatt cactttttat gatgcttccc aaggtgcctt ggcttctctt cccaactgac 480

-continued

```
aaatgcccaa gttgagaaaa atgatcataa ttttagcata aaccgagcaa tcggcgaccc    540

c                                                                    541
```

<210> SEQ ID NO 29
<211> LENGTH: 411
<212> TYPE: DNA
<213> ORGANISM: Homo sapiens

<400> SEQUENCE: 29

```
tagctgtctt cctcactctt atggcaatga ccccatatct taatggatta agataatgaa     60

agtgtatttc ttacactctg tatctatcac cagaagctga ggtgatagcc cgcttgtcat    120

tgtcatccat attctgggac tcaggcggga actttctgga atattgccag ggagcatggc    180

agaggggcac agtgcattct gggggaatgc acattggctc agcctgggta atgagtgata    240

tacattacct ctgttcacaa ctcattgccc agcaccagtc acaaggcccc accaaatacc    300

agagcccaag aaatgtagtc ctgttgatat ggttttgctg tgtcccaacc caaatctcat    360

cttgaattgt aagctcccat aattcccatg tgttgtggga gggacctggt g             411
```

<210> SEQ ID NO 30
<211> LENGTH: 511
<212> TYPE: DNA
<213> ORGANISM: Homo sapiens

<400> SEQUENCE: 30

```
atcatgagga tgttaccaaa gggatggtac taaaccattt gtattcgtct gttttcacac     60

tgctttgaag atactacctg agactgggta atttataaac aaaagagatt taattgactc    120

acagttctgc atggctgaag aggcctcagg aaacttacag tcatggtgga aggcaaagga    180

ggagcaaggc atgtcttaca tgtcagtagg agagagagcg agagcaggag aacctgccac    240

ttataaacca ttcagatctc ataactccct atcatgagaa aaacatggag gaaaccaccc    300

tcatgatcca atcacctccc gccaggtccc tccctcgaca cgtggggatt ataattcagg    360

attagaggga cacagagaca aaccatatca tcattcatga gaaatccacc ctcatagtcc    420

aatcagctcc taccaggccc cacctccaac actggggatt gcaattcaac atgagatttg    480

gatggggaca cagattcaaa ccatatcata c                                   511
```

<210> SEQ ID NO 31
<211> LENGTH: 827
<212> TYPE: DNA
<213> ORGANISM: Homo sapiens

<400> SEQUENCE: 31

```
catggccttt ctccttagag gccagaggtg ctgccctggc tgggagtgaa gctccaggca     60

ctaccagctt tcctgatttt cccgtttggt ccatgtgaag agctaccacg agccccagcc    120

tcacagtgtc cactcaaggg cagcttggtc ctcttgtcct gcagaggcag gctggtgtga    180

ccctgggaac ttgacccggg aacaacaggt ggcccagagt gagtgtggcc tggcccctca    240

acctagtgtc cgtcctcctc tctcctggag ccagtcttga gtttaaaggc attaagtgtt    300

agatacaagc tccttgtggc tggaaaaaca cccctctgct gataaagctc agggggcact    360

gaggaagcag aggccccttg ggggtgccct cctgaagaga gcgtcaggcc atcagctctg    420

tccctctggt gctcccacgt ctgttcctca ccctccatct ctgggagcag ctgcacctga    480

ctggccacgc gggggcagtg gaggcacagg ctcagggtgg ccgggctacc tggcacccta    540
```

-continued

```
tggcttacaa agtagagttg gcccagtttc cttccacctg aggggagcac tctgactcct    600

aacagtcttc cttgccctgc catcatctgg ggtggctggc tgtcaagaaa ggccgggcat    660

gctttctaaa cacagccaca ggaggcttgt agggcatctt ccaggtgggg aaacagtctt    720

agataagtaa ggtgacttgc ctaaggcctc ccagcaccct tgatcttgga gtctcacagc    780

agactgcatg tsaacaactg gaaccgaaaa catgcctcag tataaaa                  827
```

<210> SEQ ID NO 32
<211> LENGTH: 291
<212> TYPE: DNA
<213> ORGANISM: Homo sapiens

<400> SEQUENCE: 32

```
ccagaacctc cttctctttg gagaatgggg aggcctcttg gagacacaga gggtttcacc     60

ttggatgacc tctagagaaa ttgcccaaga agcccacctt ctggtcccaa cctgcagacc    120

ccacagcagt cagttggtca ggccctgctg tagaaggtca cttggctcca ttgcctgctt    180

ccaaccaatg ggcaggagag aaggccttta tttctcgccc acccattctc ctgtaccagc    240

acctccgttt tcagtcagyg ttgtccagca acggtaccgt ttacacagtc a             291
```

<210> SEQ ID NO 33
<211> LENGTH: 491
<212> TYPE: DNA
<213> ORGANISM: Homo sapiens

<400> SEQUENCE: 33

```
tgcatgtagt tttatttatg tgttttsgtc tggaaaacca agtgtcccag cagcatgact     60

gaacatcact cacttcccct acttgatcta caaggccaac gccgagagcc cagaccagga    120

ttccaaacac actgcacgag aatattgtgg atccgctgtc aggtaagtgt ccgtcactga    180

cccaracgct gttacgtggc acatgactgt acagtgccac gtaacagcac tgtacttttc    240

tcccatgaac agttacctgc catgtatcta catgattcag aacattttga acagttaatt    300

ctgacacttg aataatccca tcaaaaaccg taaaatcact ttgatgtttg taacgacaac    360

atagcatcac tttacgacag aatcatctgg aaaaacagaa caacgaatac atacatctta    420

aaaaatgctg ggtgggccca ggcacagctt cacgcctgta atcccagcac tttgggaggc    480

ttaagcgggt g                                                         491
```

<210> SEQ ID NO 34
<211> LENGTH: 521
<212> TYPE: DNA
<213> ORGANISM: Homo sapiens
<220> FEATURE:
<221> NAME/KEY: misc_feature
<222> LOCATION: 453, 476, 487
<223> OTHER INFORMATION: n = A,T,C or G

<400> SEQUENCE: 34

```
tggggcggaa agaagccaag gccaaggagc tggtgcggca gctgcagctg gaggccgagg 60

agcagaggaa gcagaagaag cggcagagtg tgtcgggcct gcacagatac cttcacttgc 120

tggatggaaa tgaaaattac ccgtgtcttg tggatgcaga cggtgatgtg atttccttcc 180

caccaataac caacagtgag aagacaaagg ttaagaaaac gacttctgat ttgtttttgg 240

aagtaacaag tgccaccagt ctgcagattt gcaaggatgt catggatgcc ctcattctga 300

aaatggcaag aaatgaaaaa gtacacttta gaaaataaag aggaaggatc actctcagat 360

actgaagccg atgcagtctc tggacaactt ccagatccca caacgaatcc cagtgctgga 420
```

-continued aaggacgggc ccttccttct ggtggtggaa cangtcccgg tggtggatct tggaanggaa 480
cctgaangtg gtgtaccccg tccaaggccg accttggcca c 521

<210> SEQ ID NO 35
<211> LENGTH: 161
<212> TYPE: DNA
<213> ORGANISM: Homo sapiens
<220> FEATURE:
<221> NAME/KEY: misc_feature
<222> LOCATION: 18
<223> OTHER INFORMATION: n = A,T,C or G

<400> SEQUENCE: 35
tcccgcgctc gcagggcncg tgccacctgc cygtccgccc gctcgctcgc tcgcccgccg 60
cgccgcgctg ccgaccgyca gcatgctgcc gagagtgggc tgccccgcgc tgccgctgcc 120
gccgccgccg ctgctgccgc tgctgccgct gctgctgctg c 161

<210> SEQ ID NO 36
<211> LENGTH: 341
<212> TYPE: DNA
<213> ORGANISM: Homo sapiens

<400> SEQUENCE: 36
ggcgggtagg catggaactg agaagaacga agaagctttc agactacgtg gggaagaatg 60
aaaaaaccaa aattatcgcc aagattcagc aaaggggaca gggagctcca gcccgagagc 120
ctattattag cagtgaggag cagaagcagc tgatgctgta ctatcacaga agacaagagg 180
agctcaagag attggaagaa aatgatgatg atgcctattt aaactcacca tgggcggata 240
acactgcttt gaaaagacat tttcatggag tgaaagacat aaagtggaga ccaagatgaa 300
gttcaccagc tgatgacact tccaaagaga ttagctcacc t 341

<210> SEQ ID NO 37
<211> LENGTH: 521
<212> TYPE: DNA
<213> ORGANISM: Homo sapiens
<220> FEATURE:
<221> NAME/KEY: misc_feature
<222> LOCATION: 516
<223> OTHER INFORMATION: n = A,T,C or G

<400> SEQUENCE: 37
tctgaaggtt aaatgtttca tctaaatagg gataatgrta aacacctata gcatagagtt 60
gtttgagatt aaatgagata atacatgtaa aattatgtgc ctggcataca gcaagattgt 120
tgttgttgtt gatgatgatg atgatgatga taatattttt ctatccccag tgcacaactg 180
cttgaaccta ttagataatc aatacatgtt tcttgaactg agatcaattt ccccatgttg 240
tctgactgat gaagccctac attttcttct agaggagatg acatttgagc aagatcttaa 300
agaaaatcag atgccttcac ctgaccactg cttggtgatc ccatggcact ttgtacatct 360
ctccattagc tctcatctca ccagcccatc attattgtat gtgctgcctt ctgaagcttg 420
cagctggcta ccatcmggta gaataaaaat catcctttca taaaatagtg accctccttt 480
tttatttgca tttcccaaag ccaagcaccg tggganggta g 521

<210> SEQ ID NO 38
<211> LENGTH: 461
<212> TYPE: DNA
<213> ORGANISM: Homo sapiens -continued

<400> SEQUENCE: 38
tatgaagaag ggaaaagaag ataatttgtg aaagaaatgg gtccagttac tagtctttga 60
aaagggtcag tctgtagctc ttcttaatga gaataggcag ctttcagttg ctcagggtca 120
gatttcctta gtggtgtatc taatcacagg aaacatctgt ggttccctcc agtctctttc 180
tgggggactt gggcccactt ctcatttcat ttaattagag gaaatagaac tcaaagtaca 240
atttactgtt gtttaacaat gccacaaaga catggttggg agctatttct tgatttgtgt 300
aaaatgctgt ttttgtgtgc tcataatggt tccaaaaatt gggtgctggc caaagagaga 360
tactgttaca gaagccagca agaagacctc tgttcattca cacccccggg gatatcagga 420
attgactcca gtgtgtgcaa atccagtttg gcctatcttc t 461

<210> SEQ ID NO 39
<211> LENGTH: 769
<212> TYPE: DNA
<213> ORGANISM: Homo sapiens

<400> SEQUENCE: 39
tgagggactg attggtttgc tctctgctat tcaattcccc aagcccactt gttcctgcag 60
cgtcctcctt ctcattccct ttagttgtac cctctctttc atctgagacc tttccttctt 120
gatgtcgcct tttcttcttc ttgctttttc tgatgttctg ctcagcatgt tctgggtgct 180
tctcatctgc atcattcctt tcagatgctg tagcttcttc ctcctctttc tgcctccttt 240
tctttttctt ttttttgggg ggcttgctct ctgactgcag ttgaggggcc ccagggtcct 300
ggcctttgag acgagccagg aaggcctgct cctgggcctc taggcgagca agcttggcct 360
tcattgtgat cccaagacgg gcagccttgt gtgctgttcg cccctcacag gcttggagca 420
gcatctcatc agtcagaatc tttggggact tggacccctg gttgtcgtca tcactgcagc 480
tctccaagtc tttgtttggc ttctctccac ctgaagtcaa tgtagccatc ttcacaaact 540
tctgatacag caagttgggc ttgggatgat tataacgggt ggtctcctta gaaaggctcc 600
ttatctgtac tccatcctgc ccagtttcca ctaccaagtt ggccgcagtc ttgttgaaga 660
gctcattcca ccagtggttt gtgaactcct tggcagggtc atgtcctacc ccatgagtgt 720
cttgcttcag ygtcaccctg agagcctgag tgataccatt ctccttccg 769

<210> SEQ ID NO 40
<211> LENGTH: 292
<212> TYPE: DNA
<213> ORGANISM: Homo sapiens

<400> SEQUENCE: 40
gacaacatga aataaatcct agaggacaaa attaaactca atagagtgta gtctagttaa 60
aaactcgaaa aatgagcaag tctggtggga gtggaggaag ggctatacta taaatccaag 120
tgggcctcct gatcttaaca agccatgctc attatacaca tctctgaact ggacatacca 180
cctttacgca ggaaacaggg cttggaactt ctaagggaaa ttaacatgca ccacccacat 240
ctaacctacc tgccgggtag gtaccatccc tgcttcgctg aaatcagtgc tc 292

<210> SEQ ID NO 41
<211> LENGTH: 406
<212> TYPE: DNA
<213> ORGANISM: Homo sapiens

<400> SEQUENCE: 41
ttggaattaa ataaacctgg aacagggaag gtgaaagttg gagtgagatg tcttccatat 60

-continued

```
ctataccttt gtgcacagtt gaatgggaac tgtttgggtt tagggcatct tagagttgat    120

tgatggaaaa agcagacagg aactggtggg aggtcaagtg gggaagttgg tgaatgtgga    180

ataacttacc tttgtgctcc acttaaacca gatgtgttgc agctttcctg acatgcaagg    240

atctacttta attccacact ctcattaata aattgaataa aagggaatgt tttggcacct    300

gatataatct gccaggctat gtgacagtag gaaggaatgg tttcccctaa caagcccaat    360

gcactggtct gactttataa attatttaat aaaatgaact attatc                   406
```

<210> SEQ ID NO 42
<211> LENGTH: 381
<212> TYPE: DNA
<213> ORGANISM: Homo sapiens

<400> SEQUENCE: 42

```
aaactggacc tgcaacaggg acatgaattt actgcarggt ctgagcaagc tcagcccctc     60

tacctcaggg ccccacagcc atgactacct cccccaggag cgggagggtg aagggggcct    120

gtctctgcaa gtggagccag agtggaggaa tgagctctga agacacagca cccagccttc    180

tcgcaccagc caagccttaa ctgcctgcct gaccctgaac cagaacccag ctgaactgcc    240

cctccaaggg acaggaaggc tgggggaggg agtttacaac ccaagccatt ccaccccctc    300

ccctgctggg gagaatgaca catcaagctg ctaacaattg gggaaggggg aaggaagaaa    360

actctgaaaa caaaatcttg t                                              381
```

<210> SEQ ID NO 43
<211> LENGTH: 451
<212> TYPE: DNA
<213> ORGANISM: Homo sapiens

<400> SEQUENCE: 43

```
catgcgtttc accactgttg gccaggctgg tctcgaactc ctggcctcaa gcaatccacc     60

cgcctcagcc tccaaaagtg ctgggattac agatgtgagc catggcacca tgccaaaagg    120

ctatattcct ggctctgtgt ttccgagact gcttttaatc ccaacttctc tacatttaga    180

ttaaaaaata ttttattcat ggtcaatctg gaacataatt actgcatctt aagtttccac    240

tgatgtatat agaaggctaa aggcacaatt tttatcaaat ctagtagagt aaccaaacat    300

aaaatcatta attactttca acttaataac taattgacat tcctcaaaag agctgttttc    360

aatcctgata ggttctttat tttttcaaaa tatatttgcc atgggatgct aatttgcaat    420

aaggcgcata atgagaatac cccaaactgg a                                   451
```

<210> SEQ ID NO 44
<211> LENGTH: 521
<212> TYPE: DNA
<213> ORGANISM: Homo sapiens

<400> SEQUENCE: 44

```
gttggacccc cagggactgg aaagacactt cttgcccgag ctgtggcggg agaagctgat     60

gttccttttt attatgcttc tggatccgaa tttgatgaga tgtttgtggg tgtgggagcc    120

agccgtatca gaaatctttt tagggaagca aaggcgaatg ctccttgtgt tatatttatt    180

gatgaattag attctgttgg tgggaagaga attgaatctc caatgcatcc atattcaagg    240

cagaccataa atcaacttct tgctgaaatg gatggtttta aacccaatga aggagttatc    300

ataataggag ccacaaactt cccagaggca ttagataatg ccttaatacc gtcctggtcg    360
```

-continued ttttgacatg caagttacag ttccaaggcc agatgtaaaa ggtcgaacag aaattttgaa 420
atggtatctc aataaaataa agtttgatca atcccgttga tccagaaatt atagcctcga 480
ggtactggtg gcttttccgg aagcagagtt gggagaatct t 521

<210> SEQ ID NO 45
<211> LENGTH: 585
<212> TYPE: DNA
<213> ORGANISM: Homo sapiens

<400> SEQUENCE: 45
gcctacaaca tccagaaaga gtctaccctg cacctggtgc tscgtctcag aggtgggatg 60
cagatcttcg tgaagaccct gactggtaag accatcactc tcgaagtgga gccgagtgac 120
accatygaga acgtcaaagc aaagatccar gacaaggaag gcrtycctcc tgaccagcag 180
aggttgatct ttgccggaaa gcagctggaa gatggdcgca ccctgtctga ctacaacatc 240
cagaaagagt cyaccctgca cctggtgctc cgtctcagag gtgggatgca ratcttcgtg 300
aagaccctga ctggtaagac catcaccctc gaggtggagc ccagtgacac catcgagaat 360
gtcaaggcaa agatccaaga taaggaaggc atccctcctg atcagcagag gttgatcttt 420
gctgggaaac agctggaaga tggacgcacc ctgtctgact acaacatcca gaaagagtcc 480
actctgcact tggtcctgcg cttgaggggg ggtgtctaag tttccccttt taaggtttcm 540
acaaatttca ttgcactttc ctttcaataa agttgttgca ttccc 585

<210> SEQ ID NO 46
<211> LENGTH: 481
<212> TYPE: DNA
<213> ORGANISM: Homo sapiens

<400> SEQUENCE: 46
gaactgggcc ctgagcccaa gtcatgcctt gtgtccgcat ctgccgtgtc acctctgtkc 60
ctgcccctca cccctccctc ctggtcttct gagccagcac catctccaaa tagcctattc 120
cttcctgcaa atcacacaca catgcgggcc acacatacct gctgccctgg agatggggaa 180
gtaggagaga tgaatagagg cccatacatt gtacagaagg aggggcaggt gcagataaaa 240
gcagcagacc cagcggcagc tgaggtgcat ggagcacggt tggggccggc attgggctga 300
gcacctgatg ggcctcatct cgtgaatcct cgaggcagcg ccacagcaga ggagttaagt 360
ggcacctggg ccgagcagag caggagactg agggtcagag tggaggctaa gctgccctgg 420
aactcctcaa tcttgcctgc cccctagtat gaagcccccct tcctgcccct acaattcctg 480
a 481

<210> SEQ ID NO 47
<211> LENGTH: 461
<212> TYPE: DNA
<213> ORGANISM: Homo sapiens
<220> FEATURE:
<221> NAME/KEY: misc_feature
<222> LOCATION: 128
<223> OTHER INFORMATION: n = A,T,C or G

<400> SEQUENCE: 47
atggatctta ctttgccacc caggttggag tgcagtgctg caatcttggc tcactgcagc 60
cttaacctcc caggctcaag ctatcctcct gccaaagcct tccacatagc tgggactaca 120
ggtacacngc caccacaccc agctaaaatt tttgtatttt ttgtagagac gggatctcgc 180
cacgttgccc aggctggtcc catcctgacc tcaagcagat ctgcccacct cagcccccca 240

-continued acgtgctagg attacaggcg tgagccaccg cacccagcct ttgttttgct tttaatggaa 300
tcaccagttc ccctccgtgt ctcagcagca gctgtgagaa atgctttgca tctgtgacct 360
ttatgaaggg gaacttccat gctgaatgag ggtaggatta catgctcctg tttcccgggg 420
gtcaagaaag cctcagactc cagcatgata agcagggtga g 461

<210> SEQ ID NO 48
<211> LENGTH: 571
<212> TYPE: DNA
<213> ORGANISM: Homo sapiens

<400> SEQUENCE: 48
ataggggctt taaggaggga attcaggttc aatgaggtcg taaggccagg gctcttatcc 60
agtaagactg gggtccttag atgagaaaga gacacccgag gtccttctct ctgccgtgtg 120
aggatgcatc aagaaggcgg ccgtctgcaa gcgaaggaga ggccgcacca gaaaccgaca 180
ccttcatctt ggacttgcag cctctagaac tgagaaaata actgtctgtt ggttaagcca 240
cccagtttgt agtattctct tatggcttcc taagcagact aacaaacaaa cacccaaaat 300
taactgatgg cttcgctgtc ttctgtaaaa attgctatga gagaactttt cactcactgt 360
tttgcagttt ctccctcagt ccctggttct ttcttctcac ataatcccaa tttcaattta 420
tagttcatgg cccaggcaga gtcattcatc acggcatctc ctgagctaaa ccagcacctg 480
ctctgctcac ttcttgactg gctgctcatc atcagccctc ttgcagagat ttcatttcct 540
cccgtgccag gtacttcacg caccaagctc a 571

<210> SEQ ID NO 49
<211> LENGTH: 511
<212> TYPE: DNA
<213> ORGANISM: Homo sapiens

<400> SEQUENCE: 49
ggataatgaa gttgttttat ttagcttgga caaaaaggca tattcctcta ttttcttata 60
caacaaatat ccccaaaata aagcaagcat atatatcttg aatgtgtaat aatccagtga 120
taaacaagag cagtacttta aaagaaaaaa aaatatgtat ttctgtcagg ttaaaatgag 180
aatcaaaacc atttactctg ctaactcatt attttttgct ttctttttgg ttaagagagg 240
caatgcaata cactgaaaaa ggtttttatc ttatctggca ttggaattag acatattcaa 300
accccagccc ccatttccaa actttaagac cacaaacaag taatttactt ttctgaacat 360 tggtttttc tggaaaatgg gaattataaa atagactttg cagactctta tgagattaaa 420
taagataatg tatgaaattc tttcttcttt tttacttctt tttcctttt gagatggagt 480 ctcaccccgt cacccaggct ggagtacagt g 511

<210> SEQ ID NO 50
<211> LENGTH: 561
<212> TYPE: DNA
<213> ORGANISM: Homo sapiens

<400> SEQUENCE: 50
ccactgcact ccagcctggg tgacggagtg agactctgtc tcaaaaaaac aaacaaacaa 60
acaaacaaaa aactgaaaag gaaatagagt tcctctttcc tcatatatga atatattatt 120
tcaacagatt gttgatcacc taccatatgc ttggtattgt tctaattgct ggggatacag 180
caagaggttc tgcagaactt catggagcat gaaagtaaat aaacaaagtt aatttcaagg 240

-continued

```
ccaggcatgg ttgctcacac ctttagtccc agcactttgg gaggctgagg caggtggatc    300

acttgggccc aggagttcaa ggctgcagtg agccaagatt gtgccactac tctccaggct    360

gggcaacaga gcaagaccct gtctcagggg gaacaaaaag ttaatttcag attttgttaa    420

gtgctgtaaa ggaagtaaat aggttgatat tcaagagagc acctgaaggc caggcgtggt    480

ggctcacgcc tgtggtctaa cgctttggga agcccgagcg ggcggatcac aaggtcagga    540

gaattttggc caggcatggt g                                              561
```

<210> SEQ ID NO 51
<211> LENGTH: 451
<212> TYPE: DNA
<213> ORGANISM: Homo sapiens

<400> SEQUENCE: 51

```
agaatccatt tattgggttt taaactagtt acacaactga aatcagtttg gcactacttt     60

atacagggat tacgcctgtg tatgccgaca cttaaatact gtaccaggac cactgctgtg    120

cttaggtctg tattcagtca ttcagcatgt agatactaaa aatatactgt agtgttcctt    180

taaggaagac tgtacagggt gtgttgcaag atgacattca ccaatttgtg aattatttca    240

acccagaaga tacctttcac tctataaact tgtcataggc aaacatgtgg tgttagcatt    300

gagagatgca cacaaaaatg ttacataaaa gttcagacat tctaatgata agtgaactga    360

aaaaaaaaaa aaccccacat ctcaattttt gtaacaagat aaagaaaata atttaaaaac    420

acaaaaaatg gcattcagtg ggtacaaagc c                                   451
```

<210> SEQ ID NO 52
<211> LENGTH: 682
<212> TYPE: DNA
<213> ORGANISM: Homo sapiens

<400> SEQUENCE: 52

```
caaatattta atataaatct ttgaaacaag ttcagakgaa ataaaaatca aagtttgcaa     60

aaacgtgaag attaacttaa ttgtcaaata ttcctcattg ccccaaatca gtattttttt    120

tatttctatg caaaagtatg ccttcaaact gcttaaatga tatatgatat gatacacaaa    180

ccagttttca aatagtaaag ccagtcatct tgcaattgta agaaataggt aaaagattat    240

aagacacctt acacacacac acacacacac acacacacgt gtgcaccgcc aatgacaaaa    300

aacaatttgg cctctcctaa aataagaaca tgaagaccct taattgctgc caggagggaa    360

cactgtgtca cccctcccta caatccaggt agtttccttt aatccaatag caaatctggg    420

catatttgag aggagtgatt ctgacagcca csgttgaaat cctgtgggga accattcatg    480

tccacccact ggtgccctga aaaaatgcca ataatttttc gctcccactt ctgctgctgt    540

ctcttccaca tcctcacata gaccccagac ccgctggccc ctggctgggc atcgcattgc    600

tggtagagca agtcataggt ctcgtctttg acgtcacaga agcgatacac caaattgcct    660

ggtcggtcat tgtcataacc ag                                             682
```

<210> SEQ ID NO 53
<211> LENGTH: 311
<212> TYPE: DNA
<213> ORGANISM: Homo sapiens
<220> FEATURE:
<221> NAME/KEY: misc_feature
<222> LOCATION: 208
<223> OTHER INFORMATION: n = A,T,C or G

<400> SEQUENCE: 53

-continued

```
tttgacttta gtaggggtct gaactattta ttttactttg ccmgtaatat ttaraccyta     60

tatatctttc attatgccat cttatcttct aatgbcaagg gaacagwtgc taamctggct    120

tctgcattwa tcacattaaa aatggctttc ttggaaaatc ttcttgatat gaataaagga    180

tcttttavag ccatcattta aagcmggntt ctctccaaca cgagtctgct sasgggggk     240

gagctgtgaa ctctggctga aggctttccc atacacactg caatgacmtg gtttctgacc    300

agbgtgagtt a                                                         311
```

<210> SEQ ID NO 54
<211> LENGTH: 561
<212> TYPE: DNA
<213> ORGANISM: Homo sapiens

<400> SEQUENCE: 54

```
agagaagccc cataaatgca atcagtgtgg gaaggccttc agtcagagct caagcctttt     60

cctccatcat cgggttcata ctggagagaa accctatgta tgtaatgaat gcggcagagc    120

ctttggtttt aactctcatc ttactgaaca cgtaaggatt cacacaggag aaaaacccta    180

tgtttgtaat gagtgcggca aagcctttcg tcggagttcc actcttgttc agcatcgaag    240

agttcacact ggggagaagc cctaccagtg cgttgaatgt gggaaagctt tcagccagag    300

ctcccagctc accctacatc agccgagttc acactggaga gaagccctat gactgtggtg    360

actgtgggaa ggccttcagc cggaggtcaa ccctcattca gcatcagaaa gttcacagcg    420

gagagactcg taagtgcaga aaacatggtc cagcctttgt tcatggctcc agcctcacag    480

cagatggaca gattcccact ggagagaagc acggcagaac ctttaaccat ggtgcaaatc    540

tcattctgcg ctggacagtt c                                              561
```

<210> SEQ ID NO 55
<211> LENGTH: 811
<212> TYPE: DNA
<213> ORGANISM: Homo sapiens

<400> SEQUENCE: 55

```
gagacagggt ctcactttgt cacccaggct ggaatgcagt ggtgcgatct tacgtagctc     60

actgcagccc tgacctcctg gactcaaaca attctcctgc ctcagccctg caagtagctg    120

ggactgtggg tgcatgccac catgcctggc taacttttgt agtttttgta aagatggggt    180

tttgccatgt tgcacatgct ggtcttgaac tcctgagctc aaacgatctg cccacctcgg    240

cctcccagaa tgttgggatt acaggggtaa accaccacgc ctggccccat tagggtattc    300

ttagcatcca cttgctcact gagattaatc ataagagatg ataagcactg gaagaaaaaa    360

atttttacta ggctttggat atttttttcc tttttcagct ttatacagag gattggatct    420

ttagttttcc tttaactgat aataaaacat tgaaaggaaa taagtttacc tgagattcac    480

agagataacc ggcatcactc ccttgctcaa ttccagtctt taccacatca attattttca    540

gaggtgcagg ataaaggcct ttagtctgct ttcgcacttt ttcttccact tttttgtaaa    600

cctgttgcct gacaaatgga attgacagcg tatgccatga ctattccatt tgtcaggcat    660

acgctgtcaa tttttccacc aatcccttgt ctctctttgg agagatcttc ttatcagcta    720

gtcctttggc aaaagtaatt gcaacttctt ctaggtattc tattgtccgt tccactggtg    780

gaacccctgg gaccaggact aaaacctcca g                                   811
```

<210> SEQ ID NO 56

-continued

<211> LENGTH: 591
<212> TYPE: DNA
<213> ORGANISM: Homo sapiens
<220> FEATURE:
<221> NAME/KEY: misc_feature
<222> LOCATION: 45, 477, 490, 561
<223> OTHER INFORMATION: n = A,T,C or G

<400> SEQUENCE: 56
atctcatata tatatttctt cctgacttta tttgcttgct tctgncacgc atttaaaata 60
tcacagagac caaaatagag cggctttctg gtggaacgca tggcagtcac aggacaaaat 120
acaaaactag gggctctgt cttctcatac atcatacaat tttcaagtat tttttttatg 180
tacaaagagc tactctatct gaaaaaaaat taaaaaataa atgagacaag atagtttatg 240
catcctagga agaaagaatg ggaagaaaga acggggcagt tgggtacaga ttcctgtccc 300
ctgttcccag ggaccactac cttcctgcca ctgagttccc ccacagcctc acccatcatg 360
tcacagggca agtgccaggg taggtgggga ccagtggaga caggaaccag caacatactt 420
tggcctggaa gataaggaga aagtctcaga aacacactgg tgggaagcaa tcccacnggc 480
cgtgccccan gagcttccca cctgctgctg gctccctggg tggctttggg aacagcttgg 540
gcaggccctt ttgggtgggg nccaactggg cctttgggcc cgtgtggaaa g 591

<210> SEQ ID NO 57
<211> LENGTH: 481
<212> TYPE: DNA
<213> ORGANISM: Homo sapiens

<400> SEQUENCE: 57
aaacattgag atggaatgat agggtttccc agaatcaggt ccatatttta actaaatgaa 60
aattatgatt tatagccttc tcaaatacct gccatacttg atatctcaac cagagctaat 120
tttacctctt tacaaattaa ataagcaagt aactggatcc acaatttata atacctgtca 180
attttttctg tattaaacct ctatcatagt ttaagcctat tagggtactt aatccttaca 240
aataaacagg tttaaaatca cctcaatagg caactgccct tctggttttc ttctttgact 300
aaacaatctg aatgcttaag attttccact ttgggtgcta gcagtacaca gtgttacact 360
ctgtattcca gacttcttaa attatagaaa aaggaatgta cactttttgt attctttctg 420
agcagggccg ggaggcaaca tcatctacca tggtagggac ttgtatgcat ggactacttt 480
a 481

<210> SEQ ID NO 58
<211> LENGTH: 141
<212> TYPE: DNA
<213> ORGANISM: Homo sapiens

<400> SEQUENCE: 58
actctgtcgc ccaggctgga gcccabtggm gcgatctcga ctccctgcaa gctmcgcctc 60
acaggwtcat gccattctcc tgcctcagca tctggagtag ctgggactac aggcgccagc 120
caccatgccc agctaatttt t 141

<210> SEQ ID NO 59
<211> LENGTH: 191
<212> TYPE: DNA
<213> ORGANISM: Homo sapiens

<400> SEQUENCE: 59
accttaaaga cataggagaa tttatactgg gagagaaagc ttacaaatgt aaggtttctg 60

-continued acaagacttg ggagtgattc acacctggaa caacatactg gacttcacac tggabagaaa 120
ccttacaagt gtaatgagtg tggcaaagcc tttggcaagc agtcaacact tattcaccat 180
caggcaattc a 191

<210> SEQ ID NO 60
<211> LENGTH: 480
<212> TYPE: DNA
<213> ORGANISM: Homo sapiens

<400> SEQUENCE: 60
agtcaggatc atgatggctc agtttcccac agcgatgaat ggagggccaa atatgtgggc 60
tattacatct gaagaacgta ctaagcatga taaacagttt gataacctca aaccttcagg 120
aggttacata acaggtgatc aagcccgtac ttttttccta cagtcaggtc tgccggcccc 180
ggttttagct gaaatatggg ccttatcaga tctgaacaag gatgggaaga tggaccagca 240
agagttctct atagctatga aactcatcaa gttaaagttg cagggccaac agctgcctgt 300
agtcctccct cctatcatga aacaaccccc tatgttctct ccactaatct ctgctcgttt 360
tgggatggga agcatgccca atctgtccat tcatcagcca ttgcctccag ttgcacctat 420
agcaacaccc ttgtcttctg ctacttcagg gaccagtatt cctccctaat gatgcctgct 480

<210> SEQ ID NO 61
<211> LENGTH: 381
<212> TYPE: DNA
<213> ORGANISM: Homo sapiens

<400> SEQUENCE: 61
ctttcgattt ccttcaattt gtcacgtttg attttatgaa gttgttcaag ggctaactgc 60
tgtgtattat agctttctct gagttccttc agctgattgt taaatgaatc catttctgag 120
agcttagatg cagtttcttt ttcaagagca tctaattgtt ctttaagtct ttggcataat 180
tcttcctttt ctgatgactt tctatgaagt aaactgatcc ctgaatcagg tgtgttactg 240
agctgcatgt ttttaattct ttcgtttaat agctgcttct cagggaccag atagataagc 300
ttattttgat attccttaag ctcttggtga agttgttcga tttccataat ttccaggtca 360
cactggttat cccaaacttc t 381

<210> SEQ ID NO 62
<211> LENGTH: 906
<212> TYPE: DNA
<213> ORGANISM: Homo sapiens

<400> SEQUENCE: 62
gtggaggtga aacggaggca agaaaggggg ctacctcagg agcgagggac aaagggggcg 60
tgaggcacct aggccgcggc accccggcga caggaagccg tcctgaaccg ggctaccggg 120
taggggaagg gcccgcgtag tcctcgcagg gccccagagc tggagtcggc tccacagccc 180
cgggccgtcg gcttctcact tcctggacct ccccggcgcc cgggcctgag gactggctcg 240
gcggagggag aagaggaaac agacttgagc agctccccgt tgtctcgcaa ctccactgcc 300
gaggaactct catttcttcc ctcgctcctt cacccccccac ctcatgtaga aaggtgctga 360
agcgtccgga gggaagaaga acctgggcta ccgtcctggc cttcccmccc ccttcccggg 420
gcgctttggt gggcgtggag ttggggttgg gggggtgggt gggggttctt ttttggagtg 480
ctggggaact tttttccctt cttcaggtca ggggaaaggg aatgcccaat tcagagagac 540

-continued

```
atgggggcaa gaaggacggg agtggaggag cttctggaac tttgcagccg tcatcgggag    600

gcggcagctc taacagcaga gagcgtcacc gcttggtatc gaagcacaag cggcataagt    660

ccaaacactc caaagacatg ggttggtgga cccccgaagc agcatccctg ggcacagtta    720

tcaaaccttt ggtggagtat gatgatatca gctctgattc cgacaccttc tccgatgaca    780

tggccttcaa actagaccga agggagaacg acgaacgtcg tggatcagat cggagcgacc    840

gcctgcacaa acatcgtcac caccagcaca ggcgttcccg ggacttacta aaagctaaac    900

agaccg                                                                906
```

<210> SEQ ID NO 63
<211> LENGTH: 491
<212> TYPE: DNA
<213> ORGANISM: Homo sapiens

<400> SEQUENCE: 63

```
gacatgtttg cctgcagggg accagagaca atgggattag ccagtgctca ctgttcttta     60

tgcttccaga gaggatgggg acagctctca ggtcagaatc caggctgaga aggccatgct    120

ggttgggggc ccccggaagc acggtccgga tcctccctgg catcagcgta gacccgctgc    180

tcaggcttgg ggtaccaaac tcatgctctg tactgttttg gccccatgcg gtgagaggaa    240

aacctagaaa aagattggtc gtgctaagga atcagctgcc ccctcatcct ccgcatccaa    300

tgctggtgac aacatattcc ctctcccagg acacagactc ggtgactcca cactgggctg    360

agtggcctct ggaggctcgt ggcctaaggc agggctccgt aaggctgatc ggctgaactg    420

ggtggggtga gggtttctga cccttcgctt cccatcccat aaccgctgtc aatgagctca    480

cactgtggtc a                                                          491
```

<210> SEQ ID NO 64
<211> LENGTH: 511
<212> TYPE: DNA
<213> ORGANISM: Homo sapiens

<400> SEQUENCE: 64

```
gatggcatgg tcgttgctaa tgtgcctgct gggatggagc acttcctcct gtgagcccag     60

gggacccgcc tgtccctgga gcttggggca aggagggaag agtgatacca ggaaggtggg    120

gctgcagcca ggggccagag tcagttcagg gagtggtcct cggccctcaa agctcctccg    180

gggactgctc aggagtgatg gtgccctgga gtttgcccca acttccctgg ccaccctgga    240

aggtgcctgg ctgctccagg cctctaggct gggctgatgg gtttctccag gacacaagta    300

tcattaaagc caccctctcc tcagcttgtc aggccgcaca tgtgggacag gctgtgctca    360

caaccccctc gcctgccctg ccctccatca ggaggagcca gtggaacctt cggaaagctc    420

ccagcatctc agcagccctc aaaagtcgtc ctggggcaag ctctggttct cctgactgga    480

ggtcatctgg gcttggcctg ctctctctcg c                                    511
```

<210> SEQ ID NO 65
<211> LENGTH: 394
<212> TYPE: DNA
<213> ORGANISM: Homo sapiens

<400> SEQUENCE: 65

```
taaaaaagtg taacaaaggt ttatttagac tttcttcatg cccccagatc caggatgtct     60

atgtaaaccg ttatcttaca aagaaagcac aatatttggt ataaactaag tcagtgactt    120

gcttaactga aatagcgtcc atccaaaagt gggtttaagg taaaactacc tgacgatatt    180
```

-continued

```
ggcggggatc ctgcagtttg gactgcttgc cgggtttgtc cagggttccg ggtctgttct    240

tggcactcat ggggacaggc atcctgctcg tctgtggggc cccgctggag cccttacgtg    300

aagctgaagg tatcgaccst agggggctct agggcagtgg gaccttcatc cggaactaac    360

aagggtcggg gagaggcctc ttgggctatg tggg                                394
```

<210> SEQ ID NO 66
<211> LENGTH: 359
<212> TYPE: DNA
<213> ORGANISM: Homo sapiens

<400> SEQUENCE: 66

```
caagcgttcc tttatggatg taaattcaaa cagtcatgct gagccatccc gggctgacag     60

tcacgttwaa gacactaggt cgggcgccac agtgccaccc aaggagaaga agaatttgga    120

atttttccat gaagatgtac ggaaatctga tgttgaatat gaaaatggcc cccaaatgga    180

attccaaaag gttaccacag gggctgtaag acctagtgac cctcctaagt gggaaagagg    240

aatggagaat agtatttctg atgcatcaag aacatcagaa tataaaactg agatcataat    300

gaaggaaaat tccatatcca atatgagttt actcagagac agtagaaact attcccagg     359
```

<210> SEQ ID NO 67
<211> LENGTH: 450
<212> TYPE: DNA
<213> ORGANISM: Homo sapiens
<220> FEATURE:
<221> NAME/KEY: misc_feature
<222> LOCATION: 425
<223> OTHER INFORMATION: n = A,T,C or G

<400> SEQUENCE: 67

```
taggaataac aaatgtttat tcagaaatgg ataagtaata cataatcacc cttcatctct     60

taatgcccct tcctctcctt ctgcacagga gacacagatg ggtaacatag aggcatggga    120

agtggaggag gacacaggac tagcccacca ccttctcttc ccggtctccc aagatgactg    180

cttatagagt ggaggaggca aacaggtccc ctcaatgtac cagatggtca cctatagcac    240

cagctccaga tggccacgtg gttgcagctg gactcaatga aactctgtga caaccagaag    300

atacctgctt tgggatgaga gggaggataa agccatgcag ggaggatatt taccatccct    360

accctaagca cagtgcaagc agtgagcccc cggctcccag tacctgaaaa accaaggcct    420

actgnctttt ggatgctctc ttgggccacg                                     450
```

<210> SEQ ID NO 68
<211> LENGTH: 511
<212> TYPE: DNA
<213> ORGANISM: Homo sapiens

<400> SEQUENCE: 68

```
aagcctcctg ccctggaaat ctggagcccc ttggagctga gctggacggg gcagggaggg     60

gctgagaggc aagaccgtct ccctcctgct gcagctgctt ccccagcagc cactgctggg    120

cacagcagaa acgccagcag agaaaatggg agccgagagt ccttagccct ggagctgagg    180

ctgcctctgg gctgacccgc tggctgtacg tggccagaac tggggttggc atctggcatc    240

catttgaggc cagggtggag gaaagggagg ccaacagagg aaaacctatt cctgctgtga    300

caacacagcc cttgtcccac gcagcctaag tgcagggagc gtgatgaagt caggcagcca    360

gtcggggagg acgaggtaac tcagcagcaa tgtcaccttg tagcctatgc gctcaatggc    420
```

-continued ccggaggggc agcaaccccc cgcacacgtc agccaacagc agtgcctctg caggcaccaa 480
gagagcgatg atggacttga gcgccgtgtt c 511

<210> SEQ ID NO 69
<211> LENGTH: 511
<212> TYPE: DNA
<213> ORGANISM: Homo sapiens

<400> SEQUENCE: 69
gtttggcaga agacatgttt aataacattt tcatatttaa aaaatacagc aacaattctc 60
tatctgtcca ccatcttgcc ttgcccttcc tggggctgag gcagacaaag gaaaggtaat 120
gaggttaggg cccccaggcg ggctaagtgc tattggcctg ctcctgctca aagagagcca 180
tagccagctg ggcacggccc cctagcccct ccaggttgct gaggcggcag cggtggtaga 240
gttcttcact gagccgtggg ctgcagtctc gcagggagaa cttctgcacc agccctggct 300
ctacggcccg aaagaggtgg agccctgaga accggaggaa aacatccatc acctccagcc 360
cctccagggc ttcctcctct tcctggcctg ccagttcacc tgccagccgg gctcgggccg 420
ccaggtagtc agcgttgtag aagcagccct ccgcagaagc ctgccggtca aatctccccg 480
ctataggagc cccccgggag gggtcagcac c 511

<210> SEQ ID NO 70
<211> LENGTH: 511
<212> TYPE: DNA
<213> ORGANISM: Homo sapiens

<400> SEQUENCE: 70
caagttgaac gtcaggcttg gcagaggtgg agtgtagatg aaaacaaagg tgtgattatg 60
aagaggatgt gagtcctttg ggtgtaggag agaaaggctg ttgagcttct atttcaagat 120
acttttacct gtgcaaaaag cacattttcc acctccttct catggcattt gtgtaaggtg 180
agtatgattc ctattccatc tgcattttag aggtgaagaa taacgtacaa gggattcagt 240
gattagcaag ggacccctca ctaagtgttg atggagttag gacagagctc agctgtttga 300
atctcagagc ccaggcagct ggagctgggt aggatcctgg agctggcact aatgtgaggt 360
gcattccctc caacccaggc tcagatccgg aacctgaccg tgctgacccc cgaaggggag 420
gcagggctga gctggcccgt tgggctccct gctcctttca caccacactc tcgctttgag 480
gtgctgggct gggactactt cacagagcag c 511

<210> SEQ ID NO 71
<211> LENGTH: 511
<212> TYPE: DNA
<213> ORGANISM: Homo sapiens

<400> SEQUENCE: 71
tggcctgggc aggattggga gagaggtagc tacccggatg cagtcctttg ggatgaagac 60
tatagggtat gaccccatca tttccccaga ggtctcggcc tcctttggtg ttcagcagct 120
gcccctggag gagatctggc ctctctgtga tttcatcact gtgcacactc ctctcctgcc 180
ctccacgaca ggcttgctga atgacaacac ctttgcccag tgcaagaagg gggtgcgtgt 240
ggtgaactgt gcccgtggag ggatcgtgga cgaaggcgcc ctgctccggg ccctgcagtc 300
tggccagtgt gccggggctg cactggacgt gtttacggaa gagccgccac gggaccgggc 360
cttggtggac catgagaatg tcatcagctg tccccacctg ggtgccagca ccaaggaggc 420
tcagagccgc tgtggggagg aaattgctgt tcagttcgtg gacatggtga aggggaaatc 480

-continued tctcacgggg gttgtgaatg cccaggccct t 511

<210> SEQ ID NO 72
<211> LENGTH: 2017
<212> TYPE: DNA
<213> ORGANISM: Homo sapiens

<400> SEQUENCE: 72
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt acatcctcat 540
taccaaatgg aactgccagt ctcattcagc ctttatccat tccttattct tcttcaacat 600
tgcctcatgc atcatcttac agcctgatga tgggaggatt tggtggtgct agtatccaga 660
aggcccagtc tctgattgat ttaggatcta gtagctcaac ttcctcaact gcttccctct 720
cagggaactc acctaagaca gggacctcag agtgggcagt tcctcagcct tcaagattaa 780
agtatcggca aaaatttaat agtctagaca aaggcatgag cggatacctc tcaggttttc 840
aagctagaaa tgcccttctt cagtcaaatc tctctcaaac tcagctagct actatttgga 900
ctctggctga catcgatggt gacggacagt tgaaagctga agaatttatt ctggcgatgc 960
acctcactga catggccaaa gctggacagc cactaccact gacgttgcct cccgagcttg 1020
tccctccatc tttcagaggg ggaaagcaag ttgattctgt taatggaact ctgccttcat 1080
atcagaaaac acaagaagaa gagcctcaga agaaactgcc agttactttt gaggacaaac 1140
ggaaagccaa ctatgaacga ggaaacatgg agctggagaa gcgacgccaa gtgttgatgg 1200
agcagcagca gagggaggct gaacgcaaag cccagaaaga gaaggaagag tgggagcgga 1260
aacagagaga actgcaagag caagaatgga agaagcagct ggagttggag aaacgcttgg 1320
agaaacagag agagctggag agacagcggg aggaagagag gagaaaggag atagaaagac 1380
gagaggcagc aaaacaggag cttgagagac aacgccgttt agaatgggaa agactccgtc 1440
ggcaggagct gctcagtcag aagaccaggg aacaagaaga cattgtcagg ctgagctcca 1500
gaaagaaaag tctccacctg gaactggaag cagtgaatgg aaaacatcag cagatctcag 1560
gcagactaca agatgtccaa atcagaaagc aaacacaaaa gactgagcta gaagttttgg 1620
ataaacagtg tgacctggaa attatggaaa tcaaacaact tcaacaagag cttaaggaat 1680
atcaaaataa gcttatctat ctggtccctg agaagcagct attaaacgaa agaattaaaa 1740
acatgcagct cagtaacaca cctgattcag ggatcagttt acttcataaa aagtcatcag 1800
aaaaggaaga attatgccaa agacttaaag aacaattaga tgctcttgaa aaagaaactg 1860
catctaagct ctcagaaatg gattcattta acaatcagct gaaggaactc agagaaagct 1920
ataatacaca gcagttagcc cttgaacaac ttcataaaat caaacgtgac aaattgaagg 1980
aaatcgaaag aaaaagatta gagcaaaaaa aaaaaaa 2017

-continued

<210> SEQ ID NO 73
<211> LENGTH: 414
<212> TYPE: DNA
<213> ORGANISM: Homo sapiens

<400> SEQUENCE: 73
atggcagtga cattcaccat catgggaacc accttccctt ttcttcagga ttctctgtag 60
tggaagagag cacccagtgt tgggctgaaa acatctgaaa gtagggagaa gaacctaaaa 120
taatcagtat ctcagagggc tctaaggtgc caagaagtct cactggacat ttaagtgcca 180
acaaaggcat actttcggaa tcgccaagtc aaaactttct aacttctgtc tctctcagag 240
acaagtgaga ctcaagagtc tactgcttta gtggcaacta cagaaaactg gtgttaccca 300
gaaaaacagg agcaattaga aatggttcca atatttcaaa gctccgcaaa caggatgtgc 360
tttcctttgc ccatttaggg tttcttctct ttcctttctc tttattaacc acta 414

<210> SEQ ID NO 74
<211> LENGTH: 1567
<212> TYPE: DNA
<213> ORGANISM: Homo sapiens

<400> SEQUENCE: 74
atatctagaa gtctggagtg agcaaacaag agcaagaaac aaaaagaagc caaaagcaga 60
aggctccaat atgaacaaga taaatctatc ttcaaagaca tattagaagt tgggaaaata 120
attcatgtga actagacaag tgtgttaaga gtgataagta aaatgcacgt ggagacaagt 180
gcatccccag atctcaggga cctccccctg cctgtcacct ggggagtgag aggacaggat 240
agtgcatgtt ctttgtctct gaatttttag ttatatgtgc tgtaatgttg ctctgaggaa 300
gcccctggaa agtctatccc aacatatcca catcttatat tccacaaatt aagctgtagt 360
atgtacccta agacgctgct aattgactgc cacttcgcaa ctcaggggcg gctgcatttt 420
agtaatgggt caaatgattc actttttatg atgcttccaa aggtgccttg gcttctcttc 480
ccaactgaca aatgccaaag ttgagaaaaa tgatcataat tttagcataa acagagcagt 540
cggcgacacc gattttataa ataaactgag caccttcttt ttaaacaaac aaatgcgggt 600
ttatttctca gatgatgttc atccgtgaat ggtccaggga aggacctttc accttgacta 660
tatggcatta tgtcatcaca agctctgagg cttctccttt ccatcctgcg tggacagcta 720
agacctcagt tttcaatagc atctagagca gtgggactca gctggggtga tttcgccccc 780
catctccggg ggaatgtctg aagacaattt tgttacctca atgagggagt ggaggaggat 840
acagtgctac taccaactag tggataaagg ccagggatgc tgctcaacct cctaccatgt 900
acaggacgtc tccccattac aactacccaa tccgaagtgt caactgtgtc aggactaaga 960
aaccctggtt ttgagtagaa aagggcctgg aaagagggga gccaacaaat ctgtctgctt 1020
cctcacatta gtcattggca aataagcatt ctgtctcttt ggctgctgcc tcagcacaga 1080
gagccagaac tctatcgggc accaggataa catctctcag tgaacagagt tgacaaggcc 1140
tatgggaaat gcctgatggg attatcttca gcttgttgag cttctaagtt tctttccctt 1200
cattctaccc tgcaagccaa gttctgtaag agaaatgcct gagttctagc tcaggttttc 1260
ttactctgaa tttagatctc cagacccttc ctggccacaa ttcaaattaa ggcaacaaac 1320
atataccttc catgaagcac acacagactt ttgaaagcaa ggacaatgac tgcttgaatt 1380
gaggccttga ggaatgaagc tttgaaggaa aagaatactt tgtttccagc cccctcccca 1440
cactcttcat gtgttaacca ctgccttcct ggaccttgga gccacggtga ctgtattaca 1500

-continued

```
tgttgttata gaaaactgat tttagagttc tgatcgttca agagaatgat taaatataca   1560

tttccta                                                             1567


<210> SEQ ID NO 75
<211> LENGTH: 240
<212> TYPE: DNA
<213> ORGANISM: Homo sapiens

<400> SEQUENCE: 75

tcgagcggcc gcccgggcag gtccttcaga cttggactgt gtcacactgc caggcttcca     60

gggctccaac ttgcagacgg cctgttgtgg gacagtctct gtaatcgcga aagcaaccat    120

ggaagacctg ggggaaaaca ccatggtttt atccaccctg agatctttga acaacttcat    180

ctctcagcgt gcggagggag gctctggact ggatatttct acctcggccg cgaccacgct    240


<210> SEQ ID NO 76
<211> LENGTH: 330
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 76

tagcgyggtc gcggccgagg yctgcttytc tgtccagccc agggcctgtg gggtcagggc     60

ggtgggtgca gatggcatcc actccggtgg cttccccatc tttctctggc ctgagcaagg    120

tcagcctgca gccagagtac agagggccaa cactggtgtt cttgaacaag ggccttagca    180

ggccctgaag grccctctct gtagtgttga acttcctgga gccaggccac atgttctcct    240

cataccgcag gytagygatg gtgaagttga gggtgaaata gtattmangr agatggctgg    300

caracctgcc cgggcggccg ctcsaaatcc                                      330


<210> SEQ ID NO 77
<211> LENGTH: 361
<212> TYPE: DNA
<213> ORGANISM: Homo sapiens

<400> SEQUENCE: 77

agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                    361


<210> SEQ ID NO 78
<211> LENGTH: 356
<212> TYPE: DNA
<213> ORGANISM: Homo sapiens
<220> FEATURE:
<221> NAME/KEY: misc_feature
<222> LOCATION: 7, 346, 350, 353
<223> OTHER INFORMATION: n = A,T,C or G

<400> SEQUENCE: 78
```

-continued ttggggntttt mgagcggccg cccgggcagg taccggggtg gtcagcgagg agccattcac 60
actgaacttc accatcaaca acctgcggta tgaggagaac atgcagcacc ctggctccag 120
gaagttcaac accacggaga gggtccttca gggcctgctc aggtccctgt tcaagagcac 180
cagtgttggc cctctgtact ctggctgcag actgactttg ctcagacttg agaaacatgg 240
ggcagccact ggagtggacg ccatctgcac cctccgcctt gatcccactg gtcctggact 300
ggacagagag cggctatact gggagctgag ccagtcctct ggcggngacn ccnctt 356

<210> SEQ ID NO 79
<211> LENGTH: 226
<212> TYPE: DNA
<213> ORGANISM: Homo sapiens

<400> SEQUENCE: 79
agcgtggtcg cggccgaggt ccagtcgcag catgctcttt ctcctgccca ctggcacagt 60
gaggaagatc tctgctgtca gtgagaaggc tgtcatccac tgagatggca gtcaaaagtg 120
catttaatac acctaacgta tcgaacatca tagcttggcc caggttatct catatgtgct 180
cagaacactt acaatagcct gcagacctgc ccgggcggcc gctcga 226

<210> SEQ ID NO 80
<211> LENGTH: 444
<212> TYPE: DNA
<213> ORGANISM: Homo sapiens
<220> FEATURE:
<221> NAME/KEY: misc_feature
<222> LOCATION: 23
<223> OTHER INFORMATION: n = A,T,C or G

<400> SEQUENCE: 80
tgtggtgttg aacttcctgg agncagggtg acccatgtcc tccccatact gcaggttggt 60
gatggtgaag ttgagggtga atggtaccag gagagggcca gcagccataa ttgtsgrgck 120
gsmgmssgag gmwggwgtyy cwgaggttcy rarrtccact gtggaggtcc caggagtgct 180
ggtggtgggc acagagstcy gatgggtgaa accattgaca tagagactgt tcctgtccag 240
ggtgtagggg cccagctctt yratgycatt ggycagttkg ctyagctccc agtacagccr 300
ctctckgyyg mgwccagsgc ttttggggtc aagatgatgg atgcagatgg catccactcc 360
agtggctgct ccatccttct cggacctgag agaggtcagt ctgcagccag agtacagagg 420
gccaacactg gtgttctttg aata 444

<210> SEQ ID NO 81
<211> LENGTH: 310
<212> TYPE: DNA
<213> ORGANISM: Homo sapiens

<400> SEQUENCE: 81
tcgagcggcc gcccgggcag gtcaggaagc acattggtct tagagccact gcctcctgga 60
ttccacctgt gctgcggaca tctccaggga gtgcagaagg gaagcaggtc aaactgctca 120
gatcagtcag actggctgtt ctcagttctc acctgagcaa ggtcagtctg cagccagagt 180
acagagggcc aacactggtg ttcttgaaca agggcttgag cagaccctgc agaaccctct 240
tccgtggtgt tgaacttcct ggaaaccagg gtgttgcatg tttttcctca taatgcaagg 300
ttggtgatgg 310

<210> SEQ ID NO 82
<211> LENGTH: 571

-continued

<212> TYPE: DNA
<213> ORGANISM: Homo sapiens
<220> FEATURE:
<221> NAME/KEY: misc_feature
<222> LOCATION: 202
<223> OTHER INFORMATION: n = A,T,C or G

<400> SEQUENCE: 82
acggtttcaa tggacacttt tattgtttac ttaatggatc atcaattttg tctcactacc 60
tacaaatgga atttcatctt gtttccatgc tgagtagtga aacagtgaca aagctaatca 120
taataaccta catcaaaaga gaactaagct aacactgctc actttctttt taacaggcaa 180
aatataaata tatgcactct anaatgcaca atggtttagt cactaaaaaa ttcaaatggg 240
atcttgaaga atgtatgcaa atccagggtg cagtgaagat gagctgagat gctgtgcaac 300
tgtttaaggg ttcctggcac tgcatctctt ggccactagc tgaatcttga catggaaggt 360
tttagctaat gccaagtgga gatgcagaaa atgctaagtt gacttagggg ctgtgcacag 420
gaactaaaag gcaggaaagt actaaatatt gctgagagca tccaccccag gaaggacttt 480
accttccagg agctccaaac tggcaccacc cccagtgctc acatggctga ctttatcctc 540
cgtgttccat ttggcacagc aagtggcagt g 571

<210> SEQ ID NO 83
<211> LENGTH: 551
<212> TYPE: DNA
<213> ORGANISM: Homo sapiens

<400> SEQUENCE: 83
aaggctggtg ggtttttgat cctgctggag aacctccgct ttcatgtgga ggaagaaggg 60
aagggaaaag atgcttctgg gaacaaggtt aaagccgagc cagccaaaat agaagctttc 120
cgagcttcac tttccaagct aggggatgtc tatgtcaatg atgcttttgg cactgctcac 180
agagcccaca gctccatggt aggagtcaat ctgccacaga aggctggtgg gtttttgatg 240
aagaaggagc tgaactactt tgcaaaggcc ttggagagcc cagagcgacc cttcctggcc 300
atcctgggcg gagctaaagt tgcagacaag atccagctca tcaataatat gctggacaaa 360
gtcaatgaga tgattattgg tggtggaatg gcttttacct tccttaaggt gctcaacaac 420
atggagattg gcacttctct gtttgatgaa gagggagcca agattgtcaa agacctaatg 480
tccaaagctg agaagaatgg tgtgaagatt accttgcctg ttgactttgt cactgctgac 540
aagtttgatg a 551

<210> SEQ ID NO 84
<211> LENGTH: 571
<212> TYPE: DNA
<213> ORGANISM: Homo sapiens

<400> SEQUENCE: 84
tttgttcctt acatttttct aaagagttac ttaaatcagt caactggtct ttgagactct 60
taagttctga ttccaactta gctaattcat tctgagaact gtggtatagg tggcgtgtct 120
cttctagctg ggacaaaagt tctttgtttt ccccctgtag agtatcacag accttctgct 180
gaagctggac ctctgtctgg gccttggact cccaaatctg cttgtcatgt tcaagcctgg 240
aaatgttaat ctttaattct tccatatgga tggacatctg tctaagttga tcctttagaa 300
cactgcaatt atcttctttg agtctaattt cttcttcttt gctttgaatc gcatcactaa 360
acttcctctc ccatttctta gcttcatcta tcaccctgtc acgatcatcc tggagggaag 420

-continued

```
acatgctctt agtaaaggct gcaagctggg tcacagtact gtccaagttt tcctgaagtt    480

gctgaacttc cttgtctttc ttgttcaaag taacctgaat ctctccaatt gtctcttcca    540

agtggacttt ttctctgcgc aaagcatcca g                                   571


<210> SEQ ID NO 85
<211> LENGTH: 561
<212> TYPE: DNA
<213> ORGANISM: Homo sapiens

<400> SEQUENCE: 85

tcattgcctg tgatggcatc tggaatgtga tgagcagcca ggaagttgta gatttcattc     60

aatcaaagga ttcagcatgt ggtggaagct gtgaggcaag agaaacaaga actgtatggc    120

aagttaagaa gcacagaggc aaacaagaag gagacagaaa agcagttgca ggaagctgag    180

caagaaatgg aggaaatgaa agaaaagatg agaaagtttg ctaaatctaa acagcagaaa    240

atcctagagc tggaagaaga gaatgaccgg cttagggcag aggtgcaccc tgcaggagat    300

acagctaaag agtgtatgga aacacttctt tcttccaatg ccagcatgaa ggaagaactt    360

gaaagggtca aaatggagta tgaaaccctt tctaagaagt ttcagtcttt aatgtctgag    420

aaagactctc taagtgaaga ggttcaagat ttaaagcatc agatagaagg taatgtatct    480

aaacaagcta acctagaggc caccgagaaa catgataacc aaacgaatgt cactgaagag    540

ggaacacagt ctataccagg t                                              561


<210> SEQ ID NO 86
<211> LENGTH: 795
<212> TYPE: DNA
<213> ORGANISM: Homo sapiens

<400> SEQUENCE: 86

aagccaataa tcaccattta ttacttaata tatgccaacc actgtacttg gcagttcaca     60

aattctcacc gttacaacaa ccccatgagg tatttattcc cattctatag atagggaaac    120

cacagctcaa gtaagttagg aaactgagcc aagtatacac agaatacgaa gtggcaaaac    180

tagaaggaaa gactgacact gctatctgct ggcctccagt gtcctggctc ttttcacacg    240

ggttcaatgt ctccagcgct gctgctgctg ctgcattacc atgccctcat tgtttttctt    300

cctctggtgt tcaactgcat ccttcaaaga atctaactca ttccagagac cacttatttc    360

tttctctctt tctgaaatta cttttaataa ttcttcatga gggggaaaag aagatgcctg    420

ttggtagttt tgttgtttaa gctgctcaat ttgggactta aacaatttgt tttcatcttg    480

tacatcctgt aacagctgtg ttttgctaga aagatcactc tccctctctt ttagcatggc    540

ttctaacctc ttcaattcat tttccttttc tttcaacaca atctcaagtt cttcaaactg    600

tgatgcagaa gaggcctctt tcaagttatg ttgtgctact tcctgaacat gtgcttttaa    660

agattcattt tcttcttgaa gatcctgtaa ccacttccct gtattggcta ggtctttctc    720

tttctcttcc aaaacagcct tcatggtatt catctgttcc tcttttcctt ttaataagtt    780

caggagcttc agaac                                                     795


<210> SEQ ID NO 87
<211> LENGTH: 594
<212> TYPE: DNA
<213> ORGANISM: Homo sapiens

<400> SEQUENCE: 87

caagcttttt tttttttttt aaaaagtgtt agcattaatg ttttattgtc acgcagatgg     60
```

-continued

```
caactgggtt tatgtcttca tattttatat ttttgtaaat taaaaaaatt acaagtttta    120

aatagccaat ggctggttat attttcagaa aacatgatta gactaattca ttaatggtgg    180

cttcaagctt ttccttattg gctccagaaa attcacccac cttttgtccc ttcttaaaaa    240

actggaatgt tggcatgcat ttgacttcac actctgaagc aacatcctga cagtcatcca    300

catctacttc aaggaatatc acgttggaat acttttcaga gagggaatga aagaaaggct    360

tgatcatttt gcaaggccca caccacgtgg ctgagaagtc aactactaca agtttatcac    420

ctgcagcgtc caaggcttcc tgaaaagcag tcttgctctc gatctgcttc accatcttgg    480

ctgctggagt ctgacgagcg gctgtaagga ccgatggaaa tggatccaaa gcaccaaaca    540

gagcttcaag actcgctgct tggcttgaat tcggatccga tatcgccatg gcct          594


<210> SEQ ID NO 88
<211> LENGTH: 557
<212> TYPE: DNA
<213> ORGANISM: Homo sapiens

<400> SEQUENCE: 88

aagtgttagc attaatgttt tattgtcacg cagatggcaa ctgggtttat gtcttcatat     60

tttatatttt tgtaaattaa aaaaattmca agttttaaat agccaatggc tggttatatt    120

ttcagaaaac atgattagac taattcatta atggtggctt caagcttttc cttattggct    180

ccagaaaatt cacccacctt ttgtcccttc ttaaaaaact ggaatgttgg catgcatttg    240

acttcacact ctgaagcaac atcctgacag tcatccacat ctacttcaag gaatatcacg    300

ttggaatact tttcagagag ggaatgaaag aaaggcttga tcattttgca aggcccacac    360

cacgtggctg agaagtcaac tactacaagt ttatcacctg cagcgtccaa ggcttcctga    420

aaagcagtct tgctctcgat ctgcttcacc atcttggctg ctggagtctg acgagcggct    480

gtaaggaccg atggaaatgg atccaaagca ccaaacagag cttcaagact cgctgcttgg    540

catgaattcg gatccga                                                   557


<210> SEQ ID NO 89
<211> LENGTH: 561
<212> TYPE: DNA
<213> ORGANISM: Homo sapiens
<220> FEATURE:
<221> NAME/KEY: misc_feature
<222> LOCATION: 544, 551
<223> OTHER INFORMATION: n = A,T,C or G

<400> SEQUENCE: 89

tacaaacttt attgaaacgc acacgcgcac acacacaaac acccctgtgg atagggaaaa     60

gcacctggcc acagggtcca ctgaaacggg gaggggatgg cagcttgtaa tgtggctttt    120

gccacaaccc ccttctgaca gggaaggcct tagattgagg ccccacctcc catggtgatg    180

gggagctcag aatggggtcc agggagaatt tggttagggg gaggtgctag ggaggcatga    240

gcagagggca ccctccgagt ggggtcccga gggctgcaga gtcttcagta ctgtccctca    300

cagcagctgt ctcaaggctg ggtccctcaa aggggcgtcc cagcgcgggg cctccctgcg    360

caaacacttg gtacccctgg ctgcgcagcg gaagccagca ggacagcagt ggcgccgatc    420

agcacaacag acgccctggc ggtagggaca gcaggcccag ccctgtcggt tgtctcggca    480

gcaggtctgg ttatcatggc agaagtgtcc ttcccacact tcacgtcctt cacacccacg    540

tganggctac nggccaggaa g                                              561
```

-continued

<210> SEQ ID NO 90
<211> LENGTH: 561
<212> TYPE: DNA
<213> ORGANISM: Homo sapiens

<400> SEQUENCE: 90
cccgtgggtg ccatccacgg agttgttacc tgatctttgg aagcaggatc gcccgtctgc 60
actgcagtgg aagccccgtg ggcagcagtg atggccatcc ccgcatgcca cggcctctgg 120
gaaggggcag caactggaag tccctgagac ggtaaagatg caggagtggc cggcagagca 180
gtgggcatca acctggcagg ggccacccag atgcctgctc agtgttgtgg gccatttgtc 240
cagaagggga cggcagcagc tgtagctggc tcctccgggg tccaggcagc aggccacagg 300
gcagaactga ccatctgggc accgcgttcc agccaccagc cctgctgtta aggccaccca 360
gctcaccagg gtccacatgg tctgcctgcg tccgactccg cggtccttgg gccctgatgg 420
ttctacctgc tgtgagctgc ccagtgggaa gtatggctgc tgccaatgcc caacgccacc 480
tgctgctccg atcacctgca ctgctgcccc aagacactgt gtgtgacctg atccagagta 540
agtgcctctc caaggagaac g 561

<210> SEQ ID NO 91
<211> LENGTH: 541
<212> TYPE: DNA
<213> ORGANISM: Homo sapiens
<220> FEATURE:
<221> NAME/KEY: misc_feature
<222> LOCATION: 480, 491
<223> OTHER INFORMATION: n = A,T,C or G

<400> SEQUENCE: 91
gaatcacctt tctggtttag ctagtacttt gtacagaaca atgaggtttc ccacagcgga 60
gtctccctgg gctctgtttg gctctcggta aggcaggcct acaccttttc ctctcctcta 120
tggagagggg aatatgcatt aaggtgaaaa gtcaccttcc aaaagtgaga aagggattcg 180
attgctgctt caggactgtg gaattatttg gaatgtttta caaatggttg ctacaaaaca 240
acaaaaaagg taattacaaa atgtgtacat cacaacatgc tttttaaaga cattatgcat 300
tgtgctcaca ttcccttaaa tgttgtttcc aaaggtgctc agcctctagc ccagctggat 360
tctccgggaa gaggcagaga cagtttggcg aaaaagacac agggaaggag ggggtggtga 420
aaggagaaag cagccttcca gttaaagatc agccctcagt taaaggtcag cttcccgcan 480
gctggcctca ngcggagtct gggtcagagg gaggagcagc agcagggtgg gactggggcg 540
t 541

<210> SEQ ID NO 92
<211> LENGTH: 551
<212> TYPE: DNA
<213> ORGANISM: Homo sapiens

<400> SEQUENCE: 92
aaccggagcg cgagcagtag ctgggtgggc accatggctg ggatcaccac catcgaggcg 60
gtgaagcgca agatccaggt tctgcagcag caggcagatg atgcagagga gcgagctgag 120
cgcctccagc gagaagttga gggagaaagg cgggcccggg aacaggctga ggctgaggtg 180
gcctccttga accgtaggat ccagctggtt gaagaagagc tggaccgtgc tcaggagcgc 240
ctggccactg ccctgcaaaa gctggaagaa gctgaaaaag ctgctgatga gagtgagaga 300
ggtatgaagg ttattgaaaa ccgggcctta aaagatgaag aaaagatgga actccaggaa 360

-continued

```
atccaactca aagaagctaa gcacattgca gaagaggcag ataggaagta tgaagaggtg    420

gctcgtaagt tggtgatcat tgaaggagac ttggaacgca cagaggaacg agctgagctg    480

gcagagtccc gttgccgaga gatggatgag cagattagac tgatggacca gaacctgaag    540

tgtctgagtg c                                                         551
```

```
<210> SEQ ID NO 93
<211> LENGTH: 531
<212> TYPE: DNA
<213> ORGANISM: Homo sapiens

<400> SEQUENCE: 93

gagaacttgg cctttattgt gggcccagga gggcacaaag gtcaggaggc ccaagggagg     60

gatctggttt tctggatagc caggtcatag catgggtatc agtaggaatc cgctgtagct    120

gcacaggcct cacttgctgc agttccgggg agaacacctg cactgcatgg cgttgatgac    180

ctcgtggtac acgacagagc cattggtgca gtgcaagggc acgcgcatgg gctccgtcct    240

cgagggcagg cagcaggagc attgctcctg cacatcctcg atgtcaatgg agtacacagc    300

tttgctggca cactttccct ggcagtaatg aatgtccact tcctcttggg acttacaatc    360

tcccactttg atgtactgca ccttggctgt gatgtctttg caatcaggct cctcacatgt    420

gtcacagcag gtgcctggaa ttttcacgat tttgcctcct tcagccagac acttgtgttc    480

atcaaatggt gggcagcccg tgaccctctt ctcccagatg tactctcctc t             531
```

```
<210> SEQ ID NO 94
<211> LENGTH: 531
<212> TYPE: DNA
<213> ORGANISM: Homo sapiens
<220> FEATURE:
<221> NAME/KEY: misc_feature
<222> LOCATION: 517
<223> OTHER INFORMATION: n = A,T,C or G

<400> SEQUENCE: 94

gcctggacct tgccggatca gtgccacaca gtgacttgct tggcaaatgg ccagaccttg     60

ctgcagagtc atcgtgtcaa ttgtgaccat ggaccccggc cttcatgtgc caacagccag    120

tctcctgttc gggtggagga gacgtgtggc tgccgctgga cctgcccttg tgtgtgcacg    180

ggcagttcca ctcggcacat cgtcaccttc gatgggcaga atttcaagct tactggtagc    240

tgctcctatg tcatctttca aaacaaggag caggacctgg aagtgctcct ccacaatggg    300

gcctgcagcc ccggggcaaa acaagcctgc atgaagtcca ttgagattaa gcatgctggc    360

gtctctgctg agctgcacag taacatggag atggcagtgg atgggagact ggtccttgcc    420

ccgtacgttg gtgaaaacat ggaagtcagc atctacggcg ctatcatgta tgaagtcagg    480

tttacccatc ttggccacat cctcacatac accgccncaa aacaacgagt t             531
```

```
<210> SEQ ID NO 95
<211> LENGTH: 605
<212> TYPE: DNA
<213> ORGANISM: Homo sapiens

<400> SEQUENCE: 95

agatcaacct ctgctggtca ggaggaatgc cttccttgtc ttggatcttt gctttgacgt     60

tctcgatagt rwcaactkkr ytsramskma agkgyratgr wmttksywgw rasyktmwwm    120

rsgraraytt agacayccm cctcwgagac gsagkaccar gtgcagaggt ggactctttc    180
```

-continued tggatgttgt agtcagacag ggtgcgtcca tcttccagct gtttcccagc aaagatcaac 240
ctctgctgat caggagggat gccttcctta tcttggatct ttgccttgac attctcgatg 300
gtgtcactgg gctccacctc gagggtgatg gtcttaccag tcagggtctt cacgaagaty 360
tgcatcccac ctctgagacg gagcaccagg tgcagggtrg actctttctg gatgttgtag 420
tcagacaggg tgcgyccatc ttccagctgc tttccsagca aagatcaacc tctgctggtc 480
aggaggratg ccttccttgt cytggatctt tgcyttgacr ttctcratgg tgtcactcgg 540
ctccacttcg agagtgatgg tcttaccagt caggtcttc acgaagatct gcatcccacc 600
tctaa 605

<210> SEQ ID NO 96
<211> LENGTH: 531
<212> TYPE: DNA
<213> ORGANISM: Homo sapiens

<400> SEQUENCE: 96
aagtcacaaa cagacaaaga ttattaccag ctgcaagcta tattagaagc tgaacgaaga 60
gacagaggtc atgattctga gatgattgga gaccttcaag ctcgaattac atctttacaa 120
gaggaggtga agcatctcaa acataatctc gaaaaagtgg aaggagaaag aaaagaggct 180
caagacatgc ttaatcactc agaaaaggaa aagaataatt tagagataga tttaaactac 240
aaacttaaat cattacaaca acggttagaa caagaggtaa atgaacacaa agtaaccaaa 300
gctcgtttaa ctgacaaaca tcaatctatt gaagaggcaa agtctgtggc aatgtgtgag 360
atggaaaaaa agctgaaaga agaaagagaa gctcgagaga aggctgaaaa tcgggttgtt 420
cagattgaga aacagtgttc catgctagac gttgatctga agcaatctca gcagaaacta 480
gaacatttga ctggaaataa agaaaggatg gaggatgaag ttaagaatct a 531

<210> SEQ ID NO 97
<211> LENGTH: 1017
<212> TYPE: DNA
<213> ORGANISM: Homo sapiens
<220> FEATURE:
<221> NAME/KEY: misc_feature
<222> LOCATION: 963, 995, 1001, 1008, 1010
<223> OTHER INFORMATION: n = A,T,C or G

<400> SEQUENCE: 97
cgcctccacc atgtccatca gggtgaccca gaagtcctac aaggtgtcca cctctggccc 60
ccgggccttc agcagccgct cctacacgag tgggcccggt tcccgcatca gctcctcgag 120
cttctcccga gtgggcagca gcaactttcg cggtggcctg ggcggcggct atggtggggc 180
cagcggcatg ggaggcatca ccgcagttac ggtcaaccag agcctgctga gccccccttgt 240 cctggaggtg gaccccaaca tccaggccgt gcgcacccag gagaaggagc agatcaagac 300
cctcaacaac aagtttgcct ccttcataga caaggtacgg ttcctggagc agcagaacaa 360
gatgctggag accaagtgga gcctcctgca gcagcagaag acggctcgaa gcaacatgga 420
caacatgttc gagagctaca tcaacaccct taggcggcag ctggagactc tgggccagga 480
gaagctgaag ctggaggcgg agcttggcaa catgcagggg ctggtggagg acttcaagaa 540
caagtatgag gatgagatca ataagcgtac agagatggag aacgaatttg tcctcatcaa 600
gaaggatgtg gatgaagctt acatgaacaa ggtagagctg gagtctcgcc tggaagggct 660
gaccgacgag atcaacttcc tcaggcagct gtatgaagag gagatccggg agctgcagtc 720
ccagatctcg gacacatctg tggtgctgtc catggacaac agccgctccc tggacatgga 780

-continued

```
cagcatcatt gctgaggtca aggcacagta cgaggatatt gccaaccgca gccgggctga    840

ggctgagagc atgtaccagg tcaagtatga ggagctgcag agcctggctg ggaagcacgg    900

ggatgacctg cggcgcacaa agactgagat ctctgagatg aacccggaac atcagcccgg    960

ctncaggctg agattgaggg cctcaaaggc caganggctt ncctggangn ccgccat      1017
```

<210> SEQ ID NO 98
<211> LENGTH: 561
<212> TYPE: DNA
<213> ORGANISM: Homo sapiens

<400> SEQUENCE: 98

```
cccggagcca gccaacgagc ggaaaatggc agacaatttt tcgctccatg atgcgttatc     60

tgggtctgga aacccaaacc ctcaaggatg gcctggcgca tgggggaacc agcctgctgg    120

ggcagggggc tacccagggg cttcctatcc tggggcctac ccgggcaggg cacccccagg    180

ggcttatcct ggacaggcac ctccaggcgc ctaccctgga gcacctggag cttatcccgg    240

agcacctgca cctggagtct acccagggcc acccagcggc cctggggcct acccatcttc    300

tggacagcca agtgccaccg gagcctaccc tgccactggc cctatggcgc cccctgctgg    360

gccactgatt gtgccttata acctgccttt gcctgggggga gtggtgcctc gcatgctgat    420

aacaattctg ggcacggtga agcccaatgc aaacagaatt gctttagatt tccaaagagg    480

gaatgatgtt gccttccact ttaacccacg cttcaatgag aacaacagga gagtcattgg    540

ttgcaataca aagctggata a                                              561
```

<210> SEQ ID NO 99
<211> LENGTH: 636
<212> TYPE: DNA
<213> ORGANISM: Homo sapiens

<400> SEQUENCE: 99

```
gggaatgcaa caactttatt gaaaggaaag tgcaatgaaa tttgttgaaa ccttaaaagg     60

ggaaacttag acaccccccc tcragcgmag kaccargtgc araggtggac tctttctgga    120

tgttgtagtc agacagggtr cgwccatctt ccagctgttt yccrgcaaag atcaacctct    180

gctgatcagg aggratgcct tccttatctt ggatctttgc cttgacattc tcgatggtgt    240

cactgggctc cacctcgagg gtgatggtct taccagtcag ggtcttcacg aagatytgca    300

tcccacctct gagacggagc accaggtgca gggtrgactc tttctggatg ttgtagtcag    360

acagggtgcg yccatcttcc agctgctttc csagcaaaga tcaacctctg ctggtcagga    420

ggratgcctt ccttgtcytg gatctttgcy ttgacrttct caatggtgtc actcggctcc    480

acttcgagag tgatggtctt accagtcagg gtcttcacga agatctgcat cccacctcta    540

agacggagca ccaggtgcag ggtggactct ttctggatgg ttgtagtcag acagggtgcg    600

tccatcttcc agctgtttcc cagcaaagat caacct                             636
```

<210> SEQ ID NO 100
<211> LENGTH: 697
<212> TYPE: DNA
<213> ORGANISM: Homo sapiens

<400> SEQUENCE: 100

```
aggttgatct ttgctgggaa acagctggaa gatggacgca ccctgtctga ctacaaccat     60

ccagaaagag tccaccctgc acctggtgct ccgtcttaga ggtgggatgc agatcttcgt    120
```

-continued

```
gaagaccctg actggtaaga ccatcactct cgaagtggag ccgagtgaca ccattgagaa    180

ygtcaargca aagatccarg acaaggaagg catycctcct gaccagcaga ggttgatctt    240

tgctsggaaa gcagctggaa gatggrcgca ccctgtctga ctacaacatc cagaaagagt    300

cyaccctgca cctggtgctc cgtctcagag gtgggatgca ratcttcgtg aagaccctga    360

ctggtaagac catcaccctc gaggtggagc ccagtgacac catcgagaat gtcaaggcaa    420

agatccaaga taaggaaggc atccctcctg atcagcagag gttgatcttt gctgggaaac    480

agctggaaga tggacgcacc ctgtctgact acaacatcca gaaagagtcc acctytgcac    540

ytggtmctbc gtctyagagg kgggrtgcaa atctwmgtkw agacactcac tkkyaagryy    600

atcamcmwtg akktcgakys castkwcact wtcrakaamg tyrwwgcawa gatccmagac    660

aaggaaggca ttcctcctga ccagcagagg ttgatct                             697
```

<210> SEQ ID NO 101
<211> LENGTH: 451
<212> TYPE: DNA
<213> ORGANISM: Homo sapiens

<400> SEQUENCE: 101

```
atggagtctc actctgtcga ccaggctgga gcgctgtggt gcgatatcgg ctcactgcag     60

tctccacttc ctgggttcaa gcgatcctcc tgcctcagcc tcccgagtag ctgggactac    120

aggcaggcgt caccataatt tttgtatttt tagtagagac atggtttcgc catgttggct    180

gggctggtct cgaactcctg acctcaagtg atctgtcctg gcctcccaaa gtgttgggat    240

tacaggcgaa agccaacgct cccggccagg gaacaacttt agaatgaagg aaatatgcaa    300

aagaacatca catcaaggat caattaatta ccatctatta attactatat gtgggtaatt    360

atgactattt cccaagcatt ctacgttgac tgcttgagaa gatgtttgtc ctgcatggtg    420

gagagtggag aagggccagg attcttaggt t                                   451
```

<210> SEQ ID NO 102
<211> LENGTH: 571
<212> TYPE: DNA
<213> ORGANISM: Homo sapiens

<400> SEQUENCE: 102

```
agcgcggtct tccggcgcga gaaagctgaa ggtgatgtgg ccgccctcaa ccgacgcatc     60

cagctcgttg aggaggagtt ggacagggct caggaacgac tggccacggc cctgcagaag    120

ctggaggagg cagaaaaagc tgcagatgag agtgagagag gaatgaaggt gatagaaaac    180

cggccatga aggatgagga gaagatggag attcaggaga tgcagctcaa agaggccaag    240

cacattgcgg aagaggctga ccgcaaatac gaggaggtag ctcgtaagct ggtcatcctg    300

gagggtgagc tggagagggc agaggagcgt gcggaggtgt ctgaactaaa atgtggtgac    360

ctggaagaag aactcaagaa tgttactaac aatctgaaat ctctggaggc tgcatctgaa    420

aagtattctg aaaaggagga caaatatgaa gaagaaatta aacttctgtc tgacaaactg    480

aaagaggctg agacccgtgc tgaatttgca gagagaacgg ttgcaaaact ggaaaagaca    540

attgatgacc tggaagagaa acttgcccag c                                   571
```

<210> SEQ ID NO 103
<211> LENGTH: 451
<212> TYPE: DNA
<213> ORGANISM: Homo sapiens

<400> SEQUENCE: 103

-continued

```
gtgcacaggt cccatttatt gtagaaaata ataataatta cagtgatgaa tagctcttct     60

taaattacaa aacagaaacc acaaagaagg aagaggaaaa accccaggac ttccaagggt    120

gaagctgtcc cctcctccct gccaccctcc caggctcatt agtgtccttg gaaggggcag    180

aggactcaga ggggatcagt ctccaggggc cctgggctga agcgggtgag gcagagagtc    240

ctgaggccac agagctgggc aacctgagcc gcctctctgg ccccctcccc caccactgcc    300

caaacctgtt tacagcacct tcgcccctcc cctctaaacc cgtccatcca ctctgcactt    360

cccaggcagg tgggtgggcc aggcctcagc catactcctg ggcgcgggtt tcggtgagca    420

aggcacagtc ccagaggtga tatcaaggcc t                                   451
```

<210> SEQ ID NO 104
<211> LENGTH: 441
<212> TYPE: DNA
<213> ORGANISM: Homo sapiens

<400> SEQUENCE: 104

```
gcaaggaact ggtctgctca cacttgctgg cttgcgcatc aggactggct ttatctcctg     60

actcacggtg caaaggtgca ctctgcgaac gttaagtccg tccccagcgc ttggaatcct    120

acggccccca cagccggatc ccctcagcct tccaggtcct caactcccgt ggacgctgaa    180

caatggcctc catggggcta caggtaatgg gcatcgcgct ggccgtcctg ggctggctgg    240

ccgtcatgct gtgctgcgcg ctgcccatgt ggcgcgtgac ggccttcatc ggcagcaaca    300

ttgtcacctc gcagaccatc tgggagggcc tatggatgaa ctgcgtggtg cagagcaccg    360

gccagatgca gtgcaaggtg tacgactcgc tgctggcact gccgcaggac ctgcaggcgg    420

cccgcgccct cgtcatcatc a                                              441
```

<210> SEQ ID NO 105
<211> LENGTH: 509
<212> TYPE: DNA
<213> ORGANISM: Homo sapiens
<220> FEATURE:
<221> NAME/KEY: misc_feature
<222> LOCATION: 195
<223> OTHER INFORMATION: n = A,T,C or G

<400> SEQUENCE: 105

```
tgcaaaaggg acacaggggt tcaaaaataa aaatttctct tccccctccc caaacctgta     60

ccccagctcc ccgaccacaa ccccccttcct cccccgggga aagcaagaag gagcaggtgt    120

ggcatctgca gctgggaaga gagaggccgg ggaggtgccg agctcggtgc tggtctcttt    180

ccaaatataa atacntgtgt cagaactgga aaatcctcca gcacccacca cccaagcact    240

ctccgttttc tgccggtgtt tggagagggg cggggggcag gggcgccagg caccggctgg    300

ctgcggtcta ctgcatccgc tgggtgtgca ccccgcgagc ctcctgctgc tcattgtaga    360

agagatgaca ctcggggtcc ccccggatgg tgggggctcc ctggatcagc ttcccggtgt    420

tggggttcac acaccagcac tccccacgct gcccgttcag agacatcttg cactgtttga    480

ggttgtacag gccatgcttg tcacagttg                                      509
```

<210> SEQ ID NO 106
<211> LENGTH: 571
<212> TYPE: DNA
<213> ORGANISM: Homo sapiens

<400> SEQUENCE: 106

-continued

```
gggttggagg gactggttct ttatttcaaa aagacacttg tcaatattca gtatcaaaac      60

agttgcacta ttgatttctc tttctcccaa tcggccccaa agagaccaca taaaaggaga     120

gtacatttta agccaataag ctgcaggatg tacacctaac agacctccta gaaaccttac     180

cagaaaatgg ggactgggta gggaaggaaa cttaaaagat caacaaactg ccagcccacg     240

gactgcagag gctgtcacag ccagatgggg tggccagggt gccacaaacc caaagcaaag     300

tttcaaaata atataaaatt taaaaagttt tgtacataag ctattcaaga tttctccagc     360

actgactgat acaaagcaca attgagatgg cacttctaga gacagcagct tcaaacccag     420

aaaagggtga tgagatgagt ttcacatggc taaatcagtg gcaaaaacac agtcttcttt     480

ctttctttct ttcaaggagg caggaaagca attaagtggt cacctcaaca taagggggac     540

atgatccatt ctgtaagcag ttgtgaaggg g                                    571
```

```
<210> SEQ ID NO 107
<211> LENGTH: 555
<212> TYPE: DNA
<213> ORGANISM: Homo sapiens

<400> SEQUENCE: 107

caggaaccgg agcgcgagca gtagctgggt gggcaccatg gctgggatca ccaccatcga      60

ggcggtgaag cgcaagatcc aggttctgca gcagcaggca gatgatgcag aggagcgagc     120

tgagcgcctc cagcgagaag ttgagggaga aaggcgggcc cgggaacagg ctgaggctga     180

ggtggcctcc ttgaaccgta ggatccagct ggttgaagaa gagctggacc gtgctcagga     240

gcgcctggcc actgccctgc aaaagctgga agaagctgaa aaagctgctg atgagagtga     300

gagaggtatg aaggttattg aaaaccgggc cttaaaagat gaagaaaaga tggaactcca     360

ggaaatccaa ctcaaagaag ctaagcacat tgcagaagag gcagatagga agtatgaaga     420

ggtggctcgt aagttggtga tcattgaagg agacttggaa cgcacagagg aacgagctga     480

gctggcagag tcccgttgcc gagagatgga tgagcagatt agactgatgg accagaacct     540

gaagtgtctg agtgc                                                      555
```

```
<210> SEQ ID NO 108
<211> LENGTH: 541
<212> TYPE: DNA
<213> ORGANISM: Homo sapiens

<400> SEQUENCE: 108

atctacgtca tcaatcaggc tggagacacc atgttcaatc gagctaagct gctcaatatt      60

ggctttcaag aggccttgaa ggactatgat tacaactgct ttgtgttcag tgatgtggac     120

ctcattccga tggacgaccg taatgcctac aggtgttttt cgcagccacg gcacatttct     180

gttgcaatgg acaagttcgg gtttagcctg ccatatgttc agtattttgg aggtgtctct     240

gctctcagta aacaacagtt tcttgccatc aatggattcc ctaataatta ttggggttgg     300

ggaggagaag atgacgacat ttttaacaga ttagttcata aaggcatgtc tatatcacgt     360

ccaaatgctg tagtagggag gtgtcgaatg atccggcatt caagagacaa gaaaaatgag     420

cccaatcctc agaggtttga ccggatcgca catacaaagg aaacgatgcg cttcgatggt     480

ttgaactcac ttacctacaa ggtgttggat gtcagagata cccgttatat acccaaatca     540

c                                                                     541
```

```
<210> SEQ ID NO 109
<211> LENGTH: 411
```

-continued

<212> TYPE: DNA
<213> ORGANISM: Homo sapiens

<400> SEQUENCE: 109
ctagacctct aattaaaagg cacaatcatg ctggagaatg aacagtctga ccccgagggc 60
cacagcgaat tttagggaag gaggcaaaga ggtgagaagg gaaaggaaag aaggaaggaa 120
ggagaacaat aagaactgga gacgttgggt gggtcaggga gtgtggtgga ggctcggaga 180
gatggtaaac aaacctgact gctatgagtt ttcaacccca tagtctaggg ccatgagggc 240
gtcagttctt ggtggctgag ggtccttcca cccagcccac ctgggggagt ggagtgggga 300
gttctgccag gtaagcagat gttgtctccc aagttcctga cccagatgtc tggcaggata 360
acgctgacct gttccctcaa caagggacct gaaagtaatt ttgctcttta c 411

<210> SEQ ID NO 110
<211> LENGTH: 451
<212> TYPE: DNA
<213> ORGANISM: Homo sapiens

<400> SEQUENCE: 110
ccgaattcaa gcgtcaacga tccytccctt accatcaaat caattggcca ccaatggtac 60
tgaacctacg agtacaccga ctacgggcgg actaatcttc aactcctaca tacttccccc 120
attattccta gaaccaggcg acctgcgact ccttgacgtt gacaatcgag tagtactccc 180
gattgaagcc cccattcgta taataattac atcacaagac gtcttgcact catgagctgt 240
ccccacatta ggcttaaaaa cagatgcaat tcccggacgt ctaagccaaa ccactttcac 300
cgctacacga ccgggggtat actacggtca atgctctgaa atctgtggag caaaccacag 360
tttcatgccc atcgtcctag aattaattcc cctaaaaatc tttgaaatag ggcccgtatt 420
taccctatag caccccctct accccctcta g 451

<210> SEQ ID NO 111
<211> LENGTH: 541
<212> TYPE: DNA
<213> ORGANISM: Homo sapiens

<400> SEQUENCE: 111
gctcttcaca cttttattgt taattctctt cacatggcag atacagagct gtcgtcttga 60
agaccaccac tgaccaggaa atgccacttt tacaaaatca tccccccttt tcatgattgg 120
aacagttttc ctgaccgtct gggagcgttg aagggtgacc agcacatttg cacatgcaaa 180
aaaggagtga ccccaaggcc tcaaccacac ttcccagagc tcaccatggg ctgcaggtga 240
cttgccaggt ttggggttcg tgagctttcc ttgctgctgc ggtggggagg ccctcaagaa 300
ctgagaggcc ggggtatgct tcatgagtgt taacatttac gggacaaaag cgcatcatta 360
ggataaggaa cagccacagc acttcatgct tgtgagggtt agctgtagga gcgggtgaaa 420
ggattccagt ttatgaaaat ttaaagcaaa caacggtttt tagctgggtg ggaaacagga 480
aaactgtgat gtcggccaat gaccaccatt tttctgccca tgtgaaggtc cccatgaaac 540
c 541

<210> SEQ ID NO 112
<211> LENGTH: 521
<212> TYPE: DNA
<213> ORGANISM: Homo sapiens

<400> SEQUENCE: 112

-continued

```
caagcgcttg gcgtttggac ccagttcagt gaggttcttg ggttttgtgc ctttggggat     60

tttggtttga cccaggggtc agccttagga aggtcttcag gaggaggccg agttcccctt    120

cagtaccacc cctctctccc cactttccct ctcccggcaa catctctggg aatcaacagc    180

atattgacac gttggagccg agcctgaaca tgcccctcgg ccccagcaca tggaaaaccc    240

ccttccttgc ctaaggtgtc tgagtttctg gctcttgagg catttccaga cttgaaattc    300

tcatcagtcc attgctcttg agtctttgca gagaacctca gatcaggtgc acctgggaga    360

aagactttgt ccccacttac agatctatct cctcccttgg gaagggcagg gaatggggac    420

ggtgtatgga ggggaaggga tctcctgcgc ccttcattgc cacacttggt gggaccatga    480

acatctttag tgtctgagct tctcaaatta ctgcaatagg a                        521
```

<210> SEQ ID NO 113
<211> LENGTH: 568
<212> TYPE: DNA
<213> ORGANISM: Homo sapiens

<400> SEQUENCE: 113

```
agcgtcaaat cagaatggaa aagactcaaa accatcatca acaccaagat caaaaggaca     60

agratccttc aagaaacagg aaaaaactcc taaaacacca aaaggaccta gttctgtaga    120

agacattaaa gcaaaaatgc aagcaagtat agaaaaaggt ggttctcttc ccaaagtgga    180

agccaaattc atcaattatg tgaagaattg cttccggatg actgaccaag aggctattca    240

agatctctgg cagtggagga agtctcttta agaaaatagt ttaaacaatt tgttaaaaaa    300

ttttccgtct tatttcattt ctgtaacagt tgatatctgg ctgtcctttt tataatgcag    360

agtgagaact ttccctaccg tgtttgataa atgttgtcca ggttctattg ccaagaatgt    420

gttgtccaaa atgcctgttt agtttttaaa gatggaactc caccctttgc ttggttttaa    480

gtatgtatgg aatgttatga taggacatag tagtagcggt ggtcagacat ggaaatggtg    540

ggsmgacaaa aatatacatg tgaaataa                                       568
```

<210> SEQ ID NO 114
<211> LENGTH: 483
<212> TYPE: DNA
<213> ORGANISM: Homo sapiens

<400> SEQUENCE: 114

```
tccgaattcc aagcgaatta tggacaaacg attcctttta gaggattact tttttcaatt     60

tcggttttag taatctaggc tttgcctgta aagaatacaa cgatggattt taaatactgt    120

ttgtggaatg tgtttaaagg attgattcta gaacctttgt atatttgata gtatttctaa    180

ctttcatttc tttactgttt gcagttaatg ttcatgttct gctatgcaat cgtttatatg    240

cacgtttctt taattttttt agattttcct ggatgtatag tttaaacaac aaaaagtcta    300

tttaaaactg tagcagtagt ttacagttct agcaaagagg aaagttgtgg ggttaaactt    360

tgtattttct ttcttataga ggcttctaaa aaggtatttt tatatgttct ttttaacaaa    420

tattgtgtac aacctttaaa acatcaatgt ttggatcaaa acaagaccca gcttattttc    480

tgc                                                                  483
```

<210> SEQ ID NO 115
<211> LENGTH: 521
<212> TYPE: DNA
<213> ORGANISM: Homo sapiens

<400> SEQUENCE: 115

-continued

```
tgtggtggcg cgggctgagg tggaggccca ggactctgac cctgcccctg ccttcagcaa     60

ggcccccggc agcgccggcc actacgaact gccgtgggtt gaaaaatata ggccagtaaa    120

gctgaatgaa attgtcggga atgaagacac cgtgagcagg ctagaggtct ttgcaaggga    180

aggaaatgtg cccaacatca tcattgcggg ccctccagga accggcaaga ccacaagcat    240

tctgtgcttg gcccgggccc tgctgggccc agcactcaaa gatgccatgt tggaactcaa    300

tgcttcaaat gacaggggca ttgacgttgt gaggaataaa attaaaatgt ttgctcaaca    360

aaaagtcact cttcccaaag gccgacataa gatcatcatt ctggatgaag cagacagcat    420

gaccgacgga gcccagcaag ccttgaggag aaccatggaa atctactcta aaaccactcg    480

ttcgcccttg cttgtaatgc ttcggataag atcatcgagc c                        521
```

<210> SEQ ID NO 116
<211> LENGTH: 501
<212> TYPE: DNA
<213> ORGANISM: Homo sapiens

<400> SEQUENCE: 116

```
ctttgcaaag cttttatttc atgtctgcgg catggaatcc acctgcacat ggcatcttag     60

ctgtgaagga gaaagcagtg cacgagaagg aatgagtggg cggaaccaac ggcctccaca    120

agctgccttc cagcagcctg ccaaggccat ggcagagaga gactgcaaac aaacacaagc    180

aaacagagtc tcttcacagc tggagtctga aagctcatag tggcatgtgt gaatctgaca    240

aaattaaaag tgtgcatagt ccattacatg cataaaacac taataataat cctgtttaca    300

cgtgactgca gcaggcaggt ccagctccac cactgccctc ctgccacatc acatcaagtg    360

ccatggttta gagggttttt catatgtaat tcttttattc tgtaaaaggt aacaaaatat    420

acagaacaaa actttccctt tttaaaacta atgttacaaa tctgtattat cacttggata    480

taaatagtat ataagctgat c                                              501
```

<210> SEQ ID NO 117
<211> LENGTH: 451
<212> TYPE: DNA
<213> ORGANISM: Homo sapiens
<220> FEATURE:
<221> NAME/KEY: misc_feature
<222> LOCATION: 320
<223> OTHER INFORMATION: n = A,T,C or G

<400> SEQUENCE: 117

```
caagggatat atgttgaggg tacrgrgtga cactgaacag atcacaaagc acgagaaaca     60

ttagttctct ccctccccag cgtctccttc gtctccctgg ttttccgatg tccacagagt    120

gagattgtcc ctaagtaact gcatgatcag agtgctgkct ttataagact cttcattcag    180

cgtatccaat tcagcaattg cttcatcaaa tgccgttttt gccaggctac aggccttttc    240

aggagagttt agaatctcat agtaaaagac tgagaaattt agtgccagac caagacgaat    300

tgggtgtgta ggctgcattn ctttcttact aatttcaaat gcttcctggt aagcctgctg    360

ggagttcgac acaagtggtt tgtttgttgc tccagatgcc acttcagaaa gatacctaaa    420

ataatctcct ttcattttca aagtagaaca c                                   451
```

<210> SEQ ID NO 118
<211> LENGTH: 501
<212> TYPE: DNA
<213> ORGANISM: Homo sapiens -continued

<400> SEQUENCE: 118

```
tccggagccg gggtagtcgc cgccgccgcc gccggtgcag ccactgcagg caccgctgcc     60

gccgcctgag tagtgggctt aggaaggaag aggtcatctc gctcggagct tcgctcggaa    120

gggtctttgt tccctgcagc cctcccacgg gaatgacaat ggataaaagt gagctggtac    180

agaaagccaa actcgctgag caggctgagc gatatgatga tatggctgca gccatgaagg    240

cagtcacaga acaggggcat gaactctcca acgaagagag aaatctgctc tctgttgcct    300

acaagaatgt ggtaaggccg cccgccgctc ttcctggcgt gtcatctcca gcattgagca    360

gaaaacagag aggaatgaga agaagcagca gatgggcaaa gagtaccgtg agaagataga    420

ggcagaactg caggacatct gcaatgatgt tctggagctt gttggacaaa tatcttattc    480

caatgctaca caacccagaa a                                              501
```

<210> SEQ ID NO 119
<211> LENGTH: 391
<212> TYPE: DNA
<213> ORGANISM: Homo sapiens

<400> SEQUENCE: 119

```
aaaaagcagc argttcaaca caaaatagaa atctcaaatg taggatagaa caaaaccaag     60

tgtgtgaggg gggaagcaac agcaaaagga agaaatgaga tgttgcaaaa aagatggagg    120

agggttcccc tctcctctgg ggactgactc aaacactgat gtggcagtat acaccattcc    180

agagtcaggg gtgttcattc ttttttggga gtaagaaaag gtggggatta agaagacgtt    240

tctggaggct tagggaccaa ggctggtctc tttccccct cccaaccccc ttgatccctt    300

tctctgatca ggggaaagga gctcgaatga gggaggtaga gttggaaagg gaaaggattc    360

cacttgacag aatgggacag actccttccc a                                   391
```

<210> SEQ ID NO 120
<211> LENGTH: 421
<212> TYPE: DNA
<213> ORGANISM: Homo sapiens
<220> FEATURE:
<221> NAME/KEY: misc_feature
<222> LOCATION: 409
<223> OTHER INFORMATION: n = A,T,C or G

<400> SEQUENCE: 120

```
tggcaatagc acagccatcc aggagctctt cargcgcatc tcggagcagt tcactgccat     60

gttccgccgg aaggccttcc tccactggta cacaggcgag ggcatggacg agatggagtt    120

caccgaggct gagagcaaca tgaacgacct cgtctctgag tatcaagcag taccaggatg    180

ccaccgcaga agaggaggag gatttcggtg aggaggccga agaggaggcc taaggcagag    240

cccccatcac ctcaggcttc tcagttccct tagccgtctt actcaactgc ccctttcctc    300

tccctcagaa tttgtgtttg ctgcctctat cttgtttttt gtttttttctt ctggggggggt    360

ctagaacagt gcctggcaca tagtaggcgc tcaataaata cttggttgnt gaatgtctcc    420

t                                                                    421
```

<210> SEQ ID NO 121
<211> LENGTH: 206
<212> TYPE: DNA
<213> ORGANISM: Homo sapiens

<400> SEQUENCE: 121

```
agctggcgct agggctcggt tgtgaaatac agcgtrgtca gcccttgcgc tcagtgtaga     60
```

-continued

```
aacccacgcc tgtaaggtcg gtcttcgtcc atctgctttt ttctgaaata cactaagagc    120

agccacaaaa ctgtaacctc aaggaaacca taaagcttgg agtgccttaa tttttaacca    180

gtttccaata aaacggttta ctacct                                          206


<210> SEQ ID NO 122
<211> LENGTH: 131
<212> TYPE: DNA
<213> ORGANISM: Homo sapiens

<400> SEQUENCE: 122

ggagatgaag atgaggaagc tgagtcagct acgggcargc gggcagctga agatgatgag     60

gatgacgatg tcgataccaa gaagcagaag accgacgagg atgactagac agcaaaaaag    120

gaaaagttaa a                                                          131


<210> SEQ ID NO 123
<211> LENGTH: 231
<212> TYPE: DNA
<213> ORGANISM: Homo sapiens
<220> FEATURE:
<221> NAME/KEY: misc_feature
<222> LOCATION: 166, 202, 222, 225
<223> OTHER INFORMATION: n = A,T,C or G

<400> SEQUENCE: 123

gatgaaaatt aaatacttaa attaatcaaa aggcactacg ataccaccta aaacctactg     60

cctcagtggc agtakgctaa kgaagatcaa gctacagsac atyatctaat atgaatgtta    120

gcaattacat akcargaagc atgtttgctt tccagaagac tatggnacaa tggtcattwg    180

ggcccaagag gatatttggc cnggaaagga tcaagataga tnaangtaaa g              231


<210> SEQ ID NO 124
<211> LENGTH: 521
<212> TYPE: DNA
<213> ORGANISM: Homo sapiens
<220> FEATURE:
<221> NAME/KEY: misc_feature
<222> LOCATION: 284, 412, 513
<223> OTHER INFORMATION: n = A,T,C or G

<400> SEQUENCE: 124

gagtagcaac gcaaagcgct tggtattgag tctgtgggsg acttcggttc cggtctctgc     60

agcagccgtg atcgcttagt ggagtgctta gggtagttgg ccaggatgcc gaatatcaaa    120

atcttcagca ggcagctccc accaggactt atctcasaaa attgctgacc gcctgggcct    180

ggagctaggc aaggtggtga ctaagaaatt cagcaaccag gagacctgtg tggaaattgg    240

tgaaagtgta ccgtggagag gatgtctaca ttgttcagag tggntgtggc gaaatcaatg    300

acaatttaat ggagcttttg atcatgatta atgcctgcaa gattgcttca gccagccggg    360

ttactgcagt catcccatgc ttcccttatg ccccggcagg ataagaaaga tnagagccgg    420

gccgccaatc tcagccaagc ttggtgcaaa tatgctatct gtagcagtgc agatcatatt    480

atcaccatgg acctacatgc ttctcaaatt canggctttt t                         521


<210> SEQ ID NO 125
<211> LENGTH: 341
<212> TYPE: DNA
<213> ORGANISM: Homo sapiens
<220> FEATURE:
<221> NAME/KEY: misc_feature
<222> LOCATION: 277
```

-continued

<223> OTHER INFORMATION: n = A,T,C or G

<400> SEQUENCE: 125
atgcaaaagg ggacacaggg ggttcaaaaa taaaaatttc tcttcccccct ccccaaacct 60 gtaccccagc tccccgacca caaccccctt cctcccccgg ggaaagcaag aaggagcagg 120
tgtggcatct gcagctggga agagagaggc cggggaggtg ccgagctcgg tgctggtctc 180
tttccaaata taaatacgtg tgtcagaact ggaaaatcct ccagcaccca ccacccaagc 240
actctccgtt ttctgccggt gtttggagag gggcggnggg caggggcgcc aggcaccggc 300
tggctgcggt ctactgcatc cgctgggtgt gcacccccgcg a 341

<210> SEQ ID NO 126
<211> LENGTH: 521
<212> TYPE: DNA
<213> ORGANISM: Homo sapiens
<220> FEATURE:
<221> NAME/KEY: misc_feature
<222> LOCATION: 353, 399, 455
<223> OTHER INFORMATION: n = A,T,C or G

<400> SEQUENCE: 126
aggttggaga aggtcatgca ggtgcagatt gtccaggskc agccacaggg tcaagcccaa 60
caggcccaga gtggcactgg acagaccatg caggtgatgc agcagatcat cactaacaca 120
ggagagatcc agcagatccc ggtgcagctg aatgccggcc agctgcagta tatccgctta 180
gcccagcctg tatcaggcac tcaagttgtg cagggacaga tccagacact tgccaccaat 240
gctcaacaga ttacacagac agaggtccag caaggacagc agcagttcaa gccagttcac 300
aagatggaca gcagctctac cagatccagc aagtcaccat gcctgcgggc cangacctcg 360
ccagcccatg ttcatccagt caagccaacc agcccttcna cgggcaggcc ccccaggtga 420
ccggcgactg aagggcctga gctggcaagg ccaangacac ccaacacaat ttttgccata 480
cagcccccag gcaatgggca cagcctttct tcccagagga c 521

<210> SEQ ID NO 127
<211> LENGTH: 351
<212> TYPE: DNA
<213> ORGANISM: Homo sapiens

<400> SEQUENCE: 127
tgagatttat tgcatttcat gcagcttgaa gtccatgcaa aggrgactag cacagttttt 60
aatgcattta aaaaataaaa gggaggtggg cagcaaacac acaaagtcct agtttcctgg 120
gtccctggga gaaaagagtg tggcaatgaa tccacccact ctccacaggg aataaatctg 180
tctcttaaat gcaaagaatg tttccatggc ctctggatgc aaatacacag agctctgggg 240
tcagagcaag ggatggggag aggaccacga gtgaaaaagc agctacacac attcacctaa 300
ttccatctga gggcaagaac aacgtggcaa gtcttggggg tagcagctgt t 351

<210> SEQ ID NO 128
<211> LENGTH: 521
<212> TYPE: DNA
<213> ORGANISM: Homo sapiens

<400> SEQUENCE: 128
tccagacatg ctcctgtcct aggcggggag caggaaccag acctgctatg ggaagcagaa 60
agagttaagg gaaggtttcc tttcattcct gttccttctc ttttgctttt gaacagtttt 120
taaatatact aatagctaag tcatttgcca gccaggtccc ggtgaacagt agagaacaag 180

-continued

```
gagcttgcta agaattaatt ttgctgtttt tcaccccatt caaacagagc tgccctgttc    240
cctgatggag ttccattcct gccagggcac ggctgagtaa cacgaagcca ttcaagaaag    300
gcgggtgtga aatcactgcc accccatgga cagacccctc actcttcctt cttagccgca    360
gcgctactta ataaatatat ttatactttg aaattatgat aaccgatttt tcccatgcgg    420
catcctaagg gcacttgcca gctcttatcc ggacagtcaa gcactgttgt tggacaacag    480
ataaaggaaa agaaaaagaa gaaaacaacc gcaacttctg t                        521
```

<210> SEQ ID NO 129
<211> LENGTH: 521
<212> TYPE: DNA
<213> ORGANISM: Homo sapiens

<400> SEQUENCE: 129

```
tgagacggac cactggcctg gtcccccctc atktgctgtc gtaggacctg acatgaaacg     60
cagatctagt ggcagagagg aagatgatga ggaacttctg agacgtcggc agcttcaaga    120
agagcaatta atgaagctta actcaggcct gggacagttg atcttgaaag aagagatgga    180
gaaagagagc cgggaaaggt catctctgtt agccagtcgc tacgattctc ccatcaactc    240
agcttcacat attccatcat ctaaaactgc atctctccct ggctatggaa gaaatgggct    300
tcaccggcct gtttctaccg acttcgctca gtataacagc tatggggatg tcagcggggg    360
agtgcgagat taccagacac ttccagatgg ccacatgcct gcaatgagaa tggaccgagg    420
agtgtctatg cccaacatgt tggaaccaaa gatatttcca tatgaaatgc tcatggtgac    480
caacagaggg ccgaaaccaa atctcagaga ggtggacaga a                        521
```

<210> SEQ ID NO 130
<211> LENGTH: 270
<212> TYPE: DNA
<213> ORGANISM: Homo sapiens

<400> SEQUENCE: 130

```
tcactttatt tttcttgtat aaaaacccta tgttgtagcc acagctggag cctgagtccg     60
ctgcacggag actctggtgt gggtcttgac gaggtggtca gtgaactcct gatagggaga    120
cttggtgaat acagtctcct tccagaggtc gggggtcagg tagctgtagg tcttagaaat    180
ggcatcaaag gtggccttgg cgaagttgcc cagggtggca gtgcagcccc gggctgaggt    240
gtagcagtca tcgataccag ccatcatgag                                     270
```

<210> SEQ ID NO 131
<211> LENGTH: 341
<212> TYPE: DNA
<213> ORGANISM: Homo sapiens

<400> SEQUENCE: 131

```
ctggaatata gacccgtgat cgacaaaact ttgaacgagg ctgactgtgc caccgtcccg     60
ccagccattc gctcctactg atgagacaag atgtggtgat gacagaatca gcttttgtaa    120
ttatgtataa tagctcatgc atgtgtccat gtcataactg tcttcatacg cttctgcact    180
ctggggaaga aggagtacat tgaagggaga ttggcaccta gtggctggga gcttgccagg    240
aacccagtgg ccagggagcg tggcacttac ctttgtccct tgcttcattc ttgtgagatg    300
ataaaactgg gcacagctct taaataaaat ataaatgaac a                        341
```

<210> SEQ ID NO 132

-continued

<211> LENGTH: 844
<212> TYPE: DNA
<213> ORGANISM: Homo sapiens
<220> FEATURE:
<221> NAME/KEY: misc_feature
<222> LOCATION: 37
<223> OTHER INFORMATION: n = A,T,C or G

<400> SEQUENCE: 132
tgaatgggga ggagctgacc caggaaatgg agcttgngga gaccaggcct gcaggggatg 60
gaaccttcca gaagtgggca tctgtggtgg tgcctcttgg gaaggagcag aagtacacat 120
gccatgtgga acatgagggg ctgcctgagc ccctcaccct gagatggggc aaggaggagc 180
ctccttcatc caccaagact aacacagtaa tcattgctgt tccggttgtc cttggagctg 240
tggtcatcct tggagctgtg atggcttttg tgatgaagag gaggagaaac acaggtggaa 300
aaggagggga ctatgctctg gctccaggct cccagagctc tgatatgtct ctcccagatt 360
gtaaagtgtg aagacagctg cctggtgtgg acttggtgac agacaatgtc ttcacacatc 420
tcctgtgaca tccagagacc tcagttctct ttagtcaagt gtctgatgtt ccctgtgagt 480
ctgcgggctc aaagtgaaga actgtggagc ccagtccacc cctgcacacc aggaccctat 540
ccctgcactg ccctgtgttc ccttccacag ccaaccttgc tgctccagcc aaacattggt 600
ggacatctgc agcctgtcag ctccatgcta ccctgacctt caactcctca cttccacact 660
gagaataata atttgaatgt gggtggctgg agagatggct cagcgctgac tgctcttcca 720
aaggtcctga gttcaaatcc cagcaaccac atggtggctc acaaccatct gtaatgggat 780
ctaataccct cttctgcagt gtctgaagac asctacagtg tacttacata taataataaa 840
taag 844

<210> SEQ ID NO 133
<211> LENGTH: 601
<212> TYPE: DNA
<213> ORGANISM: Homo sapiens

<400> SEQUENCE: 133
ggccgggcgc gcgcgccccc gccacacgca cgccgggcgt gccagtttat aaagggagag 60
agcaagcagc gagtcttgaa gctctgtttg gtgctttgga tccatttcca tcggtcctta 120
cagccgctcg tcagactcca gcagccaaga tggtgaagca gatcgagagc aagactgctt 180
ttcaggaagc cttggacgct gcaggtgata aacttgtagt agttgacttc tcagccacgt 240
ggtgtgggcc ttgcaaaatg atcaagcctt tctttcattc cctctctgaa aagtattcca 300
acgtgatatt ccttgaagta gatgtggatg actgtcagga tgttgcttca gagtgtgaag 360
tcaaatgcat gccaacattc cagtttttta agaagggaca aaaggtgggt gaattttctg 420
gagccaataa ggaaaagctt gaagccacca ttaatgaatt agtctaatca tgttttctga 480
aaatataacc agccattggc tatttaaaac ttgtaatttt tttaatttac aaaaatataa 540
aatatgaaga cataaacccm gttgccatct gcgtgacaat aaaacattaa tgctaacact 600
t 601

<210> SEQ ID NO 134
<211> LENGTH: 421
<212> TYPE: DNA
<213> ORGANISM: Homo sapiens

<400> SEQUENCE: 134
tcacataaga aatttaagca agttacrcta tcttaaaaaa cacaacgaat gcattttaat 60

-continued agagaaaccc ttccctccct ccacctccct cccccaccct cctcatgaat taagaatcta 120
agagaagaag taaccataaa accaagtttt gtggaatcca tcatccagag tgcttacatg 180
gtgattaggt taatattgcc ttcttacaaa atttctattt taaaaaaaat tataaccttg 240
attgcttatt acaaaaaaat tcagtacaaa agttcaatat attgaaaaat gcttttcccc 300
tccctcacag caccgtttta tatatagcag agaataatga agagattgct agtctagatg 360
gggcaatctt caaattacac caagacgcac agtggtttat ttaccctccc cttctcataa 420
g 421

<210> SEQ ID NO 135
<211> LENGTH: 511
<212> TYPE: DNA
<213> ORGANISM: Homo sapiens

<400> SEQUENCE: 135
ggaaaggatt caagaattag aggacttgct tgctrragaa aaagacaact ctcgtcgcat 60
gctgacagac aaagagagag agatggcgga aataagggat caaatgcagc aacagctgaa 120
tgactatgaa cagcttcttg atgtaaagtt agccctggac atggaaatca gtgcttacag 180
gaaactctta gaaggcgaag aagagaggtt gaagctgtct ccaagccctt cttcccgtgt 240
gacagtatcc cgagcatcct caagtcgtag tgtaccgtac aactagagga aagcggaaga 300
gggttgatgt ggaagaatca gaggcgaagt agtagtgtta gcatctctca ttccgcctca 360
accactggaa atgtttgcat cgaagaaatt gatgttgatg ggaaatttat cccgcttgaa 420
gaacacttct gaacaggatc aaccaatggg aaggcttggg agatgatcag aaaaattgga 480
gacacatcag tcagttataa atatacctca a 511

<210> SEQ ID NO 136
<211> LENGTH: 341
<212> TYPE: DNA
<213> ORGANISM: Homo sapiens

<400> SEQUENCE: 136
catgggtttc accaggttgg ccaggctgct cttgaactsc tgacctcagg tgatccaccc 60
gcctcggcct cccaaagtgc tgggattaca ggcgtgagcc accacgcccg gcccccaaag 120
ctgtttcttt tgtctttagc gtaaagctct cctgccatgc agtatctaca taactgacgt 180
gactgccagc aagctcagtc actccgtggt ctttttctct ttccagttct tctctctctc 240
ttcaagttct gcctcagtga aagctgcagg tccccagtta agtgatcagg tgagggttct 300
ttgaacctgg ttctatcagt cgaattaatc cttcatgatg g 341

<210> SEQ ID NO 137
<211> LENGTH: 551
<212> TYPE: DNA
<213> ORGANISM: Homo sapiens

<400> SEQUENCE: 137
gatgtgttgg accctctgtg tcaaaaaaaa cctcacaaag aatcccctgc tcattacaga 60
agaagatgca tttaaaatat gggttatttt caacttttta tctgaggaca agtatccatt 120
aattattgtg tcagaagaga ttgaatacct gcttaagaag cttacagaag ctatgggagg 180
aggttggcag caagaacaat ttgaacatta taaaatcaac tttgatgaca gtaaaaatgg 240
cctttctgca tgggaactta ttgagcttat tggaaatgga cagtttagca aaggcatgga 300

-continued

```
ccggcagact gtgtctatgg caattaatga agtctttaat gaacttatat tagatgtgtt    360

aaagcagggt tacatgatga aaaagggcca cagacggaaa aactggactg aaagatggtt    420

tgtactaaaa cccaacataa tttcttacta tgtgagtgag gatctgaagg ataagaaagg    480

agacattctc ttggatgaaa attgctgtgt agaagtcctt gcctgacaaa agatggaaag    540

aaatgccttt t                                                         551
```

```
<210> SEQ ID NO 138
<211> LENGTH: 531
<212> TYPE: DNA
<213> ORGANISM: Homo sapiens
<220> FEATURE:
<221> NAME/KEY: misc_feature
<222> LOCATION: 490
<223> OTHER INFORMATION: n = A,T,C or G

<400> SEQUENCE: 138

gactggttct ttatttcaaa aagacacttg tcaatattca gtrtcaaaac agttgcacta     60

ttgatttctc tttctcccaa tcggccccaa agagaccaca taaaaggaga gtacatttta    120

agccaataag ctgcaggatg tacacctaac agacctccta gaaaccttac cagaaaatgg    180

ggactgggta gggaaggaaa cttaaaagat caacaaactg ccagcccacg gactgcagag    240

gctgtcacag ccagatgggg tggccagggt gccacaaacc caaagcaaag tttcaaaata    300

atataaaatt taaaaagttt tgtacataag ctattcaaga tttctccagc actgactgat    360

acaaagcaca attgagatgg cacttctaga gacagcagct tcaaacccag aaaagggtga    420

tgagatgaag tttcacatgg ctaaatcagt ggcaaaaaca cagtcttctt tctttctttc    480

tttcaaggan gcaggaaagc aattaagtgg tcaccttaac ataaggggga c             531
```

```
<210> SEQ ID NO 139
<211> LENGTH: 521
<212> TYPE: DNA
<213> ORGANISM: Homo sapiens
<220> FEATURE:
<221> NAME/KEY: misc_feature
<222> LOCATION: 517
<223> OTHER INFORMATION: n = A,T,C or G

<400> SEQUENCE: 139

tgggtgggca ccatggctgg gatcaccacc atcgaggcgg tgaagcgcaa gatccaggtt     60

ctgcagcagc aggcagatga tgcagaggag cgagctgagc gcctccagcg agaagttgag    120

ggagaaaggc gggcccggga acaggctgag gctgaggtgg cctccttgaa ccgtaggatc    180

cagctggttg aagaagagct ggaccgtgct caggagcgcc tggccactgc cctgcaaaag    240

ctggaagaag ctgaaaaagc tgctgatgag agtgagagag gtatgaaggt tattgaaaac    300

cgggccttaa aagatgaaga aaagatggaa ctccaggaaa tccaactcaa agaagctaag    360

cacattgcag aagaggcaga taggaagtat gaagaggtgg ctcgtaagtt ggtgatcatt    420

gaaggagact tggaaccgca cagaaggaac gagcttgagc ttggcaaaag tcccgttgcc    480

cagagatggg atgaaccaga ttagactgat ggaccanaac c                        521
```

```
<210> SEQ ID NO 140
<211> LENGTH: 571
<212> TYPE: DNA
<213> ORGANISM: Homo sapiens
<220> FEATURE:
<221> NAME/KEY: misc_feature
<222> LOCATION: 7
<223> OTHER INFORMATION: n = A,T,C or G
```

-continued

<400> SEQUENCE: 140
aggggcngcg ggtgcgtggg ccactgggtg accgacttag cctggccaga ctctcagcac 60
ctggaagcgc cccgagagtg acagcgtgag gctgggaggg aggacttggc ttgagcttgt 120
taaactctgc tctgagcctc cttgtcgcct gcatttagat ggctcccgca aagaagggtg 180
gcgagaagaa aaagggccgt tctgccatca acgaagtggt aacccgagaa tacaccatca 240
acattcacaa gcgcatccat ggagtgggct tcaagaagcg tgcacctcgg gcactcaaag 300
agattcggaa atttgccatg aaggagatgg gaactccaga tgtgcgcatt gacaccaggc 360
tcaacaaagc tgtctgggcc aaaggaataa ggaatgtgcc ataccgaatc cggtgtgcgg 420
ctgtccagaa aacgtaatga ggatgaagat tcaccaaata agctatatac tttggttacc 480
tatgtacctg ttaccacttt caaaaatcta cagacagtca atgtggatga gaactaatcg 540
ctgatcgtca gatcaaataa agttataaaa t 571

<210> SEQ ID NO 141
<211> LENGTH: 531
<212> TYPE: DNA
<213> ORGANISM: Homo sapiens

<400> SEQUENCE: 141
tcgggagcca cacttggccc tcttcctctc caaagsgcca gaacctcctt ctctttggag 60
aatggggagg cctcttggag acacagaggg tttcaccttg gatgacctct agagaaattg 120
cccaagaagc ccaccttctg gtcccaacct gcagacccca cagcagtcag ttggtcaggc 180
cctgctgtag aaggtcactt ggctccattg cctgcttcca accaatgggc aggagagaag 240
gcctttattt ctcgcccacc cattcctcct gtaccagcac ctccgttttc agtcagtgtt 300
gtccagcaac ggtaccgttt acacagtcac ctcagacaca ccatttcacc tcccttgcca 360
agctgttagc cttagagtga ttgcagtgaa cactgtttac acaccgtgaa tccattccca 420
tcagtccatt ccagttggca ccagcctgaa ccatttggta cctggtgtta actggagtcc 480
tgtttacaag gtggagtcgg ggcttgctga cttctcttca tttgagggca c 531

<210> SEQ ID NO 142
<211> LENGTH: 491
<212> TYPE: DNA
<213> ORGANISM: Homo sapiens
<220> FEATURE:
<221> NAME/KEY: misc_feature
<222> LOCATION: 410
<223> OTHER INFORMATION: n = A,T,C or G

<400> SEQUENCE: 142
acctagacag aaggtgggtg agggaggact ggtaggaggc tgaggcaatt ccttggtagt 60
ttgtcctgaa accctactgg agaagtcagc atgaggcacc tactgagaga agtgcccaga 120
aactgctgac tgcatctgtt aagagttaac agtaaagagg tagaagtgtg tttctgaatc 180
agagtggaag cgtctcaagg gtcccacagt ggaggtccct gagctacctc ccttccgtga 240
gtgggaagag tgaagcccat gaagaactga gatgaagcaa ggatggggtt cctgggctcc 300
aggcaagggc tgtgctctct gcagcaggga gccccacgag tcagaagaaa agaactaatc 360
atttgttgca agaaaccttg cccggatact agcggaaaac tggaggcggn ggtgggggca 420
caggaaagtg gaagtgattt gatggagagc agagaagcct atgcacagtg gccgagtcca 480
cttgtaaagt g 491

-continued

<210> SEQ ID NO 143
<211> LENGTH: 515
<212> TYPE: DNA
<213> ORGANISM: Homo sapiens

<400> SEQUENCE: 143
ttcaagcaat tgtaacaagt atatgtagat tagagtgagc aaaatcatat acaattttca 60
tttccagttg ctattttcca aattgttctg taatgtcgtt aaaattactt aaaaattaac 120
aaagccaaaa attatattta tgacaagaaa gccatcccta cattaatctt acttttccac 180
tcaccggccc atctccttcc tctttttcct aactatgcca ttaaaactgt tctactgggc 240
cgggcgtgtg gctcatgcct gtaatcccag cattttggga ggccaaggca ggcggatcat 300
gaggtcaaga gattgagacc atcctggcca acatggtgaa accccgcctc gactaagaat 360
acaaaaatta gctgggcatg gtggcgcatg cctgtagtct cagctactcg ggaggctgag 420
gcagaagaat cgcttgaacc cgggaggcag aggatgcagt gagccccgat cgcgccactg 480
cactctagcc tgggcgacag actgagactc tgctc 515

<210> SEQ ID NO 144
<211> LENGTH: 340
<212> TYPE: DNA
<213> ORGANISM: Homo sapiens

<400> SEQUENCE: 144
tgtgccagtc tacaggccta tcagcagcga ctccttcagc aacagatggg gtcccctgtt 60
cagcccaacc ccatgagccc ccagcagcat atgctcccaa atcaggccca gtccccacac 120
ctacaaggcc agcagatccc taattctctc tccaatcaag tgcgctctcc ccagcctgtc 180
ccttctccac ggccacagtc ccagcccccc cactccagtc cttccccaag gatgcagcct 240
cagccttctc cacaccacgt ttccccacag acaagttccc cacatcctgg actggtagtt 300
gcccaggcca accccatgga acaagggcat tttgccagcc 340

<210> SEQ ID NO 145
<211> LENGTH: 630
<212> TYPE: DNA
<213> ORGANISM: Homo sapiens

<400> SEQUENCE: 145
tgtaaaaact tgtttttaat tttgtataaa ataaaggtgg tccatgccca cgggggctgt 60
aggaaatcca agcagaccag ctggggtggg gggatgtagc ctacctcggg ggactgtctg 120
tcctcaaaac gggctgagaa ggcccgtcag gggcccaggt cccacagaga ggcctgggat 180
actcccccaa cccgaggggc agactgggca gtggggagcc cccatcgtgc cccagaggtg 240
gccacaggct gaaggagggg cctgaggcac cgcagcctgc aacccccagg gctgcagtcc 300
actaactttt tacagaataa aaggaacatg gggatgggga aaaaagcacc aggtcaggca 360
gggcccgagg gccccagatc ccaggagggc caggactcag gatgccagca ccaccctagc 420
agctcccaca gctcctggca caggaggccg ccacggattg gcacaggccg ctgctggcca 480
tcacgccaca tttggagaac ttgtcccgac agaggtcagc tcggaggagc tcctcgtggg 540
cacacactgt acgaacacag atctccttgt taatgacgta cacacggcgg aggctgcggg 600
gacagggcac gggaggtctc agccccactt 630

<210> SEQ ID NO 146
<211> LENGTH: 521

-continued

<212> TYPE: DNA
<213> ORGANISM: Homo sapiens

<400> SEQUENCE: 146
atggctgctg gatttaggtg gtaatagggg ctgtgggcca taaatctgaa gccttgagaa 60
ccttgggtct ggagagccat gaagagggaa ggaaaagagg gcaagtcctg aacctaacca 120
atgacctgat ggattgctcg accaagacac agaagtgaag tctgtgtctg tgcacttccc 180
acagactgga gtttttggtg ctgaatagag ccagttgcta aaaaattggg ggtttggtga 240
agaaatctga ttgttgtgtg tattcaatgt gtgattttaa aaataaacag caacaacaat 300
aaaaaccctg actggctgtt ttttccctgt attctttaca actatttttt gaccctctga 360
aaattattat acttcaccta aatggaagac tgctgtgttt gtggaaattt tgtaattttt 420
taatttattt tattctctct ccttttttatt ttgcctgcag aatccgttga gagactaata 480
aggcttaata tttaattgat ttgtttaata tgtatataaa t 521

<210> SEQ ID NO 147
<211> LENGTH: 562
<212> TYPE: DNA
<213> ORGANISM: Homo sapiens

<400> SEQUENCE: 147
ggcatgcgag cgcactcggc ggacgcaagg gcggcgggga gcacacggag cactgcaggc 60
gccgggttgg gacagcgtct tcgctgctgc tggatagtcg tgttttcggg gatcgaggat 120
actcaccaga aaccgaaaat gccgaaacca atcaatgtcc gagttaccac catggatgca 180
gagctggagt ttgcaatcca gccaaataca actggaaaac agctttttga tcaggtggta 240
aagactatcg gcctccggga agtgtggtac tttggcctcc actatgtgga taataaagga 300
tttcctacct ggctgaagct ggataagaag gtgtctgccc aggaggtcag gaaggagaat 360
cccctccagt tcaagttccg ggccaaagtt ctaccctgaa gatgtggctg aggagctcat 420
ccaggacatc acccagaaac ttttcttcct tcaagtgaag gaaggaatcc ttagcgatga 480
gatctactgc ccccccttgar actgccgtgc tcttggggtc ctacgcttgt gcatgccaag 540
tttggggact accaccaaga ag 562

<210> SEQ ID NO 148
<211> LENGTH: 820
<212> TYPE: DNA
<213> ORGANISM: Homo sapiens

<400> SEQUENCE: 148
gaaggagtcg ggatactcag cattgatgca ccccaatttc aaagcggcat tcttcggcag 60
gtctctggga caatctctag ggtcactacc tggaaactcg ttagggtaca actgaatgct 120
gaaaggaaag aacacctgca gaaccggaca gaaattcacc ccggcgatca gctgattgat 180
ctcggtcgac cagaagtcat ggctaaagat gacgaggacg ttgtcaattc cctgggcttt 240
tcgaagtgag tccagcagca gtctgaggta ttcgggccgg ttatgcacct ggaccaccag 300
caccagctcc cggggggccc aggtgccagc cttatctaca ttcctcaggg tctgatcaaa 360
gttcagctgg tacaccaggg accggtaccg cagcgtcagg ttgtccgctc gggctggggg 420
accgccggga ccagggaagc cgccgacacg ttggagaccc tgcggatgcc cacagccaca 480
gaggggtggt ccccaccgcg gccgccggca ccccgcgcgg gttcggcgtc cagcaacggt 540
ggggcgaggg cctcgttctt cctttgtcgc ccattgctgc tccagaggac gaagccgcag 600

-continued

```
gcggccacca cgagcgtcag gattagcacc ttccgtttgt agatgcggaa cctcatggtc    660

tccagggccg ggagcgcagc tacagctcga gcgtcggcgc cgccgctagg agccgcggct    720

cggcttcgtc tccgtcctct ccattcagca ccacgggtcc cggaaaaagc tcagccscgg    780

tcccaaccgc accctagctt cgttacctgc gcctcgcttg                          820
```

<210> SEQ ID NO 149
<211> LENGTH: 501
<212> TYPE: DNA
<213> ORGANISM: Homo sapiens

<400> SEQUENCE: 149

```
cagattttta tttgcagtcg tcactggggc cgtttcttgc tgcttatttg tctgctagcc     60

tgctcttcca gctgcatggc caggcgcaag gccttgatga catctcgcag ggctgagaaa    120

tgcttggctt gctgggccag agcagattcc gctttgttca caaaggtctc caggtcatag    180

tctggctgct cggtcatctc agagagctca agccagtctg gtccttgctg tatgatctcc    240

ttgagctctt ccatagcctt ctcctccagc tccctgatct gagtcatggc ttcgttaaag    300

ctggacatct gggaagacag ttcctcctct tccttggata aattgcctgg aatcagcgcc    360

ccgttagagc aggcttccat ctcttctgtt tccatttgaa tcaactgctc tccactgggc    420

ccactgtggg ggctcagctc cttgaccctg ctgcatatct taagggtgtt taaaggatat    480

tcacaggagc ttatgcctgg t                                              501
```

<210> SEQ ID NO 150
<211> LENGTH: 511
<212> TYPE: DNA
<213> ORGANISM: Homo sapiens
<220> FEATURE:
<221> NAME/KEY: misc_feature
<222> LOCATION: 457, 479
<223> OTHER INFORMATION: n = A,T,C or G

<400> SEQUENCE: 150

```
ctcctcttgg tacatgaacc caagttgaaa gtggacttaa caaagtatct ggagaaccaa     60

gcattctgct ttgactttgc atttgatgaa acagcttcga atgaagttgt ctacaggttc    120

acagcaaggc cactggtaca gacaatcttt gaaggtggaa aagcaacttg ttttgcatat    180

ggccagacag gaagtggcaa gacacatact atgggcggag acctctctgg gaaagcccag    240

aatgcatcca aagggatcta tgccatggcc ttccgggacg tcttcttctg aagaatcaac    300

cctgctaccg gaagttgggc ctggaagtct atgtgacatt cttcgagatc tacaatggga    360

agctgtttga cctgctcaac aagaaggcca agcttgcgcg tgctggaaga cggcaagcaa    420

caggtgcaag tggtgggggc ttgcaggaac atctggntaa ctctgcttga tgatggcant    480

caagatgatc gacatgggca gcgcctgcag a                                   511
```

<210> SEQ ID NO 151
<211> LENGTH: 566
<212> TYPE: DNA
<213> ORGANISM: Homo sapiens

<400> SEQUENCE: 151

```
tcccgaattc aagcgacaaa ttggawagtg aaatggaaga tgcctatcat gaacatcagg     60

caaatctttt gcgccaagat ctgatgagac gacaggaaga attaagacgc atggaagaac    120

ttcacaatca agaaatgcag aaacgtaaag aaatgcaatt gaggcaagag gaggaacgac    180

gtagaagaga ggaagagatg atgattcgtc aacgtgagat ggaagaacaa atgaggcgcc    240
```

-continued

```
aaagagagga aagttacagc cgaatgggct acatggatcc acgggaaaga gacatgcgaa    300

tgggtggcgg aggagcaatg aacatgggag atccctatgg ttcaggaggc cagaaatttc    360

cacctctagg aggtggtggt ggcataggtt atgaagctaa tcctggcgtt ccaccagcaa    420

ccatgagtgg ttccatgatg ggaagtgaca tgcgtactga gcgctttggg cagggaggtg    480

cggggcctgt gggtggacag ggtcctagag gaatggggcc tggaactcca gcaggatatg    540

gtagagggag agaagagtac gaaggc                                         566
```

<210> SEQ ID NO 152
<211> LENGTH: 518
<212> TYPE: DNA
<213> ORGANISM: Homo sapiens

<400> SEQUENCE: 152

```
ttcgtgaaga ccctgactgg taagaccatc actctcgaag tggagcccga gtgacaccat     60

tgagaatgtc aaggcaaaga tccaagacaa ggaaggcatc cctcctgacc agcakaggtt    120

gatctttgct gggaaacagc tggaagatgg acgcaccctg tctgactaca acatccagaa    180

agagtccacc ctgcacctgg tgctccgtct cagaggtggg atgcaaatct tcgtgaagac    240

cctgactggt aagaccatca ccctcgaggt ggagcccagt gacaccatcg agaatgtcaa    300

ggcaaagatc caagataagg aaggcatccc tcctgatcag cagaggttga tctttgctgg    360

gaaacagctg gaagatggac gcaccctgtc tgactacaac atccagaaag agtccactct    420

gcacttggtc ctgcgcttga ggggggggtgt ctaagtttcc ccttttaagg tttcaacaaa    480

tttcattgca ctttcctttc aataaagttg ttgcattc                            518
```

<210> SEQ ID NO 153
<211> LENGTH: 542
<212> TYPE: DNA
<213> ORGANISM: Homo sapiens

<400> SEQUENCE: 153

```
gcgcgggtgc gtgggccact gggtgaccga cttagcctgg ccagactctc agcacctgga     60

agcgccccga gagtgacagc gtgaggctgg gagggaggac ttggcttgag cttgttaaac    120

tctgctctga gcctccttgt cgcctgcatt tagatggctc ccgcaaagaa gggtggcgag    180

aagaaaaagg gccgttctgc catcaacgaa gtggtaaccc gagaatacac catcaacatt    240

cacaagcgca tccatggagt gggcttcaag aagcgtgcac ctcgggcact caaagagatt    300

cggaaatttg ccatgaagga gatgggaact ccagatgtgc gcattgacac caggctcaac    360

aaagctgtct gggccaaagg aataaggaat gtgccatacc gaatccgtgt gcggctgtcc    420

agaaaacgta atgaggatga agattcacca aataagctat atactttggt tacctatgta    480

cctgttacca ctttcaaaaa tctacagaca gtcaatgtgg atgagaacta atcgctgatc    540

gt                                                                   542
```

<210> SEQ ID NO 154
<211> LENGTH: 411
<212> TYPE: DNA
<213> ORGANISM: Homo sapiens

<400> SEQUENCE: 154

```
aattctttat ttaaatcaac aaactcatct tcctcaagcc ccagaccatg gtaggcagcc     60

ctccctctcc atcccctcac cccacccctt agccacagtg aagggaatgg aaaatgagaa    120
```

-continued

```
gccacgaggg cccctgccag ggaaggctgc cccagatgtg tggtgagcac agtcagtgca    180

gctgtggctg gggcagcagc tgccacaggc tcctccctat aaattaagtt cctgcagcca    240

cagctgtggg agaagcatac ttgtagaagc aaggccagtc cagcatcaga aggcagaggc    300

agcatcagtg actcccagcc atggaatgaa cggaggacac agagctcaga gacagaacag    360

gccaggggga agaaggagag acagaatagg ccagggcatg gcggtgaggg a             411
```

<210> SEQ ID NO 155
<211> LENGTH: 421
<212> TYPE: DNA
<213> ORGANISM: Homo sapiens
<220> FEATURE:
<221> NAME/KEY: misc_feature
<222> LOCATION: 173
<223> OTHER INFORMATION: n = A,T,C or G

<400> SEQUENCE: 155

```
tgatgaatct gggtgggctg gcagtagccc gagatgatgg gctcttctct ggggatccca     60

actggttccc taagaaatcc aaggagaatc ctcggaactt ctcggataac cagctgcaag    120

agggcaagaa cgtgatcggg ttacagatgg gcaccaaccg cggggcgtct cangcaggca    180

tgactggcta cgggatgcca cgccagatcc tctgatccca ccccaggcct tgcccctgcc    240

ctcccacgaa tggttaatat atatgtagat atatatttta gcagtgacat tcccagagag    300

ccccagagct ctcaagctcc tttctgtcag ggtggggggt tcaagcctgt cctgtcacct    360

ctgaagtgcc tgctggcatc ctctccccca tgcttactaa tacattccct tccccatagc    420

c                                                                    421
```

<210> SEQ ID NO 156
<211> LENGTH: 670
<212> TYPE: DNA
<213> ORGANISM: Homo sapiens

<400> SEQUENCE: 156

```
agcggagctc cctcccctgg tggctacaac ccacacacgc caggctcagg catcgagcag     60

aactccagcg actgggtaac cactgacatt caggtgaagg tgcgggacac ctacctggat    120

acacaggtgg tgggacagac aggtgtcatc cgcagtgtca cgggggggcat gtgctctgtg    180

tacctgaagg acagtgagaa ggttgtcagc atttccagtg agcacctgga gcctatcacc    240

cccaccaaga acaacaaggt gaaagtgatc ctgggcgagg atcgggaagc cacgggcgtc    300

ctactgagca ttgatggtga ggatggcatt gtccgtatgg accttgatga gcagctcaag    360

atcctcaacc tccgcttcct ggggaagctc ctggaagcct gaagcaggca gggccggtgg    420

acttcgtcgg atgaagagtg atcctccttc cttccctggc ccttggctgt gacacaagat    480

cctcctgcag ggctaggcgg attgttctgg atttcctttt gtttttcctt ttaggtttcc    540

atcttttccc tccctggtgc tcattggaat ctgagtagag tctgggggag ggtccccacc    600

ttcctgtacc tcctccccac agcttgcttt tgttgtaccg tctttcaata aaaagaagct    660

gtttggtcta                                                           670
```

<210> SEQ ID NO 157
<211> LENGTH: 421
<212> TYPE: DNA
<213> ORGANISM: Homo sapiens

<400> SEQUENCE: 157

```
ggttcacagc actgctgctt gtgtgttgcc ggccaggaat tccaggctca caaggctatc     60
```

-continued

```
ttagcagctc gttctccggt ttttagtgcc atgtttgaac atgaaatgga ggagagcaaa    120

aagaatcgag ttgaaatcaa tgatgtggag cctgaagttt ttaaggaaat gatgtgcttc    180

atttacacgg ggaaggctcc aaacctcgac aaaatggctg atgatttgct ggcagctgct    240

gacaagtatg ccctggagcg cttaaaggtc atgtgtgagg atgccctctg cagtaacctg    300

tccgtggaga acgctgcaga aattctcatc ctggccgacc tccacagtgc agatcagttg    360

aaaactcagg cagtggattt catcaactat catgcttcgg atgtcttgga gacctcttgg    420

g                                                                    421
```

<210> SEQ ID NO 158
<211> LENGTH: 321
<212> TYPE: DNA
<213> ORGANISM: Homo sapiens

<400> SEQUENCE: 158

```
tcgtagccat tttctgcttc ctttggagaa tgacgccaca ctgactgctc attgtcgttg     60

gttccatgcc aattggtgaa atagaacctc atccggtagt ggagccggag ggacatcttg    120

tcatcaacgg tgatggtgcg atttggagca taccagagct tggtgttctc gccatacagg    180

gcaaagaggt tgtgacaaag aggagagata cggcatgcct gtgcagccct gatgcacagt    240

tcctctgctg tgtactctcc actgcccagc cggaggggct ccctgtccga cagatagaag    300

atcacttcca cccctggctt g                                              321
```

<210> SEQ ID NO 159
<211> LENGTH: 596
<212> TYPE: DNA
<213> ORGANISM: Homo sapiens

<400> SEQUENCE: 159

```
tggcacactg ctcttaagaa actatgawga tctgagattt ttttgtgtat gtttttgact     60

cttttgagtg gtaatcatat gtgtctttat agatgtacat acctccttgc acaaatggag    120

gggaattcat tttcatcact gggagtgtcc ttagtgtata aaaaccatgc tggtatatgg    180

cttcaagttg taaaaatgaa agtgacttta aaagaaaata ggggatggtc caggatctcc    240

actgataaga ctgtttttaa gtaacttaag gacctttggg tctacaagta tatgtgaaaa    300

aaatgagact tactgggtga ggaaattcat tgtttaaaga tggtcgtgtg tgtgtgtgtg    360

tgtgtgtgtg ttgtgttgtg ttttgttttt taagggaggg aatttattat ttaccgttgc    420

ttgaaattac tgkgtaaata tatgtytgat aatgatttgc tytttgvcma ctaaaattag    480

gvctgtataa gtwctaratg cmtccctggg kgttgatytt ccmagatatt gatgatamcc    540

cttaaaattg taaccygcct ttttcccttt gctytcmatt aaagtctatt cmaaag        596
```

<210> SEQ ID NO 160
<211> LENGTH: 515
<212> TYPE: DNA
<213> ORGANISM: Homo sapiens

<400> SEQUENCE: 160

```
gggggtaggc tctttattag acggttattg ctgtactaca gggtcagagt gcagtgtaag     60

cagtgtcaga ggcccgcgtt cagcccaaga atgtggattt tctctcccta ttgatcacag    120

tgggtgggtt tcttcagaaa agccccagag gcagggacca gtgagctcca aggttagaag    180

tggaactgga aggcttcagt cacatgctgc ttccacgctt ccaggctggg cagcaaggag    240

gagatgccca tgacgtgcca ggtctcccca tctgacacca gtgaagtctg gtaggacagc    300
```

-continued agccgcacgc ctgcctctgc caggaggcca atcatggtag gcagcattgc agggtcagag 360
gtctgagtcc ggaataggag caggggcagg tccctgcgga gaggcacttc tggcctgaag 420
acagctccat tgagcccctg cagtacaggy gtagtgcctt ggaccaagcc cacagcctgg 480
taaggggcgc ctgccagggc cacggccagg aggca 515

<210> SEQ ID NO 161
<211> LENGTH: 936
<212> TYPE: DNA
<213> ORGANISM: Homo sapiens

<400> SEQUENCE: 161
taatttctta gtcgtttgga atccttaagc atgcaaaagc tttgaacaga agggttcaca 60
aaggaaccag ggttgtctta tggcatccag ttaagccaga gctgggaatg cctctgggtc 120
atccacatca ggagcagaag cacttgactt gtcggtcctg ctgccacggt ttgggcgccc 180
accacgccca cgtccacctc gtcctcccct gccgccacgt cctgggcggc caaggtctcc 240
aaaattgatc tccagctgag acgttatatc atttgctggc ttccggaaat gatggtccat 300
aaccgaatct tcagcatgag cctcttcact ctttgattta tgaagaacaa atcccttctt 360
ccactgccca tcagcacctt catttggttt tcggatatta aattctactt ttgcccggtc 420
cttattttga atagccttcc actcatccaa agtcatctct tttggaccct cctcttttac 480
ctcttcaact tcattctcct tattttcagt gtctgccact ggatgatgtt cttcaccttc 540
aggtgtttcc tcagtcacat ttgattgatc caagtcagtt aattcgtctt tgacagttcc 600
ccagttgtga gatccgctac ctccacgttt gtcctcgtgc ttcaggccag atctatcact 660
tccactatgc ctatcaaatt cacgtttgcc acgagaatca aatccatctc ctcggcccat 720
tccacgtcca cggccccctc gacctcttcc aagaccacca cgacctcgaa taggtcggtc 780
aataatcggt ctatcaactg aaaattcgcc tccttcaccc ttttcttcaa gtggcttttc 840
gaatcttcgt tcacgaggtg gtcgcctttc tggtcttcta tcaattattt tcccttcacc 900
ctgaagttgt tgatcaggtc ttcttccaac tcgtgc 936

<210> SEQ ID NO 162
<211> LENGTH: 950
<212> TYPE: DNA
<213> ORGANISM: Homo sapiens

<400> SEQUENCE: 162
aagcggatgg acctgagtca gccgaatcct agccccttcc cttgggcctg ctgtggtgct 60
cgacatcagt gacagacgga agcagcagac catcaaggct acgggaggcc cggggcgctt 120
gcgaagatga agtttggctg cctctccttc cggcagcctt atgctggctt tgtcttaaat 180
ggaatcaaga ctgtggagac gcgctggcgt cctctgctga gcagccagcg gaactgtacc 240
atcgccgtcc acattgctca cagggactgg gaaggcgatg cctgtcggga gctgctggtg 300
gagagactcg ggatgactcc tgctcagatt caggccttgc tcaggaaagg ggaaaagttt 360
ggtcgaggag tgatagcggg actcgttgac attggggaaa ctttgcaatg ccccgaagac 420
ttaactcccg atgaggttgt ggaactagaa aatcaagctg cactgaccaa cctgaagcag 480
aagtacctga ctgtgatttc aaaccccagg tggttactgg agcccatacc taggaaagga 540
ggcaaggatg tattccaggt agacatccca gagcacctga tccctttggg gcatgaagtg 600
tgacaagtgt gggctcctga aaggaatgtt ccrgagaaac cagctaaatc atggcacctt 660

-continued caatttgcca tcgtgacgca gacctgtata aattaggtta aagatgaatt tccactgctt 720
tggagagtcc cacccactaa gcactgtgca tgtaaacagg ttcctttgct cagatgaagg 780
aagtaggggg tggggctttc cttgtgtgat gcctccttag gcacacaggc aatgtctcaa 840
gtactttgac cttagggtag aaggcaaagc tgccagtaaa tgtctcagca ttgctgctaa 900
ttttggtcct gctagtttct ggattgtaca aataaatgtg ttgtagatga 950

<210> SEQ ID NO 163
<211> LENGTH: 475
<212> TYPE: DNA
<213> ORGANISM: Homo sapiens
<220> FEATURE:
<221> NAME/KEY: misc_feature
<222> LOCATION: 301, 317, 331, 458, 464, 470
<223> OTHER INFORMATION: n = A,T,C or G

<400> SEQUENCE: 163
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtgt 180
acacctgtgg ttctcggggc tgccctttgg ctttggagat ggttttctcg atgggggctg 240
ggagggcttt gttggagacc ttgcacttgt actccttgcc attcaaccag tcctggtgca 300
ngacggtgag gacgctnacc acacggtacg ngctggtgta ctgctcctcc cgcggctttg 360
tcttggcatt atgcacctcc acgccgtcca cgtaccaatt gaacttgacc tcagggtctt 420
cgtggctcac gtccaccacc acgcatgtaa cctcaaanct cggncgcgan cacgc 475

<210> SEQ ID NO 164
<211> LENGTH: 476
<212> TYPE: DNA
<213> ORGANISM: Homo sapiens

<400> SEQUENCE: 164
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgtgtggtc agcgtcctca ccgtcctgca 180
ccaggactgg ctgaatggca aggagtacaa gtgcaaggtc tccaacaaag ccctcccagc 240
ccccatcgag aaaaccatct ccaaagccaa agggcagccc cgagaaccac aggtgtacac 300
cctgccccca tcccgggagg agatgaccaa gaaccaggtc agcctgacct gcctggtcaa 360
aggcttctat cccagcgaca tcgcccgtgg agtgggagag caatgggcag ccggagaaca 420
actacaagac cacgcctccc gtgctggact ccgacacctg ccgggcggcc gctcga 476

<210> SEQ ID NO 165
<211> LENGTH: 256
<212> TYPE: DNA
<213> ORGANISM: Homo sapiens
<220> FEATURE:
<221> NAME/KEY: misc_feature
<222> LOCATION: 10, 37, 249
<223> OTHER INFORMATION: n = A,T,C or G

<400> SEQUENCE: 165
agcgtggttn cggccgaggt cccaaccaag gctgcancct ggatgccatc aaagtcttct 60
gcaacatgga gactggtgag acctgcgtgt accccactca gcccagtgtg gcccagaaga 120
actggtacat cagcaagaac cccaaggaca agaggcatgt ctggttcggc gagagcatga 180

-continued ccgatggatt ccagttcgag tatggcggcc agggctccga ccctgccgat gtggacctgc 240
ccgggcggnc gctcga 256

<210> SEQ ID NO 166
<211> LENGTH: 332
<212> TYPE: DNA
<213> ORGANISM: Homo sapiens

<400> SEQUENCE: 166
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgg gcggccgctc ga 332

<210> SEQ ID NO 167
<211> LENGTH: 332
<212> TYPE: DNA
<213> ORGANISM: Homo sapiens
<220> FEATURE:
<221> NAME/KEY: misc_feature
<222> LOCATION: 77, 109, 136, 184, 198
<223> OTHER INFORMATION: n = A,T,C or G

<400> SEQUENCE: 167
tcgagcggtc gcccgggcag gtccacatcg gcagggtcgg agccctggcc gccatactcg 60
aactggaatc catcggncat gctctcgccg aaccagacat gcctcttgnc cttggggttc 120
ttgctgatgt accagntctt ctgggccaca ctgggctgag tggggtacac gcaggtctca 180
ccantctcca tgttgcanaa gactttgatg gcatccaggt tgcagccttg gttggggtca 240
atccagtact ctccactctt ccagacagag tggcacatct tgaggtcacg gcaggtgcgg 300
gcggggttct tgacctcggt cgcgaccacg ct 332

<210> SEQ ID NO 168
<211> LENGTH: 276
<212> TYPE: DNA
<213> ORGANISM: Homo sapiens
<220> FEATURE:
<221> NAME/KEY: misc_feature
<222> LOCATION: 72, 84
<223> OTHER INFORMATION: n = A,T,C or G

<400> SEQUENCE: 168
tcgagcggcc gcccgggcag gtcctcctca gagcggtagc tgttcttatt gccccggcag 60
cctccataga tnaagttatt gcangagttc ctctccacgt caaagtacca gcgtgggaag 120
gatgcacggc aaggcccagt gactgcgttg gcggtgcagt attcttcata gttgaacata 180
tcgctggagt ggacttcaga atcctgcctt ctgggagcac ttgggacaga ggaatccgct 240
gcattcctgc tggtggacct cggccgcgac cacgct 276

<210> SEQ ID NO 169
<211> LENGTH: 276
<212> TYPE: DNA
<213> ORGANISM: Homo sapiens

<400> SEQUENCE: 169

-continued

```
agcgtggtcg cggccgaggt ccaccagcag gaatgcagcg gattcctctg tcccaagtgc     60

tcccagaagg caggattctg aagaccactc cagcgatatg ttcaactatg aagaatactg    120

caccgccaac gcagtcactg ggccttgccg tgcatccttc ccacgctggt actttgacgt    180

ggagaggaac tcctgcaata acttcatcta tggaggctgc cggggcaata agaacagcta    240

ccgctctgag gaggacctgc ccgggcggcc gctcga                              276
```

<210> SEQ ID NO 170
<211> LENGTH: 332
<212> TYPE: DNA
<213> ORGANISM: Homo sapiens
<220> FEATURE:
<221> NAME/KEY: misc_feature
<222> LOCATION: 294
<223> OTHER INFORMATION: n = A,T,C or G

<400> SEQUENCE: 170

```
tcgagcggcc gcccgggcag gtccacatcg gcagggtcgg agccctggcc gccatactcg     60

aactggaatc catcggtcat gctctcgccg aaccagacat gcctcttgtc cttggggttc    120

ttgctgatgt accagttctt ctgggccaca ctgggctgag tggggtacac gcaggtctca    180

ccagtctcca tgttgcagaa gactttgatg gcatccaggt tgcagccttg gttggggtca    240

atccagtact ctccactctt ccagccagaa tggcacatct tgaggtcacg gcangtgcgg    300

gcggggttct tgacctcggc cgcgaccacg ct                                  332
```

<210> SEQ ID NO 171
<211> LENGTH: 333
<212> TYPE: DNA
<213> ORGANISM: Homo sapiens

<400> SEQUENCE: 171

```
agcgtggtcg cggccgaggt caagaaaccc cgccccgcacc tgccgtgacc tcaagatgtg    60

ccactctggc tggaagagtg gagagtactg gattgacccc aaccaaggct gcaacctgga    120

tgccatcaaa gtcttctgca acatggagac tggtgagacc tgcgtgtacc ccactcagcc    180

cagtgtggcc cagaagaact ggtacatcag caagaacccc aaggacaaga ggcatgtctg    240

gctcggcgag agcatgaccg atggattcca gttcgagtat ggcggccagg gctccgaccc    300

tgccgatgtg gacctgcccg ggcggccgct cga                                 333
```

<210> SEQ ID NO 172
<211> LENGTH: 527
<212> TYPE: DNA
<213> ORGANISM: Homo sapiens
<220> FEATURE:
<221> NAME/KEY: misc_feature
<222> LOCATION: 46, 125, 140, 148, 220, 229, 291, 388, 456
<223> OTHER INFORMATION: n = A,T,C or G

<400> SEQUENCE: 172

```
agcgtggtcg cggccgaggt cctgtcagag tggcactggt agaagntcca ggaaccctga     60

actgtaaggg ttcttcatca gtgccaacag gatgacatga aatgatgtac tcagaagtgt    120

cctgnaatgg ggcccatgan atggttgnct gagagagagc ttcttgtcct acattcggcg    180

ggtatggtct tggcctatgc cttatggggg tggccgttgn gggcggtgng gtccgcctaa    240

aaccatgttc ctcaaagatc atttgttgcc caacactggg ttgctgacca naagtgccag    300

gaagctgaat accatttcca gtgtcatacc cagggtgggt gacgaaaggg gtcttttgaa    360

ctgtggaagg aacatccaag atctctgntc catgaagatt ggggtgtgga agggttacca    420
```

-continued gttggggaag ctcgctgtct ttttccttcc aatcangggc tcgctcttct gaatattctt 480
cagggcaatg acataaattg tatattcggt tcccggttcc aggccag 527

<210> SEQ ID NO 173
<211> LENGTH: 635
<212> TYPE: DNA
<213> ORGANISM: Homo sapiens
<220> FEATURE:
<221> NAME/KEY: misc_feature
<222> LOCATION: 444, 453, 517, 540, 546, 551, 573, 593
<223> OTHER INFORMATION: n = A,T,C or G

<400> SEQUENCE: 173
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgangaacat ggntttaggc ggaccacacc ggccacaacg 480
ggcaccccca taaggcatag gccaagaaca tacccgncga atgtaggaca agaagctctn 540
tctcanacaa ncatctcatg ggccccattc cangacactt ctgagtacat canttcatgg 600
catcctggtg gcactgataa aaacccttac agtta 635

<210> SEQ ID NO 174
<211> LENGTH: 572
<212> TYPE: DNA
<213> ORGANISM: Homo sapiens
<220> FEATURE:
<221> NAME/KEY: misc_feature
<222> LOCATION: 457, 511, 520, 552, 568
<223> OTHER INFORMATION: n = A,T,C or G

<400> SEQUENCE: 174
agcgtggtcg cgggcgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct acattcggcg 180
ggtatggtct tggcctatgc cttatggggg tggccgttgt gggcggtgtg gtccgcctaa 240
aaccatgttc ctcaaagatc atttgttgcc caacactggg ttgctgacca gaagtgccag 300
gaagctgaat accatttcca gtgtcatacc cagggtgggt gacgaaaggg gtcttttgaa 360
ctgtggaagg aacatccaag atctctggtc catgaagatt ggggtgtgga agggttacca 420
gttggggaag ctcgtctgtc tttttccttc caatcanggg ctcgctcttc tgattattct 480
tcagggcaat gacataaatt gtatattcgg ntcccgggtn cagccaataa taataaccct 540
ctgtgacacc anggcggggc cgaagganca ct 572

<210> SEQ ID NO 175
<211> LENGTH: 372
<212> TYPE: DNA
<213> ORGANISM: Homo sapiens
<220> FEATURE:
<221> NAME/KEY: misc_feature
<222> LOCATION: 247

-continued

<223> OTHER INFORMATION: n = A,T,C or G

<400> SEQUENCE: 175
agcgtggtcg cggccgaggt cctcaccaga ggtaccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg tcatttcaga tgtgattcat ctagatggtg ccatgacaat 300
ggtgtgaact acaagattgg agagaagtgg gaccgtcagg gagaaaatgg acctgcccgg 360
gcggccgctc ga 372

<210> SEQ ID NO 176
<211> LENGTH: 372
<212> TYPE: DNA
<213> ORGANISM: Homo sapiens
<220> FEATURE:
<221> NAME/KEY: misc_feature
<222> LOCATION: 251
<223> OTHER INFORMATION: n = A,T,C or G

<400> SEQUENCE: 176
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ntgacagagt tgcccacggt aacaacctct tcccgaacct tatgcctctg 300
ctggtctttc agtgcctcca ctatgatgtt gtaggtggta cctctggtga ggacctcggc 360
cgcgaccacg ct 372

<210> SEQ ID NO 177
<211> LENGTH: 269
<212> TYPE: DNA
<213> ORGANISM: Homo sapiens
<220> FEATURE:
<221> NAME/KEY: misc_feature
<222> LOCATION: 94, 225
<223> OTHER INFORMATION: n = A,T,C or G

<400> SEQUENCE: 177
agcgtggccg cggccgaggt ccattggctg gaacggcatc aacttggaag ccagtgatcg 60
tctcagcctt ggttctccag ctaatggtga tggnggtctc agtagcatct gtcacacgag 120
cccttcttgg tgggctgaca ttctccagag tggtgacaac accctgagct ggtctgcttg 180
tcaaagtgtc cttaagagca tagacactca cttcatattt ggcgnccacc ataagtcctg 240
atacaaccac ggaatgacct gtcaggaac 269

<210> SEQ ID NO 178
<211> LENGTH: 529
<212> TYPE: DNA
<213> ORGANISM: Homo sapiens

<400> SEQUENCE: 178
tcgagcggcc gcccgggcag gtcctcagac cgggttctga gtacacagtc agtgtggttg 60
ccttgcacga tgatatggag agccagcccc tgattggaac ccagtccaca gctattcctg 120
caccaactga cctgaagttc actcaggtca cacccacaag cctgagcgcc cagtggacac 180

-continued

```
cacccaatgt tcagctcact ggatatcgag tgcgggtgac ccccaaggag aagaccggac    240
caatgaaaga aatcaacctt gctcctgaca gctcatccgt ggttgtatca ggacttatgg    300
cggccaccaa atatgaagtg agtgtctatg ctcttaagga cactttgaca agcagaccag    360
ctcagggtgt tgtcaccact ctggagaatg tcagcccacc aagaagggct cgtgtgacag    420
atgctactga gaccaccatc accattagct ggagaaccaa gactgagacg atcactggct    480
tccaagttga tgccgttcca gccaatggac ctcggccgcg accacgctt                529
```

<210> SEQ ID NO 179
<211> LENGTH: 454
<212> TYPE: DNA
<213> ORGANISM: Homo sapiens
<220> FEATURE:
<221> NAME/KEY: misc_feature
<222> LOCATION: 64
<223> OTHER INFORMATION: n = A,T,C or G

<400> SEQUENCE: 179

```
agcgtggtcg cggccgaggt ctggccgaac tgccagtgta cagggaagat gtacatgtta     60
tagntcttct cgaagtcccg ggccagcagc tccacggggt ggtctcctgc ctccaggcgc    120
ttctcattct catggatctt cttcacccgc agcttctgct tctcagtcag aaggttgttg    180
tcctcatccc tctcatacag ggtgaccagg acgttcttga gccagtcccg catgcgcagg    240
gggaattcgg tcagctcaga gtccaggcaa ggggggatgt atttgcaagg cccgatgtag    300
tccaagtgga gcttgtggcc cttcttggtg ccctccaagg tgcactttgt ggcaaagaag    360
tggcaggaag agtcgaaggt cttgttgtca ttgctgcaca ccttctcaaa ctcgccaatg    420
ggggctgggc agacctgccc gggcggccgc tcga                                454
```

<210> SEQ ID NO 180
<211> LENGTH: 454
<212> TYPE: DNA
<213> ORGANISM: Homo sapiens
<220> FEATURE:
<221> NAME/KEY: misc_feature
<222> LOCATION: 55, 299, 317, 332, 342, 348
<223> OTHER INFORMATION: n = A,T,C or G

<400> SEQUENCE: 180

```
tcgagcggcc gcccgggcag gtctgcccag cccccattgg cgagtttgag aaggngtgca     60
gcaatgacaa caagaccttc gactcttcct gccacttctt tgccacaaag tgcaccctgg    120
agggcaccaa gaagggccac aagctccacc tggactacat cgggccttgc aaatacatcc    180
ccccttgcct ggactctgag ctgaccgaat tccccctgcg catgcgggac tggctcaaga    240
acgtcctggt caccctgtat gagagggatg aggacaacaa ccttctgact gagaagcana    300
agctgcgggt gaagaanatc catgagaatg anaagcgcct gnaggcanga gaccaccccg    360
tggagctgct ggcccgggac ttcgagaaga actataacat gtacatcttc cctgtacact    420
ggcagttcgg ccagacctcg gccgcgacca cgct                                454
```

<210> SEQ ID NO 181
<211> LENGTH: 102
<212> TYPE: DNA
<213> ORGANISM: Homo sapiens
<220> FEATURE:
<221> NAME/KEY: misc_feature
<222> LOCATION: 8, 47, 60, 67
<223> OTHER INFORMATION: n = A,T,C or G -continued

<400> SEQUENCE: 181
agcgtggntg cggacgacgc ccacaaagcc attgtatgta gttttanttc agctgcaaan 60
aataccncca gcatccacct tactaaccag catatgcaga ca 102

<210> SEQ ID NO 182
<211> LENGTH: 337
<212> TYPE: DNA
<213> ORGANISM: Homo sapiens
<220> FEATURE:
<221> NAME/KEY: misc_feature
<222> LOCATION: 169, 195, 253, 314
<223> OTHER INFORMATION: n = A,T,C or G

<400> SEQUENCE: 182
tcgagcggtc gcccgggcag gtctgggcgg atagcaccgg gcatattttg gaatggatga 60
ggtctggcac cctgagcagc ccagcgagga cttggtctta gttgagcaat ttggctagga 120
ggatagtatg cagcacggtt ctgagtctgt gggatagctg ccatgaagna acctgaagga 180
ggcgctggct ggtangggtt gattacaggg ctgggaacag ctcgtacact tgccattctc 240
tgcatatact ggntagtgag gcgagcctgg cgctcttctt tgcgctgagc taaagctaca 300
tacaatggct ttgnggacct cggccgcgac cacgctt 337

<210> SEQ ID NO 183
<211> LENGTH: 374
<212> TYPE: DNA
<213> ORGANISM: Homo sapiens

<400> SEQUENCE: 183
tcgagcggcc gcccgggcag gtccattttc tccctgacgg tcccacttct ctccaatctt 60
gtagttcaca ccattgtcat gacaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagaag ttgcccacgg taacaacctc ttcccgaacc ttatgcctct 300
gctggtcttt caagtgcctc cactatgatg ttgtaggtgg cacctctggt gaggacctcg 360
gccgcgacca cgct 374

<210> SEQ ID NO 184
<211> LENGTH: 375
<212> TYPE: DNA
<213> ORGANISM: Homo sapiens
<220> FEATURE:
<221> NAME/KEY: misc_feature
<222> LOCATION: 30, 174, 248, 285, 306, 332, 345, 368
<223> OTHER INFORMATION: n = A,T,C or G

<400> SEQUENCE: 184
agcgtggttt gcggccgagg tcctcaccan aggtgccacc tacaacatca tagtggaggc 60
actgaaagac cagcagaggc ataaggttcg ggaagaggtt gttaccgtgg gcaactctgt 120
caacgaaggc ttgaaccaac ctacggatga ctcgtgcttt gacccctaca cagnttccca 180
ttatgccgtt ggagatgagt gggaacgaat gtctgaatca ggctttaaac tgttgtgcca 240
gtgcttangc tttggaagtg gtcatttcag atgtgattca tctanatggt gtcatgacaa 300
tggtgngaac tacaagattg gagagaagtg gnaccgtcag ggganaaaat ggacctgccc 360
gggcggcncg ctcga 375

-continued

<210> SEQ ID NO 185
<211> LENGTH: 148
<212> TYPE: DNA
<213> ORGANISM: Homo sapiens
<220> FEATURE:
<221> NAME/KEY: misc_feature
<222> LOCATION: 28, 36, 86
<223> OTHER INFORMATION: n = A,T,C or G

<400> SEQUENCE: 185
agcgtggtcg cggccgaggt ctggcttnct gctcangtga ttatcctgaa ccatccaggc 60
caaataagcg ccggctatgc ccctgnattg gattgccaca cggctcacat tgcatgcaag 120
tttgctgagc tgaaggaaaa gattgatc 148

<210> SEQ ID NO 186
<211> LENGTH: 397
<212> TYPE: DNA
<213> ORGANISM: Homo sapiens
<220> FEATURE:
<221> NAME/KEY: misc_feature
<222> LOCATION: 78
<223> OTHER INFORMATION: n = A,T,C or G

<400> SEQUENCE: 186
tcgagcggcc gcccgggcag gtccaattga aacaaacagt tctgagaccg ttcttccacc 60
actgattaag agtggggngg cgggtattag ggataatatt catttagcct tctgagcttt 120
ctgggcagac ttggtgacct tgccagctcc agcagccttc tggtccactg ctttgatgac 180
acccaccgca actgtctgtc tcatatcacg aacagcaaag cgacccaaag gtggatagtc 240
tgagaagctc tcaacacaca tgggcttgcc aggaaccata tcaacaatgg gcagcatcac 300
cagacttcaa gaatttaagg gccatcttcc agctttttac cagaacggcg atcaatcttt 360
tccttcagct cagcaaactt gcatgcaatg tgagccg 397

<210> SEQ ID NO 187
<211> LENGTH: 584
<212> TYPE: DNA
<213> ORGANISM: Homo sapiens
<220> FEATURE:
<221> NAME/KEY: misc_feature
<222> LOCATION: 145, 286, 363, 365, 425, 433, 452, 462, 471, 512, 514,
534, 536, 540, 565, 583
<223> OTHER INFORMATION: n = A,T,C or G

<400> SEQUENCE: 187
tcgagcggcc gcccgggcag gtccagaggg ctgtgctgaa gtttgctgct gccactggag 60
ccactccaat tgctggccgc ttcactcctg gaaccttcac taaccagatc caggcagcct 120
tccgggagcc acggcttctt gtggntactg accccagggc tgaccaccag cctctcacgg 180
aggcatctta tgttaaccta cctaccattg cgctgtgtaa cacagattct cctctgcgct 240
atgtggacat tgccatccca tgcaacaaca agggagctca ctcagngggg tttgatgtgg 300
tggatgctgg ctcgggaagt tctgcgcatg cgtggcacca tttcccgtga acacccatgg 360
gangncatgc ctgatctgga cttctacaga gatcctgaag agattgaaaa agaagaacag 420
gctgnttgct ganaaagcaa gtgaccaagg angaaatttc angggtgaaa nggactgctc 480
ccgctcctga attcactgct actcaacctg angntgcaga ctggtcttga aggngnacan 540
gggccctctg ggcctattta agcancttcg gtcgcgaaca cgnt 584

<210> SEQ ID NO 188
<211> LENGTH: 579

-continued

<212> TYPE: DNA
<213> ORGANISM: Homo sapiens
<220> FEATURE:
<221> NAME/KEY: misc_feature
<222> LOCATION: 7, 136, 486
<223> OTHER INFORMATION: n = A,T,C or G

<400> SEQUENCE: 188
agcgtgngtc gcggccgagg tgctgaatag gcacagaggg cacctgtaca ccttcagacc 60
agtctgcaac ctcaggctga gtagcagtga actcaggagc gggagcagtc cattcaccct 120
gaaattcctc cttggncact gccttctcag cagcagcctg ctcttctttt tcaatctctt 180
caggatctct gtagaagtac agatcaggca tgacctccca tgggtgttca cgggaaatgg 240
tgccacgcat gcgcagaact tcccgagcca gcatccacca catcaaaccc actgagtgag 300
ctcccttgtt gttgcatggg atgggcaatg tccacatagc gcagaggaga atctgtgtta 360
cacagcgcaa tggtaggtag gttaacataa gatgcctccg cgagaagctg gtggtcagcc 420
ctggggtcaa gtaaccacaa gaagccgtgg ctcccggaag gctgcctgga tctggttagt 480
gaaggntcca ggagtgaagc ggccaacaat tggagtggct tcagtggcaa gcagcaaact 540
tcagcacaag ccctctggac ctgcccggcg gccgctcga 579

<210> SEQ ID NO 189
<211> LENGTH: 374
<212> TYPE: DNA
<213> ORGANISM: Homo sapiens
<220> FEATURE:
<221> NAME/KEY: misc_feature
<222> LOCATION: 41, 280, 314, 330, 350, 353
<223> OTHER INFORMATION: n = A,T,C or G

<400> SEQUENCE: 189
tcgagcggcc gcccgggcag gtccattttc tccctgacgg ncccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctcn tccccgaacc ttatgcctct 300
gctgggcttt cagngcctcc actatgatgn tgtagggggg cacctctggn gangacctcg 360
gccgcgacca cgct 374

<210> SEQ ID NO 190
<211> LENGTH: 373
<212> TYPE: DNA
<213> ORGANISM: Homo sapiens
<220> FEATURE:
<221> NAME/KEY: misc_feature
<222> LOCATION: 247, 304, 306, 332, 337
<223> OTHER INFORMATION: n = A,T,C or G

<400> SEQUENCE: 190
agcgtggtcg cggccgaggt cctcaccaga ggtgccacct acaacatcat agtggaggca 60
ctgaaagacc agcagaggca taaggctcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg gtcatttcag atgtgattca tctagatggt gccatgacaa 300
tggngngaac tacaagattg gagagaagtg gnaccgncag ggagaaaatg gacctgcccg 360

-continued ggcggccgct cga 373

<210> SEQ ID NO 191
<211> LENGTH: 354
<212> TYPE: DNA
<213> ORGANISM: Homo sapiens
<220> FEATURE:
<221> NAME/KEY: misc_feature
<222> LOCATION: 218, 299, 306, 326, 333, 337, 341
<223> OTHER INFORMATION: n = A,T,C or G

<400> SEQUENCE: 191
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggntg caaccttggt tggggtcaat 240
ccagtactct ccactcttcc agccagagtg gcacatcttg aggtcacggc aggtgcggnc 300
gggggntttt gcggctgccc tctggncttc ggntgtnctc natctgctgg ctca 354

<210> SEQ ID NO 192
<211> LENGTH: 587
<212> TYPE: DNA
<213> ORGANISM: Homo sapiens
<220> FEATURE:
<221> NAME/KEY: misc_feature
<222> LOCATION: 276
<223> OTHER INFORMATION: n = A,T,C or G

<400> SEQUENCE: 192
tcgagcggcc gcccgggcag gtctcgcggt cgcactggtg atgctggtcc tgttggtccc 60
cccggccctc ctggacctcc tggccccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagncgca agaaccccgc ccgcacctgc 300
cgtgacctca agatgtgcca ctctgactgg aagagtggag agtactggat tgaccccaac 360
caagctgcaa cctggatgcc atcaaagtct tctgcaacat ggagactggt gagacctgcg 420
tgtaccccac tcagcccagt gtggcccaaa agaactggta catcagcaag aaccccaagg 480
acaagaagca tgtctggttc ggcgagaaca tgaccgatgg attccagttc gagtatggcg 540
ggcagggctc cgaccctgcc gatggggacc ttggccgcga acacgct 587

<210> SEQ ID NO 193
<211> LENGTH: 98
<212> TYPE: DNA
<213> ORGANISM: Homo sapiens
<220> FEATURE:
<221> NAME/KEY: misc_feature
<222> LOCATION: 8, 9, 33, 58, 71, 90
<223> OTHER INFORMATION: n = A,T,C or G

<400> SEQUENCE: 193
agcgtggnng cggccgaggt ataaatatcc agnccatatc ctccctccac acgctganag 60
atgaagctgt ncaaagatct cagggtggan aaaaccat 98

<210> SEQ ID NO 194
<211> LENGTH: 240
<212> TYPE: DNA
<213> ORGANISM: Homo sapiens -continued

<400> SEQUENCE: 194
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg ggggaaaaca ccatggtttt atccaccctg agatctttga acaacttcat 180
ctctcagcgt gcggagggag gctctggact ggatatttct acctcggccg cgaccacgct 240

<210> SEQ ID NO 195
<211> LENGTH: 400
<212> TYPE: DNA
<213> ORGANISM: Homo sapiens
<220> FEATURE:
<221> NAME/KEY: misc_feature
<222> LOCATION: 22, 37, 39, 105, 268, 276, 302, 323, 331, 335, 347, 351, 371, 378
<223> OTHER INFORMATION: n = A,T,C or G

<400> SEQUENCE: 195
cgagcgggcg accgggcagg tncagactcc aatccanana accatcaagc cagatgtcag 60
aagctacacc atcacaggtt tacaaccagg cactgactac aaganctacc tgcacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240
acgtgccagg attaccggta catcatcnag tatganaagc ctgggcctcc tcccagagaa 300
gnggtccctc ggccccgccc tgntgtccca naggntacta ttactgngcc ngcaaccggc 360
aaccgatatc nattttgnca ttggccttca acaataatta 400

<210> SEQ ID NO 196
<211> LENGTH: 494
<212> TYPE: DNA
<213> ORGANISM: Homo sapiens
<220> FEATURE:
<221> NAME/KEY: misc_feature
<222> LOCATION: 19, 83, 168, 252, 271, 292, 430
<223> OTHER INFORMATION: n = A,T,C or G

<400> SEQUENCE: 196
agcgtggttc gcggccgang tcctgtcaga gtggcactgg tagaagttcc aggaaccctg 60
aactgtaagg gttcttcatc agngccaaca ggatgacatg aaatgatgta ctcagaagtg 120
tcctggaatg gggcccatga gatggttgtc tgagagagag cttcttgncc tgtctttttc 180
cttccaatca ggggctcgct cttctgatta ttcttcaggg caatgacata aattgtatat 240
tcgggtcccg gntccaggcc agtaatagta ncctctgtga caccagggcg gngccgaggg 300
accacttctc tgggaggaga cccaggcttc tcatacttga tgatgtaacc ggtaatcctg 360
gcacgtggcg gctgccatga taccagcaag gaattggggt gtggtggcca ggaaacgcag 420
gttggatggn gcatcaatgg cagtggaggc cgtcgatgac cacaggggga gctccgacat 480
tgtcattcaa ggtg 494

<210> SEQ ID NO 197
<211> LENGTH: 118
<212> TYPE: DNA
<213> ORGANISM: Homo sapiens
<220> FEATURE:
<221> NAME/KEY: misc_feature
<222> LOCATION: 8, 71, 96
<223> OTHER INFORMATION: n = A,T,C or G

<400> SEQUENCE: 197
agcgtggncg cggccgaggt gcagcgcggg ctgtgccacc ttctgctctc tgcccaacga 60
taaggagggt ncctgccccc aggagaacat taactntccc cagctcggcc tctgccgg 118

<210> SEQ ID NO 198
<211> LENGTH: 403
<212> TYPE: DNA
<213> ORGANISM: Homo sapiens
<220> FEATURE:
<221> NAME/KEY: misc_feature
<222> LOCATION: 41, 53, 98, 195, 350
<223> OTHER INFORMATION: n = A,T,C or G

<400> SEQUENCE: 198
tcgagcggcc gcccgggcag gttttttttg ctgaaagtgg ntactttatt ggntgggaaa 60
gggagaagct gtggtcagcc caagagggaa tacagagncc cgaaaaaggg gagggcaggt 120
gggctggaac cagacgcagg gccaggcaga aactttctct cctcactgct cagcctggtg 180
gtggctggag ctcanaaatt gggagtgaca caggacacct tcccacagcc attgcggcgg 240
catttcatct ggccaggaca ctggctgtcc acctggcact ggtcccgaca gaagcccgag 300
ctggggaaag ttaatgttca cctgggggca ggaaccctcc ttatcattgn gcagagagca 360
gaaggtggca cagcccgcgc tgcacctcgg ccgcgaccac gct 403

<210> SEQ ID NO 199
<211> LENGTH: 167
<212> TYPE: DNA
<213> ORGANISM: Homo sapiens
<220> FEATURE:
<221> NAME/KEY: misc_feature
<222> LOCATION: 92, 107
<223> OTHER INFORMATION: n = A,T,C or G

<400> SEQUENCE: 199
tcgagcggcc gcccgggcag gtccaccata agtcctgata caaccacgga tgagctgtca 60
ggagcaaggt tgatttcttt cattggtccg gncttctcct tgggggncac ccgcactcga 120
tatccagtga gctgaacatt gggtggcgtc cactgggcgc tcaggct 167

<210> SEQ ID NO 200
<211> LENGTH: 252
<212> TYPE: DNA
<213> ORGANISM: Homo sapiens
<220> FEATURE:
<221> NAME/KEY: misc_feature
<222> LOCATION: 210, 226, 227, 230, 236
<223> OTHER INFORMATION: n = A,T,C or G

<400> SEQUENCE: 200
tcgagcggtt cgcccgggca ggtccaccac acccaattcc ttgctggtat catggcagcc 60
gccacgtgcc aggattaccg gctacatcat caagtatgag aagcctgggt ctcctcccag 120
agaagcggtc cctcggcccc gccctggtgt cacagaggct actattactg gcctggaacc 180
gggaaccgaa tatacaattt atgtcattgn cctgaagaat aatcannaan agcgancccc 240
tgattggaag ga 252

<210> SEQ ID NO 201
<211> LENGTH: 91
<212> TYPE: DNA
<213> ORGANISM: Homo sapiens

<400> SEQUENCE: 201

-continued agcgtggtcg cggccgaggt tgtacaagct tttttttttt tttttttttt tttttttttt 60
tttttttttt tttttttttt tttttttttt t 91

<210> SEQ ID NO 202
<211> LENGTH: 368
<212> TYPE: DNA
<213> ORGANISM: Homo sapiens
<220> FEATURE:
<221> NAME/KEY: misc_feature
<222> LOCATION: 9, 354
<223> OTHER INFORMATION: n = A,T,C or G

<400> SEQUENCE: 202
tcgagcggnc gcccgggcag gtctgccaac accaagattg gcccccgccg catccacaca 60
gtccgtgtgc ggggaggtaa caagaaatac cgtgccctga ggttggacgt ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatcgac 240
agcacaccgt accgacagtg gtacgagtcc cactatgcgc tgcccctggg ccgcaagaag 300
ggagccaagc tgactcctga ggaagaagag attttaaaca aaaaacgatc taanaaaaaa 360
aaaacaat 368

<210> SEQ ID NO 203
<211> LENGTH: 340
<212> TYPE: DNA
<213> ORGANISM: Homo sapiens

<400> SEQUENCE: 203
agcgtggtcg cggccgaggt gaaatggtat tcagcttcct ggcacttctg gtcagcaacc 60
cagtgttggg caacaaatga tctttgagga acatggtttt aggcggacca caccgcccac 120
aacggccacc cccataaggc ataggccaag accatacccg ccgaatgtag gacaagaagc 180
tctctctcag acaaccatct catgggcccc attccaggac acttctgagt acatcatttc 240
atgtcatcct gttggcactg atgaagaacc cttacagttc agggttcctg gaacttctac 300
cagtgccact ctgacaggac ctgcccgggc ggccgctcga 340

<210> SEQ ID NO 204
<211> LENGTH: 341
<212> TYPE: DNA
<213> ORGANISM: Homo sapiens

<400> SEQUENCE: 204
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc acctcggccg cgaccacgct a 341

<210> SEQ ID NO 205
<211> LENGTH: 770
<212> TYPE: DNA
<213> ORGANISM: Homo sapiens
<220> FEATURE:
<221> NAME/KEY: misc_feature
<222> LOCATION: 529, 591, 623, 626, 629, 630, 656, 702, 709, 712, 717,
743, 746, 749, 759, 762, 766

-continued

<223> OTHER INFORMATION: n = A,T,C or G

<400> SEQUENCE: 205
tcgagcggcc gcccgggcag gtctcccttc ttgcggccca ggggcagcgc atagtgggac 60
tcgtaccact gtcggtacgg tgtgctgtcg atgagcacga tgcaattctt caccagggtc 120
ttggtacgaa ccagctcgtt attagatgca ttgtagacaa catcgatgat ccttgtttta 180
cgagtacaac actctgagcc ccaggagaaa ttccccacgt ccaacctcag ggcacggtat 240
ttcttgttac ctccccgcac acggactgtg tggatgcggc gggggccaag ctgactcctg 300
aggaagaaga gattttaaac aaaaaacgat ctaaaaaaat tcagaagaaa tatgatgaaa 360
ggaaaaagaa tgccaaaatc agcagtctcc tggaggagca gttccagcag ggcaagcttc 420
ttgcgtgcat cgcttcaagg ccgggacagt gtgaccgagc agatggctat gtgctagagg 480
gcaaagaagt ggagttctat cttaagaaaa tcagggccca gaatggtgng tcttcaacta 540
atccaaaggg gagtttcaga ccagtgcaat cagcaaaaac attgatactg ntggccaaat 600
ttattggtgc agggcttgca cantangann ggctgggtct tggggcttgg attggnacaa 660
gctttggcag ccttttcttt ggttttgcca aaaacctttt gntgaagang anacctnggg 720
cggacccctt aaccgattcc acnccnggng gcgttctang gncccncttg 770

<210> SEQ ID NO 206
<211> LENGTH: 810
<212> TYPE: DNA
<213> ORGANISM: Homo sapiens
<220> FEATURE:
<221> NAME/KEY: misc_feature
<222> LOCATION: 574, 621, 625, 636, 668, 673, 704, 728, 743, 767, 772,
786, 789, 807, 809, 810
<223> OTHER INFORMATION: n = A,T,C or G

<400> SEQUENCE: 206
agcgtggtcg cggccgaggt ctgctgcttc agcgaagggt ttctggcata accaatgata 60
aggctgccaa agactgttcc aataccagca ccagaaccag ccactcctac tgttgcagca 120
cctgcaccaa taaatttggc agcagtatca atgtctctgc tgattgcact ggtctgaaac 180
tccctttgga ttagctgaga cacaccattc tgggccctga ttttcctaag atagaactcc 240
aactctttgc cctctagcac atagccatct gctcggtcac actgtcccgg ccttgaagcg 300
atgcacgcaa gaagcttgcc ctgctggaac tgctcctcca ggagactgct gattttggca 360
ttctttttcc tttcatcata tttcttctga atttttttag atcgtttttt gtttaaaatc 420
tcttcttcct caggagtcag cttggccccc gccgcatcca cacagtccgt gtgcggggag 480
gtaacaagaa ataccgtgcc ctgaggttgg acgtggggaa tttctcctgg ggctcagagt 540
ggtgtactcg taaaacaagg atcatcgatg gtgnctacaa tgcatctaat aacgagctgg 600
gtcggaccca aagaacctgg ngaanaaatg gatcgnctca tcgacaggac accgtacccg 660
acaggggnac gantcccact atgcgcttgc ccctgggccg caanaaagga aaactgcccg 720
ggcggccntc gaaagcccaa ttntggaaaa aatccatcac actgggnggc cngtcgagca 780
tgcatntana ggggcccatt ccccctnann 810

<210> SEQ ID NO 207
<211> LENGTH: 257
<212> TYPE: DNA
<213> ORGANISM: Homo sapiens

<400> SEQUENCE: 207

-continued

```
tcgagcggcc gcccgggcag gtccccaacc aaggctgcaa cctggatgcc atcaaagtct     60

tctgcaacat ggagactggt gagacctgcg tgtaccccac tcagcccagt gtggcccaga    120

agaactggta catcagcaag aaccccaagg acaagaggca tgtctggttc ggcgagagca    180

tgaccgatgg attccagttc gagtatggcg gccagggctc cgaccctgcc gatgtggacc    240

tcggccgcga ccacgct                                                   257
```

```
<210> SEQ ID NO 208
<211> LENGTH: 257
<212> TYPE: DNA
<213> ORGANISM: Homo sapiens

<400> SEQUENCE: 208

agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggacctg    240

cccgggcggc cgctcga                                                   257
```

```
<210> SEQ ID NO 209
<211> LENGTH: 747
<212> TYPE: DNA
<213> ORGANISM: Homo sapiens
<220> FEATURE:
<221> NAME/KEY: misc_feature
<222> LOCATION: 453, 538, 540, 542, 546, 554, 556, 598, 659, 670, 679,
      689, 693, 711, 723, 724, 731, 747
<223> OTHER INFORMATION: n = A,T,C or G

<400> SEQUENCE: 209

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agacccctttt cgtcacccac   360

cctgggtatg acactggaaa tggtattcag cttcctggca cttctggtca gcaacccagt    420

gttgggcaac aaatgatctt tgaggaacat ggntttaggc ggaccacacc gcccacaacg    480

gccaccccca taaggcatag gccaagacca tacccgccga atgtaggaca agaagctntn    540

tntcanacac catntnatgg gccccattcc aggacacttc tgagtacatc atttatgnca    600

tctgtggcac ttgatgaaaa cccttacagt tcagggttct ggaactttta ccaggcctnt    660

tacaggactn ggccggacnc cttaagccna ttncaccctg ggcgttcta nggtcccact     720

cgnncactgg ngaaaatggc tactgtn                                        747
```

```
<210> SEQ ID NO 210
<211> LENGTH: 872
<212> TYPE: DNA
<213> ORGANISM: Homo sapiens
<220> FEATURE:
<221> NAME/KEY: misc_feature
<222> LOCATION: 165, 174, 181, 256, 260, 269, 271, 277, 286, 289, 294,
      298, 300, 301, 303, 308, 311, 321, 325, 328, 329, 333, 338, 342,
      346, 349, 351, 357, 359, 364, 366, 379, 385, 395, 396, 397,
      407, 408, 410, 414, 415, 429, 431, 434, 435, 440, 443
<223> OTHER INFORMATION: n = A,T,C or G
```

-continued

<220> FEATURE:
<221> NAME/KEY: misc_feature
<222> LOCATION: 444, 446, 447, 448, 449, 450, 451, 464, 470, 472, 475, 479, 483, 484, 485, 488, 494, 496, 497, 504, 508, 509, 511, 513, 517, 522, 524, 526, 532, 533, 542, 543, 553, 559, 566, 567, 571, 572, 578, 582, 588, 591, 594, 595, 596, 600, 606
<223> OTHER INFORMATION: n = A,T,C or G
<220> FEATURE:
<221> NAME/KEY: misc_feature
<222> LOCATION: 612, 614, 617, 618, 629, 630, 631, 652, 654, 655, 661, 663, 664, 666, 671, 673, 678, 679, 681, 688, 690, 691, 698, 706, 707, 708, 714, 719, 721, 723, 726, 741, 751, 761, 762, 769, 770, 778, 779, 781, 782, 785, 791, 802, 807, 808, 812
<223> OTHER INFORMATION: n = A,T,C or G
<220> FEATURE:
<221> NAME/KEY: misc_feature
<222> LOCATION: 815, 820, 827, 828, 838, 841, 844, 851, 857, 864, 866, 869, 872
<223> OTHER INFORMATION: n = A,T,C or G

<400> SEQUENCE: 210

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgngaaac tccnaggaca    180

ngagggctaa attccatgaa gtttgtggat ggcctgatga tccacaatcg gagaccctgt    240

taactactac cgtctnaccn cctgctgtnc ncccccnttt ctgctnaana catngggntn    300

ntncttgncc ntccttgggt ngaanatnna atngcctncc cnttcntanc nctactngnt    360

ccananttgg cctttaaana atccnccttg ccttnnncac tgttcanntn tttnntcgta    420

aaccctatna nttnnattan atnntnnnnn nctcaccccc ctcntcattn anccnatang    480

ctnnnaantc cttnanncct cccncccnnt ncnctcntac tnantncttc tnncccatta    540

cnnagctctt tcntttaana taatgnngcc nngctctnca tntctacnat ntgnnnaatn    600

cccccncccc cnancgnntt tttgacctnn naacctcctt tcctcttccc tncnnaaatt    660

ncnnanttcc ncnttccnnc ntttcggntn ntcccatnct ttccannnct tcantctanc    720

ncnctncaac ttattttcct ntcatccctt nttctttaca nnccccctnn tctactcnnc    780

nnttncatta natttgaaac tnccacnnct anttncctcn ctctacnntt ttattttncg    840

ntcnctctac ntaatanttt aatnanttnt cn                                  872
```

<210> SEQ ID NO 211
<211> LENGTH: 517
<212> TYPE: DNA
<213> ORGANISM: Homo sapiens
<220> FEATURE:
<221> NAME/KEY: misc_feature
<222> LOCATION: 462, 464, 506
<223> OTHER INFORMATION: n = A,T,C or G

<400> SEQUENCE: 211

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120

tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacaa gcagtgtcaa cgtagtaagt taacagggtc tccgctgtgg    300

atcatcaggc catccacaaa cttcatggat ttagccctct gtcctcggag tttcccagac    360

accacaacct cgcagccttt ggccccactc tccatgatga accgcagcac accatagcag    420

gccctccgca caagcaagcc ctcctaagaa tttgtaacgc ananactctg ctggcaatgg    480
```

cacacaaacc tctagtggac ctcggncgcg accacgc 517

<210> SEQ ID NO 212
<211> LENGTH: 695
<212> TYPE: DNA
<213> ORGANISM: Homo sapiens
<220> FEATURE:
<221> NAME/KEY: misc_feature
<222> LOCATION: 432, 476, 522, 547, 621, 624, 647, 679
<223> OTHER INFORMATION: n = A,T,C or G

<400> SEQUENCE: 212
tcgagcggcc gcccgggcag gtctggtcca ggatagcctg cgagtcctcc tactgctact 60
ccagacttga catcatatga atcatactgg ggagaatagt tctgaggacc agtagggcat 120
gattcacaga ttccaggggg gccaggagaa ccaggggacc ctggttgtcc tggaatacca 180
gggtcaccat ttctcccagg aataccagga gggcctggat ctcccttggg gccttgaggt 240
ccttgaccat taggagggcg agtaggagca gttggaggct gtgggcaaac tgcacaacat 300
tctccaaatg gaatttctgg gttggggcag tctaattctt gatccgtcac atattatgtc 360
atcgcagaga acggatcctg agtcacagac acatatttgg catggttctg gcttccagac 420
atctctatcc gncataggac tgaccaagat gggaacatcc tccttcaaca agcttnctgt 480
tgtgccaaaa ataatagtgg gatgaagcag accgagaagt anccagctcc cctttttgca 540
caaagcntca tcatgtctaa atatcagaca tgagacttct ttgggcaaaa aaggagaaaa 600
agaaaaagca gttcaaagta nccnccatca agttggttcc ttgcccnttc agcacccggg 660
ccccgttata aaacacctng ggccggaccc ccctt 695

<210> SEQ ID NO 213
<211> LENGTH: 804
<212> TYPE: DNA
<213> ORGANISM: Homo sapiens
<220> FEATURE:
<221> NAME/KEY: misc_feature
<222> LOCATION: 552, 555, 592, 624, 629, 633, 658, 695, 697, 698, 700,
702, 745, 753, 755, 762, 773, 786, 788, 793, 795
<223> OTHER INFORMATION: n = A,T,C or G

<400> SEQUENCE: 213
agcgtggtcg cggccgaggt gttttatgac gggcccggtg ctgaagggca gggaacaact 60
tgatggtgct actttgaact gcttttcttt tctccttttt gcacaaagag tctcatgtct 120
gatatttaga catgatgagc tttgtgcaaa aggggagctg gctacttctc gctctgcttc 180
atcccactat tattttggca caacaggaag ctgttgaagg aggatgttcc catcttggtc 240
agtcctatgc ggatagagat gtctggaagc cagaaccatg ccaaatatgt gtctgtgact 300
caggatccgt tctctgcgat gacataatat gtgacgatca agaattagac tgccccaacc 360
cagaaattcc atttggagaa tgttgtgcag tttgcccaca gcctccaact gctcctactc 420
gccctcctaa tggtcaagga cctcaaggcc ccaagggaga tccaggccct cctggtattc 480
ctgggagaaa tggtgaccct ggtattccag gacaaccagg gtcccctggt tctcctggcc 540
cccctggaat cnggngaatc atgccctact ggtcctcaaa ctattctccc anatgattca 600
tatgatgtca agtctgggat agcnagtang ganggactcg caggctattc tggaccanac 660
ctgccggggg ggcgttcgaa agcccgaatc tgcananntn cnttcacact ggcggccgtc 720
gagctgcttt aaaagggcca ttccnccttt agngnggggg antacaatta ctnggcggcg 780
ttttanancg cgngnctggg aaat 804

-continued

<210> SEQ ID NO 214
<211> LENGTH: 594
<212> TYPE: DNA
<213> ORGANISM: Homo sapiens
<220> FEATURE:
<221> NAME/KEY: misc_feature
<222> LOCATION: 452, 509, 585
<223> OTHER INFORMATION: n = A,T,C or G

<400> SEQUENCE: 214
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagagtg gcacatcttg aggtcacggc aggtgcgggc 300
ggggttcttg cggctgccct ctgggctccg gatgttctcg atctgctggc tcaggctctt 360
gagggtggtg tccacctcga ggtcacggtc acgaaccaca ttggcatcat cagcccggta 420
gtagcggcca ccatcgtgag ccttctcttg angtggctgg ggcaggaact gaagtcgaaa 480
ccagcgctgg gaggaccagg gggaccaana ggtccaggaa gggcccgggg gggaccaaca 540
ggaccagcat caccaagtgc gacccgcgag aacctgcccg gccgnccgct cgaa 594

<210> SEQ ID NO 215
<211> LENGTH: 590
<212> TYPE: DNA
<213> ORGANISM: Homo sapiens
<220> FEATURE:
<221> NAME/KEY: misc_feature
<222> LOCATION: 8, 9
<223> OTHER INFORMATION: n = A,T,C or G

<400> SEQUENCE: 215
tcgagcgnnc gcccgggcag gtctcgcggt cgcactggtg atgctggtcc tgttggtccc 60
cccggccctc ctggacctcc tggtccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagccgca agaaccccgc ccgcacctgc 300
cgtgacctca agatgtgcca ctctgactgg aagagtggag agtactggat tgaccccaac 360
caaggctgca acctggatgc catcaaagtc ttctgcaaca tggagactgg tgagacctgc 420
gtgtacccca ctcagcccag tgtggcccag aagaactggt acatcagcaa gaaccccaag 480
gacaagaggc atgtctggtt cggcgagagc atgaccgatg gattccagtt cgagtatggc 540
ggccagggct cccaccctgc cgatgtggac ctccggccgc gaccaccctt 590

<210> SEQ ID NO 216
<211> LENGTH: 801
<212> TYPE: DNA
<213> ORGANISM: Homo sapiens
<220> FEATURE:
<221> NAME/KEY: misc_feature
<222> LOCATION: 2, 22, 25, 26, 328, 373, 385, 440, 473, 534, 571, 572, 573, 582, 587, 589, 593, 600, 605, 617, 633, 642, 653, 672, 681, 685, 696, 699, 709, 715, 717, 726, 731, 739, 742, 745, 758, 769, 772, 778, 780, 788, 789, 791, 793, 796
<223> OTHER INFORMATION: n = A,T,C or G

<400> SEQUENCE: 216

-continued

```
tngagcggcc gcccgggcag gntgnnaacg ctggtcctgc tggtcctcct ggcaaggctg     60
gtgaagatgg tcaccctgga aaacccggac gacctggtga gagaggagtt gttggaccac    120
agggtgctcg tggtttccct ggaactcctg gacttcctgg cttcaaaggc attaggggac    180
acaatggtct ggatggattg aagggacagc ccggtgctcc tggtgtgaag ggtgaacctg    240
gtgcccctgg tgaaaatgga actccaggtc aaacaggagc ccgtgggctt cctggtgaga    300
gaggaccgtg ttggtgcccc tggcccanac ctcggccgcg accacgctaa gcccgaattt    360
ccagcacact ggnggccgtt actantggat ccgagctcgg taccaagctt ggcgtaatca    420
tggtcatagc tgtttcctgn gtgaaattgt tatccgctca caatttcaca cancatacga    480
agccggaaag cataaagtgt aaagccttgg ggtgctaatg agtgagctaa ctcncattaa    540
attgcgttgc gctcactgcc cgcttttcca nnngggaaac cntggcntng ccngcttgcn    600
ttaantgaaa tccgccnacc cccggggaaa agncggtttg cngtattggg gcnctttttc    660
cctttcctcg gnttacttga nttantgggc tttggncgnt tcgggttgng gcgancnggt    720
tcaacntcac nccaaaggng gnaanacggt tttcccanaa tccgggggnt ancccaangn    780
aaaacatnng ncnaangggc t                                              801
```

<210> SEQ ID NO 217
<211> LENGTH: 349
<212> TYPE: DNA
<213> ORGANISM: Homo sapiens
<220> FEATURE:
<221> NAME/KEY: misc_feature
<222> LOCATION: 10, 157, 170
<223> OTHER INFORMATION: n = A,T,C or G

<400> SEQUENCE: 217

```
agcgtggttn gcggccgagg tctgggccag gggcaccaac acgtcctctc tcaccaggaa     60
gcccacgggc tcctgtttga cctggagttc cattttcacc aggggcacca ggttcaccct    120
tcacaccagg agcaccgggc tgtcccttca atccatncag accattgtgn cccctaatgc    180
ctttgaagcc aggaagtcca ggagttccag ggaaaccacc gagcaccctg tggtccaaca    240
actcctctct caccaggtcg tccgggtttt ccagggtgac catcttcacc agccttgcca    300
ggaggaccag caggaccagc gttaccaacc tgcccgggcg gccgctcga                349
```

<210> SEQ ID NO 218
<211> LENGTH: 372
<212> TYPE: DNA
<213> ORGANISM: Homo sapiens

<400> SEQUENCE: 218

```
tcgagcggcc gcccgggcag gtccattttc tccctgacgg tcccacttct ctccaatctt     60
gtagttcaca ccattgtcat ggcaccatct agatgaatca catctgaaat gaccacttcc    120
aaagcctaag cactggcaca acagtttaaa gcctgattca gacattcgtt cccactcatc    180
tccaacggca taatgggaaa ctgtgtaggg gtcaaagcac gagtcatccg taggttggtt    240
caagccttcg ttgacagagt tgcccacggt aacaacctct tcccgaacct tatgcctctg    300
ctggtctttc agtgcctcca ctatgatgtt gtaggtggca cctctggtga ggacctcggc    360
cgcgaccacg ct                                                        372
```

<210> SEQ ID NO 219
<211> LENGTH: 374
<212> TYPE: DNA

-continued

<213> ORGANISM: Homo sapiens

<400> SEQUENCE: 219
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaag atgtgattca tctagatggt gccatgacaa 300
tggtgtgaac tacaagattg gagagaagtg ggaccgtcag ggagaaaatg gacctgcccg 360
ggccggccgc tcga 374

<210> SEQ ID NO 220
<211> LENGTH: 828
<212> TYPE: DNA
<213> ORGANISM: Homo sapiens
<220> FEATURE:
<221> NAME/KEY: misc_feature
<222> LOCATION: 8, 9, 557, 571, 587, 588, 601, 642, 643, 647, 654, 664, 681, 688, 698, 719, 720, 725, 734, 738, 743, 744, 757, 765, 773, 778, 780, 782, 783, 793, 798, 805, 809, 822, 827
<223> OTHER INFORMATION: n = A,T,C or G

<400> SEQUENCE: 220
tcgagcgnnc gcccgggcag gtccagtagt gccttcggga ctgggttcac ccccaggtct 60
gcggcagttg tcacagcgcc agccccgctg gcctccaaag catgtgcagg agcaaatggc 120
accgagatat tccttctgcc actgttctcc tacgtggtat gtcttcccat catcgtaaca 180
cgttgcctca tgagggtcac acttgaattc tccttttccg ttcccaagac atgtgcagct 240
catttggctg gctctatagt ttggggaaag tttgttgaaa ctgtgccact gacctttact 300
tcctccttct ctactggagc tttcgtacct tccacttctg ctgttggtaa aatggtggat 360
cttctatcaa tttcattgac agtacccact tctcccaaac atccagggaa atagtgattt 420
cagagcgatt aggagaacca aattatgggg cagaaataag gggcttttcc acaggttttc 480
ctttggagga agatttcagt ggtgacttta aaagaatact caacagtgtc ttcatcccca 540
tagcaaaaga agaaacngta aatgatggaa ngcttctgga gatgccnnca tttaagggac 600
ncccagaact tcaccatcta caggacctac ttcagtttac annaagncac atantctgac 660
tcanaaagga cccaagtagc nccatggnca gcactttnag cctttcccct ggggaaaann 720
ttacnttctt aaancctngg ccnngacccc cttaagncca aattntggaa aanttccntn 780
cnnctggggg gcngttcnac atgcntttna agggcccaat tnccccnt 828

<210> SEQ ID NO 221
<211> LENGTH: 476
<212> TYPE: DNA
<213> ORGANISM: Homo sapiens

<400> SEQUENCE: 221
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtgt 180
acacctgtgg ttctcggggc tgccctttgg ctttggagat ggttttctcg atgggggctg 240
ggagggcttt gttggagacc ttgcacttgt actccttgcc attcagccag tcctggtgca 300
ggacggtgag gacgctgacc acacggtacg tgctgttgta ctgctcctcc cgcggctttg 360

-continued

```
tcttggcatt atgcacctcc acgccgtcca cgtaccagtt gaacttgacc tcagggtctt    420

cgtggctcac gtccaccacc acgcatgtaa cctcagacct cggccgcgac cacgct        476


<210> SEQ ID NO 222
<211> LENGTH: 477
<212> TYPE: DNA
<213> ORGANISM: Homo sapiens

<400> SEQUENCE: 222

agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgtgtggtc agcgtcctca ccgtcctgca    180

ccaggactgg ctgaatggca aggagtacaa gtgcaaggtc tccaacaaag ccctcccagc    240

ccccatcgag aaaaccatct ccaaagccaa agggcaagcc ccgagaacca caggtgtaca    300

ccctgccccc atcccgggag gagatgacca agaaccaggt cagcctgacc tgcctggtca    360

aaggcttcta tcccagcgac atcgccgtgg agtgggagag caatgggcag ccggagaaca    420

actacaagac cacgcctccc gtgctggact ccgacacctg cccgggcggc cgctcga       477


<210> SEQ ID NO 223
<211> LENGTH: 361
<212> TYPE: DNA
<213> ORGANISM: Homo sapiens

<400> SEQUENCE: 223

tcgagcggcc gcccgggcag gttgaatggc tcctcgctga ccacccccggt gctggtggtg     60

ggtacagagc tccgatgggt gaaaccattg acatagagac tgtccctgtc cagggtgtag    120

gggcccagct cagtgatgcc gtgggtcagc tggctcagct tccagtacag ccgctctctg    180

tccagtccag ggcttttggg gtcaggacga tgggtgcaga cagcatccac tctggtggct    240

gccccatcct tctcaggcct gagcaaggtc agtctgcaac cagagtacag agagctgaca    300

ctggtgttct tgaacaaggg cataagcaga ccctgaagga cacctcggcc gcgaccacgc    360

t                                                                    361


<210> SEQ ID NO 224
<211> LENGTH: 361
<212> TYPE: DNA
<213> ORGANISM: Homo sapiens

<400> SEQUENCE: 224

agcgtggtcg cggccgaggt gtccttcagg gtctgcttat gcccttgttc aagaacacca     60

gtgtcagctc tctgtactct ggttgcagac tgaccttgct caggcctgag aaggatgggg    120

cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                    361


<210> SEQ ID NO 225
<211> LENGTH: 766
<212> TYPE: DNA
<213> ORGANISM: Homo sapiens
<220> FEATURE:
```

<221> NAME/KEY: misc_feature
<222> LOCATION: 574, 610, 631, 643, 657, 660, 666, 688, 712, 735, 747
<223> OTHER INFORMATION: n = A,T,C or G

<400> SEQUENCE: 225

```
agcgtggtcg cggccgaggt cctgtcagag tggcactggt agaagttcca ggaaccctga     60
actgtaaggg ttcttcatca gtgccaacag gatgacatga aatgatgtac tcagaagtgt    120
cctggaatgg ggcccatgag atggttgtct gagagagagc ttcttgtcct acattcggcg    180
ggtatggtct tggcctatgc cttatggggg tggccgttgt gggcggtgtg gtccgcctaa    240
aaccatgttc ctcaaagatc atttgttgcc caacactggg ttgctgacca gaagtgccag    300
gaagctgaat accatttcca gtgtcatacc cagggtgggt gacgaaaggg gtcttttgaa    360
ctgtggaagg aacatccaag atctctggtc catgaagatt ggggtgtgga agggttacca    420
gttggggaag ctcgtctgtc tttttccttc caatcagggg ctcgctcttc tgattattct    480
tcagggcaat gacataaatt gtatattcgg tcccggttcc aggccagtaa tagtagcctc    540
tgtgacacca gggcggggcc gagggaccct tctnttggaa gagaccagct tctcatactt    600
gatgatgagn ccggtaatcc tggcacgtgg nggttgcatg atnccaccaa ggaaatnggn    660
gggggnggac ctgcccggcg gccgttcnaa agcccaattc cacacacttg gnggccgtac    720
tatggatccc actcngtcca acttggngga atatggcata actttt                   766
```

<210> SEQ ID NO 226
<211> LENGTH: 364
<212> TYPE: DNA
<213> ORGANISM: Homo sapiens

<400> SEQUENCE: 226

```
tcgagcggcc gcccgggcag gtccttgacc ttttcagcaa gtgggaaggt gtaatccgtc     60
tccacagaca aggccaggac tcgtttgtac ccgttgatga tagaatgggg tactgatgca    120
acagttgggt agccaatctg cagacagaca ctggcaacat tgcggacacc ctccaggaag    180
cgagaatgca gagtttcctc tgtgatatca agcacttcag ggttgtagat gctgccattg    240
tcgaacacct gctggatgac cagcccaaag gagaaggggg agatgttgag catgttcagc    300
agcgtggctt cgctggctcc cactttgtct ccagtcttga tcagacctcg gccgcgacca    360
cgct                                                                 364
```

<210> SEQ ID NO 227
<211> LENGTH: 275
<212> TYPE: DNA
<213> ORGANISM: Homo sapiens

<400> SEQUENCE: 227

```
agcgtggtcg cggccgaggt ctgtcctaca gtcctcagga ctctactccc tcagcagcgt     60
ggtgaccgtg ccctccagca acttcggcac ccagacctac acctgcaacg tagatcacaa    120
gcccagcaac accaaggtgg acaagagagt tgagcccaaa tcttgtgaca aaactcacac    180
atgcccaccg tgcccagcac ctgaactcct ggggggaccg tcagtcttcc tcttcccccg    240
catccccctt ccaaacctgc ccgggcggcc gctcg                               275
```

<210> SEQ ID NO 228
<211> LENGTH: 275
<212> TYPE: DNA
<213> ORGANISM: Homo sapiens

<400> SEQUENCE: 228

-continued

```
cgagcggccg cccgggcagg tttggaaggg ggatgcgggg gaagaggaag actgacggtc     60

cccccaggag ttcaggtgct gggcacggtg ggcatgtgtg agttttgtca caagatttgg    120

gctcaactct cttgtccacc ttggtgttgc tgggcttgtg atctacgttg caggtgtagg    180

tctgggtgcc gaagttgctg gagggcacgg tcaccacgct gctgagggag tagagtcctg    240

aggactgtag gacagacctc ggccgcgacc acgct                               275


<210> SEQ ID NO 229
<211> LENGTH: 40
<212> TYPE: DNA
<213> ORGANISM: Homo sapiens
<220> FEATURE:
<221> NAME/KEY: misc_feature
<222> LOCATION: 1, 4, 5, 13, 15, 17, 29
<223> OTHER INFORMATION: n = A,T,C or G

<400> SEQUENCE: 229

nggnnggtcc ggncngncag gaccactcnt cttcgaaata                          40


<210> SEQ ID NO 230
<211> LENGTH: 208
<212> TYPE: DNA
<213> ORGANISM: Homo sapiens

<400> SEQUENCE: 230

agcgtggtcg cggccgaggt cctcacttgc ctcctgcaaa gcaccgatag ctgcgctctg     60

gaagcgcaga tctgttttaa agtcctgagc aatttctcgc accagacgct ggaagggaag    120

tttgcgaatc agaagttcag tggacttctg ataacgtcta atttcacgga gcgccacagt    180

accaggacct gcccgggcgg ccgctcga                                       208


<210> SEQ ID NO 231
<211> LENGTH: 208
<212> TYPE: DNA
<213> ORGANISM: Homo sapiens
<220> FEATURE:
<221> NAME/KEY: misc_feature
<222> LOCATION: 33
<223> OTHER INFORMATION: n = A,T,C or G

<400> SEQUENCE: 231

tcgagcggcc gcccgggcag gtcctggtac tgnggcgctc cgtgaaatta gacgttatca     60

gaagtccact gaacttctga ttcgcaaact tcccttccag cgtctggtgc gagaaattgc    120

tcaggacttt aaaacagatc tgcgcttcca gagcgcagct atcggtgctt tgcaggaggc    180

aagtgaggac ctcggccgcg accacgct                                       208


<210> SEQ ID NO 232
<211> LENGTH: 332
<212> TYPE: DNA
<213> ORGANISM: Homo sapiens

<400> SEQUENCE: 232

tcgagcggcc gcccgggcag gtccacatcg gcagggtcgg agccctggcc gccatactcg     60

aactggaatc catcggtcat gctctcgccg aaccagacat gcctcttgtc cttggggttc    120

ttgctgatgt accagttctt ctgggccaca ctgggctgag tggggtacac gcaggtctca    180

ccagtctcca tgttgcagaa gactttgatg gcatccaggt tgcagccttg gttggggtca    240

atccagtact ctccactctt ccagtcagag tggcacatct tgaggtcacg gcaggtgcgg    300
```

-continued gcggggttct tgacctcggc cgcgaccacg ct 332

<210> SEQ ID NO 233
<211> LENGTH: 415
<212> TYPE: DNA
<213> ORGANISM: Homo sapiens
<220> FEATURE:
<221> NAME/KEY: misc_feature
<222> LOCATION: 6, 15, 19, 21
<223> OTHER INFORMATION: n = A,T,C or G

<400> SEQUENCE: 233
gtgggnttga acccntttna nctccgcttg gtaccgagct cggatccact agtaacggcc 60
gccagtgtgc tggaattcgg cttagcgtgg tcgcggccga ggtcaagaac cccgcccgca 120
cctgccgtga cctcaagatg tgccactctg actggaagag tggagagtac tggattgacc 180
ccaaccaagg ctgcaacctg gatgccatca aagtcttctg caacatggag actggtgaga 240
cctgcgtgta ccccactcag cccagtgtgg cccagaagaa ctggtacatc agcaagaacc 300
ccaaggacaa gaggcatgtc tggttcggcg agagcatgac cgatggattc cagttcgagt 360
atggcggcca gggctccgac cctgccgatg tggacctgcc cgggcggccg ctcga 415

<210> SEQ ID NO 234
<211> LENGTH: 776
<212> TYPE: DNA
<213> ORGANISM: Homo sapiens
<220> FEATURE:
<221> NAME/KEY: misc_feature
<222> LOCATION: 505, 550, 574, 601, 604, 608, 612, 649, 656, 657, 680, 711, 750, 776
<223> OTHER INFORMATION: n = A,T,C or G

<400> SEQUENCE: 234
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
ggaccaggac caacaaaaac taaaactgca ggtccagatc aaacagaaat gactattgaa 420
ggcttgcagc ccacagtgga gtatgtggtt aagtgtctat gctcagaatc caagcggaga 480
gaagtcagcc tctggttcag actgnaagta accaacattg atcgcctaaa ggactggcat 540
tcactgatgn ggatgccgat tccatcaaaa ttgnttggga aaacccacag gggcaagttt 600
ncangtcnag gnggacctac tcgagccctg aggatggaat ccttgactnt tccttnncct 660
gatggggaaa aaaaaccttn aaaacttgaa ggacctgccc gggcggccgt ncaaaaccca 720
attccacccc cttgggggcg ttctatgggn cccactcgga ccaaacttgg ggtaan 776

<210> SEQ ID NO 235
<211> LENGTH: 805
<212> TYPE: DNA
<213> ORGANISM: Homo sapiens
<220> FEATURE:
<221> NAME/KEY: misc_feature
<222> LOCATION: 637, 684, 705, 724, 733, 756, 778, 793, 796, 804
<223> OTHER INFORMATION: n = A,T,C or G

<400> SEQUENCE: 235

-continued

```
tcgagcggcc gcccgggcag gtccttgcag ctctgcagtg tcttcttcac catcaggtgc     60
agggaatagc tcatggattc catcctcagg gctcgagtag gtcaccctgt acctggaaac    120
ttgcccctgt gggctttccc aagcaatttt gatggaatcg gcatccacat cagtgaatgc    180
cagtccttta gggcgatcaa tgttggttac tgcagtctga accagaggct gactctctcc    240
gcttggattc tgagcataga cactaaccac atactccact gtgggctgca agccttcaat    300
agtcatttct gtttgatctg gacctgcagt tttagttttt gttggtcctg gtccattttt    360
gggagtggtg gttactctgt aaccagtaac aggggaactt gaaggcagcc acttgacact    420
aatgctgttg tcctgaacat cggtcacttg catctgggat ggtttgtcaa tttctgttcg    480
gtaattaatg gaaattggct tgctgcttgc ggggcttgtc tccacggcca gtgacagcat    540
acacagtgat ggtataatca actccaggtt taagccgctg atggtagctg aaactttgct    600
ccaggcacaa gtgaactcct gacagggcta tttcctnctg ttctccgtaa gtgatcctgt    660
aatatctcac tgggacagca ggangcattc caaaacttcg ggcgngaccc cctaagccga    720
attntgcaat atncatcaca ctggcgggcg ctcgancatt cattaaaagg cccaatcncc    780
cctataggga gtntantaca attng                                          805
```

<210> SEQ ID NO 236
<211> LENGTH: 262
<212> TYPE: DNA
<213> ORGANISM: Homo sapiens

<400> SEQUENCE: 236

```
tcgagcggcc gcccgggcag gtcacttttg gtttttggtc atgttcggtt ggtcaaagat     60
aaaaactaag tttgagagat gaatgcaaag gaaaaaaata ttttccaaag tccatgtgaa    120
attgtctccc attttttgg cttttgaggg ggttcagttt gggttgcttg tctgtttccg    180
ggttgggggg aaagttggtt gggtgggagg gagccaggtt gggatggagg gagtttacag    240
gaagcagaca gggccaacgt cg                                             262
```

<210> SEQ ID NO 237
<211> LENGTH: 372
<212> TYPE: DNA
<213> ORGANISM: Homo sapiens

<400> SEQUENCE: 237

```
agcgtggtcg cggccgaggt cctcaccaga ggtgccacct acaacatcat agtggaggca     60
ctgaaagacc agcagaggca taaggttcgg gaagaggttg ttaccgtggg caactctgtc    120
aacgaaggct tgaaccaacc tacggatgac tcgtgctttg acccctacac agtttcccat    180
tatgccgttg gagatgagtg ggaacgaatg tctgaatcag gctttaaact gttgtgccag    240
tgcttaggct ttggaagtgg tcatttcaga tgtgattcat ctagatggtg ccatgacaat    300
ggtgtgaact acaagattgg agagaagtgg gaccgtcagg gagaaaatgg acctgcccgg    360
gcggccgctc ga                                                        372
```

<210> SEQ ID NO 238
<211> LENGTH: 372
<212> TYPE: DNA
<213> ORGANISM: Homo sapiens

<400> SEQUENCE: 238

```
tcgagcggcc gcccgggcag gtccattttc tccctgacgg tcccacttct ctccaatctt     60
gtagttcaca ccattgtcat ggcaccatct agatgaatca catctgaaat gaccacttcc    120
```

-continued

```
aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgcccacggt aacaacctct tcccgaacct tatgcctctg    300

ctggtctttc agtgcctcca ctatgatgtt gtaggtggca cctctggtga ggacctcggc    360

cgcgaccacg ct                                                        372
```

<210> SEQ ID NO 239
<211> LENGTH: 720
<212> TYPE: DNA
<213> ORGANISM: Homo sapiens
<220> FEATURE:
<221> NAME/KEY: misc_feature
<222> LOCATION: 478, 557, 563, 566, 620, 660, 663, 672, 673, 684, 693, 695
<223> OTHER INFORMATION: n = A,T,C or G

<400> SEQUENCE: 239

```
tcgagcggcc gcccgggcag gtccaccata agtcctgata caaccacgga tgagctgtca     60

ggagcaaggt tgatttcttt cattggtccg gtcttctcct tgggggtcac ccgcactcga    120

tatccagtga gctgaacatt gggtggtgtc cactgggcgc tcaggcttgt gggtgtgacc    180

tgagtgaact tcaggtcagt tggtgcagga atagtggtta ctgcagtctg aaccagaggc    240

tgactctctc cgcttggatt ctgagcatag acactaacca catactccac tgtgggctgc    300

aagccttcaa tagtcatttc tgtttgatct ggacctgcag ttttagtttt tgttggtcct    360

ggtccatttt tgggagtggt ggttactctg taaccagtaa caggggaact tgaaggcagc    420

cacttgacac taatgctgtt gtcctgaaca tcggtcactt gcatctggga tggtttgnca    480

atttctgttc ggtaattaat ggaaattggc ttgctgcttg cggggctgtc tccacggcca    540

gtgacagcat acacagngat ggnatnatca actccaagtt taaggccctg atggtaactt    600

taaacttgct cccagccagn gaacttccgg acagggtatt tcttctggtt ttccgaaagn    660

gancctggaa tnntctcctt gganccagaag gancntccaa aacttgggcc ggaacccctt    720
```

<210> SEQ ID NO 240
<211> LENGTH: 691
<212> TYPE: DNA
<213> ORGANISM: Homo sapiens
<220> FEATURE:
<221> NAME/KEY: misc_feature
<222> LOCATION: 564, 582, 640, 651, 666, 669, 690
<223> OTHER INFORMATION: n = A,T,C or G

<400> SEQUENCE: 240

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcagggg ctcgctcttc tgattattct    480

tcagggcaat gacataaatt gtatattcgg ttcccggttc caggccagta atagtagcct    540

cttgtgacac caggcggggc ccanggacca cttctctggg angagaccca gcttctcata    600
```

-continued cttgatgatg taacccggta atcctgcacg tggcggctgn catgatacca ncaaggaatt 660
gggtgnggng gacctgcccg gcggccctcn a 691

<210> SEQ ID NO 241
<211> LENGTH: 808
<212> TYPE: DNA
<213> ORGANISM: Homo sapiens
<220> FEATURE:
<221> NAME/KEY: misc_feature
<222> LOCATION: 680, 715, 721, 728, 735, 749, 757, 762, 772, 776, 779,
781, 792, 796, 800, 808
<223> OTHER INFORMATION: n = A,T,C or G

<400> SEQUENCE: 241
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
ggaccaggac caacaaaaac taaaactgca ggtccagatc aaacagaaat gactattgaa 420
ggcttgcagc ccacagtgga gtatgtggtt agtgtctatg ctcagaatcc aagcggagag 480
agtcagcctc tggttcagac tgcagtaacc actattcctg caccaactga cctgaagttc 540
actcaggtca cacccacaag cctgagccgc cagtggacac cacccaatgt tcactcactg 600
gatatcgagt gcgggtgacc cccaaggaga agacccggac ccatgaaaga aatcaacctt 660
gctcctgaca gctcatccgn gggtgtatca ggacttatgg gggactgccc cggcnggccg 720
ntcgaaancg aattntgaaa tttccttcnc actgggnggc gnttcgagct tncttntana 780
nggcccaatt cncctntagn gggtcgtn 808

<210> SEQ ID NO 242
<211> LENGTH: 26
<212> TYPE: DNA
<213> ORGANISM: Homo sapiens
<220> FEATURE:
<221> NAME/KEY: misc_feature
<222> LOCATION: 22
<223> OTHER INFORMATION: n = A,T,C or G

<400> SEQUENCE: 242
agcgtggtcg cggccgaggt cnagga 26

<210> SEQ ID NO 243
<211> LENGTH: 697
<212> TYPE: DNA
<213> ORGANISM: Homo sapiens
<220> FEATURE:
<221> NAME/KEY: misc_feature
<222> LOCATION: 496, 541, 624, 662, 679, 688
<223> OTHER INFORMATION: n = A,T,C or G

<400> SEQUENCE: 243
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240

-continued attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgaggaacat ggttttaggc ggaccacacc gcccacaacg 480
ggcaccccca taaggnatag gccaagacca taccccgccg aatgtaggac aagaagctct 540
ntctcaacaa ccatctcatg ggccccattc caggacactt ctgagtacat catttcatgt 600
catcctggtg ggcacttgat gaanaaccct tacagttcag ggttcctgga acttctacca 660
gngccacttc tgacagganc ttgggcgnga ccaccct 697

<210> SEQ ID NO 244
<211> LENGTH: 373
<212> TYPE: DNA
<213> ORGANISM: Homo sapiens

<400> SEQUENCE: 244
agcgtggtcg cggccgaggt ccattttctc cctgacggtc ccacttctct ccaatcttgt 60
agttcacacc attgtcatgg caccatctag atgaatcaca tctgaaatga ccacttccaa 120
agcctaagca ctggcacaac agtttaaagc ctgattcaga cattcgttcc cactcatctc 180
caacggcata atgggaaact gtgtaggggt caaagcacga gtcatccgta ggttggttca 240
agccttcgtt gacagagttg cccacggtaa caacctcttc ccgaacctta tgcctctgct 300
ggtctttcag tgcctccact atgatgttgt aggtggcacc tctggtgagg acctgcccgg 360
gcggcccgct cga 373

<210> SEQ ID NO 245
<211> LENGTH: 307
<212> TYPE: DNA
<213> ORGANISM: Homo sapiens

<400> SEQUENCE: 245
agcgtggtcg cggccgaggt gtgccccaga ccaggaattc ggcttcgacg ttggccctgt 60
ctgcttcctg taaactccct ccatcccaac ctggctccct cccacccaac caactttccc 120
cccaacccgg aaacagacaa gcaacccaaa ctgaaccccc tcaaaagcca aaaaaatggg 180
agacaatttc acatggactt tggaaaatat ttttttcctt tgcattcatc tctcaaactt 240
agtttttatc tttgaccaac cgaacatgac caaaaaccaa aagtgacctg cccgggcggc 300
cgctcga 307

<210> SEQ ID NO 246
<211> LENGTH: 372
<212> TYPE: DNA
<213> ORGANISM: Homo sapiens

<400> SEQUENCE: 246
tcgagcggcc gcccgggcag gtcctcacca gaggtgccac ctacaacatc atagtggagg 60
cactgaaaga ccagcagagg cataaggttc gggaagaggt tgttaccgtg ggcaactctg 120
tcaacgaagg cttgaaccaa cctacggatg actcgtgctt tgacccctac acagtttccc 180
attatgccgt tggagatgag tgggaacgaa tgtctgaatc aggctttaaa ctgttgtgcc 240
agtgcttagg ctttggaagt ggtcatttca gatgtgattc atctagatgg tgccatgaca 300
atggtgtgaa ctacaagatt ggagagaagt gggaccgtca gggagaaaat ggacctcggc 360

-continued cgcgaccacg ct 372

<210> SEQ ID NO 247
<211> LENGTH: 348
<212> TYPE: DNA
<213> ORGANISM: Homo sapiens
<220> FEATURE:
<221> NAME/KEY: misc_feature
<222> LOCATION: 284, 297, 299, 322, 325, 338, 342, 345
<223> OTHER INFORMATION: n = A,T,C or G

<400> SEQUENCE: 247
tcgagcggcc gcccgggcag gtaccggggt ggtcagcgag gagccattca cactgaactt 60
caccatcaac aacctgcggt atgaggagaa catgcagcac cctggctcca ggaagttcaa 120
caccacggag agggtccttc agggcctgct caggtccctg ttcaagagca ccagtgttgg 180
ccctctgtac tctggctgca gactgacttt gctcagacct gagaaacatg gggcagccac 240
tggagtggac gccatctgca ccctccgcct tgatcccact ggtnctggac tggacanana 300
gcggctatac ttgggagctg anccnaacct ttggcggnga cnccnctt 348

<210> SEQ ID NO 248
<211> LENGTH: 304
<212> TYPE: DNA
<213> ORGANISM: Homo sapiens
<220> FEATURE:
<221> NAME/KEY: misc_feature
<222> LOCATION: 125
<223> OTHER INFORMATION: n = A,T,C or G

<400> SEQUENCE: 248
gaggactggc tcagctccca gtatagccgc tctctgtcca gtccaggacc agtgggatca 60
aggcggaggg tgcagatggc gtccactcca gtggctgccc catgtttctc aagtctgagc 120
aaagncagtc tgcagccaga gtacagaggg ccaacactgg tgctcttgaa cagggacctg 180
agcaggccct gaaggaccct ctccgtggtg ttgaacttcc tggagccagg gtgctgcatg 240
ttctcctcat accgcaggtt gttgatggtg aagttcagtg tgaatggctc ctcgctgacc 300
accc 304

<210> SEQ ID NO 249
<211> LENGTH: 400
<212> TYPE: DNA
<213> ORGANISM: Homo sapiens
<220> FEATURE:
<221> NAME/KEY: misc_feature
<222> LOCATION: 308, 310, 312, 320, 331, 336, 383, 392, 396
<223> OTHER INFORMATION: n = A,T,C or G

<400> SEQUENCE: 249
agcgtggtcg cggccgaggt ccaccacacc caattccttg ctggtatcat ggcagccgcc 60
acgtgccagg attaccggct acatcatcaa gtatgagaag cctgggtctc ctcccagaga 120
agtggtccct cggccccgcc ctggtgtcac agaggctact attactggcc tggaaccggg 180
aaccgaatat acaatttatg tcattgccct gaagaataat cagaagagcg agcccctgat 240
tggaaggaaa aagacagacg agcttcccca actggtaacc cttccacacc ccaatcttca 300
tggaccanan ancttggatn gtcctttcac nggttnaaaa aaccctttc gcccccccac 360 cttggggatt aaccttggga aangggatt tnaccnttcc 400

<210> SEQ ID NO 250
<211> LENGTH: 400

-continued

```
<212> TYPE: DNA
<213> ORGANISM: Homo sapiens
<220> FEATURE:
<221> NAME/KEY: misc_feature
<222> LOCATION: 338, 357, 361, 369, 388, 394
<223> OTHER INFORMATION: n = A,T,C or G

<400> SEQUENCE: 250

tcgagcggcc gcccgggcag gtcctgtcag agtggcactg gtagaagttc caggaaccct     60

gaactgtaag ggttcttcat cagtgccaac aggatgacat gaaatgatgt actcagaagt    120

gtcctggaat ggggcccatg agatggttgt ctgagagaga gcttcttgtc ctacattcgg    180

cgggtatggt cttggcctat gccttatggg ggtggccgtt gtgggcggtg tggtccgcct    240

aaaaccatgt tcctcaaaga tcatttgttg cccaacactg ggttgctgac cagaagtgcc    300

aggaagctga ataccatttc cagtgtcata cccagggngg gtgaccaaag ggggtcnttt    360

ngacctggng aaaggaacca tccaaaanct ctgncccatg                          400


<210> SEQ ID NO 251
<211> LENGTH: 514
<212> TYPE: DNA
<213> ORGANISM: Homo sapiens
<220> FEATURE:
<221> NAME/KEY: misc_feature
<222> LOCATION: 8, 107, 312, 338, 351, 352, 357, 363, 366, 373, 380,
      405, 421, 444, 508
<223> OTHER INFORMATION: n = A,T,C or G

<400> SEQUENCE: 251

agcgtggncg cggccgaggt ctgaggatgt aaactcttcc caggggaagg ctgaagtgct     60

gaccatggtg ctactgggtc cttctgagtc agatatgtga ctgatgngaa ctgaagtagg    120

tactgtagat ggtgaagtct gggtgtccct aaatgctgca tctccagagc cttccatcat    180

taccgtttct tcttttgcta tgggatgaga cactgttgag tattctctaa agtcaccact    240

gaaatcttcc tccaaaggaa aacctgtgga aaagcccctt atttctgccc cataatttgg    300

ttctcctaat cnctctgaaa tcactatttc cctggaangt ttgggaaaaa nngggcnacc    360

tgncantgga aantggatan aaagatccca ccattttacc caacnagcag aaagtgggaa    420

nggtaccgaa aagctccaag taanaaaaag gagggaagta aaggtcaagt gggcaccagt    480

ttcaaacaaa actttcccca aactatanaa ccca                                514


<210> SEQ ID NO 252
<211> LENGTH: 501
<212> TYPE: DNA
<213> ORGANISM: Homo sapiens
<220> FEATURE:
<221> NAME/KEY: misc_feature
<222> LOCATION: 20, 21, 25, 44, 343, 347, 356, 362, 387, 391, 398, 409,
      428, 430, 453, 494
<223> OTHER INFORMATION: n = A,T,C or G

<400> SEQUENCE: 252

aagcggccgc ccgggcaggn ncagnagtgc cttcgggact gggntcaccc ccaggtctgc     60

ggcagttgtc acagcgccag ccccgctggc ctccaaagca tgtgcaggag caaatggcac    120

cgagatattc cttctgccac tgttctccta cgtggtatgt cttcccatca tcgtaacacg    180

ttgcctcatg agggtcacac ttgaattctc cttttccgtt cccaagacat gtgcagctca    240

tttggctggc tctatagttt ggggaaagtt tgttgaaact gtgccactga cctttacttc    300

ctccttctct actggagctt tccgtacctt ccacttctgc tgntggnaaa aagggnggaa    360
```

-continued

```
cntcttatca atttcattgg acagtanccc nctttctncc caaaacatnc aagggaaaat    420

attgattncn agagcggatt aaggaacaac ccnaattatg ggggccagaa ataaaggggg    480

cttttccaca ggtnttttcc t                                              501
```

<210> SEQ ID NO 253
<211> LENGTH: 226
<212> TYPE: DNA
<213> ORGANISM: Homo sapiens

<400> SEQUENCE: 253

```
tcgagcggcc gcccgggcag gtctgcaggc tattgtaagt gttctgagca catatgagat     60

aacctgggcc aagctatgat gttcgatacg ttaggtgtat taaatgcact tttgactgcc    120

atctcagtgg atgacagcct tctcactgac agcagagatc ttcctcactg tgccagtggg    180

caggagaaag agcatgctgc gactggacct cggccgcgac cacgct                   226
```

<210> SEQ ID NO 254
<211> LENGTH: 226
<212> TYPE: DNA
<213> ORGANISM: Homo sapiens

<400> SEQUENCE: 254

```
agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226
```

<210> SEQ ID NO 255
<211> LENGTH: 427
<212> TYPE: DNA
<213> ORGANISM: Homo sapiens
<220> FEATURE:
<221> NAME/KEY: misc_feature
<222> LOCATION: 327, 403
<223> OTHER INFORMATION: n = A,T,C or G

<400> SEQUENCE: 255

```
cgagcggccg cccgggcagg tccagactcc aatccagaga accaccaagc cagatgtcag     60

aagctacacc atcacaggtt tacaaccagg cactgactac aagatctacc tgtacacctt    120

gaatgacaat gctcggagct cccctgtggt catcgacgcc tccactgcca ttgatgcacc    180

atccaacctg cgtttcctgg ccaccacacc caattccttg ctggtatcat ggcagccgcc    240

acgtgccagg attaccggct acatcatcaa gtatgagaag cctgggtctc ctcccagaga    300

agtggtccct cggccccgcc ctggtgncac agaagctact attactggcc tggaaccggg    360

aaccgaatat acaatttatg tcattgccct gaagaataat canaagagcg agcccctgat    420

tggaagg                                                              427
```

<210> SEQ ID NO 256
<211> LENGTH: 535
<212> TYPE: DNA
<213> ORGANISM: Homo sapiens
<220> FEATURE:
<221> NAME/KEY: misc_feature
<222> LOCATION: 347, 456, 475
<223> OTHER INFORMATION: n = A,T,C or G

<400> SEQUENCE: 256

```
agcgtggtcg cggccgaggt cctgtcagag tggcactggt agaagttcca ggaaccctga     60
```

-continued

```
actgtaaggg ttcttcatca gtgccaacag gatgacatga aatgatgtac tcagaagtgt    120

cctggaatgg ggcccatgag atggttgtct gagagagagc ttcttgtcct gtctttttcc    180

ttccaatcag gggctcgctc ttctgattat tcttcagggc aatgacataa attgtatatt    240

cggttcccgg ttccaggcca gtaatagtag cctctgtgac accagggcgg ggccgaggga    300

ccacttctct gggaggagac ccaggcttct catacttgat gatgtanccg gtaatcctgg    360

caccgtggcg gctgccatga taccagcaag gaattgggtg tggtggccaa gaaacgcagg    420

ttggatggtg catcaatggc agtggaggcg tcgatnacca caggggagct ccgancattg    480

tcattcaagg tggacaggta gaatcttgta atcaggtgcc tggtttgtaa acctg         535
```

<210> SEQ ID NO 257
<211> LENGTH: 544
<212> TYPE: DNA
<213> ORGANISM: Homo sapiens
<220> FEATURE:
<221> NAME/KEY: misc_feature
<222> LOCATION: 495, 511
<223> OTHER INFORMATION: n = A,T,C or G

<400> SEQUENCE: 257

```
tcgagcggcc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtggcccaga agaactggta catcagcaag    300

aaccccaagg acaagaagca tgtctggttc ggcgaaagca tgaccgatgg attccagttc    360

gagtatggcg gccagggctc cgaccctgcc gatgtggacc tcggccgcga ccacgctaag    420

cccgaattcc agcacactgg cggccgttac tagtgggatc cgagcttcgg taccaagctt    480

ggcgtaatca tgggncatag ctgtttcctg ngtgaaaatg gtattccgct tcacaatttc    540

ccac                                                                 544
```

<210> SEQ ID NO 258
<211> LENGTH: 418
<212> TYPE: DNA
<213> ORGANISM: Homo sapiens

<400> SEQUENCE: 258

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaagctctt    360

gaagggtggt gtccacctcg aggtcacggt cacgaaacct gcccgggcgg ccgctcga      418
```

<210> SEQ ID NO 259
<211> LENGTH: 377
<212> TYPE: DNA
<213> ORGANISM: Homo sapiens
<220> FEATURE:
<221> NAME/KEY: misc_feature
<222> LOCATION: 320, 326, 342, 352

-continued

<223> OTHER INFORMATION: n = A,T,C or G

<400> SEQUENCE: 259
agcgtggtcg cggccgaggt caagaacccc gcccgcacct gccgtgacct caagatgtgc 60
cactctgact ggaagagtgg agagtactgg attgacccca accaaggctg caacctggat 120
gccatcaaag tcttctgcaa catggagact ggtgagacct gcgtgtaccc cactcagccc 180
agtgtggccc agaagaactg gtacatcagc aagaacccca aggacaagag gcatgtctgg 240
ttcggcgaga gcatgaccga tggattccag ttcgagtatg gcggccaggg ctccgaccct 300
gccgatgtgg acctgcccgn gccggnccgc tcgaaaagcc cnaatttcca gncacacttg 360
gccggccgtt actactg 377

<210> SEQ ID NO 260
<211> LENGTH: 332
<212> TYPE: DNA
<213> ORGANISM: Homo sapiens

<400> SEQUENCE: 260
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 261
<211> LENGTH: 94
<212> TYPE: DNA
<213> ORGANISM: Homo sapiens

<400> SEQUENCE: 261
cgagcggccg cccgggcagg tccccccct tttttttttt tttttttttt tttttttttt 60
tttttttttt tttttttttt tttttttttt tttt 94

<210> SEQ ID NO 262
<211> LENGTH: 650
<212> TYPE: DNA
<213> ORGANISM: Homo sapiens
<220> FEATURE:
<221> NAME/KEY: misc_feature
<222> LOCATION: 412, 582, 612, 641, 646
<223> OTHER INFORMATION: n = A,T,C or G

<400> SEQUENCE: 262
agcgtggtcg cggccgaggt ctggcattcc ttcgacttct ctccagccga gcttcccaga 60
acatcacata tcactgcaaa aatagcattg catacatgga tcaggccagt ggaaatgtaa 120
agaaggccct gaagctgatg gggtcaaatg aaggtgaatt caaggctgaa ggaaatagca 180
aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgctttttat 360
aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480
gtttggaaac agtataattt gacaaagaaa aaaggatact tctctttttt tggctggtcc 540
accaaataca attcaaaagg ctttttggtt ttattttttt anccaattcc aatttcaaaa 600
tgtctcaatg gngcttataa taaaataaac tttcaccctt nttttntgat 650

<210> SEQ ID NO 263
<211> LENGTH: 573
<212> TYPE: DNA
<213> ORGANISM: Homo sapiens
<220> FEATURE:
<221> NAME/KEY: misc_feature
<222> LOCATION: 453, 458, 544
<223> OTHER INFORMATION: n = A,T,C or G

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagaa gtaaccacca ctcccaaaaa 360
tggaccagga ccaacaaaaa ctaaaactgc aggtccagat caaacagaaa atggactatt 420
gaaggcttgc agcccacagt ggaagtatgt ggntaggngt ctatgctcag aatcccaagc 480
cggagaaagt cagccttctg gtttagactg cagtaaccaa cattgatcgc cctaaaggac 540
tggncattca cttggatggt ggatgtccaa ttc 573

<210> SEQ ID NO 264
<211> LENGTH: 550
<212> TYPE: DNA
<213> ORGANISM: Homo sapiens
<220> FEATURE:
<221> NAME/KEY: misc_feature
<222> LOCATION: 39, 174, 352, 526
<223> OTHER INFORMATION: n = A,T,C or G

<400> SEQUENCE: 264
tcgagcggcc gcccgggcag gtccttgcag ctctgcagng tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagngaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tggtggtcct gncccatttt 360
tgggaagtgg ggggttactc tgtaaccagt aacaggggaa cttgaaggca gccacttgac 420
actaatgctg ttgtcctgaa catcggtcac ttgcatctgg ggatggtttt gacaatttct 480
ggttcggcaa attaatggaa attggcttgc tgcttggcgg ggctgnctcc acgggccagt 540
gacagcatac 550

<210> SEQ ID NO 265
<211> LENGTH: 596
<212> TYPE: DNA
<213> ORGANISM: Homo sapiens
<220> FEATURE:
<221> NAME/KEY: misc_feature
<222> LOCATION: 347, 352, 353, 534, 555, 587
<223> OTHER INFORMATION: n = A,T,C or G -continued

<400> SEQUENCE: 265
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tgttggncct gnnccatttt 360
tggggaaggg gtggttactc ttgtaaccag taacagggga acttgaagca gccacttgac 420
actaatgctg gtggcctgaa catcggtcac ttgcatctgg gatggtttgg tcaatttctg 480
ttcggtaatt aatgggaaat tggcttactg gcttgcgggg gctgtctcca cggncagtga 540
caagcataca caggngatgg gtataatcaa ctccaggttt aaggccnctg atggta 596

<210> SEQ ID NO 266
<211> LENGTH: 506
<212> TYPE: DNA
<213> ORGANISM: Homo sapiens
<220> FEATURE:
<221> NAME/KEY: misc_feature
<222> LOCATION: 393, 473
<223> OTHER INFORMATION: n = A,T,C or G

<400> SEQUENCE: 266
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agtaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
gggaccagga ccaacaaaaa actaaaactg canggtccag atcaaacaga aatgactatt 420
gaaggcttgc agcccacagt ggagtatgtg ggttagtgtc tatgctcaga atnccaagcg 480
gagagagtca gcctctggtt cagact 506

<210> SEQ ID NO 267
<211> LENGTH: 548
<212> TYPE: DNA
<213> ORGANISM: Homo sapiens
<220> FEATURE:
<221> NAME/KEY: misc_feature
<222> LOCATION: 346, 358, 432, 510, 512
<223> OTHER INFORMATION: n = A,T,C or G

<400> SEQUENCE: 267
tcgagcggcc gcccgggcag gtcagcgctc tcaggacgtc accaccatgg cctgggctct 60
gctcctcctc accctcctca ctcagggcac agggtcctgg gcccagtctg ccctgactca 120
gcctccctcc gcgtccgggt ctcctggaca gtcagtcacc atctcctgca ctggaaccag 180
cagtgacgtt ggtgcttatg aatttgtctc ctggtaccaa caacacccag gcaaggcccc 240
caaactcatg atttctgagg tcactaagcg gccctcaggg gtccctgatc gcttctctgg 300
ctccaagtct ggcaacacgg cctccctgac cgtctctggg ctccangctg aggatgangc 360
tgattattac tggaagctca tatgcaggca acaacaattg ggtgttcggc ggaagggacc 420
aagctgaccg tnctaaggtc aagcccaagg cttgcccccc tcggtcactc tgttcccacc 480

-continued

```
ctcctctgaa gaagctttca agccaacaan gncacactgg gtgtgtctca taagtggact    540

ttctaccc                                                             548


<210> SEQ ID NO 268
<211> LENGTH: 584
<212> TYPE: DNA
<213> ORGANISM: Homo sapiens
<220> FEATURE:
<221> NAME/KEY: misc_feature
<222> LOCATION: 98, 380, 421, 454, 495, 506, 512, 561, 565, 579
<223> OTHER INFORMATION: n = A,T,C or G

<400> SEQUENCE: 268

agcgtggtcg cggccgaggt ctgtagcttc tgtgggactt ccactgctca ggcgtcaggc     60

tcaggtagct gctggccgcg tacttgttgt tgctttgntt ggagggtgtg gtggtctcca    120

ctcccgcctt gacggggctg ctatctgcct tccaggccac tgtcacggct cccgggtaga    180

agtcacttat gagacacacc agtgtggcct tgttggcttg aagctcctca gaggagggtg    240

ggaacagagt gaccgagggg gcagccttgg gctgacctag gacggtcagc ttggtccctc    300

cgccgaacac ccaattgttg ttgcctgcat atgagctgca gtaataatca gcctcatcct    360

cagcctggag cccagagacn gtcaagggag gcccgtgttt gccaagactt ggaagccaga    420

naagcgatca gggacccctg agggccgctt tacngacctc aaaaaatcat gaatttgggg    480

ggcctttgcc tgggngttgg ttggtnacca gnaaaacaaa atttcataaa gcaccaacgt    540

cactgctggt ttccagtgca ngaanatggt gaactgaant gtcc                     584


<210> SEQ ID NO 269
<211> LENGTH: 368
<212> TYPE: DNA
<213> ORGANISM: Homo sapiens
<220> FEATURE:
<221> NAME/KEY: misc_feature
<222> LOCATION: 265, 329
<223> OTHER INFORMATION: n = A,T,C or G

<400> SEQUENCE: 269

agcgtggtcg cggccgaggt ccagcatcag gagccccgcc ttgccggctc tggtcatcgc     60

ctttcttttt gtggcctgaa acgatgtcat caattcgcag tagcagaact gccgtctcca    120

ctgctgtctt ataagtctgc agcttcacag ccaatggctc ccatatgccc agttccttca    180

tgtccaccaa agtacccgtc tcaccattta caccccaggt ctcacagttc tcctgggtgt    240

gcttggcccg aagggaggta agtanacgga tggtgctggt cccacagttc tggatcaggg    300

tacgaggaat gacctctagg gcctgggcna caagccctgt atggacctgc ccgggcgggc    360

ccgctcga                                                             368


<210> SEQ ID NO 270
<211> LENGTH: 368
<212> TYPE: DNA
<213> ORGANISM: Homo sapiens
<220> FEATURE:
<221> NAME/KEY: misc_feature
<222> LOCATION: 54, 163, 219, 229, 316
<223> OTHER INFORMATION: n = A,T,C or G

<400> SEQUENCE: 270

tcgagcggcc gcccgggcag gtccatacag ggctgttgcc caggccctag aggncattcc     60

ttgtaccctg atccagaact gtgggaccag caccatccgt ctacttacct cccttcgggc    120
```

-continued

```
caagcacacc caggagaact gtgagacctg gggtgtaaat ggngagacgg gtactttggt    180

ggacatgaag gaactgggca tatgggagcc attggctgng aagctgcana cttataagac    240

agcagtggag acggcagttc tgctactgcg aattgatgac atcgtttcag gccacaaaaa    300

gaaaggcgat gaccanagcc ggcaaggcgg ggcttcctga tgctggacct cggccgccga    360

ccacgctt                                                              368
```

<210> SEQ ID NO 271
<211> LENGTH: 424
<212> TYPE: DNA
<213> ORGANISM: Homo sapiens
<220> FEATURE:
<221> NAME/KEY: misc_feature
<222> LOCATION: 279, 329, 362, 384, 400
<223> OTHER INFORMATION: n = A,T,C or G

<400> SEQUENCE: 271

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgggaaac tccgaggaca    180

gagggctaaa tccatgaagt ttgtggatgg cctgatgatc cacagcggag accctgttaa    240

ctactacgtt gacactgctg tgcgccacgt gttgctcana cagggtgtgc tgggcatcaa    300

ggtgaagatc atgctgccct gggacccanc tggcaaaaat ggcccttaaa aaccccttgc    360

cntgaccacg tgaaccattt gtgngaaccc caagatgaan atacttgccc accaccccc    420

attc                                                                  424
```

<210> SEQ ID NO 272
<211> LENGTH: 541
<212> TYPE: DNA
<213> ORGANISM: Homo sapiens
<220> FEATURE:
<221> NAME/KEY: misc_feature
<222> LOCATION: 422, 442, 510, 513, 515, 525
<223> OTHER INFORMATION: n = A,T,C or G

<400> SEQUENCE: 272

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120

tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacag cagtgtcaac gtagtagtta acagggtctc cgctgtggat    300

catcaggcca tccacaaact tcatggattt agccctctgt cctcggagtt tcccaaaaca    360

ccacaacctc gccagccttt gggccccact tcttcatgaa tgaaaccgca gcacaccatt    420

ancaaggccc ttccgcacag gnaagccctt cctaaggagt tttgtaaacg caaaaaactc    480

ttgcctgggg caaatgggca cacagacctn tantnggacc ttggnccgcg aaccaccgct    540

t                                                                     541
```

<210> SEQ ID NO 273
<211> LENGTH: 579
<212> TYPE: DNA
<213> ORGANISM: Homo sapiens
<220> FEATURE:
<221> NAME/KEY: misc_feature
<222> LOCATION: 223, 265, 277, 308, 329, 346, 360, 366, 429, 448, 517,
524, 531, 578

-continued

<223> OTHER INFORMATION: n = A,T,C or G

<400> SEQUENCE: 273
agcgtggtcg cggccgaggt ctggccctcc tggcaaggct ggtgaagatg gtcaccctgg 60
aaaacccgga cgacctggtg agagaggagt tgttggacca cagggtgctc gtggtttccc 120
tggaactcct ggacttcctg gcttcaaagg cattagggga cacaatggtc tggatggatt 180
gaagggacag cccggtgctc ctggtgtgaa gggtgaacct ggngcccctg gtgaaaatgg 240
aactccaggt caaacaggag cccgngggct tcctggngag agaggacgtg ttggtgcccc 300
tggcccanac ctgcccgggc ggccgctcna aaagccgaaa tccagnacac tggcggccgn 360
tactantgga atccgaactt cggtaccaaa gcttggccgt aatcatggcc atagcttgtt 420
ccctggggng gaaattggta ttccgctncc aattccacac aacataccga acccggaaag 480
cattaaagtg taaaagccct ggggggggcct aaatgangtg agcntaactc ncatttaatt 540
ggcgttgcgc ttcactgccc cgcttttcca gtccgggna 579

<210> SEQ ID NO 274
<211> LENGTH: 330
<212> TYPE: DNA
<213> ORGANISM: Homo sapiens
<220> FEATURE:
<221> NAME/KEY: misc_feature
<222> LOCATION: 171
<223> OTHER INFORMATION: n = A,T,C or G

<400> SEQUENCE: 274
tcgagcggcc gcccgggcag gtctgggcca ggggcaccaa cacgtcctct ctcaccagga 60
agcccacggg ctcctgtttg acctggagtt ccattttcac caggggcacc aggttcaccc 120
ttcacaccag gagcaccggg ctgtcccttc aatccatcca gaccattgtg nccccctaatg 180
cctttgaagc caggaagtcc aggagttcca gggaaaccac gagcaccctg tggtccaaca 240
actcctctct caccaggtcg tccgggtttt ccagggtgac catcttcacc agccttgcca 300
ggagggccag acctcggccg cgaccacgct 330

<210> SEQ ID NO 275
<211> LENGTH: 97
<212> TYPE: DNA
<213> ORGANISM: Homo sapiens
<220> FEATURE:
<221> NAME/KEY: misc_feature
<222> LOCATION: 2, 35, 72
<223> OTHER INFORMATION: n = A,T,C or G

<400> SEQUENCE: 275
ancgtggtcg cggccgaggt cctcaccaga ggtgncacct acaacatcat agtggaggca 60
ctgaaagacc ancagaggca taaggttcgg gaagagg 97

<210> SEQ ID NO 276
<211> LENGTH: 610
<212> TYPE: DNA
<213> ORGANISM: Homo sapiens
<220> FEATURE:
<221> NAME/KEY: misc_feature
<222> LOCATION: 358, 360, 363, 382, 424, 433, 464, 468, 477, 491, 499,
511, 558, 584, 588, 590
<223> OTHER INFORMATION: n = A,T,C or G

<400> SEQUENCE: 276
tcgagcggcc gcccgggcag gtccattttc tccctgacgg tcccacttct ctccaatctt 60

-continued

```
gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgtccacggt aacaacctct tcccgaacct tatgcctctg    300

ctggtctttc agtgcctcca ctatgatgtt gtaggtggca cctctggtga ggacctcngn    360

ccngaacaac gcttaagccc gnattctgca gaataatccc atcacacttg gcggccgctt    420

cgancatgca tcntaaaagg ggccccaatt tccccttat aagngaancc gtatttncca    480

atttcactgg ncccgccgnt tttacaaacg ncggtgaact ggggaaaaac cctggcggtt    540

acccaacttt aatcgccntt ggcagcacaa tccccccttt tcgnccancn tgggcgtaaa    600

taaccgaaaa                                                           610
```

<210> SEQ ID NO 277
<211> LENGTH: 38
<212> TYPE: DNA
<213> ORGANISM: Homo sapiens
<220> FEATURE:
<221> NAME/KEY: misc_feature
<222> LOCATION: 2, 5, 18, 21, 31
<223> OTHER INFORMATION: n = A,T,C or G

<400> SEQUENCE: 277

```
ancgnggtcg cggccgangt nttttttctt nttttttt                             38
```

<210> SEQ ID NO 278
<211> LENGTH: 443
<212> TYPE: DNA
<213> ORGANISM: Homo sapiens
<220> FEATURE:
<221> NAME/KEY: misc_feature
<222> LOCATION: 156, 212, 233, 245, 327, 331, 336, 361, 364, 381, 391,
397, 419, 437
<223> OTHER INFORMATION: n = A,T,C or G

<400> SEQUENCE: 278

```
agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgggnggtc agcgtcctca ccgtcctgca    180

ccagaattgg ttgaatggca aggagtacaa gngcaaggtt tccaacaaag ccntcccagc    240

ccccntcgaa aaaaccattt ccaaagccaa agggcagccc cgagaaccac aggtgtacac    300

cctgccccca tcccgggagg aaaagancaa naaccnggtt cagccttaac ttgcttggtc    360

naangctttt tatcccaacg nacttccccc ntggaantgg gaaaaaccaa tgggccaanc    420

cgaaaaacaa ttacaanaac ccc                                            443
```

<210> SEQ ID NO 279
<211> LENGTH: 348
<212> TYPE: DNA
<213> ORGANISM: Homo sapiens
<220> FEATURE:
<221> NAME/KEY: misc_feature
<222> LOCATION: 219, 256, 291, 297, 307, 314, 317
<223> OTHER INFORMATION: n = A,T,C or G

<400> SEQUENCE: 279

```
tcgagcggcc gcccgggcag gtgtcggagt ccagcacggg aggcgtggtc ttgtagttgt     60

tctccggctg cccattgctc tcccactcca cggcgatgtc gctgggatag aagcctttga    120
```

-continued

```
ccaggcaggt caggctgacc tggttcttgg tcatctcctc ccgggatggg ggcagggtga    180

acacctgggg ttctcggggc ttgccctttg gttttgaana tggttttctc gatgggggct    240

ggaagggctt tgttgnaaac cttgcacttg actccttgcc attcacccag ncctggngca    300

ggacggngag gacnctnacc acacggaacc gggctggtgg actgctcc                  348
```

```
<210> SEQ ID NO 280
<211> LENGTH: 149
<212> TYPE: DNA
<213> ORGANISM: Homo sapiens
<220> FEATURE:
<221> NAME/KEY: misc_feature
<222> LOCATION: 18, 34, 51, 118, 120, 140
<223> OTHER INFORMATION: n = A,T,C or G

<400> SEQUENCE: 280

agcgtggtcg cggacgangt cctgtcagag tggnactggt agaagttcca ngaaccctga     60

actgtaaggg ttcttcatca gtgccaacag gatgacatga aatgatgtac tcagaagngn    120

cctggaatgg ggcccatgan atggttgcc                                       149
```

```
<210> SEQ ID NO 281
<211> LENGTH: 404
<212> TYPE: DNA
<213> ORGANISM: Homo sapiens
<220> FEATURE:
<221> NAME/KEY: misc_feature
<222> LOCATION: 383, 386, 388, 393
<223> OTHER INFORMATION: n = A,T,C or G

<400> SEQUENCE: 281

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaagaata atcagaagag cgagcccctg    240

attggaagga aaaagacaga cgagcttccc caactggtaa cccttccaca ccccaatctt    300

catggaccag agatcttgga tgttccttcc acagttcaaa agaccccttt cggcaccccc    360

cctgggtatg aacctgggaa aanggnantt aanctttcct ggca                      404
```

```
<210> SEQ ID NO 282
<211> LENGTH: 507
<212> TYPE: DNA
<213> ORGANISM: Homo sapiens
<220> FEATURE:
<221> NAME/KEY: misc_feature
<222> LOCATION: 320, 341, 424, 450, 459, 487, 498
<223> OTHER INFORMATION: n = A,T,C or G

<400> SEQUENCE: 282

agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaaggtn ccctggtact gggttacaga ntaaccacca ctcccaaaaa    360

tggaccagga accacaaaaa cttaaactgc agggtccaga tcaaaacaga aatgactatt    420

gaangcttgc agcccacagt gggagtatgn gggtagtgnc tatgcttcag aatccaagcg    480
```

-continued gaaaaangtc aagccttntg ggttcaa 507

<210> SEQ ID NO 283
<211> LENGTH: 325
<212> TYPE: DNA
<213> ORGANISM: Homo sapiens
<220> FEATURE:
<221> NAME/KEY: misc_feature
<222> LOCATION: 216, 292, 303, 304
<223> OTHER INFORMATION: n = A,T,C or G

<400> SEQUENCE: 283
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagnctga accagaggct gactctctcc 240
gcttggattc tgagcataga cactaaccac atactccact gtgggctgca anccttcaat 300
aanncatttc tgtttgatct ggacc 325

<210> SEQ ID NO 284
<211> LENGTH: 331
<212> TYPE: DNA
<213> ORGANISM: Homo sapiens
<220> FEATURE:
<221> NAME/KEY: misc_feature
<222> LOCATION: 54, 59, 63, 121, 312, 327
<223> OTHER INFORMATION: n = A,T,C or G

<400> SEQUENCE: 284
tcgagcggcc gcccgggcag gtctggtggg gtcctggcac acgcacatgg gggngttgnt 60
ctnatccagc tgcccagccc ccattggcga gtttgagaag gtgtgcagca atgacaacaa 120
naccttcgac tcttcctgcc acttctttgc cacaaagtgc accctggagg gcaccaagaa 180
gggccacaag ctccacctgg actacatcgg gccttgcaaa tacatccccc cttgcctgga 240
ctctgagctg accgaattcc cccttgcgca tgcgggactg gctcaagaac cgtcctggca 300
cccttgtatg anagggatga agacacnacc c 331

<210> SEQ ID NO 285
<211> LENGTH: 509
<212> TYPE: DNA
<213> ORGANISM: Homo sapiens
<220> FEATURE:
<221> NAME/KEY: misc_feature
<222> LOCATION: 316, 319, 327, 329, 339, 344, 357, 384, 398, 427, 443, 450, 478
<223> OTHER INFORMATION: n = A,T,C or G

<400> SEQUENCE: 285
agcgtggtcg cggccgaggt ctgtcctaca gtcctcagga ctctactccc tcagcagcgt 60
ggtgaccgtg ccctccagca acttcggcac ccagacctac acctgcaacg tagatcacaa 120
gcccagcaac accaaggtgg acaagagagt tgagcccaaa tcttgtgaca aaactcacac 180
atgcccaccg tgcccagcac ctgaactcct ggggggaccg tcagtcttcc tcttcccccg 240
catccccctt ccaaacctgc ccgggcggcc gctcgaaagc cgaattccag cacactggcg 300
gccggtacta gtgganccna acttggnanc caacctggng gaantaatgg gcataanctg 360
tttctggggg gaaattggta tccngtttac aattcccnca caacatacga gccggaagca 420
taaaagngta aaagcctggg ggnggcctan tgaagtgaag ctaaactcac attaattngc 480

-continued gttgccgctc actggcccgc ttttccagc 509

<210> SEQ ID NO 286
<211> LENGTH: 336
<212> TYPE: DNA
<213> ORGANISM: Homo sapiens
<220> FEATURE:
<221> NAME/KEY: misc_feature
<222> LOCATION: 188, 251, 267
<223> OTHER INFORMATION: n = A,T,C or G

<400> SEQUENCE: 286
tcgagcggcc gcccgggcag gtttggaagg gggatgcggg ggaagaggaa gactgacggt 60
ccccccagga gttcaggtgc tgggcacggt gggcatgtgt gagttttgtc acaagatttg 120
ggctcaactc tcttgtccac cttggtgttg ctgggcttgt gatctacgtt gcaggtgtag 180
gtctgggngc cgaagttgct ggagggcacg gtcaccacgc tgctgaggga gtagagtcct 240
gaggactgta ngacagacct cggccgngac cacgctaagc cgaattctgc agatatccat 300
cacactggcg gccgctccga gcatgcattt tagagg 336

<210> SEQ ID NO 287
<211> LENGTH: 30
<212> TYPE: DNA
<213> ORGANISM: Homo sapiens
<220> FEATURE:
<221> NAME/KEY: misc_feature
<222> LOCATION: 8, 18
<223> OTHER INFORMATION: n = A,T,C or G

<400> SEQUENCE: 287
agcgtggncg cggacganga caacaacccc 30

<210> SEQ ID NO 288
<211> LENGTH: 316
<212> TYPE: DNA
<213> ORGANISM: Homo sapiens
<220> FEATURE:
<221> NAME/KEY: misc_feature
<222> LOCATION: 22, 130
<223> OTHER INFORMATION: n = A,T,C or G

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapiens
<220> FEATURE:
<221> NAME/KEY: misc_feature
<222> LOCATION: 36, 165, 191, 195, 218, 235
<223> OTHER INFORMATION: n = A,T,C or G

<400> SEQUENCE: 289
agcgtggtcg cggccgaggt ccagcctgga gataanggtg aaggtggtgc ccccggactt 60

-continued

```
ccaggtatag ctggacctcg tggtagccct ggtgagagag gtgaaactgg ccctccagga    120

cctgctggtt tccctggtgc tcctggacag aatggtgaac ctggnggtaa aggagaaaga    180

ggggctccgg ntganaaagg tgaaggaggc cctcctgnat tggcaggggc cccangactt    240

agaggtggag ctggcccccc tggccccgaa ggaggaaagg gtgctgctgg tcctcctggg    300

ccacctgg                                                             308
```

```
<210> SEQ ID NO 290
<211> LENGTH: 324
<212> TYPE: DNA
<213> ORGANISM: Homo sapiens
<220> FEATURE:
<221> NAME/KEY: misc_feature
<222> LOCATION: 184
<223> OTHER INFORMATION: n = A,T,C or G

<400> SEQUENCE: 290

tcgagcggcc gcccgggcag gtctgggcca ggaggaccaa taggaccagt aggacccctt     60

gggccatctt tccctgggac accatcagca cctggaccgc ctggttcacc cttgtcaccc    120

tttggaccag gacttccaag acctcctctt tctccaggca ttccttgcag accaggagta    180

ccancagcac caggtggccc aggaggacca gcagcaccct ttcctccttc gggaccaggg    240

ggaccagctc cacctctaag tcctggggcc cctgccaatc caggagggcc tccttcacct    300

ttctcacccg gagcccctct ttct                                           324
```

```
<210> SEQ ID NO 291
<211> LENGTH: 278
<212> TYPE: DNA
<213> ORGANISM: Homo sapiens
<220> FEATURE:
<221> NAME/KEY: misc_feature
<222> LOCATION: 249, 267
<223> OTHER INFORMATION: n = A,T,C or G

<400> SEQUENCE: 291

tcgagcggcc gcccgggcag gtccaccggg atattcgggg gtctggcagg aatgggaggc     60

atccagaacg agaaggagac catgcaaagc ctgaacgacc gcctggcctc ttacctggac    120

agagtgagga gcctggagac cgacaaccgg aggctggaga gcaaaatccg ggagcacttg    180

gagaagaagg gaccccaggt cagagactgg agccattact tcaagatcat cgaggacctg    240

agggctcana tcttcgcaaa tactgcngac aatgcccg                             278
```

```
<210> SEQ ID NO 292
<211> LENGTH: 299
<212> TYPE: DNA
<213> ORGANISM: Homo sapiens
<220> FEATURE:
<221> NAME/KEY: misc_feature
<222> LOCATION: 6, 19, 25, 51, 53, 61, 63, 70, 109, 136, 157, 241,
      276
<223> OTHER INFORMATION: n = A,T,C or G

<400> SEQUENCE: 292

atgcgnggtc gcggccgang accanctctg gctcatactt gactctaaag ncntcaccag     60

nanttacggn cattgccaat ctgcagaacg atgcgggcat tgtccgcant atttgcgaag    120

atctgagccc tcaggncctc gatgatcttg aagtaanggc tccagtctct gacctggggt    180

cccttcttct ccaagtgctc ccggattttg ctctccagcc tccggttctc ggtctccaag    240

ncttctcact ctgtccagga aaagaggcca ggcggncgat cagggctttt gcatggact     299
```

-continued

<210> SEQ ID NO 293
<211> LENGTH: 101
<212> TYPE: DNA
<213> ORGANISM: Homo sapiens

<400> SEQUENCE: 293
agcgtggtcg cggccgaggt tgtacaagct tttttttttt tttttttttt tttttttttt 60
tttttttttt tttttttttt tttttttttt tttttttttt t 101

<210> SEQ ID NO 294
<211> LENGTH: 285
<212> TYPE: DNA
<213> ORGANISM: Homo sapiens
<220> FEATURE:
<221> NAME/KEY: misc_feature
<222> LOCATION: 64, 103, 110, 237, 282
<223> OTHER INFORMATION: n = A,T,C or G

<400> SEQUENCE: 294
tcgagcggcc gcccgggcag gtctgccaac accaagattg gccccgccg catccacaca 60 gttngtgtgc ggggaggtaa caagaaatac cgtgccctga ggntggacgn ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatngac 240
agcacaccgt accgacagtg ggtaccgaag tcccactatg cncct 285

<210> SEQ ID NO 295
<211> LENGTH: 216
<212> TYPE: DNA
<213> ORGANISM: Homo sapiens

<400> SEQUENCE: 295
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaag 216

<210> SEQ ID NO 296
<211> LENGTH: 414
<212> TYPE: DNA
<213> ORGANISM: Homo sapiens
<220> FEATURE:
<221> NAME/KEY: misc_feature
<222> LOCATION: 7, 10, 33, 61, 62, 63, 88, 109, 122, 255, 298, 307,
340, 355, 386, 393
<223> OTHER INFORMATION: n = A,T,C or G

<400> SEQUENCE: 296
agcgtgntcn cggccgagga tggggaagct cgnctgtctt tttccttcca atcaggggct 60
nnntcttctg attattcttc agggcaanga cataaattgt atattcggnt cccggttcca 120
gnccagtaat agtagcctct gtgacaccag ggcggggccg agggaccact tctctgggag 180
gagacccagg cttctcatac ttgatgatga agccggtaat cctggcacgt gggcggctgc 240
catgatacca ccaangaatt gggtgtggtg gacctgcccg ggcgggccgc tcgaaaancc 300
gaattcntgc aagaatatcc atcacacttg ggcgggccgn tcgaaccatg catcntaaaa 360
gggccccaat ttcccccta ttaggngaag ccncatttaa caaattccac ttgg 414

<210> SEQ ID NO 297

-continued

<211> LENGTH: 376
<212> TYPE: DNA
<213> ORGANISM: Homo sapiens
<220> FEATURE:
<221> NAME/KEY: misc_feature
<222> LOCATION: 312, 326, 335, 361
<223> OTHER INFORMATION: n = A,T,C or G

<400> SEQUENCE: 297
tcgagcggcc gcccgggcag gtctcgcggt cgcactggtg atgctggtcc tgttggtccc 60
cccggccctc ctggacctcc tggtccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagccttgag 240
ccagcagaat cgaaaacatt cggaacccaa gaagggcaag cccgcaaaga aaccccgccc 300
gcacctggcc gngaacctcc aagaangtgc ccacntcttg actgggaaaa aaagggaaaa 360
ntacttggaa ttggac 376

<210> SEQ ID NO 298
<211> LENGTH: 357
<212> TYPE: DNA
<213> ORGANISM: Homo sapiens
<220> FEATURE:
<221> NAME/KEY: misc_feature
<222> LOCATION: 345, 346
<223> OTHER INFORMATION: n = A,T,C or G

<400> SEQUENCE: 298
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagaagt ggcacatctt gaggtcacgg cagggtgcgg 300
gcggggttct tgcgggctgc ccttctgggc tcccggaatg ttctnngaac ttgctgg 357

<210> SEQ ID NO 299
<211> LENGTH: 307
<212> TYPE: DNA
<213> ORGANISM: Homo sapiens
<220> FEATURE:
<221> NAME/KEY: misc_feature
<222> LOCATION: 281, 285, 306
<223> OTHER INFORMATION: n = A,T,C or G

<400> SEQUENCE: 299
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgggaaac tccgaggaca 180
gagggctaaa tccatgaagt ttgtggatgg cctgatgatc cacagcggag accctgttaa 240
ctactacgtt gacacttgct tgtgcgccac gtgttgctca nacangggtg ggctgggcat 300 caaggng 307

<210> SEQ ID NO 300
<211> LENGTH: 351
<212> TYPE: DNA
<213> ORGANISM: Homo sapiens

<400> SEQUENCE: 300

-continued

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120

tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacag caagtgtcaa cgtaagtaag ttaacagggt ctccgctgtg    300

gatcatcagg ccatccacaa acttcatgga tttaaccctc tgtcctcgga g             351
```

```
<210> SEQ ID NO 301
<211> LENGTH: 330
<212> TYPE: DNA
<213> ORGANISM: Homo sapiens

<400> SEQUENCE: 301

tcgagcggcc gcccgggcag gtgtttcaga ggttccaagg tccactgtgg aggtcccagg     60

agtgctggtg gtgggcacag aggtccgatg ggtgaaacca ttgacataga gactgttcct    120

gtccagggtg taggggccca gctctttgat gccattggcc agttggctca gctcccagta    180

cagccgctct ctgttgagtc cagggctttt ggggtcaaga tgatggatgc agatggcatc    240

cactccagtg gctgctccat ccttctcgga cctgagagag gtcagtctgc agccagagta    300

cagagggcca acactggtgt tctttgaata                                     330
```

```
<210> SEQ ID NO 302
<211> LENGTH: 317
<212> TYPE: DNA
<213> ORGANISM: Homo sapiens
<220> FEATURE:
<221> NAME/KEY: misc_feature
<222> LOCATION: 129, 295
<223> OTHER INFORMATION: n = A,T,C or G

<400> SEQUENCE: 302

agcgtggtcg cggccgaggt ctgtactggg agctaagcaa actgaccaat gacattgaag     60

agctgggccc ctacaccctg gacaggaaca gtctctatgt caatggtttc acccatcaga    120

gctctgtgnc caccaccagc actcctggga cctccacagt ggatttcaga acctcaggga    180

ctccatcctc cctctccagc cccacaatta tggctgctgg ccctctcctg gtaccattca    240

ccctcaactt caccatcacc aacctgcagt atggggagga catgggtcac cctgnctcca    300

ggaagttcaa caccaca                                                   317
```

```
<210> SEQ ID NO 303
<211> LENGTH: 283
<212> TYPE: DNA
<213> ORGANISM: Homo sapiens
<220> FEATURE:
<221> NAME/KEY: misc_feature
<222> LOCATION: 139, 146, 195
<223> OTHER INFORMATION: n = A,T,C or G

<400> SEQUENCE: 303

tcgagcggcc gcccggacag gtctgggcgg atagcaccgg gcatattttg gaatggatga     60

ggtctggcac cctgagcagt ccagcgagga cttggtctta gttgagcaat ttggctagga    120

ggatagtatg cagcacggnt ctgagnctgt gggatagctg ccatgaagta acctgaagga    180

ggtgctggct ggtangggtt gattacaggg ttgggaacag ctcgtacact tgccattctc    240

tgcatatact ggttagtgag gtgagcctgg ccctcttctt ttg                      283
```

<210> SEQ ID NO 304
<211> LENGTH: 72
<212> TYPE: DNA
<213> ORGANISM: Homo sapiens
<220> FEATURE:
<221> NAME/KEY: misc_feature
<222> LOCATION: 59
<223> OTHER INFORMATION: n = A,T,C or G

<400> SEQUENCE: 304
agcgtggtcg cggccgaggt gagccacagg tgaccggggc tgaagctggg gctgctggnc 60
ctgctggtcc tg 72

<210> SEQ ID NO 305
<211> LENGTH: 245
<212> TYPE: DNA
<213> ORGANISM: Homo sapiens
<220> FEATURE:
<221> NAME/KEY: misc_feature
<222> LOCATION: 5, 11, 22, 98, 102
<223> OTHER INFORMATION: n = A,T,C or G

<400> SEQUENCE: 305
cagcngctcc nacggggcct gngggaccaa caacaccgtt ttcaccctta ggccctttgg 60
ctcctctttc tcctttagca ccaggttgac cagcagcncc ancaggacca gcaaatccat 120
tggggccagc aggaccgacc tcaccacgtt caccagggct tccccgagga ccagcaggac 180
cagcaggacc agcagcccca gcttcgcccc ggtcacctgt ggctcacctc ggccgcgacc 240
acgct 245

<210> SEQ ID NO 306
<211> LENGTH: 246
<212> TYPE: DNA
<213> ORGANISM: Homo sapiens
<220> FEATURE:
<221> NAME/KEY: misc_feature
<222> LOCATION: 144, 159
<223> OTHER INFORMATION: n = A,T,C or G

<400> SEQUENCE: 306
tcgagcggtc gcccgggcag gtccaccggg atagccgggg gtctggcagg aatgggaggc 60
atccagaacg agaaggagac catgcaaagc ctgaacgacc gcctggcctc ttacctggac 120
agagtgagga gcctggagac cganaaccgg aggctggana gcaaaatccg ggagcacttg 180
gagaagaagg gaccccaggt caagagactg gagccattac ttcaagatca tcgagggacc 240
tggagg 246

<210> SEQ ID NO 307
<211> LENGTH: 333
<212> TYPE: DNA
<213> ORGANISM: Homo sapiens
<220> FEATURE:
<221> NAME/KEY: misc_feature
<222> LOCATION: 5
<223> OTHER INFORMATION: n = A,T,C or G

<400> SEQUENCE: 307
agcgnggtcg cggccgaggt ccagctctgt ctcatacttg actctaaagt catcagcagc 60
aagacgggca ttgtcaatct gcagaacgat gcgggcattg tccgcagtat ttgcgaagat 120
ctgagccctc aggtcctcga tgatcttgaa gtaatggctc cagtctctga cctggggtcc 180

-continued

```
cttcttctcc aagtgctccc ggattttgct ctccagcctc cggttctcgg tctccaggct    240

cctcactctg tccaggtaag aaggcccagg cggtcgttca ggctttgcat ggtctccttc    300

tcgttctgga tgcctcccat tcctgccaga ccc                                 333


<210> SEQ ID NO 308
<211> LENGTH: 310
<212> TYPE: DNA
<213> ORGANISM: Homo sapiens

<400> SEQUENCE: 308

tcgagcggcc gcccgggcag gtcaggaagc acattggtct tagagccact gcctcctgga     60

ttccacctgt gctgcggaca tctccaggga gtgcagaagg gaagcaggtc aaactgctca    120

gatcagtcag actggctgtt ctcagttctc acctgagcaa ggtcagtctg cagccagagt    180

acagagggcc aacactggtg ttcttgaaca agggcttgag cagaccctgc agaaccctct    240

tccgtggtgt tgaacttcct ggaaaccagg gtgttgcatg tttttcctca taatgcaagg    300

ttggtgatgg                                                           310

<210> SEQ ID NO 309
<211> LENGTH: 429
<212> TYPE: DNA
<213> ORGANISM: Homo sapiens

<400> SEQUENCE: 309

agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacaccg caggtctcac    180

cagtctccat gttgcagaag actttgatgg catccaggtt gcagccttgg ttggggtcaa    240

tccagtactc tccactcttc cagtcagaag tgggcacatc ttgaggtcac cggcaggtgc    300

cgggccgggg gttcttgcgg cttgccctct gggctccgga tgttctcgat ctgcttggct    360

caggctcttg agggtgggtg tccacctcga ggtcacggtc accgaaacct gcccgggcgg    420

cccgctcga                                                            429


<210> SEQ ID NO 310
<211> LENGTH: 430
<212> TYPE: DNA
<213> ORGANISM: Homo sapiens
<220> FEATURE:
<221> NAME/KEY: misc_feature
<222> LOCATION: 342
<223> OTHER INFORMATION: n = A,T,C or G

<400> SEQUENCE: 310

tcgagcggtc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtgggcccag aagaaactgg tacatcagca    300

aggaacccca aggacaagag gcattgtctt ggttcggcga gnagcatgac ccgatggatt    360

ccagtttcga gtattggcgg ccagggcttc ccgacccttg ccgatgtgga cctcggccgc    420

gaccaccgct                                                           430


<210> SEQ ID NO 311
```

-continued

<211> LENGTH: 2996
<212> TYPE: DNA
<213> ORGANISM: Homo sapiens

<400> SEQUENCE: 311
cagccaccgg agtggatgcc atctgcaccc accgccctga ccccacaggc cctgggctgg 60
acagagagca gctgtatttg gagctgagcc agctgaccca cagcatcact gagctgggcc 120
cctacaccct ggacagggac agtctctatg tcaatggttt cacacagcgg agctctgtgc 180
ccaccactag cattcctggg acccccacag tggacctggg aacatctggg actccagttt 240
ctaaacctgg tccctcggct gccagccctc tcctggtgct attcactctc aacttcacca 300
tcaccaacct gcggtatgag gagaacatgc agcaccctgg ctccaggaag ttcaacacca 360
cggagagggt ccttcagggc ctggtccctg ttcaagagca ccagtgttgg ccctctgtac 420
tctggctgca gactgacttt gctcaggcct gaaaaggatg ggacagccac tggagtggat 480
gccatctgca cccaccaccc tgaccccaaa agccctaggc tggacagaga gcagctgtat 540
tgggagctga gccagctgac ccacaatatc actgagctgg gcccctatgc cctggacaac 600
gacagcctct ttgtcaatgg tttcactcat cggagctctg tgtccaccac cagcactcct 660
gggaccccca cagtgtatct gggagcatct aagactccag cctcgatatt tggcccttca 720
gctgccagcc atctcctgat actattcacc ctcaacttca ccatcactaa cctgcggtat 780
gaggagaaca tgtggcctgg ctccaggaag ttcaacacta cagagagggt ccttcagggc 840
ctgctaaggc ccttgttcaa gaacaccagt gttggccctc tgtactctgg ctgcaggctg 900
accttgctca ggccagagaa agatggggaa gccaccggag tggatgccat ctgcacccac 960
cgccctgacc ccacaggccc tgggctggac agagagcagc tgtatttgga gctgagccag 1020
ctgacccaca gcatcactga gctgggcccc tacacactgg acagggacag tctctatgtc 1080
aatggtttca cccatcggag ctctgtaccc accaccagca ccggggtggt cagcgaggag 1140
ccattcacac tgaacttcac catcaacaac ctgcgctaca tggcggacat gggccaaccc 1200
ggctccctca agttcaacat cacagacaac gtcatgaagc acctgctcag tcctttgttc 1260
cagaggagca gcctgggtgc acggtacaca ggctgcaggg tcatcgcact aaggtctgtg 1320
aagaacggtg ctgagacacg ggtggacctc ctctgcacct acctgcagcc cctcagcggc 1380
ccaggtctgc ctatcaagca ggtgttccat gagctgagcc agcagaccca tggcatcacc 1440
cggctgggcc cctactctct ggacaaagac agcctctacc ttaacggtta caatgaacct 1500
ggtccagatg agcctcctac aactcccaag ccagccacca cattcctgcc tcctctgtca 1560
gaagccacaa cagccatggg gtaccacctg aagaccctca cactcaactt caccatctcc 1620
aatctccagt attcaccaga tatgggcaag ggctcagcta cattcaactc caccgagggg 1680
gtccttcagc acctgctcag acccttgttc cagaagagca gcatgggccc cttctacttg 1740
ggttgccaac tgatctccct caggcctgag aaggatgggg cagccactgg tgtggacacc 1800
acctgcacct accaccctga ccctgtgggc cccgggctgg acatacagca gctttactgg 1860
gagctgagtc agctgaccca tggtgtcacc caactgggct tctatgtcct ggacagggat 1920
agcctcttca tcaatggcta tgcaccccag aatttatcaa tccggggcga gtaccagata 1980
aatttccaca ttgtcaactg gaacctcagt aatccagacc ccacatcctc agagtacatc 2040
accctgctga gggacatcca ggacaaggtc accacactct acaaaggcag tcaactacat 2100
gacacattcc gcttctgcct ggtcaccaac ttgacgatgg actccgtgtt ggtcactgtc 2260
aaggcattgt tctcctccaa tttggacccc agcctggtgg agcaagtctt tctagataag 2220

-continued

```
accctgaatg cctcattcca ttggctgggc tccacctacc agttggtgga catccatgtg   2280

acagaaatgg agtcatcagt ttatcaacca acaagcagct ccagcaccca gcacttctac   2340

ctgaatttca ccatcaccaa cctaccatat tcccaggaca aagcccagcc aggcaccacc   2400

aattaccaga ggaacaaaag gaatattgag gatgcgctca accaactctt ccgaaacagc   2460

agcatcaaga gttatttttc tgactgtcaa gtttcaacat tcaggtctgt ccccaacagg   2520

caccacaccg gggtggactc cctgtgtaac ttctcgccac tggctcggag agtagacaga   2580

gttgccatct atgaggaatt tctgcggatg acccggaatg gtacccagct gcagaacttc   2640

accctggaca ggagcagtgt ccttgtggat gggtattttc ccaacagaaa tgagccctta   2700

actgggaatt ctgaccttcc cttctgggct gtcatcctca tcggcttggc aggactcctg   2760

ggactcatca catgcctgat ctgcggtgtc ctggtgacca cccgccggcg gaagaaggaa   2820

ggagaataca acgtccagca acagtgccca ggctactacc agtcacacct agacctggag   2880

gatctgcaat gactggaact tgccggtgcc tggggtgcct ttcccccagc cagggtccaa   2940

agaagcttgg ctggggcaga aataaaccat attggtcgga cacaaaaaaa aaaaaa       2996
```

```
<210> SEQ ID NO 312
<211> LENGTH: 914
<212> TYPE: PRT
<213> ORGANISM: Homo sapiens

<400> SEQUENCE: 312

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240
```

-continued

```
Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655
```

-continued

```
Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
    770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
    850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln
```

<210> SEQ ID NO 313
<211> LENGTH: 656
<212> TYPE: DNA
<213> ORGANISM: Homo sapiens

<400> SEQUENCE: 313

```
acagccagtc ggagctgcaa gtgttctggg tggatcgcgy atatgcactc aaaatgctct     60

ttgtaaagga aagccacaac atgtccaagg gacctgaggc gacttggagg ctgagcaaag    120

tgcagtttgt ctacgactcc tcggagaaaa cccacttcaa agacgcagtc agtgctggga    180

agcacacagc caactcgcac cacctctctg ccttggtcac ccccgctggg aagtcctatg    240

agtgtcaagc tcaacaaacc atttcactgg cctctagtga tccgcagaag acggtcacca    300

tgatcctgtc tgcggtccac atccaacctt ttgacattat ctcagatttt gtcttcagtg    360

aagagcataa atgcccagtg gatgagcggg agcaactgga agaaaccttg cccctgattt    420

tggggctcat cttgggcctc gtcatcatgg taacactcgc gatttaccac gtccaccaca    480

aaatgactgc caaccaggtg cagatccctc gggacagatc ccagtataag cacatgggct    540

agaggccgtt aggcaggcac cccctattcc tgctccccca actggatcag gtagaacaac    600

aaaagcactt ttccatcttg tacacgagat acaccaacat agctacaatc aaacag        656
```

-continued

<210> SEQ ID NO 314
<211> LENGTH: 519
<212> TYPE: DNA
<213> ORGANISM: Homo sapiens

<400> SEQUENCE: 314
tgtgcgtgga ccagtcagct tccgggtgtg actggagcag ggcttgtcgt cttcttcaga 60
gtcactttgc aggggttggt gaagctgctc ccatccatgt acagctccca gtctactgat 120
gtttaaggat ggtctcggtg gttaggccca ctagaataaa ctgagtccaa tacctctaca 180
cagttatgtt taactgggct ctctgacacc gggaggaagg tggcggggtt taggtgttgc 240
aaacttcaat ggttatgcgg ggatgttcac agagcaagct ttggtatcta gctagtctag 300
cattcattag ctaatggtgt cctttggtat ttattaaaat caccacagca taggggggact 360 ttatgtttag gttttgtcta agagttagct tatctgcttc ttgtgctaac agggctattg 420
ctaccaggga ctttggacat gggggccagc gtttggaaac ctcatctagt ttttttgaga 480
gataggccac tggccttgga cctcggccgc gaccacgct 519

<210> SEQ ID NO 315
<211> LENGTH: 441
<212> TYPE: DNA
<213> ORGANISM: Homo sapiens

<400> SEQUENCE: 315
cacagagcgt ttattgacac caccactcct gaaaattggg atttcttatt aggttcccct 60
aaaagttccc atgttgatta catgtaaata gtcacatata tacaatgaag gcagtttctt 120
cagaggcaac cagggtttat agtgctaggt aaatgtcatc tcttttgtgc tactgactca 180
ttgtcaaacg tctctgcact gttttcagcc tctccacgtt gcctctgtcc tgcttcttag 240
ttccttcttt gtgacaaacc aaaagaataa gaggatttag aacaggactg cttttcccct 300
atgatttaaa aattccaatg actttcgccc ttgggagaaa tttccaagga aatctctctc 360
gctcgctctc tccgttttcc tttgtgagct tctgggggag ggttagtggt gactttttga 420
tacgaaaaaa tgcattttgt g 441

<210> SEQ ID NO 316
<211> LENGTH: 247
<212> TYPE: DNA
<213> ORGANISM: Homo sapiens

<400> SEQUENCE: 316
tggcgcggct gctggatttc accttcttgc acctgccggt gagcgcctgg ggtctaaagg 60
ggcgggatac tccattatgg cccctcgccc tgtagggctg gaatagttag aaaaggcaac 120
ccagtctagc ttggtaagaa gagagacatg cccccaacct cggcgccctt tttcctcacg 180
atctgctgtc cttacttcag cgactgcagg agcttcacct gcaagaaaac agcattgagc 240
tgctgac 247

<210> SEQ ID NO 317
<211> LENGTH: 409
<212> TYPE: DNA
<213> ORGANISM: Homo sapiens

<400> SEQUENCE: 317
tgacagggct cctggagttg ttaagtcacc aagtagctgc aggggatgga cactgcccca 60

-continued

```
cacgatgtgg gatgaacagc agccttggtt tgtagcccag ggtgtccatg gatttgaccc    120

gaatgctccc tggaggccct gtggcgagga caggcactgg atggtccaga ccctctggct    180

ggaggagtgg tggagccagg actgggcctt cagccatgag ggctagaata acctgacctc    240

ttgcattcta acactgggtc attaatgaca cctttccagt ggatgttgca aaaaccaaca    300

ctgtcaggaa cctggccctg ggagggctca ggtgagctca caaggagagg tcaagccaag    360

ccaaagggta ggkaacacac aacaccaggg gaaaccagcc cccaaacca                409
```

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: 6, 17, 24, 271
<223> OTHER INFORMATION: n = A,T,C or G

<400> SEQUENCE: 318

```
caaggnagat cttaagnggg gtcntatgta agtgtgctcc tggctccagg gttcctggag     60

cctcacgagg tcaggggaac ccttgtagaa ctccaccagc agcatcatct cgtgaaggat    120

gtcattggtc aggaagctgt cctggacgta ggccatctcc acatccatgg ggatgccata    180

gtcactgggc ctttgctcgg gaggaggcat cacccagaaa ggcgagatct tggactcggg    240

gcctgggttg ccagaatagt aaggggagca nagcagggcg aggcagggct ggaagccatt    300

gctggagccc tgcagccgca                                                320
```

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: 172
<223> OTHER INFORMATION: n = A,T,C or G

<400> SEQUENCE: 319

```
tgaagcaata gcgcccccat tttacaggcg gagcatggaa gccagagagg tgggtggggg     60

agggggtcct tccctggctc aggcagatgg gaagatgagg aagccgctga agacgctgtc    120

ggcctcagag ccctggtaaa tgtgaccctt tttggggtct ttttcaaccc anacctggtc    180

accctgctgc agacctcggc cgcgaccacg ct                                  212
```

<210> SEQ ID NO 320
<211> LENGTH: 769
<212> TYPE: DNA
<213> ORGANISM: Homo sapiens

<400> SEQUENCE: 320

```
tggaggtgta gcagtgagag gagatytcag gcaagagtgt cacagcagag ccctaaascc     60

tccaactcac cagtgagaga tgagactgcc cagtactcag ccttcatctc ctgggccacc    120

tggagggcgt ctttctccat cagcgcatac tgagcagggg tactcagatc cttcttggaa    180

cctacaagga agagaagcac actggaaggg tcattctcct tcagggcatc ggccagccac    240

tgcctgccat gggaggtgga aagtaaggga tgagtgagtc tgcagggccc ctcccactga    300

cattcatagg cccaattacc ccctctctgg tcctacatgc attcttcttc ttcctgacca    360

cccctctgtt ctgaaccctc tcttcccgga gcctcccatt atattgcagg atgctcactt    420

acttggtatg ttccagagat gccacatcat tcaggttgaa gacaatgatg atggcttgga    480
```

-continued agagtggcag aaacagcccc aggttgacag ggaagacact actgctcatt tccccaatcc 540
ttccagctcc atatgagaaa gccatgtgca ctctgagacc cacctacccc acttcaccca 600
gccccttacc ttgagctcct ctatagtagg ttgatgcaat gcatttgaac ctctcctgcc 660
cagcggtatc ccaactggaa ggaaggaaga gtgaagcaca ggtatgtatc ttgggggtg 720 tgggtgctgg ggagaaggga tagctggaag gggtgtggaa gcactcaca 769

<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: 633, 666
<223> OTHER INFORMATION: n = A,T,C or G

<400> SEQUENCE: 321
tgggctgtgg gcggcacctg tgctctgcag gccagacagc gatagaagcc tttgtctgtg 60
cctactcccc cggaggcaac tgggaggtca acgggaagac aatcatcccc tataagaagg 120
gtgcctggtg ttcgctctgc acagccagtg tctcaggctg cttcaaagcc tgggaccatg 180 cagggggct ctgtgaggtc cccaggaatc cttgtcgcat gagctgccag aaccatggac 240
gtctcaacat cagcacctgc cactgccact gtccccctgg ctacacgggc agatactgcc 300
aagtgaggtg cagcctgcag tgtgtgcacg gccggttccg ggaggaggag tgctcgtgcg 360
tctgtgacat cggctacggg ggagcccagt gtgccaccaa ggtgcatttt cccttccaca 420
cctgtgacct gaggatcgac ggagactgct tcatggtgtc ttcagaggca gacacctatt 480
acagaagcca ggatgaaatg tcagaggaat ggcggggtgc tggcccagat caagagccag 540
aaagtgcagg acatcctcgc cttctatctg ggccgcctgg agaccaccaa cgaggtgact 600
gacagtgact ttgagaccag gaacttctgg atngggctca cctacaagac cgccaaggac 660
tccttncgct gggccacagg ggagcaccag 690

<210> SEQ ID NO 322
<211> LENGTH: 104
<212> TYPE: DNA
<213> ORGANISM: Homo sapiens

<400> SEQUENCE: 322
gtcgcaagcc ggagcaccac catgtagcct ttcccgaagt accggacctt ctcctcctcc 60
acgctcacat cacggacatc atggagcagg accaccacct ggtc 104

<210> SEQ ID NO 323
<211> LENGTH: 118
<212> TYPE: DNA
<213> ORGANISM: Homo sapiens

<400> SEQUENCE: 323
gggccctggg cgcttccaaa tgacccagga ggtggtctgc gacgaatgcc ctaatgtcaa 60
actagtgaat gaagaacgaa cactggaagt agaaatagag cctggggtga gagacgga 118

<210> SEQ ID NO 324
<211> LENGTH: 354
<212> TYPE: DNA
<213> ORGANISM: Homo sapiens

<400> SEQUENCE: 324

-continued

```
tgctctccgg gagcttgaag aagaaactgg ctacaaaggg gacattgccg aatgttctcc     60

agcggtctgt atggacccag gcttgtcaaa ctgtactata cacatcgtga cagtcaccat    120

taacggagat gatgccgaaa acgcaaggcc gaagccaaag ccaggggatg gagagtttgt    180

ggaagtcatt tctttaccca agaatgacct gctgcagaga cttgatgctc tggtagctga    240

agaacatctc acagtggacg ccagggtcta ttcctacgct ctagcgctga aacatgcaaa    300

tgcaaagcca tttgaagtgc ccttcttgaa attttaagcc caaatatgac actg          354
```

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 325

```
ncatgcttga atgggctcct ggtgagagat tgccccctgg tggtgaaaca atcgtgtgtg     60

cccactgata ccaagaccaa tgaaagagac acagttaagc agcaatccat ctcatttcca    120

ggcacttcaa taggtcgctg attggtcctt gcaccagcag tggtagtcgt acctatttca    180

gagaggtctg aaattcaggt tcttagtttg ccagggacag gccctacctt atattttttt    240

ccatcttcat catccacttc tgcttacagt ttgctgctta caataactta atgatggatt    300

gagttatctg ggtggtctct agccatctgg gcagtgtggt tctgtctaac caaagggcat    360

tggcctcaaa ccctgcattt ggtttagggg ctaacagagc tcctcagata atcttcacac    420

acatgtaact gctggagatc ttattctatt atgaataaga aacgagaagt ttttccaaag    480

tgttagtcag gatctgaagg ctgtcattca gataacccag cttttccttt tggcttttag    540

cccattcaga ctttgccaga gtcaagccaa ggattgcttt tttgctacag ttttctgcca    600

aatggcctag ttcctgagta cctggaaacc agagagaaag ag                       642
```

<210> SEQ ID NO 326
<211> LENGTH: 455
<212> TYPE: DNA
<213> ORGANISM: Homo sapiens

<400> SEQUENCE: 326

```
tccgtgagga tgagcttcga gtccttcacc aggcactgca ggggcacagt cacgtcaatc     60

accttcacct tctcgctctt cctgctcttg tcattgacaa acttcccgta ccaggcattg    120

acgatgatga ggcccattct ggactcttct gcctcaatta tccttcggac agattcctgc    180

atcagccgga cagcggactc cgcctcttgc ttcttctgca gcacatcggt ggcggcgctt    240

tccctctgct tctccaattc cttctctttc tgagccctga ggtatggttt gatgatcaga    300

cggtgcatgg caaagtagac cactagaggc cccacggtgg catagaacat ggcgctgggc    360

agaagctggt ccgtcaagtg aatagggaag aagtatgtct gactggccct gttgagcttg    420

actttgagag aaacgccctg tggaactcca acgct                               455
```

<210> SEQ ID NO 327
<211> LENGTH: 321
<212> TYPE: DNA
<213> ORGANISM: Homo sapiens

<400> SEQUENCE: 327

-continued

```
ttcactgtga actcgcagtc ctcgatgaac tcgcacagat gtgacagccc tgtctccttg     60

ctctctgagt tctcttcaat gatgctgatg atgcagtcca cgatagcgcg cttatactca    120

aagccaccct cttcccgcag catggtgaac aggaagttca taaggacggc gtgtttgcga    180

ggatatttct gacacagggc actgatggcc tggacaacca ccaccttgaa ttcatccgag    240

atttctgaca tgaaggagga gatctgcttc atgaggcggt cgatgctgct ctcgctgccc    300

gtcttaagga gggtggtgat g                                              321
```

```
<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: 302, 311
<223> OTHER INFORMATION: n = A,T,C or G

<400> SEQUENCE: 328

tgcaggaggg gccatggggg ctgtgaatgg gatgcagccc catggtgtcc ctgataaatc     60

cagtgtgcag tctgatgaag tctgggtggg tgtggtctac gggctggcag ctaccatgat    120

ccaagaggta atgcactcct tttcccatct ctccaccatc tgtatcctgg ccmagaaaaa    180

cttcccttca aaccaaccaa aatttccttt caaaggcata acccaaatgc catccttggt    240

ccggtctaat aaagcctccc ccatttttcc cctggtatgc attcccaggc tccctggcct    300

tncagggctt nctgtctgtg ggtcatagtt tatctcctcc cacttgctgg gagctccttg    360

aaggcaaaga ctctactgcc tccatctatc cagtggaagt ggctcttcag agggtgccaa    420

gttagtatgt atgactgtca tctctcccaa cagggcctga cttggsaggg cttcca        476
```

```
<210> SEQ ID NO 329
<211> LENGTH: 340
<212> TYPE: DNA
<213> ORGANISM: Homo sapiens

<400> SEQUENCE: 329

cgagggagat tgccagcacc ctgatggaga gtgagatgat ggagatcttg tcagtgctag     60

ctaagggtga ccacagccct gtcacaaggg ctgctgcagc ctgcctggac aaagcagtgg    120

aatatgggct tatccaaccc aaccaagatg gagagtgagg gggttgtccc tgggcccaag    180

gctcatgcac acgctaccta ttgtggcacg gagagtaagg acggaagcag ctttggctgg    240

tggtggctgg catgcccaat actcttgccc atcctcgctt gctgccctag gatgtcctct    300

gttctgagtc agcggccacg ttcagtcaca cagccctgct                         340
```

```
<210> SEQ ID NO 330
<211> LENGTH: 277
<212> TYPE: DNA
<213> ORGANISM: Homo sapiens

<400> SEQUENCE: 330

tgtcaccatc acattggtgc caaataccca gaagacatcg tagatgaaga gtccgcccag     60

caggatgcag ccagtgctga cattgttgag gtgcaggagc tctactccat taagggagaa    120

ggccaggcca aaaaggttgt tggcaatcca gtgcttcctc agcaggtacc agacgccaac    180

gatgctgctc aggcccaggc acaccaggtc cttggtgtca aattcataat tgatgatctc    240
```

-continued ctccttgttt tcccagaacc ctgtgtgaag agcagac 277

<210> SEQ ID NO 331
<211> LENGTH: 136
<212> TYPE: DNA
<213> ORGANISM: Homo sapiens

<400> SEQUENCE: 331
ttgcttccca cctcctttct ctgtcctctc ctgaggttct gccttacaat ggggacactg 60
atacaaacca cacacacaat gaggatgaaa acagataaca ggtaaaatga cctcacctgc 120
ccgggcggcc gctcga 136

<210> SEQ ID NO 332
<211> LENGTH: 184
<212> TYPE: DNA
<213> ORGANISM: Homo sapiens

<400> SEQUENCE: 332
ttgtgagata aacgcagata ctgcaatgca ttaaaacgct tgaaatactc atcagggatg 60
ttgctgatct tattgttgtc taagtagaga gttagaagag agacagggag accagaaggc 120
agtctggcta tctgattgaa gctcaagtca aggtattcga gtgatttaag acctttaaaa 180
gcag 184

<210> SEQ ID NO 333
<211> LENGTH: 384
<212> TYPE: DNA
<213> ORGANISM: Homo sapiens

<400> SEQUENCE: 333
cggaaaactt cgaggaattg ctcaaagtgc tgggggtgaa tgtgatgctg aggaagattg 60
ctgtggctgc agcgtccaag ccagcagtgg agatcaaaca ggagggagac actttctaca 120
tcaaaacctc caccaccgtg cgcaccacag agattaactt caaggttggg gaggagtttg 180
aggagcagac tgtggatggg aggccctgta agagcctggt gaaatgggag agtgagaata 240
aaatggtctg tgagcagaag ctcctgaagg gagagggccc caagacctcg tggaccagag 300
aactgaccaa cgatggggaa ctgatcctga ccatgacggc ggatgacgtt gtgtgcacca 360
gggtctacgt ccgagagtga gcgg 384

<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: 2, 165
<223> OTHER INFORMATION: n = A,T,C or G

<400> SEQUENCE: 334
cnacaaacag agcagacacc ctggatccgg tcctgctact ggccaggacg gctggaccgt 60
aaaattgaat ttccacttcc tgaccgccgc cagaagagat tgattttctc cactatcact 120
agcaagatga acctctctga ggaggttgac ttggaagact atgtngccc 169

<210> SEQ ID NO 335
<211> LENGTH: 185
<212> TYPE: DNA
<213> ORGANISM: Homo sapiens

<400> SEQUENCE: 335
ccaggtttgc agcccaggct gcacatcagg ggactgcctc gcaatacttc atgctgttgc 60
tgctgactga tggtgctgtg acggatgtgg aagccacacg tgaggctgtg gtgcgtgcct 120
cgaacctgcc catgtcagtg atcattgtgg gtgtgggtgg tgctgacttt gaggccatgg 180
agcag 185

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: 26
<223> OTHER INFORMATION: n = A,T,C or G

<400> SEQUENCE: 336
ctgcccctgc cttacggcgg ccaganacac acccaggatg gcattggccc caaacttgga 60
tttgttctca gtcccatcca actccagcat caggttgtcc agtttctctt gctccaccac 120
agagagacct gagctgatga gggctggcgc gatggtggag ttgatgtggt ccactgcctt 180
caggacacct ttgcctaagt aacgctgttt gtctccatcc ctcagctcca gggcctcata 240
gatgcccgta gaggctccac tgggcactgc agcccggaaa agacctttgg cagtatagag 300
atccacctcc actgtggggt tcccgcggga gtccaggatc tcccgggccc agatcttc 358

<210> SEQ ID NO 337
<211> LENGTH: 271
<212> TYPE: DNA
<213> ORGANISM: Homo sapiens
<220> FEATURE:
<221> NAME/KEY: misc_feature
<222> LOCATION: 17
<223> OTHER INFORMATION: n = A,T,C or G

<400> SEQUENCE: 337
cacaaagcca ccagccnggg aaatcagaat ttacttgatg caactgactt gtaatagcca 60
gaaatcctgc ccagcatggg attcagaacc tggtctgcaa ccaaatccac cgtcaaagtt 120
catacaggat aaaacaaatt caattgcctt ttccacatta atagcatcaa gcttccccaa 180
caaagccaaa gttgccaccg cacaaaaaga gaatcttgtg tcaatttctc cctactttat 240
aaaagtagat ttttcacatc ccatgaagca g 271

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: 15, 17, 18
<223> OTHER INFORMATION: n = A,T,C or G

<400> SEQUENCE: 338
ctgtgctccc gactngnnca tctcaggtac caccgactgc actgggcggg gccctctggg 60
gggaaaggct ccacggggca gggatacatc tcgaggccag tcatcctctg gaggcagccc 120
aatcaggtca aagattttgc ccaactggtc ggcttcagag tttccacaga agagaggctt 180
tcgacgaaac atctctgcaa agatacagcc aacactccac atgtccacag gtgttgcata 240
tgtggactgc agaagaactt cgggagctcg gtaccagagt gtaacaacca cgggtgtaag 300
tgccatctgg tagctgtaga ttctgg 326

-continued

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: 47, 54, 60, 69, 90, 91, 96, 113, 117, 119, 195
<223> OTHER INFORMATION: n = A,T,C or G

<400> SEQUENCE: 339
ttcacctgag gactcatttc gtgccctttg ttgacttcaa gcaaagncct tcanggtctn 60
caaggacgnc acatttccac ttgcgaatgn nctcanggct catcttgaag aanaagnanc 120
ccaagtgctg gatcccagac tcgggggtaa ccttgtgggt aagagctcat ccagtttatg 180
ctttaggacg tccanctact cgggggagct ggaagcctgc gtggatgcgg ccctgctgga 240
cctcggccgc gaccacgcta 260

<210> SEQ ID NO 340
<211> LENGTH: 220
<212> TYPE: DNA
<213> ORGANISM: Homo sapiens
<220> FEATURE:
<221> NAME/KEY: misc_feature
<222> LOCATION: 15, 18
<223> OTHER INFORMATION: n = A,T,C or G

<400> SEQUENCE: 340
ctggaagccc ggctnggnct ggcagcggaa ggagccaggc aggttcacgc agcggtgctg 60
gcagtagcgg tagcggcact cgtctatgtc cacacactcg ggcccgatct tgcggtaacc 120
atcagggcag gtgcactgat aggagccagg caagttatgg cagtcctggc tggggcgaca 180
gtcgtgcagg gcctgggcac actcgtccac atccacacag 220

<210> SEQ ID NO 341
<211> LENGTH: 384
<212> TYPE: DNA
<213> ORGANISM: Homo sapiens

<400> SEQUENCE: 341
ctgctaccag gggagcgaga gctgactatc ccagcctcgg ctaatgtatt ctacgccatg 60
gatggagctt cacacgattt cctcctgcgg cagcggcgaa ggtcctctac tgctacaccg 120
ggcgtcacca gtggcccgtc tgcctcagga actcctccga gtgagggagg agggggctcc 180
tttcccagga tcaaggccac agggaggaag attgcacggg cactgttctg aggaggaagc 240
cccgttggct tacagaagtc atggtgttca taccagatgt gggtagccat cctgaatggt 300
ggcaattata tcacattgag acagaaattc agaaagggag ccagccaccc tggggcagtg 360
aagtgccact ggtttaccag acag 384

<210> SEQ ID NO 342
<211> LENGTH: 245
<212> TYPE: DNA
<213> ORGANISM: Homo sapiens

<400> SEQUENCE: 342
ctggctaagc tcatcattgt tactggtggg caccatgtcc ttgaagcttc aggcaagcaa 60
tgtaaccaac aagaatgacc ccaagtccat caactctcga gtcttcattg gaaacctcaa 120
cacagctctg gtgaagaaat cagatgtgga gaccatcttc tctaagtatg gccgtgtggc 180

-continued

```
cggctgttct gtgcacaagg gctatgcctt tgttcagtac tccaatgagc gccatgcccg    240

ggcag                                                                245


<210> SEQ ID NO 343
<211> LENGTH: 611
<212> TYPE: DNA
<213> ORGANISM: Homo sapiens

<400> SEQUENCE: 343

ccaaaaaaat caagatttaa tttttttatt tgcactgaaa aactaatcat aactgttaat     60

tctcagccat ctttgaagct tgaaagaaga gtctttggta ttttgtaaac gttagcagac    120

tttcctgcca gtgtcagaaa atcctattta tgaatcctgt cggtattcct tggtatctga    180

aaaaaatacc aaatagtacc atacatgagt tatttctaag tttgaaaaat aaaaagaaat    240

tgcatcacac taattacaaa atacaagttc tggaaaaaat atttttcttc attttaaaac    300

ttttttaac taataatggc tttgaaagaa gaggcttaat ttgggggtgg taactaaaat     360

caaaagaaat gattgacttg agggtctctg tttggtaaga atacatcatt agcttaaata    420

agcagcagaa ggttagtttt aattatgtag cttctgttaa tattaagtgt tttttgtctg    480

ttttacctca atttgaacag ataagtttgc ctgcatgctg gacatgcctc agaaccatga    540

atagcccgta ctagatcttg ggaacatgga tcttagagtc ctttggaata agttcttata    600

taaatacccc c                                                         611


<210> SEQ ID NO 344
<211> LENGTH: 311
<212> TYPE: DNA
<213> ORGANISM: Homo sapiens
<220> FEATURE:
<221> NAME/KEY: misc_feature
<222> LOCATION: 1, 275, 284, 296, 297, 300
<223> OTHER INFORMATION: n = A,T,C or G

<400> SEQUENCE: 344

nctcgaaaaa gcccaagaca gcagaagcag acacctccag tgaactagca aagaaaagca     60

aagaagtatt cagaaaagag atgtcccagt tcatcgtcca gtgcctgaac ccttaccgga    120

aacctgactg caaagtggga agaattacca caactgaaga ctttaaacat ctggctcgca    180

agctgactca cggtgttatg aataaggagc tgaagtactg taagaatcct gaggacctgg    240

agtgcaatga gaatgtgaaa cacaaaacca aggantacat taanaagtac atgcannaan    300

tttggggctt g                                                         311


<210> SEQ ID NO 345
<211> LENGTH: 201
<212> TYPE: DNA
<213> ORGANISM: Homo sapiens

<400> SEQUENCE: 345

cacacggtca tcccgactgc caacctggag gcccaggccc tgtggaagga gccgggcagc     60

aatgtcacca tgagtgtgga tgctgagtgt gtgcccatgg tcagggacct tctcaggtac    120

ttctactccc gaaggattga catcaccctg tcgtcagtca agtgcttcca caagctggcc    180

tctgcctatg gggccaggca g                                              201


<210> SEQ ID NO 346
<211> LENGTH: 370
<212> TYPE: DNA
<213> ORGANISM: Homo sapiens
```

<400> SEQUENCE: 346
ctgctccagg gcgtggtgtg ccttcgtggc ctctgcctcc tccgaggagc caggctgtgt 60
tctcttcaga atgttctgga gcagcagttt gaggcgggtg atgcgttgga agggcagaat 120
cagaaaggac ttgagggaaa ggcgctggca gacggggtcg ctctccagct tctccaagac 180
ctcccggaaa ttgctgttgc tattcatcag gctctggaag gtgcgttcct gataggtctg 240
gttggtgaca taaggcaggt agacccggcg gaagtctggg gcgtggttca ggactacgtc 300
acatacttgg aaggagaaga tattgttctc aaagttctct tccaggtctg aaaggaacgt 360
ggcgctgacg 370

<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: 416
<223> OTHER INFORMATION: n = A,T,C or G

<400> SEQUENCE: 347
ctgttgtgct gtgtatggac gtgggcttta ccatgagtaa ctccattcct ggtatagaat 60
ccccatttga acaagcaaag aaggtgataa ccatgtttgt acagcgacag gtgtttgctg 120
agaacaagga tgagattgct ttagtcctgt ttggtacaga tggcactgac aatccccttt 180
ctggtgggga tcagtatcag aacatcacag tgcacagaca tctgatgcta ccagattttg 240
atttgctgga ggacattgaa agcaaaatcc aaccaggttc tcaacaggct gacttcctgg 300
atgcactaat cgtgagcatg gatgtgattc aacatgaaac aataggaaag aagtttggag 360
aagaggcata ttgaaatatt cactgacctc aagcagcccg attcagcaaa agtcan 416

<210> SEQ ID NO 348
<211> LENGTH: 351
<212> TYPE: DNA
<213> ORGANISM: Homo sapiens

<400> SEQUENCE: 348
gtacaggaga ggatggcagg tgcagagcgg gcactgagct ctgcaggtga aagggctcgg 60
cagttggatg ctctcctgga ggctctgaaa ttgaaacggg caggaaatag tctggcagcc 120
tctacagcag aagaaacggc aggcagtgcc cagggacgag caggagacag atgccttcct 180
cttgtctcaa ctgcaaagag gcgttccttc ctctttcact aatcctcctc agcacagacc 240
ctttacgggt gtcaggctgg gggacagtaa ggtctttccc ttcccacaag gccatatctc 300
aggctgtctc agtgggggga aaccttggac aatacccggg ctttcttggg c 351

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: 1
<223> OTHER INFORMATION: n = A,T,C or G

<400> SEQUENCE: 349
nccgggacat ctccaccctc aacagtggca agaagagcct ggagactgaa cacaaggcct 60
tgaccagtga gattgcactg ctgcagtcca ggctgaagac agagggctct gatctgtgcg 120

-continued acagagtgag cgaaatgcag aagctggatg cacaggtcaa ggagctggtg ctgaagtcgg 180
cggtggaggc tgagcgcctg gtggctg 207

<210> SEQ ID NO 350
<211> LENGTH: 323
<212> TYPE: DNA
<213> ORGANISM: Homo sapiens

<400> SEQUENCE: 350
ccatacaggg ctgttgccca ggccctagag gtcattcctc gtaccctgat ccagaactgt 60
ggggccagca ccatccgtct acttacctcc cttcgggcca agcacaccca ggagaactgt 120
gagacctggg gtgtaaatgg tgagacgggt actttggtgg acatgaagga actgggcata 180
tgggagccat tggctgtgaa gctgcagact tataagacag cagtggagac ggcagttctg 240
ctactgcgaa ttgatgacat cgtttcaggc cacgaaaaga aaggcgatga ccagagccgg 300
caaggcgggg ctcctgatgc tgg 323

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: 12, 25, 39, 42
<223> OTHER INFORMATION: n = A,T,C or G

<400> SEQUENCE: 351
cgccgcatcc cntggtccct tccantccct tttcctttnt cngggaacgt gtatgcggtt 60
tgtttttgtt ttgtagggtt tttttccttc tccacctctc cctgtctctt ttgctccatg 120
ttgtccgttt ctgtggggtt aggtttatgt ttttaatcat ctgaggtcac gtctatttcc 180
tccggactcg cctgcttggt ggcgattctc caccggttaa tatggtgcgt ccctttttttc 240 ttttgttgcg aatctgagcc ttcttcctcc agcttctgcc ttttgaactt tgttcttcgg 300
ttctgaaacc atacttttac ctgagtttcc gtgaggctga ggctgtgtgc caa 353

<210> SEQ ID NO 352
<211> LENGTH: 467
<212> TYPE: DNA
<213> ORGANISM: Homo sapiens

<400> SEQUENCE: 352
ctgcccacac tgatcacttg cgagatgtcc ttagggtaca agaacaggaa ttgaagtctg 60
aatttgagca gaacctgtct gagaaactct ctgaacaaga attacaattt cgtcgtctca 120
gtcaagagca agttgacaac tttactctgg atataaatac tgcctatgcc agactcagag 180
gaatcgaaca ggctgttcag agccatgcag ttgctgaaga ggaagccaga aaagcccacc 240
aactctggct ttcagtggag gcattaaagt acagcatgaa gacctcatct gcagaaacac 300
ctactatccc gctgggtagt gcagttgagg ccatcaaagc caactgttct gataatgaat 360
tcacccaagc tttaaccgca gctatccctc cagagtccct gacccgtggg gtgtacagtg 420
aagagaccct tagagcccgt ttctatgctg ttcaaaaact ggcccga 467

<210> SEQ ID NO 353
<211> LENGTH: 350
<212> TYPE: DNA
<213> ORGANISM: Homo sapiens

<400> SEQUENCE: 353

-continued

```
ctgctgcagc cacagtagtt cctcccatgg tgggtggccc tcctggtcct gctggcccag     60

gaaatctgtc cccaccagga acagcccctg gaaaacggcc ccgtcctcta ccaccttgtg    120

gaaatgctgc acgggaactg cctcctggag gaccagcttt accttcccca gacatttgtc    180

ctgattgtgt agttttcctg gactgcattt caaattgact caggaactgt ttattgcatg    240

gagttacaac aggattctga ccatgaagtt ctcttttagg taacagatcc attaactttt    300

ttgaagatgc ttcagatcca acaccaacaa gggcaaaccc ctttgactgg               350
```

<210> SEQ ID NO 354
<211> LENGTH: 351
<212> TYPE: DNA
<213> ORGANISM: Homo sapiens

<400> SEQUENCE: 354

```
atttagatga gatctgaggc atggagacat ggagacagta tacagactcc tagatttaag     60

ttttaggttt tttgcttttc taatcaccaa ttcttatata caatgtatat tttagactcg    120

agcagatgat catcttcatc ttaagtcatt ccttttgact gagtatggca ggattagagg    180

gaatggcagt atagatcaat gtctttttct gtaaagtata ggaaaaacca gagaggaaaa    240

aaagagctga caattggaag gtagtagaaa attgacgata atttcttctt aacaaataat    300

agttgtatat acaaggaggc tagtcaacca gattttattt gttgagggcg a             351
```

<210> SEQ ID NO 355
<211> LENGTH: 308
<212> TYPE: DNA
<213> ORGANISM: Homo sapiens

<400> SEQUENCE: 355

```
ttttggcgca agttttacag attttattaa agtcgaagct attggtcttg gaagatgaaa     60

atgcaaatgt tgatgaggtg gaattgaagc cagatacctt aataaaatta tatcttggtt    120

ataaaaataa gaaattaagg gttaacatca atgtgccaat gaaaaccgaa cagaagcagg    180

aacaagaaac cacacacaaa aacatcgagg aagaccgcaa actactgatt caggcggcca    240

tcgtgagaat catgaagatg aggaaggttc tgaaacacca gcagttactt ggcgaggtcc    300

tcactcag                                                             308
```

<210> SEQ ID NO 356
<211> LENGTH: 207
<212> TYPE: DNA
<213> ORGANISM: Homo sapiens

<400> SEQUENCE: 356

```
ctgtcccaag tgctcccaga aggcaggatt ctgaagacca ctccagcgat atgttcaact     60

atgaagaata ctgcaccgcc aacgcagtca ctgggccttg ccgtgcatcc ttcccacgct    120

ggtactttga cgtggagagg aactcctgca ataacttcat ctatggaggc tgccggggca    180

ataagaacag ctaccgctct gaggagg                                        207
```

<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: 25, 29
<223> OTHER INFORMATION: n = A,T,C or G -continued

<400> SEQUENCE: 357

```
tcgaccacgc cctcgtagcg catgngctnc aggacgatgc tcagagtgat gaacaccccg     60

gtgcggccca cgccagcact gcagtgcacc gtgataggcc catcctgtcc aaactgctcc    120

ttggtcttat gcacctgccc gatgaagtca atgaatccct cgcctgtctt gggcacgccc    180

tgctctgg                                                             188
```

<210> SEQ ID NO 358
<211> LENGTH: 291
<212> TYPE: DNA
<213> ORGANISM: Homo sapiens

<400> SEQUENCE: 358

```
ctgggagcat cggcaagcta ctgccttaaa atccgatctc cccgagtgca caatttctgt     60

ccctttttaag ggttcacaac actaaagatt tcacatgaaa gggttgtgat tgatttgagc    120

aggcaggcgg tacgtgacag gggctgcatg caccggtggt cagagagaaa cagaacaggg    180

cagggaattt cacaatgttc ttctatacaa tggctggaat ctatgaataa catcagtttc    240

taagttatgg gttgattttt aactactggg tttaggccag gcaggcccag g             291
```

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: 79, 98, 100
<223> OTHER INFORMATION: n = A,T,C or G

<400> SEQUENCE: 359

```
gccaccacac tccagcctgg gcaatacagc aagactgtct caaaaaaaaa aaaaaaaaaa     60

cccaaaaaaa ctcaaaaang taatgaatga tacccaangn gccttttcta gaaaaag       117
```

<210> SEQ ID NO 360
<211> LENGTH: 394
<212> TYPE: DNA
<213> ORGANISM: Homo sapiens

<400> SEQUENCE: 360

```
ctgttcctct ggggtggtcc agttctagag tgggagaaag ggagtcaggc gcattgggaa     60

tcgtggttcc agtctggttg cagaatctgc acatttgcca agaaattttc cctgtttgga    120

aagtttgccc cagctttccc gggcacacca ccttttgtcc caagtgtctg ccggtcgacc    180

aatctgcctg ccacacattg accaagccag acccggttca cccagctcga ggatcccagg    240

ttgaagagtg gccccttgag gccctggaaa gaccaatcac tggacttctt cccttgagag    300

tcagaggtca cccgtgattc tgcctgcacc ttatcattga tctgcagtga tttctgcaaa    360

tcaagagaaa ctctgcaggg cactcccctg tttc                                394
```

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: 28, 31
<223> OTHER INFORMATION: n = A,T,C or G

<400> SEQUENCE: 361

```
ctgggcggat agcaccgggc atattttntt natggatgag gtctggcacc ctgagcagtc     60
```

-continued

```
cagcgaggac ttggtcttag ttgagcaatt tggctaggag gatagtatgc agcacggttc    120

tgagtctgtg ggatagctgc catgaagtaa cctgaaggag gtgctggctg gtaggggttg    180

attacagggt tgggaacagc tcgtacactt gccattctct gcatatactg gttagtgagg    240

tgagcctggc gctcttcttt gcgctgagct aaagctacat acaatggctt tgtggacctc    300

ggccgcgacc acgctaagcc gaattccagc acactggcgg ccgttactag tggatccgag    360

ctcggtacca agcttggcgt aatcatggtc atag                                394
```

<210> SEQ ID NO 362
<211> LENGTH: 268
<212> TYPE: DNA
<213> ORGANISM: Homo sapiens

<400> SEQUENCE: 362

```
ctgcgcgtgg accagtcagc ttccgggtgt gactggagca gggcttgtcg tcttcttcag     60

agtcactttg caggggttgg tgaagctgct cccatccatg tacagctccc agtctactga    120

tgtttaagga tggtctcggt ggttaggccc actagaataa actgagtcca atacctctac    180

acagttatgt ttaactgggc tctctgacac cgggaggaag gtggcggggt ttaggtgttg    240

caaacttcaa tggttatgcg gggatgtt                                       268
```

<210> SEQ ID NO 363
<211> LENGTH: 323
<212> TYPE: DNA
<213> ORGANISM: Homo sapiens

<400> SEQUENCE: 363

```
ccttgacctt ttcagcaagt gggaaggtgt aatccgtctc cacagacaag gccaggactc     60

gtttgtaccc gttgatgata gaatggggta ctgatgcaac agttgggtag ccaatctgca    120

gacagacact ggcaacattg cggacaccct ccaggaagcg agaatgcaga gtttcctctg    180

tgatatcaag cacttcaggg ttgtagatgc tgccattgtc gaacacctgc tggatgacca    240

gcccaaagga gaagggggag atgttgagca tgttcagcag cgtggcttcg ctggctccca    300

ctttgtctcc agtcttgatc aga                                            323
```

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: 29
<223> OTHER INFORMATION: n = A,T,C or G

<400> SEQUENCE: 364

```
ccaagctctc catcgtcccc gtgcgcagng gctactgggg gaacaagatc ggcaagcccc     60

acactgtccc ttgcaaggtg acaggccgct gcggctctgt gctggtacgc ctcatcactg    120

cacccagggg cactggcatc gtctccgcac ctgtgcctaa gaagctgctc atgatggctg    180

gcatcgatga ctgctacacc tcagcccggg gctgcactgc caccctgggc aacttcgcca    240

aggccacctt tgatgccatt tctaagacct acagctacct gacccccgac ctctggaagg    300

agactgtatt caccaagtct ccctatcagg agttcactga ccacctcgtc aagacccaca    360

ccagagtctc cgtgcagcgg actcaggctc cag                                 393
```

<210> SEQ ID NO 365

-continued

<211> LENGTH: 371
<212> TYPE: DNA
<213> ORGANISM: Homo sapiens

<400> SEQUENCE: 365
cctcctcaga gcggtagctg ttcttattgc cccggcagcc tccatagatg aagttattgc 60
aggagttcct ctccacgtca aagtaccagc gtgggaagga tgcacggcaa ggcccagtga 120
ctgcgttggc ggtgcagtat tcttcatagt tgaacatatc gctggagtgg tcttcagaat 180
cctgccttct gggagcactt gggacagagg aatccgctgc attcctgctg gtggacctcg 240
gccgcgacca cgctaagccg aattccagca cactggcggc cgttactagt ggatccgagc 300
tcggtaccaa gcttggcgta atcatggtca tagctgtttc ctgtgtgaaa ttgttatccg 360
ctcacaattc c 371

<210> SEQ ID NO 366
<211> LENGTH: 393
<212> TYPE: DNA
<213> ORGANISM: Homo sapiens

<400> SEQUENCE: 366
atttcttgcc agatgggagc tctttggtga agactccttt cgggaaaagt tttttggctt 60
cttcttcagg gatggttgga aggaccatca cactatcccc atccttccaa tcaactgggg 120
tggcaaccct tttttctgct gtcagctgga gagagatgac taccctgaga atctcatcaa 180
agttcctgcc agtggtagct gggtagagga tagacagctt cagcttctta tcaggaccaa 240
aaacaaacac cacacgagct gccacaggca tgccctttc atccttctct gctggatcca 300
gcatgcccaa caggatggca agctcccgat tcctatcatc gatgatggga aaaggtaact 360
tttctgtggg ctcttcacaa ttgtaagcat tga 393

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: 34, 54, 55
<223> OTHER INFORMATION: n = A,T,C or G

<400> SEQUENCE: 367
ccagctctgt ctcatacttg actctaaagt cttnagcagc aagacgggca ttgnnaatct 60
gcagaacgat gcgggcattg tccacagtat ttgcgaagat ctgagccctc aggtcctcga 120
tgatcttgaa gtaatggctc cagtctctga cctggggtcc cttcttctcc aagtgctccc 180
ggattttgct ctccagcctc cggttctcgg tctccaggct cctcactctg tccaggtaag 240
aggccaggcg gtcgttcagg ctttgcatgg tctccttctc gttctggatg cctcccattc 300
ctgccagacc cccggctatc ccggtgg 327

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: 24
<223> OTHER INFORMATION: n = A,T,C or G

<400> SEQUENCE: 368
ctggagaagg acttcagcag tttnaagaag tactgccaag tcatccgtgt cattgcccac 60

-continued

```
acccagatgc gcctgcttcc tctgcgccag aagaaggccc acctgatgga gatccaggtg    120
aacggaggca ctgtggccga gaagctggac tgggcccgcg agaggcttga gcagcaggta    180
cctgtgaacc aagtgtttgg gcaggatgag atgatcgacg tcatcggggt gaccaagggc    240
aaaggctaca aggggtcac cagtcgttgg cacaccaaga agctgccccg caagacccac     300
cgagga                                                               306
```

<210> SEQ ID NO 369
<211> LENGTH: 394
<212> TYPE: DNA
<213> ORGANISM: Homo sapiens

<400> SEQUENCE: 369

```
tcgacccaca ccggaacacg gagagctggg ccagcattgg cacttgatag gatttcccgt     60
cggctgccac gaaagtgcgt ttctttgtgt tctcgggttg gaaccgtgat ttccacagac    120
ccttgaaata cactgcgttg acgaggacca gtctggtgag cacaccatca ataagatctg    180
gggacagcag attgtcaatc atatccctgg tttcattttt aacccatgca ttgatggaat    240
cacaggcaga ggctggatcc tcaaagttca cattccggac ctcacactgg aacacatctt    300
tgttccttgt aacaaaaggc acttcaattt cagaggcatt cttaacaaac acggcgttag    360
ccactgtcac aatgtcttta ttcttcttgg agac                                394
```

<210> SEQ ID NO 370
<211> LENGTH: 653
<212> TYPE: DNA
<213> ORGANISM: Homo sapiens

<400> SEQUENCE: 370

```
ccaccacacc caattccttg ctggtatcat ggcagccgcc acgtgccagg attaccggct     60
acatcatcaa gtatgagaag cctgggtctc ctcccagaga agtggtccct cggccccgcc    120
ctggtgtcac agaggctact attactggcc tggaaccggg aaccgaatat acaatttatg    180
tcattgccct gaagaataat cagaagagcg agcccctgat tggaaggaaa aagacagacg    240
agcttcccca actggtaacc cttccacacc ccaatcttca tggaccagag atcttggatg    300
ttccttccac agttcaaaag accccttttcg tcacccaccc tgggtatgac actggaaatg   360
gtattcagct tcctggcact tctggtcagc aacccagtgt tgggcaacaa atgatctttg    420
aggaacatgg ttttaggcgg accacaccgc ccacaacggc cacccccata aggcataggc    480
caagaccata cccgccgaat gtaggacaag aagctctctc tcagacaacc atctcatggg    540
ccccattcca ggacacttct gagtacatca tttcatgtca tcctgttggc actgatgaag    600
aacccttaca gttcagggtt cctggaactt ctaccagtgc cactctgaca gga           653
```

<210> SEQ ID NO 371
<211> LENGTH: 268
<212> TYPE: DNA
<213> ORGANISM: Homo sapiens

<400> SEQUENCE: 371

```
ctgcccagcc cccattggcg agtttgagaa ggtgtgcagc aatgacaaca agaccttcga     60
ctcttcctgc cacttctttg ccacaaagtg caccctggag ggcaccaaga agggccacaa    120
gctccacctg gactacatcg ggccttgcaa atacatcccc ccttgcctgg actctgagct    180
gaccgaattc cccctgcgca tgcgggactg gctcaagaac gtcctggtca ccctgtatga    240
```

-continued gagggatgag gacaacaacc ttctgact 268

<210> SEQ ID NO 372
<211> LENGTH: 392
<212> TYPE: DNA
<213> ORGANISM: Homo sapiens

<400> SEQUENCE: 372
gctggtgccc ctggtgaacg tggacctcct ggattggcag gggccccagg acttagaggt 60
ggaactggtc cccctggtcc cgaaggagga aagggtgctg ctggtcctcc tgggccacct 120
ggtgctgctg gtactcctgg tctgcaagga atgcctggag aaagaggagg tcttggaagt 180
cctggtccaa agggtgacaa gggtgaacca ggcggtccag gtgctgatgg tgtcccaggg 240
aaagatggcc caaggggtcc tactggtcct attggtcctc ctggcccagc tggccagcct 300
ggagataagg gtgaaggtgg tgccccccgga cttccaggta tagctggacc tcgtggtagc 360
cctggtgaga gaggtgaaac ctcggccgcg ac 392

<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: 30
<223> OTHER INFORMATION: n = A,T,C or G

<400> SEQUENCE: 373
ccaagcgctc agatcggcaa ggggcaccan ttttgatctg cccagtgcac agccccacaa 60
ccaggtcagc gatgaaggta tcttcagtct cccccgaacg atgagacacc atgacgcccc 120
aaccattggc ctgggccagc ttgcacgcct gaagagactc ggtcacggag ccaatctggt 180
tgactttgag caggaggcag ttgcaggact tctcgttcac ggccttggcg atcctctttg 240
ggttggtcac tgtgagatca tcccccacta cctggattcc tgcactggct gtgaacttct 300
gccaagctcc ccagtcatcc tggtcaaagg gatcttcgat agacaccact gggtagtcct 360
tgatgaagga cttgtacagg tcagccag 388

<210> SEQ ID NO 374
<211> LENGTH: 393
<212> TYPE: DNA
<213> ORGANISM: Homo sapiens

<400> SEQUENCE: 374
ctgacgaccg cgtgaacccc tgcattgggg gtgtcatcct cttccatgag acactctacc 60
agaaggcgga tgatgggcgt cccttccccc aagttatcaa atccaagggc ggtgttgtgg 120
gcatcaaggt agacaagggc gtggtccccc tggcagggac aaatggcgag actaccaccc 180
aagggttgga tgggctgtct gagcgctgtg cccagtacaa gaaggacgga gctgacttcg 240
ccaagtggcg ttgtgtgctg aagattgggg aacacacccc ctcagccctc gccatcatgg 300
aaaatgccaa tgttctggcc cgttatgcca gtatctgcca gcagaatggc attgtgccca 360
tcgtggagcc tgagatcctc cctgatgggg acc 393

<210> SEQ ID NO 375
<211> LENGTH: 394
<212> TYPE: DNA
<213> ORGANISM: Homo sapiens
<220> FEATURE:
<221> NAME/KEY: misc_feature -continued
<222> LOCATION: 30, 33
<223> OTHER INFORMATION: n = A,T,C or G

<400> SEQUENCE: 375
ccacaaatgg cgtggtccat gtcatcaccn ttnttctgca gcctccagcc aacagacctc 60
aggaaagagg ggatgaactt gcagactctg cgcttgagat cttcaaacaa gcatcagcgt 120
tttccagggc ttcccagagg tctgtgcgac tagcccctgt ctatcaaaag ttattagaga 180
ggatgaagca ttagcttgaa gcactacagg aggaatgcac cacggcagct ctccgccaat 240
ttctctcaga tttccacaga gactgtttga atgttttcaa aaccaagtat cacactttaa 300
tgtacatggg ccgcaccata atgagatgtg agccttgtgc atgtggggga ggagggagag 360
agatgtactt tttaaatcat gttcccccta aaca 394

<210> SEQ ID NO 376
<211> LENGTH: 392
<212> TYPE: DNA
<213> ORGANISM: Homo sapiens
<220> FEATURE:
<221> NAME/KEY: misc_feature
<222> LOCATION: 30
<223> OTHER INFORMATION: n = A,T,C or G

<400> SEQUENCE: 376
ctgcccagcc cccattggcg agtttgattn ggtgtgcagc aatgacaaca agaccttcga 60
ctcttcctgc cacttctttg ccacaaagtg caccctggag ggcaccaaga agggccacaa 120
gctccacctg gactacatcg ggccttgcaa atacatcccc ccttgcctgg actctgagct 180
gaccgaattc cccctgcgca tgcgggactg gctcaagaac gtcctggtca ccctgtatga 240
gagggatgag gacaacaacc ttctgactga gaagcagaag ctgcgggtga agaagatcca 300
tgagaatgag aagcgcctgg aggcaggaga ccacccccgtg gagctgctgg cccgggactt 360
cgagaagaac tataacatgt acatcttccc tg 392

<210> SEQ ID NO 377
<211> LENGTH: 292
<212> TYPE: DNA
<213> ORGANISM: Homo sapiens

<400> SEQUENCE: 377
caatgtttga tgcttaaccc ccccaatttc tgtgagatgg atggccagtg caagcgtgac 60
ttgaagtgtt gcatgggcat gtgtgggaaa tcctgcgttt cccctgtgaa agcttgattc 120
ctgccatatg gaggaggctc tggagtcctg ctctgtgtgg tccaggtcct ttccaccctg 180
agacttggct ccaccactga tatcctcctt tggggaaagg cttggcacac agcaggcttt 240
caagaagtgc cagttgatca atgaataaat aaacgagcct atttctcttt gc 292

<210> SEQ ID NO 378
<211> LENGTH: 395
<212> TYPE: DNA
<213> ORGANISM: Homo sapiens

<400> SEQUENCE: 378
ctgctgcttc agcgaagggt ttctggcata tccaatgata aggctgccaa agactgttcc 60
aataccagca ccagaaccag ccactcctac tgttgcagca cctgcaccaa taaatttggc 120
agcagtatca atgtctctgc tgattgcact ggtctgaaac tccctttgga ttagctgaga 180
cacaccattc tgggccctga ttttcctaag atagaactcc aactctttgc cctctagcac 240

-continued

```
atagccatct gctcggccac actgtcccgg ccttgaagcg atgcacgcaa gaagcttgcc    300

ctgctggaac tgctcctcca ggagactgct gattttggca ttctttttcc tttcatcata    360

tttcttctga attttttaga tcgtttttttg tttaa                               395
```

<210> SEQ ID NO 379
<211> LENGTH: 223
<212> TYPE: DNA
<213> ORGANISM: Homo sapiens

<400> SEQUENCE: 379

```
ccagatgaaa tgctgccgca atggctgtgg gaaggtgtcc tgtgtcactc ccaatttctg     60

agctccagcc accaccaggc tgagcagtga ggagagaaag tttctgcctg gccctgcatc    120

tggttccagc ccacctgccc tcccctttttt cgggactctg tattccctct tgggctgacc    180

acagcttctc cctttcccaa ccaataaagt aaccactttc agc                       223
```

<210> SEQ ID NO 380
<211> LENGTH: 317
<212> TYPE: DNA
<213> ORGANISM: Homo sapiens
<220> FEATURE:
<221> NAME/KEY: misc_feature
<222> LOCATION: 30, 32
<223> OTHER INFORMATION: n = A,T,C or G

<400> SEQUENCE: 380

```
tcgaccacag tattccaacc ctcctgtgcn tngagaagtg atggagggtg ctgacaacca     60

gggtgcagga gaacaaggta gaccagtgag gcagaatatg tatcggggat atagaccacg    120

attccgcagg ggccctcctc gccaaagaca gcctagagag gacggcaatg aagaagataa    180

agaaaatcaa ggagatgaga cccaaggtca gcagccacct caacgtcggt accgccgcaa    240

cttcaattac cgacgcagac gcccagaaaa ccctaaacca caagatggca aagagacaaa    300

agcagccgat ccaccag                                                   317
```

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: 29, 30, 31
<223> OTHER INFORMATION: n = A,T,C or G

<400> SEQUENCE: 381

```
cctgaaggaa gagctggcct acctgaatnn naaccatgag gaggaaatca gtacgctgag     60

gggccaagtg ggaggccagg tcagtgtgga ggtggattcc gctccgggca ccgatctcgc    120

caagatcctg agtgacatgc gaagccaata tgaggtcatg gccgagcaga accggaagga    180

tgctgaagcc tggttcacca gccggactga agaattgaac cgggaggtcg ctggccacac    240

ggagcagctc cagatgagca ggtccgaggt tactgacctg cggcgcaccc ttcagggtct    300

tgagattgag ctgcagtcac agacctcggc cgcgaccacg ctaagccgaa ttccagcaca    360

ctggcggccg ttactagtgg atccgagctc gg                                   392
```

<210> SEQ ID NO 382
<211> LENGTH: 234
<212> TYPE: DNA
<213> ORGANISM: Homo sapiens

<400> SEQUENCE: 382

-continued

```
cctcgatgtc taaatgagcg tggtaaagga tggtgcctgc tggggtctcg tagatacctc     60

gggacttcat tccaatgaag cggttctcca cgatgtcaat acggcccacg ccatgcttgc    120

ccgcgacttc gttcaggtac atgaagagct ccaaggaggt ctggtgggtg gtgccatcct    180

tgacgttggt caccttcaca gggacccctt ttttgaactc catctccaga atgt          234
```

```
<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: 66
<223> OTHER INFORMATION: n = A,T,C or G

<400> SEQUENCE: 383

ccttgacctt ttcagcaagt gggaaggtgt tttccgtctc cacagacaag gccaggactc     60

gtttgnaccc gttgatgata gaatggggta ctgatgcaac agttgggtag ccaatctgca    120

gacagacact ggcaacattg cggacaccca ggatttcaat ggtgcccctg gagattttag    180

tggtgatacc taaagcctgg aaaaaggagg tcttctcggg cccgagacca gtgttctggg    240

ctggcacagt gacttcacat ggggcaatgg caccagcacg ggcagcagac ctgcccgggc    300

ggccgctcga aagccgaatt ccagcacact ggcggccgtt actagtggat ccgagctcgg    360

taccaagctt ggcgtaatca tggtcatagc tgtttc                              396
```

```
<210> SEQ ID NO 384
<211> LENGTH: 396
<212> TYPE: DNA
<213> ORGANISM: Homo sapiens

<400> SEQUENCE: 384

gctgaatagg cacagagggc acctgtacac cttcagacca gtctgcaacc tcaggctgag     60

tagcagtgaa ctcaggagcg ggagcagtcc attcaccctg aaattcctcc ttggtcactg    120

ccttctcagc agcagcctgc tcttcttttt caatctcttc aggatctctg tagaagtaca    180

gatcaggcat gacctcccat gggtgttcac gggaaatggt gccacgcatg cgcagaactt    240

cccgagccag catccaccac atcaaaccca ctgagtgagc tcccttgttg ttgcatggga    300

tggcaatgtc cacatagcgc agaggagaat ctgtgttaca cagcgcaatg gtaggtaggt    360

taacataaga tgcctccgtg agaggctggt ggtcag                              396
```

```
<210> SEQ ID NO 385
<211> LENGTH: 2943
<212> TYPE: DNA
<213> ORGANISM: Homo sapiens

<400> SEQUENCE: 385

cagccaccgg agtggatgcc atctgcaccc accgccctga ccccacaggc cctgggctgg     60

acagagagca gctgtatttg gagctgagcc agctgaccca cagcatcact gagctgggcc    120

cctacaccct ggacagggac agtctctatg tcaatggttt cacacagcgg agctctgtgc    180

ccaccactag cattcctggg acccccacag tggacctggg aacatctggg actccagttt    240

ctaaacctgg tccctcggct gccagccctc tcctggtgct attcactctc aacttcacca    300

tcaccaacct gcggtatgag gagaacatgc agcaccctgg ctccaggaag ttcaacacca    360

cggagagggt ccttcagggc ctggtccctg ttcaagagca ccagtgttgg ccctctgtac    420
```

-continued

```
tctggctgca gactgacttt gctcaggcct gaaaaggatg ggacagccac tggagtggat    480
gccatctgca cccaccaccc tgaccccaaa agccctaggc tggacagaga gcagctgtat    540
tgggagctga gccagctgac ccacaatatc actgagctgg gcccctatgc cctggacaac    600
gacagcctct ttgtcaatgg tttcactcat cggagctctg tgtccaccac cagcactcct    660
gggacccccca cagtgtatct gggagcatct aagactccag cctcgatatt tggcccttca    720
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctccctca agttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc cccgggctgg acatacagca gctttactgg   1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca acaagcagct ccagcaccca gcacttctac   2340
ctgaatttca ccatcaccaa cctaccatat tcccaggaca aagcccagcc aggcaccacc   2400
aattaccaga ggaacaaaag gaatattgag gatgcggcac cacaccgggg tggactccct   2460
gtgtaacttc tcgccactgg ctcggagagt agacagagtt gccatctatg aggaatttct   2520
gcggatgacc cggaatggta cccagctgca gaacttcacc ctggacagga gcagtgtcct   2580
tgtggatggg tattttccca acagaaatga gcccttaact gggaattctg accttccctt   2640
ctgggctgtc atcctcatcg gcttggcagg actcctggga ctcatcacat gcctgatctg   2700
cggtgtcctg gtgaccaccc gccggcggaa gaaggaagga gaatacaacg tccagcaaca   2760
gtgcccaggc tactaccagt cacacctaga cctggaggat ctgcaatgac tggaacttgc   2820
```

-continued cggtgcctgg ggtgcctttc ccccagccag ggtccaaaga agcttggctg gggcagaaat 2880
aaaccatatt ggtcggaaaa aaaaaaaaaa aaaaaaaaaa aaaaaaaaaa aaaaaaaaaa 2940
aaa 2943

<210> SEQ ID NO 386
<211> LENGTH: 2608
<212> TYPE: DNA
<213> ORGANISM: Homo sapiens

<400> SEQUENCE: 386
gttcaagagc accagtgttg gccctctgta ctctggctgc agactgactt tgctcaggcc 60
tgaaaaggat gggacagcca ctggagtgga tgccatctgc acccaccacc ctgaccccaa 120
aagccctagg ctggacagag agcagctgta ttgggagctg agccagctga cccacaatat 180
cactgagctg ggcccctatg ccctggacaa cgacagcctc tttgtcaatg gtttcactca 240
tcggagctct gtgtccacca ccagcactcc tgggaccccc acagtgtatc tgggagcatc 300
taagactcca gcctcgatat ttggcccttc agctgccagc catctcctga tactattcac 360
cctcaacttc accatcacta acctgcggta tgaggagaac atgtggcctg gctccaggaa 420
gttcaacact acagagaggg tccttcaggg cctgctaagg cccttgttca agaacaccag 480
tgttggccct ctgtactctg gctgcaggct gaccttgctc aggccagaga aagatgggga 540
agccaccgga gtggatgcca tctgcaccca ccgccctgac cccacaggcc ctgggctgga 600
cagagagcag ctgtatttgg agctgagcca gctgacccac agcatcactg agctgggccc 660
ctacacactg gacagggaca gtctctatgt caatggtttc acccatcgga gctctgtacc 720
caccaccagc accggggtgg tcagcgagga gccattcaca ctgaacttca ccatcaacaa 780
cctgcgctac atggcggaca tgggccaacc cggctccctc aagttcaaca tcacagacaa 840
cgtcatgaag cacctgctca gtcctttgtt ccagaggagc agcctgggtg cacggtacac 900
aggctgcagg gtcatcgcac taaggtctgt gaagaacggt gctgagacac gggtggacct 960
cctctgcacc tacctgcagc ccctcagcgg cccaggtctg cctatcaagc aggtgttcca 1020
tgagctgagc cagcagaccc atggcatcac ccggctgggc ccctactctc tggacaaaga 1080
cagcctctac cttaacggtt acaatgaacc tggtccagat gagcctccta caactcccaa 1140
gccagccacc acattcctgc ctcctctgtc agaagccaca acagccatgg ggtaccacct 1200
gaagaccctc acactcaact tcaccatctc caatctccag tattcaccag atatgggcaa 1260
gggctcagct acattcaact ccaccgaggg ggtccttcag cacctgctca gacccttgtt 1320
ccagaagagc agcatgggcc ccttctactt gggttgccaa ctgatctccc tcaggcctga 1380
gaaggatggg gcagccactg gtgtggacac cacctgcacc taccaccctg accctgtggg 1440
ccccgggctg gacatacagc agctttactg ggagctgagt cagctgaccc atggtgtcac 1500
ccaactgggc ttctatgtcc tggacaggga tagcctcttc atcaatggct atgcacccca 1560
gaatttatca atccggggcg agtaccagat aaatttccac attgtcaact ggaacctcag 1620
taatccagac cccacatcct cagagtacat caccctgctg agggacatcc aggacaaggt 1680
caccacactc tacaaaggca gtcaactaca tgacacattc cgcttctgcc tggtcaccaa 1740
cttgacgatg gactccgtgt tggtcactgt caaggcattg ttctcctcca atttggaccc 1800
cagcctggtg gagcaagtct ttctagataa gaccctgaat gcctcattcc attggctggg 1860
ctccacctac cagttggtgg acatccatgt gacagaaatg gagtcatcag tttatcaacc 1920

-continued

```
aacaagcagc tccagcaccc agcacttcta cctgaatttc accatcacca acctaccata   1980

ttcccaggac aaagcccagc caggcaccac caattaccag aggaacaaaa ggaatattga   2040

ggatgcgctc aaccaactct tccgaaacag cagcatcaag agttattttt ctgactgtca   2100

agtttcaaca ttcaggtctg tccccaacag gcaccacacc ggggtggact ccctgtgtaa   2160

cttctcgcca ctggctcgga gagtagacag agttgccatc tatgaggaat ttctgcggat   2220

gacccggaat ggtacccagc tgcagaactt caccctggac aggagcagtg tccttgtgga   2280

tgggtatttt cccaacagaa atgagccctt aactgggaat tctgaccttc ccttctgggc   2340

tgtcatcctc atcggcttgg caggactcct gggactcatc acatgcctga tctgcggtgt   2400

cctggtgacc acccgccggc ggaagaagga aggagaatac aacgtccagc aacagtgccc   2460

aggctactac cagtcacacc tagacctgga ggatctgcaa tgactggaac ttgccggtgc   2520

ctggggtgcc tttcccccag ccagggtcca aagaagcttg gctggggcag aaataaacca   2580

tattggtcgg acacaaaaaa aaaaaaaa                                       2608
```

<210> SEQ ID NO 387
<211> LENGTH: 1761
<212> TYPE: DNA
<213> ORGANISM: Homo sapiens

<400> SEQUENCE: 387

```
ctgaacttca ccatcaacaa cctgcgctac atggcggaca tgggccaacc cggctccctc     60

aagttcaaca tcacagacaa cgtcatgaag cacctgctca gtcctttgtt ccagaggagc    120

agcctgggtg cacggtacac aggctgcagg gtcatcgcac taaggtctgt gaagaacggt    180

gctgagacac gggtggacct cctctgcagg taggtgcaga ggaggtccac ggcatcaccc    240

ggctgggccc ctactctctg gacaaagaca gcctctacct taacgctccc aagccagcca    300

ccacattcct gcctcctctg tcagaagcca caacagccat ggggtaccac ctgaagaccc    360

tcacactcaa cttcaccatc tccaatctcc agtattcacc agatatgggc aagggctcag    420

ctacattcaa ctccaccgag ggggtccttc agcacctgct cagacccttg ttccagaaga    480

gcagcatggg ccccttctac ttgggttgcc aactgatctc cctcaggcct gagaaggatg    540

gggcagccac tggtgtggac accacctgca cctaccaccc tgaccctgtg ggccccgggc    600

tggacataca gcagctttac tgggagctga gtcagctgac ccatggtgtc acccaactgg    660

gcttctatgt cctggacagg gatagcctct tcatcaatgg ctatgcaccc cagaatttat    720

caatccgggg cgagtaccag ataaatttcc acattgtcaa ctggaacctc agtaatccag    780

accccacatc ctcagagtac atcaccctgc tgagggacat ccaggacaag gtcaccacac    840

tctacaaagg cagtcaacta catgacacat tccgcttctg cctggtcacc aacttgacga    900

tggactccgt gttggtcact gtcaaggcat tgttctcctc caatttggac cccagcctgg    960

tggagcaagt ctttctagat aagaccctga atgcctcatt ccattggctg ggctccacct   1020

accagttggt ggacatccat gtgacagaaa tggagtcatc agtttatcaa ccaacaagca   1080

gctccagcac ccagcacttc tacctgaatt tcaccatcac caacctacca tattcccagg   1140

acaaagccca gccaggcacc accaattacc agaggaacaa aaggaatatt gaggatgcgc   1200

tcaaccaact cttccgaaac agcagcatca agagttattt ttctgactgt caagtttcaa   1260

cattcaggtc tgtccccaac aggcaccaca ccggggtgga ctccctgtgt aacttctcgc   1320

cactggctcg gagagtagac agagttgcca tctatgagga atttctgcgg atgacccgga   1380

atggtaccca gctgcagaac ttcaccctgg acaggagcag tgtccttgtg gatgggtatt   1440
```

-continued

```
ttcccaacag aaatgagccc ttaactggga attctgacct tcccttctgg gctgtcatcc   1500

tcatcggctt ggcaggactc ctgggactca tcacatgcct gatctgcggt gtcctggtga   1560

ccacccgccg gcggaagaag gaaggagaat acaacgtcca gcaacagtgc ccaggctact   1620

accagtcaca cctagacctg gaggatctgc aatgactgga acttgccggt gcctggggtg   1680

cctttccccc agccagggtc caaagaagct tggctggggc agaaataaac catattggtc   1740

ggacacaaaa aaaaaaaaaa a                                             1761
```

<210> SEQ ID NO 388
<211> LENGTH: 772
<212> TYPE: PRT
<213> ORGANISM: Homo sapiens

<400> SEQUENCE: 388

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
```

-continued 305 310 315 320

Pro Thr Thr Ser Thr Gly Val Val Ser Glu Glu Pro Phe Thr Leu Asn
325 330 335

Phe Thr Ile Asn Asn Leu Arg Tyr Met Ala Asp Met Gly Gln Pro Gly
340 345 350

Ser Leu Lys Phe Asn Ile Thr Asp Asn Val Met Lys His Leu Leu Ser
355 360 365

Pro Leu Phe Gln Arg Ser Ser Leu Gly Ala Arg Tyr Thr Gly Cys Arg
370 375 380

Val Ile Ala Leu Arg Ser Val Lys Asn Gly Ala Glu Thr Arg Val Asp
385 390 395 400

Leu Leu Cys Thr Tyr Leu Gln Pro Leu Ser Gly Pro Gly Leu Pro Ile
405 410 415

Lys Gln Val Phe His Glu Leu Ser Gln Gln Thr His Gly Ile Thr Arg
420 425 430

Leu Gly Pro Tyr Ser Leu Asp Lys Asp Ser Leu Tyr Leu Asn Gly Tyr
435 440 445

Asn Glu Pro Gly Pro Asp Glu Pro Pro Thr Thr Pro Lys Pro Ala Thr
450 455 460

Thr Phe Leu Pro Pro Leu Ser Glu Ala Thr Thr Ala Met Gly Tyr His
465 470 475 480

Leu Lys Thr Leu Thr Leu Asn Phe Thr Ile Ser Asn Leu Gln Tyr Ser
485 490 495

Pro Asp Met Gly Lys Gly Ser Ala Thr Phe Asn Ser Thr Glu Gly Val
500 505 510

Leu Gln His Leu Leu Arg Pro Leu Phe Gln Lys Ser Ser Met Gly Pro
515 520 525

Phe Tyr Leu Gly Cys Gln Leu Ile Ser Leu Arg Pro Glu Lys Asp Gly
530 535 540

Ala Ala Thr Gly Val Asp Thr Thr Cys Thr Tyr His Pro Asp Pro Val
545 550 555 560

Gly Pro Gly Leu Asp Ile Gln Gln Leu Tyr Trp Glu Leu Ser Gln Leu
565 570 575

Thr His Gly Val Thr Gln Leu Gly Phe Tyr Val Leu Asp Arg Asp Ser
580 585 590

Leu Phe Ile Asn Gly Tyr Ala Pro Gln Asn Leu Ser Ile Arg Gly Glu
595 600 605

Tyr Gln Ile Asn Phe His Ile Val Asn Trp Asn Leu Ser Asn Pro Asp
610 615 620

Pro Thr Ser Ser Glu Tyr Ile Thr Leu Leu Arg Asp Ile Gln Asp Lys
625 630 635 640

Val Thr Thr Leu Tyr Lys Gly Ser Gln Leu His Asp Thr Phe Arg Phe
645 650 655

Cys Leu Val Thr Asn Leu Thr Met Asp Ser Val Leu Val Thr Val Lys
660 665 670

Ala Leu Phe Ser Ser Asn Leu Asp Pro Ser Leu Val Glu Gln Val Phe
675 680 685

Leu Asp Lys Thr Leu Asn Ala Ser Phe His Trp Leu Gly Ser Thr Tyr
690 695 700

Gln Leu Val Asp Ile His Val Thr Glu Met Glu Ser Ser Val Tyr Gln
705 710 715 720

Pro Thr Ser Ser Ser Ser Thr Gln His Phe Tyr Leu Asn Phe Thr Ile
725 730 735

-continued

```
Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Ala Pro His Arg Gly
        755                 760                 765

Gly Leu Pro Val
    770


<210> SEQ ID NO 389
<211> LENGTH: 833
<212> TYPE: PRT
<213> ORGANISM: Homo sapiens

<400> SEQUENCE: 389

Phe Lys Ser Thr Ser Val Gly Pro Leu Tyr Ser Gly Cys Arg Leu Thr
 1               5                  10                  15

Leu Leu Arg Pro Glu Lys Asp Gly Thr Ala Thr Gly Val Asp Ala Ile
            20                  25                  30

Cys Thr His His Pro Asp Pro Lys Ser Pro Arg Leu Asp Arg Glu Gln
        35                  40                  45

Leu Tyr Trp Glu Leu Ser Gln Leu Thr His Asn Ile Thr Glu Leu Gly
    50                  55                  60

Pro Tyr Ala Leu Asp Asn Asp Ser Leu Phe Val Asn Gly Phe Thr His
65                  70                  75                  80

Arg Ser Ser Val Ser Thr Thr Ser Thr Pro Gly Thr Pro Thr Val Tyr
                85                  90                  95

Leu Gly Ala Ser Lys Thr Pro Ala Ser Ile Phe Gly Pro Ser Ala Ala
            100                 105                 110

Ser His Leu Leu Ile Leu Phe Thr Leu Asn Phe Thr Ile Thr Asn Leu
        115                 120                 125

Arg Tyr Glu Glu Asn Met Trp Pro Gly Ser Arg Lys Phe Asn Thr Thr
    130                 135                 140

Glu Arg Val Leu Gln Gly Leu Leu Arg Pro Leu Phe Lys Asn Thr Ser
145                 150                 155                 160

Val Gly Pro Leu Tyr Ser Gly Cys Arg Leu Thr Leu Leu Arg Pro Glu
                165                 170                 175

Lys Asp Gly Glu Ala Thr Gly Val Asp Ala Ile Cys Thr His Arg Pro
            180                 185                 190

Asp Pro Thr Gly Pro Gly Leu Asp Arg Glu Gln Leu Tyr Leu Glu Leu
        195                 200                 205

Ser Gln Leu Thr His Ser Ile Thr Glu Leu Gly Pro Tyr Thr Leu Asp
    210                 215                 220

Arg Asp Ser Leu Tyr Val Asn Gly Phe Thr His Arg Ser Ser Val Pro
225                 230                 235                 240

Thr Thr Ser Thr Gly Val Val Ser Glu Glu Pro Phe Thr Leu Asn Phe
                245                 250                 255

Thr Ile Asn Asn Leu Arg Tyr Met Ala Asp Met Gly Gln Pro Gly Ser
            260                 265                 270

Leu Lys Phe Asn Ile Thr Asp Asn Val Met Lys His Leu Leu Ser Pro
        275                 280                 285

Leu Phe Gln Arg Ser Ser Leu Gly Ala Arg Tyr Thr Gly Cys Arg Val
    290                 295                 300

Ile Ala Leu Arg Ser Val Lys Asn Gly Ala Glu Thr Arg Val Asp Leu
305                 310                 315                 320

Leu Cys Thr Tyr Leu Gln Pro Leu Ser Gly Pro Gly Leu Pro Ile Lys
```

-continued

```
                325                 330                 335

Gln Val Phe His Glu Leu Ser Gln Gln Thr His Gly Ile Thr Arg Leu
            340                 345                 350

Gly Pro Tyr Ser Leu Asp Lys Asp Ser Leu Tyr Leu Asn Gly Tyr Asn
        355                 360                 365

Glu Pro Gly Pro Asp Glu Pro Pro Thr Thr Pro Lys Pro Ala Thr Thr
    370                 375                 380

Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
            420                 425                 430

Gln His Leu Leu Arg Pro Leu Phe Gln Lys Ser Ser Met Gly Pro Phe
        435                 440                 445

Tyr Leu Gly Cys Gln Leu Ile Ser Leu Arg Pro Glu Lys Asp Gly Ala
    450                 455                 460

Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
                485                 490                 495

His Gly Val Thr Gln Leu Gly Phe Tyr Val Leu Asp Arg Asp Ser Leu
            500                 505                 510

Phe Ile Asn Gly Tyr Ala Pro Gln Asn Leu Ser Ile Arg Gly Glu Tyr
        515                 520                 525

Gln Ile Asn Phe His Ile Val Asn Trp Asn Leu Ser Asn Pro Asp Pro
    530                 535                 540

Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
                565                 570                 575

Leu Val Thr Asn Leu Thr Met Asp Ser Val Leu Val Thr Val Lys Ala
            580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Ser Thr Gln His Phe Tyr Leu Asn Phe Thr Ile Thr
                645                 650                 655

Asn Leu Pro Tyr Ser Gln Asp Lys Ala Gln Pro Gly Thr Thr Asn Tyr
            660                 665                 670

Gln Arg Asn Lys Arg Asn Ile Glu Asp Ala Leu Asn Gln Leu Phe Arg
        675                 680                 685

Asn Ser Ser Ile Lys Ser Tyr Phe Ser Asp Cys Gln Val Ser Thr Phe
    690                 695                 700

Arg Ser Val Pro Asn Arg His His Thr Gly Val Asp Ser Leu Cys Asn
705                 710                 715                 720

Phe Ser Pro Leu Ala Arg Arg Val Asp Arg Val Ala Ile Tyr Glu Glu
                725                 730                 735

Phe Leu Arg Met Thr Arg Asn Gly Thr Gln Leu Gln Asn Phe Thr Leu
            740                 745                 750
```

-continued

```
Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800

Leu Val Thr Thr Arg Arg Arg Lys Lys Glu Gly Glu Tyr Asn Val Gln
                805                 810                 815

Gln Gln Cys Pro Gly Tyr Tyr Gln Ser His Leu Asp Leu Glu Asp Leu
            820                 825                 830

Gln


<210> SEQ ID NO 390
<211> LENGTH: 438
<212> TYPE: PRT
<213> ORGANISM: Homo sapiens

<400> SEQUENCE: 390

Met Gly Tyr His Leu Lys Thr Leu Thr Leu Asn Phe Thr Ile Ser Asn
 1               5                  10                  15

Leu Gln Tyr Ser Pro Asp Met Gly Lys Gly Ser Ala Thr Phe Asn Ser
            20                  25                  30

Thr Glu Gly Val Leu Gln His Leu Leu Arg Pro Leu Phe Gln Lys Ser
        35                  40                  45

Ser Met Gly Pro Phe Tyr Leu Gly Cys Gln Leu Ile Ser Leu Arg Pro
    50                  55                  60

Glu Lys Asp Gly Ala Ala Thr Gly Val Asp Thr Thr Cys Thr Tyr His
65                  70                  75                  80

Pro Asp Pro Val Gly Pro Gly Leu Asp Ile Gln Gln Leu Tyr Trp Glu
                85                  90                  95

Leu Ser Gln Leu Thr His Gly Val Thr Gln Leu Gly Phe Tyr Val Leu
            100                 105                 110

Asp Arg Asp Ser Leu Phe Ile Asn Gly Tyr Ala Pro Gln Asn Leu Ser
        115                 120                 125

Ile Arg Gly Glu Tyr Gln Ile Asn Phe His Ile Val Asn Trp Asn Leu
    130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
    210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
        275                 280                 285
```

-continued

```
Asn Gln Leu Phe Arg Asn Ser Ser Ile Lys Ser Tyr Phe Ser Asp Cys
    290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335

Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Phe
        355                 360                 365

Pro Asn Arg Asn Glu Pro Leu Thr Gly Asn Ser Asp Leu Pro Phe Trp
    370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                405                 410                 415

Glu Tyr Asn Val Gln Gln Gln Cys Pro Gly Tyr Tyr Gln Ser His Leu
            420                 425                 430

Asp Leu Glu Asp Leu Gln
        435
```

<210> SEQ ID NO 391
<211> LENGTH: 2627
<212> TYPE: DNA
<213> ORGANISM: Homo sapiens

<400> SEQUENCE: 391

```
ccacgcgtcc gcccacgcgt ccggaaggca gcggcagctc cactcagcca gtacccagat     60

acgctgggaa ccttccccag ccatggcttc cctggggcag atcctcttct ggagcataat    120

tagcatcatc attattctgg ctggagcaat tgcactcatc attggctttg gtatttcagg    180

gagacactcc atcacagtca ctactgtcgc ctcagctggg aacattgggg aggatggaat    240

cctgagctgc acttttgaac ctgacatcaa ctttctgat atcgtgatac aatggctgaa    300

ggaaggtgtt ttaggcttgg tccatgagtt caaagaaggc aaagatgagc tgtcggagca    360

ggatgaaatg ttcagaggcc ggacagcagt gtttgctgat caagtgatag ttggcaatgc    420

ctctttgcgg ctgaaaaacg tgcaactcac agatgctggc acctacaaat gttatatcat    480

cacttctaaa ggcaagggga atgctaacct tgagtataaa actggagcct tcagcatgcc    540

ggaagtgaat gtggactata atgccagctc agagaccttg cggtgtgagg ctccccgatg    600

gttcccccag cccacagtgg tctgggcatc ccaagttgac cagggagcca acttctcgga    660

agtctccaat accagctttg agctgaactc tgagaatgtg accatgaagg ttgtgtctgt    720

gctctacaat gttacgatca acaacacata ctcctgtatg attgaaaatg acattgccaa    780

agcaacaggg gatatcaaag tgacagaatc ggagatcaaa aggcggagtc acctacagct    840

gctaaactca aaggcttctc tgtgtgtctc ttctttcttt gccatcagct gggcacttct    900

gcctctcagc ccttacctga tgctaaaata atgtgccttg gccacaaaaa agcatgcaaa    960

gtcattgtta caacagggat ctacagaact atttcaccac cagatatgac ctagttttat   1020

atttctggga ggaaatgaat tcatatctag aagtctggag tgagcaaaca agagcaagaa   1080

acaaaaagaa gccaaaagca gaaggctcca atatgaacaa gataaatcta tcttcaaaga   1140

catattagaa gttgggaaaa taattcatgt gaactagaca agtgtgttaa gagtgataag   1200
```

-continued

```
taaaatgcac gtggagacaa gtgcatcccc agatctcagg gacctccccc tgcctgtcac   1260
ctggggagtg agaggacagg atagtgcatg ttctttgtct ctgaattttt agttatatgt   1320
gctgtaatgt tgctctgagg aagcccctgg aaagtctatc ccaacatatc cacatcttat   1380
attccacaaa ttaagctgta gtatgtaccc taagacgctg ctaattgact gccacttcgc   1440
aactcagggg cggctgcatt ttagtaatgg gtcaaatgat tcacttttta tgatgcttcc   1500
aaaggtgcct tggcttctct tcccaactga caaatgccaa agttgagaaa aatgatcata   1560
attttagcat aaacagagca gtcggcgaca ccgattttat aaataaactg agcaccttct   1620
ttttaaacaa acaaatgcgg gtttatttct cagatgatgt tcatccgtga atggtccagg   1680
gaaggacctt tcaccttgac tatatggcat tatgtcatca caagctctga ggcttctcct   1740
ttccatcctg cgtggacagc taagacctca gttttcaata gcatctagag cagtgggact   1800
cagctggggt gatttcgccc cccatctccg ggggaatgtc tgaagacaat tttggttacc   1860
tcaatgaggg agtggaggag gatacagtgc tactaccaac tagtggataa aggccaggga   1920
tgctgctcaa cctcctacca tgtacaggac gtctccccat tacaactacc caatccgaag   1980
tgtcaactgt gtcaggacta agaaaccctg gttttgagta gaaaagggcc tggaaagagg   2040
ggagccaaca aatctgtctg cttcctcaca ttagtcattg gcaaataagc attctgtctc   2100
tttggctgct gcctcagcac agagagccag aactctatcg ggcaccagga taacatctct   2160
cagtgaacag agttgacaag gcctatggga aatgcctgat gggattatct tcagcttgtt   2220
gagcttctaa gtttctttcc cttcattcta ccctgcaagc caagttctgt aagagaaatg   2280
cctgagttct agctcaggtt ttcttactct gaatttagat ctccagaccc ttcctggcca   2340
caattcaaat taaggcaaca aacatatacc ttccatgaag cacacacaga cttttgaaag   2400
caaggacaat gactgcttga attgaggcct tgaggaatga agctttgaag gaaaagaata   2460
ctttgtttcc agccccttc ccacactctt catgtgttaa ccactgcctt cctggacctt   2520
ggagccacgg tgactgtatt acatgttgtt atagaaaact gattttagag ttctgatcgt   2580
tcaagagaat gattaaatat acatttccta caccaaaaaa aaaaaaa                 2627
```

<210> SEQ ID NO 392
<211> LENGTH: 309
<212> TYPE: PRT
<213> ORGANISM: Homo sapiens

<400> SEQUENCE: 392

```
His Ala Ser Ala His Ala Ser Gly Arg Gln Arg Gln Leu His Ser Ala
 1               5                  10                  15

Ser Thr Gln Ile Arg Trp Glu Pro Ser Pro Ala Met Ala Ser Leu Gly
            20                  25                  30

Gln Ile Leu Phe Trp Ser Ile Ile Ser Ile Ile Ile Ile Leu Ala Gly
        35                  40                  45

Ala Ile Ala Leu Ile Ile Gly Phe Gly Ile Ser Gly Arg His Ser Ile
    50                  55                  60

Thr Val Thr Thr Val Ala Ser Ala Gly Asn Ile Gly Glu Asp Gly Ile
65                  70                  75                  80

Leu Ser Cys Thr Phe Glu Pro Asp Ile Lys Leu Ser Asp Ile Val Ile
                85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
        115                 120                 125
```

-continued

```
Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175

Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
    290                 295                 300

Tyr Leu Met Leu Lys
305


<210> SEQ ID NO 393
<211> LENGTH: 282
<212> TYPE: PRT
<213> ORGANISM: Homo sapiens

<400> SEQUENCE: 393

Met Ala Ser Leu Gly Gln Ile Leu Phe Trp Ser Ile Ile Ser Ile Ile
 1               5                  10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
```

-continued

```
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280


<210> SEQ ID NO 394
<211> LENGTH: 20
<212> TYPE: PRT
<213> ORGANISM: Homo sapiens

<400> SEQUENCE: 394

Met Ala Ser Leu Gly Gln Ile Leu Phe Trp Ser Ile Ile Ser Ile Ile
 1               5                  10                  15

Ile Ile Leu Ala
            20


<210> SEQ ID NO 395
<211> LENGTH: 20
<212> TYPE: PRT
<213> ORGANISM: Homo sapiens

<400> SEQUENCE: 395

Ile Ile Ile Leu Ala Gly Ala Ile Ala Leu Ile Ile Gly Phe Gly Ile
 1               5                  10                  15

Ser Gly Arg His
            20


<210> SEQ ID NO 396
<211> LENGTH: 20
<212> TYPE: PRT
<213> ORGANISM: Homo sapiens

<400> SEQUENCE: 396

Ile Ser Gly Arg His Ser Ile Thr Val Thr Thr Val Ala Ser Ala Gly
 1               5                  10                  15

Asn Ile Gly Glu
            20


<210> SEQ ID NO 397
<211> LENGTH: 20
<212> TYPE: PRT
<213> ORGANISM: Homo sapiens

<400> SEQUENCE: 397

Gly Asn Ile Gly Glu Asp Gly Ile Leu Ser Cys Thr Phe Glu Pro Asp
 1               5                  10                  15

Ile Lys Leu Ser
            20


<210> SEQ ID NO 398
<211> LENGTH: 20
```

-continued

<212> TYPE: PRT
<213> ORGANISM: Homo sapiens

<400> SEQUENCE: 398

Asp Ile Lys Leu Ser Asp Ile Val Ile Gln Trp Leu Lys Glu Gly Val
1 5 10 15

Leu Gly Leu Val
20

<210> SEQ ID NO 399
<211> LENGTH: 20
<212> TYPE: PRT
<213> ORGANISM: Homo sapiens

<400> SEQUENCE: 399

Val Leu Gly Leu Val His Glu Phe Lys Glu Gly Lys Asp Glu Leu Ser
1 5 10 15

Glu Gln Asp Glu
20

<210> SEQ ID NO 400
<211> LENGTH: 20
<212> TYPE: PRT
<213> ORGANISM: Homo sapiens

<400> SEQUENCE: 400

Ser Glu Gln Asp Glu Met Phe Arg Gly Arg Thr Ala Val Phe Ala Asp
1 5 10 15

Gln Val Ile Val
20

<210> SEQ ID NO 401
<211> LENGTH: 20
<212> TYPE: PRT
<213> ORGANISM: Homo sapiens

<400> SEQUENCE: 401

Asp Gln Val Ile Val Gly Asn Ala Ser Leu Arg Leu Lys Asn Val Gln
1 5 10 15

Leu Thr Asp Ala
20

<210> SEQ ID NO 402
<211> LENGTH: 21
<212> TYPE: PRT
<213> ORGANISM: Homo sapiens

<400> SEQUENCE: 402

Val Gln Leu Thr Asp Ala Gly Thr Tyr Lys Cys Tyr Ile Ile Thr Ser
1 5 10 15

Lys Gly Lys Gly Asn
20

<210> SEQ ID NO 403
<211> LENGTH: 20
<212> TYPE: PRT
<213> ORGANISM: Homo sapiens

<400> SEQUENCE: 403

Lys Gly Lys Gly Asn Ala Asn Leu Glu Tyr Lys Thr Gly Ala Phe Ser
1 5 10 15

Met Pro Glu Val

-continued

20

<210> SEQ ID NO 404
<211> LENGTH: 20
<212> TYPE: PRT
<213> ORGANISM: Homo sapiens

<400> SEQUENCE: 404

Ser Met Pro Glu Val Asn Val Asp Tyr Asn Ala Ser Ser Glu Thr Leu
1 5 10 15

Arg Cys Glu Ala
20

<210> SEQ ID NO 405
<211> LENGTH: 20
<212> TYPE: PRT
<213> ORGANISM: Homo sapiens

<400> SEQUENCE: 405

Leu Arg Cys Glu Ala Pro Arg Trp Phe Pro Gln Pro Thr Val Val Trp
1 5 10 15

Ala Ser Gln Val
20

<210> SEQ ID NO 406
<211> LENGTH: 20
<212> TYPE: PRT
<213> ORGANISM: Homo sapiens

<400> SEQUENCE: 406

Trp Ala Ser Gln Val Asp Gln Gly Ala Asn Phe Ser Glu Val Ser Asn
1 5 10 15

Thr Ser Phe Glu
20

<210> SEQ ID NO 407
<211> LENGTH: 20
<212> TYPE: PRT
<213> ORGANISM: Homo sapiens

<400> SEQUENCE: 407

Asn Thr Ser Phe Glu Leu Asn Ser Glu Asn Val Thr Met Lys Val Val
1 5 10 15

Ser Val Leu Tyr
20

<210> SEQ ID NO 408
<211> LENGTH: 20
<212> TYPE: PRT
<213> ORGANISM: Homo sapiens

<400> SEQUENCE: 408

Val Ser Val Leu Tyr Asn Val Thr Ile Asn Asn Thr Tyr Ser Cys Met
1 5 10 15

Ile Glu Asn Asp
20

<210> SEQ ID NO 409
<211> LENGTH: 20
<212> TYPE: PRT
<213> ORGANISM: Homo sapiens

<400> SEQUENCE: 409

-continued

```
Met Ile Glu Asn Asp Ile Ala Lys Ala Thr Gly Asp Ile Lys Val Thr
 1               5                  10                  15

Glu Ser Glu Ile
            20


<210> SEQ ID NO 410
<211> LENGTH: 20
<212> TYPE: PRT
<213> ORGANISM: Homo sapiens

<400> SEQUENCE: 410

Thr Glu Ser Glu Ile Lys Arg Arg Ser His Leu Gln Leu Leu Asn Ser
 1               5                  10                  15

Lys Ala Ser Leu
            20


<210> SEQ ID NO 411
<211> LENGTH: 20
<212> TYPE: PRT
<213> ORGANISM: Homo sapiens

<400> SEQUENCE: 411

Ser Lys Ala Ser Leu Cys Val Ser Ser Phe Phe Ala Ile Ser Trp Ala
 1               5                  10                  15

Leu Leu Pro Leu
            20


<210> SEQ ID NO 412
<211> LENGTH: 20
<212> TYPE: PRT
<213> ORGANISM: Homo sapiens

<400> SEQUENCE: 412

Ser Ser Phe Phe Ala Ile Ser Trp Ala Leu Leu Pro Leu Ser Pro Tyr
 1               5                  10                  15

Leu Met Leu Lys
            20


<210> SEQ ID NO 413
<211> LENGTH: 35
<212> TYPE: PRT
<213> ORGANISM: Homo sapiens

<400> SEQUENCE: 413

Ile Ser Gly Arg His Ser Ile Thr Val Thr Thr Val Ala Ser Ala Gly
 1               5                  10                  15

Asn Ile Gly Glu Asp Gly Ile Leu Ser Cys Thr Phe Glu Pro Asp Ile
            20                  25                  30

Lys Leu Ser
        35


<210> SEQ ID NO 414
<211> LENGTH: 35
<212> TYPE: PRT
<213> ORGANISM: Homo sapiens

<400> SEQUENCE: 414

Val Leu Gly Leu Val His Glu Phe Lys Glu Gly Lys Asp Glu Leu Ser
 1               5                  10                  15

Glu Gln Asp Glu Met Phe Arg Gly Arg Thr Ala Val Phe Ala Asp Gln
            20                  25                  30
```

-continued

```
Val Ile Val
        35


<210> SEQ ID NO 415
<211> LENGTH: 65
<212> TYPE: PRT
<213> ORGANISM: Homo sapiens

<400> SEQUENCE: 415

Lys Gly Lys Gly Asn Ala Asn Leu Glu Tyr Lys Thr Gly Ala Phe Ser
 1               5                  10                  15

Met Pro Glu Val Asn Val Asp Tyr Asn Ala Ser Ser Glu Thr Leu Arg
            20                  25                  30

Cys Glu Ala Pro Arg Trp Phe Pro Gln Pro Thr Val Val Trp Ala Ser
        35                  40                  45

Gln Val Asp Gln Gly Ala Asn Phe Ser Glu Val Ser Asn Thr Ser Phe
    50                  55                  60

Glu
65


<210> SEQ ID NO 416
<211> LENGTH: 10
<212> TYPE: PRT
<213> ORGANISM: Homo sapiens

<400> SEQUENCE: 416

Lys Leu Ser Asp Ile Val Ile Gln Trp Leu
 1               5                  10


<210> SEQ ID NO 417
<211> LENGTH: 10
<212> TYPE: PRT
<213> ORGANISM: Homo sapiens

<400> SEQUENCE: 417

Ser Leu Gly Gln Ile Leu Phe Trp Ser Ile
 1               5                  10


<210> SEQ ID NO 418
<211> LENGTH: 10
<212> TYPE: PRT
<213> ORGANISM: Homo sapiens

<400> SEQUENCE: 418

Leu Leu Asn Ser Lys Ala Ser Leu Cys Val
 1               5                  10


<210> SEQ ID NO 419
<211> LENGTH: 10
<212> TYPE: PRT
<213> ORGANISM: Homo sapiens

<400> SEQUENCE: 419

Ser Leu Cys Val Ser Ser Phe Phe Ala Ile
 1               5                  10


<210> SEQ ID NO 420
<211> LENGTH: 10
<212> TYPE: PRT
<213> ORGANISM: Homo sapiens

<400> SEQUENCE: 420
```

-continued

```
Val Leu Tyr Asn Val Thr Ile Asn Asn Thr
 1              5                   10


<210> SEQ ID NO 421
<211> LENGTH: 10
<212> TYPE: PRT
<213> ORGANISM: Homo sapiens

<400> SEQUENCE: 421

Ile Leu Phe Trp Ser Ile Ile Ser Ile Ile
 1              5                   10


<210> SEQ ID NO 422
<211> LENGTH: 10
<212> TYPE: PRT
<213> ORGANISM: Homo sapiens

<400> SEQUENCE: 422

Leu Leu Pro Leu Ser Pro Tyr Leu Met Leu
 1              5                   10


<210> SEQ ID NO 423
<211> LENGTH: 10
<212> TYPE: PRT
<213> ORGANISM: Homo sapiens

<400> SEQUENCE: 423

Cys Met Ile Glu Asn Asp Ile Ala Lys Ala
 1              5                   10


<210> SEQ ID NO 424
<211> LENGTH: 10
<212> TYPE: PRT
<213> ORGANISM: Homo sapiens

<400> SEQUENCE: 424

Lys Thr Gly Ala Phe Ser Met Pro Glu Val
 1              5                   10


<210> SEQ ID NO 425
<211> LENGTH: 10
<212> TYPE: PRT
<213> ORGANISM: Homo sapiens

<400> SEQUENCE: 425

Trp Ala Leu Leu Pro Leu Ser Pro Tyr Leu
 1              5                   10


<210> SEQ ID NO 426
<211> LENGTH: 10
<212> TYPE: PRT
<213> ORGANISM: Homo sapiens

<400> SEQUENCE: 426

Ile Ile Leu Ala Gly Ala Ile Ala Leu Ile
 1              5                   10


<210> SEQ ID NO 427
<211> LENGTH: 10
<212> TYPE: PRT
<213> ORGANISM: Homo sapiens

<400> SEQUENCE: 427

Gln Leu Thr Asp Ala Gly Thr Tyr Lys Cys
 1              5                   10
```

<210> SEQ ID NO 428
<211> LENGTH: 10
<212> TYPE: PRT
<213> ORGANISM: Homo sapiens

<400> SEQUENCE: 428

```
Ala Leu Leu Pro Leu Ser Pro Tyr Leu Met
 1               5                   10
```

<210> SEQ ID NO 429
<211> LENGTH: 10
<212> TYPE: PRT
<213> ORGANISM: Homo sapiens

<400> SEQUENCE: 429

```
Gln Leu Leu Asn Ser Lys Ala Ser Leu Cys
 1               5                   10
```

<210> SEQ ID NO 430
<211> LENGTH: 10
<212> TYPE: PRT
<213> ORGANISM: Homo sapiens

<400> SEQUENCE: 430

```
Ile Leu Ser Cys Thr Phe Glu Pro Asp Ile
 1               5                   10
```

<210> SEQ ID NO 431
<211> LENGTH: 10
<212> TYPE: PRT
<213> ORGANISM: Homo sapiens

<400> SEQUENCE: 431

```
Trp Leu Lys Glu Gly Val Leu Gly Leu Val
 1               5                   10
```

<210> SEQ ID NO 432
<211> LENGTH: 10
<212> TYPE: PRT
<213> ORGANISM: Homo sapiens

<400> SEQUENCE: 432

```
Leu Gln Leu Leu Asn Ser Lys Ala Ser Leu
 1               5                   10
```

<210> SEQ ID NO 433
<211> LENGTH: 10
<212> TYPE: PRT
<213> ORGANISM: Homo sapiens

<400> SEQUENCE: 433

```
Gln Ile Leu Phe Trp Ser Ile Ile Ser Ile
 1               5                   10
```

<210> SEQ ID NO 434
<211> LENGTH: 10
<212> TYPE: PRT
<213> ORGANISM: Homo sapiens

<400> SEQUENCE: 434

```
Gly Ile Ser Gly Arg His Ser Ile Thr Val
 1               5                   10
```

-continued

<210> SEQ ID NO 435
<211> LENGTH: 10
<212> TYPE: PRT
<213> ORGANISM: Homo sapiens

<400> SEQUENCE: 435

Phe Glu Pro Asp Ile Lys Leu Ser Asp Ile
1 5 10

<210> SEQ ID NO 436
<211> LENGTH: 9
<212> TYPE: PRT
<213> ORGANISM: Homo sapiens

<400> SEQUENCE: 436

Ala Leu Leu Pro Leu Ser Pro Tyr Leu
1 5

<210> SEQ ID NO 437
<211> LENGTH: 9
<212> TYPE: PRT
<213> ORGANISM: Homo sapiens

<400> SEQUENCE: 437

Ser Leu Cys Val Ser Ser Phe Phe Ala
1 5

<210> SEQ ID NO 438
<211> LENGTH: 9
<212> TYPE: PRT
<213> ORGANISM: Homo sapiens

<400> SEQUENCE: 438

Ile Leu Phe Trp Ser Ile Ile Ser Ile
1 5

<210> SEQ ID NO 439
<211> LENGTH: 9
<212> TYPE: PRT
<213> ORGANISM: Homo sapiens

<400> SEQUENCE: 439

Gln Leu Leu Asn Ser Lys Ala Ser Leu
1 5

<210> SEQ ID NO 440
<211> LENGTH: 9
<212> TYPE: PRT
<213> ORGANISM: Homo sapiens

<400> SEQUENCE: 440

Lys Val Val Ser Val Leu Tyr Asn Val
1 5

<210> SEQ ID NO 441
<211> LENGTH: 9
<212> TYPE: PRT
<213> ORGANISM: Homo sapiens

<400> SEQUENCE: 441

Ile Leu Ala Gly Ala Ile Ala Leu Ile
1 5

<210> SEQ ID NO 442
<211> LENGTH: 9

-continued

<212> TYPE: PRT
<213> ORGANISM: Homo sapiens

<400> SEQUENCE: 442

Trp Leu Lys Glu Gly Val Leu Gly Leu
 1               5

<210> SEQ ID NO 443
<211> LENGTH: 9
<212> TYPE: PRT
<213> ORGANISM: Homo sapiens

<400> SEQUENCE: 443

Ile Ile Leu Ala Gly Ala Ile Ala Leu
 1               5

<210> SEQ ID NO 444
<211> LENGTH: 9
<212> TYPE: PRT
<213> ORGANISM: Homo sapiens

<400> SEQUENCE: 444

Asn Val Thr Met Lys Val Val Ser Val
 1               5

<210> SEQ ID NO 445
<211> LENGTH: 9
<212> TYPE: PRT
<213> ORGANISM: Homo sapiens

<400> SEQUENCE: 445

Glu Met Phe Arg Gly Arg Thr Ala Val
 1               5

<210> SEQ ID NO 446
<211> LENGTH: 9
<212> TYPE: PRT
<213> ORGANISM: Homo sapiens

<400> SEQUENCE: 446

Ala Val Phe Ala Asp Gln Val Ile Val
 1               5

<210> SEQ ID NO 447
<211> LENGTH: 9
<212> TYPE: PRT
<213> ORGANISM: Homo sapiens

<400> SEQUENCE: 447

Leu Leu Pro Leu Ser Pro Tyr Leu Met
 1               5

<210> SEQ ID NO 448
<211> LENGTH: 9
<212> TYPE: PRT
<213> ORGANISM: Homo sapiens

<400> SEQUENCE: 448

Leu Leu Asn Ser Lys Ala Ser Leu Cys
 1               5

<210> SEQ ID NO 449
<211> LENGTH: 9
<212> TYPE: PRT
<213> ORGANISM: Homo sapiens

<400> SEQUENCE: 449

Val Ile Gln Trp Leu Lys Glu Gly Val
 1               5

<210> SEQ ID NO 450
<211> LENGTH: 9
<212> TYPE: PRT
<213> ORGANISM: Homo sapiens

<400> SEQUENCE: 450

Ala Ile Ser Trp Ala Leu Leu Pro Leu
 1               5

<210> SEQ ID NO 451
<211> LENGTH: 9
<212> TYPE: PRT
<213> ORGANISM: Homo sapiens

<400> SEQUENCE: 451

Ser Leu Gly Gln Ile Leu Phe Trp Ser
 1               5

<210> SEQ ID NO 452
<211> LENGTH: 9
<212> TYPE: PRT
<213> ORGANISM: Homo sapiens

<400> SEQUENCE: 452

Ile Ala Leu Ile Ile Gly Phe Gly Ile
 1               5

<210> SEQ ID NO 453
<211> LENGTH: 9
<212> TYPE: PRT
<213> ORGANISM: Homo sapiens

<400> SEQUENCE: 453

Cys Thr Phe Glu Pro Asp Ile Lys Leu
 1               5

<210> SEQ ID NO 454
<211> LENGTH: 9
<212> TYPE: PRT
<213> ORGANISM: Homo sapiens

<400> SEQUENCE: 454

Ile Val Gly Asn Ala Ser Leu Arg Leu
 1               5

<210> SEQ ID NO 455
<211> LENGTH: 9
<212> TYPE: PRT
<213> ORGANISM: Homo sapiens

<400> SEQUENCE: 455

Gly Gln Ile Leu Phe Trp Ser Ile Ile
 1               5

<210> SEQ ID NO 456
<211> LENGTH: 3447
<212> TYPE: DNA
<213> ORGANISM: Homo sapiens

<400> SEQUENCE: 456

-continued

```
atgcccttgt tcaagaacac cagtgtcagc tctctgtact ctggttgcag actgaccttg     60
ctcaggcctg agaaggatgg ggcagccacc agagtggatg ctgtctgcac ccatcgtcct    120
gaccccaaaa gccctggact ggacagagag cggctgtact ggaagctgag ccagctgacc    180
cacggcatca ctgagctggg cccctacacc ctggacaggc acagtctcta tgtcaatggt    240
ttcacccatc agagctctat gacgaccacc agaactcctg atacctccac aatgcacctg    300
gcaacctcga gaactccagc ctccctgtct ggacctacga ccgccagccc tctcctggtg    360
ctattcacaa ttaacttcac catcactaac ctgcggtatg aggagaacat gcatcaccct    420
ggctctagaa agtttaacac cacggagaga gtccttcagg gtctgctcag gcctgtgttc    480
aagaacacca gtgttggccc tctgtactct ggctgcagac tgaccttgct caggcccaag    540
aaggatgggg cagccaccaa agtggatgcc atctgcacct accgccctga tcccaaaagc    600
cctggactgg acagagagca gctatactgg gagctgagcc agctaaccca cagcatcact    660
gagctgggcc cctacaccct ggacagggac agtctctatg tcaatggttt cacacagcgg    720
agctctgtgc ccaccactag cattcctggg acccccacag tggacctggg aacatctggg    780
actccagttt ctaaacctgg tccctcggct gccagccctc tcctggtgct attcactctc    840
aacttcacca tcaccaacct gcggtatgag gagaacatgc agcaccctgg ctccaggaag    900
ttcaacacca cggagagggt ccttcagggc ctgctcaggt ccctgttcaa gagcaccagt    960
gttggccctc tgtactctgg ctgcagactg actttgctca ggcctgaaaa ggatgggaca   1020
gccactggag tggatgccat ctgcacccac caccctgacc ccaaaagccc taggctggac   1080
agagagcagc tgtattggga gctgagccag ctgacccaca atatcactga gctgggccac   1140
tatgccctgg acaacgacag cctctttgtc aatggtttca ctcatcggag ctctgtgtcc   1200
accaccagca ctcctgggac ccccacagtg tatctgggag catctaagac tccagcctcg   1260
atatttggcc cttcagctgc cagccatctc ctgatactat tcaccctcaa cttcaccatc   1320
actaacctgc ggtatgagga gaacatgtgg cctggctcca ggaagttcaa cactacagag   1380
agggtccttc agggcctgct aaggcccttg ttcaagaaca ccagtgttgg ccctctgtac   1440
tctggctcca ggctgacctt gctcaggcca gagaaagatg gggaagccac cggagtggat   1500
gccatctgca cccaccgccc tgaccccaca ggccctgggc tggacagaga gcagctgtat   1560
ttggagctga gccagctgac ccacagcatc actgagctgg gcccctacac actggacagg   1620
gacagtctct atgtcaatgg tttcacccat cggagctctg tacccaccac cagcaccggg   1680
gtggtcagcg aggagccatt cacactgaac ttcaccatca acaacctgcg ctacatggcg   1740
gacatgggcc aacccggctc cctcaagttc aacatcacag acaacgtcat gaagcacctg   1800
ctcagtcctt tgttccagag gagcagcctg ggtgcacggt acacaggctg cagggtcatc   1860
gcactaaggt ctgtgaagaa cggtgctgag acacgggtgg acctcctctg cacctacctg   1920
cagcccctca gcggcccagg tctgcctatc aagcaggtgt tccatgagct gagccagcag   1980
acccatggca tcacccggct gggcccctac tctctggaca aagacagcct ctaccttaac   2040
ggttacaatg aacctggtct agatgagcct cctacaactc ccaagccagc caccacattc   2100
ctgcctcctc tgtcagaagc cacaacagcc atggggtacc acctgaagac cctcacactc   2160
aacttcacca tctccaatct ccagtattca ccagatatgg gcaagggctc agctacattc   2220
aactccaccg aggggtcct  tcagcacctg ctcagaccct tgttccagaa gagcagcatg   2280
ggccccttct acttgggttg ccaactgatc tccctcaggc ctgagaagga tggggcagcc   2340
```

-continued

```
actggtgtgg acaccacctg cacctaccac cctgaccctg tgggccccgg gctggacata   2400
cagcagcttt actgggagct gagtcagctg acccatggtg tcacccaact gggcttctat   2460
gtcctggaca gggatagcct cttcatcaat ggctatgcac cccagaattt atcaatccgg   2520
ggcgagtacc agataaattt ccacattgtc aactggaacc tcagtaatcc agaccccaca   2580
tcctcagagt acatcaccct gctgagggac atccaggaca aggtcaccac actctacaaa   2640
ggcagtcaac tacatgacac attccgcttc tgcctggtca ccaacttgac gatggactcc   2700
gtgttggtca ctgtcaaggc attgttctcc tccaatttgg accccagcct ggtggagcaa   2760
gtctttctag ataagaccct gaatgcctca ttccattggc tgggctccac ctaccagttg   2820
gtggacatcc atgtgacaga aatggagtca tcagtttatc aaccaacaag cagctccagc   2880
acccagcact tctacccgaa tttcaccatc accaacctac catattccca ggacaaagcc   2940
cagccaggca ccaccaatta ccagaggaac aaaaggaata ttgaggatgc gctcaaccaa   3000
ctcttccgaa acagcagcat caagagttat ttttctgact gtcaagtttc aacattcagg   3060
tctgtcccca acaggcacca caccggggtg gactccctgt gtaacttctc gccactggct   3120
cggagagtag acagagttgc catctatgag gaatttctgc ggatgacccg gaatggtacc   3180
cagctgcaga acttcaccct ggacaggagc agtgtccttg tggatgggta ttctcccaac   3240
agaaatgagc ccttaactgg gaattctgac cttcccttct gggctgtcat cttcatcggc   3300
ttggcaggac tcctgggact catcacatgc ctgatctgcg gtgtcctggt gaccacccgc   3360
cggcggaaga aggaaggaga atacaacgtc cagcaacagt gcccaggcta ctaccagtca   3420
cacctagacc tggaggatct gcaatga                                      3447
```

<210> SEQ ID NO 457
<211> LENGTH: 3557
<212> TYPE: DNA
<213> ORGANISM: Homo sapiens

<400> SEQUENCE: 457

```
gagagggtcc ttcagggtct gcttatgccc ttgttcaaga acaccagtgt cagctctctg     60
tactctggtt gcagactgac cttgctcagg cctgagaagg atggggcagc caccagagtg    120
gatgctgtct gcacccatcg tcctgacccc aaaagccctg gactggacag agagcggctg    180
tactggaagc tgagccagct gacccacggc atcactgagc tgggcccccta caccctggac    240
aggcacagtc tctatgtcaa tggtttcacc catcagagct ctatgacgac caccagaact    300
cctgatacct ccacaatgca cctggcaacc tcgagaactc cagcctccct gtctggacct    360
acgaccgcca gccctctcct ggtgctattc acaattaact tcaccatcac taacctgcgg    420
tatgaggaga acatgcatca ccctggctct agaaagttta acaccacgga gagagtcctt    480
cagggtctgc tcaggcctgt gttcaagaac accagtgttg gccctctgta ctctggctgc    540
agactgacct tgctcaggcc caagaaggat ggggcagcca ccaaagtgga tgccatctgc    600
acctaccgcc ctgatcccaa aagccctgga ctggacagag agcagctata ctgggagctg    660
agccagctaa cccacagcat cactgagctg ggcccctaca ccctggacag ggacagtctc    720
tatgtcaatg gtttcacaca gcggagctct gtgcccacca ctagcattcc tgggaccccc    780
acagtggacc tgggaacatc tgggactcca gtttctaaac ctggtccctc ggctgccagc    840
cctctcctgg tgctattcac tctcaacttc accatcacca acctgcggta tgaggagaac    900
atgcagcacc ctggctccag gaagttcaac accacggaga gggtccttca gggcctgctc    960
aggtccctgt tcaagagcac cagtgttggc cctctgtact ctggctgcag actgactttg   1020
```

-continued

```
ctcaggcctg aaaaggatgg gacagccact ggagtggatg ccatctgcac ccaccaccct   1080
gaccccaaaa gccctaggct ggacagagag cagctgtatt gggagctgag ccagctgacc   1140
cacaatatca ctgagctggg ccactatgcc ctggacaacg acagcctctt tgtcaatggt   1200
ttcactcatc ggagctctgt gtccaccacc agcactcctg ggacccccac agtgtatctg   1260
ggagcatcta agactccagc ctcgatattt ggcccttcag ctgccagcca tctcctgata   1320
ctattcaccc tcaacttcac catcactaac ctgcggtatg aggagaacat gtggcctggc   1380
tccaggaagt tcaacactac agagagggtc cttcagggcc tgctaaggcc cttgttcaag   1440
aacaccagtg ttggccctct gtactctggc tccaggctga ccttgctcag gccagagaaa   1500
gatggggaag ccaccggagt ggatgccatc tgcacccacc gccctgaccc cacaggccct   1560
gggctggaca gagagcagct gtatttggag ctgagccagc tgacccacag catcactgag   1620
ctgggcccct acacactgga cagggacagt ctctatgtca atggtttcac ccatcggagc   1680
tctgtaccca ccaccagcac cggggtggtc agcgaggagc cattcacact gaacttcacc   1740
atcaacaacc tgcgctacat ggcggacatg ggccaacccg gctccctcaa gttcaacatc   1800
acagacaacg tcatgaagca cctgctcagt cctttgttcc agaggagcag cctgggtgca   1860
cggtacacag gctgcagggt catcgcacta aggtctgtga agaacggtgc tgagacacgg   1920
gtggacctcc tctgcaccta cctgcagccc ctcagcggcc caggtctgcc tatcaagcag   1980
gtgttccatg agctgagcca gcagacccat ggcatcaccc ggctgggccc ctactctctg   2040
gacaaagaca gcctctacct taacggttac aatgaacctg gtctagatga gcctcctaca   2100
actcccaagc cagccaccac attcctgcct cctctgtcag aagccacaac agccatgggg   2160
taccacctga agaccctcac actcaacttc accatctcca atctccagta ttcaccagat   2220
atgggcaagg gctcagctac attcaactcc accgaggggg tccttcagca cctgctcaga   2280
cccttgttcc agaagagcag catgggcccc ttctacttgg gttgccaact gatctccctc   2340
aggcctgaga aggatggggc agccactggt gtggacacca cctgcaccta ccaccctgac   2400
cctgtgggcc ccgggctgga catacagcag ctttactggg agctgagtca gctgacccat   2460
ggtgtcaccc aactgggctt ctatgtcctg gacagggata gcctcttcat caatggctat   2520
gcaccccaga atttatcaat ccggggcgag taccagataa atttccacat tgtcaactgg   2580
aacctcagta atccagaccc cacatcctca gagtacatca ccctgctgag ggacatccag   2640
gacaaggtca ccacactcta caaaggcagt caactacatg acacattccg cttctgcctg   2700
gtcaccaact tgacgatgga ctccgtgttg gtcactgtca aggcattgtt ctcctccaat   2760
ttggacccca gcctggtgga gcaagtcttt ctagataaga ccctgaatgc ctcattccat   2820
tggctgggct ccacctacca gttggtggac atccatgtga cagaaatgga gtcatcagtt   2880
tatcaaccaa caagcagctc cagcacccag cacttctacc cgaatttcac catcaccaac   2940
ctaccatatt cccaggacaa agcccagcca ggcaccacca attaccagag gaacaaaagg   3000
aatattgagg atgcgctcaa ccaactcttc cgaaacagca gcatcaagag ttatttttct   3060
gactgtcaag tttcaacatt caggtctgtc cccaacaggc accacaccgg ggtggactcc   3120
ctgtgtaact tctcgccact ggctcggaga gtagacagag ttgccatcta tgaggaattt   3180
ctgcggatga cccggaatgg tacccagctg cagaacttca ccctggacag gagcagtgtc   3240
cttgtggatg ggtattctcc caacagaaat gagcccttaa ctgggaattc tgaccttccc   3300
ttctgggctg tcatcttcat cggcttggca ggactcctgg gactcatcac atgcctgatc   3360
```

-continued

```
tgcggtgtcc tggtgaccac ccgccggcgg aagaaggaag gagaatacaa cgtccagcaa   3420

cagtgcccag gctactacca gtcacaccta gacctggagg atctgcaatg actggaactt   3480

gccggtgcct ggggtgcctt tcccccagcc agggtccaaa gaagcttggc tggggcagaa   3540

ataaaccata ttggtcg                                                  3557


<210> SEQ ID NO 458
<211> LENGTH: 1148
<212> TYPE: PRT
<213> ORGANISM: Homo sapiens

<400> SEQUENCE: 458

Met Pro Leu Phe Lys Asn Thr Ser Val Ser Ser Leu Tyr Ser Gly Cys
1               5                   10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Thr
    50                  55                  60

Glu Leu Gly Pro Tyr Thr Leu Asp Arg His Ser Leu Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125

Thr Asn Leu Arg Tyr Glu Glu Asn Met His His Pro Gly Ser Arg Lys
    130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
        195                 200                 205

Tyr Trp Glu Leu Ser Gln Leu Thr His Ser Ile Thr Glu Leu Gly Pro
    210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg Ser Leu Phe Lys Ser Thr Ser
305                 310                 315                 320

Val Gly Pro Leu Tyr Ser Gly Cys Arg Leu Thr Leu Leu Arg Pro Glu
                325                 330                 335
```

-continued

```
Lys Asp Gly Thr Ala Thr Gly Val Asp Ala Ile Cys Thr His His Pro
            340                 345                 350

Asp Pro Lys Ser Pro Arg Leu Asp Arg Glu Gln Leu Tyr Trp Glu Leu
        355                 360                 365

Ser Gln Leu Thr His Asn Ile Thr Glu Leu Gly His Tyr Ala Leu Asp
    370                 375                 380

Asn Asp Ser Leu Phe Val Asn Gly Phe Thr His Arg Ser Ser Val Ser
385                 390                 395                 400

Thr Thr Ser Thr Pro Gly Thr Pro Thr Val Tyr Leu Gly Ala Ser Lys
                405                 410                 415

Thr Pro Ala Ser Ile Phe Gly Pro Ser Ala Ala Ser His Leu Leu Ile
            420                 425                 430

Leu Phe Thr Leu Asn Phe Thr Ile Thr Asn Leu Arg Tyr Glu Glu Asn
        435                 440                 445

Met Trp Pro Gly Ser Arg Lys Phe Asn Thr Thr Glu Arg Val Leu Gln
    450                 455                 460

Gly Leu Leu Arg Pro Leu Phe Lys Asn Thr Ser Val Gly Pro Leu Tyr
465                 470                 475                 480

Ser Gly Ser Arg Leu Thr Leu Leu Arg Pro Glu Lys Asp Gly Glu Ala
                485                 490                 495

Thr Gly Val Asp Ala Ile Cys Thr His Arg Pro Asp Pro Thr Gly Pro
            500                 505                 510

Gly Leu Asp Arg Glu Gln Leu Tyr Leu Glu Leu Ser Gln Leu Thr His
        515                 520                 525

Ser Ile Thr Glu Leu Gly Pro Tyr Thr Leu Asp Arg Asp Ser Leu Tyr
    530                 535                 540

Val Asn Gly Phe Thr His Arg Ser Ser Val Pro Thr Thr Ser Thr Gly
545                 550                 555                 560

Val Val Ser Glu Glu Pro Phe Thr Leu Asn Phe Thr Ile Asn Asn Leu
                565                 570                 575

Arg Tyr Met Ala Asp Met Gly Gln Pro Gly Ser Leu Lys Phe Asn Ile
            580                 585                 590

Thr Asp Asn Val Met Lys His Leu Leu Ser Pro Leu Phe Gln Arg Ser
        595                 600                 605

Ser Leu Gly Ala Arg Tyr Thr Gly Cys Arg Val Ile Ala Leu Arg Ser
    610                 615                 620

Val Lys Asn Gly Ala Glu Thr Arg Val Asp Leu Leu Cys Thr Tyr Leu
625                 630                 635                 640

Gln Pro Leu Ser Gly Pro Gly Leu Pro Ile Lys Gln Val Phe His Glu
                645                 650                 655

Leu Ser Gln Gln Thr His Gly Ile Thr Arg Leu Gly Pro Tyr Ser Leu
            660                 665                 670

Asp Lys Asp Ser Leu Tyr Leu Asn Gly Tyr Asn Glu Pro Gly Leu Asp
        675                 680                 685

Glu Pro Pro Thr Thr Pro Lys Pro Ala Thr Thr Phe Leu Pro Pro Leu
    690                 695                 700

Ser Glu Ala Thr Thr Ala Met Gly Tyr His Leu Lys Thr Leu Thr Leu
705                 710                 715                 720

Asn Phe Thr Ile Ser Asn Leu Gln Tyr Ser Pro Asp Met Gly Lys Gly
                725                 730                 735

Ser Ala Thr Phe Asn Ser Thr Glu Gly Val Leu Gln His Leu Leu Arg
            740                 745                 750

Pro Leu Phe Gln Lys Ser Ser Met Gly Pro Phe Tyr Leu Gly Cys Gln
```

-continued

```
        755                 760                 765

Leu Ile Ser Leu Arg Pro Glu Lys Asp Gly Ala Ala Thr Gly Val Asp
    770                 775                 780

Thr Thr Cys Thr Tyr His Pro Asp Pro Val Gly Pro Gly Leu Asp Ile
785                 790                 795                 800

Gln Gln Leu Tyr Trp Glu Leu Ser Gln Leu Thr His Gly Val Thr Gln
                805                 810                 815

Leu Gly Phe Tyr Val Leu Asp Arg Asp Ser Leu Phe Ile Asn Gly Tyr
            820                 825                 830

Ala Pro Gln Asn Leu Ser Ile Arg Gly Glu Tyr Gln Ile Asn Phe His
        835                 840                 845

Ile Val Asn Trp Asn Leu Ser Asn Pro Asp Pro Thr Ser Ser Glu Tyr
    850                 855                 860

Ile Thr Leu Leu Arg Asp Ile Gln Asp Lys Val Thr Thr Leu Tyr Lys
865                 870                 875                 880

Gly Ser Gln Leu His Asp Thr Phe Arg Phe Cys Leu Val Thr Asn Leu
                885                 890                 895

Thr Met Asp Ser Val Leu Val Thr Val Lys Ala Leu Phe Ser Ser Asn
            900                 905                 910

Leu Asp Pro Ser Leu Val Glu Gln Val Phe Leu Asp Lys Thr Leu Asn
        915                 920                 925

Ala Ser Phe His Trp Leu Gly Ser Thr Tyr Gln Leu Val Asp Ile His
    930                 935                 940

Val Thr Glu Met Glu Ser Ser Val Tyr Gln Pro Thr Ser Ser Ser Ser
945                 950                 955                 960

Thr Gln His Phe Tyr Pro Asn Phe Thr Ile Thr Asn Leu Pro Tyr Ser
                965                 970                 975

Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
        995                 1000                1005

Ser Tyr Phe Ser Asp Cys Gln Val Ser Thr Phe Arg Ser Val Pro Asn
    1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
                1045                1050                1055

Arg Asn Gly Thr Gln Leu Gln Asn Phe Thr Leu Asp Arg Ser Ser Val
            1060                1065                1070

Leu Val Asp Gly Tyr Ser Pro Asn Arg Asn Glu Pro Leu Thr Gly Asn
        1075                1080                1085

Ser Asp Leu Pro Phe Trp Ala Val Ile Phe Ile Gly Leu Ala Gly Leu
    1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Gln Cys Pro Gly
                1125                1130                1135

Tyr Tyr Gln Ser His Leu Asp Leu Glu Asp Leu Gln
            1140                1145
```

<210> SEQ ID NO 459
<211> LENGTH: 1156
<212> TYPE: PRT
<213> ORGANISM: Homo sapiens -continued

<400> SEQUENCE: 459

```
Glu Arg Val Leu Gln Gly Leu Leu Met Pro Leu Phe Lys Asn Thr Ser
 1               5                  10                  15

Val Ser Ser Leu Tyr Ser Gly Cys Arg Leu Thr Leu Leu Arg Pro Glu
            20                  25                  30

Lys Asp Gly Ala Ala Thr Arg Val Asp Ala Val Cys Thr His Arg Pro
        35                  40                  45

Asp Pro Lys Ser Pro Gly Leu Asp Arg Glu Arg Leu Tyr Trp Lys Leu
    50                  55                  60

Ser Gln Leu Thr His Gly Ile Thr Glu Leu Gly Pro Tyr Thr Leu Asp
65                  70                  75                  80

Arg His Ser Leu Tyr Val Asn Gly Phe Thr His Gln Ser Ser Met Thr
                85                  90                  95

Thr Thr Arg Thr Pro Asp Thr Ser Thr Met His Leu Ala Thr Ser Arg
            100                 105                 110

Thr Pro Ala Ser Leu Ser Gly Pro Thr Thr Ala Ser Pro Leu Leu Val
        115                 120                 125

Leu Phe Thr Ile Asn Phe Thr Ile Thr Asn Leu Arg Tyr Glu Glu Asn
    130                 135                 140

Met His His Pro Gly Ser Arg Lys Phe Asn Thr Thr Glu Arg Val Leu
145                 150                 155                 160

Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Lys Val Asp Ala Ile Cys Thr Tyr Arg Pro Asp Pro Lys Ser
        195                 200                 205

Pro Gly Leu Asp Arg Glu Gln Leu Tyr Trp Glu Leu Ser Gln Leu Thr
    210                 215                 220

His Ser Ile Thr Glu Leu Gly Pro Tyr Thr Leu Asp Arg Asp Ser Leu
225                 230                 235                 240

Tyr Val Asn Gly Phe Thr Gln Arg Ser Ser Val Pro Thr Thr Ser Ile
                245                 250                 255

Pro Gly Thr Pro Thr Val Asp Leu Gly Thr Ser Gly Thr Pro Val Ser
            260                 265                 270

Lys Pro Gly Pro Ser Ala Ala Ser Pro Leu Leu Val Leu Phe Thr Leu
        275                 280                 285

Asn Phe Thr Ile Thr Asn Leu Arg Tyr Glu Glu Asn Met Gln His Pro
    290                 295                 300

Gly Ser Arg Lys Phe Asn Thr Thr Glu Arg Val Leu Gln Gly Leu Leu
305                 310                 315                 320

Arg Ser Leu Phe Lys Ser Thr Ser Val Gly Pro Leu Tyr Ser Gly Cys
                325                 330                 335

Arg Leu Thr Leu Leu Arg Pro Glu Lys Asp Gly Thr Ala Thr Gly Val
            340                 345                 350

Asp Ala Ile Cys Thr His His Pro Asp Pro Lys Ser Pro Arg Leu Asp
        355                 360                 365

Arg Glu Gln Leu Tyr Trp Glu Leu Ser Gln Leu Thr His Asn Ile Thr
    370                 375                 380

Glu Leu Gly His Tyr Ala Leu Asp Asn Asp Ser Leu Phe Val Asn Gly
385                 390                 395                 400

Phe Thr His Arg Ser Ser Val Ser Thr Thr Ser Thr Pro Gly Thr Pro
```

-continued

```
                405                 410                 415

Thr Val Tyr Leu Gly Ala Ser Lys Thr Pro Ala Ser Ile Phe Gly Pro
            420                 425                 430

Ser Ala Ala Ser His Leu Leu Ile Leu Phe Thr Leu Asn Phe Thr Ile
        435                 440                 445

Thr Asn Leu Arg Tyr Glu Glu Asn Met Trp Pro Gly Ser Arg Lys Phe
    450                 455                 460

Asn Thr Thr Glu Arg Val Leu Gln Gly Leu Leu Arg Pro Leu Phe Lys
465                 470                 475                 480

Asn Thr Ser Val Gly Pro Leu Tyr Ser Gly Ser Arg Leu Thr Leu Leu
                485                 490                 495

Arg Pro Glu Lys Asp Gly Glu Ala Thr Gly Val Asp Ala Ile Cys Thr
            500                 505                 510

His Arg Pro Asp Pro Thr Gly Pro Gly Leu Asp Arg Glu Gln Leu Tyr
        515                 520                 525

Leu Glu Leu Ser Gln Leu Thr His Ser Ile Thr Glu Leu Gly Pro Tyr
    530                 535                 540

Thr Leu Asp Arg Asp Ser Leu Tyr Val Asn Gly Phe Thr His Arg Ser
545                 550                 555                 560

Ser Val Pro Thr Thr Ser Thr Gly Val Val Ser Glu Glu Pro Phe Thr
                565                 570                 575

Leu Asn Phe Thr Ile Asn Asn Leu Arg Tyr Met Ala Asp Met Gly Gln
            580                 585                 590

Pro Gly Ser Leu Lys Phe Asn Ile Thr Asp Asn Val Met Lys His Leu
        595                 600                 605

Leu Ser Pro Leu Phe Gln Arg Ser Ser Leu Gly Ala Arg Tyr Thr Gly
    610                 615                 620

Cys Arg Val Ile Ala Leu Arg Ser Val Lys Asn Gly Ala Glu Thr Arg
625                 630                 635                 640

Val Asp Leu Leu Cys Thr Tyr Leu Gln Pro Leu Ser Gly Pro Gly Leu
                645                 650                 655

Pro Ile Lys Gln Val Phe His Glu Leu Ser Gln Gln Thr His Gly Ile
            660                 665                 670

Thr Arg Leu Gly Pro Tyr Ser Leu Asp Lys Asp Ser Leu Tyr Leu Asn
        675                 680                 685

Gly Tyr Asn Glu Pro Gly Leu Asp Glu Pro Pro Thr Thr Pro Lys Pro
    690                 695                 700

Ala Thr Thr Phe Leu Pro Pro Leu Ser Glu Ala Thr Thr Ala Met Gly
705                 710                 715                 720

Tyr His Leu Lys Thr Leu Thr Leu Asn Phe Thr Ile Ser Asn Leu Gln
                725                 730                 735

Tyr Ser Pro Asp Met Gly Lys Gly Ser Ala Thr Phe Asn Ser Thr Glu
            740                 745                 750

Gly Val Leu Gln His Leu Leu Arg Pro Leu Phe Gln Lys Ser Ser Met
        755                 760                 765

Gly Pro Phe Tyr Leu Gly Cys Gln Leu Ile Ser Leu Arg Pro Glu Lys
    770                 775                 780

Asp Gly Ala Ala Thr Gly Val Asp Thr Thr Cys Thr Tyr His Pro Asp
785                 790                 795                 800

Pro Val Gly Pro Gly Leu Asp Ile Gln Gln Leu Tyr Trp Glu Leu Ser
                805                 810                 815

Gln Leu Thr His Gly Val Thr Gln Leu Gly Phe Tyr Val Leu Asp Arg
            820                 825                 830
```

-continued

Asp Ser Leu Phe Ile Asn Gly Tyr Ala Pro Gln Asn Leu Ser Ile Arg
        835                 840                 845

Gly Glu Tyr Gln Ile Asn Phe His Ile Val Asn Trp Asn Leu Ser Asn
    850                 855                 860

Pro Asp Pro Thr Ser Ser Glu Tyr Ile Thr Leu Leu Arg Asp Ile Gln
865                 870                 875                 880

Asp Lys Val Thr Thr Leu Tyr Lys Gly Ser Gln Leu His Asp Thr Phe
                885                 890                 895

Arg Phe Cys Leu Val Thr Asn Leu Thr Met Asp Ser Val Leu Val Thr
            900                 905                 910

Val Lys Ala Leu Phe Ser Ser Asn Leu Asp Pro Ser Leu Val Glu Gln
        915                 920                 925

Val Phe Leu Asp Lys Thr Leu Asn Ala Ser Phe His Trp Leu Gly Ser
    930                 935                 940

Thr Tyr Gln Leu Val Asp Ile His Val Thr Glu Met Glu Ser Ser Val
945                 950                 955                 960

Tyr Gln Pro Thr Ser Ser Ser Ser Thr Gln His Phe Tyr Pro Asn Phe
                965                 970                 975

Thr Ile Thr Asn Leu Pro Tyr Ser Gln Asp Lys Ala Gln Pro Gly Thr
            980                 985                 990

Thr Asn Tyr Gln Arg Asn Lys Arg Asn Ile Glu Asp Ala Leu Asn Gln
        995                 1000                1005

Leu Phe Arg Asn Ser Ser Ile Lys Ser Tyr Phe Ser Asp Cys Gln Val
    1010                1015                1020

Ser Thr Phe Arg Ser Val Pro Asn Arg His His Thr Gly Val Asp Ser
1025                1030                1035                1040

Leu Cys Asn Phe Ser Pro Leu Ala Arg Arg Val Asp Arg Val Ala Ile
                1045                1050                1055

Tyr Glu Glu Phe Leu Arg Met Thr Arg Asn Gly Thr Gln Leu Gln Asn
            1060                1065                1070

Phe Thr Leu Asp Arg Ser Ser Val Leu Val Asp Gly Tyr Ser Pro Asn
        1075                1080                1085

Arg Asn Glu Pro Leu Thr Gly Asn Ser Asp Leu Pro Phe Trp Ala Val
    1090                1095                1100

Ile Phe Ile Gly Leu Ala Gly Leu Leu Gly Leu Ile Thr Cys Leu Ile
1105                1110                1115                1120

Cys Gly Val Leu Val Thr Thr Arg Arg Arg Lys Lys Glu Gly Glu Tyr
                1125                1130                1135

Asn Val Gln Gln Gln Cys Pro Gly Tyr Tyr Gln Ser His Leu Asp Leu
            1140                1145                1150

Glu Asp Leu Gln
        1155

<210> SEQ ID NO 460
<211> LENGTH: 79
<212> TYPE: PRT
<213> ORGANISM: Homo sapiens

<400> SEQUENCE: 460

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser

-continued

```
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp
65                  70                  75


<210> SEQ ID NO 461
<211> LENGTH: 313
<212> TYPE: PRT
<213> ORGANISM: Homo sapiens

<400> SEQUENCE: 461

Met Pro Leu Phe Lys Asn Thr Ser Val Ser Ser Leu Tyr Ser Gly Cys
 1               5                  10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Thr
    50                  55                  60

Glu Leu Gly Pro Tyr Thr Leu Asp Arg His Ser Leu Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125

Thr Asn Leu Arg Tyr Glu Glu Asn Met His His Pro Gly Ser Arg Lys
    130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
        195                 200                 205

Tyr Trp Glu Leu Ser Gln Leu Thr His Ser Ile Thr Glu Leu Gly Pro
    210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg
305                 310


<210> SEQ ID NO 462
<211> LENGTH: 2996
```

-continued

<212> TYPE: DNA
<213> ORGANISM: Homo sapiens

<400> SEQUENCE: 462
cagccaccgg agtggatgcc atctgcaccc accgccctga ccccacaggc cctgggctgg 60
acagagagca gctgtatttg gagctgagcc agctgaccca cagcatcact gagctgggcc 120
cctacaccct ggacagggac agtctctatg tcaatggttt cacacagcgg agctctgtgc 180
ccaccactag cattcctggg acccccacag tggacctggg aacatctggg actccagttt 240
ctaaacctgg tccctcggct gccagccctc tcctggtgct attcactctc aacttcacca 300
tcaccaacct gcggtatgag gagaacatgc agcaccctgg ctccaggaag ttcaacacca 360
cggagagggt ccttcagggc ctggtccctg ttcaagagca ccagtgttgg ccctctgtac 420
tctggctgca gactgacttt gctcaggcct gaaaaggatg ggacagccac tggagtggat 480
gccatctgca cccaccaccc tgaccccaaa agccctaggc tggacagaga gcagctgtat 540
tgggagctga gccagctgac ccacaatatc actgagctgg gcccctatgc cctggacaac 600
gacagcctct ttgtcaatgg tttcactcat cggagctctg tgtccaccac cagcactcct 660
gggaccccca cagtgtatct gggagcatct aagactccag cctcgatatt tggcccttca 720
gctgccagcc atctcctgat actattcacc ctcaacttca ccatcactaa cctgcggtat 780
gaggagaaca tgtggcctgg ctccaggaag ttcaacacta cagagagggt ccttcagggc 840
ctgctaaggc ccttgttcaa gaacaccagt gttggccctc tgtactctgg ctgcaggctg 900
accttgctca ggccagagaa agatggggaa gccaccggag tggatgccat ctgcacccac 960
cgccctgacc ccacaggccc tgggctggac agagagcagc tgtatttgga gctgagccag 1020
ctgacccaca gcatcactga gctgggcccc tacacactgg acagggacag tctctatgtc 1080
aatggtttca cccatcggag ctctgtaccc accaccagca ccggggtggt cagcgaggag 1140
ccattcacac tgaacttcac catcaacaac ctgcgctaca tggcggacat gggccaaccc 1200
ggctccctca agttcaacat cacagacaac gtcatgaagc acctgctcag tcctttgttc 1260
cagaggagca gcctgggtgc acggtacaca ggctgcaggg tcatcgcact aaggtctgtg 1320
aagaacggtg ctgagacacg ggtggacctc ctctgcacct acctgcagcc cctcagcggc 1380
ccaggtctgc ctatcaagca ggtgttccat gagctgagcc agcagaccca tggcatcacc 1440
cggctgggcc cctactctct ggacaaagac agcctctacc ttaacggtta caatgaacct 1500
ggtccagatg agcctcctac aactcccaag ccagccacca cattcctgcc tcctctgtca 1560
gaagccacaa cagccatggg gtaccacctg aagaccctca cactcaactt caccatctcc 1620
aatctccagt attcaccaga tatgggcaag ggctcagcta cattcaactc caccgagggg 1680
gtccttcagc acctgctcag acccttgttc cagaagagca gcatgggccc cttctacttg 1740
ggttgccaac tgatctccct caggcctgag aaggatgggg cagccactgg tgtggacacc 1800
acctgcacct accaccctga ccctgtgggc cccgggctgg acatacagca gctttactgg 1860
gagctgagtc agctgaccca tggtgtcacc caactgggct tctatgtcct ggacagggat 1920
agcctcttca tcaatggcta tgcaccccag aatttatcaa tccggggcga gtaccagata 1980
aatttccaca ttgtcaactg gaacctcagt aatccagacc ccacatcctc agagtacatc 2040
accctgctga gggacatcca ggacaaggtc accacactct acaaaggcag tcaactacat 2100
gacacattcc gcttctgcct ggtcaccaac ttgacgatgg actccgtgtt ggtcactgtc 2160
aaggcattgt tctcctccaa tttggacccc agcctggtgg agcaagtctt tctagataag 2220

-continued

```
accctgaatg cctcattcca ttggctgggc tccacctacc agttggtgga catccatgtg   2280

acagaaatgg agtcatcagt ttatcaacca acaagcagct ccagcaccca gcacttctac   2340

ctgaatttca ccatcaccaa cctaccatat tcccaggaca aagcccagcc aggcaccacc   2400

aattaccaga ggaacaaaag gaatattgag gatgcgctca accaactctt ccgaaacagc   2460

agcatcaaga gttatttttc tgactgtcaa gtttcaacat tcaggtctgt ccccaacagg   2520

caccacaccg gggtggactc cctgtgtaac ttctcgccac tggctcggag agtagacaga   2580

gttgccatct atgaggaatt tctgcggatg acccggaatg gtacccagct gcagaacttc   2640

accctggaca ggagcagtgt ccttgtggat gggtattttc ccaacagaaa tgagccctta   2700

actgggaatt ctgaccttcc cttctgggct gtcatcctca tcggcttggc aggactcctg   2760

ggactcatca catgcctgat ctgcggtgtc ctggtgacca cccgccggcg gaagaaggaa   2820

ggagaataca acgtccagca acagtgccca ggctactacc agtcacacct agacctggag   2880

gatctgcaat gactggaact tgccggtgcc tggggtgcct ttcccccagc cagggtccaa   2940

agaagcttgg ctggggcaga aataaaccat attggtcgga cacaaaaaaa aaaaaa       2996
```

```
<210> SEQ ID NO 463
<211> LENGTH: 3557
<212> TYPE: DNA
<213> ORGANISM: Homo sapiens

<400> SEQUENCE: 463

gagagggtcc ttcagggtct gcttatgccc ttgttcaaga acaccagtgt cagctctctg     60

tactctggtt gcagactgac cttgctcagg cctgagaagg atggggcagc caccagagtg    120

gatgctgtct gcacccatcg tcctgacccc aaaagccctg gactggacag agagcggctg    180

tactggaagc tgagccagct gacccacggc atcactgagc tgggccccta caccctggac    240

aggcacagtc tctatgtcaa tggtttcacc catcagagct ctatgacgac caccagaact    300

cctgatacct ccacaatgca cctggcaacc tcgagaactc cagcctccct gtctggacct    360

acgaccgcca gccctctcct ggtgctattc acaattaact tcaccatcac taacctgcgg    420

tatgaggaga acatgcatca ccctggctct agaaagttta acaccacgga gagagtcctt    480

cagggtctgc tcaggcctgt gttcaagaac accagtgttg gccctctgta ctctggctgc    540

agactgacct tgctcaggcc caagaaggat ggggcagcca ccaaagtgga tgccatctgc    600

acctaccgcc ctgatcccaa aagccctgga ctggacagag agcagctata ctgggagctg    660

agccagctaa cccacagcat cactgagctg ggcccctaca ccctggacag ggacagtctc    720

tatgtcaatg gtttcacaca gcggagctct gtgcccacca ctagcattcc tgggaccccc    780

acagtggacc tgggaacatc tgggactcca gtttctaaac ctggtccctc ggctgccagc    840

cctctcctgg tgctattcac tctcaacttc accatcacca acctgcggta tgaggagaac    900

atgcagcacc ctggctccag gaagttcaac accacggaga gggtccttca gggcctgctc    960

aggtccctgt tcaagagcac cagtgttggc cctctgtact ctggctgcag actgactttg   1020

ctcaggcctg aaaaggatgg gacagccact ggagtggatg ccatctgcac ccaccaccct   1080

gaccccaaaa gccctaggct ggacagagag cagctgtatt gggagctgag ccagctgacc   1140

cacaatatca ctgagctggg ccactatgcc ctggacaacg acagcctctt tgtcaatggt   1200

ttcactcatc ggagctctgt gtccaccacc agcactcctg ggacccccac agtgtatctg   1260

ggagcatcta agactccagc ctcgatattt ggcccttcag ctgccagcca tctcctgata   1320

ctattcaccc tcaacttcac catcactaac ctgcggtatg aggagaacat gtggcctggc   1380
```

-continued

```
tccaggaagt tcaacactac agagagggtc cttcagggcc tgctaaggcc cttgttcaag   1440
aacaccagtg ttggccctct gtactctggc tccaggctga ccttgctcag gccagagaaa   1500
gatggggaag ccaccggagt ggatgccatc tgcacccacc gccctgaccc cacaggccct   1560
gggctggaca gagagcagct gtatttggag ctgagccagc tgacccacag catcactgag   1620
ctgggcccct acacactgga cagggacagt ctctatgtca atggtttcac ccatcggagc   1680
tctgtaccca ccaccagcac cggggtggtc agcgaggagc cattcacact gaacttcacc   1740
atcaacaacc tgcgctacat ggcggacatg ggccaacccg gctccctcaa gttcaacatc   1800
acagacaacg tcatgaagca cctgctcagt cctttgttcc agaggagcag cctgggtgca   1860
cggtacacag gctgcagggt catcgcacta aggtctgtga agaacggtgc tgagacacgg   1920
gtggacctcc tctgcaccta cctgcagccc ctcagcggcc caggtctgcc tatcaagcag   1980
gtgttccatg agctgagcca gcagacccat ggcatcaccc ggctgggccc ctactctctg   2040
gacaaagaca gcctctacct taacggttac aatgaacctg gtctagatga gcctcctaca   2100
actcccaagc cagccaccac attcctgcct cctctgtcag aagccacaac agccatgggg   2160
taccacctga agaccctcac actcaacttc accatctcca atctccagta ttcaccagat   2220
atgggcaagg gctcagctac attcaactcc accgaggggg tccttcagca cctgctcaga   2280
cccttgttcc agaagagcag catgggcccc ttctacttgg gttgccaact gatctccctc   2340
aggcctgaga aggatggggc agccactggt gtggacacca cctgcaccta ccaccctgac   2400
cctgtgggcc ccgggctgga catacagcag ctttactggg agctgagtca gctgacccat   2460
ggtgtcaccc aactgggctt ctatgtcctg gacagggata gcctcttcat caatggctat   2520
gcaccccaga atttatcaat ccggggcgag taccagataa atttccacat tgtcaactgg   2580
aacctcagta atccagaccc cacatcctca gagtacatca ccctgctgag ggacatccag   2640
gacaaggtca ccacactcta caaaggcagt caactacatg acacattccg cttctgcctg   2700
gtcaccaact tgacgatgga ctccgtgttg gtcactgtca aggcattgtt ctcctccaat   2760
ttggacccca gcctggtgga gcaagtcttt ctagataaga ccctgaatgc ctcattccat   2820
tggctgggct ccacctacca gttggtggac atccatgtga cagaaatgga gtcatcagtt   2880
tatcaaccaa caagcagctc cagcacccag cacttctacc cgaatttcac catcaccaac   2940
ctaccatatt cccaggacaa agcccagcca ggcaccacca attaccagag gaacaaaagg   3000
aatattgagg atgcgctcaa ccaactcttc cgaaacagca gcatcaagag ttatttttct   3060
gactgtcaag tttcaacatt caggtctgtc cccaacaggc accacaccgg ggtggactcc   3120
ctgtgtaact tctcgccact ggctcggaga gtagacagag ttgccatcta tgaggaattt   3180
ctgcggatga cccggaatgg tacccagctg cagaacttca ccctggacag gagcagtgtc   3240
cttgtggatg ggtattctcc caacagaaat gagcccttaa ctgggaattc tgaccttccc   3300
ttctgggctg tcatcttcat cggcttggca ggactcctgg gactcatcac atgcctgatc   3360
tgcggtgtcc tggtgaccac ccgccggcgg aagaaggaag gagaatacaa cgtccagcaa   3420
cagtgcccag gctactacca gtcacaccta gacctggagg atctgcaatg actggaactt   3480
gccggtgcct ggggtgcctt tcccccagcc agggtccaaa gaagcttggc tggggcagaa   3540
ataaaccata ttggtcg                                                  3557
```

<210> SEQ ID NO 464
<211> LENGTH: 2712
<212> TYPE: DNA

-continued

<213> ORGANISM: Homo sapiens

<400> SEQUENCE: 464
aggacatgcg tcaccctggc tccaggaagt tcaacaccac agagagggtc ctgcagggtc 60
tgcttggtcc cttgttcaag aactccagtg tcggccctct gtactctggc tgcagactga 120
tctctctcag gtctgagaag gatggggcag ccactggagt ggatgccatc tgcacccacc 180
accttaaccc tcaaagcctg gactggacag ggagcagctg tactggcagc tgagccagat 240
gaccaatggc atcaaagagc tgggccccta caccctggac cggaacagtc tctacgtcaa 300
tggtttcacc catcggagct ctgggctcac caccagcact ccttggactt ccacagttga 360
ccttggaacc tcagggactc catcccccgt ccccagcccc acaactgctg gccctctcct 420
ggtgccattc accctaaact tcaccatcac caacctgcag tatgaggagg acatgcatcg 480
ccctggatct aggaagttca acgccacaga gagggtcctg cagggtctgc ttagtcccat 540
attcaagaac tccagtgttg gccctctgta ctctggctgc agactgacct ctctcaggcc 600
cgagaaggat ggggcagcaa ctggaatgga tgctgtctgc ctctaccacc ctaatcccaa 660
aagacctggg ctggacagag agcagctgta ctgggagcta agccagctga cccacaacat 720
cactgagctg ggcccctaca gcctggacag ggacagtctc tatgtcaatg gtttcaccca 780
tcagaactct gtgcccacca ccagtactcc tgggacctcc acagtgtact gggcaaccac 840
tgggactcca tcctccttcc ccggccacac agagcctggc cctctcctga taccattcac 900
attcaacttt accatcacca acctgcatta tgaggaaaac atgcaacacc ctggttccag 960
gaagttcaac gccacagaga gggtcctgca gggtctgctt agtcccatat tcaagaactc 1020
cagtgttggc cctctgtact ctggctgcag actgacctct ctcaggcccg agaaggatgg 1080
ggcagcaact ggaatggatg ctgtctgtct ctaccgaccc taatcccatc ggacctgggc 1140
tggacagaga gcagctgtac tgggagctga gccagctgac ccacgacatc actgagctgg 1200
gcccctacag ccctggacag ggacagtctc tatgtcaatg gtttcaccca tcagaactct 1260
gtgcccacca ccagtactcc tgggacctcc acagtgtact gggcaaccac tgggactcca 1320
tcctccttcc ccggccacac agagcctggc cctctcctga taccattcac tttcaacttt 1380
accatcacca acctgcatta tgaggaaaac atgcaacacc tggttccagg aagttcaaca 1440
ccacggagag ggttctgcag ggtctgctca cgcccttgtt caagaacacc agtgttggcc 1500
ctctgtactc tggctgcaga ctgaccttgc tcagacctga gaagcaggag gcagccactg 1560
gagtggacac catctgcact caccgccttg accctctaaa ccctggactg gacagagagc 1620
agctatactg ggagctgagc aaactgaccc gtggcatcat cgagctgggc ccctacctcc 1680
tggacagagg cagtctctat gtcaatggtt tcacccatcg gaactttgtg cccatcacca 1740
gcactcctgg gacctccaca gtacacctag gaacctctga aactccatcc tccctaccta 1800
gacccatagt gcctggccct ctcctggtgc cattcaccct caacttcacc atcaccaact 1860
tgcagtatga ggaggccatg cgacaccctg gctccaggaa gttcaatacc acggagaggg 1920
tcctacaggg tctgctcagg cccttgttca agaataccag tatcggccct ctgtactcca 1980
gctgcagact gaccttgctc aggccagaga aggacaaggc agccaccaga gtggatgcca 2040
tctgtaccca ccaccctgac cctcaaagcc ctggactgaa cagagagcag ctgtactggg 2100
agctgagcca gctgacccac ggcatcactg agctgggccc ctacaccctg gacaggcaca 2160
gtctctatgt caatggtttc acccatcaga gccccatacc aaccaccagc actcctgata 2220
cctccacaat gcacctggga acctcgagaa ctccagcctc cctgtctgga cctacgaccg 2280

-continued ccagccctct cctggtgcta ttcacaatta acttcaccat cactaacctg cggtatgagg 2340
agaacatgca tcaccgctgg ctctagaaag tttaacacca cggagagagt ccttcagggt 2400
ctgctcaggc ctgtgttcaa agaacaccag tgttggccct ctgtactctg gctgcagact 2460
gaccttgctc aggcccgaga aggatggggc agccacgcaa agtggatgcc atctgcacct 2520
accgccctga tcccaaaagc cctggactgg acagagagca gctatactgg gagctgagcc 2580
agggtgatgc atgttctcct catatcgcag gttagtgatg gtgaagttaa ttgtgaatag 2640
caccaggaga gggctggcgg tcatgggtcc agacagggag cctggagttc tcgaggttgc 2700
caggtgcatg tc 2712

<210> SEQ ID NO 465
<211> LENGTH: 1175
<212> TYPE: DNA
<213> ORGANISM: Homo sapiens

<400> SEQUENCE: 465
gaggtatgct aactactact attatttagt aggctttgtt agaaacttct gttgttatag 60
tcaagggacg catggaaact ttttatatta ttctctcttt aaatcctgtt gcatatgttt 120
agaagtaggc cttttggaaa tatataaagt tctccacttt tgaacatgtt gtttctttcc 180
cacctccacg acagctgcca gccctctcct ggtgctattc actctcaact tcaccatcac 240
caacctgcgg tatgaggaga acatgcagca ccctggctcc aggaagttca acactacaga 300
gagggtcctt cagggcctgc taaggccctt gttcaagaac accagtgttg gccctctgta 360
ctctggctgc aggctgacct tgctcaggcc agagaaagat ggggaagcca ccggagtgga 420
tgccatctgc acccaccgcc ctgaccccac aggccctggg ctggacagag agcagctgta 480
tttggagctg agccagctga cccacagcat cactgagctg ggcccctaca cactggacag 540
ggacagtctc tatgtcaatg gtttcaccca tcggagctct gtacccacca ccagcaccgg 600
ggtggtcagc gaggagccat tcacactgaa cttcaccatc aacaacctgc gctacatggc 660
ggacatgggc caacccggct ccctcaagtt caacatcaca gacaacgtca tgaagcacct 720
gctcagtcct ttgttccaga ggagcagcct gggtgcacgg tacacaggct gcagggtcat 780
cgcactaagg tctgtgaaga acggtgctga gacacgggtg gacctcctct gcacctacct 840
gcagcccctc agcggcccag gtctgcctat caagcaggtg ttccatgagc tgagccagca 900
gacccatggc atcacccggc tgggccccta ctctctggac aaagacagcc tctaccttaa 960
cggttacaat gaacctggtc cagatgagcc tcctacaact cccaagccag ccaccacatt 1020
cctgcctcct ctgtcagaag ccacaacagc catggggtac cacctgaaga ccctcacact 1080
caattcacat ctccaatctc cagtattcac cagatatggg caagggctca aggtacattc 1140
aatccaccga ggggggtcct tcagcaactg gtcag 1175

<210> SEQ ID NO 466
<211> LENGTH: 1959
<212> TYPE: DNA
<213> ORGANISM: Homo sapiens

<400> SEQUENCE: 466
catccccagc tcgaacagca gccacagtcc cattcatggt gccattcacc ctcaacttca 60
actcatcacc aacctgcagt acgaggagga catgcggcac ctggttccag gaagttcaac 120
gcgcacagag agagaactgc agggtcgtgc tcaaacccta gatcaggaat agcagtctgg 180

-continued

```
aatacctcta ttcaggctgc agactagcct cactcaggcc agagaaggat agctcagcca    240
cggcagtgga tgccatctgc acacatcgcc ctgaccctga agacctcgga ctggacagag    300
agcgactgta ctgggagctg agcaatctga caaatggcat ccaggagctg ggcccctaca    360
ccctggaccg gaacagtctc tatgtcaatg gtttcaccca tcgaagctct atgcccacca    420
ccagcactcc tgggacctcc acagtggatg tgggaacctc agggactcca tcctccagcc    480
ccagccccac gactgctggc cctctcctga tgccgttcac cctcaacttc accatcacca    540
acctgcagta cgaggaggac atgcgtcgca ctggctccag gaagttcaac accatggaga    600
gtgtcctgca gggtctgctc aagcccttgt tcaagaacac cagtgttggc cctctgtact    660
ctggctgcag attgaccttg ctcaggccca agaaagatgg ggcagccact ggagtggatg    720
ccatctgcac ccaccgcctt gaccccaaaa gccctggact caacagggag cagctgtact    780
gggagctaag caaactgacc aatgacattg aagagctggg cccctacacc ctggacagga    840
acagtctcta tgtcaatggt ttcacccatc agagctctgt gtccaccacc agcactcctg    900
ggacctccac agtggatctc agaacctcag tggactccat cctccctctc cagccccaca    960
attatggctg ctggccctct cctggtacca ttcaccctca acttcaccat caccaacctg   1020
cagtatgggg aggacatggg tcaccctggc tccaggaagt tcaacaccac agagagggtc   1080
ctgcagggtc tgcttggtcc catattcaag aacaccagtg ttggccctct gtactctggc   1140
tgcagactga cctctctcag gtccaagaag gatggagcag ccactggagt ggatgccatc   1200
tgcatccatc atcttgaccc caaaagccct ggactcaaca gagagcggct gtactgggag   1260
ctgagccaac tgaccaatgg catcaaagag ctgggcccct acaccctgga caggaacagt   1320
ctctatgtca atggtttcac ccatcggacc tctgtgccca ccaccagtac tcctgggacc   1380
tccacagtgt actgggcaac cactgggact ccatcctccc tccccgccac acagagcctg   1440
gccctctcct gataccattc acattcaact ttaccatcac ctacctgcat tatagaggaa   1500
aacatgcaac acccgtggtt ccaggaacga tgtcaacacc acaggagagg gttctgcagg   1560
gtcttcgctc acgcccattg ttacaagaac accagtagtt ggccctctgt actctggctg   1620
cagaatgacc ttgctcagac ctgagaagca ggaggcaaca cactggaatg gacaccatct   1680
gtatccacca gcgttagatc ccatcaggac ctggactgga cagagagcag gctatactgg   1740
gagctagagc cagctgaccc acagcatcac agagctggga ccctacagcc ctggataggg   1800
acagtctcta tgtcaatggc ttcaaccctt ggagctctgt gccaaccacc agcactcctg   1860
ggacctccac agtgcacctg gcaacctctg ggactccatc ctccctgcct ggccacacag   1920
cccctgtccc tctcttgata ccattcaccc tcaacttac                          1959
```

<210> SEQ ID NO 467
<211> LENGTH: 1636
<212> TYPE: DNA
<213> ORGANISM: Homo sapiens

<400> SEQUENCE: 467

```
gacctcctct gcacctacct gcagcccctc agcggcccag gtctgcctat caagcaggtg     60
ttccatgagc tgagccagca gacccatggc atcacccggc tgggccccta ctctctggac    120
aaagacagcc tctaccttaa cggttacaat gaacctggtc cagatgagcc tcctacaact    180
cccaagccag ccaccacatt cctgcctcct ctgtcagaag ccacaacagc catggggtac    240
cacctgaaga ccctcacact caacttcacc atctccaatc tccagtattc accagatatg    300
ggcaagggct cagctacatt caactccacc gaggggtcc ttcagcacct gctcagaccc     360
```

-continued ttgttccaga agagcagcat gggccccttc tacttgggtt gccaactgat ctccctcagg 420
cctgagaagg atggggcagc cactggtgtg gacaccacct gcacctacca ccctgaccct 480
gtgggccccg ggctggacat acagcagctt tactgggagc tgagtcagct gacccatggt 540
gtcacccaac tgggcttcta tgtcctggac agggatagcc tcttcatcaa tggctatgca 600
ccccagaatt tatcaatccg gggcgagtac cagataaatt tccacattgt caactggaac 660
ctcagtaatc cagaccccac atcctcagag tacatcaccc tgctgaggga catccaggac 720
aaggtcacca cactctacaa aggcagtcaa ctacatgaca cattccgctt ctgcctggtc 780
accaacttga cgatggactc cgtgttggtc actgtcaagg cattgttctc ctccaatttg 840
gaccccagcc tggtggagca agtctttcta gataagaccc tgaatgcctc attccattgg 900
ctgggctcca cctaccagtt ggtggacatc catgtgacag aaatggagtc atcagtttat 960
caaccaacaa gcagctccag cacccagcac ttctacctga atttcaccat caccaaccta 1020
ccatattccc aggacaaagc ccagccaggc accaccaatt accagaggaa caaaaggaat 1080
attgaggatg cgctcaacca actcttccga aacagcagca tcaagagtta tttttctgac 1140
tgtcaagttt caacattcag gtctgtcccc aacaggcacc acaccggggt ggactccctg 1200
tgtaacttct cgccactggc tcggagagta gacagagttg ccatctatga ggaatttctg 1260
cggatgaccc ggaatggtac ccagctgcag aacttcaccc tggacaggag cagtgtcctt 1320
gtggatgggt attctcccaa cagaaatgag ccccttaactg ggaattctga ccttcccttc 1380
tgggctgtca tcctcatcgg cttggcagga ctcctgggac tcatcacatg cctgatctgc 1440
ggtgtcctgg tgaccacccg ccggcggaag aaggaaggag aatacaacgt ccagcaacag 1500
tgcccaggct actaccagtc acacctagac ctggaggatc tgcaatgact ggaacttgcc 1560
ggtgcctggg gtgcctttcc cccagccagg gtccaaagaa gcttggctgg ggcagaaata 1620
aaccatattg gtcgga 1636

<210> SEQ ID NO 468
<211> LENGTH: 231
<212> TYPE: DNA
<213> ORGANISM: Homo sapiens

<400> SEQUENCE: 468
actacatgac acattccgct tctgcctggt caccaacttg acaaatggag tcatcagttt 60
atcaaccaac aagcagctcc agcacccagc acttctacct gaatttcacc atcaccaacc 120
taccatattc ccaggacaaa gcccagccag gcaccaccaa ttaccagagg aacaaaagga 180
atattgagga tgcgctcaac caactcttcc gaaacagcag catcgagagt t 231

<210> SEQ ID NO 469
<211> LENGTH: 607
<212> TYPE: DNA
<213> ORGANISM: Homo sapiens

<400> SEQUENCE: 469
atgaagagct atcgctgtcc aggacataga agcccagttg ggtgacacca tgggtcagct 60
gactcagctc ccagtaaagc tgctgtatgt ccagcccggg gcccacaggg tcagggtggt 120
aggtgcaggt ggtgtccaca ccagtggctg ccccatcctt ctcaggccag gtgctgaagg 180
accccctcgg tggagttgaa tgtagctgag cccttgccca tatctggtga atactggaga 240
ttggagatgg tgaagttgag tgtgagggtc ttcaggtggt accccatggc tgttgtggct 300

-continued

```
tctgacagag gaggcaggaa tgtggtggct ggcttgggag ttgtaggagg ctcatctgga    360

ccaggttcat tgtaaccgtt aaggtagagg ctgtctttgt ccagagagta ggggcccagc    420

cgggtgatgc catgggtctg ctggctcagc tcatggaaca cctgcttgat aggcagacct    480

gggccgctga ggggctgcag gtaggtgcag aggaggtcca cccgtgtctc agcaccgttc    540

ttcacagacc ttagtgcgat gaccctgcag cctgtgtacc gtgcacccag gctgctcctc    600

tggaaca                                                              607
```

<210> SEQ ID NO 470
<211> LENGTH: 981
<212> TYPE: DNA
<213> ORGANISM: Homo sapiens

<400> SEQUENCE: 470

```
ggtaaccaca gctgacccat ggcatcaaag agctgggccc ctacaccctg gacaggaaca     60

gtctctatgt caatggtttc acccatcgga gctctgtggc ccccaccagc actcctggga    120

cctccacagt ggaccttggg acctcaggga ctccatcctc cctccccagc cccacaacag    180

ctgttcctct cctggtgccg ttcaccctca actttaccat caccaatctg cagtatgggg    240

aggacatgcg tcaccctggc tccaggaagt tcaacaccac agagagggtc ctgcagggtc    300

tgcttggtcc cttgttcaag aactccagtg tcggccctct gtactctggc tgcagactga    360

tctctctcag gtctgagaag gatggggcag ccactggagt ggatgccatc tgcacccacc    420

accttaaccc tcaaagccct ggactggaca gggagcagct gtactggcag ctgagccaga    480

gaccacaacc tcatttatca cctattctga gacacacaca agttcagcca ttccaactct    540

ccctgtctcc ccctggtgca tcaaagatgc tgacctcact ggtcatcagt tctgggacag    600

acagcactac aactttccca acactgacgg agaccccata tgaaccagag acaacagcca    660

tacagctcat tcatcctgca gagaccaaca caatggttcc caggacaact cccaagtttt    720

cccatagtaa gtcagacacc acactcccag tagccatcac cagtcctggg ccagaagcca    780

gttcagctgt ttcaacgaca actatctcac ctgatatgtc agatctggtg acctcactgg    840

tccctagttc tgggacagac accagtacaa ccttcccaac attgagtgag accccatatg    900

aaccagagac tacagccacg tggctcactc atcctgcaga aaccagaaca acggtttctg    960

ggacaattcc caacttttcc c                                              981
```

<210> SEQ ID NO 471
<211> LENGTH: 959
<212> TYPE: DNA
<213> ORGANISM: Homo sapiens

<400> SEQUENCE: 471

```
cagatggcat ccactccggt ggcttcccca tctttctctg gcctgagcaa ggtcagcctg     60

cagccagagt acagagggcc aacactggtg ttcttgaaca agggccttag caggccctga    120

aggaccctct ctgtagtgtt gaacttcctg gagccaggcc acatgttctc ctcataccgc    180

aggttagtga tggtgaagtt gagggtgaat agtatcagga gatggctggc agctgaaggg    240

ccaaatatcg aggctggagt cttagatgct cccagataca ctgtgggggt cccaggagtg    300

ctggtggtgg acacagagct ccgatgagtg aaaccattga caaagaggct gtcgttgtcc    360

agggcatagg ggcccagctc agtgatattg tgggtcagct ggctcagctc ccaatacagc    420

tgctctctgt ccagcctagg gcttttgggg tcagggtggt gggtgcagat ggcatccact    480

ccagtggctg tcccatcctt ttcaggcctg agcaaagtca gtctgcagcc agagtacaga    540
```

-continued

```
gggccaacac tggtgctctt gaacagggac ctgagcaggc cctgaaggac cctctccgtg    600

gtgttgaact tcctggagcc agggtgctgc atgttctcct cataccgcag gttggtgatg    660

gtgaagttga gagtgaatag caccaggaga gggctggcag ccgagggacc aggtttagaa    720

actggagtcc cagatgttcc caggtccact gtgggggtcc caggaatgct agtggtgggc    780

acagagctcc gctgtgtgaa accattgaca tagagactgt ccctgtccag ggtgtagggg    840

cccagctcag tgatgctgtg ggttagctgg ctcagctccc agtatagctg ctctctgtcc    900

agtccagggc ttttgggatc agggcggtag gtgcagatgg catccacttt ggtggctgc     959
```

<210> SEQ ID NO 472
<211> LENGTH: 1315
<212> TYPE: DNA
<213> ORGANISM: Homo sapiens

<400> SEQUENCE: 472

```
ccaccgtctt gaccccaaaa gccctggagt ggacagggag cagctatact gggagctgag     60

ccagctgacc aatggcatca aagagctggg cccctacacc tggacaggaa cagtctctat    120

gtcaatggtt tcacccatcg gacctctgtg cccaccacca gcactcctgg gacctccaca    180

gtggaccttg gaacctcagg gactccattc tccctcccaa gccccgcaac tgctggccct    240

ctcctggtgc tgttcaccct caacttcacc atcaccaacc tgaagtatga ggaggacatg    300

catcgccctg gctccaggaa gttcaacacc actgagaggg tcctgcagac tctgcttggt    360

cctatgttca agaacaccag tgttggcctt ctgtactctg gctgcagact gaccttgctc    420

aggtccgaga aggatggagc agccactgga gtggatgcca tctgcaccca ccgtcttgac    480

cccaaaagcc ctggagtgga cagggagcag ctatactggg agctgagcca gctgaccaat    540

ggcatcaaag agctgggccc ctacaccctg gacaggaaca gtctctatgt caatggtttc    600

acccattgga tccctgtgcc caccagcagc actcctggga cctccacagt ggaccttggg    660

tcagggactc catcctccct ccccagcccc acaactgctg gccctctcct ggtgccgttc    720

accctcaact tcaccatcac caacctgaag tacgaggagg acatgcattg ccctggctcc    780

aggaagttca acaccacaga gagagtcctg cagagtctgc ttggtcccat gttcaagaac    840

accagtgttg gccctctgta ctctggctgc agactgacct tgctcaggtc cgagaaggat    900

ggagcagcca ctggagtgga tgccatctgc acccaccgtc ttgaccccaa aagcctggag    960

tggacaggga gcagctatac tgggagctga gccagctgac caatgccatc aaagagctgg   1020

gtccctacac cctggacagc aacagtcttc tatgtcaatg gtttcaccca tcagacctct   1080

gcgcccaaca ccagcactcc tgggacctcc acagtggacc ttgggacctc agggactcca   1140

tcctccctcc ccagccctac atctgctggc cctctcctgg tgccattcac cctcaacttc   1200

accatcacca acctgcagta cgaggaggac atgcatcacc caggctccag gaagttcaac   1260

accacggagc gggtcctgca gggtctgctt ggtcccatgt tcaagaacac tacga        1315
```

<210> SEQ ID NO 473
<211> LENGTH: 689
<212> TYPE: DNA
<213> ORGANISM: Homo sapiens

<400> SEQUENCE: 473

```
acggcatcag gagagggcca gcagtcgtgg ggctggggct ggaggatgga gtccctgagg     60

ttcccacatc cactgtggag gtcccaggag tgctggtggt gggcatagag cttcgatggg    120
```

-continued

```
tgaaaccatt gacatagaga ctgttccggt ccagggtgta ggggcccagc tcagtgatgc    180

cgtgggtcag ctggctcagc tcccagtaca gctgctctct gttcagtcca gggctttgag    240

ggtcagggtg gtgggtacag atggcatcca ctctggtggc tgccttgtcc ttctctggcc    300

ttgagcaagg tcagtctgca gcctgagagc taacagaggt ccgataactg gtattcttga    360

acaagggcct agagcagaac cctgtaggac catcgccgtg gtatatgaac ttcctagagc    420

caggatttcg cacggccatc actcatactg caacttgctg atggcaaagt tgaggataaa    480

cggcaccagg agagggccag ccacttatgg gtctaggtag ggaggatgga gtttcagagg    540

ttctcgagat ccactgtgga ggtcccagga gtgctggtgg tggacacaga gctctgatgg    600

gtgaaaccat tgacatagag actgttcctg tccagggtgt aggggcccag ctcttcaatg    660

tcattggtca gtttgcttag ctcccagta                                       689
```

<210> SEQ ID NO 474
<211> LENGTH: 495
<212> TYPE: DNA
<213> ORGANISM: Homo sapiens

<400> SEQUENCE: 474

```
gtggatatga gttgaatact cactgctggt ggtggacaca gagctctgat gggtgaaacc     60

tgcatagaga aggagggagg agagtgggta agagacaagg agaggtgggg gaccaaatgg    120

aggtcaatgc taccctggtg caatgaaccg agtttcatgg tacagggaca attgaagatt    180

ttctatcagc atcctcacat caggaaagaa tgccctgagg gaacacagtc catgatggta    240

aggaaaccat gaagtccaga ccttagtcat cccatgtaga gcacatgaca gaattttcaa    300

aggccaggca gggagtgtga cctctagtta gagattagag gctgcccagc aagggggaag    360

agatttcaac cacatcacag ccactcacca ttgacataga gactgttcct gtccagggtg    420

taggggccca gctcttcaat gtcattggtc agtttgctta gctcccagta cagctgctcc    480

ctgttgagtc caggg                                                      495
```

<210> SEQ ID NO 475
<211> LENGTH: 192
<212> TYPE: DNA
<213> ORGANISM: Homo sapiens

<400> SEQUENCE: 475

```
agtgcccagg ctactaccag tcacacctag acctggagga tctgcaatga ctggaacttg     60

ccggtgcctg ggatagcct  cttcatcaat ggctatgcac cccagaattt atcaatccgg    120

ggcgagtacc agataaattt ccacattgtc aactggaacc tcagtaatcc agaccccaca    180

tcctcagagt ac                                                         192
```

<210> SEQ ID NO 476
<211> LENGTH: 500
<212> TYPE: DNA
<213> ORGANISM: Homo sapiens

<400> SEQUENCE: 476

```
ccggtggctg ccccacgttt ttcaggcctg agcaaggtca gtctgcagcc agagtacaga     60

gggccaacac tggtgctctt gaacaagggc ttgagcagac cctgcaggac tctctccgtg    120

gtgttgaact tcctggaacc agggtgacgc atgtcctcct catactgcag gttggtgata    180

gtgaagttga gggtgaatgg caccaggaga gggccagggc tgtgtggcca gggagggagg    240

ctggagtccc agaggtttcc aggtgcactg cagaggtccc aggaatactg gtggttggca    300
```

-continued

```
cagagctccg atgggtgaag ccattgacat agagactgtc cctgtccagg tgtaggggcc    360

cagctctgta acgctgttgg tcagctggct cagctcccag tatagccgct ctctgtccag    420

tccaggacca gtgggatcaa ggcggagggt gcagatggcg tccactccag tggctgcccc    480

atgtttctca ggtctgagca                                                500


<210> SEQ ID NO 477
<211> LENGTH: 191
<212> TYPE: DNA
<213> ORGANISM: Homo sapiens

<400> SEQUENCE: 477

gaggtatgct aactactact attatttagt aggctttgtt agaaacttct gttgttatag     60

tcaagggacg catggaaact ttttatatta ttctctcttt aaatcctgtt gcatatgttt    120

agaagtaggc cttttggaaa tatataaagt tctccacttt tgaacatgtt gtttctttcc    180

cacctccacg a                                                         191


<210> SEQ ID NO 478
<211> LENGTH: 914
<212> TYPE: PRT
<213> ORGANISM: Homo sapiens

<400> SEQUENCE: 478

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
```

-continued

```
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670
```

-continued

```
Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
    770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
    850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln


<210> SEQ ID NO 479
<211> LENGTH: 1148
<212> TYPE: PRT
<213> ORGANISM: Homo sapiens

<400> SEQUENCE: 479

Met Pro Leu Phe Lys Asn Thr Ser Val Ser Ser Leu Tyr Ser Gly Cys
 1               5                  10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Thr
    50                  55                  60

Glu Leu Gly Pro Tyr Thr Leu Asp Arg His Ser Leu Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125
```

-continued

```
Thr Asn Leu Arg Tyr Glu Glu Asn Met His His Pro Gly Ser Arg Lys
    130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
        195                 200                 205

Tyr Trp Glu Leu Ser Gln Leu Thr His Ser Ile Thr Glu Leu Gly Pro
    210                 215                 220

Tyr Thr Leu Asp Arg Asp Ser Leu Tyr Val Asn Gly Phe Thr Gln Arg
225                 230                 235                 240

Ser Ser Val Pro Thr Thr Ser Ile Pro Gly Thr Pro Thr Val Asp Leu
                245                 250                 255

Gly Thr Ser Gly Thr Pro Val Ser Lys Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg Ser Leu Phe Lys Ser Thr Ser
305                 310                 315                 320

Val Gly Pro Leu Tyr Ser Gly Cys Arg Leu Thr Leu Leu Arg Pro Glu
                325                 330                 335

Lys Asp Gly Thr Ala Thr Gly Val Asp Ala Ile Cys Thr His His Pro
            340                 345                 350

Asp Pro Lys Ser Pro Arg Leu Asp Arg Glu Gln Leu Tyr Trp Glu Leu
        355                 360                 365

Ser Gln Leu Thr His Asn Ile Thr Glu Leu Gly His Tyr Ala Leu Asp
    370                 375                 380

Asn Asp Ser Leu Phe Val Asn Gly Phe Thr His Arg Ser Ser Val Ser
385                 390                 395                 400

Thr Thr Ser Thr Pro Gly Thr Pro Thr Val Tyr Leu Gly Ala Ser Lys
                405                 410                 415

Thr Pro Ala Ser Ile Phe Gly Pro Ser Ala Ala Ser His Leu Leu Ile
            420                 425                 430

Leu Phe Thr Leu Asn Phe Thr Ile Thr Asn Leu Arg Tyr Glu Glu Asn
        435                 440                 445

Met Trp Pro Gly Ser Arg Lys Phe Asn Thr Thr Glu Arg Val Leu Gln
    450                 455                 460

Gly Leu Leu Arg Pro Leu Phe Lys Asn Thr Ser Val Gly Pro Leu Tyr
465                 470                 475                 480

Ser Gly Ser Arg Leu Thr Leu Leu Arg Pro Glu Lys Asp Gly Glu Ala
                485                 490                 495

Thr Gly Val Asp Ala Ile Cys Thr His Arg Pro Asp Pro Thr Gly Pro
            500                 505                 510

Gly Leu Asp Arg Glu Gln Leu Tyr Leu Glu Leu Ser Gln Leu Thr His
        515                 520                 525

Ser Ile Thr Glu Leu Gly Pro Tyr Thr Leu Asp Arg Asp Ser Leu Tyr
    530                 535                 540
```

-continued

```
Val Asn Gly Phe Thr His Arg Ser Ser Val Pro Thr Thr Ser Thr Gly
545                 550                 555                 560

Val Val Ser Glu Glu Pro Phe Thr Leu Asn Phe Thr Ile Asn Asn Leu
                565                 570                 575

Arg Tyr Met Ala Asp Met Gly Gln Pro Gly Ser Leu Lys Phe Asn Ile
            580                 585                 590

Thr Asp Asn Val Met Lys His Leu Leu Ser Pro Leu Phe Gln Arg Ser
        595                 600                 605

Ser Leu Gly Ala Arg Tyr Thr Gly Cys Arg Val Ile Ala Leu Arg Ser
    610                 615                 620

Val Lys Asn Gly Ala Glu Thr Arg Val Asp Leu Leu Cys Thr Tyr Leu
625                 630                 635                 640

Gln Pro Leu Ser Gly Pro Gly Leu Pro Ile Lys Gln Val Phe His Glu
                645                 650                 655

Leu Ser Gln Gln Thr His Gly Ile Thr Arg Leu Gly Pro Tyr Ser Leu
            660                 665                 670

Asp Lys Asp Ser Leu Tyr Leu Asn Gly Tyr Asn Glu Pro Gly Leu Asp
        675                 680                 685

Glu Pro Pro Thr Thr Pro Lys Pro Ala Thr Thr Phe Leu Pro Pro Leu
    690                 695                 700

Ser Glu Ala Thr Thr Ala Met Gly Tyr His Leu Lys Thr Leu Thr Leu
705                 710                 715                 720

Asn Phe Thr Ile Ser Asn Leu Gln Tyr Ser Pro Asp Met Gly Lys Gly
                725                 730                 735

Ser Ala Thr Phe Asn Ser Thr Glu Gly Val Leu Gln His Leu Leu Arg
            740                 745                 750

Pro Leu Phe Gln Lys Ser Ser Met Gly Pro Phe Tyr Leu Gly Cys Gln
        755                 760                 765

Leu Ile Ser Leu Arg Pro Glu Lys Asp Gly Ala Ala Thr Gly Val Asp
    770                 775                 780

Thr Thr Cys Thr Tyr His Pro Asp Pro Val Gly Pro Gly Leu Asp Ile
785                 790                 795                 800

Gln Gln Leu Tyr Trp Glu Leu Ser Gln Leu Thr His Gly Val Thr Gln
                805                 810                 815

Leu Gly Phe Tyr Val Leu Asp Arg Asp Ser Leu Phe Ile Asn Gly Tyr
            820                 825                 830

Ala Pro Gln Asn Leu Ser Ile Arg Gly Glu Tyr Gln Ile Asn Phe His
        835                 840                 845

Ile Val Asn Trp Asn Leu Ser Asn Pro Asp Pro Thr Ser Ser Glu Tyr
    850                 855                 860

Ile Thr Leu Leu Arg Asp Ile Gln Asp Lys Val Thr Thr Leu Tyr Lys
865                 870                 875                 880

Gly Ser Gln Leu His Asp Thr Phe Arg Phe Cys Leu Val Thr Asn Leu
                885                 890                 895

Thr Met Asp Ser Val Leu Val Thr Val Lys Ala Leu Phe Ser Ser Asn
            900                 905                 910

Leu Asp Pro Ser Leu Val Glu Gln Val Phe Leu Asp Lys Thr Leu Asn
        915                 920                 925

Ala Ser Phe His Trp Leu Gly Ser Thr Tyr Gln Leu Val Asp Ile His
    930                 935                 940

Val Thr Glu Met Glu Ser Ser Val Tyr Gln Pro Thr Ser Ser Ser Ser
945                 950                 955                 960

Thr Gln His Phe Tyr Pro Asn Phe Thr Ile Thr Asn Leu Pro Tyr Ser
```

-continued

```
                965                 970                 975

Gln Asp Lys Ala Gln Pro Gly Thr Thr Asn Tyr Gln Arg Asn Lys Arg
            980                 985                 990

Asn Ile Glu Asp Ala Leu Asn Gln Leu Phe Arg Asn Ser Ser Ile Lys
        995                 1000                1005

Ser Tyr Phe Ser Asp Cys Gln Val Ser Thr Phe Arg Ser Val Pro Asn
    1010                1015                1020

Arg His His Thr Gly Val Asp Ser Leu Cys Asn Phe Ser Pro Leu Ala
1025                1030                1035                1040

Arg Arg Val Asp Arg Val Ala Ile Tyr Glu Glu Phe Leu Arg Met Thr
                1045                1050                1055

Arg Asn Gly Thr Gln Leu Gln Asn Phe Thr Leu Asp Arg Ser Ser Val
            1060                1065                1070

Leu Val Asp Gly Tyr Ser Pro Asn Arg Asn Glu Pro Leu Thr Gly Asn
        1075                1080                1085

Ser Asp Leu Pro Phe Trp Ala Val Ile Phe Ile Gly Leu Ala Gly Leu
    1090                1095                1100

Leu Gly Leu Ile Thr Cys Leu Ile Cys Gly Val Leu Val Thr Thr Arg
1105                1110                1115                1120

Arg Arg Lys Lys Glu Gly Glu Tyr Asn Val Gln Gln Gln Cys Pro Gly
                1125                1130                1135

Tyr Tyr Gln Ser His Leu Asp Leu Glu Asp Leu Gln
            1140                1145


<210> SEQ ID NO 480
<211> LENGTH: 230
<212> TYPE: PRT
<213> ORGANISM: Homo sapiens

<400> SEQUENCE: 480

Met His Arg Pro Gly Ser Arg Lys Phe Asn Thr Thr Glu Arg Val Leu
 1               5                  10                  15

Gln Thr Leu Leu Gly Pro Met Phe Lys Asn Thr Ser Val Gly Leu Leu
            20                  25                  30

Tyr Ser Gly Cys Arg Leu Thr Leu Leu Arg Ser Glu Lys Asp Gly Ala
        35                  40                  45

Ala Thr Gly Val Asp Ala Ile Cys Thr His Arg Leu Asp Pro Lys Ser
    50                  55                  60

Pro Gly Val Asp Arg Glu Gln Leu Tyr Trp Glu Leu Ser Gln Leu Thr
65                  70                  75                  80

Asn Gly Ile Lys Glu Leu Gly Pro Tyr Thr Leu Asp Arg Asn Ser Leu
                85                  90                  95

Tyr Val Asn Gly Phe Thr His Trp Ile Pro Val Pro Thr Ser Ser Thr
            100                 105                 110

Pro Gly Thr Ser Thr Val Asp Leu Gly Ser Gly Thr Pro Ser Ser Leu
        115                 120                 125

Pro Ser Pro Thr Thr Ala Gly Pro Leu Leu Val Pro Phe Thr Leu Asn
    130                 135                 140

Phe Thr Ile Thr Asn Leu Lys Tyr Glu Glu Asp Met His Cys Pro Gly
145                 150                 155                 160

Ser Arg Lys Phe Asn Thr Thr Glu Arg Val Leu Gln Ser Leu Leu Gly
                165                 170                 175

Pro Met Phe Lys Asn Thr Ser Val Gly Pro Leu Tyr Ser Gly Cys Arg
            180                 185                 190
```

-continued

```
Leu Thr Leu Leu Arg Ser Glu Lys Asp Gly Ala Ala Thr Gly Val Asp
        195                 200                 205

Ala Ile Cys Thr His Arg Leu Asp Pro Lys Ser Leu Glu Trp Thr Gly
    210                 215                 220

Ser Ser Tyr Thr Gly Ser
225                 230


<210> SEQ ID NO 481
<211> LENGTH: 210
<212> TYPE: PRT
<213> ORGANISM: Homo sapiens

<400> SEQUENCE: 481

Met Gln His Pro Gly Ser Arg Lys Phe Asn Thr Thr Glu Arg Val Leu
 1               5                  10                  15

Gln Gly Leu Leu Arg Ser Leu Phe Lys Ser Thr Ser Val Gly Pro Leu
            20                  25                  30

Tyr Ser Gly Cys Arg Leu Thr Leu Leu Arg Pro Glu Lys Asp Gly Thr
        35                  40                  45

Ala Thr Gly Val Asp Ala Ile Cys Thr His His Pro Asp Pro Lys Ser
    50                  55                  60

Pro Arg Leu Asp Arg Glu Gln Leu Tyr Trp Glu Leu Ser Gln Leu Thr
65                  70                  75                  80

His Asn Ile Thr Glu Leu Gly Pro Tyr Ala Leu Asp Asn Asp Ser Leu
                85                  90                  95

Phe Val Asn Gly Phe Thr His Arg Ser Ser Val Ser Thr Thr Ser Thr
            100                 105                 110

Pro Gly Thr Pro Thr Val Tyr Leu Gly Ala Ser Lys Thr Pro Ala Ser
        115                 120                 125

Ile Phe Gly Pro Ser Ala Ala Ser His Leu Leu Ile Leu Phe Thr Leu
    130                 135                 140

Asn Phe Thr Ile Thr Asn Leu Arg Tyr Glu Glu Asn Met Trp Pro Gly
145                 150                 155                 160

Ser Arg Lys Phe Asn Thr Thr Glu Arg Val Leu Gln Gly Leu Leu Arg
                165                 170                 175

Pro Leu Phe Lys Asn Thr Ser Val Gly Pro Leu Tyr Ser Gly Cys Arg
            180                 185                 190

Leu Thr Leu Leu Arg Pro Glu Lys Asp Gly Glu Ala Thr Gly Val Asp
        195                 200                 205

Ala Ile
    210


<210> SEQ ID NO 482
<211> LENGTH: 97
<212> TYPE: PRT
<213> ORGANISM: Homo sapiens

<400> SEQUENCE: 482

Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60
```

-continued

```
Ala Pro Gly Ser Ser Thr Pro Arg Arg Gly Ser Phe Arg Ala Cys Ser
65                  70                  75                  80

Gly Pro Cys Ser Arg Ala Pro Val Leu Ala Leu Cys Thr Leu Ala Ala
                85                  90                  95

Asp


<210> SEQ ID NO 483
<211> LENGTH: 438
<212> TYPE: PRT
<213> ORGANISM: Homo sapiens

<400> SEQUENCE: 483

Met Gly Tyr His Leu Lys Thr Leu Thr Leu Asn Phe Thr Ile Ser Asn
 1               5                  10                  15

Leu Gln Tyr Ser Pro Asp Met Gly Lys Gly Ser Ala Thr Phe Asn Ser
            20                  25                  30

Thr Glu Gly Val Leu Gln His Leu Leu Arg Pro Leu Phe Gln Lys Ser
        35                  40                  45

Ser Met Gly Pro Phe Tyr Leu Gly Cys Gln Leu Ile Ser Leu Arg Pro
    50                  55                  60

Glu Lys Asp Gly Ala Ala Thr Gly Val Asp Thr Thr Cys Thr Tyr His
65                  70                  75                  80

Pro Asp Pro Val Gly Pro Gly Leu Asp Ile Gln Gln Leu Tyr Trp Glu
                85                  90                  95

Leu Ser Gln Leu Thr His Gly Val Thr Gln Leu Gly Phe Tyr Val Leu
            100                 105                 110

Asp Arg Asp Ser Leu Phe Ile Asn Gly Tyr Ala Pro Gln Asn Leu Ser
        115                 120                 125

Ile Arg Gly Glu Tyr Gln Ile Asn Phe His Ile Val Asn Trp Asn Leu
    130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
    210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
        275                 280                 285

Asn Gln Leu Phe Arg Asn Ser Ser Ile Lys Ser Tyr Phe Ser Asp Cys
    290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335
```

-continued

```
Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Ser
        355                 360                 365

Pro Asn Arg Asn Glu Pro Leu Thr Gly Asn Ser Asp Leu Pro Phe Trp
    370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                405                 410                 415

Glu Tyr Asn Val Gln Gln Gln Cys Pro Gly Tyr Tyr Gln Ser His Leu
            420                 425                 430

Asp Leu Glu Asp Leu Gln
        435


<210> SEQ ID NO 484
<211> LENGTH: 216
<212> TYPE: PRT
<213> ORGANISM: Homo sapiens

<400> SEQUENCE: 484

Met Thr Leu Lys Ser Trp Ala Pro Thr Pro Trp Thr Gly Thr Val Ser
 1               5                  10                  15

Met Ser Met Val Ser Pro Ile Arg Ala Leu Cys Pro Pro Pro Ala Leu
            20                  25                  30

Leu Gly Pro Pro Gln Trp Ile Ser Glu Pro Gln Trp Thr Pro Ser Ser
        35                  40                  45

Leu Ser Ser Pro Thr Ile Met Ala Ala Gly Pro Leu Leu Val Pro Phe
    50                  55                  60

Thr Leu Asn Phe Thr Ile Thr Asn Leu Gln Tyr Gly Glu Asp Met Gly
65                  70                  75                  80

His Pro Gly Ser Arg Lys Phe Asn Thr Thr Glu Arg Val Leu Gln Gly
                85                  90                  95

Leu Leu Gly Pro Ile Phe Lys Asn Thr Ser Val Gly Pro Leu Tyr Ser
            100                 105                 110

Gly Cys Arg Leu Thr Ser Leu Arg Ser Lys Lys Asp Gly Ala Ala Thr
        115                 120                 125

Gly Val Asp Ala Ile Cys Ile His His Leu Asp Pro Lys Ser Pro Gly
    130                 135                 140

Leu Asn Arg Glu Arg Leu Tyr Trp Glu Leu Ser Gln Leu Thr Asn Gly
145                 150                 155                 160

Ile Lys Glu Leu Gly Pro Tyr Thr Leu Asp Arg Asn Ser Leu Tyr Val
                165                 170                 175

Asn Gly Phe Thr His Arg Thr Ser Val Pro Thr Thr Ser Thr Pro Gly
            180                 185                 190

Thr Ser Thr Val Tyr Trp Ala Thr Thr Gly Thr Pro Ser Ser Leu Pro
        195                 200                 205

Ala Thr Gln Ser Leu Ala Leu Ser
    210                 215


<210> SEQ ID NO 485
<211> LENGTH: 268
<212> TYPE: PRT
<213> ORGANISM: Homo sapiens

<400> SEQUENCE: 485
```

-continued

```
Met Pro Thr Thr Ser Thr Pro Gly Thr Ser Thr Val Asp Val Gly Thr
 1               5                  10                  15

Ser Gly Thr Pro Ser Ser Ser Pro Ser Pro Thr Thr Ala Gly Pro Leu
            20                  25                  30

Leu Met Pro Phe Thr Leu Asn Phe Thr Ile Thr Asn Leu Gln Tyr Glu
        35                  40                  45

Glu Asp Met Arg Arg Thr Gly Ser Arg Lys Phe Asn Thr Met Glu Ser
    50                  55                  60

Val Leu Gln Gly Leu Leu Lys Pro Leu Phe Lys Asn Thr Ser Val Gly
65                  70                  75                  80

Pro Leu Tyr Ser Gly Cys Arg Leu Thr Leu Leu Arg Pro Lys Lys Asp
                85                  90                  95

Gly Ala Ala Thr Gly Val Asp Ala Ile Cys Thr His Arg Leu Asp Pro
            100                 105                 110

Lys Ser Pro Gly Leu Asn Arg Glu Gln Leu Tyr Trp Glu Leu Ser Lys
        115                 120                 125

Leu Thr Asn Asp Ile Glu Glu Leu Gly Pro Tyr Thr Leu Asp Arg Asn
    130                 135                 140

Ser Leu Tyr Val Asn Gly Phe Thr His Gln Ser Ser Val Ser Thr Thr
145                 150                 155                 160

Ser Thr Pro Gly Thr Ser Thr Val Asp Leu Arg Thr Ser Val Asp Ser
                165                 170                 175

Ile Leu Pro Leu Gln Pro His Asn Tyr Gly Cys Trp Pro Ser Pro Gly
            180                 185                 190

Thr Ile His Pro Gln Leu His His His Gln Pro Ala Val Trp Gly Gly
        195                 200                 205

His Gly Ser Pro Trp Leu Gln Glu Val Gln His His Arg Glu Gly Pro
    210                 215                 220

Ala Gly Ser Ala Trp Ser His Ile Gln Glu His Gln Cys Trp Pro Ser
225                 230                 235                 240

Val Leu Trp Leu Gln Thr Asp Leu Ser Gln Val Gln Glu Gly Trp Ser
                245                 250                 255

Ser His Trp Ser Gly Cys His Leu His Pro Ser Ser
            260                 265
```

<210> SEQ ID NO 486
<211> LENGTH: 304
<212> TYPE: PRT
<213> ORGANISM: Homo sapiens

<400> SEQUENCE: 486

```
Met Gln His Pro Gly Ser Arg Lys Phe Asn Thr Thr Glu Arg Val Leu
 1               5                  10                  15

Gln Gly Leu Leu Arg Pro Leu Phe Lys Asn Thr Ser Val Gly Pro Leu
            20                  25                  30

Tyr Ser Gly Cys Arg Leu Thr Leu Leu Arg Pro Glu Lys Asp Gly Glu
        35                  40                  45

Ala Thr Gly Val Asp Ala Ile Cys Thr His Arg Pro Asp Pro Thr Gly
    50                  55                  60

Pro Gly Leu Asp Arg Glu Gln Leu Tyr Leu Glu Leu Ser Gln Leu Thr
65                  70                  75                  80

His Ser Ile Thr Glu Leu Gly Pro Tyr Thr Leu Asp Arg Asp Ser Leu
                85                  90                  95

Tyr Val Asn Gly Phe Thr His Arg Ser Ser Val Pro Thr Thr Ser Thr
            100                 105                 110
```

-continued

```
Gly Val Val Ser Glu Glu Pro Phe Thr Leu Asn Phe Thr Ile Asn Asn
        115                 120                 125

Leu Arg Tyr Met Ala Asp Met Gly Gln Pro Gly Ser Leu Lys Phe Asn
    130                 135                 140

Ile Thr Asp Asn Val Met Lys His Leu Leu Ser Pro Leu Phe Gln Arg
145                 150                 155                 160

Ser Ser Leu Gly Ala Arg Tyr Thr Gly Cys Arg Val Ile Ala Leu Arg
                165                 170                 175

Ser Val Lys Asn Gly Ala Glu Thr Arg Val Asp Leu Leu Cys Thr Tyr
            180                 185                 190

Leu Gln Pro Leu Ser Gly Pro Gly Leu Pro Ile Lys Gln Val Phe His
        195                 200                 205

Glu Leu Ser Gln Gln Thr His Gly Ile Thr Arg Leu Gly Pro Tyr Ser
    210                 215                 220

Leu Asp Lys Asp Ser Leu Tyr Leu Asn Gly Tyr Asn Glu Pro Gly Pro
225                 230                 235                 240

Asp Glu Pro Pro Thr Thr Pro Lys Pro Ala Thr Thr Phe Leu Pro Pro
                245                 250                 255

Leu Ser Glu Ala Thr Thr Ala Met Gly Tyr His Leu Lys Thr Leu Thr
            260                 265                 270

Leu Asn Ser His Leu Gln Ser Pro Val Phe Thr Arg Tyr Gly Gln Gly
        275                 280                 285

Leu Lys Val His Ser Ile His Arg Gly Gly Ser Phe Ser Asn Trp Ser
    290                 295                 300


<210> SEQ ID NO 487
<211> LENGTH: 294
<212> TYPE: PRT
<213> ORGANISM: Homo sapiens

<400> SEQUENCE: 487

Met Thr Asn Gly Ile Lys Glu Leu Gly Pro Tyr Thr Leu Asp Arg Asn
 1               5                  10                  15

Ser Leu Tyr Val Asn Gly Phe Thr His Arg Ser Ser Gly Leu Thr Thr
            20                  25                  30

Ser Thr Pro Trp Thr Ser Thr Val Asp Leu Gly Thr Ser Gly Thr Pro
        35                  40                  45

Ser Pro Val Pro Ser Pro Thr Thr Ala Gly Pro Leu Leu Val Pro Phe
    50                  55                  60

Thr Leu Asn Phe Thr Ile Thr Asn Leu Gln Tyr Glu Glu Asp Met His
65                  70                  75                  80

Arg Pro Gly Ser Arg Lys Phe Asn Ala Thr Glu Arg Val Leu Gln Gly
                85                  90                  95

Leu Leu Ser Pro Ile Phe Lys Asn Ser Ser Val Gly Pro Leu Tyr Ser
            100                 105                 110

Gly Cys Arg Leu Thr Ser Leu Arg Pro Glu Lys Asp Gly Ala Ala Thr
        115                 120                 125

Gly Met Asp Ala Val Cys Leu Tyr His Pro Asn Pro Lys Arg Pro Gly
    130                 135                 140

Leu Asp Arg Glu Gln Leu Tyr Trp Glu Leu Ser Gln Leu Thr His Asn
145                 150                 155                 160

Ile Thr Glu Leu Gly Pro Tyr Ser Leu Asp Arg Asp Ser Leu Tyr Val
                165                 170                 175

Asn Gly Phe Thr His Gln Asn Ser Val Pro Thr Thr Ser Thr Pro Gly
```

-continued

```
            180                 185                 190

Thr Ser Thr Val Tyr Trp Ala Thr Thr Gly Thr Pro Ser Ser Phe Pro
        195                 200                 205

Gly His Thr Glu Pro Gly Pro Leu Leu Ile Pro Phe Thr Phe Asn Phe
    210                 215                 220

Thr Ile Thr Asn Leu His Tyr Glu Glu Asn Met Gln His Pro Gly Ser
225                 230                 235                 240

Arg Lys Phe Asn Ala Thr Glu Arg Val Leu Gln Gly Leu Leu Ser Pro
                245                 250                 255

Ile Phe Lys Asn Ser Ser Val Gly Pro Leu Tyr Ser Gly Cys Arg Leu
            260                 265                 270

Thr Ser Leu Arg Pro Glu Lys Asp Gly Ala Ala Thr Gly Met Asp Ala
        275                 280                 285

Val Cys Leu Tyr Arg Pro
    290


<210> SEQ ID NO 488
<211> LENGTH: 233
<212> TYPE: PRT
<213> ORGANISM: Homo sapiens

<400> SEQUENCE: 488

Ser Leu Val Glu Gln Val Phe Leu Asp Lys Thr Leu Asn Ala Ser Phe
 1               5                  10                  15

His Trp Leu Gly Ser Thr Tyr Gln Leu Val Asp Ile His Val Thr Glu
            20                  25                  30

Met Glu Ser Ser Val Tyr Gln Pro Thr Ser Ser Ser Ser Thr Gln His
        35                  40                  45

Phe Tyr Leu Asn Phe Thr Ile Thr Asn Leu Pro Tyr Ser Gln Asp Lys
    50                  55                  60

Ala Gln Pro Gly Thr Thr Asn Tyr Gln Arg Asn Lys Arg Asn Ile Glu
65                  70                  75                  80

Asp Ala Leu Asn Gln Leu Phe Arg Asn Ser Ser Ile Lys Ser Tyr Phe
                85                  90                  95

Ser Asp Cys Gln Val Ser Thr Phe Arg Ser Val Pro Asn Arg His His
            100                 105                 110

Thr Gly Val Asp Ser Leu Cys Asn Phe Ser Pro Leu Ala Arg Arg Val
        115                 120                 125

Asp Arg Val Ala Ile Tyr Glu Glu Phe Leu Arg Met Thr Arg Asn Gly
    130                 135                 140

Thr Gln Leu Gln Asn Phe Thr Leu Asp Arg Ser Ser Val Leu Val Asp
145                 150                 155                 160

Gly Tyr Phe Pro Asn Arg Asn Glu Pro Leu Thr Gly Asn Ser Asp Leu
                165                 170                 175

Pro Phe Trp Ala Val Ile Leu Ile Gly Leu Ala Gly Leu Leu Gly Leu
            180                 185                 190

Ile Thr Cys Leu Ile Cys Gly Val Leu Val Thr Thr Arg Arg Arg Lys
        195                 200                 205

Lys Glu Gly Glu Tyr Asn Val Gln Gln Gln Cys Pro Gly Tyr Tyr Gln
    210                 215                 220

Ser His Leu Asp Leu Glu Asp Leu Gln
225                 230


<210> SEQ ID NO 489
<211> LENGTH: 178
```

-continued

<212> TYPE: PRT
<213> ORGANISM: Homo sapiens

<400> SEQUENCE: 489

Ser Leu Val Glu Gln Val Phe Leu Asp Lys Thr Leu Asn Ala Ser Phe
1 5 10 15

His Trp Leu Gly Ser Thr Tyr Gln Leu Val Asp Ile His Val Thr Glu
20 25 30

Met Glu Ser Ser Val Tyr Gln Pro Thr Ser Ser Ser Ser Thr Gln His
35 40 45

Phe Tyr Leu Asn Phe Thr Ile Thr Asn Leu Pro Tyr Ser Gln Asp Lys
50 55 60

Ala Gln Pro Gly Thr Thr Asn Tyr Gln Arg Asn Lys Arg Asn Ile Glu
65 70 75 80

Asp Ala Leu Asn Gln Leu Phe Arg Asn Ser Ser Ile Lys Ser Tyr Phe
85 90 95

Ser Asp Cys Gln Val Ser Thr Phe Arg Ser Val Pro Asn Arg His His
100 105 110

Thr Gly Val Asp Ser Leu Cys Asn Phe Ser Pro Leu Ala Arg Arg Val
115 120 125

Asp Arg Val Ala Ile Tyr Glu Glu Phe Leu Arg Met Thr Arg Asn Gly
130 135 140

Thr Gln Leu Gln Asn Phe Thr Leu Asp Arg Ser Ser Val Leu Val Asp
145 150 155 160

Gly Tyr Phe Pro Asn Arg Asn Glu Pro Leu Thr Gly Asn Ser Asp Leu
165 170 175

Pro Phe

<210> SEQ ID NO 490
<211> LENGTH: 15
<212> TYPE: PRT
<213> ORGANISM: Homo sapiens

<400> SEQUENCE: 490

Thr Cys Gly Met Arg Arg Thr Cys Ser Thr Leu Ala Pro Gly Ser
1 5 10 15

<210> SEQ ID NO 491
<211> LENGTH: 15
<212> TYPE: PRT
<213> ORGANISM: Homo sapiens

<400> SEQUENCE: 491

Cys Arg Leu Thr Leu Leu Arg Pro Glu Lys Asp Gly Thr Ala Thr
1 5 10 15

<210> SEQ ID NO 492
<211> LENGTH: 15
<212> TYPE: PRT
<213> ORGANISM: Homo sapiens

<400> SEQUENCE: 492

Asp Gly Thr Ala Thr Gly Val Asp Ala Ile Cys Thr His His Pro
1 5 10 15

<210> SEQ ID NO 493
<211> LENGTH: 15
<212> TYPE: PRT
<213> ORGANISM: Homo sapiens -continued

<400> SEQUENCE: 493

Cys Thr His His Pro Asp Pro Lys Ser Pro Arg Leu Asp Arg Glu
1 5 10 15

<210> SEQ ID NO 494
<211> LENGTH: 15
<212> TYPE: PRT
<213> ORGANISM: Homo sapiens

<400> SEQUENCE: 494

Arg Leu Asp Arg Glu Gln Leu Tyr Trp Glu Leu Ser Gln Leu Thr
1 5 10 15

<210> SEQ ID NO 495
<211> LENGTH: 15
<212> TYPE: PRT
<213> ORGANISM: Homo sapiens

<400> SEQUENCE: 495

Leu Gly Pro Tyr Ala Leu Asp Asn Asp Ser Leu Phe Val Asn Gly
1 5 10 15

<210> SEQ ID NO 496
<211> LENGTH: 15
<212> TYPE: PRT
<213> ORGANISM: Homo sapiens

<400> SEQUENCE: 496

Ser Val Ser Thr Thr Ser Thr Pro Gly Thr Pro Thr Tyr Val Leu
1 5 10 15

<210> SEQ ID NO 497
<211> LENGTH: 15
<212> TYPE: PRT
<213> ORGANISM: Homo sapiens

<400> SEQUENCE: 497

Leu Arg Pro Glu Lys Asp Gly Glu Ala Thr Gly Val Asp Ala Ile
1 5 10 15

<210> SEQ ID NO 498
<211> LENGTH: 15
<212> TYPE: PRT
<213> ORGANISM: Homo sapiens

<400> SEQUENCE: 498

Asp Pro Thr Gly Pro Gly Leu Asp Arg Glu Gln Leu Tyr Leu Glu
1 5 10 15

<210> SEQ ID NO 499
<211> LENGTH: 15
<212> TYPE: PRT
<213> ORGANISM: Homo sapiens

<400> SEQUENCE: 499

Leu Asp Arg Asp Ser Leu Tyr Val Asn Gly Phe Thr His Arg Ser
1 5 10 15

<210> SEQ ID NO 500
<211> LENGTH: 15
<212> TYPE: PRT
<213> ORGANISM: Homo sapiens

<400> SEQUENCE: 500

-continued

```
Gly Pro Tyr Ser Leu Asp Lys Asp Ser Leu Tyr Leu Asn Gly Tyr
 1               5                  10                  15


<210> SEQ ID NO 501
<211> LENGTH: 15
<212> TYPE: PRT
<213> ORGANISM: Homo sapiens

<400> SEQUENCE: 501

Tyr Leu Asn Gly Tyr Asn Glu Pro Gly Pro Asp Glu Pro Pro Thr
 1               5                  10                  15


<210> SEQ ID NO 502
<211> LENGTH: 15
<212> TYPE: PRT
<213> ORGANISM: Homo sapiens

<400> SEQUENCE: 502

Ala Thr Phe Asn Ser Thr Glu Gly Val Leu Gln His Leu Leu Arg
 1               5                  10                  15


<210> SEQ ID NO 503
<211> LENGTH: 15
<212> TYPE: PRT
<213> ORGANISM: Homo sapiens

<400> SEQUENCE: 503

Gln Leu Ile Ser Leu Arg Pro Glu Lys Asp Gly Ala Ala Thr Gly
 1               5                  10                  15


<210> SEQ ID NO 504
<211> LENGTH: 15
<212> TYPE: PRT
<213> ORGANISM: Homo sapiens

<400> SEQUENCE: 504

Gly Ala Ala Thr Gly Val Asp Thr Thr Cys Thr Tyr His Pro Asp
 1               5                  10                  15


<210> SEQ ID NO 505
<211> LENGTH: 15
<212> TYPE: PRT
<213> ORGANISM: Homo sapiens

<400> SEQUENCE: 505

Thr Tyr His Pro Asp Pro Val Gly Pro Gly Leu Asp Ile Gln Gln
 1               5                  10                  15


<210> SEQ ID NO 506
<211> LENGTH: 15
<212> TYPE: PRT
<213> ORGANISM: Homo sapiens

<400> SEQUENCE: 506

Leu Asp Ile Gln Gln Leu Tyr Trp Glu Leu Ser Gln Leu Thr His
 1               5                  10                  15


<210> SEQ ID NO 507
<211> LENGTH: 15
<212> TYPE: PRT
<213> ORGANISM: Homo sapiens

<400> SEQUENCE: 507

His Ile Val Asn Trp Asn Leu Ser Asn Pro Asp Pro Thr Ser Ser
 1               5                  10                  15
```

-continued

<210> SEQ ID NO 508
<211> LENGTH: 15
<212> TYPE: PRT
<213> ORGANISM: Homo sapiens

<400> SEQUENCE: 508

Asp Pro Thr Ser Ser Glu Tyr Ile Thr Leu Leu Arg Asp Ile Gln
1 5 10 15

<210> SEQ ID NO 509
<211> LENGTH: 15
<212> TYPE: PRT
<213> ORGANISM: Homo sapiens

<400> SEQUENCE: 509

Leu Arg Asp Ile Gln Asp Lys Val Thr Thr Leu Tyr Lys Gly Ser
1 5 10 15

<210> SEQ ID NO 510
<211> LENGTH: 15
<212> TYPE: PRT
<213> ORGANISM: Homo sapiens

<400> SEQUENCE: 510

Leu Tyr Lys Gly Ser Gln Leu His Asp Thr Phe Arg Phe Cys Leu
1 5 10 15

<210> SEQ ID NO 511
<211> LENGTH: 15
<212> TYPE: PRT
<213> ORGANISM: Homo sapiens

<400> SEQUENCE: 511

Asp Lys Ala Gln Pro Gly Thr Thr Asn Tyr Gln Arg Asn Lys Arg
1 5 10 15

<210> SEQ ID NO 512
<211> LENGTH: 450
<212> TYPE: DNA
<213> ORGANISM: Homo sapiens

<400> SEQUENCE: 512
gttacaatga acctggtcca gatgagcctc ctacaactcc caagccagcc accacattcc 60
tgcctcctct gtcagaagcc acaacagcca tggggtacca cctgaagacc ctcacactca 120
acttcaccat ctccaatctc cagtattcac cagatatggg caagggctca gctacattca 180
actccaccga gggggtcctt cagcacctgc tcagaccctt gttccagaag agcagcatgg 240
gccccttcta cttgggttgc caactgatct ccctcaggcc tgagaaggat ggggcagcca 300
ctggtgtgga caccacctgc acctaccacc ctgaccctgt gggccccggg ctggacatac 360
agcagcttta ctgggagctg agtcagctga cccatggtgt cacccaactg ggcttctatg 420
tcctggacag ggatagcctc ttcatcaatg 450

<210> SEQ ID NO 513
<211> LENGTH: 402
<212> TYPE: DNA
<213> ORGANISM: Homo sapiens

<400> SEQUENCE: 513
gtttcaccca tcggagctct gtacccacca ccagcaccgg ggtggtcagc gaggagccat 60

-continued

```
tcacactgaa cttcaccatc aacaacctgc gctacatggc ggacatgggc caacccggct    120

ccctcaagtt caacatcaca gacaacgtca tgaagcacct gctcagtcct ttgttccaga    180

ggagcagcct gggtgcacgg tacacaggct gcagggtcat cgcactaagg tctgtgaaga    240

acggtgctga gacacgggtg gacctcctct gcacctacct gcagcccctc agcggcccag    300

gtctgcctat caagcaggtg ttccatgagc tgagccagca gacccatggc atcacccggc    360

tgggccccta ctctctggac aaagacagcc tctaccttaa cg                       402
```

```
<210> SEQ ID NO 514
<211> LENGTH: 465
<212> TYPE: DNA
<213> ORGANISM: Homo sapiens

<400> SEQUENCE: 514

gtttcactca tcggagctct gtgtccacca ccagcactcc tgggaccccc acagtgtatc     60

tgggagcatc taagactcca gcctcgatat ttggcccttc agctgccagc catctcctga    120

tactattcac cctcaacttc accatcacta acctgcggta tgaggagaac atgtggcctg    180

gctccaggaa gttcaacact acagagaggg tccttcaggg cctgctaagg cccttgttca    240

agaacaccag tgttggccct ctgtactctg gctgcaggct gaccttgctc aggccagaga    300

aagatgggga agccaccgga gtggatgcca tctgcaccca ccgccctgac cccacaggcc    360

ctgggctgga cagagagcag ctgtatttgg agctgagcca gctgacccac agcatcactg    420

agctgggccc ctacacactg gacagggaca gtctctatgt caatg                    465
```

```
<210> SEQ ID NO 515
<211> LENGTH: 463
<212> TYPE: DNA
<213> ORGANISM: Homo sapiens

<400> SEQUENCE: 515

gtttcacaca gcggagctct gtgcccacca ctagcattcc tgggaccccc acagtggacc     60

tgggaacatc tgggactcca gtttctaaac ctggtccctc ggctgccagc cctctcctgg    120

tgctattcac tctcaacttc accatcacca acctgcggta tgaggagaac atgcagcacc    180

ctggctccag gaagttcaac accacggaga gggtccttca gggcctggtc cctgttcaag    240

agcaccagtg ttggccctct gtactctggc tgcagactga ctttgctcag gcctgaaaag    300

gatgggacag ccactggagt ggatgccatc tgcacccacc accctgaccc caaaagccct    360

aggctggaca gagagcagct gtattgggag ctgagccagc tgacccacaa tatcactgag    420

ctgggcccct atgccctgga caacgacagc ctctttgtca atg                      463
```

```
<210> SEQ ID NO 516
<211> LENGTH: 156
<212> TYPE: DNA
<213> ORGANISM: Homo sapiens

<400> SEQUENCE: 516

cagccaccgg agtggatgcc atctgcaccc accgccctga ccccacaggc cctgggctgg     60

acagagagca gctgtatttg gagctgagcc agctgaccca cagcatcact gagctgggcc    120

cctacaccct ggacagggac agtctctatg tcaatg                              156
```

```
<210> SEQ ID NO 517
<211> LENGTH: 450
<212> TYPE: DNA
<213> ORGANISM: Homo sapiens
```

-continued

<400> SEQUENCE: 517
gttacaatga acctggtcta gatgagcctc ctacaactcc caagccagcc accacattcc 60
tgcctcctct gtcagaagcc acaacagcca tggggtacca cctgaagacc ctcacactca 120
acttcaccat ctccaatctc cagtattcac cagatatggg caagggctca gctacattca 180
actccaccga gggggtcctt cagcacctgc tcagaccctt gttccagaag agcagcatgg 240
gccccttcta cttgggttgc caactgatct ccctcaggcc tgagaaggat ggggcagcca 300
ctggtgtgga caccacctgc acctaccacc ctgaccctgt gggccccggg ctggacatac 360
agcagcttta ctgggagctg agtcagctga cccatggtgt cacccaactg ggcttctatg 420
tcctggacag ggatagcctc ttcatcaatg 450

<210> SEQ ID NO 518
<211> LENGTH: 402
<212> TYPE: DNA
<213> ORGANISM: Homo sapiens

<400> SEQUENCE: 518
gtttcaccca tcggagctct gtacccacca ccagcaccgg ggtggtcagc gaggagccat 60
tcacactgaa cttcaccatc aacaacctgc gctacatggc ggacatgggc caacccggct 120
ccctcaagtt caacatcaca gacaacgtca tgaagcacct gctcagtcct ttgttccaga 180
ggagcagcct gggtgcacgg tacacaggct gcagggtcat cgcactaagg tctgtgaaga 240
acggtgctga gacacgggtg gacctcctct gcacctacct gcagcccctc agcggcccag 300
gtctgcctat caagcaggtg ttccatgagc tgagccagca gacccatggc atcacccggc 360
tgggccccta ctctctggac aaagacagcc tctaccttaa cg 402

<210> SEQ ID NO 519
<211> LENGTH: 465
<212> TYPE: DNA
<213> ORGANISM: Homo sapiens

<400> SEQUENCE: 519
gtttcactca tcggagctct gtgtccacca ccagcactcc tgggaccccc acagtgtatc 60
tgggagcatc taagactcca gcctcgatat ttggcccttc agctgccagc catctcctga 120
tactattcac cctcaacttc accatcacta acctgcggta tgaggagaac atgtggcctg 180
gctccaggaa gttcaacact acagagaggg tccttcaggg cctgctaagg cccttgttca 240
agaacaccag tgttggccct ctgtactctg gctccaggct gaccttgctc aggccagaga 300
aagatgggga agccaccgga gtggatgcca tctgcaccca ccgccctgac cccacaggcc 360
ctgggctgga cagagagcag ctgtatttgg agctgagcca gctgacccac agcatcactg 420
agctgggccc ctacacactg gacagggaca gtctctatgt caatg 465

<210> SEQ ID NO 520
<211> LENGTH: 468
<212> TYPE: DNA
<213> ORGANISM: Homo sapiens

<400> SEQUENCE: 520
gtttcacaca gcggagctct gtgcccacca ctagcattcc tgggaccccc acagtggacc 60
tgggaacatc tgggactcca gtttctaaac ctggtccctc ggctgccagc cctctcctgg 120
tgctattcac tctcaacttc accatcacca acctgcggta tgaggagaac atgcagcacc 180

-continued

```
ctggctccag gaagttcaac accacggaga gggtccttca gggcctgctc aggtccctgt    240

tcaagagcac cagtgttggc cctctgtact ctggctgcag actgactttg ctcaggcctg    300

aaaaggatgg gacagccact ggagtggatg ccatctgcac ccaccaccct gaccccaaaa    360

gccctaggct ggacagagag cagctgtatt gggagctgag ccagctgacc cacaatatca    420

ctgagctggg ccactatgcc ctggacaacg acagcctctt tgtcaatg                 468
```

<210> SEQ ID NO 521
<211> LENGTH: 468
<212> TYPE: DNA
<213> ORGANISM: Homo sapiens

<400> SEQUENCE: 521

```
gtttcaccca tcagagctct atgacgacca ccagaactcc tgatacctcc acaatgcacc     60

tggcaacctc gagaactcca gcctccctgt ctggacctac gaccgccagc cctctcctgg    120

tgctattcac aattaacttc accatcacta acctgcggta tgaggagaac atgcatcacc    180

ctggctctag aaagtttaac accacggaga gagtccttca gggtctgctc aggcctgtgt    240

tcaagaacac cagtgttggc cctctgtact ctggctgcag actgaccttg ctcaggccca    300

agaaggatgg ggcagccacc aaagtggatg ccatctgcac ctaccgccct gatcccaaaa    360

gccctggact ggacagagag cagctatact gggagctgag ccagctaacc cacagcatca    420

ctgagctggg cccctacacc ctggacaggg acagtctcta tgtcaatg                 468
```

<210> SEQ ID NO 522
<211> LENGTH: 262
<212> TYPE: DNA
<213> ORGANISM: Homo sapiens

<400> SEQUENCE: 522

```
gagagggtcc ttcagggtct gcttatgccc ttgttcaaga acaccagtgt cagctctctg     60

tactctggtt gcagactgac cttgctcagg cctgagaagg atggggcagc caccagagtg    120

gatgctgtct gcacccatcg tcctgacccc aaaagccctg gactggacag agagcggctg    180

tactggaagc tgagccagct gacccacggc atcactgagc tgggccccta caccctggac    240

aggcacagtc tctatgtcaa tg                                             262
```

<210> SEQ ID NO 523
<211> LENGTH: 302
<212> TYPE: DNA
<213> ORGANISM: Homo sapiens

<400> SEQUENCE: 523

```
aggacatgcg tcaccctggc tccaggaagt tcaacaccac agagagggtc ctgcagggtc     60

tgcttggtcc cttgttcaag aactccagtg tcggccctct gtactctggc tgcagactga    120

tctctctcag gtctgagaag gatggggcag ccactggagt ggatgccatc tgcacccacc    180

accttaaccc tcaaagcctg gactggacag ggagcagctg tactggcagc tgagccagat    240

gaccaatggc atcaaagagc tgggccccta caccctggac cggaacagtc tctacgtcaa    300
tg                                                                   302
```

<210> SEQ ID NO 524
<211> LENGTH: 468
<212> TYPE: DNA
<213> ORGANISM: Homo sapiens

<400> SEQUENCE: 524

-continued

```
gtttcaccca tcggagctct gggctcacca ccagcactcc ttggacttcc acagttgacc     60

ttggaacctc agggactcca tcccccgtcc ccagccccac aactgctggc cctctcctgg    120

tgccattcac cctaaacttc accatcacca acctgcagta tgaggaggac atgcatcgcc    180

ctggatctag gaagttcaac gccacagaga gggtcctgca gggtctgctt agtcccatat    240

tcaagaactc cagtgttggc cctctgtact ctggctgcag actgacctct ctcaggcccg    300

agaaggatgg ggcagcaact ggaatggatg ctgtctgcct ctaccaccct aatcccaaaa    360

gacctgggct ggacagagag cagctgtact gggagctaag ccagctgacc cacaacatca    420

ctgagctggg cccctacagc ctggacaggg acagtctcta tgtcaatg                 468
```

<210> SEQ ID NO 525
<211> LENGTH: 470
<212> TYPE: DNA
<213> ORGANISM: Homo sapiens

<400> SEQUENCE: 525

```
gtttcaccca tcagaactct gtgcccacca ccagtactcc tgggacctcc acagtgtact     60

gggcaaccac tgggactcca tcctccttcc ccggccacac agagcctggc cctctcctga    120

taccattcac attcaacttt accatcacca acctgcatta tgaggaaaac atgcaacacc    180

ctggttccag gaagttcaac gccacagaga gggtcctgca gggtctgctt agtcccatat    240

tcaagaactc cagtgttggc cctctgtact ctggctgcag actgacctct ctcaggcccg    300

agaaggatgg ggcagcaact ggaatggatg ctgtctgtct ctaccgaccc taatcccatc    360

ggacctgggc tggacagaga gcagctgtac tgggagctga gccagctgac ccacgacatc    420

actgagctgg gcccctacag ccctggacag ggacagtctc tatgtcaatg               470
```

<210> SEQ ID NO 526
<211> LENGTH: 467
<212> TYPE: DNA
<213> ORGANISM: Homo sapiens

<400> SEQUENCE: 526

```
gtttcaccca tcagaactct gtgcccacca ccagtactcc tgggacctcc acagtgtact     60

gggcaaccac tgggactcca tcctccttcc ccggccacac agagcctggc cctctcctga    120

taccattcac tttcaacttt accatcacca acctgcatta tgaggaaaac atgcaacacc    180

tggttccagg aagttcaaca ccacggagag ggttctgcag ggtctgctca cgcccttgtt    240

caagaacacc agtgttggcc ctctgtactc tggctgcaga ctgaccttgc tcagacctga    300

gaagcaggag gcagccactg gagtggacac catctgcact caccgccttg accctctaaa    360

ccctggactg gacagagagc agctatactg ggagctgagc aaactgaccc gtggcatcat    420

cgagctgggc ccctacctcc tggacagagg cagtctctat gtcaatg                  467
```

<210> SEQ ID NO 527
<211> LENGTH: 468
<212> TYPE: DNA
<213> ORGANISM: Homo sapiens

<400> SEQUENCE: 527

```
gtttcaccca tcggaacttt gtgcccatca ccagcactcc tgggacctcc acagtacacc     60

taggaacctc tgaaactcca tcctccctac ctagacccat agtgcctggc cctctcctgg    120

tgccattcac cctcaacttc accatcacca acttgcagta tgaggaggcc atgcgacacc    180

ctggctccag gaagttcaat accacggaga gggtcctaca gggtctgctc aggcccttgt    240
```

-continued

```
tcaagaatac cagtatcggc cctctgtact ccagctgcag actgaccttg ctcaggccag    300

agaaggacaa ggcagccacc agagtggatg ccatctgtac ccaccaccct gaccctcaaa    360

gccctggact gaacagagag cagctgtact gggagctgag ccagctgacc cacggcatca    420

ctgagctggg cccctacacc ctggacaggc acagtctcta tgtcaatg                 468
```

<210> SEQ ID NO 528
<211> LENGTH: 537
<212> TYPE: DNA
<213> ORGANISM: Homo sapiens

<400> SEQUENCE: 528

```
gtttcaccca tcagagcccc ataccaacca ccagcactcc tgatacctcc acaatgcacc     60

tgggaacctc gagaactcca gcctccctgt ctggacctac gaccgccagc cctctcctgg    120

tgctattcac aattaacttc accatcacta acctgcggta tgaggagaac atgcatcacc    180

gctggctcta gaaagtttaa caccacggag agagtccttc agggtctgct caggcctgtg    240

ttcaaagaac accagtgttg gccctctgta ctctggctgc agactgacct tgctcaggcc    300

cgagaaggat ggggcagcca cgcaaagtgg atgccatctg cacctaccgc cctgatccca    360

aaagccctgg actggacaga gagcagctat actgggagct gagccagggt gatgcatgtt    420

ctcctcatat cgcaggttag tgatggtgaa gttaattgtg aatagcacca ggagagggct    480

ggcggtcatg ggtccagaca gggagcctgg agttctcgag gttgccaggt gcatgtc       537
```

<210> SEQ ID NO 529
<211> LENGTH: 231
<212> TYPE: DNA
<213> ORGANISM: Homo sapiens

<400> SEQUENCE: 529

```
tgttccagag gagcagcctg ggtgcacggt acacaggctg cagggtcatc gcactaaggt     60

ctgtgaagaa cggtgctgag acacgggtgg acctcctctg cacctacctg cagcccctca    120

gcggcccagg tctgcctatc aagcaggtgt tccatgagct gagccagcag acccatggca    180

tcacccggct gggcccctac tctctggaca aagacagcct ctaccttaac g             231
```

<210> SEQ ID NO 530
<211> LENGTH: 376
<212> TYPE: DNA
<213> ORGANISM: Homo sapiens

<400> SEQUENCE: 530

```
gttacaatga acctggtcca gatgagcctc ctacaactcc caagccagcc accacattcc     60

tgcctcctct gtcagaagcc acaacagcca tggggtacca cctgaagacc ctcacactca    120

acttcaccat ctccaatctc cagtattcac cagatatggg caagggctca gctacattca    180

actccaccga gggggtcctt cagcacctgg cctgagaagg atggggcagc cactggtgtg    240

gacaccacct gcacctacca ccctgaccct gtgggccccg ggctggacat acagcagctt    300

tactgggagc tgagtcagct gacccatggt gtcacccaac tgggcttcta tgtcctggac    360

agcgatagct cttcat                                                    376
```

<210> SEQ ID NO 531
<211> LENGTH: 75
<212> TYPE: DNA
<213> ORGANISM: Homo sapiens -continued

<400> SEQUENCE: 531
ggtaaccaca gctgacccat ggcatcaaag agctgggccc ctacaccctg gacaggaaca 60
gtctctatgt caatg 75

<210> SEQ ID NO 532
<211> LENGTH: 906
<212> TYPE: DNA
<213> ORGANISM: Homo sapiens

<400> SEQUENCE: 532
gtttcaccca tcggagctct gtggccccca ccagcactcc tgggacctcc acagtggacc 60
ttgggacctc agggactcca tcctccctcc ccagccccac aacagctgtt cctctcctgg 120
tgccgttcac cctcaacttt accatcacca atctgcagta tggggaggac atgcgtcacc 180
ctggctccag gaagttcaac accacagaga gggtcctgca gggtctgctt ggtcccttgt 240
tcaagaactc cagtgtcggc cctctgtact ctggctgcag actgatctct ctcaggtctg 300
agaaggatgg ggcagccact ggagtggatg ccatctgcac ccaccacctt aaccctcaaa 360
gccctggact ggacagggag cagctgtact ggcagctgag ccagagacca caacctcatt 420
tatcacctat tctgagacac acacaagttc agccattcca actctccctg tctccccctg 480
gtgcatcaaa gatgctgacc tcactggtca tcagttctgg gacagacagc actacaactt 540
tcccaacact gacggagacc ccatatgaac cagagacaac agccatacag ctcattcatc 600
ctgcagagac caacacaatg gttcccagga caactcccaa gttttcccat agtaagtcag 660
acaccacact cccagtagcc atcaccagtc ctgggccaga agccagttca gctgtttcaa 720
cgacaactat ctcacctgat atgtcagatc tggtgacctc actggtccct agttctggga 780
cagacaccag tacaaccttc ccaacattga gtgagacccc atatgaacca gagactacag 840
ccacgtggct cactcatcct gcagaaacca gaacaacggt ttctgggaca attcccaact 900
tttccc 906

<210> SEQ ID NO 533
<211> LENGTH: 404
<212> TYPE: DNA
<213> ORGANISM: Homo sapiens

<400> SEQUENCE: 533
gtttcaccca tcggagctct gtggccccca ccagcactcc tgggacctcc acagtggacc 60
ttgggacctc agggactcca tcctccctcc ccagccccac aacagctgtt cctctcctgg 120
tgccgttcac cctcaacttt accatcacca atctgcagta tggggaggac atgcgtcacc 180
ctggctccag gaagttcaac accacagaga gggtcctgca gggtctgctt ggtcccttgt 240
tcaagaactc cagtgtcggc cctctgtact ctggctgcag actgatctct ctcaggtctg 300
agaaggatgg ggcagccact ggagtggatg ccatctgcac ccaccacctt aaccctcaaa 360
gccctggact ggacagggag cagctgtact ggcagctgag ccag 404

<210> SEQ ID NO 534
<211> LENGTH: 157
<212> TYPE: DNA
<213> ORGANISM: Homo sapiens

<400> SEQUENCE: 534
gcagccacca aagtggatgc catctgcacc taccgccctg atcccaaaag ccctggactg 60
gacagagagc agctatactg ggagctgagc cagctaaccc acagcatcac tgagctgggc 120

-continued ccctacaccc tggacaggga cagtctctat gtcaatg 157

<210> SEQ ID NO 535
<211> LENGTH: 468
<212> TYPE: DNA
<213> ORGANISM: Homo sapiens

<400> SEQUENCE: 535
gtttcacaca gcggagctct gtgcccacca ctagcattcc tgggaccccc acagtggacc 60
tgggaacatc tgggactcca gtttctaaac ctggtccctc ggctgccagc cctctcctgg 120
tgctattcac tctcaacttc accatcacca acctgcggta tgaggagaac atgcagcacc 180
ctggctccag gaagttcaac accacggaga gggtccttca gggcctgctc aggtccctgt 240
tcaagagcac cagtgttggc cctctgtact ctggctgcag actgactttg ctcaggcctg 300
aaaaggatgg gacagccact ggagtggatg ccatctgcac ccaccaccct gaccccaaaa 360
gccctaggct ggacagagag cagctgtatt gggagctgag ccagctgacc cacaatatca 420
ctgagctggg cccctatgcc ctggacaacg acagcctctt tgtcaatg 468

<210> SEQ ID NO 536
<211> LENGTH: 334
<212> TYPE: DNA
<213> ORGANISM: Homo sapiens

<400> SEQUENCE: 536
gtttcactca tcggagctct gtgtccacca ccagcactcc tgggaccccc acagtgtatc 60
tgggagcatc taagactcca gcctcgatat ttggcccttc agctgccagc catctcctga 120
tactattcac cctcaacttc accatcacta acctgcggta tgaggagaac atgtggcctg 180
gctccaggaa gttcaacact acagagaggg tccttcaggg cctgctaagg cccttgttca 240
agaacaccag tgttggccct ctgtactctg gctgcaggct gaccttgctc aggccagaga 300
aagatgggga agccaccgga gtggatgcca tctg 334

<210> SEQ ID NO 537
<211> LENGTH: 127
<212> TYPE: DNA
<213> ORGANISM: Homo sapiens

<400> SEQUENCE: 537
ccaccgtctt gaccccaaaa gccctggagt ggacagggag cagctatact gggagctgag 60
ccagctgacc aatggcatca aagagctggg cccctacacc tggacaggaa cagtctctat 120
gtcaatg 127

<210> SEQ ID NO 538
<211> LENGTH: 468
<212> TYPE: DNA
<213> ORGANISM: Homo sapiens

<400> SEQUENCE: 538
gtttcaccca tcggacctct gtgcccacca ccagcactcc tgggacctcc acagtggacc 60
ttggaacctc agggactcca ttctccctcc caagccccgc aactgctggc cctctcctgg 120
tgctgttcac cctcaacttc accatcacca acctgaagta tgaggaggac atgcatcgcc 180
ctggctccag gaagttcaac accactgaga gggtcctgca gactctgctt ggtcctatgt 240
tcaagaacac cagtgttggc cttctgtact ctggctgcag actgaccttg ctcaggtccg 300

-continued agaaggatgg agcagccact ggagtggatg ccatctgcac ccaccgtctt gaccccaaaa 360
gccctggagt ggacagggag cagctatact gggagctgag ccagctgacc aatggcatca 420
aagagctggg cccctacacc ctggacagga acagtctcta tgtcaatg 468

<210> SEQ ID NO 539
<211> LENGTH: 465
<212> TYPE: DNA
<213> ORGANISM: Homo sapiens

<400> SEQUENCE: 539
gtttcaccca ttggatccct gtgcccacca gcagcactcc tgggacctcc acagtggacc 60
ttgggtcagg gactccatcc tccctcccca gccccacaac tgctggccct ctcctggtgc 120
cgttcaccct caacttcacc atcaccaacc tgaagtacga ggaggacatg cattgccctg 180
gctccaggaa gttcaacacc acagagagag tcctgcagag tctgcttggt cccatgttca 240
agaacaccag tgttggccct ctgtactctg gctgcagact gaccttgctc aggtccgaga 300
aggatggagc agccactgga gtggatgcca tctgcaccca ccgtcttgac cccaaaagcc 360
tggagtggac agggagcagc tatactggga gctgagccag ctgaccaatg ccatcaaaga 420
gctgggtccc tacaccctgg acagcaacag tcttctatgt caatg 465

<210> SEQ ID NO 540
<211> LENGTH: 255
<212> TYPE: DNA
<213> ORGANISM: Homo sapiens

<400> SEQUENCE: 540
gtttcaccca tcagacctct gcgcccaaca ccagcactcc tgggacctcc acagtggacc 60
ttgggacctc agggactcca tcctccctcc ccagccctac atctgctggc cctctcctgg 120
tgccattcac cctcaacttc accatcacca acctgcagta cgaggaggac atgcatcacc 180
caggctccag gaagttcaac accacggagc gggtcctgca gggtctgctt ggtcccatgt 240
tcaagaacac tacga 255

<210> SEQ ID NO 541
<211> LENGTH: 390
<212> TYPE: DNA
<213> ORGANISM: Homo sapiens

<400> SEQUENCE: 541
catccccagc tcgaacagca gccacagtcc cattcatggt gccattcacc ctcaacttca 60
actcatcacc aacctgcagt acgaggagga catgcggcac ctggttccag gaagttcaac 120
gcgcacagag agagaactgc agggtcgtgc tcaaacccta gatcaggaat agcagtctgg 180
aatacctcta ttcaggctgc agactagcct cactcaggcc agagaaggat agctcagcca 240
cggcagtgga tgccatctgc acacatcgcc ctgaccctga agacctcgga ctggacagag 300
agcgactgta ctgggagctg agcaatctga caaatggcat ccaggagctg ggcccctaca 360
ccctggaccg gaacagtctc tatgtcaatg 390

<210> SEQ ID NO 542
<211> LENGTH: 468
<212> TYPE: DNA
<213> ORGANISM: Homo sapiens

<400> SEQUENCE: 542
gtttcaccca tcgaagctct atgcccacca ccagcactcc tgggacctcc acagtggatg 60

-continued

```
tgggaacctc agggactcca tcctccagcc ccagccccac gactgctggc cctctcctga    120
tgccgttcac cctcaacttc accatcacca acctgcagta cgaggaggac atgcgtcgca    180
ctggctccag gaagttcaac accatggaga gtgtcctgca gggtctgctc aagcccttgt    240
tcaagaacac cagtgttggc cctctgtact ctggctgcag attgaccttg ctcaggccca    300
agaaagatgg ggcagccact ggagtggatg ccatctgcac ccaccgcctt gaccccaaaa    360
gccctggact caacagggag cagctgtact gggagctaag caaactgacc aatgacattg    420
aagagctggg cccctacacc ctggacagga acagtctcta tgtcaatg                 468
```

<210> SEQ ID NO 543
<211> LENGTH: 475
<212> TYPE: DNA
<213> ORGANISM: Homo sapiens

<400> SEQUENCE: 543

```
gtttcaccca tcagagctct gtgtccacca ccagcactcc tgggacctcc acagtggatc     60
tcagaacctc agtggactcc atcctccctc tccagcccca caattatggc tgctggccct    120
ctcctggtac cattcaccct caacttcacc atcaccaacc tgcagtatgg ggaggacatg    180
ggtcaccctg gctccaggaa gttcaacacc acagagaggg tcctgcaggg tctgcttggt    240
cccatattca agaacaccag tgttggccct ctgtactctg gctgcagact gacctctctc    300
aggtccaaga aggatggagc agccactgga gtggatgcca tctgcatcca tcatcttgac    360
cccaaaagcc ctggactcaa cagagagcgg ctgtactggg agctgagcca actgaccaat    420
ggcatcaaag agctgggccc ctacaccctg gacaggaaca gtctctatgt caatg         475
```

<210> SEQ ID NO 544
<211> LENGTH: 485
<212> TYPE: DNA
<213> ORGANISM: Homo sapiens

<400> SEQUENCE: 544

```
gtttcaccca tcggacctct gtgcccacca ccagtactcc tgggacctcc acagtgtact     60
gggcaaccac tgggactcca tcctccctcc ccgccacaca gagcctggcc ctctcctgat    120
accattcaca ttcaacttta ccatcaccta cctgcattat agaggaaaac atgcaacacc    180
cgtggttcca ggaacgatgt caacaccaca ggagagggtt ctgcagggtc ttcgctcacg    240
cccattgtta caagaacacc agtagttggc cctctgtact ctggctgcag aatgaccttg    300
ctcagacctg agaagcagga ggcaacacac tggaatggac accatctgta tccaccagcg    360
ttagatccca tcaggacctg gactggacag agagcaggct atactgggag ctagagccag    420
ctgacccaca gcatcacaga gctgggaccc tacagccctg gatagggaca gtctctatgt    480
caatg                                                                485
```

<210> SEQ ID NO 545
<211> LENGTH: 141
<212> TYPE: DNA
<213> ORGANISM: Homo sapiens

<400> SEQUENCE: 545

```
gcttcaaccc ttggagctct gtgccaacca ccagcactcc tgggacctcc acagtgcacc     60
tggcaacctc tgggactcca tcctccctgc ctggccacac agcccctgtc cctctcttga    120
taccattcac cctcaactta c                                              141
```

-continued

<210> SEQ ID NO 546
<211> LENGTH: 142
<212> TYPE: DNA
<213> ORGANISM: Homo sapiens

<400> SEQUENCE: 546
gacctcctct gcacctacct gcagcccctc agcggcccag gtctgcctat caagcaggtg 60
ttccatgagc tgagccagca gacccatggc atcacccggc tgggccccta ctctctggac 120
aaagacagcc tctaccttaa cg 142

<210> SEQ ID NO 547
<211> LENGTH: 185
<212> TYPE: DNA
<213> ORGANISM: Homo sapiens

<400> SEQUENCE: 547
gttcttaccc aggccagaga aggatagctc agccacggca gtggatgcca tctgcacaca 60
tcgccctgac cctgaagacc tcggactgga cagagagcga ctgtactggg agctgagcaa 120
tctgacaaat ggcatccagg agctgggccc ctacaccctg gaccggaaca gtctctatgt 180
caatg 185

<210> SEQ ID NO 548
<211> LENGTH: 462
<212> TYPE: DNA
<213> ORGANISM: Homo sapiens

<400> SEQUENCE: 548
gtttcaccca tcgaagctct atgcccacca ccagcactcc tgggacctcc acagtggatg 60
tgggaacctc agggactcca tcctccagcc ccagccccac gactgctggc cctctcctga 120
tgccgttcac cctcaacttc accatcacca acctgcagta cgaggaggac atgcgtcgca 180
ctggctccag gaagttcaac accatggaga gtgtcctgca gggtctgccc ttgttcaaga 240
acaccagtgt tggccctctg tactctggct gcagattgac cttgctcagg cccgagaaag 300
atggggcagc cactggagtg gatgccatct gcacccaccg ccttgacccc aaaagccctg 360
gactcaacag ggagcagctg tactgggagc taagcaaact gaccaatgac attgaagagc 420
tgggccccta caccctggac aggaacagtc tctatgtcaa tg 462

<210> SEQ ID NO 549
<211> LENGTH: 400
<212> TYPE: DNA
<213> ORGANISM: Homo sapiens

<400> SEQUENCE: 549
actccatcct ccctctccag ccccacaatt atggctgctg gccctctcct ggtaccattc 60
accctcaact tcaccatcac caacctgcag tatggggagg acatgggtca ccctggctcc 120
aggaagttca acaccacaga gagggtcctg cagggtctgc ttggtcccat attcaagaac 180
accagtgttg gccctctgta ctctggctgc agactgacct ctctcaggtc tgagaaggat 240
ggagcagcca ctggagtgga tgccatctgc atccatcatc ttgaccccaa aagccctgga 300
ctcaacagag agcggctgta ctgggagctg agccaactga ccaatggcat caaagagctg 360
ggcccctaca ccctggacag gaacagtctc tatgtcaatg 400

<210> SEQ ID NO 550
<211> LENGTH: 468

-continued

<212> TYPE: DNA
<213> ORGANISM: Homo sapiens

<400> SEQUENCE: 550
gtttcaccca tcggacctct gtgcccacca gcagcactcc tgggacctcc acagtggacc 60
ttggaacctc agggactcca ttctccctcc caagccccgc aactgctggc cctctcctgg 120
tgctgttcac cctcaacttc accatcacca acctgaagta tgaggaggac atgcatcgcc 180
ctggctccag gaagttcaac accactgaga gggtcctgca gactctgctt ggtcctatgt 240
tcaagaacac cagtgttggc cttctgtact ctggctgcag actgaccttg ctcaggtccg 300
agaaggatgg agcagtcact ggagtggatg ccatctgcac ccaccgtctt gaccccaaaa 360
gccctggagt ggacagggag cagctatact gggagctgag ccagctgacc aatggcatca 420
aagagctggg cccctacacc ctggacaggc acagtctcta tgtcaatg 468

<210> SEQ ID NO 551
<211> LENGTH: 366
<212> TYPE: DNA
<213> ORGANISM: Homo sapiens

<400> SEQUENCE: 551
ctgctggccc tctcctggtg ctgttcaccc tcaacttcac catcaccaac ctgaagtatg 60
aggaggacat gcatcgccct ggctccagga agttcaacac cactgagagg gtcctgcaga 120
ctctgcgtgg tcctatgttc aagaacacca gtggtggcct tctgtactct ggctgcagac 180
tgaccttgct caggtccgag aaggatggag cagccactgg agtggatgcc atctgcaccc 240
accgtcttga ccccaaaagc cctggagtgg acagggagca gctatactgg gagctgagcc 300
agctgaccaa tggcatcaaa gagctgggcc cctacaccct ggacaggaac agtctctatg 360
tcaatg 366

<210> SEQ ID NO 552
<211> LENGTH: 465
<212> TYPE: DNA
<213> ORGANISM: Homo sapiens

<400> SEQUENCE: 552
gtttcaccca ttggatccct gtgcccacca gcagcactcc tgggacctcc acagtggacc 60
ttgggtcagg gactccatcc tccctcccca gccccacaac tgctggccct ctcctggtgc 120
cattcaccct caacttcacc atcaccaacc tgcagtacga ggaggacatg catcacccag 180
gctccaggaa gttcaacacc acggagcggg tcctgcaggg tctgcttggt cccatgttca 240
agaacaccag tgtcggcctt ctgtactctg gctgcagact gaccttgctc aggcctgaga 300
agaatggggc agccactgga atggatgcca tctgcagcca ccgtcttgac cccaaaagcc 360
ctggactcaa cagagagcag ctgtactggg agctgagcca gctgacccat ggcatcaaag 420
agctgggccc ctacaccctg gacaggcaca gtctctatgt caatg 465

<210> SEQ ID NO 553
<211> LENGTH: 401
<212> TYPE: DNA
<213> ORGANISM: Homo sapiens

<400> SEQUENCE: 553
aacgattcga ccttctcctg ggacctccac agtggacctt gggtcaggga ctccatcctc 60
cctccccagc cccacaactg ctggccctct cctggtgccg ttcaccctca acttcaccat 120

-continued

```
caccaacctg gagtacgagg aggacatgca ttgccctggc tccaggaagt tcaacaccac    180

agagagagtc ctgcagagtc tgcttggtcc catgttcaag aacaccagtg ttggccctct    240

gtactctggc tgcagactga ccttgctcag gtccgagaag gatggagcag ccactggagt    300

ggatgccatc tgcacccacc gtcttgaccc caaaagccct ggagtggaca gggagcagct    360

atactgggag ctgagccagc tgaccaatgg catcaaagaa a                        401
```

<210> SEQ ID NO 554
<211> LENGTH: 385
<212> TYPE: DNA
<213> ORGANISM: Homo sapiens

<400> SEQUENCE: 554

```
tcctgggacc tccacagtgg accttgggtc ctcagggact ccatcctccc tccccagccc     60

tacatctgct ggccctctcc tggtgccatt caccctcaac ttcaccatca ccaacctgca    120

gtacgaggag gacatgcatc acccaggctc caggaagttc aacaccacgg agcgggtcct    180

gcagggtctg cttggtccca tgttcaagaa caccagtgtc ggccttctgt actctggctg    240

cagactgacc ttgctcaggc ctgagaagaa tggggcagcc actggaatgg atgccatctg    300

cagccaccgt cttgacccca aaagccctgg actcaacaga gagcagctgt actgggagct    360

gagccagctg acccatggca tcaaa                                          385
```

<210> SEQ ID NO 555
<211> LENGTH: 173
<212> TYPE: DNA
<213> ORGANISM: Homo sapiens

<400> SEQUENCE: 555

```
gtctgagaag gatggggcag ccactggagt ggatgccatc tgcacccacc accttaaccc     60

tcaaagccct ggactggaca gggagcagct gtactggcag ctgagccaga tgaccaatgg    120

catcaaagag ctgggcccct acaccctgga ccggaacagt ctctacgtca atg           173
```

<210> SEQ ID NO 556
<211> LENGTH: 468
<212> TYPE: DNA
<213> ORGANISM: Homo sapiens

<400> SEQUENCE: 556

```
gtttcaccca tcggagctct gggctcacca ccagcactcc ttggacttcc acagttgacc     60

ttggaacctc agggactcca tccccgtcc ccagccccac aactgctggc cctctcctgg     120

tgccattcac cctaaacttc accatcacca acctgcagta tgaggaggac atgcatcgcc    180

ctggatctag gaagttcaac gccacagaga gggtcctgca gggtctgctt agtcccatat    240

tcaagaactc cagtgttggc cctctgtact ctggctgcag actgacctct ctcaggcccg    300

agaaggatgg ggcagcaact ggaatggatg ctgtctgcct ctaccaccct aatcccaaaa    360

gacctgggct ggacagagag cagctgtact gggagctaag ccagctgacc cacaacatca    420

ctgagctggg cccctacagc ctggacaggc acagtctcta tgtcaatg                 468
```

<210> SEQ ID NO 557
<211> LENGTH: 468
<212> TYPE: DNA
<213> ORGANISM: Homo sapiens

<400> SEQUENCE: 557

```
gtttcaccca tcagaactct gtgcccacca ccagtactcc tgggacctcc acagtgtact     60
```

-continued gggcaaccac tgggactcca tcctccttcc ccggccacac agagcctggc cctctcctga 120
taccattcac tttcaacttt accatcacca acctgcatta tgaggaaaac atgcaacacc 180
ctggttccag gaagttcaac accacggaga gggttctgca gggtctgctc acgcccttgt 240
tcaagaacac cagtgttggc cctctgtact ctggctgcag actgaccttg ctcagacctg 300
agaagcagga ggcagccact ggagtggaca ccatctgtac ccaccgcgtt gatcccatcg 360
gacctggact ggacagagag cggctatact gggagctgag ccagctgacc aacagcatca 420
cagagctggg accctacacc ctggataggg acagtctcta tgtcaatg 468

<210> SEQ ID NO 558
<211> LENGTH: 468
<212> TYPE: DNA
<213> ORGANISM: Homo sapiens

<400> SEQUENCE: 558
gcttcaaccc ttggagctct gtgccaacca ccagcactcc tgggacctcc acagtgcacc 60
tggcaacctc tgggactcca tcctccctgc ctggccacac agcccctgtc cctctcttga 120
taccattcac cctcaacttt accatcacca acctgcatta tgaagaaaac atgcaacacc 180
ctggttccag gaagttcaac accacggaga gggttctgca gggtctgctc aagcccttgt 240
tcaagagcac cagcgttggc cctctgtact ctggctgcag actgaccttg ctcagacctg 300
agaaacatgg ggcagccact ggagtggacg ccatctgcac cctccgcctt gatcccactg 360
gtcctggact ggacagagag cggctatact gggagctgag ccagctgacc aacagcgtta 420
cagagctggg cccctacacc ctggacaggg acagtctcta tgtcaatg 468

<210> SEQ ID NO 559
<211> LENGTH: 468
<212> TYPE: DNA
<213> ORGANISM: Homo sapiens

<400> SEQUENCE: 559
gcttcaccca tcggagctct gtgccaacca ccagtattcc tgggacctct gcagtgcacc 60
tggaaacctc tgggactcca gcctccctcc ctggccacac agcccctggc cctctcctgg 120
tgccattcac cctcaacttc actatcacca acctgcagta tgaggaggac atgcgtcacc 180
ctggttccag gaagttcaac accacggaga gagtcctgca gggtctgctc aagcccttgt 240
tcaagagcac cagtgttggc cctctgtact ctggctgcag actgaccttg ctcaggcctg 300
aaaaacgtgg ggcagccacc ggcgtggaca ccatctgcac tcaccgcctt gaccctctaa 360
accctggact ggacagagag cagctatact gggagctgag caaactgacc tgtggcatca 420
tcgagctggg cccctacctc ctggacagag gcagtctcta tgtcaatg 468

<210> SEQ ID NO 560
<211> LENGTH: 468
<212> TYPE: DNA
<213> ORGANISM: Homo sapiens

<400> SEQUENCE: 560
gtttcaccca tcggaacttt gtgcccatca ccagcactcc tgggacctcc acagtacacc 60
taggaacctc tgaaactcca tcctccctac ctagacccat agtgcctggc cctctcctgg 120
tgccattcac cctcaacttc accatcacca acttgcagta tgaggaggcc atgcgacacc 180
ctggctccag gaagttcaat accacggaga gggtcctaca gggtctgctc aggcccttgt 240

-continued tcaagaatac cagtatcggc cctctgtact ccagctgcag actgaccttg ctcaggccag 300
agaaggacaa ggcagccacc agagtggatg ccatctgtac ccaccaccct gaccctcaaa 360
gccctggact gaacagagag cagctgtact gggagctgag ccagctgacc cacggcatca 420
ctgagctggg cccctacacc ctggacaggg acagtctcta tgtcgatg 468

<210> SEQ ID NO 561
<211> LENGTH: 468
<212> TYPE: DNA
<213> ORGANISM: Homo sapiens

<400> SEQUENCE: 561
gtttcactca ttggagcccc ataccaacca ccagcactcc tgggacctcc atagtgaacc 60
tgggaacctc tgggatccca ccttccctcc ctgaaactac agccaccggc cctctcctgg 120
tgccattcac actcaacttc accatcacta acctacagta tgaggagaac atgggtcacc 180
ctggctccag gaagttcaac atcacggaga gtgttctgca gggtctgctc aagcccttgt 240
tcaagagcac cagtgttggc cctctgtatt ctggctgcag actgaccttg ctcaggcctg 300
agaaggacgg agtagccacc agagtggacg ccatctgcac ccaccgccct gaccccaaaa 360
tccctgggct agacagacag cagctatact gggagctgag ccagctgacc cacagcatca 420
ctgagctggg accctacacc ctggataggg acagtctcta tgtcaatg 468

<210> SEQ ID NO 562
<211> LENGTH: 407
<212> TYPE: DNA
<213> ORGANISM: Homo sapiens

<400> SEQUENCE: 562
gtttcaccca gcggagctct gtgcccacca ccagcaccac tggccctgtc ctgctgccat 60
tcaccctcaa ttttaccatc attaacctgc agtatgagga ggacatgcat cgccctggct 120
ccaggaagtt caacaccacg gagagggtcc ttcagggtct gcttatgccc ttgttcaaga 180
acaccagtgt cagctctctg tactctggtt gcagactgac cttgctcagg cctgagaagg 240
atggggcagc caccagagtg gatgctgtct gcacccatcg tcctgacccc aaaagccctg 300
gactggacag agagcggctg tactggaagc tgagccagct gacccacggc atcactgagc 360
tgggccccta caccctggac aggcacagtc tctatgtcaa tggtttc 407

<210> SEQ ID NO 563
<211> LENGTH: 468
<212> TYPE: DNA
<213> ORGANISM: Homo sapiens

<400> SEQUENCE: 563
gtttcaccca tcagagctct atgacgacca ccagaactcc tgatacctcc acaatgcacc 60
tggcaacctc gagaactcca gcctccctgt ctggacctac gaccgccagc cctctcctgg 120
tgctattcac aattaacttc accatcacta acctgcggta tgaggagaac atgcatcacc 180
ctggctctag aaagtttaac accacggaga gagtccttca gggtctgctc aggcctgtgt 240
tcaagaacac cagtgttggc cctctgtact ctggctgcag actgaccttg ctcaggccca 300
agaaggatgg ggcagccacc aaagtggatg ccatctgcac ctaccgccct gatcccaaaa 360
gccctggact ggacagagag cagctatact gggagctgag ccagctaacc cacagcatca 420
ctgagctggg cccctacacc ctggacaggg acagtctcta tgtcaatg 468

-continued

<210> SEQ ID NO 564
<211> LENGTH: 468
<212> TYPE: DNA
<213> ORGANISM: Homo sapiens

<400> SEQUENCE: 564
gtttcacaca gcggagctct gtgcccacca ctagcattcc tgggaccccc acagtggacc 60
tgggaacatc tgggactcca gtttctaaac ctggtccctc ggctgccagc cctctcctgg 120
tgctattcac tctcaacttc accatcacca acctgcggta tgaggagaac atgcagcacc 180
ctggctccag gaagttcaac accacggaga gggtccttca gggcctgctc aggtccctgt 240
tcaagagcac cagtgttggc cctctgtact ctggctgcag actgactttg ctcaggcctg 300
aaaaggatgg gacagccact ggagtggatg ccatctgcac ccaccaccct gaccccaaaa 360
gccctaggct ggacagagag cagctgtatt gggagctgag ccagctgacc cacaatatca 420
ctgagctggg ccactatgcc ctggacaacg acagcctctt tgtcaatg 468

<210> SEQ ID NO 565
<211> LENGTH: 465
<212> TYPE: DNA
<213> ORGANISM: Homo sapiens

<400> SEQUENCE: 565
gtttcactca tcggagctct gtgtccacca ccagcactcc tgggaccccc acagtgtatc 60
tgggagcatc taagactcca gcctcgatat ttggcccttc agctgccagc catctcctga 120
tactattcac cctcaacttc accatcacta acctgcggta tgaggagaac atgtggcctg 180
gctccaggaa gttcaacact acagagaggg tccttcaggg cctgctaagg cccttgttca 240
agaacaccag tgttggccct ctgtactctg gctgcaggct gaccttgctc aggccagaga 300
aagatgggga agccaccgga gtggatgcca tctgcaccca ccgccctgac ccccacaggcc 360 ctgggctgga cagagagcag ctgtatttgg agctgagcca gctgacccac agcatcactg 420
agctgggccc ctacacactg gacagggaca gtctctatgt caatg 465

<210> SEQ ID NO 566
<211> LENGTH: 402
<212> TYPE: DNA
<213> ORGANISM: Homo sapiens

<400> SEQUENCE: 566
gtttcaccca tcggagctct gtacccacca ccagcaccgg ggtggtcagc gaggagccat 60
tcacactgaa cttcaccatc aacaacctgc gctacatggc ggacatgggc caacccggct 120
ccctcaagtt caacatcaca gacaacgtca tgaagcacct gctcagtcct ttgttccaga 180
ggagcagcct gggtgcacgg tacacaggct gcagggtcat cgcactaagg tctgtgaaga 240
acggtgctga gacacgggtg gacctcctct gcacctacct gcagcccctc agcggcccag 300
gtctgcctat caagcaggtg ttccatgagc tgagccagca gacccatggc atcacccggc 360
tgggccccta ctctctggac aaagacagcc tctaccttaa cg 402

<210> SEQ ID NO 567
<211> LENGTH: 450
<212> TYPE: DNA
<213> ORGANISM: Homo sapiens

<400> SEQUENCE: 567
gttacaatga acctggtcta gatgagcctc ctacaactcc caagccagcc accacattcc 60

-continued

```
tgcctcctct gtcagaagcc acaacagcca tggggtacca cctgaagacc ctcacactca    120

acttcaccat ctccaatctc cagtattcac cagatatggg caagggctca gctacattca    180

actccaccga gggggtcctt cagcacctgc tcagaccctt gttccagaag agcagcatgg    240

gccccttcta cttgggttgc caactgatct ccctcaggcc tgagaaggat ggggcagcca    300

ctggtgtgga caccacctgc acctaccacc ctgaccctgt gggccccggg ctggacatac    360

agcagcttta ctgggagctg agtcagctga cccatggtgt cacccaactg ggcttctatg    420

tcctggacag ggatagcctc ttcatcaatg                                     450
```

<210> SEQ ID NO 568
<211> LENGTH: 1060
<212> TYPE: DNA
<213> ORGANISM: Homo sapiens
<220> FEATURE:
<221> NAME/KEY: misc_feature
<222> LOCATION: 406,742,801
<223> OTHER INFORMATION: n = A,T,C or G

<400> SEQUENCE: 568

```
gctatgcacc ccagaattta tcaatccggg gcgagtacca gataaatttc cacattgtca     60

actggaacct cagtaatcca gaccccacat cctcagagta catcaccctg ctgagggaca    120

tccaggacaa ggtcaccaca ctctacaaag gcagtcaact acatgacaca ttccgcttct    180

gcctggtcac caacttgacg atggactccg tgttggtcac tgtcaaggca ttgttctcct    240

ccaatttgga ccccagcctg gtggagcaag tctttctaga taagaccctg aatgcctcat    300

tccattggct gggctccacc taccagttgg tggacatcca tgtgacagaa atggagtcat    360

cagtttatca accaacaagc agctccagca cccagcactt ctaccygaat ttcaccatca    420

ccaacctacc atattcccag gacaaagccc agccaggcac caccaattac cagaggaaca    480

aaaggaatat tgaggatgcg ctcaaccaac tcttccgaaa cagcagcatc aagagttatt    540

tttctgactg tcaagtttca acattcaggt ctgtccccaa caggcaccac accggggtgg    600

actccctgtg taacttctcg ccactggctc ggagagtaga cagagttgcc atctatgagg    660

aatttctgcg gatgacccgg aatggtaccc agctgcagaa cttcaccctg gacaggagca    720

gtgtccttgt ggatgggtat tytcccaaca gaaatgagcc cttaactggg aattctgacc    780

ttcccttctg ggctgtcatc ytcatcggct tggcaggact cctgggactc atcacatgcc    840

tgatctgcgg tgtcctggtg accacccgcc ggcggaagaa ggaaggagaa tacaacgtcc    900

agcaacagtg cccaggctac taccagtcac acctagacct ggaggatctg caatgactgg    960

aacttgccgg tgcctggggt gcctttcccc cagccagggt ccaaagaagc ttggctgggg   1020

cagaaataaa ccatattggt cggacacaaa aaaaaaaaaa                          1060
```

<210> SEQ ID NO 569
<211> LENGTH: 10622
<212> TYPE: DNA
<213> ORGANISM: Homo sapiens
<220> FEATURE:
<221> NAME/KEY: misc_feature
<222> LOCATION: 1,691,1164,1165,1730,2015,2149,2785,3044,3163,
4483,4632,4825,4841,4849,4883,4915,4932,4947,6355,
6370,7716,8210,9131,9968,10304,10363
<223> OTHER INFORMATION: n = A,T,C or G

<400> SEQUENCE: 569

```
ncatccccag ctcgaacagc agccacagtc ccattcatgg tgccattcac cctcaacttc     60

aactcatcac caacctgcag tacgaggagg acatgcggca cctggttcca ggaagttcaa    120
```

-continued

```
cgcgcacaga gagagaactg cagggtcgtg ctcaaaccct agatcaggaa tagcagtctg    180
gaatacctct attcaggctg cagactagcc tcactcaggc cagagaagga tagctcagcc    240
acggcagtgg atgccatctg cacacatcgc cctgaccctg aagacctcgg actggacaga    300
gagcgactgt actgggagct gagcaatctg acaaatggca tccaggagct gggcccctac    360
accctggacc ggaacagtct ctatgtcaat ggtttcaccc atcgaagctc tatgcccacc    420
accagcactc ctgggacctc cacagtggat gtgggaacct cagggactcc atcctccagc    480
cccagcccca cgactgctgg ccctctcctg atgccgttca ccctcaactt caccatcacc    540
aacctgcagt acgaggagga catgcgtcgc actggctcca ggaagttcaa caccatggag    600
agtgtcctgc agggtctgct caagcccttg ttcaagaaca ccagtgttgg ccctctgtac    660
tctggctgca gattgacctt gctcaggccc ragaaagatg gggcagccac tggagtggat    720
gccatctgca cccaccgcct tgaccccaaa agccctggac tcaacaggga gcagctgtac    780
tgggagctaa gcaaactgac caatgacatt gaagagctgg gcccctacac cctggacagg    840
aacagtctct atgtcaatgg tttcacccat cagagctctg tgtccaccac cagcactcct    900
gggacctcca cagtggatct cagaacctca gtgactccat cctccctctc cagccccaca    960
attatggctg ctggccctct cctggtacca ttcaccctca acttcaccat caccaacctg   1020
cagtatgggg aggacatggg tcaccctggc tccaggaagt tcaacaccac agagagggtc   1080
ctgcagggtc tgcttggtcc catattcaag aacaccagtg ttggccctct gtactctggc   1140
tgcagactga cctctctcag gtcyragaag gatggagcag ccactggagt ggatgccatc   1200
tgcatccatc atcttgaccc caaaagccct ggactcaaca gagagcggct gtactgggag   1260
ctgagccaac tgaccaatgg catcaaagag ctgggcccct acaccctgga caggaacagt   1320
ctctatgtca atgctgctgg ccctctcctg gtgctgttca ccctcaactt caccatcacc   1380
aacctgaagt atgaggagga catgcatcgc cctggctcca ggaagttcaa caccactgag   1440
agggtcctgc agactctgcg tggtcctatg ttcaagaaca ccagtggtgg ccttctgtac   1500
tctggctgca gactgacctt gctcaggtcc gagaaggatg gagcagccac tggagtggat   1560
gccatctgca cccaccgtct tgaccccaaa agccctggag tggacaggga gcagctatac   1620
tgggagctga gccagctgac caatggcatc aaagagctgg gcccctacac cctggacagg   1680
aacagtctct atgtcaatgg tttcacccat cggacctctg tgcccaccas cagcactcct   1740
gggacctcca cagtggacct tggaacctca gggactccat tctccctccc aagccccgca   1800
actgctggcc ctctcctggt gctgttcacc ctcaacttca ccatcaccaa cctgaagtat   1860
gaggaggaca tgcatcgccc tggctccagg aagttcaaca ccactgagag ggtcctgcag   1920
actctgcttg gtcctatgtt caagaacacc agtgttggcc ttctgtactc tggctgcaga   1980
ctgaccttgc tcaggtccga gaaggatgga gcagycactg gagtggatgc catctgcacc   2040
caccgtcttg accccaaaag ccctggagtg gacagggagc agctatactg ggagctgagc   2100
cagctgacca atggcatcaa agagctgggc ccctacaccc tggacaggma cagtctctat   2160
gtcaatggtt tcacccattg gatccctgtg cccaccagca gcactcctgg gacctccaca   2220
gtggaccttg ggtcagggac tccatcctcc ctccccagcc ccacaactgc tggccctctc   2280
ctggtgccat tcaccctcaa cttcaccatc accaacctgc agtacgagga ggacatgcat   2340
cacccaggct ccaggaagtt caacaccacg gagcgggtcc tgcagggtct gcttggtccc   2400
atgttcaaga acaccagtgt cggccttctg tactctggct gcagactgac cttgctcagg   2460
```

-continued

```
cctgagaaga atggggcagc cactggaatg gatgccatct gcagccaccg tcttgacccc   2520
aaaagccctg gactcaacag agagcagctg tactgggagc tgagccagct gacccatggc   2580
atcaaagagc tgggccccta caccctggac aggcacagtc tctatgtcaa tggtttcacc   2640
cattggatcc ctgtgcccac cagcagcact cctgggacct ccacagtgga ccttgggtca   2700
gggactccat cctccctccc cagccccaca actgctggcc ctctcctggt gccgttcacc   2760
ctcaacttca ccatcaccaa cctgragtac gaggaggaca tgcattgccc tggctccagg   2820
aagttcaaca ccacagagag agtcctgcag agtctgcttg gtcccatgtt caagaacacc   2880
agtgttggcc ctctgtactc tggctgcaga ctgaccttgc tcaggtccga gaaggatgga   2940
gcagccactg gagtggatgc catctgcacc caccgtcttg accccaaaag ccctggagtg   3000
gacagggagc agctatactg ggagctgagc cagctgacca atgscatcaa agagctgggt   3060
ccctacaccc tggacagcaa cagtctctat gtcaatggtt tcacccatca gacctctgcg   3120
cccaacacca gcactcctgg gacctccaca gtggaccttg ggwcctcagg gactccatcc   3180
tccctcccca gccctacatc tgctggccct ctcctggtgc cattcaccct caacttcacc   3240
atcaccaacc tgcagtacga ggaggacatg catcacccag gctccaggaa gttcaacacc   3300
acggagcggg tcctgcaggg tctgcttggt cccatgttca agaacaccag tgtcggcctt   3360
ctgtactctg gctgcagact gaccttgctc aggcctgaga agaatggggc agccactgga   3420
atggatgcca tctgcagcca ccgtcttgac ccccaaaagcc ctggactcaa cagagagcag   3480
ctgtactggg agctgagcca gctgacccat ggcatcaaag agctgggccc ctacaccctg   3540
gacaggaaca gtctctatgt caatggtttc acccatcgga gctctgtggc ccccaccagc   3600
actcctggga cctccacagt ggaccttggg acctcaggga ctccatcctc cctccccagc   3660
cccacaacag ctgttcctct cctggtgccg ttcaccctca actttaccat caccaatctg   3720
cagtatgggg aggacatgcg tcaccctggc tccaggaagt tcaacaccac agagagggtc   3780
ctgcagggtc tgcttggtcc cttgttcaag aactccagtg tcggccctct gtactctggc   3840
tgcagactga tctctctcag gtctgagaag gatggggcag ccactggagt ggatgccatc   3900
tgcacccacc accttaaccc tcaaagccct ggactggaca gggagcagct gtactggcag   3960
ctgagccaga tgaccaatgg catcaaagag ctgggcccct acaccctgga ccggaacagt   4020
ctctacgtca atggtttcac ccatcggagc tctgggctca ccaccagcac tccttggact   4080
tccacagttg accttggaac ctcagggact ccatcccccg tccccagccc cacaactgct   4140
ggccctctcc tggtgccatt caccctaaac ttcaccatca ccaacctgca gtatgaggag   4200
gacatgcatc gccctggatc taggaagttc aacgccacag agagggtcct gcagggtctg   4260
cttagtccca tattcaagaa ctccagtgtt ggccctctgt actctggctg cagactgacc   4320
tctctcaggc ccgagaagga tggggcagca actggaatgg atgctgtctg cctctaccac   4380
cctaatccca aaagacctgg gctggacaga gagcagctgt actgggagct aagccagctg   4440
acccacaaca tcactgagct gggcccctac agcctggaca ggsacagtct ctatgtcaat   4500
ggtttcaccc atcagaactc tgtgcccacc accagtactc ctgggacctc cacagtgtac   4560
tgggcaacca ctgggactcc atcctccttc cccggccaca cagagcctgg ccctctcctg   4620
ataccattca cwttcaactt taccatcacc aacctgcatt atgaggaaaa catgcaacac   4680
cctggttcca ggaagttcaa caccacggag agggttctgc agggtctgct cacgcccttg   4740
ttcaagaaca ccagtgttgg ccctctgtac tctggctgca gactgacctt gctcagacct   4800
gagaagcagg aggcagccac tggartggac accatctgta yccaccgcst tgatcccatc   4860
```

-continued

```
ggacctggac tggacagaga gcrgctatac tgggagctga gccagctgac ccacrgcatc   4920
acagagctgg gmccctacac cctggayagg gacagtctct atgtcaatgg cttcaaccct   4980
tggagctctg tgccaaccac cagcactcct gggacctcca cagtgcacct ggcaacctct   5040
gggactccat cctccctgcc tggccacaca gcccctgtcc ctctcttgat accattcacc   5100
ctcaacttta ccatcaccaa cctgcattat gaagaaaaca tgcaacaccc tggttccagg   5160
aagttcaaca ccacggagag ggttctgcag ggtctgctca agcccttgtt caagagcacc   5220
agcgttggcc ctctgtactc tggctgcaga ctgaccttgc tcagacctga gaaacatggg   5280
gcagccactg gagtggacgc catctgcacc ctccgccttg atcccactgg tcctggactg   5340
gacagagagc ggctatactg ggagctgagc cagctgacca acagcgttac agagctgggc   5400
ccctacaccc tggacaggga cagtctctat gtcaatggct tcacccatcg gagctctgtg   5460
ccaaccacca gtattcctgg gacctctgca gtgcacctgg aaacctctgg gactccagcc   5520
tccctccctg gccacacagc cctggccct ctcctggtgc cattcaccct caacttcact   5580
atcaccaacc tgcagtatga ggaggacatg cgtcaccctg gttccaggaa gttcaacacc   5640
acggagagag tcctgcaggg tctgctcaag cccttgttca agagcaccag tgttggccct   5700
ctgtactctg gctgcagact gaccttgctc aggcctgaaa aacgtggggc agccaccggc   5760
gtggacacca tctgcactca ccgccttgac cctctaaacc ctggactgga cagagagcag   5820
ctatactggg agctgagcaa actgacctgt ggcatcatcg agctgggccc ctacctcctg   5880
gacagaggca gtctctatgt caatggtttc acccatcgga actttgtgcc catcaccagc   5940
actcctggga cctccacagt acacctagga acctctgaaa ctccatcctc cctacctaga   6000
cccatagtgc ctggccctct cctggtgcca ttcaccctca acttcaccat caccaacttg   6060
cagtatgagg aggccatgcg acaccctggc tccaggaagt tcaataccac ggagagggtc   6120
ctacagggtc tgctcaggcc cttgttcaag aataccagta tcggccctct gtactccagc   6180
tgcagactga ccttgctcag gccagagaag gacaaggcag ccaccagagt ggatgccatc   6240
tgtacccacc accctgaccc tcaaagccct ggactgaaca gagagcagct gtactgggag   6300
ctgagccagc tgacccacgg catcactgag ctgggcccct acaccctgga caggsacagt   6360
ctctatgtcr atggtttcac tcattggagc cccataccaa ccaccagcac tcctgggacc   6420
tccatagtga acctgggaac ctctgggatc ccaccttccc tccctgaaac tacagccacc   6480
ggccctctcc tggtgccatt cacactcaac ttcaccatca ctaacctaca gtatgaggag   6540
aacatgggtc accctggctc caggaagttc aacatcacgg agagtgttct gcagggtctg   6600
ctcaagccct tgttcaagag caccagtgtt ggccctctgt attctggctg cagactgacc   6660
ttgctcaggc ctgagaagga cggagtagcc accagagtgg acgccatctg cacccaccgc   6720
cctgacccca aaatccctgg gctagacaga cagcagctat actgggagct gagccagctg   6780
acccacagca tcactgagct gggaccctac accctggata gggacagtct ctatgtcaat   6840
ggtttcaccc agcggagctc tgtgcccacc accagcactc ctgggacttt cacagtacag   6900
ccggaaacct ctgagactcc atcatccctc cctggcccca cagccactgg ccctgtcctg   6960
ctgccattca ccctcaattt taccatcatt aacctgcagt atgaggagga catgcatcgc   7020
cctggctcca ggaagttcaa caccacggag agggtccttc agggtctgct tatgcccttg   7080
ttcaagaaca ccagtgtcag ctctctgtac tctggttgca gactgacctt gctcaggcct   7140
gagaaggatg gggcagccac cagagtggat gctgtctgca cccatcgtcc tgaccccaaa   7200
```

-continued

```
agccctggac tggacagaga gcggctgtac tggaagctga gccagctgac ccacggcatc   7260
actgagctgg gcccctacac cctggacagg cacagtctct atgtcaatgg tttcacccat   7320
cagagctcta tgacgaccac cagaactcct gatacctcca caatgcacct ggcaacctcg   7380
agaactccag cctccctgtc tggacctacg accgccagcc ctctcctggt gctattcaca   7440
attaacttca ccatcactaa cctgcggtat gaggagaaca tgcatcaccc tggctctaga   7500
aagtttaaca ccacggagag agtccttcag ggtctgctca ggcctgtgtt caagaacacc   7560
agtgttggcc ctctgtactc tggctgcaga ctgaccttgc tcaggcccaa gaaggatggg   7620
gcagccacca aagtggatgc catctgcacc taccgccctg atcccaaaag ccctggactg   7680
gacagagagc agctatactg ggagctgagc cagctraccc acagcatcac tgagctgggc   7740
ccctacaccc tggacaggga cagtctctat gtcaatggtt tcacacagcg gagctctgtg   7800
cccaccacta gcattcctgg gacccccaca gtggacctgg gaacatctgg gactccagtt   7860
tctaaacctg gtccctcggc tgccagccct ctcctggtgc tattcactct caacttcacc   7920
atcaccaacc tgcggtatga ggagaacatg cagcaccctg gctccaggaa gttcaacacc   7980
acggagaggg tccttcaggg cctgctcagg tccctgttca agagcaccag tgttggccct   8040
ctgtactctg gctgcagact gactttgctc aggcctgaaa aggatgggac agccactgga   8100
gtggatgcca tctgcaccca ccaccctgac cccaaaagcc ctaggctgga cagagagcag   8160
ctgtattggg agctgagcca gctgacccac aatatcactg agctgggccm ctatgccctg   8220
gacaacgaca gcctctttgt caatggtttc actcatcgga gctctgtgtc caccaccagc   8280
actcctggga cccccacagt gtatctggga gcatctaaga ctccagcctc gatatttggc   8340
ccttcagctg ccagccatct cctgatacta ttcaccctca acttcaccat cactaacctg   8400
cggtatgagg agaacatgtg gcctggctcc aggaagttca acactacaga gagggtcctt   8460
cagggcctgc taaggccctt gttcaagaac accagtgttg gccctctgta ctctggctgc   8520
aggctgacct tgctcaggcc agagaaagat ggggaagcca ccggagtgga tgccatctgc   8580
acccaccgcc ctgaccccac aggccctggg ctggacagag agcagctgta tttggagctg   8640
agccagctga cccacagcat cactgagctg ggcccctaca cactggacag ggacagtctc   8700
tatgtcaatg gtttcaccca tcggagctct gtacccacca ccagcaccgg ggtggtcagc   8760
gaggagccat tcacactgaa cttcaccatc aacaacctgc gctacatggc ggacatgggc   8820
caacccggct ccctcaagtt caacatcaca gacaacgtca tgaagcacct gctcagtcct   8880
ttgttccaga ggagcagcct gggtgcacgg tacacaggct gcagggtcat cgcactaagg   8940
tctgtgaaga acggtgctga gacacgggtg gacctcctct gcacctacct gcagcccctc   9000
agcggcccag gtctgcctat caagcaggtg ttccatgagc tgagccagca gacccatggc   9060
atcacccggc tgggccccta ctctctggac aaagacagcc tctaccttaa cggttacaat   9120
gaacctggtc yagatgagcc tcctacaact cccaagccag ccaccacatt cctgcctcct   9180
ctgtcagaag ccacaacagc catggggtac cacctgaaga ccctcacact caacttcacc   9240
atctccaatc tccagtattc accagatatg ggcaagggct cagctacatt caactccacc   9300
gagggggtcc ttcagcacct gctcagaccc ttgttccaga agagcagcat gggccccttc   9360
tacttgggtt gccaactgat ctccctcagg cctgagaagg atggggcagc cactggtgtg   9420
gacaccacct gcacctacca ccctgaccct gtgggccccg ggctggacat acagcagctt   9480
tactgggagc tgagtcagct gacccatggt gtcacccaac tgggcttcta tgtcctggac   9540
agggatagcc tcttcatcaa tggctatgca ccccagaatt tatcaatccg gggcgagtac   9600
```

-continued

```
cagataaatt tccacattgt caactggaac ctcagtaatc cagaccccac atcctcagag   9660
tacatcaccc tgctgaggga catccaggac aaggtcacca cactctacaa aggcagtcaa   9720
ctacatgaca cattccgctt ctgcctggtc accaacttga cgatggactc cgtgttggtc   9780
actgtcaagg cattgttctc ctccaatttg gaccccagcc tggtggagca agtctttcta   9840
gataagaccc tgaatgcctc attccattgg ctgggctcca cctaccagtt ggtggacatc   9900
catgtgacag aaatggagtc atcagtttat caaccaacaa gcagctccag cacccagcac   9960
ttctaccyga atttcaccat caccaaccta ccatattccc aggacaaagc ccagccaggc  10020
accaccaatt accagaggaa caaaaggaat attgaggatg cgctcaacca actcttccga  10080
aacagcagca tcaagagtta tttttctgac tgtcaagttt caacattcag gtctgtcccc  10140
aacaggcacc acaccggggt ggactccctg tgtaacttct cgccactggc tcggagagta  10200
gacagagttg ccatctatga ggaatttctg cggatgaccc ggaatggtac ccagctgcag  10260
aacttcaccc tggacaggag cagtgtcctt gtggatgggt attytcccaa cagaaatgag  10320
cccttaactg ggaattctga ccttcccttc tgggctgtca tcytcatcgg cttggcagga  10380
ctcctgggac tcatcacatg cctgatctgc ggtgtcctgg tgaccacccg ccggcggaag  10440
aaggaaggag aatacaacgt ccagcaacag tgcccaggct actaccagtc acacctagac  10500
ctggaggatc tgcaatgact ggaacttgcc ggtgcctggg gtgcctttcc cccagccagg  10560
gtccaaagaa gcttggctgg ggcagaaata aaccatattg gtcggacaca aaaaaaaaaa  10620
aa                                                                 10622
```

<210> SEQ ID NO 570
<211> LENGTH: 469
<212> TYPE: DNA
<213> ORGANISM: Homo sapiens
<220> FEATURE:
<221> NAME/KEY: misc_feature
<222> LOCATION: 71,92,93,120,124,168,178,218,230,300,
321,350,387,412,414,415,422,423,451
<223> OTHER INFORMATION: n = A,T,C or G

<400> SEQUENCE: 570

```
gtttcaccca tcggagctct gtgcccacca ccagcactcc tgggacctcc acagtggacc     60
tgggaacctc wgggactcca tcctccctcc cyrgccccac agctgctggc cctctcctgr    120
tgcyattcac cctcaacttc accatcacca acctgcagta tgaggagrac atgcatcrcc    180
ctggctccag gaagttcaac accacggaga gggtcctkca gggtctgcty aggtcccttg    240
ttcaagaaca ccagtgttgg ccctctgtac tctggctgca gactgacctt gctcaggccy    300
gagaaggatg gggcagccac yggagtggat gccatctgca cccaccgccy tgaccccaaa    360
agccctggac tggacagaga gcagctrtac tgggagctga gccagctgac cmayrgcatc    420
amwgagctgg gcccctacac cctggacagg racagtctct atgtcaatg             469
```

<210> SEQ ID NO 571
<211> LENGTH: 130
<212> TYPE: PRT
<213> ORGANISM: Homo sapiens
<220> FEATURE:
<221> NAME/KEY: variant
<222> LOCATION: 69,107,110
<223> OTHER INFORMATION: Xaa = Any amino acid

<400> SEQUENCE: 571

His Pro Gln Leu Glu Gln Gln Pro Gln Ser His Ser Trp Cys His Ser

-continued

```
                5                   10                  15

Pro Ser Thr Ser Thr His His Gln Pro Ala Val Arg Gly Gly His Ala
            20                  25                  30

Ala Pro Gly Ser Arg Lys Phe Asn Ala His Arg Glu Arg Thr Ala Gly
        35                  40                  45

Ser Cys Ser Asn Pro Arg Ser Gly Ile Ala Val Trp Asn Thr Ser Ile
    50                  55                  60

Gln Ala Ala Asp Xaa Pro His Ser Gly Gln Arg Arg Ile Ala Gln Pro
65                  70                  75                  80

Arg Gln Trp Met Pro Ser Ala His Ile Ala Leu Thr Leu Lys Thr Ser
                85                  90                  95

Asp Trp Thr Glu Ser Asp Cys Thr Gly Ser Xaa Ala Ile Xaa Gln Met
            100                 105                 110

Ala Ser Arg Ser Trp Ala Pro Thr Pro Trp Thr Gly Thr Val Ser Met
        115                 120                 125

Ser Met
    130
```

```
<210> SEQ ID NO 572
<211> LENGTH: 130
<212> TYPE: PRT
<213> ORGANISM: Homo sapiens
<220> FEATURE:
<221> NAME/KEY: variant
<222> LOCATION: 1,58,78,92,94
<223> OTHER INFORMATION: Xaa = Any amino acid

<400> SEQUENCE: 572

Xaa Ile Pro Ser Ser Asn Ser Ser His Ser Pro Ile His Gly Ala Ile
                5                   10                  15

His Pro Gln Leu Gln Leu Ile Thr Asn Leu Gln Tyr Glu Glu Asp Met
            20                  25                  30

Arg His Leu Val Pro Gly Ser Ser Thr Arg Thr Glu Arg Glu Leu Gln
        35                  40                  45

Gly Arg Ala Gln Thr Leu Asp Gln Glu Xaa Gln Ser Gly Ile Pro Leu
    50                  55                  60

Phe Arg Leu Gln Thr Ser Leu Thr Gln Ala Arg Glu Gly Xaa Leu Ser
65                  70                  75                  80

His Gly Ser Gly Cys His Leu His Thr Ser Pro Xaa Pro Xaa Arg Pro
                85                  90                  95

Arg Thr Gly Gln Arg Ala Thr Val Leu Gly Ala Glu Gln Ser Asp Lys
            100                 105                 110

Trp His Pro Gly Ala Gly Pro Leu His Pro Gly Pro Glu Gln Ser Leu
        115                 120                 125

Cys Gln
    130
```

```
<210> SEQ ID NO 573
<211> LENGTH: 130
<212> TYPE: PRT
<213> ORGANISM: Homo sapiens
<220> FEATURE:
<221> NAME/KEY: variant
<222> LOCATION: 1,54
<223> OTHER INFORMATION: Xaa = Any amino acid

<400> SEQUENCE: 573

Xaa Ser Pro Ala Arg Thr Ala Ala Thr Val Pro Phe Met Val Pro Phe
                5                   10                  15
```

-continued

```
Thr Leu Asn Phe Asn Ser Ser Pro Thr Cys Ser Thr Arg Arg Thr Cys
            20                  25                  30

Gly Thr Trp Phe Gln Glu Val Gln Arg Ala Gln Arg Glu Asn Cys Arg
        35                  40                  45

Val Val Leu Lys Pro Xaa Ile Arg Asn Ser Ser Leu Glu Tyr Leu Tyr
    50                  55                  60

Ser Gly Cys Arg Leu Ala Ser Leu Arg Pro Glu Lys Asp Ser Ser Ala
65                  70                  75                  80

Thr Ala Val Asp Ala Ile Cys Thr His Arg Pro Asp Pro Glu Asp Leu
                85                  90                  95

Gly Leu Asp Arg Glu Arg Leu Tyr Trp Glu Leu Ser Asn Leu Thr Asn
            100                 105                 110

Gly Ile Gln Glu Leu Gly Pro Tyr Thr Leu Asp Arg Asn Ser Leu Tyr
        115                 120                 125

Val Asn
    130


<210> SEQ ID NO 574
<211> LENGTH: 156
<212> TYPE: PRT
<213> ORGANISM: Homo sapiens
<220> FEATURE:
<221> NAME/KEY: variant
<222> LOCATION: 101
<223> OTHER INFORMATION: Xaa = Any amino acid

<400> SEQUENCE: 574

Gly Phe Thr His Arg Ser Ser Met Pro Thr Thr Ser Thr Pro Gly Thr
                5                   10                  15

Ser Thr Val Asp Val Gly Thr Ser Gly Thr Pro Ser Ser Ser Pro Ser
            20                  25                  30

Pro Thr Thr Ala Gly Pro Leu Leu Met Pro Phe Thr Leu Asn Phe Thr
        35                  40                  45

Ile Thr Asn Leu Gln Tyr Glu Glu Asp Met Arg Arg Thr Gly Ser Arg
    50                  55                  60

Lys Phe Asn Thr Met Glu Ser Val Leu Gln Gly Leu Leu Lys Pro Leu
65                  70                  75                  80

Phe Lys Asn Thr Ser Val Gly Pro Leu Tyr Ser Gly Cys Arg Leu Thr
                85                  90                  95

Leu Leu Arg Pro Xaa Lys Asp Gly Ala Ala Thr Gly Val Asp Ala Ile
            100                 105                 110

Cys Thr His Arg Leu Asp Pro Lys Ser Pro Gly Leu Asn Arg Glu Gln
        115                 120                 125

Leu Tyr Trp Glu Leu Ser Lys Leu Thr Asn Asp Ile Glu Glu Leu Gly
    130                 135                 140

Pro Tyr Thr Leu Asp Arg Asn Ser Leu Tyr Val Asn
145                 150                 155


<210> SEQ ID NO 575
<211> LENGTH: 158
<212> TYPE: PRT
<213> ORGANISM: Homo sapiens
<220> FEATURE:
<221> NAME/KEY: variant
<222> LOCATION: 103
<223> OTHER INFORMATION: Xaa = Any amino acid

<400> SEQUENCE: 575
```

-continued

```
Gly Phe Thr His Gln Ser Ser Val Ser Thr Thr Ser Thr Pro Gly Thr
                5                   10                  15

Ser Thr Val Asp Leu Arg Thr Ser Val Thr Pro Ser Ser Leu Ser Ser
            20                  25                  30

Pro Thr Ile Met Ala Ala Gly Pro Leu Leu Val Pro Phe Thr Leu Asn
        35                  40                  45

Phe Thr Ile Thr Asn Leu Gln Tyr Gly Glu Asp Met Gly His Pro Gly
    50                  55                  60

Ser Arg Lys Phe Asn Thr Thr Glu Arg Val Leu Gln Gly Leu Leu Gly
65                  70                  75                  80

Pro Ile Phe Lys Asn Thr Ser Val Gly Pro Leu Tyr Ser Gly Cys Arg
                85                  90                  95

Leu Thr Ser Leu Arg Ser Xaa Lys Asp Gly Ala Ala Thr Gly Val Asp
            100                 105                 110

Ala Ile Cys Ile His His Leu Asp Pro Lys Ser Pro Gly Leu Asn Arg
        115                 120                 125

Glu Arg Leu Tyr Trp Glu Leu Ser Gln Leu Thr Asn Gly Ile Lys Glu
    130                 135                 140

Leu Gly Pro Tyr Thr Leu Asp Arg Asn Ser Leu Tyr Val Asn
145                 150                 155


<210> SEQ ID NO 576
<211> LENGTH: 122
<212> TYPE: PRT
<213> ORGANISM: Homo sapiens

<400> SEQUENCE: 576

Ala Ala Gly Pro Leu Leu Val Leu Phe Thr Leu Asn Phe Thr Ile Thr
                5                   10                  15

Asn Leu Lys Tyr Glu Glu Asp Met His Arg Pro Gly Ser Arg Lys Phe
            20                  25                  30

Asn Thr Thr Glu Arg Val Leu Gln Thr Leu Arg Gly Pro Met Phe Lys
        35                  40                  45

Asn Thr Ser Gly Gly Leu Leu Tyr Ser Gly Cys Arg Leu Thr Leu Leu
    50                  55                  60

Arg Ser Glu Lys Asp Gly Ala Ala Thr Gly Val Asp Ala Ile Cys Thr
65                  70                  75                  80

His Arg Leu Asp Pro Lys Ser Pro Gly Val Asp Arg Glu Gln Leu Tyr
                85                  90                  95

Trp Glu Leu Ser Gln Leu Thr Asn Gly Ile Lys Glu Leu Gly Pro Tyr
            100                 105                 110

Thr Leu Asp Arg Asn Ser Leu Tyr Val Asn
        115                 120


<210> SEQ ID NO 577
<211> LENGTH: 156
<212> TYPE: PRT
<213> ORGANISM: Homo sapiens
<220> FEATURE:
<221> NAME/KEY: variant
<222> LOCATION: 11,106,151
<223> OTHER INFORMATION: Xaa = Any amino acid

<400> SEQUENCE: 577

Gly Phe Thr His Arg Thr Ser Val Pro Thr Xaa Ser Thr Pro Gly Thr
                5                   10                  15

Ser Thr Val Asp Leu Gly Thr Ser Gly Thr Pro Phe Ser Leu Pro Ser
            20                  25                  30
```

-continued

```
Pro Ala Thr Ala Gly Pro Leu Leu Val Leu Phe Thr Leu Asn Phe Thr
        35                  40                  45

Ile Thr Asn Leu Lys Tyr Glu Glu Asp Met His Arg Pro Gly Ser Arg
    50                  55                  60

Lys Phe Asn Thr Thr Glu Arg Val Leu Gln Thr Leu Leu Gly Pro Met
65                  70                  75                  80

Phe Lys Asn Thr Ser Val Gly Leu Leu Tyr Ser Gly Cys Arg Leu Thr
                85                  90                  95

Leu Leu Arg Ser Glu Lys Asp Gly Ala Xaa Thr Gly Val Asp Ala Ile
            100                 105                 110

Cys Thr His Arg Leu Asp Pro Lys Ser Pro Gly Val Asp Arg Glu Gln
        115                 120                 125

Leu Tyr Trp Glu Leu Ser Gln Leu Thr Asn Gly Ile Lys Glu Leu Gly
    130                 135                 140

Pro Tyr Thr Leu Asp Arg Xaa Ser Leu Tyr Val Asn
145                 150                 155


<210> SEQ ID NO 578
<211> LENGTH: 155
<212> TYPE: PRT
<213> ORGANISM: Homo sapiens

<400> SEQUENCE: 578

Gly Phe Thr His Trp Ile Pro Val Pro Thr Ser Ser Thr Pro Gly Thr
                5                   10                  15

Ser Thr Val Asp Leu Gly Ser Gly Thr Pro Ser Ser Leu Pro Ser Pro
            20                  25                  30

Thr Thr Ala Gly Pro Leu Leu Val Pro Phe Thr Leu Asn Phe Thr Ile
        35                  40                  45

Thr Asn Leu Gln Tyr Glu Glu Asp Met His His Pro Gly Ser Arg Lys
    50                  55                  60

Phe Asn Thr Thr Glu Arg Val Leu Gln Gly Leu Leu Gly Pro Met Phe
65                  70                  75                  80

Lys Asn Thr Ser Val Gly Leu Leu Tyr Ser Gly Cys Arg Leu Thr Leu
                85                  90                  95

Leu Arg Pro Glu Lys Asn Gly Ala Ala Thr Gly Met Asp Ala Ile Cys
            100                 105                 110

Ser His Arg Leu Asp Pro Lys Ser Pro Gly Leu Asn Arg Glu Gln Leu
        115                 120                 125

Tyr Trp Glu Leu Ser Gln Leu Thr His Gly Ile Lys Glu Leu Gly Pro
    130                 135                 140

Tyr Thr Leu Asp Arg His Ser Leu Tyr Val Asn
145                 150                 155


<210> SEQ ID NO 579
<211> LENGTH: 155
<212> TYPE: PRT
<213> ORGANISM: Homo sapiens
<220> FEATURE:
<221> NAME/KEY: variant
<222> LOCATION: 52,138
<223> OTHER INFORMATION: Xaa = Any amino acid

<400> SEQUENCE: 579

Gly Phe Thr His Trp Ile Pro Val Pro Thr Ser Ser Thr Pro Gly Thr
                5                   10                  15

Ser Thr Val Asp Leu Gly Ser Gly Thr Pro Ser Ser Leu Pro Ser Pro
```

-continued

```
            20                  25                  30

Thr Thr Ala Gly Pro Leu Leu Val Pro Phe Thr Leu Asn Phe Thr Ile
        35                  40                  45

Thr Asn Leu Xaa Tyr Glu Glu Asp Met His Cys Pro Gly Ser Arg Lys
    50                  55                  60

Phe Asn Thr Thr Glu Arg Val Leu Gln Ser Leu Leu Gly Pro Met Phe
65                  70                  75                  80

Lys Asn Thr Ser Val Gly Pro Leu Tyr Ser Gly Cys Arg Leu Thr Leu
                85                  90                  95

Leu Arg Ser Glu Lys Asp Gly Ala Ala Thr Gly Val Asp Ala Ile Cys
            100                 105                 110

Thr His Arg Leu Asp Pro Lys Ser Pro Gly Val Asp Arg Glu Gln Leu
        115                 120                 125

Tyr Trp Glu Leu Ser Gln Leu Thr Asn Xaa Ile Lys Glu Leu Gly Pro
    130                 135                 140

Tyr Thr Leu Asp Ser Asn Ser Leu Tyr Val Asn
145                 150                 155


<210> SEQ ID NO 580
<211> LENGTH: 156
<212> TYPE: PRT
<213> ORGANISM: Homo sapiens
<220> FEATURE:
<221> NAME/KEY: variant
<222> LOCATION: 23
<223> OTHER INFORMATION: Xaa = Any amino acid

<400> SEQUENCE: 580

Gly Phe Thr His Gln Thr Ser Ala Pro Asn Thr Ser Thr Pro Gly Thr
                  5                  10                  15

Ser Thr Val Asp Leu Gly Xaa Ser Gly Thr Pro Ser Ser Leu Pro Ser
            20                  25                  30

Pro Thr Ser Ala Gly Pro Leu Leu Val Pro Phe Thr Leu Asn Phe Thr
        35                  40                  45

Ile Thr Asn Leu Gln Tyr Glu Glu Asp Met His His Pro Gly Ser Arg
    50                  55                  60

Lys Phe Asn Thr Thr Glu Arg Val Leu Gln Gly Leu Leu Gly Pro Met
65                  70                  75                  80

Phe Lys Asn Thr Ser Val Gly Leu Leu Tyr Ser Gly Cys Arg Leu Thr
                85                  90                  95

Leu Leu Arg Pro Glu Lys Asn Gly Ala Ala Thr Gly Met Asp Ala Ile
            100                 105                 110

Cys Ser His Arg Leu Asp Pro Lys Ser Pro Gly Leu Asn Arg Glu Gln
        115                 120                 125

Leu Tyr Trp Glu Leu Ser Gln Leu Thr His Gly Ile Lys Glu Leu Gly
    130                 135                 140

Pro Tyr Thr Leu Asp Arg Asn Ser Leu Tyr Val Asn
145                 150                 155


<210> SEQ ID NO 581
<211> LENGTH: 156
<212> TYPE: PRT
<213> ORGANISM: Homo sapiens

<400> SEQUENCE: 581

Gly Phe Thr His Arg Ser Ser Val Ala Pro Thr Ser Thr Pro Gly Thr
                  5                  10                  15
```

-continued

```
Ser Thr Val Asp Leu Gly Thr Ser Gly Thr Pro Ser Ser Leu Pro Ser
            20                  25                  30

Pro Thr Thr Ala Val Pro Leu Leu Val Pro Phe Thr Leu Asn Phe Thr
        35                  40                  45

Ile Thr Asn Leu Gln Tyr Gly Glu Asp Met Arg His Pro Gly Ser Arg
    50                  55                  60

Lys Phe Asn Thr Thr Glu Arg Val Leu Gln Gly Leu Leu Gly Pro Leu
65                  70                  75                  80

Phe Lys Asn Ser Ser Val Gly Pro Leu Tyr Ser Gly Cys Arg Leu Ile
                85                  90                  95

Ser Leu Arg Ser Glu Lys Asp Gly Ala Ala Thr Gly Val Asp Ala Ile
            100                 105                 110

Cys Thr His His Leu Asn Pro Gln Ser Pro Gly Leu Asp Arg Glu Gln
        115                 120                 125

Leu Tyr Trp Gln Leu Ser Gln Met Thr Asn Gly Ile Lys Glu Leu Gly
    130                 135                 140

Pro Tyr Thr Leu Asp Arg Asn Ser Leu Tyr Val Asn
145                 150                 155


<210> SEQ ID NO 582
<211> LENGTH: 156
<212> TYPE: PRT
<213> ORGANISM: Homo sapiens
<220> FEATURE:
<221> NAME/KEY: variant
<222> LOCATION: 151
<223> OTHER INFORMATION: Xaa = Any amino acid

<400> SEQUENCE: 582

Gly Phe Thr His Arg Ser Ser Gly Leu Thr Thr Ser Thr Pro Trp Thr
                5                   10                  15

Ser Thr Val Asp Leu Gly Thr Ser Gly Thr Pro Ser Pro Val Pro Ser
            20                  25                  30

Pro Thr Thr Ala Gly Pro Leu Leu Val Pro Phe Thr Leu Asn Phe Thr
        35                  40                  45

Ile Thr Asn Leu Gln Tyr Glu Glu Asp Met His Arg Pro Gly Ser Arg
    50                  55                  60

Lys Phe Asn Ala Thr Glu Arg Val Leu Gln Gly Leu Leu Ser Pro Ile
65                  70                  75                  80

Phe Lys Asn Ser Ser Val Gly Pro Leu Tyr Ser Gly Cys Arg Leu Thr
                85                  90                  95

Ser Leu Arg Pro Glu Lys Asp Gly Ala Ala Thr Gly Met Asp Ala Val
            100                 105                 110

Cys Leu Tyr His Pro Asn Pro Lys Arg Pro Gly Leu Asp Arg Glu Gln
        115                 120                 125

Leu Tyr Trp Glu Leu Ser Gln Leu Thr His Asn Ile Thr Glu Leu Gly
    130                 135                 140

Pro Tyr Ser Leu Asp Arg Xaa Ser Leu Tyr Val Asn
145                 150                 155


<210> SEQ ID NO 583
<211> LENGTH: 156
<212> TYPE: PRT
<213> ORGANISM: Homo sapiens
<220> FEATURE:
<221> NAME/KEY: variant
<222> LOCATION: 109,114,117,128,139
<223> OTHER INFORMATION: Xaa = Any amino acid
```

-continued

<400> SEQUENCE: 583

```
Gly Phe Thr His Gln Asn Ser Val Pro Thr Thr Ser Thr Pro Gly Thr
                  5                  10                  15

Ser Thr Val Tyr Trp Ala Thr Thr Gly Thr Pro Ser Ser Phe Pro Gly
             20                  25                  30

His Thr Glu Pro Gly Pro Leu Leu Ile Pro Phe Thr Phe Asn Phe Thr
         35                  40                  45

Ile Thr Asn Leu His Tyr Glu Glu Asn Met Gln His Pro Gly Ser Arg
     50                  55                  60

Lys Phe Asn Thr Thr Glu Arg Val Leu Gln Gly Leu Leu Thr Pro Leu
 65                  70                  75                  80

Phe Lys Asn Thr Ser Val Gly Pro Leu Tyr Ser Gly Cys Arg Leu Thr
                 85                  90                  95

Leu Leu Arg Pro Glu Lys Gln Glu Ala Ala Thr Gly Xaa Asp Thr Ile
            100                 105                 110

Cys Xaa His Arg Xaa Asp Pro Ile Gly Pro Gly Leu Asp Arg Glu Xaa
        115                 120                 125

Leu Tyr Trp Glu Leu Ser Gln Leu Thr His Xaa Ile Thr Glu Leu Gly
    130                 135                 140

Pro Tyr Thr Leu Asp Arg Asp Ser Leu Tyr Val Asn
145                 150                 155
```

<210> SEQ ID NO 584
<211> LENGTH: 156
<212> TYPE: PRT
<213> ORGANISM: Homo sapiens

<400> SEQUENCE: 584

```
Gly Phe Asn Pro Trp Ser Ser Val Pro Thr Thr Ser Thr Pro Gly Thr
                        5                  10                  15

Ser Thr Val His Leu Ala Thr Ser Gly Thr Pro Ser Ser Leu Pro Gly
             20                  25                  30

His Thr Ala Pro Val Pro Leu Leu Ile Pro Phe Thr Leu Asn Phe Thr
         35                  40                  45

Ile Thr Asn Leu His Tyr Glu Glu Asn Met Gln His Pro Gly Ser Arg
     50                  55                  60

Lys Phe Asn Thr Thr Glu Arg Val Leu Gln Gly Leu Leu Lys Pro Leu
 65                  70                  75                  80

Phe Lys Ser Thr Ser Val Gly Pro Leu Tyr Ser Gly Cys Arg Leu Thr
                 85                  90                  95

Leu Leu Arg Pro Glu Lys His Gly Ala Ala Thr Gly Val Asp Ala Ile
            100                 105                 110

Cys Thr Leu Arg Leu Asp Pro Thr Gly Pro Gly Leu Asp Arg Glu Arg
        115                 120                 125

Leu Tyr Trp Glu Leu Ser Gln Leu Thr Asn Ser Val Thr Glu Leu Gly
    130                 135                 140

Pro Tyr Thr Leu Asp Arg Asp Ser Leu Tyr Val Asn
145                 150                 155
```

<210> SEQ ID NO 585
<211> LENGTH: 156
<212> TYPE: PRT
<213> ORGANISM: Homo sapiens

<400> SEQUENCE: 585

```
Gly Phe Thr His Arg Ser Ser Val Pro Thr Thr Ser Ile Pro Gly Thr
```

-continued

```
                  5                  10                  15

Ser Ala Val His Leu Glu Thr Ser Gly Thr Pro Ala Ser Leu Pro Gly
            20                  25                  30

His Thr Ala Pro Gly Pro Leu Leu Val Pro Phe Thr Leu Asn Phe Thr
        35                  40                  45

Ile Thr Asn Leu Gln Tyr Glu Glu Asp Met Arg His Pro Gly Ser Arg
    50                  55                  60

Lys Phe Asn Thr Thr Glu Arg Val Leu Gln Gly Leu Leu Lys Pro Leu
65                  70                  75                  80

Phe Lys Ser Thr Ser Val Gly Pro Leu Tyr Ser Gly Cys Arg Leu Thr
                85                  90                  95

Leu Leu Arg Pro Glu Lys Arg Gly Ala Ala Thr Gly Val Asp Thr Ile
            100                 105                 110

Cys Thr His Arg Leu Asp Pro Leu Asn Pro Gly Leu Asp Arg Glu Gln
        115                 120                 125

Leu Tyr Trp Glu Leu Ser Lys Leu Thr Cys Gly Ile Ile Glu Leu Gly
    130                 135                 140

Pro Tyr Leu Leu Asp Arg Gly Ser Leu Tyr Val Asn
145                 150                 155
```

<210> SEQ ID NO 586
<211> LENGTH: 156
<212> TYPE: PRT
<213> ORGANISM: Homo sapiens
<220> FEATURE:
<221> NAME/KEY: variant
<222> LOCATION: 151,156
<223> OTHER INFORMATION: Xaa = Any amino acid

<400> SEQUENCE: 586

```
Gly Phe Thr His Arg Asn Phe Val Pro Ile Thr Ser Thr Pro Gly Thr
                  5                  10                  15

Ser Thr Val His Leu Gly Thr Ser Glu Thr Pro Ser Ser Leu Pro Arg
            20                  25                  30

Pro Ile Val Pro Gly Pro Leu Leu Val Pro Phe Thr Leu Asn Phe Thr
        35                  40                  45

Ile Thr Asn Leu Gln Tyr Glu Glu Ala Met Arg His Pro Gly Ser Arg
    50                  55                  60

Lys Phe Asn Thr Thr Glu Arg Val Leu Gln Gly Leu Leu Arg Pro Leu
65                  70                  75                  80

Phe Lys Asn Thr Ser Ile Gly Pro Leu Tyr Ser Ser Cys Arg Leu Thr
                85                  90                  95

Leu Leu Arg Pro Glu Lys Asp Lys Ala Ala Thr Arg Val Asp Ala Ile
            100                 105                 110

Cys Thr His His Pro Asp Pro Gln Ser Pro Gly Leu Asn Arg Glu Gln
        115                 120                 125

Leu Tyr Trp Glu Leu Ser Gln Leu Thr His Gly Ile Thr Glu Leu Gly
    130                 135                 140

Pro Tyr Thr Leu Asp Arg Xaa Ser Leu Tyr Val Xaa
145                 150                 155
```

<210> SEQ ID NO 587
<211> LENGTH: 156
<212> TYPE: PRT
<213> ORGANISM: Homo sapiens

<400> SEQUENCE: 587

-continued

```
Gly Phe Thr His Trp Ser Pro Ile Pro Thr Thr Ser Thr Pro Gly Thr
                    5                   10                  15

Ser Ile Val Asn Leu Gly Thr Ser Gly Ile Pro Pro Ser Leu Pro Glu
            20                  25                  30

Thr Thr Ala Thr Gly Pro Leu Leu Val Pro Phe Thr Leu Asn Phe Thr
        35                  40                  45

Ile Thr Asn Leu Gln Tyr Glu Glu Asn Met Gly His Pro Gly Ser Arg
    50                  55                  60

Lys Phe Asn Ile Thr Glu Ser Val Leu Gln Gly Leu Leu Lys Pro Leu
65                  70                  75                  80

Phe Lys Ser Thr Ser Val Gly Pro Leu Tyr Ser Gly Cys Arg Leu Thr
                85                  90                  95

Leu Leu Arg Pro Glu Lys Asp Gly Val Ala Thr Arg Val Asp Ala Ile
            100                 105                 110

Cys Thr His Arg Pro Asp Pro Lys Ile Pro Gly Leu Asp Arg Gln Gln
        115                 120                 125

Leu Tyr Trp Glu Leu Ser Gln Leu Thr His Ser Ile Thr Glu Leu Gly
    130                 135                 140

Pro Tyr Thr Leu Asp Arg Asp Ser Leu Tyr Val Asn
145                 150                 155
```

<210> SEQ ID NO 588
<211> LENGTH: 156
<212> TYPE: PRT
<213> ORGANISM: Homo sapiens

<400> SEQUENCE: 588

```
Gly Phe Thr Gln Arg Ser Ser Val Pro Thr Thr Ser Thr Pro Gly Thr
                    5                   10                  15

Phe Thr Val Gln Pro Glu Thr Ser Glu Thr Pro Ser Ser Leu Pro Gly
            20                  25                  30

Pro Thr Ala Thr Gly Pro Val Leu Leu Pro Phe Thr Leu Asn Phe Thr
        35                  40                  45

Ile Ile Asn Leu Gln Tyr Glu Glu Asp Met His Arg Pro Gly Ser Arg
    50                  55                  60

Lys Phe Asn Thr Thr Glu Arg Val Leu Gln Gly Leu Leu Met Pro Leu
65                  70                  75                  80

Phe Lys Asn Thr Ser Val Ser Ser Leu Tyr Ser Gly Cys Arg Leu Thr
                85                  90                  95

Leu Leu Arg Pro Glu Lys Asp Gly Ala Ala Thr Arg Val Asp Ala Val
            100                 105                 110

Cys Thr His Arg Pro Asp Pro Lys Ser Pro Gly Leu Asp Arg Glu Arg
        115                 120                 125

Leu Tyr Trp Lys Leu Ser Gln Leu Thr His Gly Ile Thr Glu Leu Gly
    130                 135                 140

Pro Tyr Thr Leu Asp Arg His Ser Leu Tyr Val Asn
145                 150                 155
```

<210> SEQ ID NO 589
<211> LENGTH: 156
<212> TYPE: PRT
<213> ORGANISM: Homo sapiens

<400> SEQUENCE: 589

```
Gly Phe Thr His Gln Ser Ser Met Thr Thr Thr Arg Thr Pro Asp Thr
                    5                   10                  15
```

-continued

```
Ser Thr Met His Leu Ala Thr Ser Arg Thr Pro Ala Ser Leu Ser Gly
            20                  25                  30

Pro Thr Thr Ala Ser Pro Leu Leu Val Leu Phe Thr Ile Asn Phe Thr
        35                  40                  45

Ile Thr Asn Leu Arg Tyr Glu Glu Asn Met His His Pro Gly Ser Arg
    50                  55                  60

Lys Phe Asn Thr Thr Glu Arg Val Leu Gln Gly Leu Leu Arg Pro Val
 65                 70                  75                  80

Phe Lys Asn Thr Ser Val Gly Pro Leu Tyr Ser Gly Cys Arg Leu Thr
                85                  90                  95

Leu Leu Arg Pro Lys Lys Asp Gly Ala Ala Thr Lys Val Asp Ala Ile
            100                 105                 110

Cys Thr Tyr Arg Pro Asp Pro Lys Ser Pro Gly Leu Asp Arg Glu Gln
        115                 120                 125

Leu Tyr Trp Glu Leu Ser Gln Leu Thr His Ser Ile Thr Glu Leu Gly
    130                 135                 140

Pro Tyr Thr Leu Asp Arg Asp Ser Leu Tyr Val Asn
145                 150                 155


<210> SEQ ID NO 590
<211> LENGTH: 156
<212> TYPE: PRT
<213> ORGANISM: Homo sapiens
<220> FEATURE:
<221> NAME/KEY: variant
<222> LOCATION: 145
<223> OTHER INFORMATION: Xaa = Any amino acid

<400> SEQUENCE: 590

Gly Phe Thr Gln Arg Ser Ser Val Pro Thr Thr Ser Ile Pro Gly Thr
                  5                  10                  15

Pro Thr Val Asp Leu Gly Thr Ser Gly Thr Pro Val Ser Lys Pro Gly
            20                  25                  30

Pro Ser Ala Ala Ser Pro Leu Leu Val Leu Phe Thr Leu Asn Phe Thr
        35                  40                  45

Ile Thr Asn Leu Arg Tyr Glu Glu Asn Met Gln His Pro Gly Ser Arg
    50                  55                  60

Lys Phe Asn Thr Thr Glu Arg Val Leu Gln Gly Leu Leu Arg Ser Leu
 65                 70                  75                  80

Phe Lys Ser Thr Ser Val Gly Pro Leu Tyr Ser Gly Cys Arg Leu Thr
                85                  90                  95

Leu Leu Arg Pro Glu Lys Asp Gly Thr Ala Thr Gly Val Asp Ala Ile
            100                 105                 110

Cys Thr His His Pro Asp Pro Lys Ser Pro Arg Leu Asp Arg Glu Gln
        115                 120                 125

Leu Tyr Trp Glu Leu Ser Gln Leu Thr His Asn Ile Thr Glu Leu Gly
    130                 135                 140

Xaa Tyr Ala Leu Asp Asn Asp Ser Leu Phe Val Asn
145                 150                 155


<210> SEQ ID NO 591
<211> LENGTH: 155
<212> TYPE: PRT
<213> ORGANISM: Homo sapiens

<400> SEQUENCE: 591

Gly Phe Thr His Arg Ser Ser Val Ser Thr Thr Ser Thr Pro Gly Thr
                  5                  10                  15
```

-continued

Pro Thr Val Tyr Leu Gly Ala Ser Lys Thr Pro Ala Ser Ile Phe Gly
20 25 30

Pro Ser Ala Ala Ser His Leu Leu Ile Leu Phe Thr Leu Asn Phe Thr
35 40 45

Ile Thr Asn Leu Arg Tyr Glu Glu Asn Met Trp Pro Gly Ser Arg Lys
50 55 60

Phe Asn Thr Thr Glu Arg Val Leu Gln Gly Leu Leu Arg Pro Leu Phe
65 70 75 80

Lys Asn Thr Ser Val Gly Pro Leu Tyr Ser Gly Cys Arg Leu Thr Leu
85 90 95

Leu Arg Pro Glu Lys Asp Gly Glu Ala Thr Gly Val Asp Ala Ile Cys
100 105 110

Thr His Arg Pro Asp Pro Thr Gly Pro Gly Leu Asp Arg Glu Gln Leu
115 120 125

Tyr Leu Glu Leu Ser Gln Leu Thr His Ser Ile Thr Glu Leu Gly Pro
130 135 140

Tyr Thr Leu Asp Arg Asp Ser Leu Tyr Val Asn
145 150 155

<210> SEQ ID NO 592
<211> LENGTH: 134
<212> TYPE: PRT
<213> ORGANISM: Homo sapiens

<400> SEQUENCE: 592

Gly Phe Thr His Arg Ser Ser Val Pro Thr Thr Ser Thr Gly Val Val
5 10 15

Ser Glu Glu Pro Phe Thr Leu Asn Phe Thr Ile Asn Asn Leu Arg Tyr
20 25 30

Met Ala Asp Met Gly Gln Pro Gly Ser Leu Lys Phe Asn Ile Thr Asp
35 40 45

Asn Val Met Lys His Leu Leu Ser Pro Leu Phe Gln Arg Ser Ser Leu
50 55 60

Gly Ala Arg Tyr Thr Gly Cys Arg Val Ile Ala Leu Arg Ser Val Lys
65 70 75 80

Asn Gly Ala Glu Thr Arg Val Asp Leu Leu Cys Thr Tyr Leu Gln Pro
85 90 95

Leu Ser Gly Pro Gly Leu Pro Ile Lys Gln Val Phe His Glu Leu Ser
100 105 110

Gln Gln Thr His Gly Ile Thr Arg Leu Gly Pro Tyr Ser Leu Asp Lys
115 120 125

Asp Ser Leu Tyr Leu Asn
130

<210> SEQ ID NO 593
<211> LENGTH: 150
<212> TYPE: PRT
<213> ORGANISM: Homo sapiens
<220> FEATURE:
<221> NAME/KEY: variant
<222> LOCATION: 7
<223> OTHER INFORMATION: Xaa = Any amino acid

<400> SEQUENCE: 593

Gly Tyr Asn Glu Pro Gly Xaa Asp Glu Pro Pro Thr Thr Pro Lys Pro
5 10 15

Ala Thr Thr Phe Leu Pro Pro Leu Ser Glu Ala Thr Thr Ala Met Gly

-continued

```
            20                  25                  30

Tyr His Leu Lys Thr Leu Thr Leu Asn Phe Thr Ile Ser Asn Leu Gln
        35                  40                  45

Tyr Ser Pro Asp Met Gly Lys Gly Ser Ala Thr Phe Asn Ser Thr Glu
    50                  55                  60

Gly Val Leu Gln His Leu Leu Arg Pro Leu Phe Gln Lys Ser Ser Met
 65                  70                  75                  80

Gly Pro Phe Tyr Leu Gly Cys Gln Leu Ile Ser Leu Arg Pro Glu Lys
                85                  90                  95

Asp Gly Ala Ala Thr Gly Val Asp Thr Thr Cys Thr Tyr His Pro Asp
            100                 105                 110

Pro Val Gly Pro Gly Leu Asp Ile Gln Gln Leu Tyr Trp Glu Leu Ser
        115                 120                 125

Gln Leu Thr His Gly Val Thr Gln Leu Gly Phe Tyr Val Leu Asp Arg
    130                 135                 140

Asp Ser Leu Phe Ile Asn
145                 150


<210> SEQ ID NO 594
<211> LENGTH: 318
<212> TYPE: PRT
<213> ORGANISM: Homo sapiens
<220> FEATURE:
<221> NAME/KEY: variant
<222> LOCATION: 136,248,268
<223> OTHER INFORMATION: Xaa = Any amino acid

<400> SEQUENCE: 594

Gly Tyr Ala Pro Gln Asn Leu Ser Ile Arg Gly Glu Tyr Gln Ile Asn
                  5                  10                  15

Phe His Ile Val Asn Trp Asn Leu Ser Asn Pro Asp Pro Thr Ser Ser
            20                  25                  30

Glu Tyr Ile Thr Leu Leu Arg Asp Ile Gln Asp Lys Val Thr Thr Leu
        35                  40                  45

Tyr Lys Gly Ser Gln Leu His Asp Thr Phe Arg Phe Cys Leu Val Thr
    50                  55                  60

Asn Leu Thr Met Asp Ser Val Leu Val Thr Val Lys Ala Leu Phe Ser
 65                  70                  75                  80

Ser Asn Leu Asp Pro Ser Leu Val Glu Gln Val Phe Leu Asp Lys Thr
                85                  90                  95

Leu Asn Ala Ser Phe His Trp Leu Gly Ser Thr Tyr Gln Leu Val Asp
            100                 105                 110

Ile His Val Thr Glu Met Glu Ser Ser Val Tyr Gln Pro Thr Ser Ser
        115                 120                 125

Ser Ser Thr Gln His Phe Tyr Xaa Asn Phe Thr Ile Thr Asn Leu Pro
    130                 135                 140

Tyr Ser Gln Asp Lys Ala Gln Pro Gly Thr Thr Asn Tyr Gln Arg Asn
145                 150                 155                 160

Lys Arg Asn Ile Glu Asp Ala Leu Asn Gln Leu Phe Arg Asn Ser Ser
                165                 170                 175

Ile Lys Ser Tyr Phe Ser Asp Cys Gln Val Ser Thr Phe Arg Ser Val
            180                 185                 190

Pro Asn Arg His His Thr Gly Val Asp Ser Leu Cys Asn Phe Ser Pro
        195                 200                 205

Leu Ala Arg Arg Val Asp Arg Val Ala Ile Tyr Glu Glu Phe Leu Arg
    210                 215                 220
```

-continued

```
Met Thr Arg Asn Gly Thr Gln Leu Gln Asn Phe Thr Leu Asp Arg Ser
225                 230                 235                 240

Ser Val Leu Val Asp Gly Tyr Xaa Pro Asn Arg Asn Glu Pro Leu Thr
                245                 250                 255

Gly Asn Ser Asp Leu Pro Phe Trp Ala Val Ile Xaa Ile Gly Leu Ala
            260                 265                 270

Gly Leu Leu Gly Leu Ile Thr Cys Leu Ile Cys Gly Val Leu Val Thr
        275                 280                 285

Thr Arg Arg Arg Lys Lys Glu Gly Glu Tyr Asn Val Gln Gln Gln Cys
    290                 295                 300

Pro Gly Tyr Tyr Gln Ser His Leu Asp Leu Glu Asp Leu Gln
305                 310                 315


<210> SEQ ID NO 595
<211> LENGTH: 3451
<212> TYPE: PRT
<213> ORGANISM: Homo sapiens
<220> FEATURE:
<221> NAME/KEY: VARIANT
<222> LOCATION: 177, 335, 523, 618, 663, 875, 961, 1001, 1441, 1555,
      1560, 1563, 1574, 1585, 2065, 2070, 2683, 2990, 3269, 3381, 3401
<223> OTHER INFORMATION: Xaa = Any Amino Acid

<400> SEQUENCE: 595

Ile Arg Asn Ser Ser Leu Glu Tyr Leu Tyr Ser Gly Cys Arg Leu Ala
 1               5                  10                  15

Ser Leu Arg Pro Glu Lys Asp Ser Ser Ala Thr Ala Val Asp Ala Ile
            20                  25                  30

Cys Thr His Arg Pro Asp Pro Glu Asp Leu Gly Leu Asp Arg Glu Arg
        35                  40                  45

Leu Tyr Trp Glu Leu Ser Asn Leu Thr Asn Gly Ile Gln Glu Leu Gly
    50                  55                  60

Pro Tyr Thr Leu Asp Arg Asn Ser Leu Tyr Val Asn Gly Phe Thr His
65                  70                  75                  80

Arg Ser Ser Met Pro Thr Thr Ser Thr Pro Gly Thr Ser Thr Val Asp
                85                  90                  95

Val Gly Thr Ser Gly Thr Pro Ser Ser Ser Pro Ser Pro Thr Thr Ala
            100                 105                 110

Gly Pro Leu Leu Met Pro Phe Thr Leu Asn Phe Thr Ile Thr Asn Leu
        115                 120                 125

Gln Tyr Glu Glu Asp Met Arg Arg Thr Gly Ser Arg Lys Phe Asn Thr
    130                 135                 140

Met Glu Ser Val Leu Gln Gly Leu Leu Lys Pro Leu Phe Lys Asn Thr
145                 150                 155                 160

Ser Val Gly Pro Leu Tyr Ser Gly Cys Arg Leu Thr Leu Leu Arg Pro
                165                 170                 175

Xaa Lys Asp Gly Ala Ala Thr Gly Val Asp Ala Ile Cys Thr His Arg
            180                 185                 190

Leu Asp Pro Lys Ser Pro Gly Leu Asn Arg Glu Gln Leu Tyr Trp Glu
        195                 200                 205

Leu Ser Lys Leu Thr Asn Asp Ile Glu Glu Leu Gly Pro Tyr Thr Leu
    210                 215                 220

Asp Arg Asn Ser Leu Tyr Val Asn Gly Phe Thr His Gln Ser Ser Val
225                 230                 235                 240

Ser Thr Thr Ser Thr Pro Gly Thr Ser Thr Val Asp Leu Arg Thr Ser
                245                 250                 255
```

-continued

```
Val Thr Pro Ser Ser Leu Ser Ser Pro Thr Ile Met Ala Ala Gly Pro
            260                 265                 270

Leu Leu Val Pro Phe Thr Leu Asn Phe Thr Ile Thr Asn Leu Gln Tyr
        275                 280                 285

Gly Glu Asp Met Gly His Pro Gly Ser Arg Lys Phe Asn Thr Thr Glu
    290                 295                 300

Arg Val Leu Gln Gly Leu Leu Gly Pro Ile Phe Lys Asn Thr Ser Val
305                 310                 315                 320

Gly Pro Leu Tyr Ser Gly Cys Arg Leu Thr Ser Leu Arg Ser Xaa Lys
                325                 330                 335

Asp Gly Ala Ala Thr Gly Val Asp Ala Ile Cys Ile His His Leu Asp
            340                 345                 350

Pro Lys Ser Pro Gly Leu Asn Arg Glu Arg Leu Tyr Trp Glu Leu Ser
        355                 360                 365

Gln Leu Thr Asn Gly Ile Lys Glu Leu Gly Pro Tyr Thr Leu Asp Arg
    370                 375                 380

Asn Ser Leu Tyr Val Asn Ala Ala Gly Pro Leu Leu Val Leu Phe Thr
385                 390                 395                 400

Leu Asn Phe Thr Ile Thr Asn Leu Lys Tyr Glu Glu Asp Met His Arg
                405                 410                 415

Pro Gly Ser Arg Lys Phe Asn Thr Thr Glu Arg Val Leu Gln Thr Leu
            420                 425                 430

Arg Gly Pro Met Phe Lys Asn Thr Ser Gly Gly Leu Leu Tyr Ser Gly
        435                 440                 445

Cys Arg Leu Thr Leu Leu Arg Ser Glu Lys Asp Gly Ala Ala Thr Gly
    450                 455                 460

Val Asp Ala Ile Cys Thr His Arg Leu Asp Pro Lys Ser Pro Gly Val
465                 470                 475                 480

Asp Arg Glu Gln Leu Tyr Trp Glu Leu Ser Gln Leu Thr Asn Gly Ile
                485                 490                 495

Lys Glu Leu Gly Pro Tyr Thr Leu Asp Arg Asn Ser Leu Tyr Val Asn
            500                 505                 510

Gly Phe Thr His Arg Thr Ser Val Pro Thr Xaa Ser Thr Pro Gly Thr
        515                 520                 525

Ser Thr Val Asp Leu Gly Thr Ser Gly Thr Pro Phe Ser Leu Pro Ser
    530                 535                 540

Pro Ala Thr Ala Gly Pro Leu Leu Val Leu Phe Thr Leu Asn Phe Thr
545                 550                 555                 560

Ile Thr Asn Leu Lys Tyr Glu Glu Asp Met His Arg Pro Gly Ser Arg
                565                 570                 575

Lys Phe Asn Thr Thr Glu Arg Val Leu Gln Thr Leu Leu Gly Pro Met
            580                 585                 590

Phe Lys Asn Thr Ser Val Gly Leu Leu Tyr Ser Gly Cys Arg Leu Thr
        595                 600                 605

Leu Leu Arg Ser Glu Lys Asp Gly Ala Xaa Thr Gly Val Asp Ala Ile
    610                 615                 620

Cys Thr His Arg Leu Asp Pro Lys Ser Pro Gly Val Asp Arg Glu Gln
625                 630                 635                 640

Leu Tyr Trp Glu Leu Ser Gln Leu Thr Asn Gly Ile Lys Glu Leu Gly
                645                 650                 655

Pro Tyr Thr Leu Asp Arg Xaa Ser Leu Tyr Val Asn Gly Phe Thr His
            660                 665                 670
```

-continued

```
Trp Ile Pro Val Pro Thr Ser Ser Thr Pro Gly Thr Ser Thr Val Asp
        675                 680                 685

Leu Gly Ser Gly Thr Pro Ser Ser Leu Pro Ser Pro Thr Thr Ala Gly
    690                 695                 700

Pro Leu Leu Val Pro Phe Thr Leu Asn Phe Thr Ile Thr Asn Leu Gln
705                 710                 715                 720

Tyr Glu Glu Asp Met His His Pro Gly Ser Arg Lys Phe Asn Thr Thr
                725                 730                 735

Glu Arg Val Leu Gln Gly Leu Leu Gly Pro Met Phe Lys Asn Thr Ser
            740                 745                 750

Val Gly Leu Leu Tyr Ser Gly Cys Arg Leu Thr Leu Leu Arg Pro Glu
        755                 760                 765

Lys Asn Gly Ala Ala Thr Gly Met Asp Ala Ile Cys Ser His Arg Leu
    770                 775                 780

Asp Pro Lys Ser Pro Gly Leu Asn Arg Glu Gln Leu Tyr Trp Glu Leu
785                 790                 795                 800

Ser Gln Leu Thr His Gly Ile Lys Glu Leu Gly Pro Tyr Thr Leu Asp
                805                 810                 815

Arg His Ser Leu Tyr Val Asn Gly Phe Thr His Trp Ile Pro Val Pro
            820                 825                 830

Thr Ser Ser Thr Pro Gly Thr Ser Thr Val Asp Leu Gly Ser Gly Thr
        835                 840                 845

Pro Ser Ser Leu Pro Ser Pro Thr Thr Ala Gly Pro Leu Leu Val Pro
    850                 855                 860

Phe Thr Leu Asn Phe Thr Ile Thr Asn Leu Xaa Tyr Glu Glu Asp Met
865                 870                 875                 880

His Cys Pro Gly Ser Arg Lys Phe Asn Thr Thr Glu Arg Val Leu Gln
                885                 890                 895

Ser Leu Leu Gly Pro Met Phe Lys Asn Thr Ser Val Gly Pro Leu Tyr
            900                 905                 910

Ser Gly Cys Arg Leu Thr Leu Leu Arg Ser Glu Lys Asp Gly Ala Ala
        915                 920                 925

Thr Gly Val Asp Ala Ile Cys Thr His Arg Leu Asp Pro Lys Ser Pro
    930                 935                 940

Gly Val Asp Arg Glu Gln Leu Tyr Trp Glu Leu Ser Gln Leu Thr Asn
945                 950                 955                 960

Xaa Ile Lys Glu Leu Gly Pro Tyr Thr Leu Asp Ser Asn Ser Leu Tyr
                965                 970                 975

Val Asn Gly Phe Thr His Gln Thr Ser Ala Pro Asn Thr Ser Thr Pro
            980                 985                 990

Gly Thr Ser Thr Val Asp Leu Gly Xaa Ser Gly Thr Pro Ser Ser Leu
        995                 1000                1005

Pro Ser Pro Thr Ser Ala Gly Pro Leu Leu Val Pro Phe Thr Leu Asn
    1010                1015                1020

Phe Thr Ile Thr Asn Leu Gln Tyr Glu Glu Asp Met His His Pro Gly
1025                1030                1035                1040

Ser Arg Lys Phe Asn Thr Thr Glu Arg Val Leu Gln Gly Leu Leu Gly
                1045                1050                1055

Pro Met Phe Lys Asn Thr Ser Val Gly Leu Leu Tyr Ser Gly Cys Arg
            1060                1065                1070

Leu Thr Leu Leu Arg Pro Glu Lys Asn Gly Ala Ala Thr Gly Met Asp
        1075                1080                1085

Ala Ile Cys Ser His Arg Leu Asp Pro Lys Ser Pro Gly Leu Asn Arg
```

-continued

```
    1090                1095                1100

Glu Gln Leu Tyr Trp Glu Leu Ser Gln Leu Thr His Gly Ile Lys Glu
1105                1110                1115                1120

Leu Gly Pro Tyr Thr Leu Asp Arg Asn Ser Leu Tyr Val Asn Gly Phe
                1125                1130                1135

Thr His Arg Ser Ser Val Ala Pro Thr Ser Thr Pro Gly Thr Ser Thr
            1140                1145                1150

Val Asp Leu Gly Thr Ser Gly Thr Pro Ser Ser Leu Pro Ser Pro Thr
        1155                1160                1165

Thr Ala Val Pro Leu Leu Val Pro Phe Thr Leu Asn Phe Thr Ile Thr
    1170                1175                1180

Asn Leu Gln Tyr Gly Glu Asp Met Arg His Pro Gly Ser Arg Lys Phe
1185                1190                1195                1200

Asn Thr Thr Glu Arg Val Leu Gln Gly Leu Leu Gly Pro Leu Phe Lys
                1205                1210                1215

Asn Ser Ser Val Gly Pro Leu Tyr Ser Gly Cys Arg Leu Ile Ser Leu
            1220                1225                1230

Arg Ser Glu Lys Asp Gly Ala Ala Thr Gly Val Asp Ala Ile Cys Thr
        1235                1240                1245

His His Leu Asn Pro Gln Ser Pro Gly Leu Asp Arg Glu Gln Leu Tyr
    1250                1255                1260

Trp Gln Leu Ser Gln Met Thr Asn Gly Ile Lys Glu Leu Gly Pro Tyr
1265                1270                1275                1280

Thr Leu Asp Arg Asn Ser Leu Tyr Val Asn Gly Phe Thr His Arg Ser
                1285                1290                1295

Ser Gly Leu Thr Thr Ser Thr Pro Trp Thr Ser Thr Val Asp Leu Gly
            1300                1305                1310

Thr Ser Gly Thr Pro Ser Pro Val Pro Ser Pro Thr Thr Ala Gly Pro
        1315                1320                1325

Leu Leu Val Pro Phe Thr Leu Asn Phe Thr Ile Thr Asn Leu Gln Tyr
    1330                1335                1340

Glu Glu Asp Met His Arg Pro Gly Ser Arg Lys Phe Asn Ala Thr Glu
1345                1350                1355                1360

Arg Val Leu Gln Gly Leu Leu Ser Pro Ile Phe Lys Asn Ser Ser Val
                1365                1370                1375

Gly Pro Leu Tyr Ser Gly Cys Arg Leu Thr Ser Leu Arg Pro Glu Lys
            1380                1385                1390

Asp Gly Ala Ala Thr Gly Met Asp Ala Val Cys Leu Tyr His Pro Asn
        1395                1400                1405

Pro Lys Arg Pro Gly Leu Asp Arg Glu Gln Leu Tyr Trp Glu Leu Ser
    1410                1415                1420

Gln Leu Thr His Asn Ile Thr Glu Leu Gly Pro Tyr Ser Leu Asp Arg
1425                1430                1435                1440

Xaa Ser Leu Tyr Val Asn Gly Phe Thr His Gln Asn Ser Val Pro Thr
                1445                1450                1455

Thr Ser Thr Pro Gly Thr Ser Thr Val Tyr Trp Ala Thr Thr Gly Thr
            1460                1465                1470

Pro Ser Ser Phe Pro Gly His Thr Glu Pro Gly Pro Leu Leu Ile Pro
        1475                1480                1485

Phe Thr Phe Asn Phe Thr Ile Thr Asn Leu His Tyr Glu Glu Asn Met
    1490                1495                1500

Gln His Pro Gly Ser Arg Lys Phe Asn Thr Thr Glu Arg Val Leu Gln
1505                1510                1515                1520
```

-continued

```
Gly Leu Leu Thr Pro Leu Phe Lys Asn Thr Ser Val Gly Pro Leu Tyr
                1525                1530                1535

Ser Gly Cys Arg Leu Thr Leu Leu Arg Pro Glu Lys Gln Glu Ala Ala
            1540                1545                1550

Thr Gly Xaa Asp Thr Ile Cys Xaa His Arg Xaa Asp Pro Ile Gly Pro
        1555                1560                1565

Gly Leu Asp Arg Glu Xaa Leu Tyr Trp Glu Leu Ser Gln Leu Thr His
    1570                1575                1580

Xaa Ile Thr Glu Leu Gly Pro Tyr Thr Leu Asp Arg Asp Ser Leu Tyr
1585                1590                1595                1600

Val Asn Gly Phe Asn Pro Trp Ser Ser Val Pro Thr Thr Ser Thr Pro
                1605                1610                1615

Gly Thr Ser Thr Val His Leu Ala Thr Ser Gly Thr Pro Ser Ser Leu
            1620                1625                1630

Pro Gly His Thr Ala Pro Val Pro Leu Leu Ile Pro Phe Thr Leu Asn
        1635                1640                1645

Phe Thr Ile Thr Asn Leu His Tyr Glu Glu Asn Met Gln His Pro Gly
    1650                1655                1660

Ser Arg Lys Phe Asn Thr Thr Glu Arg Val Leu Gln Gly Leu Leu Lys
1665                1670                1675                1680

Pro Leu Phe Lys Ser Thr Ser Val Gly Pro Leu Tyr Ser Gly Cys Arg
                1685                1690                1695

Leu Thr Leu Leu Arg Pro Glu Lys His Gly Ala Ala Thr Gly Val Asp
            1700                1705                1710

Ala Ile Cys Thr Leu Arg Leu Asp Pro Thr Gly Pro Gly Leu Asp Arg
        1715                1720                1725

Glu Arg Leu Tyr Trp Glu Leu Ser Gln Leu Thr Asn Ser Val Thr Glu
    1730                1735                1740

Leu Gly Pro Tyr Thr Leu Asp Arg Asp Ser Leu Tyr Val Asn Gly Phe
1745                1750                1755                1760

Thr His Arg Ser Ser Val Pro Thr Thr Ser Ile Pro Gly Thr Ser Ala
                1765                1770                1775

Val His Leu Glu Thr Ser Gly Thr Pro Ala Ser Leu Pro Gly His Thr
            1780                1785                1790

Ala Pro Gly Pro Leu Leu Val Pro Phe Thr Leu Asn Phe Thr Ile Thr
        1795                1800                1805

Asn Leu Gln Tyr Glu Glu Asp Met Arg His Pro Gly Ser Arg Lys Phe
    1810                1815                1820

Asn Thr Thr Glu Arg Val Leu Gln Gly Leu Leu Lys Pro Leu Phe Lys
1825                1830                1835                1840

Ser Thr Ser Val Gly Pro Leu Tyr Ser Gly Cys Arg Leu Thr Leu Leu
                1845                1850                1855

Arg Pro Glu Lys Arg Gly Ala Ala Thr Gly Val Asp Thr Ile Cys Thr
            1860                1865                1870

His Arg Leu Asp Pro Leu Asn Pro Gly Leu Asp Arg Glu Gln Leu Tyr
        1875                1880                1885

Trp Glu Leu Ser Lys Leu Thr Cys Gly Ile Ile Glu Leu Gly Pro Tyr
    1890                1895                1900

Leu Leu Asp Arg Gly Ser Leu Tyr Val Asn Gly Phe Thr His Arg Asn
1905                1910                1915                1920

Phe Val Pro Ile Thr Ser Thr Pro Gly Thr Ser Thr Val His Leu Gly
                1925                1930                1935
```

-continued

```
Thr Ser Glu Thr Pro Ser Ser Leu Pro Arg Pro Ile Val Pro Gly Pro
            1940                1945                1950

Leu Leu Val Pro Phe Thr Leu Asn Phe Thr Ile Thr Asn Leu Gln Tyr
        1955                1960                1965

Glu Glu Ala Met Arg His Pro Gly Ser Arg Lys Phe Asn Thr Thr Glu
    1970                1975                1980

Arg Val Leu Gln Gly Leu Leu Arg Pro Leu Phe Lys Asn Thr Ser Ile
1985                1990                1995                2000

Gly Pro Leu Tyr Ser Ser Cys Arg Leu Thr Leu Leu Arg Pro Glu Lys
                2005                2010                2015

Asp Lys Ala Ala Thr Arg Val Asp Ala Ile Cys Thr His His Pro Asp
            2020                2025                2030

Pro Gln Ser Pro Gly Leu Asn Arg Glu Gln Leu Tyr Trp Glu Leu Ser
        2035                2040                2045

Gln Leu Thr His Gly Ile Thr Glu Leu Gly Pro Tyr Thr Leu Asp Arg
    2050                2055                2060

Xaa Ser Leu Tyr Val Xaa Gly Phe Thr His Trp Ser Pro Ile Pro Thr
2065                2070                2075                2080

Thr Ser Thr Pro Gly Thr Ser Ile Val Asn Leu Gly Thr Ser Gly Ile
                2085                2090                2095

Pro Pro Ser Leu Pro Glu Thr Thr Ala Thr Gly Pro Leu Leu Val Pro
            2100                2105                2110

Phe Thr Leu Asn Phe Thr Ile Thr Asn Leu Gln Tyr Glu Glu Asn Met
        2115                2120                2125

Gly His Pro Gly Ser Arg Lys Phe Asn Ile Thr Glu Ser Val Leu Gln
    2130                2135                2140

Gly Leu Leu Lys Pro Leu Phe Lys Ser Thr Ser Val Gly Pro Leu Tyr
2145                2150                2155                2160

Ser Gly Cys Arg Leu Thr Leu Leu Arg Pro Glu Lys Asp Gly Val Ala
                2165                2170                2175

Thr Arg Val Asp Ala Ile Cys Thr His Arg Pro Asp Pro Lys Ile Pro
            2180                2185                2190

Gly Leu Asp Arg Gln Gln Leu Tyr Trp Glu Leu Ser Gln Leu Thr His
        2195                2200                2205

Ser Ile Thr Glu Leu Gly Pro Tyr Thr Leu Asp Arg Asp Ser Leu Tyr
    2210                2215                2220

Val Asn Gly Phe Thr Gln Arg Ser Ser Val Pro Thr Thr Ser Thr Pro
2225                2230                2235                2240

Gly Thr Phe Thr Val Gln Pro Glu Thr Ser Glu Thr Pro Ser Ser Leu
                2245                2250                2255

Pro Gly Pro Thr Ala Thr Gly Pro Val Leu Leu Pro Phe Thr Leu Asn
            2260                2265                2270

Phe Thr Ile Ile Asn Leu Gln Tyr Glu Glu Asp Met His Arg Pro Gly
        2275                2280                2285

Ser Arg Lys Phe Asn Thr Thr Glu Arg Val Leu Gln Gly Leu Leu Met
    2290                2295                2300

Pro Leu Phe Lys Asn Thr Ser Val Ser Ser Leu Tyr Ser Gly Cys Arg
2305                2310                2315                2320

Leu Thr Leu Leu Arg Pro Glu Lys Asp Gly Ala Ala Thr Arg Val Asp
                2325                2330                2335

Ala Val Cys Thr His Arg Pro Asp Pro Lys Ser Pro Gly Leu Asp Arg
            2340                2345                2350

Glu Arg Leu Tyr Trp Lys Leu Ser Gln Leu Thr His Gly Ile Thr Glu
```

-continued

```
        2355                2360                2365

Leu Gly Pro Tyr Thr Leu Asp Arg His Ser Leu Tyr Val Asn Gly Phe
    2370                2375                2380

Thr His Gln Ser Ser Met Thr Thr Thr Arg Thr Pro Asp Thr Ser Thr
2385                2390                2395                2400

Met His Leu Ala Thr Ser Arg Thr Pro Ala Ser Leu Ser Gly Pro Thr
                2405                2410                2415

Thr Ala Ser Pro Leu Leu Val Leu Phe Thr Ile Asn Phe Thr Ile Thr
            2420                2425                2430

Asn Leu Arg Tyr Glu Glu Asn Met His His Pro Gly Ser Arg Lys Phe
        2435                2440                2445

Asn Thr Thr Glu Arg Val Leu Gln Gly Leu Leu Arg Pro Val Phe Lys
    2450                2455                2460

Asn Thr Ser Val Gly Pro Leu Tyr Ser Gly Cys Arg Leu Thr Leu Leu
2465                2470                2475                2480

Arg Pro Lys Lys Asp Gly Ala Ala Thr Lys Val Asp Ala Ile Cys Thr
                2485                2490                2495

Tyr Arg Pro Asp Pro Lys Ser Pro Gly Leu Asp Arg Glu Gln Leu Tyr
            2500                2505                2510

Trp Glu Leu Ser Gln Leu Thr His Ser Ile Thr Glu Leu Gly Pro Tyr
        2515                2520                2525

Thr Leu Asp Arg Asp Ser Leu Tyr Val Asn Gly Phe Thr Gln Arg Ser
    2530                2535                2540

Ser Val Pro Thr Thr Ser Ile Pro Gly Thr Pro Thr Val Asp Leu Gly
2545                2550                2555                2560

Thr Ser Gly Thr Pro Val Ser Lys Pro Gly Pro Ser Ala Ala Ser Pro
                2565                2570                2575

Leu Leu Val Leu Phe Thr Leu Asn Phe Thr Ile Thr Asn Leu Arg Tyr
            2580                2585                2590

Glu Glu Asn Met Gln His Pro Gly Ser Arg Lys Phe Asn Thr Thr Glu
        2595                2600                2605

Arg Val Leu Gln Gly Leu Leu Arg Ser Leu Phe Lys Ser Thr Ser Val
    2610                2615                2620

Gly Pro Leu Tyr Ser Gly Cys Arg Leu Thr Leu Leu Arg Pro Glu Lys
2625                2630                2635                2640

Asp Gly Thr Ala Thr Gly Val Asp Ala Ile Cys Thr His His Pro Asp
                2645                2650                2655

Pro Lys Ser Pro Arg Leu Asp Arg Glu Gln Leu Tyr Trp Glu Leu Ser
            2660                2665                2670

Gln Leu Thr His Asn Ile Thr Glu Leu Gly Xaa Tyr Ala Leu Asp Asn
        2675                2680                2685

Asp Ser Leu Phe Val Asn Gly Phe Thr His Arg Ser Ser Val Ser Thr
    2690                2695                2700

Thr Ser Thr Pro Gly Thr Pro Thr Val Tyr Leu Gly Ala Ser Lys Thr
2705                2710                2715                2720

Pro Ala Ser Ile Phe Gly Pro Ser Ala Ala Ser His Leu Leu Ile Leu
                2725                2730                2735

Phe Thr Leu Asn Phe Thr Ile Thr Asn Leu Arg Tyr Glu Glu Asn Met
            2740                2745                2750

Trp Pro Gly Ser Arg Lys Phe Asn Thr Thr Glu Arg Val Leu Gln Gly
        2755                2760                2765

Leu Leu Arg Pro Leu Phe Lys Asn Thr Ser Val Gly Pro Leu Tyr Ser
    2770                2775                2780
```

-continued

```
Gly Cys Arg Leu Thr Leu Leu Arg Pro Glu Lys Asp Gly Glu Ala Thr
2785                2790                2795                2800

Gly Val Asp Ala Ile Cys Thr His Arg Pro Asp Pro Thr Gly Pro Gly
                2805                2810                2815

Leu Asp Arg Glu Gln Leu Tyr Leu Glu Leu Ser Gln Leu Thr His Ser
            2820                2825                2830

Ile Thr Glu Leu Gly Pro Tyr Thr Leu Asp Arg Asp Ser Leu Tyr Val
        2835                2840                2845

Asn Gly Phe Thr His Arg Ser Ser Val Pro Thr Thr Ser Thr Gly Val
    2850                2855                2860

Val Ser Glu Glu Pro Phe Thr Leu Asn Phe Thr Ile Asn Asn Leu Arg
2865                2870                2875                2880

Tyr Met Ala Asp Met Gly Gln Pro Gly Ser Leu Lys Phe Asn Ile Thr
                2885                2890                2895

Asp Asn Val Met Lys His Leu Leu Ser Pro Leu Phe Gln Arg Ser Ser
            2900                2905                2910

Leu Gly Ala Arg Tyr Thr Gly Cys Arg Val Ile Ala Leu Arg Ser Val
        2915                2920                2925

Lys Asn Gly Ala Glu Thr Arg Val Asp Leu Leu Cys Thr Tyr Leu Gln
    2930                2935                2940

Pro Leu Ser Gly Pro Gly Leu Pro Ile Lys Gln Val Phe His Glu Leu
2945                2950                2955                2960

Ser Gln Gln Thr His Gly Ile Thr Arg Leu Gly Pro Tyr Ser Leu Asp
                2965                2970                2975

Lys Asp Ser Leu Tyr Leu Asn Gly Tyr Asn Glu Pro Gly Xaa Asp Glu
            2980                2985                2990

Pro Pro Thr Thr Pro Lys Pro Ala Thr Thr Phe Leu Pro Pro Leu Ser
        2995                3000                3005

Glu Ala Thr Thr Ala Met Gly Tyr His Leu Lys Thr Leu Thr Leu Asn
    3010                3015                3020

Phe Thr Ile Ser Asn Leu Gln Tyr Ser Pro Asp Met Gly Lys Gly Ser
3025                3030                3035                3040

Ala Thr Phe Asn Ser Thr Glu Gly Val Leu Gln His Leu Leu Arg Pro
                3045                3050                3055

Leu Phe Gln Lys Ser Ser Met Gly Pro Phe Tyr Leu Gly Cys Gln Leu
            3060                3065                3070

Ile Ser Leu Arg Pro Glu Lys Asp Gly Ala Ala Thr Gly Val Asp Thr
        3075                3080                3085

Thr Cys Thr Tyr His Pro Asp Pro Val Gly Pro Gly Leu Asp Ile Gln
    3090                3095                3100

Gln Leu Tyr Trp Glu Leu Ser Gln Leu Thr His Gly Val Thr Gln Leu
3105                3110                3115                3120

Gly Phe Tyr Val Leu Asp Arg Asp Ser Leu Phe Ile Asn Gly Tyr Ala
                3125                3130                3135

Pro Gln Asn Leu Ser Ile Arg Gly Glu Tyr Gln Ile Asn Phe His Ile
            3140                3145                3150

Val Asn Trp Asn Leu Ser Asn Pro Asp Pro Thr Ser Ser Glu Tyr Ile
        3155                3160                3165

Thr Leu Leu Arg Asp Ile Gln Asp Lys Val Thr Thr Leu Tyr Lys Gly
    3170                3175                3180

Ser Gln Leu His Asp Thr Phe Arg Phe Cys Leu Val Thr Asn Leu Thr
3185                3190                3195                3200
```

-continued

```
Met Asp Ser Val Leu Val Thr Val Lys Ala Leu Phe Ser Ser Asn Leu
                3205                3210                3215

Asp Pro Ser Leu Val Glu Gln Val Phe Leu Asp Lys Thr Leu Asn Ala
            3220                3225                3230

Ser Phe His Trp Leu Gly Ser Thr Tyr Gln Leu Val Asp Ile His Val
        3235                3240                3245

Thr Glu Met Glu Ser Ser Val Tyr Gln Pro Thr Ser Ser Ser Ser Thr
    3250                3255                3260

Gln His Phe Tyr Xaa Asn Phe Thr Ile Thr Asn Leu Pro Tyr Ser Gln
3265                3270                3275                3280

Asp Lys Ala Gln Pro Gly Thr Thr Asn Tyr Gln Arg Asn Lys Arg Asn
                3285                3290                3295

Ile Glu Asp Ala Leu Asn Gln Leu Phe Arg Asn Ser Ser Ile Lys Ser
            3300                3305                3310

Tyr Phe Ser Asp Cys Gln Val Ser Thr Phe Arg Ser Val Pro Asn Arg
        3315                3320                3325

His His Thr Gly Val Asp Ser Leu Cys Asn Phe Ser Pro Leu Ala Arg
    3330                3335                3340

Arg Val Asp Arg Val Ala Ile Tyr Glu Glu Phe Leu Arg Met Thr Arg
3345                3350                3355                3360

Asn Gly Thr Gln Leu Gln Asn Phe Thr Leu Asp Arg Ser Ser Val Leu
                3365                3370                3375

Val Asp Gly Tyr Xaa Pro Asn Arg Asn Glu Pro Leu Thr Gly Asn Ser
            3380                3385                3390

Asp Leu Pro Phe Trp Ala Val Ile Xaa Ile Gly Leu Ala Gly Leu Leu
        3395                3400                3405

Gly Leu Ile Thr Cys Leu Ile Cys Gly Val Leu Val Thr Thr Arg Arg
    3410                3415                3420

Arg Lys Lys Glu Gly Glu Tyr Asn Val Gln Gln Gln Cys Pro Gly Tyr
3425                3430                3435                3440

Tyr Gln Ser His Leu Asp Leu Glu Asp Leu Gln
                3445                3450
```

<210> SEQ ID NO 596
<211> LENGTH: 156
<212> TYPE: PRT
<213> ORGANISM: Homo sapiens

<400> SEQUENCE: 596

```
Gly Phe Thr His Arg Ser Ser Val Pro Thr Thr Ser Thr Pro Gly Thr
                  5                  10                  15

Ser Thr Val Asp Leu Gly Thr Ser Gly Thr Pro Ser Ser Leu Pro Ser
             20                  25                  30

Pro Thr Ala Ala Gly Pro Leu Leu Val Pro Phe Thr Leu Asn Phe Thr
         35                  40                  45

Ile Thr Asn Leu Gln Tyr Glu Glu Asp Met His His Pro Gly Ser Arg
     50                  55                  60

Lys Phe Asn Thr Thr Glu Arg Val Leu Gln Gly Leu Leu Gly Pro Leu
 65                  70                  75                  80

Phe Lys Asn Thr Ser Val Gly Pro Leu Tyr Ser Gly Cys Arg Leu Thr
                 85                  90                  95

Leu Leu Arg Pro Glu Lys Asp Gly Ala Ala Thr Gly Val Asp Ala Ile
            100                 105                 110

Cys Thr His Arg Leu Asp Pro Lys Ser Pro Gly Leu Asp Arg Glu Gln
        115                 120                 125
```

-continued

```
Leu Tyr Trp Glu Leu Ser Gln Leu Thr His Gly Ile Thr Glu Leu Gly
    130                 135                 140

Pro Tyr Thr Leu Asp Arg Asp Ser Leu Tyr Val Asn
145                 150                 155


<210> SEQ ID NO 597
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 597

Lys Ser Tyr Phe Ser Asp Cys Gln Val Ser Thr Phe Arg Ser Val Pro
 1               5                  10                  15

Asn Arg His His Thr Gly Val Asp Ser Leu Cys Asn
            20                  25


<210> SEQ ID NO 598
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 598

Phe Ser Pro Leu Ala Arg Arg Val Asp Arg Val Ala Ile Tyr Glu Glu
 1               5                  10                  15

Phe Leu Arg Met Thr Arg Asn Gly Thr Gln Leu Gln
            20                  25


<210> SEQ ID NO 599
<211> LENGTH: 28
<212> TYPE: PRT
<213> ORGANISM: Artificial Sequence
<220> FEATURE:
<223> OTHER INFORMATION: Peptide that correspond to the extracellular
      domain of O772P molecule.

<400> SEQUENCE: 599

Thr Leu Asp Arg Ser Ser Val Leu Val Asp Gly Tyr Phe Pro Asn Arg
 1               5                  10                  15

Asn Glu Pro Leu Thr Gly Asn Ser Asp Leu Pro Phe
            20                  25


<210> SEQ ID NO 600
<211> LENGTH: 20
<212> TYPE: PRT
<213> ORGANISM: Homo sapiens

<400> SEQUENCE: 600

Met Ala Ser Leu Gly Gln Ile Leu Phe Trp Ser Ile Ile Ser Ile Ile
 1               5                  10                  15

Ile Ile Leu Ala
            20


SEQ ID NO 601
LENGTH: 20
<212> TYPE: PRT
<213> ORGANISM: Homo sapiens

<400> SEQUENCE: 601
```

-continued

Ile Ile Ile Leu Ala Gly Ala Ile Ala Leu Ile Ile Gly Phe Gly Ile
1 5 10 15

Ser Gly Arg His
20

<210> SEQ ID NO 602
<211> LENGTH: 20
<212> TYPE: PRT
<213> ORGANISM: Homo sapiens

<400> SEQUENCE: 602

Ile Ser Gly Arg His Ser Ile Thr Val Thr Thr Val Ala Ser Ala Gly
1 5 10 15

Asn Ile Gly Glu
20

<210> SEQ ID NO 603
<211> LENGTH: 20
<212> TYPE: PRT
<213> ORGANISM: Homo sapiens

<400> SEQUENCE: 603

Gly Asn Ile Gly Glu Asp Gly Ile Leu Ser Cys Thr Phe Glu Pro Asp
1 5 10 15

Ile Lys Leu Ser
20

<210> SEQ ID NO 604
<211> LENGTH: 20
<212> TYPE: PRT
<213> ORGANISM: Homo sapiens

<400> SEQUENCE: 604

Asp Ile Lys Leu Ser Asp Ile Val Ile Gln Trp Leu Lys Glu Gly Val
1 5 10 15

Leu Gly Leu Val
20

<210> SEQ ID NO 605
<211> LENGTH: 20
<212> TYPE: PRT
<213> ORGANISM: Homo sapiens

<400> SEQUENCE: 605

Val Leu Gly Leu Val His Glu Phe Lys Glu Gly Lys Asp Glu Leu Ser
1 5 10 15

Glu Gln Asp Glu
20

<210> SEQ ID NO 606
<211> LENGTH: 20
<212> TYPE: PRT
<213> ORGANISM: Homo sapiens

<400> SEQUENCE: 606

Ser Glu Gln Asp Glu Met Phe Arg Gly Arg Thr Ala Val Phe Ala Asp
1 5 10 15

Gln Val Ile Val
20

<210> SEQ ID NO 607

<211> LENGTH: 20
<212> TYPE: PRT
<213> ORGANISM: Homo sapiens

<400> SEQUENCE: 607

Asp Gln Val Ile Val Gly Asn Ala Ser Leu Arg Leu Lys Asn Val Gln
1 5 10 15

Leu Thr Asp Ala
20

<210> SEQ ID NO 608
<211> LENGTH: 21
<212> TYPE: PRT
<213> ORGANISM: Homo sapiens

<400> SEQUENCE: 608

Val Gln Leu Thr Asp Ala Gly Thr Tyr Lys Cys Tyr Ile Ile Thr Ser
1 5 10 15

Lys Gly Lys Gly Asn
20

<210> SEQ ID NO 609
<211> LENGTH: 20
<212> TYPE: PRT
<213> ORGANISM: Homo sapiens

<400> SEQUENCE: 609

Lys Gly Lys Gly Asn Ala Asn Leu Glu Tyr Lys Thr Gly Ala Phe Ser
1 5 10 15

Met Pro Glu Val
20

<210> SEQ ID NO 610
<211> LENGTH: 20
<212> TYPE: PRT
<213> ORGANISM: Homo sapiens

<400> SEQUENCE: 610

Ser Met Pro Glu Val Asn Val Asp Tyr Asn Ala Ser Ser Glu Thr Leu
1 5 10 15

Arg Cys Glu Ala
20

<210> SEQ ID NO 611
<211> LENGTH: 20
<212> TYPE: PRT
<213> ORGANISM: Homo sapiens

<400> SEQUENCE: 611

Leu Arg Cys Glu Ala Pro Arg Trp Phe Pro Gln Pro Thr Val Val Trp
1 5 10 15

Ala Ser Gln Val
20

<210> SEQ ID NO 612
<211> LENGTH: 20
<212> TYPE: PRT
<213> ORGANISM: Homo sapiens

<400> SEQUENCE: 612

Trp Ala Ser Gln Val Asp Gln Gly Ala Asn Phe Ser Glu Val Ser Asn
1 5 10 15

-continued

```
Thr Ser Phe Glu
            20


<210> SEQ ID NO 613
<211> LENGTH: 20
<212> TYPE: PRT
<213> ORGANISM: Homo sapiens

<400> SEQUENCE: 613

Asn Thr Ser Phe Glu Leu Asn Ser Glu Asn Val Thr Met Lys Val Val
 1               5                   10                  15

Ser Val Leu Tyr
            20


<210> SEQ ID NO 614
<211> LENGTH: 20
<212> TYPE: PRT
<213> ORGANISM: Homo sapiens

<400> SEQUENCE: 614

Val Ser Val Leu Tyr Asn Val Thr Ile Asn Asn Thr Tyr Ser Cys Met
 1               5                   10                  15

Ile Glu Asn Asp
            20


<210> SEQ ID NO 615
<211> LENGTH: 20
<212> TYPE: PRT
<213> ORGANISM: Homo sapiens

<400> SEQUENCE: 615

Met Ile Glu Asn Asp Ile Ala Lys Ala Thr Gly Asp Ile Lys Val Thr
 1               5                   10                  15

Glu Ser Glu Ile
            20


<210> SEQ ID NO 616
<211> LENGTH: 20
<212> TYPE: PRT
<213> ORGANISM: Homo sapiens

<400> SEQUENCE: 616

Thr Glu Ser Glu Ile Lys Arg Arg Ser His Leu Gln Leu Leu Asn Ser
 1               5                   10                  15

Lys Ala Ser Leu
            20


<210> SEQ ID NO 617
<211> LENGTH: 20
<212> TYPE: PRT
<213> ORGANISM: Homo sapiens

<400> SEQUENCE: 617

Ser Lys Ala Ser Leu Cys Val Ser Ser Phe Phe Ala Ile Ser Trp Ala
 1               5                   10                  15

Leu Leu Pro Ile
            20


<210> SEQ ID NO 618
<211> LENGTH: 20
<212> TYPE: PRT
<213> ORGANISM: Homo sapiens
```

-continued

<400> SEQUENCE: 618

Ser Ser Phe Phe Ala Ile Ser Trp Ala Leu Leu Pro Leu Ser Pro Tyr
1 5 10 15

Leu Met Leu Lys
20

<210> SEQ ID NO 619
<211> LENGTH: 30
<212> TYPE: DNA
<213> ORGANISM: Artificial Sequence
<220> FEATURE:
<223> OTHER INFORMATION: PCR primer

<400> SEQUENCE: 619
cagaagctta tggcttccct ggggcagact 30

<210> SEQ ID NO 620
<211> LENGTH: 31
<212> TYPE: DNA
<213> ORGANISM: Artificial Sequence
<220> FEATURE:
<223> OTHER INFORMATION: PCR primer

<400> SEQUENCE: 620
cagcggccgc ttattttagc atcaggtaag g 31

<210> SEQ ID NO 621
<211> LENGTH: 849
<212> TYPE: DNA
<213> ORGANISM: Rhesus Monkey

<400> SEQUENCE: 621
atggcttccc tggggcagat cctcttctgg agcataatta gcatcatctt tattctggct 60
ggagcaattg cactcatcat tggctttggt atttcaggga gacactccat cacagtcact 120
actgttgcct cagctgggaa cattggggag gatggaatcc tgagctgcac ttttgaacct 180
gacatcaaac tttctgatat cgtgatacaa tggctgaagg aaggtgttat aggcttggtc 240
catgagttca aagaaggcaa agatgagctg tcggagcagg atgaaatgtt cagaggccgg 300
acagcagtgt ttgctgatca agtgatagtt ggcaatgcct ctctgcggct gaaaaatgta 360
caacttacag acgctggcac ctacaaatgt tacatcatca cttctaaagg caaggggaat 420
gctaaccttg agtataaaac tggagccttc agcatgccag aggtgaatgt ggactataac 480
gccagctcag agaccttgcg gtgtgaggct ccccgatggt tcccccagcc cacagtggtc 540
tgggcatccc aagttgacca gggagccaac ttctcggaag tctccaatac cagctttgag 600
ctgaactctg agaatgtgac catgaaggtt gtgtctgtgc tatacaatgt tacgatcaac 660
aacacatact cctgtatgat tgaaaatgac attgccaaag caacagggga tatcaaagtg 720
acagaatctg agatcaaaag acggagtcac ctacagctgc taaactcaaa ggcttctctg 780
tgtgtctctt ctttccttgc catcagctgg gcacttctgc ctctcgcccc ttacctgatg 840
ctaaaataa 849

<210> SEQ ID NO 622
<211> LENGTH: 1399
<212> TYPE: DNA
<213> ORGANISM: Mus musculus
<220> FEATURE:
<221> NAME/KEY: misc_feature
<222> LOCATION: 1093,1130,1134,1233
<223> OTHER INFORMATION: n = A,T,C or G -continued

<400> SEQUENCE: 622

```
cccgcgtccg cggacgcgtg gggcagcagg caggcagctc cactcaccaa aatctggccc      60
cacacacagc aggactgtgg gaaggaactc cctctccatg gcttccttgg ggcagatcat     120
cttttggagt attattaaca tcatcatcat cctggctggg gccatcgcac tcatcattgg     180
ctttggcatt tcaggcaagc acttcatcac ggtcacgacc ttcacctcag ctggaaacat     240
tggagaggac gggaccctga gctgcacttt tgaacctgac atcaaactca acggcatcgt     300
catccagtgg ctgaaagaag gcatcaaagg tttggtccac gagttcaaag aaggcaaaga     360
cgacctctca cagcagcatg agatgttcag aggccgcaca gcagtgtttg ctgatcaggt     420
ggtagttggc aatgcttccc tgagactgaa aaacgtgcag ctcacggatg ctggcaccta     480
cacatgttac atccgcacct caaaaggcaa agggaatgca aaccttgagt ataagaccgg     540
agccttcagt atgccagaga taaatgtgga ctataatgcc agttcagaga gtttacgctg     600
cgaggctcct cggtggttcc cccagcccac agtggcctgg gcatctcaag tcgaccaagg     660
agccaatttc tcagaagtct ccaacaccag ctttgagttg aactctgaga atgtgaccat     720
gaaggtcgta tctgtgctct acaatgtcac aatcaacaac acatactcct gtatgattga     780
aaacgacatt gccaaagcca ccggggacat caaagtgaca gattcagagg tcaaaaggcg     840
aagtcagctg cagttgctga actctgggcc ttccccgtgt gttttttctt ctgcctttgt     900
ggctggctgg gcactcctat ctctctcctg ttgcctgatg ctaagatgag ggccctggc      960
tacacaaaag catgcaacgt tgctggtcca acagaatccc ggagaactac agaaatattt    1020
tcctcaagac atgacctagt tttatatttt tagaagaaga tgaaatcatg tctagaagtc    1080
tggagagagc agncaggacc aagatgtgga aggaaaacaa aagtaacccn cagncccccc    1140
cgatcggaac aagatggacc tagaaaataa ttcaaccaaa ctagagtata ctaagtgtgc    1200
tgttacaatg tgtgtagggt aggtgtcctc ccmcatctca ggggcctccc ctggtccccc    1260
agctcctgag ttaggatggg ctgttatgat gtccctctga aggttcctgg atggttccta    1320
ctgccatata ctcattttat attcagccca ttaaaccata gtgaatgcta aaaaaaaaaa    1380
aaaaaaaaaa aaaaaaaaa                                                 1399
```

<210> SEQ ID NO 623
<211> LENGTH: 282
<212> TYPE: PRT
<213> ORGANISM: Rhesus Monkey

<400> SEQUENCE: 623

```
Met Ala Ser Leu Gly Gln Ile Leu Phe Trp Ser Ile Ile Ser Ile Ile
                5                   10                  15

Phe Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Ile Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
            100                 105                 110
```

-continued

```
Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Leu Pro Leu Ala Pro Tyr Leu Met Leu Lys
        275                 280


<210> SEQ ID NO 624
<211> LENGTH: 283
<212> TYPE: PRT
<213> ORGANISM: Mus musculus

<400> SEQUENCE: 624

Met Ala Ser Leu Gly Gln Ile Ile Phe Trp Ser Ile Ile Asn Ile Ile
                  5                  10                  15

Ile Ile Leu Ala Gly Ala Ile Ala Leu Ile Ile Gly Phe Gly Ile Ser
             20                  25                  30

Gly Lys His Phe Ile Thr Val Thr Thr Phe Thr Ser Ala Gly Asn Ile
         35                  40                  45

Gly Glu Asp Gly Thr Leu Ser Cys Thr Phe Glu Pro Asp Ile Lys Leu
     50                  55                  60

Asn Gly Ile Val Ile Gln Trp Leu Lys Glu Gly Ile Lys Gly Leu Val
 65                  70                  75                  80

His Glu Phe Lys Glu Gly Lys Asp Asp Leu Ser Gln Gln His Glu Met
                 85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
        115                 120                 125

Thr Cys Tyr Ile Arg Thr Ser Lys Gly Lys Gly Asn Ala Asn Leu Glu
    130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
```

-continued

```
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
                245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
        275                 280
```